(12) United States Patent
Horhota et al.

(10) Patent No.: US 12,180,138 B2
(45) Date of Patent: Dec. 31, 2024

(54) LIPID NANOPARTICLE COMPOSITIONS FOR DELIVERING CIRCULAR POLYNUCLEOTIDES

(71) Applicant: Orna Therapeutics, Inc., Watertown, MA (US)

(72) Inventors: Allen T. Horhota, Cambridge, MA (US); Junghoon Yang, Cambridge, MA (US); Kevin J. Kauffman, Newton, MA (US); Thomas Barnes, Cambridge, MA (US); Robert Alexander Wesselhoeft, Cambridge, MA (US); Amy M. Becker, Cambridge, MA (US); Gregory Motz, Cambridge, MA (US)

(73) Assignee: Orna Therapeutics, Inc., Watertown, MA (US)

( * ) Notice: Subject to any disclaimer, the term of this patent is extended or adjusted under 35 U.S.C. 154(b) by 0 days.

(21) Appl. No.: 18/501,955

(22) Filed: Nov. 3, 2023

(65) Prior Publication Data
US 2024/0116852 A1    Apr. 11, 2024

Related U.S. Application Data

(63) Continuation of application No. PCT/US2022/049313, filed on Nov. 8, 2022.
(Continued)

(51) Int. Cl.
| | |
|---|---|
| *C07C 229/12* | (2006.01) |
| *A61K 9/127* | (2006.01) |
| *A61K 31/7105* | (2006.01) |
| *A61K 45/06* | (2006.01) |
| *A61K 47/10* | (2017.01) |

(Continued)

(52) U.S. Cl.
CPC .......... *C07C 229/12* (2013.01); *A61K 9/1272* (2013.01); *A61K 31/7105* (2013.01); *A61K 45/06* (2013.01); *A61K 47/10* (2013.01); *A61K 47/18* (2013.01); *A61K 47/183* (2013.01); *A61K 47/24* (2013.01); *A61K 47/28* (2013.01); *A61K 47/543* (2017.08); *A61K 48/0033* (2013.01); *C07C 219/06* (2013.01); *C07C 229/22* (2013.01); *C07C 229/24* (2013.01)

(58) Field of Classification Search
CPC ... C97C 229/12; A61K 47/28; A61K 47/1183; C07C 229/12
See application file for complete search history.

(56) References Cited

FOREIGN PATENT DOCUMENTS

| WO | WO 2017/049245 A1 | 3/2017 |
|---|---|---|
| WO | WO 2018/170306 A1 | 9/2018 |

(Continued)

OTHER PUBLICATIONS

PCT International Search Report and Written Opinion, PCT Application No. PCT/US2022/049313, Mar. 17, 2023, 11 pages.
(Continued)

*Primary Examiner* — Carlos A Azpuru
(74) *Attorney, Agent, or Firm* — Fenwick & West LLP; Carl A. Morales; Cara A. Mosley

(57) ABSTRACT

Disclosed herein are novel lipids that can be used in combination with other lipid components, such as helper lipids, structural lipids, and cholesterols, to form lipid nanoparticles for delivery of therapeutic agents, such as nucleic acids (e.g., circular polynucleotides), both in vitro and in vivo.

28 Claims, 108 Drawing Sheets
Specification includes a Sequence Listing.

Related U.S. Application Data

(60) Provisional application No. 63/277,055, filed on Nov. 8, 2021.

(51) Int. Cl.
| | | |
|---|---|---|
| *A61K 47/18* | (2017.01) |
| *A61K 47/24* | (2006.01) |
| *A61K 47/28* | (2006.01) |
| *A61K 47/54* | (2017.01) |
| *A61K 48/00* | (2006.01) |
| *C07C 219/06* | (2006.01) |
| *C07C 229/22* | (2006.01) |
| *C07C 229/24* | (2006.01) |

(56) References Cited

FOREIGN PATENT DOCUMENTS

| WO | WO 2019/152557 A1 | 8/2019 |
|---|---|---|
| WO | 2020/061367 * | 3/2020 |
| WO | WO 2020/061367 A1 | 3/2020 |
| WO | WO 2020/257611 A1 | 12/2020 |
| WO | WO 2021/142280 A1 | 7/2021 |
| WO | WO 2021/178396 A1 | 9/2021 |
| WO | WO 2022/140252 A1 | 6/2022 |
| WO | WO 2022/247755 A1 | 12/2022 |

OTHER PUBLICATIONS

PCT International Preliminary Report on Patentability, PCT Application No. PCT/US2022/049313, Feb. 23, 2024, 14 pages.

PCT International Search Report and Written Opinion, PCT Application No. PCT/US2022/045408, Mar. 22, 2023, 20 pages.

PCT Written Opinion of the International Preliminary Examining Authority, PCT Application No. PCT/US2022/049313, Nov. 29, 2023, eight pages.

U.S. Appl. No. 18/501,945, filed Nov. 3, 2023, Inventors Allen T. Horhota, et al. (copy not enclosed).

U.S. Appl. No. 18/501,950, filed Nov. 3, 2023, Inventors Allen T. Horhota, et al. (copy not enclosed).

U.S. Appl. No. 18/501,958, filed Nov. 3, 2023, Inventors Allen T. Horhota, et al. (copy not enclosed).

Zhao, X. et al. "Imidazole-Based Synthetic Lipidoids for In Vivo mRNA Delivery into Primary T Lymphocytes." Angewandte Chemie International Edition, vol. 59, No. 45, Nov. 2, 2020, pp. 20083-20089.

* cited by examiner

SEQUENCE LISTING

```
Sequence total quantity: 125
SEQ ID NO: 1              moltype = AA   length = 493
FEATURE                   Location/Qualifiers
source                    1..493
                          mol_type = protein
                          organism = synthetic construct
SEQUENCE: 1
MALPVTALLL PLALLLHAAR PDIVLTQSPA SLAVSLGERA TINCRASESV SVIGAHLIHW   60
YQQKPGQPPK LLIYLASNLE TGVPARFSGS GSGTDFTLTI SSLQAEDAAI YYCLQSRIFP  120
RTFGQGTKLE IKGSTSGSGK PGSGEGSTKG QVQLVQSGSE LKKPGASVKV SCKASGYTFT  180
DYSINWVRQA PGQGLEWMGW INTETREPAY AYDFRGRFVF SLDTSVSTAY LQISSLKAED  240
TAVYYCARDY SYAMDYWGQG TLVTVSSAAA TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                    493

SEQ ID NO: 2              moltype = AA   length = 207
FEATURE                   Location/Qualifiers
source                    1..207
                          mol_type = protein
                          organism = synthetic construct
SEQUENCE: 2
KNQVEQSPQS LIILEGKNCT LQCNYTVSPF SNLRWYKQDT GRGPVSLTIM TFSENTKSNG   60
RYTATLDADT KQSSLHITAS QLSDSASYIC VVNHSGGSYI PTFGRGTSLI VHPYIQKPDP  120
AVYQLRDSKS SDKSVCLFTD FDSQTNVSQS KDSDVYITDK TVLDMRSMDF KSNSAVAWSN  180
KSDFACANAF NNSIIPEDTF FPSPESS                                     207

SEQ ID NO: 3              moltype = AA   length = 246
FEATURE                   Location/Qualifiers
source                    1..246
                          mol_type = protein
                          organism = synthetic construct
SEQUENCE: 3
DVKVTQSSRY LVKRTGEKVF LECVQDMDHE NMFWYRQDPG LGLRLIYFSY DVKMKEKGDI   60
PEGYSVSREK KERFSLILES ASTNQTSMYL CASSFLMTSG DPYEQYFGPG TRLTVTEDLK  120
NVFPPEVAVF EPSEAEISHT QKATLVCLAT GFYPDHVELS WWVNGKEVHS GVSTDPQPLK  180
EQPALNDSRY CLSSRLRVSA TFWQNPRNHF RCQVQFYGLS ENDEWTQDRA KPVTQIVSAE  240
AWGRAD                                                            246

SEQ ID NO: 4              moltype = AA   length = 115
FEATURE                   Location/Qualifiers
source                    1..115
                          mol_type = protein
                          organism = synthetic construct
SEQUENCE: 4
MQEVTQIPAA LSVPEGENLV LNCSFTDSAI YNLQWFRQDP GKGLTSLLLI QSSQREQTSG   60
RLNASLDKSS GRSTLYIAAS QPGDSATYLC AVRPTSGGSY IPTFGRGTSL IVHPY       115

SEQ ID NO: 5              moltype = AA   length = 112
FEATURE                   Location/Qualifiers
source                    1..112
                          mol_type = protein
                          organism = synthetic construct
SEQUENCE: 5
MGVTQTPKFQ VLKTGQSMTL QCAQDMNHEY MSWYRQDPGM GLRLIHYSVG AGITDQGEVP   60
NGYNVSRSTT EDFPLRLLSA APSQTSVYFC ASSYVGNTGE LFFGEGSRLT VL          112

SEQ ID NO: 6              moltype = AA   length = 166
FEATURE                   Location/Qualifiers
source                    1..166
                          mol_type = protein
                          organism = synthetic construct
SEQUENCE: 6
APPRLICDSR VLERYLLEAK EAENITTGCA EHCSLNENIT VPDTKVNFYA WKRMEVGQQA   60
VEVWQGLALL SEAVLRGQAL LVNSSQPWEP LQLHVDKAVS GLRSLTTLLR ALGAQKEAIS  120
PPDAASAAPL RTITADTFRK LFRVYSNFLR GKLKLYTGEA CRTGDR                 166

SEQ ID NO: 7              moltype = AA   length = 452
FEATURE                   Location/Qualifiers
source                    1..452
                          mol_type = protein
                          organism = synthetic construct
SEQUENCE: 7
MSTAVLENPG LGRKLSDFGQ ETSYIEDNCN QNGAISLIFS LKEEVGALAK VLRLFEENDV   60
NLTHIESRPS RLKKDEYEFF THLDKRSLPA LTNIIKILRH DIGATVHELS RDKKDTVPW   120
FPRTIQELDR FANQILSYGA ELDADHPGFK DPVYRARRKQ FADIAYNYRH GQPIPRVEYM  180
EEEKKTWGTV FKTLKSLYKT HACYEYNHIF PLLEKYCGFH EDNIPQLEDV SQFLQTCTGF  240
```

```
RLRPVAGLLS SRDFLGGLAF RVFHCTQYIR HGSKPMYTPE PDICHELLGH VPLFSDRSFA    300
QFSQEIGLAS LGAPDEYIEK LATIYWFTVE FGLCKQGDSI KAYGAGLLSS FGELQYCLSE    360
KPKLLPLELE KTAIQNYTVT EFQPLYYVAE SFNDAKEKVR NFAATIPRPF SVRYDPYTQR    420
IEVLDNTQQL KILADSINSE IGILCSALQK IK                                  452

SEQ ID NO: 8              moltype = AA  length = 1462
FEATURE                   Location/Qualifiers
source                    1..1462
                          mol_type = protein
                          organism = synthetic construct
SEQUENCE: 8
LSVKAQTAHI VLEDGTKMKG YSFGHPSSVA GEVVFNTGLG GYPEAITDPA YKGQILTMAN     60
PIIGNGGAPD TTALDELGLS KYLESNGIKV SGLLVLDYSK DYNHWLATKS LGQWLQEEKV    120
PAIYGVDTRM LTKIIRDKGT MLGKIEFEGQ PVDFVDPNKQ NLIAEVSTKD VKVYGKGNPT    180
KVVAVDCGIK NNVIRLLVKR GAEVHLVPWN HDFTKMEYDG ILIAGGPGNP ALAEPLIQNV    240
RKILESDRKE PLFGISTGNL ITGLAAGAKT YKMSMANRGQ NQPVLNITNK QAFITAQNHG    300
YALDNTLPAG WKPLFVNVND QTNEGIMHES KPFFAVQFHP EVTPGPIDTE YLFDSFFSLI    360
KKGKATTITS VLPKPALVAS RVEVSKVLIL GSGGLSIGQA GEFDYSGSQA VKAMKEENVK    420
TVLMNPNIAS VQTNEVGLKQ ADTVYFLPIT PQFVTEVIKA EQPDGLILGM GGQTALNCGV    480
ELFKRGVLKE YGVKVLGTSV ESIMATEDRQ LFSDKLNEIN EKIAPSFAVE SIEDALKAAD    540
TIGYPVMIRS AYALGGLGSG ICPNRETLMD LSTKAFAMTN QILVEKSVTG WKEIEYEVVR    600
DADDNCVTVC NMENVDAMGV HTGDSIVVVAP AQTLSNADDQ MLRRTSINVV RHLGIVGECN    660
IQFALHPTSM EYCIIEVNAR LSRSSALASK ATGYPLAFIA AKIALGIPLP EIKNVVSGKT    720
SACFEPSLDY MVTKIPRWDL DRFHGTSSRI GSSMKSVGEV MAIGRTFEES FQKALRMCHP    780
SIEGFTPRLP MNKEWPSNLD LRKELSEPSS TRIYAIAKAI DDNMSLDEIE KLTYIDKWFL    840
YKMRDILNME KTLKGLNSES MTEETLKRAK EIGFSDKQIS KCLGLTEAQT RELRLKKNIH    900
PWVKQIDTLA AEYPSVTNYL YVTYNGQEHD VNFDDHGMMV LGCGPYHIGS SVEFDWCAVS    960
SIRTLRQLGK KTVVVNCNPE TVSTDFDECD KLYFEELSLE RILDIYHQEA CGGCIISVGG   1020
QIPNNLAVPL YKNGVKIMGT SPLQIDRAED RSIFSAVLDE LKVAQAPWKA VNTLNEALEF   1080
AKSVDYPCLL RPSYVLSGSA MNVVFSEDEM KKFLEEATRV SQEHPVVLTK FVEGAREVEM   1140
DAVGKDGRVI SHAISEHVED AGVHSGDATL MLPTQTISQG AIEKVKDATR KIAKAFAISG   1200
PFNVQPLVKG NDVLVIECNL RASRSFPFVS KTLGVDFIDV ATKVMIGENV DEKHLPTLDH   1260
PIIPADYVAI KAPMFSWPRL RDADPILRCE MASTGEVACF GEGIHTAFLK AMLSTGFKIP   1320
QKGILIGIQQ SFRPRFLGVA EQLHHNEGFKL FATEATSDWL NANNVPATPV AWPSQEGQNP   1380
SLSSIRKLIR DGSIDLVINL PNNNTKFVHD NYVIRRTAVD SGIPLLTNFQ VTKLFAEAVQ   1440
KSRKVDSKSL FHYRQYSAGK AA                                            1462

SEQ ID NO: 9              moltype = AA  length = 1053
FEATURE                   Location/Qualifiers
source                    1..1053
                          mol_type = protein
                          organism = synthetic construct
SEQUENCE: 9
MKRNYILGLD IGITSVGYGI IDYETRDVID AGVRLFKEAN VENNEGRRSK RGARRLKRRR     60
RHRIQRVKKL LFDYNLLTDH SELSGINPYE ARVKGLSQKL SEEEFSAALL HLAKRRGVHN    120
VNEVEEDTGN ELSTKEQISR NSKALEEKYV AELQLERLKK DGEVRGSINR FKTSDYVKEA    180
KQLLKVQKAY HQLDQSFIDT YIDLLETRRT YYEGPGEGSP FGWKDIKEWY EMLMGHCTYF    240
PEELRSVKYA YNADLYNALN DLNNLVITRD ENEKLEYYEK FQIIENVFKQ KKKPTLKQIA    300
KEILVNEEDI KGYRVTSTGK PEFTNLKVYH DIKDITARKE IIENAELLDQ IAKILTIYQS    360
SEDIQEELTN LNSELTQEEI EQISNLKGYT GTHNLSLKAI NLILDELWHT NDNQIAIFNR    420
LKLVPKKVDL SQQKEIPTTL VDDFILSPVV KRSFIQSIKV INAIIKKYGL PNDIIIELAR    480
EKNSKDAQKM INEMQKRNRQ TNERIEEIIR TTGKENAKYL IEKIKLHDMQ EGKCLYSLEA    540
IPLEDLLNNP FNYEVDHIIP RSVSFDNSFN NKVLVKQEEN SKKGNRTPFQ YLSSSDSKIS    600
YETFKKHILN LAKGKGRISK TKKEYLLEER DINRFSVQKD FINRNLVDTR YATRGLMNLL    660
RSYFRVNNLD VKVKSINGGF TSFLRRKWKF KKERNKGVHK HAEDALIIAN ADFIFKEWKK    720
LDKAKKVMEN QMFEEKQAES MPEIETEQEY KEIFITPHQI KHIKDFKDYK YSHRVDKKPN    780
RELINDTLYS TRKDDKGNTL IVNNLNGLYD KDNDKLKKLI NKSPEKLLMY HHDPQTYQKL    840
KLIMEQYGDE KNPLYKYYEE TGNYLTKYSK KDNGPVIKKI KYYGNKLNAH LDITDDYPNS    900
RNKVVKLSLK PYRFDVYLDN GVYKFVTVKN LDVIKKENYY EVNSKCYEEA KKLKKISNQA    960
EFIASFYNND LIKINGELYR VIGVNNDLLN RIEVNMIDIT YREYLENMND KRPPRIIKTI   1020
ASKTQSIKKY STDILGNLYE VKSKKHPQII KKG                                1053

SEQ ID NO: 10             moltype = AA  length = 1353
FEATURE                   Location/Qualifiers
source                    1..1353
                          mol_type = protein
                          organism = synthetic construct
SEQUENCE: 10
AAGGILHLEL LVAVGPDVFQ AHQEDTERYV LTNLNIGAEL LRDPSLGAQF RVHLVKMVIL     60
TEPEGAPNIT ANLTSSLLSV CGWSQTINPE DDTDPGHADL VLYITRFDLE LPDGNRQVRG    120
VTQLGGACSP TWSCLITEDT GFDLGVTIAH EIGHSFGLEH DGAPGSGCGP SGHVMASDGA    180
APRAGLAWSP CSRRQLLSLL SAGRARCVWD PPRPQPGSAG HPPDAQPGLY YSANEQCRVA    240
FGPKAVACTF AREHLDMCQA LSCHTDPLDQ SSCRLLVPL LDGTECGVEK WCSKGRCRSL    300
VELTPIAAVH GRWSSWGPRS CSVSRCGGGV VTRRRQCNNP RPAFGGRACV GADLQAEMCN    360
TQACEKTQLE FMSQQCARTD GQPLRSSPGG ASFYHWGAAV PHSQGDALCR HMCRAIGESF    420
IMKRGDSFLD GTRCMPSGPR EDGTLSLCVS GSCRTFGCDG RMDSQQVWDR CQVCGGDNST    480
CSPRKGSFTA GRAREYVTFL TVTPNLTSVY IANHRPLFTH LAVRIGGRYV VAGKMSISPN    540
TTYPSLLEDG RVEYRVALTE DRLPRLEEIR IWGPLQEDAD IQVYRRYGEE YGNLTRPDIT    600
FTYFQPKPRQ AWVWAAVRGP CSVSCGAGLR WVNYSCLDQA RKELVETVQC QGSQQPPAWP    660
```

```
EACVLEPCPP YWAVGDFGPC SASCGGGLRE RPVRCVEAQG SLLKTLPPAR CRAGAQQPAV      720
ALETCNPQPC PARWEVSEPS SCTSAGGAGL ALENETCVPG ADGLEAPVTE GPGSVDEKLP      780
APEPCVGMSC PPGWGHLDAT SAGEKAPSPW GSIRTGAQAA HVWTPAAGSC SVSCGRGLME      840
LRFLCMDSAL RVPVQEELCG LASKPGSRRE VCQAVPCPAR WQYKLAACSV SCGRGVVRRI      900
LYCARAHGED DGEEILLDTQ CQGLPRPEPQ EACSLEPCPP RWKVMSLGPC SASCGLGTAR      960
RSVACVQLDQ GQDVEVDEAA CAALVRPEAS VPCLIADCTY RWHVGTWMEC SVSCGDGIQR     1020
RRDTCLGPQA QAPVPADFCQ HLPKPVTVRG CWAGPCVGQG TPSLVPHEEA AAPGRTTATP     1080
AGASLEWSQA RGLLFSPAPQ PRRLLPGPQE NSVQSSACGR QHLEPTGTID MRGPGQADCA     1140
VAIGRPLGEV VTLRVLESSL NCSAGDMLLL WGRLTWRKMC RKLLDMTFSS KTNTLVVRQR     1200
CGRPGGGVLL RYGSQLAPET FYRECDMQLF GPWGEIVSPS LSPATSNAGG CRLFINVAPH     1260
ARIAIHALAT NMGAGTEGAN ASYILIRDTH SLRTTAFHGQ QVLYWESESS QAEMEFSEGF     1320
LKAQASLRGQ YWTLQSWVPE MQDPQSWKGK EGT                                  1353

SEQ ID NO: 11              moltype = AA  length = 431
FEATURE                    Location/Qualifiers
source                     1..431
                           mol_type = protein
                           organism = synthetic construct
SEQUENCE: 11
MPNPRPGKPS APSLALGPSP GASPSWRAAP KASDLLGARG PGGTFQGRDL RGGAHASSSS       60
LNPMPPSQLQ LPTLPLVMVA PSGARLGPLP HLQALLQDRP HFMHQLSTVD AHARTPVLQV      120
HPLESPAMIS LTPPTTATGV FSLKARPGLP PGINVASLEW VSREPALLCT FPNPSAPRKD      180
STLSAVPQSS YPLLANGVCK WPGCEKVFEE PEDFLKHCQA DHLLDEKGRA QCLLQREMVQ      240
SLEQQLVLEK EKLSAMQAHL AGKMALTKAS SVASSDKGSC CIVAAGSQGP VVPAWSGPRE      300
APDSLFAVRR HLWGSHGNST FPEFLHNMDY FKFHNMRPPF TYATLIRWAI LEAPEKQRTL      360
NEIYHWFTRM PAFFRNHPAT WKNAIRHNLS LHKCFVRVES EKGAVWTDE LEFRKKRSQR      420
PSRCSNPTPG P                                                          431

SEQ ID NO: 12              moltype = AA  length = 160
FEATURE                    Location/Qualifiers
source                     1..160
                           mol_type = protein
                           organism = synthetic construct
SEQUENCE: 12
SPGQGTQSEN SCTHFPGNLP NMLRDLRDAF SRVKTFFQMK DQLDNLLLKE SLLEDFKGYL       60
GCQALSEMIQ FYLEEVMPQA ENQDPDIKAH VNSLGENLKT LRLRLRRCHR FLPCENKSKA      120
VEQVKNAFNK LQEKGIYKAM SEFDIFINYI EAYMTMKIRN                            160

SEQ ID NO: 13              moltype = AA  length = 133
FEATURE                    Location/Qualifiers
source                     1..133
                           mol_type = protein
                           organism = synthetic construct
SEQUENCE: 13
APTSSSTKKT QLQLEHLLLD LQMILNGINN YKNPKLTRML TFKFYMPKKA TELKHLQCLE       60
EELKPLEEVL NLAQSKNFHL RPRDLISNIN VIVLELKGSE TTFMCEYADE TATIVEFLNR      120
WITFCQSIIS TLT                                                        133

SEQ ID NO: 14              moltype = AA  length = 329
FEATURE                    Location/Qualifiers
source                     1..329
                           mol_type = protein
                           organism = synthetic construct
SEQUENCE: 14
MKFGSKIRRL AVAAVAGAIA LGASFAVAQA PTFFRIGTGG TAGTYYPIGG LIANAISGAG       60
EKGVPGLVAT AVSSNGSVAN INAIKSGALE SGFTQSDVAY WAYNGTGLYD GKGKVEDLRL      120
LATLYPETIH IVARKDANIK SVADLKGKRV SLDEPGSGTI VDARIVLEAY GLTEDDIKAE      180
HLKPGPAGER LKDGALDAYF FVGGYPTGAI SELAISNGIS LVPISGPEAD KILEKYSFFS      240
KDVVPAGAYK DVAETPTLAV AAQWVTSAKQ PDDLIYNITK VLWNEDTRKA LDAGHAKGKL      300
IKLDSATSSL GIPLHPGAER FYKEAGVLK                                       329

SEQ ID NO: 15              moltype = AA  length = 402
FEATURE                    Location/Qualifiers
source                     1..402
                           mol_type = protein
                           organism = synthetic construct
SEQUENCE: 15
MKKLLKSALL FAATGSALSL QALPVGNPAE PSLLIDGTMW EGASGDPCDP CATWCDAISI       60
RAGYYGDYVF DRVLKVDVNK TFSGMAATPT QATGNASNTN QPEANGRPNI AYGRHMQDAE      120
WFSNAAFLAL NIWDRFDIFC TLGASNGYFK ASSAAFNLVG LIGFSAASSI STDLPMQLPN      180
VGITQGVVEF YTDTSFSWSV GARGALWECG CATLGAEFQY AQSNPKIEML NVTSSPAQFV      240
IHKPRGYKGA SSNFPLPITA GTTEATDTKS ATIKYHEWQV GLALSYRLNM LVPYIGVNWS      300
RATFDADTIR IAQPKLKSEI LNITTWNPSL IGSTTALPNN SGKDVLSDVL QIASIQINKM      360
KSRKACGVAV GATLIDADKW SITGEARLIN ERAAHMNAQF RF                        402

SEQ ID NO: 16              moltype = AA  length = 370
FEATURE                    Location/Qualifiers
source                     1..370
                           mol_type = protein
```

```
                       organism = synthetic construct
SEQUENCE: 16
MKKLALVLGL LLVVGSVASA KEVMPAPTPA PEKVVEYVEK PVIVYRDREV APAWRPNGSV    60
DVQYRWYGEV EKKNPKDDKD ENWATGKVNA GRLQTLTKVN FTEKQTLEVR TRNHHTLNDT   120
DANNKKSNGA ADEYRLRHFY NFGKLGSSKV NATSRVEFKQ KTNDGEKSLG ASVLFDFADY   180
IYSNNFFKVD KLGLRPGYKY VWKGHGNGEE GTPTVHNEYH LAFESDFTLP FNFALNLEYD   240
LSYNRYREKF ETTDGLKKAE WYGELTAVLS NYTPLYKAGA FELGFNAEGG YDTYNMHQYK   300
RIGGEDGTSV DRRDYELYLE PTLQVSYKPT DFVKLYAAAG ADYRNRITGE SEVKRWRWQP   360
TASAGMKVTF                                                         370

SEQ ID NO: 17          moltype = AA  length = 495
FEATURE                Location/Qualifiers
source                 1..495
                       mol_type = protein
                       organism = synthetic construct
SEQUENCE: 17
MNQHFDVLII GAGLSGIGTA CHVTAEFPDK TIALLERRER LGGTWDLFRY PGVRSDSDMF    60
TFGYKFRPWR DVKVLADGAS IRQYIADTAT EFGVDEKIHY GLKVNTAEWS SRQCRWTVAG   120
VHEATGETRT YTCDYLISCT GYYNYDAGYL PDFPGVHRFG GRCVHPQHWP EDLDYSGKKV   180
VVIGSGATAV TLVPAMAGSN PGSAAHVTML QRSPSYIFSL PAVDKISEVL GRFLPDRWVY   240
EFGRRRNIAI QRKLYQACRR WPKLMRRLLL WEVRRRLGRS VDMSNFTPNY LPWDERLCAV   300
PNGDLFKTLA SGAASVVTDQ IETFTEKGIL CKSGREIEAD IIVTATGLNI QMLGGMRLIV   360
DGAEYQLPEK MTYKGVLLEN APNLAWIIGY TNASWTLKSD IAGAYLCRLL RHMADNGYTV   420
ATPRDAQDCA LDVGMFDQLN SGYVKRGQDI MPRQGSKHPW RVLMHYEKDA KILLEDPIDD   480
GVLHFAAAAQ DHAAA                                                   495

SEQ ID NO: 18          moltype = AA  length = 95
FEATURE                Location/Qualifiers
source                 1..95
                       mol_type = protein
                       organism = synthetic construct
SEQUENCE: 18
MTEQQWNFAG IEAAASAIQG NVTSIHSLLD EGKQSLTKLA AAWGGSGSEA YQGVQQKWDA    60
TATELNNALQ NLARTISEAG QAMASTEGNV TGMFA                              95

SEQ ID NO: 19          moltype = AA  length = 311
FEATURE                Location/Qualifiers
source                 1..311
                       mol_type = protein
                       organism = synthetic construct
SEQUENCE: 19
MKKSLIALTL AALPVAAMAD VTLYGTIKAG VETYRFVAHN GAQASGVETA TEIADLGSKI    60
GFKGQEDLGN GLKAIWQLEQ KAYVSGTNTG WGNRQSFIGL KGGFGKVRVG RLNSVLKDTG   120
GFNPWEGKSE YLSLSNIARP EERPISVRYD SPEFAGFSGS VQYVPNDNSG ENKSESYHAG   180
FNYKNSGFFV QYAGSYKRHN YTTEKHQIHR LVGGYDHDAL YASVAVQQQD AKLAWPDDNS   240
HNSQTEVATT VAYRFGNVTP RVSYAHGFKG SVYEANHDNT YDQVVVGAEY DFSKRTSALV   300
SAGWLQEGKG A                                                       311

SEQ ID NO: 20          moltype = AA  length = 107
FEATURE                Location/Qualifiers
source                 1..107
                       mol_type = protein
                       organism = synthetic construct
SEQUENCE: 20
FVGYKPYSQN PRDYFVPDNE LPPLVHSGFN PSFIATVSHE KGSGDTSEFE ITYGRNMDVT    60
HATRRTTHYG NSYLEGSRIH NAFVNRNYTV KYEVNWKTHE IKVKGHN                107

SEQ ID NO: 21          moltype = AA  length = 301
FEATURE                Location/Qualifiers
source                 1..301
                       mol_type = protein
                       organism = synthetic construct
SEQUENCE: 21
EVKLSGDARM GVMYNGDDWN FSSRSRVLFT MSGTTDSGLE FGASFKAHES VGAETGEDGT    60
VFLSGAFGKI EMGDALGASE ALFGDLYEVG YTDLDDDRGGN DIPYLTGDER LTAEDNPVLL  120
YTYSAGAFSV AASMSDGKVG ETSEDDAQEM AVAAAYTFGN YTVGLGYEKI DSPDTALMAD   180
MEQLELAAIA KFGATNVKAY YADGELDRDF ARAVFDLTPV AAAATAVDHK AYGLSVDSTF   240
GATTVGGYVQ VLDIDTIDDV TYYGLGASYD LGGGASIVGG IADNDLPNSD MVADLGVKFK   300
F                                                                  301

SEQ ID NO: 22          moltype = AA  length = 346
FEATURE                Location/Qualifiers
source                 1..346
                       mol_type = protein
                       organism = synthetic construct
SEQUENCE: 22
MKKTAIAIAV ALAGFATVAQ AAPKDNTWYT GAKLGWSQYH DTGFINNNGP THENQLGAGA    60
FGGYQVNPYV GFEMGDWLG RMPYKGSVEN GAYKAQGVQL TAKLGYPITD DLDIYTRLGG   120
MVWRADTKSN VYGKNHDTGV SPVFAGGVEY AITPEIATRL EYQWTNNIGD AHTIGTRPDN   180
```

```
GMLSLGVSYR  FGQGEAAPVV  APAPAPAPEV  QTKHFTLKSD  VLFNFNKATL  KPEGQAALDQ   240
LYSQLSNLDP  KDGSVVVLGY  TDRIGSDAYN  QGLSERRAQS  VVDYLISKGI  PADKISARGM   300
GESNPVTGNT  CDNVKQRAAL  IDCLAPDRRV  EIEVKGIKDV  VTQPQA                   346

SEQ ID NO: 23           moltype = AA   length = 87
FEATURE                 Location/Qualifiers
source                  1..87
                        mol_type = protein
                        organism = synthetic construct
SEQUENCE: 23
AGVATATGTK  SATINYHEWQ  VGASLSYRLN  SLVPYIGVQW  SRATFDADNI  RIAQPKLPTA    60
VLNLTAWNPS  LLGNATALST  TDSFSDF                                          87

SEQ ID NO: 24           moltype = AA   length = 631
FEATURE                 Location/Qualifiers
source                  1..631
                        mol_type = protein
                        organism = synthetic construct
SEQUENCE: 24
MTTYQDDFYQ  AVNGKWAETA  VIPDDKPRTG  GFSDLADEIE  ALMLDTTDAW  LAGENIPDDA    60
ILKNFVKFHR  LVADYAKRDE  VGVSPILPLI  EEYQSLKSFS  EFVANIAKYE  LAGLPNEFPF   120
SVAPDFMNAQ  LNVLWAEAPS  ILLPDTTYYE  EGNEKAEELR  GIWRQSQEKL  LPQFGFSTEE   180
IKDLLDKVIE  LDKQLAKYVL  SREEGSEYAK  LYHPYVWADF  KKLAPELPLD  SIFEKILGQV   240
PDKVIVPEER  FWTEFAATYY  SEANWDLLKA  NLIVDAANAY  NAYLTDDIRV  ESGAYSRALS   300
GTPQAMDKQK  AAFYLAQGPF  SQALGLWYAG  QKFSPEAKAD  VESKVARMIE  VYKSRLETAD   360
WLAPATREKA  ITKLNVITPH  IGYPEKLPET  YAKKVIDESL  SLVENAQNLA  KITIAHTWSK   420
WNKPVDRSEW  HMPAHLVNAY  YDPQQNQIVF  PAAILQEPFY  SLDQSSSANY  GGIGAVIAHE   480
ISHAFDTNGA  SFDEHGSLND  WWTQEDYAAF  KERTDKIVAQ  FDGLESHGAK  VNGKLTVSEN   540
VADLGGVACA  LEAAQSEEDF  SARDFFINFA  TIWRMKAREE  YMQMLASIDV  HAPGELRTNV   600
TLTNFDAFHE  TFDIKEGDAM  WRAPKDRVII  W                                   631

SEQ ID NO: 25           moltype = AA   length = 341
FEATURE                 Location/Qualifiers
source                  1..341
                        mol_type = protein
                        organism = synthetic construct
SEQUENCE: 25
MNKTLIALAV  SAAAVATGAY  ADGINQSGDK  AGSTVYSAKG  TSLEVGGRAE  ARLSLKDGKA    60
QDNSRVRLNF  LGKAEINDSL  YGVGFYEGEF  TTNDQGKNAS  NNSLDNRYTY  AGIGGTYGEV   120
TYGKNDGALG  VITDFTDIMS  YHGNTAAEKI  AVADRVDNML  AYKGQFGDLG  VKASYRFADR   180
NAVDAMGNVV  TETNAAKYSD  NGEDGYSLSA  IYTFGDTGFN  VGAGYADQDD  QNEYMLAASY   240
RMENLYFAGL  FTDGELAKDV  DYTGYELAAG  YKLGQAAFTA  TYNNAETAKE  TSADNFAIDA   300
TYYFKPNFRS  YISYQFNLLD  SDKVGKVASE  DELAIGLRYD  F                       341

SEQ ID NO: 26           moltype = AA   length = 160
FEATURE                 Location/Qualifiers
source                  1..160
                        mol_type = protein
                        organism = synthetic construct
SEQUENCE: 26
MKGGAGVPDL  PSLDASGVRL  AIVASSWHGK  ICDALLDGAR  KVAAGCGLDD  PTVVRVLGAI    60
EIPVVAQELA  RNHDAVVALG  VVIRGQTPHF  DYVCDAVTQG  LTRVSLDSST  PIANGVLTTN   120
TEEQALDRAG  LPTSAEDKGA  QATVAALATA  LTLRELRAHS                          160

SEQ ID NO: 27           moltype = AA   length = 150
FEATURE                 Location/Qualifiers
source                  1..150
                        mol_type = protein
                        organism = synthetic construct
SEQUENCE: 27
MKKLTKVLLV  AGSVAVLAAC  GSSKKDESAG  QMFGGYSVQD  LQQRYNTVYF  GFDKYNIEGE    60
YVQILDAHAA  FLNATPATKV  VVEGNTDERG  TPEYNIALGQ  RRADAVKHYL  SAKGVQAGQV   120
STVSYGEEKP  AVLGHDEAAY  SKNRRAVLAY                                      150

SEQ ID NO: 28           moltype = AA   length = 177
FEATURE                 Location/Qualifiers
source                  1..177
                        mol_type = protein
                        organism = synthetic construct
SEQUENCE: 28
MGISKASLLS  LAAAGIVLAG  CQSSRLGNLD  NVSPPPPPAP  VNAVPAGTVQ  KGNLDSPTQF    60
PNAPSTDMSA  QSGTQVASLP  PASAPDLTPG  AVAGVWNASL  GGQSCKIATP  QTKYGQYRA   120
GPLRCPGELA  NLASWAVNGK  QLVLYDANGG  TVASLYSSGQ  GRFDGQTTGG  QAVTLSR     177

SEQ ID NO: 29           moltype = AA   length = 359
FEATURE                 Location/Qualifiers
source                  1..359
                        mol_type = protein
                        organism = synthetic construct
```

```
SEQUENCE: 29
MQILADLLNT IPAIDSTAMS RAQRHIDGLL KPVGSLGKLE VLAIQLAGMP GLNGIPHVGK    60
KAVLVMCADH GVWEEGVAIS PKEVTAIQAE NMTRGTTGVC VLAEQAGANV HVIDVGIDTA   120
EPIPGLINMR VARGSGNIAS APAMSRRQAE KLLLDVICYT QELAKNGVTL FGVGELGMAN   180
TTPAAAIVST ITGRDPEEVV GIGANLPTDK LANKIDVVRR AITLNQPNPQ DGVDVLAKVG   240
GFDLVGIAGV MLGAASCGLP VLLDGFLSYA AALAACQMSP AIKPYLIPSH LSAEKGARIA   300
LSHLGLEPYL NMEMRLGEGS GAALAMPIIE AACAIYNNMG ELAASNIVLP GNTTSDLNS    359

SEQ ID NO: 30               moltype = AA  length = 172
FEATURE                     Location/Qualifiers
source                      1..172
                            mol_type = protein
                            organism = synthetic construct
SEQUENCE: 30
MKNARTTLIA AAIAGTLVTT SPAGIANADD AGLDPNAAAG PDAVGFDPNL PPAPDAAPVD    60
TPPAPEDAGF DPNLPPPLAP DFLSPPAEEA PPVPVAYSVN WDAIAQCESG GNWSINTGNG   120
YYGGLRFTAG TWRANGGSGS AANASREEQI RVAENVLRSQ GIRAWPVCGR RG           172

SEQ ID NO: 31               moltype = AA  length = 130
FEATURE                     Location/Qualifiers
source                      1..130
                            mol_type = protein
                            organism = synthetic construct
SEQUENCE: 31
MAKLSTDELL DAFKEMTLLE LSDFVKKFEE TFEVTAAAPV AVAAAGAAPA GAAVEAAEEQ    60
SEFDVILEAA GDKKIGVIKV VREIVSGLGL KEAKDLVDGA PKPLLEKVAK EAADEAKAKL   120
EAAGATVTVK                                                           130

SEQ ID NO: 32               moltype = AA  length = 199
FEATURE                     Location/Qualifiers
source                      1..199
                            mol_type = protein
                            organism = synthetic construct
SEQUENCE: 32
MAENSNIDDI KAPLLAALGA ADLALATVNE LITNLRERAE ETRTDTRSRV EESRARLTKL    60
QEDLPEQLTE LREKFTAEEL RKAAEGYLEA ATSRYNELVE RGEAAALERLR SQQSFEEVSA   120
RAEGYVDQAV ELTQEALGTV ASQTRAVGER AAKLVGIELP KKAAPAKKAA PAKKAAPAKK   180
AAAKKAPAKK AAAKKVTQK                                                 199

SEQ ID NO: 33               moltype = AA  length = 594
FEATURE                     Location/Qualifiers
source                      1..594
                            mol_type = protein
                            organism = synthetic construct
SEQUENCE: 33
MNKIYRIIWN SALNAWVAVS ELTRNHTKRA SATVATAVLA TLLFATVQAS TTDDDDLYLE    60
PVQRTAVVLS FRSDKEGTGE KEVTEKLSNWG VYFDKKGVLT AGTITLKAGD NLKIKQNTNE   120
NTNASSFTYS LKKDLTDLTS VGTEKLSFSA NSNKVNITSD TKGLNFAKKT AETNGDTTVH   180
LNGIGSTLTD TLLNTGATTN VTNDNVTDDE KKRAASVKDV LNAGWNIKGV KPGTTASDNV   240
DFVRTYDTVE FLSADTKTTT VNVESKDNGK RTEVKIGAKT SVIKEKDGKL VTGKDKGEND   300
SSTDKGEGLV TAKEVIDAVN KAGWRMKTTT ANGQTGQANK FETVTSGTNV TFASGKGTTA   360
TVSKDDQGNI TVMYDVNVGD ALNVNQLQNS GWNLDSKAVA GSSGKVISGN VSPSKGKMDE   420
TVNINAGNNI EITRNGKNID IATSMTPQFS SVSLGAGADA PTLSVDDEGA LNVGSKDANK   480
PVRITNVAPG VKEGDVTNVA QLKGVAQNLN NHIDNVDGNA RAGIAQAIAT AGLVQAYLPG   540
KSMMAIGGGT YRGEAGYAIG YSSISDGGNW IIKGTASGNS RGHFGASASV GYQW          594

SEQ ID NO: 34               moltype = AA  length = 376
FEATURE                     Location/Qualifiers
source                      1..376
                            mol_type = protein
                            organism = synthetic construct
SEQUENCE: 34
MAKQDYYEIL GVSKTAEERE IRKAYKRLAM KYHPDRNQGD KEAEAKFKEI KEAYEVLTDS    60
QKRAAYDQYG HAAFEQGGMG GGGFGGGADF SDIFGDVFGD IFGGGRGRQR AARGADLRYN   120
MELTLEEAVR GVTKEIRIPT LEECDVCHGS GAKPGTQPQT CPTCHGSGQV QMRQGFFAVQ   180
QTCPHCQGRG TLIKDPCNKC HGHGRVERSK TLSVKIPAGV DTGDRIRLAG EGEAGEHGAP   240
AGDLYVQVQV KQHPIFEREG NNLYCEVPIN FAMAALGGEI EVPTLDGRVK LKVPGETQTG   300
KLFRMRGKGV KSVRGGAQGD LLCRVVVETP VGLNERQKQL LQELQESFGG PTGEHNSPRS   360
KSFFDGVKKF FDDLTR                                                    376

SEQ ID NO: 35               moltype = AA  length = 471
FEATURE                     Location/Qualifiers
source                      1..471
                            mol_type = protein
                            organism = synthetic construct
SEQUENCE: 35
MANKAVNDFI LAMNYDKKKL LTHQGESIEN RFIKEGNQLP DEFVVIERKK RSLSTNTSDI    60
SVTATNDSRL YPGALLVVDE TLLENNPTLL AVDRAPMTYS IDLPGLASSD SFLQVEDPSN   120
SSVRGAVNDL LAKWHQDYGQ VNNVPARMQY EKITAHSMEQ LKVKFGSDFE KTGNSLDIDF   180
```

```
NSVHSGEKQI QIVNFKQIYY TVSVDAVKNP GDVFQDTVTV EDLKQRGISA ERPLVYISSV  240
AYGRQVYLKL ETTSKSDEVE AAFEALIKGV KVAPQTEWKQ ILDNTEVKAV ILGGDPSSGA  300
RVVTGKVDMV EDLIQEGSRF TADHPGLPIS YTTSFLRDNV VATFQNSTDY VETKVTAYRN  360
GDLLLDHSGA YVAQYYITWD ELSYDHQGKE VLTPKAWDRN GQDLTAHFTT SIPLKGNVRN  420
LSVKIRECTG LAWEWWRTVY EKTDLPLVRK RTISIWGTTL YPQVEDKVEN D           471

SEQ ID NO: 36         moltype = AA  length = 498
FEATURE               Location/Qualifiers
source                1..498
                      mol_type = protein
                      organism = synthetic construct
SEQUENCE: 36
MAQVINTNSL SLITQNNINK NQSALSSSIE RLSSGLRINS AKDDAAGQAI ANRFTSNIKG   60
LTQAARNAND GISVAQTTEG ALSEINNNLQ RVRELTVQAT TGTNSESDLS SIQDEIKSRL  120
DEIDRVSGQT QFNGVNVLAK NGSMKIQVGA NDNQTITIDL KQIDAKTLGL DGFSVKNNDT  180
VTTSAPVTAF GATTTNNIKL TGITLSTEAA TDTGGTNPAS IEGVYTDNGN DYYAKITGGD  240
NDGKYYAVTV ANDGTVTMAT GATANATVTD ANTTKATTIT SGGTPVQIDN TAGSATANLG  300
AVSLVKLQDS KGNDTDTYAL KDTNGNLYAA DVNETTGAVS VKTITYTDSS GAASSPTAVK  360
LGGDDGKTEV VDIDGKTYDS ADLNGGNLQT GLTAGGEALT AVANGKTTDP LKALDDAIAS  420
VDKFRSSLGA VQNRLDSAVT NLNNTTTNLS EAQSRIQDAD YATEVSNMSK AQIIQQAGNS  480
VLAKANQVPQ QVLSLLQG                                                498

SEQ ID NO: 37         moltype = AA  length = 189
FEATURE               Location/Qualifiers
source                1..189
                      mol_type = protein
                      organism = synthetic construct
SEQUENCE: 37
MASPFALLMV LVVLSCKSSC SLGCDLPETH SLDNRRTLML LAQMSRISPS SCLMDRHDFG   60
FPQEEFDGNQ FQKAPAISVL HELIQQIFNL FTTKDSSAAW DEDLLDKFCT ELYQQLNDLE  120
ACVMQEERVG ETPLMNADSI LAVKKYFRRI TLYLTEKKYS PCAWEVVRAE IMRSLSLSTN  180
LQERLRRKE                                                          189

SEQ ID NO: 38         moltype = AA  length = 166
FEATURE               Location/Qualifiers
source                1..166
                      mol_type = protein
                      organism = synthetic construct
SEQUENCE: 38
MKYTSYILAF QLCIVLGSLG CYCQDPYVKE AENLKKYFNA GHSDVADNGT LFLGILKNWK   60
EESDRKIMQS QIVSFYFKLF KNFKDDQSIQ KSVETIKEDM NVKFFNSNKK KRDDFEKLTN  120
YSVTDLNVQR KAIHELIQVM AELSPAAKTG KRKRSQMLFR GRRASQ                 166

SEQ ID NO: 39         moltype = AA  length = 153
FEATURE               Location/Qualifiers
source                1..153
                      mol_type = protein
                      organism = synthetic construct
SEQUENCE: 39
MYRMQLLSCI ALSLALVTNS APTSSSTKKT QLQLEHLLLD LQMILNGINN YKNPKLTRML   60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                               153

SEQ ID NO: 40         moltype = AA  length = 39
FEATURE               Location/Qualifiers
source                1..39
                      mol_type = protein
                      organism = synthetic construct
SEQUENCE: 40
MWPPGSASQP PPSPAAATGL HPAARPVSLQ CRLSMCPAR                          39

SEQ ID NO: 41         moltype = AA  length = 338
FEATURE               Location/Qualifiers
source                1..338
                      mol_type = protein
                      organism = synthetic construct
SEQUENCE: 41
MGKKQNRKTG NSKTQSASPP PKERSSSPAT EQSWMENDFD ELREEGFRRS NYSELREDIQ   60
TKGKEVENFE KNLEECITRI SNTEKCLKEL MELKTKTREL REECRSLRSR CDQLEERVSA  120
MEDEMNEMKR EGKFREKRIK RNEQTLQEIW DYVKRPNLRL IGVPESDVEN GTKLENTLQD  180
IIQENFPNLA RQANVQIQEI QRTPQRYSSR RATPRHIIVR FTKVEMKEKM LRAAREKGRV  240
TLKGKPIRLT ADLLAETLQA RREWGPIFNI LKGKNFQPRI SYPAKLSFIS EGEIKYFIDK  300
QMLRDFVTTR PALKELLKEA LNMERNNRYQ LLQNHAKM                          338

SEQ ID NO: 42         moltype = AA  length = 162
FEATURE               Location/Qualifiers
source                1..162
                      mol_type = protein
                      organism = synthetic construct
```

```
SEQUENCE: 42
MRISKPHLRS ISIQCYLCLL LNSHFLTEAG IHVFILGCFS AGLPKTEANW VNVISDLKKI    60
EDLIQSMHID ATLYTESDVH PSCKVTAMKC FLLELQVISL ESGDASIHDT VENLIILANN   120
SLSSNGNVTE SGCKECEELE EKNIKEFLQS FVHIVQMFIN TS                     162

SEQ ID NO: 43          moltype = AA   length = 193
FEATURE                Location/Qualifiers
source                 1..193
                       mol_type = protein
                       organism = synthetic construct
SEQUENCE: 43
MAAEPVEDNC INFVAMKFID NTLYFIAEDD ENLESDYFGK LESKLSVIRN LNDQVLFIDQ    60
GNRPLFEDMT DSDCRDNAPR TIFIISMYKD SQPRGMAVTI SVKCEKISTL SCENKIISFK   120
EMNPPDNIKD TKSDIIFFQR SVPGHDNKMQ FESSSYEGYF LACEKERDLF KLILKKEDEL   180
GDRSIMFTVQ NED                                                     193

SEQ ID NO: 44          moltype = AA   length = 162
FEATURE                Location/Qualifiers
source                 1..162
                       mol_type = protein
                       organism = synthetic construct
SEQUENCE: 44
MRSSPGNMER IVICLMVIFL GTLVHKSSSQ GQDRHMIRMR QLIDIVDQLK NYVNDLVPEF    60
LPAPEDVETN CEWSAFSCFQ KAQLKSANTG NNERIINVSI KKLKRKPPST NAGRRQKHRL   120
TCPSCDSYEK KPPKEFLERF KSLLQKMIHQ HLSSRTHGSE DS                     162

SEQ ID NO: 45          moltype = AA   length = 144
FEATURE                Location/Qualifiers
source                 1..144
                       mol_type = protein
                       organism = synthetic construct
SEQUENCE: 45
MWLQSLLLLG TVACSISAPA RSPSPSTQPW EHVNAIQEAR RLLNLSRDTA AEMNETVEVI    60
SEMFDLQEPT CLQTRLELYK QGLRGSLTKL KGPLTMMASH YKQHCPPTPE TSCATQIITF   120
ESFKENLKDF LLVIPFDCWE PVQE                                         144

SEQ ID NO: 46          moltype = AA   length = 269
FEATURE                Location/Qualifiers
source                 1..269
                       mol_type = protein
                       organism = synthetic construct
SEQUENCE: 46
MAEVPELASE MMAYYSGNED DLFFEADGPK QMKCSFQDLD LCPLDGGIQL RISDHHYSKG    60
FRQAASVVVA MDKLRKMLVP CPQTFQENDL STFFPFIFEE EPIFFDTWDN EAYVHDAPVR   120
SLNCTLRDSQ QKSLVMSGPY ELKALHLQGQ DMEQQVVFSM SFVQGEESND KIPVALGLKE   180
KNLYLSCVLK DDKPTLQLES VDPKNYPKKK MEKRFVFNKI EINNKLEFES AQFPNWYIST   240
SQAENMPVFL GGTKGGQDIT DFTMQFVSS                                    269

SEQ ID NO: 47          moltype = AA   length = 212
FEATURE                Location/Qualifiers
source                 1..212
                       mol_type = protein
                       organism = synthetic construct
SEQUENCE: 47
MNSFSTSAFG PVAFSLGLLL VLPAAFPAPV PPGEDSKDVA APHRQPLTSS ERIDKQIRYI    60
LDGISALRKE TCNKSNMCES SKEALAENNL NLPKMAEKDG CFQSGFNEET CLVKIITGLL   120
EFEVYLEYLQ NRFESSEEQA RAVQMSTKVL IQFLQKKAKN LDAITTPDPT TNASLLTKLQ   180
AQNQWLQDMT THLILRSFKE FLQSSLRALR QM                                212

SEQ ID NO: 48          moltype = AA   length = 233
FEATURE                Location/Qualifiers
source                 1..233
                       mol_type = protein
                       organism = synthetic construct
SEQUENCE: 48
MSTESMIRDV ELAEEALPKK TGGPQGSRRC LFLSLFSFLI VAGATTLFCL LHFGVIGPQR    60
EEFPRDLSLI SPLAQAVRSS SRTPSDKPVA HVVANPQAEG QLQWLNRRAN ALLANGVELR   120
DNQLVVPSEG LYLIYSQVLF KGQGCPSTHV LLTHTISRIA VSYQTKVNLL SAIKSPCQRE   180
TPEGAEAKPW YEPIYLGGVF QLEKGDRLSA EINRPDYLDF AESGQVYFGI IAL          233

SEQ ID NO: 49          moltype = AA   length = 177
FEATURE                Location/Qualifiers
source                 1..177
                       mol_type = protein
                       organism = synthetic construct
SEQUENCE: 49
MFHVSFRYIF GLPPLILVLL PVASSDCDIE GKDGKQYESV LMVSIDQLLD SMKEIGSNCL    60
NNEFNFFKRH ICDANKEGMF LFRAARKLRQ FLKMNSTGDF DLHLLKVSEG TTILLNCTGQ   120
VKGRKPAALG EAQPTKSLEE NKSLKEQKKL NDLCFLKRLL QEIKTCWNKI LMGTKEH      177
```

```
SEQ ID NO: 50            moltype = AA   length = 155
FEATURE                  Location/Qualifiers
source                   1..155
                         mol_type = protein
                         organism = synthetic construct
SEQUENCE: 50
MTPGKTSLVS LLLLLSLEAI VKAGITIPRN PGCPNSEDKN FPRTVMVNLN IHNRNTNTNP    60
KRSSDYYNRS TSPWNLHRNE DPERYPSVIW EAKCRHLGCI NADGNVDYHM NSVPIQQEIL   120
VLRREPPHCP NSFRLEKILV SVGCTCVTPI VHHVA                              155

SEQ ID NO: 51            moltype = AA   length = 235
FEATURE                  Location/Qualifiers
source                   1..235
                         mol_type = protein
                         organism = synthetic construct
SEQUENCE: 51
MTVLAPAWSP TTYLLLLLLL SSGLSGTQDC SFQHSPISSD FAVKIRELSD YLLQDYPVTV    60
ASNLQDEELC GGLWRLVLAQ RWMERLKTVA GSKMQGLLER VNTEIHFVTK CAFQPPPSCL   120
RFVQTNISRL LQETSEQLVA LKPWITRQNF SRCLELQCQP DSSTLPPPWS PRPLEATAPT   180
APQPPLLLLL LLPVGLLLLA AAWCLHWQRT RRRTPRPGEQ VPPVPSPQDL LLVEH        235

SEQ ID NO: 52            moltype = AA   length = 448
FEATURE                  Location/Qualifiers
source                   1..448
                         mol_type = protein
                         organism = synthetic construct
SEQUENCE: 52
QVQLVESGGG VVQPGRSLRL SCAASGFTFS SYTMHWVRQA PGKGLEWVTF ISYDGNNKYY    60
ADSVKGRFTI SRDNSKNTLY LQMNSLRAED TAIYYCARTG WLGPFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                      448

SEQ ID NO: 53            moltype = AA   length = 440
FEATURE                  Location/Qualifiers
source                   1..440
                         mol_type = protein
                         organism = synthetic construct
SEQUENCE: 53
QVQLVESGGG VVQPGRSLRL DCKASGITFS NSGMHWVRQA PGKGLEWVAV IWYDGSKRYY    60
ADSVKGRFTI SRDNSKNTLF LQMNSLRAED TAVYYCATND DYWGQGTLVT VSSASTKGPS   120
VFPLAPCSRS TSESTAALGC LVKDYFPEPV TVSWNSGALT SGVHTFPAVL QSSGLYSLSS   180
VVTVPSSSLG TKTYTCNVDH KPSNTKVDKR VESKYGPPCP PCPAPEFLGG PSVFLFPPKP   240
KDTLMISRTP EVTCVVVDVS QEDPEVQFNW YVDGVEVHNA KTKPREEQFN STYRVVSVLT   300
VLHQDWLNGK EYKCKVSNKG LPSSIEKTIS KAKGQPREPQ VYTLPPSQEE MTKNQVSLTC   360
LVKGFYPSDI AVEWESNGQP ENNYKTTPPV LDSDGSFFLY SRLTVDKSRW QEGNVFSCSV   420
MHEALHNHYT QKSLSLSLGK                                               440

SEQ ID NO: 54            moltype = AA   length = 442
FEATURE                  Location/Qualifiers
source                   1..442
                         mol_type = protein
                         organism = synthetic construct
SEQUENCE: 54
EVQLVQSGAE VKKPGESLRI SCKGSGYSFS TYWISWVRQM PGKGLEWMGK IYPGDSYTNY    60
SPSFQGQVTI SADKSISTAY LQWSSLKASD TAMYYCARGY GIFDWGQGT LVTVSSASTK    120
GPSVFPLAPC SRSTSESTAA LGCLVKDYFP EPVTVSWNSG ALTSGVHTFP AVLQSSGLYS   180
LSSVVTVPSS NFGTQTYTCN VDHKPSNTKV DKTVERKCCV ECPPCPAPPV AGPSVFLFPP   240
KPKDTLMISR TPEVTCVVVD VSHEDPEVQF NWYVDGVEVH NAKTKPREEQ FNSTFRVVSV   300
LTVVHQDWLN GKEYKCKVSN KGLPAPIEKT ISKTKGQPRE PQVYTLPPSR EEMTKNQVSL   360
TCLVKGFYPS DIAVEWESNG QPENNYKTTP PMLDSDGSFF LYSKLTVDKS RWQQGNVFSC   420
SVMHEALHNH YTQKSLSLSP GK                                            442

SEQ ID NO: 55            moltype = DNA   length = 625
FEATURE                  Location/Qualifiers
source                   1..625
                         mol_type = unassigned DNA
                         organism = unidentified
                         note = AP1.0 sequence
SEQUENCE: 55
attctcgggc tacggccctg gagccactcc ggctcctaaa gatttagaag tttgagcaca    60
cccgccact agggccccc atccaggggg gcaacgggca agcacttctg tttcccggt     120
atgatctgat aggctgtaac cacggctgaa acagagatta tcgttatccg cttcactact   180
tcgagaagcc tagtaatgat gggtgaaatt gaatccgttg atccggtgtc tccccccacac  240
cagaaactca tgatgagggt tgccatcccg gctacggcga cgtagcgggc atccctgcgc   300
```

```
tggcatgagg cctcttagga ggacggatga tatggatctt gtcgtgaaga gcctattgag    360
ctagtgtcga ctcctccgcc cccgtgaatg cggctaatcc taaccccgga gcaggtgggt    420
ccaatccagg gcctggcctg tcgtaatgcg taagtctggg acggaaccga ctactttcgg    480
gaaggcgtgt ttccatttgt tcattatttg tgtgtttatg gtgacaactc tgggtaaacg    540
ttctattgcg tttattgaga gattcccaac aattgaacaa acgagaacta cctgttttat    600
taaatttaca cagagaagaa ttaca                                          625

SEQ ID NO: 56          moltype = DNA   length = 549
FEATURE                Location/Qualifiers
source                 1..549
                       mol_type = other DNA
                       organism = unidentified
                       note = CK1.0 sequence
SEQUENCE: 56
gtggccacgc ccgggccacc gatacttccc ttcactcctt cgggactgtt ggggaggaac    60
acaacagggc tccctgtttt tcccattcct tcccccttt cccaaccca accgccgtat     120
ctggtggcgg caagacacac gggtctttcc ctctaaagca caattgtgtg tgtgtcccag    180
gtcctcctgc gtacggtgcg ggagtgctcc cacccaactg ttgtaagcct gtccaacgcg    240
tcgtcctggc aagactatga cgtcgcatgt tccgctgcgg atgccgaccg ggtaaccggt    300
tccccagtgt gtgtagtgcg atcttccagg tcctcctggt tggcgttgtc cagaaactgc    360
ttcaggtaag tggggtgtgc ccaatcccta caaaggttga ttctttcacc accttaggaa    420
tgctccggag gtaccccagc aacagctggg atctgaccgg aggctaattg tctacggtg     480
gtgtttcctt tttcttttca cacaactcta ctgctgacaa ctcactgact atccacttgc    540
tctgtcacg                                                            549

SEQ ID NO: 57          moltype = DNA   length = 630
FEATURE                Location/Qualifiers
source                 1..630
                       mol_type = unassigned DNA
                       organism = unidentified
                       note = PV1.0 sequence
SEQUENCE: 57
aacaaaaggc tacaccactt gggctacggc ccgcgccacc ttgtggcgca aagacattag    60
aagaatagca taccgcccac tagggccctg cagccagcag ggtaacgggc aagcacttct    120
gtctccccgg tagaacggta taggctgtac ccacggccga aaactgaact atcgttaccc    180
gactccgtac ttcgcaaagc ttagtaggaa actggaaagt tcgagttatt gacccggagt    240
gttccccca ctccagaaac gcgtgatgag ggttgccacc ccgaccatgg cgacatggtg     300
ggcatccctg cgctggcacg cggcctctaa gaggataact cgctcctact ggtaaccgaa    360
gagcccgtg agctacggtt tattcctccg cctccctgaa tgcgggctaat cctaacccat    420
gagcagttgc catagatcca tatggtggac tgtcgtaacg cgtaagttgt gggcggaacc    480
gactactttg ggatggcgtg tttccttgtt ttctccattt gttgttgtat ggtgacaagt    540
tatagatctc gatctatagc gtttcttgag agatttccaa acatttattc aagtcgtaca    600
attcttgtgt ttaagcagta cagtgtaacc                                     630

SEQ ID NO: 58          moltype = DNA   length = 653
FEATURE                Location/Qualifiers
source                 1..653
                       mol_type = unassigned DNA
                       organism = unidentified
                       note = SV1.0 sequence
SEQUENCE: 58
tctgtcctca ccccatcttc ccttctttcc tgcaccgtta cgcttactcg catgtgcatt    60
gagtggtgca cgtgcttgaa caaacagcta cactcacatg ggggcgggtt ttcccgccct    120
gcggcctctc gcgaggccca ccctcccct tcctcccata actacagtgc tttggtaggt     180
aagcatcctg atccccgcg gaagctgctc acgtggcaac tgtggggacc cagacaggtt     240
atcaaaggca cccggtcttt ccgccttcag gagtatccct gctagtgaat tctagtaggg    300
ctctgcttgg tgccaacctc cccaaatgc gcgtgcggg agtgctcttc cccaactcac      360
cctagtatcc tctcatgtgt gtgcttggtc agcatatctg agacgatgtt ccgctgtccc    420
agaccagtcc agtaatggac gggccagtgt gcgtagtcgt cttccggctt gtccggcgca    480
tgtttggtga accggtgggg taaggttggt gtgcccaacg cccgtacttt ggtgatacct    540
caagaccacc caggaatgcc agggaggtac cccgcttcac agcgggatct gaccctgggc    600
taattgtcta cggtggttct tcttgcttcc acttctttct actgttcgcc acc           653

SEQ ID NO: 59          moltype = DNA   length = 635
FEATURE                Location/Qualifiers
source                 1..635
                       mol_type = genomic DNA
                       organism = Caprine kobuvirus
                       strain = 5delta40
SEQUENCE: 59
gtggccacgc ccgggccacc gatacttccc ttcactcctt cgggactgtt ggggaggaac    60
acaacagggc tccctgtttt tcccattcct tcccccttt cccaaccca accgccgtat     120
ctggtggcgg caagacacac gggtctttcc ctctaaagca caattgtgtg tgtgtcccag    180
gtcctcctgc gtacggtgcg ggagtgctcc cacccaactg ttgtaagcct gtccaacgcg    240
tcgtcctggc aagactatga cgtcgcatgt tccgctgcgg atgccgaccg ggtaaccggt    300
tccccagtgt gtgtagtgcg atcttccagg tcctcctggt tggcgttgtc cagaaactgc    360
ttcaggtaag tggggtgtgc ccaatcccta caaaggttga ttctttcacc accttaggaa    420
tgctccggag gtaccccagc aacagctggg atctgaccgg aggctaattg tctacggtg     480
gtgtttcctt tttcttttca cacaactcta ctgctgacaa ctcactgact atccacttgc    540
```

```
tctcttgtgc ctttctgctc tggttcaagt tccttgattg tttttgactg cttttcactg  600
cttttcttct cacaatcctt gctcagttca aagtc                             635

SEQ ID NO: 60          moltype = DNA  length = 513
FEATURE                Location/Qualifiers
source                 1..513
                       mol_type = genomic DNA
                       organism = Caprine kobuvirus
                       strain = 5delta40/3delta122
SEQUENCE: 60
gtggccacgc ccgggccacc gatacttccc ttcactcctt cgggactgtt ggggaggaac  60
acaacagggc tcccctgttt tcccattcct tccccctttt cccaacccca accgccgtat  120
ctggtggcgg caagacacac gggtctttcc ctctaaagca caattgtgtg tgtgtcccag  180
gtcctcctgc gtacggtgcg ggagtgctcc cacccaactg ttgtaagcct gtccaacgcg  240
tcgtcctggc aagactatga cgtcgcatgt tccgctgcgg atgccgaccg ggtaaccggt  300
tccccagtgt gtgtagtgcg atcttccagg tcctcctggt tggcgttgtc cagaaactgc  360
ttcaggtaag tggggtgtgc ccaatcccta caaaggttga ttctttcacc accttaggaa  420
tgctccggag gtaccccagc aacagctggg atctgaccgg aggctaattg tctacgggtg  480
gtgtttcctt tttcttttca cacaactaaa gtc                               513

SEQ ID NO: 61          moltype = DNA  length = 549
FEATURE                Location/Qualifiers
source                 1..549
                       mol_type = genomic DNA
                       organism = Caprine kobuvirus
                       strain = 5delta40/3delta86_Distal
SEQUENCE: 61
gtggccacgc ccgggccacc gatacttccc ttcactcctt cgggactgtt ggggaggaac  60
acaacagggc tcccctgttt tcccattcct tccccctttt cccaacccca accgccgtat  120
ctggtggcgg caagacacac gggtctttcc ctctaaagca caattgtgtg tgtgtcccag  180
gtcctcctgc gtacggtgcg ggagtgctcc cacccaactg ttgtaagcct gtccaacgcg  240
tcgtcctggc aagactatga cgtcgcatgt tccgctgcgg atgccgaccg ggtaaccggt  300
tccccagtgt gtgtagtgcg atcttccagg tcctcctggt tggcgttgtc cagaaactgc  360
ttcaggtaag tggggtgtgc ccaatcccta caaaggttga ttctttcacc accttaggaa  420
tgctccggag gtaccccagc aacagctggg atctgaccgg aggctaattg tctacgggtg  480
gtgtttcctt tttcttttca cacaactcta ctgctgacaa ctcactgact atccacttgc  540
tctaaagtc                                                          549

SEQ ID NO: 62          moltype = DNA  length = 513
FEATURE                Location/Qualifiers
source                 1..513
                       mol_type = genomic DNA
                       organism = Caprine kobuvirus
                       strain = 5delta40/3delta122_Kozak
SEQUENCE: 62
gtggccacgc ccgggccacc gatacttccc ttcactcctt cgggactgtt ggggaggaac  60
acaacagggc tcccctgttt tcccattcct tccccctttt cccaacccca accgccgtat  120
ctggtggcgg caagacacac gggtctttcc ctctaaagca caattgtgtg tgtgtcccag  180
gtcctcctgc gtacggtgcg ggagtgctcc cacccaactg ttgtaagcct gtccaacgcg  240
tcgtcctggc aagactatga cgtcgcatgt tccgctgcgg atgccgaccg ggtaaccggt  300
tccccagtgt gtgtagtgcg atcttccagg tcctcctggt tggcgttgtc cagaaactgc  360
ttcaggtaag tggggtgtgc ccaatcccta caaaggttga ttctttcacc accttaggaa  420
tgctccggag gtaccccagc aacagctggg atctgaccgg aggctaattg tctacgggtg  480
gtgtttcctt tttcttttca cacaactgcc acc                               513

SEQ ID NO: 63          moltype = DNA  length = 549
FEATURE                Location/Qualifiers
source                 1..549
                       mol_type = genomic DNA
                       organism = Caprine kobuvirus
                       strain = 5delta40/3delta86 Proximal
SEQUENCE: 63
gtggccacgc ccgggccacc gatacttccc ttcactcctt cgggactgtt ggggaggaac  60
acaacagggc tcccctgttt tcccattcct tccccctttt cccaacccca accgccgtat  120
ctggtggcgg caagacacac gggtctttcc ctctaaagca caattgtgtg tgtgtcccag  180
gtcctcctgc gtacggtgcg ggagtgctcc cacccaactg ttgtaagcct gtccaacgcg  240
tcgtcctggc aagactatga cgtcgcatgt tccgctgcgg atgccgaccg ggtaaccggt  300
tccccagtgt gtgtagtgcg atcttccagg tcctcctggt tggcgttgtc cagaaactgc  360
ttcaggtaag tggggtgtgc ccaatcccta caaaggttga ttctttcacc accttaggaa  420
tgctccggag gtaccccagc aacagctggg atctgaccgg aggctaattg tctacgggtg  480
gtgtttcctt tttcttttca cacaactttc actgcttttc ttctcacaat ccttgctcag  540
ttcaaagtc                                                          549

SEQ ID NO: 64          moltype = DNA  length = 678
FEATURE                Location/Qualifiers
source                 1..678
                       mol_type = genomic DNA
                       organism = Picornavirales sp.
                       note = isolate RtNn-PicoV/HuB2015-3 polyprotein gene-1
```

```
SEQUENCE: 64
tgaaccgtta cgcaccactc agttggtgtt tggtggcacc aatgatgaaa caaaaggcta    60
caccacttgg gctacggccc gcgccacctt gtggcgcaaa gacattagaa gaatagcata   120
ccgcccacta gggccctgca gccagcaggg taacgggcaa gcacttctgt ctccccgta    180
gaacggtata ggctgtaccc acggccgaaa actgaactat cgttacccga ctccgtactt   240
cgcaaagctt agtaggaaac tggaaagttc gagttattga cccggagtgt tccccccact   300
ccagaaacgc gtgatgaggg ttgccacccc gaccatggcg acatggtggg catccctgcg   360
ctggcacgcg gcctctaaga ggataactcg ctcctactgg taaccgaaga gccccgtgag   420
ctacggttta ttcctccgcc tccctgaatg cggctaatcc taacccatga gcagttgcca   480
tagatccata tggtggactg tcgtaacgcg taagttgtgg gcggaaccga ctactttggg   540
atggcgtgtt tccttgtttt ctccatttgt tgttgtatgg tgacaagtta tagatctcga   600
tctatagcgt ttcttgagag atttccaaac atttattcaa gtcgtacaat tcttgtgttt   660
aagcagtaca gtgtaagg                                                 678

SEQ ID NO: 65             moltype = DNA  length = 630
FEATURE                   Location/Qualifiers
source                    1..630
                          mol_type = genomic DNA
                          organism = Parabovirus sp.
                          strain = 5delta48
SEQUENCE: 65
aacaaaaggc tacaccactt gggctacggc ccgcgccacc ttgtggcgca aagacattag    60
aagaatagca taccgcccac tagggccctg cagccagcag ggtaacgggc aagcacttct   120
gtctccccgg tagaacggta taggctgtac ccacggccga aaactgaact atcgttaccc   180
gactccgtac ttcgcaaagc ttagtaggaa actggaaagt tcgagttatt gacccggagt   240
gttcccccca ctccagaaac gcgtgatgag ggttgccacc ccgaccatgg cgacatggtt   300
ggcatccctg cgctggcacg cggcctctaa gaggataact cgctcctact ggtaaccgaa   360
gagccccgtg agctacggtt tattcctccg cctccctgaa tgcggctaat cctaacccat   420
gagcagttgc catagatcca tatggtggac tgtcgtaacg cgtaagttgt gggcggaacc   480
gactactttg ggatggcgtg tttccttgtt ttctccattt gttgttgtat ggtgacaagt   540
tatagatctc gatctatagc gtttcttgag agatttccaa acatttattc aagtcgtaca   600
attcttgtgt ttaagcagta cagtgtaagg                                    630

SEQ ID NO: 66             moltype = DNA  length = 611
FEATURE                   Location/Qualifiers
source                    1..611
                          mol_type = genomic DNA
                          organism = Parabovirus sp.
                          strain = 5delta67
SEQUENCE: 66
tgggctacgg cccgcgccac cttgtggcgc aaagacatta gaagaatagc ataccgccca    60
ctagggccct gcagccagca gggtaacggg caagcacttc tgtctccccg gtagaacggt   120
ataggctgta cccacggccg aaaactgaac tatcgttacc cgactccgta cttcgcaaag   180
cttagtagga aactggaaag ttcgagttat tgacccggag tgttcccccc actccagaaa   240
cgcgtgatga gggttgccac cccgaccatg gcgacatggt gggcatccct gcgctggcac   300
gcggcctcta agaggataac tcgctcctac tggtaaccga agagccccgt gagctacggt   360
ttattcctcc gcctccctga atgcggctaa tcctaaccca tgagcagttg ccatagatcc   420
atatggtgga ctgtcgtaac gcgtaagttg tgggcggaac cgactacttt gggatggcgt   480
gtttccttgt tttctccatt tgttgttgta tggtgacaag ttatagatct cgatctatag   540
cgtttcttga gagatttcca aacatttatt caagtcgtac aattcttgtg tttaagcagt   600
acagtgtaag g                                                        611

SEQ ID NO: 67             moltype = DNA  length = 618
FEATURE                   Location/Qualifiers
source                    1..618
                          mol_type = genomic DNA
                          organism = Parabovirus sp.
                          strain = 3delta60
SEQUENCE: 67
tgaaccgtta cgcaccactc agttggtgtt tggtggcacc aatgatgaaa caaaaggcta    60
caccacttgg gctacggccc gcgccacctt gtggcgcaaa gacattagaa gaatagcata   120
ccgcccacta gggccctgca gccagcaggg taacgggcaa gcacttctgt ctccccgta    180
gaacggtata ggctgtaccc acggccgaaa actgaactat cgttacccga ctccgtactt   240
cgcaaagctt agtaggaaac tggaaagttc gagttattga cccggagtgt tccccccact   300
ccagaaacgc gtgatgaggg ttgccacccc gaccatggcg acatggtggg catccctgcg   360
ctggcacgcg gcctctaaga ggataactcg ctcctactgg taaccgaaga gccccgtgag   420
ctacggttta ttcctccgcc tccctgaatg cggctaatcc taacccatga gcagttgcca   480
tagatccata tggtggactg tcgtaacgcg taagttgtgg gcggaaccga ctactttggg   540
atggcgtgtt tccttgtttt ctccatttgt tgttgtatgg tgacaagtta tagatctcga   600
tctatagcgt ttgtaagg                                                 618

SEQ ID NO: 68             moltype = DNA  length = 826
FEATURE                   Location/Qualifiers
source                    1..826
                          mol_type = genomic DNA
                          organism = Apodemus agrarius picornavirus
                          note = strain Longquan-Aa118 polyprotein 1
SEQUENCE: 68
tttgaaaggg gtgcggatat catggcgttt ctcgccatga tatccgcaca ttgcaaaccc    60
```

```
atattgcata cccactgggt atgcattatg gggaggcccc tttcacccct cccccccaa   120
ttacctttc cccctctagt aaccatacgc tttactcagc gtaactactc cgggttacgt   180
gatgaagaag aggctacgga gattctcggg ctacggccct ggagccactc cggctcctaa   240
agatttagaa gtttgagcac acccgcccac tagggccccc catccagggg ggcaacgggc   300
aagcacttct gtttcccccgg tatgatctga taggctgtaa ccacggctga aacagagatt   360
atcgttatcc gcttcactac ttcgagaagc ctagtaatga tgggtgaaat tgaatccgtt   420
gatccggtgt ctcccccaca ccagaaactc atgatgaggg ttgccatccc ggctacggcg   480
acgtagcggg catccctgcg ctggcatgag gcctcttagg aggacggatg atatggatct   540
tgtcgtgaag agcctattga gctagtgtcg actcctccgc cccgtgaat gcggctaatc   600
ctaaccccgg agcaggtggg tccaatccag ggcctggcct gtcgtaatgc gtaagtctgg   660
gacggaaccg actactttcg ggaaggcgtg tttccatttg ttcattattt gtgtgtttat   720
ggtgacaact ctgggtaaac gttctattgc gtttattgag agattcccaa caattgaaca   780
aacgagaact acctgtttta ttaaatttac acagagaaga attaca              826

SEQ ID NO: 69            moltype = DNA   length = 721
FEATURE                  Location/Qualifiers
source                   1..721
                         mol_type = genomic DNA
                         organism = Apodemus picornavirus
                         strain = 5delta105
SEQUENCE: 69
cccctcccc cccaattacc ttttccccct ctagtaacca tacgctttac tcagcgtaac   60
tactccgggt tacgtgatga agaagaggct acggagattc tcgggctacg gcctggagc   120
cactccggct cctaaagatt tagaagtttg agcacacccg cccactaggg cccccatcc   180
aggggggcaa cgggcaagca cttctgtttc ccggtatga tctgataggc tgtaaccacg   240
gctgaaacag agattatcgt tatccgcttc actacttcga gaagcctagt aatgatgggt   300
gaaattgaat ccgttgatcc ggtgtctccc ccacaccaga aactcatgat gagggttgcc   360
atcccggcta cggcgacgta gcgggcatcc ctgcgctggc atgaggcctc ttaggaggac   420
ggatgatatg gatcttgtcg tgaagagcct attgagctag tgtcgactcc tccgcccccg   480
tgaatgcggc taatcctaac cccggaagcag gtgggtccaa tccagggcct ggcctgtcgt   540
aatgcgtaag tctgggacgg aaccgactac tttcggaag cgtgtttcc atttgttcat   600
tatttgtgtg tttatggtga caactctggg taaacgttct attgcgttta ttgagagatt   660
cccaacaatt gaacaaacga gaactacctg ttttattaaa tttacacaga gaagaattac   720
a                                                                  721

SEQ ID NO: 70            moltype = DNA   length = 625
FEATURE                  Location/Qualifiers
source                   1..625
                         mol_type = genomic DNA
                         organism = Apodemus picornavirus
                         strain = 5delta201
SEQUENCE: 70
attctcgggc tacggccctg gagccactcc ggctcctaaa gatttagaag tttgagcaca   60
cccgcccact agggcccccc atccaggggg gcaacgggca agcacttctg tttcccggt   120
atgatctgat aggctgtaac cacggctgaa acagagatta tcgttatccg cttcactact   180
tcgagaagc tagtaatgat gggtgaaatt gaatccgtt atccggtgtc tcccccacac   240
cagaaactca tgatgagggt tgccatcccg gctacggcga cgtagcgggc atccctgcg   300
tggcatgagg cctcttagga ggacggatga tatggatctt gtcgtgaaga gcctattgag   360
ctagtgtcga ctcctccgcc cccgtgaatg cggctaatcc taaccccgga gcaggtgggt   420
ccaatccagg gcctggcctg tcgtaatgcg taagtctggg acggaaccga ctactttcgg   480
gaaggcgtgt ttccatttgt tcattatttg tgtgtttatg gtgacaactc tgggtaaacg   540
ttctattgcg tttattgaga gattcccaac aattgaacaa acgagaacta cctgttttat   600
taaatttaca cagagaagaa ttaca                                        625

SEQ ID NO: 71            moltype = DNA   length = 766
FEATURE                  Location/Qualifiers
source                   1..766
                         mol_type = genomic DNA
                         organism = Kobuvirus sp.
                         note = SZAL6-KoV/2011/HUN- complete genome.1
SEQUENCE: 71
tttcacaccc tcttttccgg tggtccggac ccagaccacc gttactccat tcagctactt   60
cggtacctgt tcggaggaat taaacgggca ccctacccaa gggttacatg ggaccatatt   120
cctcctcccc tgtaacttta agttttgtgc ccgtattctt gactccaggc gtgatcttg   180
tcgcccgtcc tgtgaacaaa cagctagaca ctttcctccc ctccctctgg gctgctccgg   240
cagtccactc cctcccccca gcgtaacatg ccccgctgga gtgatgcacc tggaagtcgt   300
ggacgtgggt tagtaacttc ggtgaaaacc cactataatg acaactggtt gaccccccaca   360
ctcaaaggac tcgagtcttt ctcccttaag gctagcccgg ccacatgaat ttgcagctgg   420
caactagtga gtccaccatg tcccgcaacc tcggctgcgg agtgctgttc cccaagcgta   480
tgccttcctt ctgtaagagt gcgcctggca agcacatctg agaagtcgtt ccgctgcgtc   540
gtgccaacct ggcgacaggt gacccagtgt gcgtagactt cttccggatt cgtccggctc   600
ttctctagga aacatgcgtg taaggttcat gtgccaaagc cctgcgcgcg tgttcttctc   660
actgccctag gaatgtgccg caggtacccc tacttcggta gggatctgag cggtagctaa   720
ttgtctacgg gtagtttcat ttccatcttc tcttcaggtc gacatc                 766

SEQ ID NO: 72            moltype = DNA   length = 608
FEATURE                  Location/Qualifiers
source                   1..608
                         mol_type = genomic DNA
```

```
                        organism = Kobuvirus sp.
                        strain = SZAL6 5delta158
SEQUENCE: 72
ttgactccag gcggatgttg tgtcgcccgt cctgtgaaca acagctaga cactttcctc    60
ccctccctct gggctgctcc ggcagtccac tccctcccccc cagcgtaaca tgccccgctg   120
gagtgatgca cctggaagtc gtggacgtgg gttagtaact tcggtgaaaa cccactataa   180
tgacaactgg ttgaccccca cactcaaagg actcgagtct ttctccctta aggctagccc   240
ggccacatga atttgcagct ggcaactagt gagtccacca tgtcccgcaa cctcggctgc   300
ggagtgctgt tccccaagcg tatgccttcc ttctgtaaga gtgcgcctgg caagcacatc   360
tgagaagtcg ttccgctgcg tcgtgccaac ctggcgacag gtgacccagt gtcgtagac    420
ttcttccgga ttcgtccggc tcttctctag gaaacatgcg tgtaaggttc atgtgccaaa   480
gccctgcgcg cggtgttctt ctactgccct aggaatgtgc cgcaggtacc cctacttcgg   540
tagggatctg agcggtagct aattgtctac gggtagtttc atttccatct tctcttcagg   600
tcgacatc                                                            608

SEQ ID NO: 73            moltype = DNA   length = 690
FEATURE                  Location/Qualifiers
source                   1..690
                        mol_type = genomic DNA
                        organism = Kobuvirus sp.
                        strain = SZAL6 5delta76
SEQUENCE: 73
gaattaaacg ggcaccctac ccaagggtta catgggacca tattcctcct ccctgtaac    60
tttaagtttt gtgcccgtat tcttgactcc aggcggatgt tgtgtcgccc gtcctgtgaa   120
caaacagcta gacactttcc tcccctccct ctgggctgct ccggcagtcc actccctccc   180
cccagcgtaa catgccccgc tggagtgatg cacctggaag tcgtggacgt gggttagtaa   240
cttcggtgaa aacccactat aatgacaact ggttgacccc cacactcaaa ggactcgagt   300
cttttctccct taaggctagc ccggccacat gaatttgcag ctggcaacta gtgagtccac   360
catgtcccgc aacctcggct gcggagtgct gttcccaag cgtatgcctt ccttctgtaa    420
gagtgcgcct ggcaagcaca tctgagaagt cgttccgctg cgtcgtgcca acctggcgac   480
aggtgaccca gtgtgcgtag acttcttccg gattcgtccg gctcttctct aggaaacatg   540
cgtgtaaggt tcatgtgcca aagccctgcg cgcggtgttc ttctactgcc ctaggaatgt   600
gccgcaggta cccctacttc ggtagggatc tgagcggtag ctaattgtct acgggtagtt   660
tcatttccat cttctcttca ggtcgacatc                                    690

SEQ ID NO: 74            moltype = DNA   length = 729
FEATURE                  Location/Qualifiers
source                   1..729
                        mol_type = genomic DNA
                        organism = Kobuvirus sp.
                        strain = SZAL6 3delta37
SEQUENCE: 74
tttcacaccc tcttttccgg tggtccggac ccagaccacc gttactccat tcagctactt    60
cggtacctgt tcggaggaat taaacgggca ccctacccaa gggttacatg ggaccatatt   120
cctcctcccc tgtaacttta agttttgtgc ccgtattctt gactccaggc ggatgttgtg   180
tcgcccgtct gtgaacaaa cagctagaca ctttcctccc ctccctctgg gctgctccgg    240
cagtccactc cctcccccca gcgtaacatg ccccgctgga gtgatgcacc tggaagtcgt   300
ggacgtgggt tagtaacttc ggtgaaaacc cactataatg acaactggtt gaccccaca    360
ctcaaaggac tcgagtcttt ctcccttaag gctagcccgg ccacatgaat tgcagctgg    420
caactagtga gtccaccatg tcccgcaacc tcggctgcgg agtgctgttc cccaagcgta   480
tgccttcctt ctgtaagagt gcgcctggca agcacatctg agaagtcgtt ccgctgcgtc   540
gtgccaacct ggcgacaggt gacccagtgt gcgtagactt cttccggatt cgtccggctc   600
ttctctagga aacatgcgtg taaggttcat gtgccaaagc cctgcgcgcg tgttcttct    660
actgccctag gaatgtgccg caggtacccc tacttcggta gggatctgag cggtagctaa   720
ttggacatc                                                           729

SEQ ID NO: 75            moltype = DNA   length = 650
FEATURE                  Location/Qualifiers
source                   1..650
                        mol_type = genomic DNA
                        organism = Salivirus sp.
                        strain = SZ1
SEQUENCE: 75
tctgtcctca ccccatcttc ccttcttttcc tgcaccgtta cgcttactcg catgtgcatt    60
gagtggtgca cgtgcttgaa caaacagcta cactcacatg ggggcgggtt ttcccgccct   120
gcggcctctc gcgaggccca cccctccccct tcctcccata actacagtgc tttggtaggt   180
aagcatcctg atccccgcg gaagctgctc acgtggcaac tgtggggacc cagacaggtt    240
atcaaaggca cccggtcttc ccgccttcag gagtatccgt gctagtgaat tctagtaggg   300
ctctgcttgg tgccaacctc cccccaaatgc gcgctgcggg agtgctcttc cccaactgac   360
cctagtatcc tctcatgtgt gtgcttggtc agcatatctg agacgatgtt ccgctgtccc   420
agaccagtcc agtaatggac gggccagtgt gcgtagtcgt cttccggctt gtccggcgca   480
tgtttggtga accggtgggg taaggttggt gtgcccaacg cccgtacttt ggtgataccct   540
caagaccacc caggaatgcc agggaggtac cccgcttcac agcgggatct gaccctggc    600
taattgtcta cggtggttct tcttgcttcc acttcttttct actgttcatg              650

SEQ ID NO: 76            moltype = DNA   length = 508
FEATURE                  Location/Qualifiers
source                   1..508
                        mol_type = genomic DNA
```

```
                        organism = Crohivirus B
SEQUENCE: 76
gtataagaga caggtgtttg ccttgtcttc ggactggcat cttgggacca acccccnttt    60
tccccagcca tggttaaat ggcaataaag gacgtaacaa ctttgtaacc attaagcttt    120
gtaattttgt aaccactaag ctttgtgcac ataatgtaac catcaagctt gttagtccca    180
gcaggaggtt tgcatgcttg tagccgaaat ggggctcgac cccccatagt aggatacttg    240
atttttgcatt ccattgtgga cctgcaaact ctacacatag aggctttgtc ttgcatctaa    300
acacctgagt acagtgtgta cctagaccct atagtacggg aggaccgttt gtttcctcaa    360
taaccctaca taataggcta ggtgggcatg cccaatttgc aagatcccag actggggtc    420
ggtctgggca gggttagatc cctgttagct actgcctgat agggtggtgc tcaaccatgt    480
gtagtttaaa ttgagctgtt catatacc                                      508

SEQ ID NO: 77           moltype = DNA   length = 457
FEATURE                 Location/Qualifiers
source                  1..457
                        mol_type = genomic DNA
                        organism = Crohivirus B
                        strain = 5delta51
SEQUENCE: 77
ccccctttt ccccagccat gggttaaatg gcaataaagg acgtaacaac tttgtaacca    60
ttaagctttg taattttgta accactaagc tttgtgcaca taatgtaacc atcaagcttg    120
ttagtcccag caggaggttt gcatgcttgt agccgaaatg gggctcgacc ccccatagta    180
ggatacttga ttttgcattc cattgtggac ctgcaaactc tacacataga ggctttgtct    240
tgcatctaaa cacctgagta cagtgtgtac ctagacccta tagtacggga ggaccgtttg    300
tttcctcaat aaccctacat aataggctag gtgggcatgc ccaatttgca agatcccaga    360
ctggggtcg gtctgggcag ggttagatcc ctgttagcta ctgcctgata gggtggtgct    420
caaccatgtg tagtttaaat tgagctgttc atatacc                            457

SEQ ID NO: 78           moltype = DNA   length = 742
FEATURE                 Location/Qualifiers
source                  1..742
                        mol_type = genomic DNA
                        organism = Coxsackievirus B3
                        note = clone CV-B3/28 2A C107S- complete genome.1
SEQUENCE: 78
ttaaaacagc ctgtgggttg atcccaccca cagggcccat tgggcgctag cactctggta    60
tcacggtacc tttgtgcgcc tgttttatac ccctcccccc aactgtaact tagaagtaac    120
acacaccgat caacagtcag cgtggcacac cagccacgtt tgatcaagc acttctgtta    180
ccccggactg agtatcaata gactgctcac gcggttgaag gagaaagcgt tcgttatccg    240
gccaactact tcgaaaaacc tagtaacacc gtgaagttg cagagtgttt cgctcagcac    300
tacccccagtg tagatcaggt cgatgagtca ccgcattccc cacgggcgac cgtggcggtg    360
gctgcgttgg cggcctgccc atggggaaac ccatgggacg ctctaataca gacatggtgc    420
gaagagtcta ttgagctagt tggtagtcct ccggccccg aatgcggcta atcctaactg    480
cggagcacac accctcaagc cagagggcag tgtgtcgtaa cggcaactc tgcagcggaa    540
ccgactactt tgggtgtccg tgtttcattt tattcctata ctggctgctt atggtgacaa    600
ttgagagatt gttaccatat agctattgga ttggccatcc ggtgaccaat agagctatta    660
tatctcttt tgttgggttt ataccactta gcttgaaaga ggttaaaaca ttacaattca    720
ttgttaagtt gaatacagca aa                                            742

SEQ ID NO: 79           moltype = DNA   length = 651
FEATURE                 Location/Qualifiers
source                  1..651
                        mol_type = genomic DNA
                        organism = Coxsackievirus B3
                        strain = 3delta91
SEQUENCE: 79
ttaaaacagc ctgtgggttg atcccaccca cagggcccat tgggcgctag cactctggta    60
tcacggtacc tttgtgcgcc tgttttatac ccctcccccc aactgtaact tagaagtaac    120
acacaccgat caacagtcag cgtggcacac cagccacgtt tgatcaagc acttctgtta    180
ccccggactg agtatcaata gactgctcac gcggttgaag gagaaagcgt tcgttatccg    240
gccaactact tcgaaaaacc tagtaacacc gtgaagttg cagagtgttt cgctcagcac    300
tacccccagtg tagatcaggt cgatgagtca ccgcattccc cacgggcgac cgtggcggtg    360
gctgcgttgg cggcctgccc atggggaaac ccatgggacg ctctaataca gacatggtgc    420
gaagagtcta ttgagctagt tggtagtcct ccggccccg aatgcggcta atcctaactg    480
cggagcacac accctcaagc cagagggcag tgtgtcgtaa cggcaactc tgcagcggaa    540
ccgactactt tgggtgtccg tgtttcattt tattcctata ctggctgctt atggtgacaa    600
ttgagagatt gttaccatat agctattgga ttggccatcc ggtgaagcaa a             651

SEQ ID NO: 80           moltype = DNA   length = 721
FEATURE                 Location/Qualifiers
source                  1..721
                        mol_type = genomic DNA
                        organism = Saffold virus
SEQUENCE: 80
cacttattta attcggcctt ttgtgacaag cccctcggtg aaagaacctc tctcttttcg    60
acgtggttgg aattgccatc atttccgacg aaagtgctat catgcctccc cgattatgtg    120
atgttttctg ccctgctggg cggagcattc tcggttgag aaaccttgaa tcttttctctt    180
tggaaccttg gttcccccgg tctaagccgc ttggaatatg caggggttat ttcttgatc    240
ttatttctac ttttgcgggt tctatccgta aaaagggtac gtgctgcccc ttcctttctct    300
```

```
ggagaattca cacggcggtc tttccgtctc tcaacaagtg tgaatgcagc atgccggaaa    360
cggtgaagaa aacagttttc tgtggaaatt tagagtgcac atcgaaacag ctgtagcgac    420
ctcacagtag cagcggactc ccctcttggc gacaagagcc tctgcggcca aaagcccgt     480
ggataagatc cactgctgtg agcggtgcaa ccccagcacc ctggttcgat gatcattctc    540
tatggaacca gaaaatggtt ttctcaagcc ctccggtaga gaagccaaga atgtcctgaa    600
ggtaccccgc gtgcgggatc tgatcaggag accaattggc ggtgctttac actgtcactt    660
tggtttaaaa attgtcacag cttctccaaa ccaagtggtc ttggttttcc aattttgttg    720
a                                                                    721

SEQ ID NO: 81           moltype = DNA   length = 675
FEATURE                 Location/Qualifiers
source                  1..675
                        mol_type = genomic DNA
                        organism = Saffold virus
                        strain = 5delta46
SEQUENCE: 81
cctctctctt ttcgacgtgg ttggaattgc catcatttcc gacgaaagtg ctatcatgcc     60
tccccgatta tgtgatgttt tctgccctgc tgggcggagc attctcgggt tgagaaacct    120
tgaatctttt tctttggaac cttggttccc ccggtctaag ccgcttggaa tatgacaggg    180
ttatttcctt gatcttattt ctactttgc gggttctatc cgtaaaaagg gtacgtgctg     240
cccctccctt ctctggagaa ttcacacggc ggtctttccg tctctcaaca agtgtgaatg    300
cagcatgccg gaaacggtga agaaaacagt ttttctgtga aatttagagt gcacatcgaa    360
acagctgtag cgacctcaca gtagcagcgg actcccctct tggcgacaag agcctctgcg    420
gccaaaagcc ccgtgggataa gatccactgc tgtgagcggt gcaaccccag cacctggtt    480
cgatgatcat tctctatgga accagaaaat ggttttctca gccctccgg tagagaagcc    540
aagaatgtcc tgaaggtacc ccgcgtgcgg gatctgatca ggagaccaat tggcggtgct    600
ttacactgtc actttggttt aaaaattgtc acagcttctc caaaccaagt ggtcttggtt    660
ttccaatttt gttga                                                     675

SEQ ID NO: 82           moltype = DNA   length = 628
FEATURE                 Location/Qualifiers
source                  1..628
                        mol_type = genomic DNA
                        organism = Saffold virus
                        strain = 5delta93
SEQUENCE: 82
gtgctatcat gcctccccga ttatgtgatg ttttctgccc tgctgggcgg agcattctcg     60
ggttgagaaa ccttgaatct tttctttgg aaccttggtt ccccggtct aagccgcttg    120
gaatatgaca gggttatttt cttgatctta tttctacttt tgcgggttct atccgtaaaa    180
agggtacgtg ctgccccctc cttctctgga gaattcacac ggcggtcttt ccgtctctca    240
acaagtgtga atgcagcatg ccggaaacgg tgaagaaaac agtttctgt ggaaatttag    300
agtgcacatc gaaacagctg tagcgacctc acagtagcag cggactcccc tcttggcgac    360
aagagcctct gcggccaaaa gccccgtgga taagatccac tgctgtgagc ggtgcaaccc    420
cagcaccctg gttcgatgat cattctctat ggaaccagaa aatggttttc tcaagccctc    480
cggtagagaa gccaagaatg tcctgaaggt accccgcgtg cgggatctga tcaggagacc    540
aattggcggt gctttacact gtcactttgg ttttaaaaatt gtcacagctt ctccaaacca    600
agtggtcttg gttttccaat tttgttga                                       628

SEQ ID NO: 83           moltype = DNA   length = 674
FEATURE                 Location/Qualifiers
source                  1..674
                        mol_type = genomic DNA
                        organism = Saffold virus
                        note = 3delta47
SEQUENCE: 83
cacttattta attcggcctt ttgtgacaag cccctcggtg aaagaacctc tctcttttcg     60
acgtggttgg aattgccatc atttccgacg aaagtgctat catgcctccc cgattatgtg    120
atgttttctg ccctgctggg cggagcattc tcggggtgag aaaccttgaa tcttttctt    180
tggaaccttg gttcccccgg tctaagccgc ttggaatatg acagggttat tttcttgatc    240
ttatttctac ttttgcgggt tctatccgta aaaagggtac gtgctgcccc ttcctctct    300
ggagaattca cacggcggtc tttccgtctc tcaacaagtg tgaatgcagc atgccggaaa    360
cggtgaagaa aacagttttc tgtggaaatt tagagtgcac atcgaaacag ctgtagcgac    420
ctcacagtag cagcggactc ccctcttggc gacaagagcc tctgcggcca aaagcccgt     480
ggataagatc cactgctgtg agcggtgcaa ccccagcacc ctggttcgat gatcattctc    540
tatggaacca gaaaatggtt ttctcaagcc ctccggtaga gaagccaaga atgtcctgaa    600
ggtaccccgc gtgcgggatc tgatcaggag accaattggc ggtgctttac actgtcactt    660
tggtttaatg ttga                                                      674

SEQ ID NO: 84           moltype = DNA   length = 726
FEATURE                 Location/Qualifiers
source                  1..726
                        mol_type = genomic DNA
                        organism = Saffold virus
                        note = Kozak
SEQUENCE: 84
cacttattta attcggcctt ttgtgacaag cccctcggtg aaagaacctc tctcttttcg     60
acgtggttgg aattgccatc atttccgacg aaagtgctat catgcctccc cgattatgtg    120
atgttttctg ccctgctggg cggagcattc tcggggtgag aaaccttgaa tcttttctt    180
tggaaccttg gttcccccgg tctaagccgc ttggaatatg acagggttat tttcttgatc    240
```

```
ttatttctac ttttgcgggt tctatccgta aaaagggtac gtgctgcccc ttccttctct    300
ggagaattca cacggcgtc tttcgtctc tcaacaagtg tgaatgcagc atgccgaaa      360
cggtgaagaa aacagttttc tgtggaaatt tagagtgcac atcgaaacag ctgtagcgac    420
ctcacagtag cagcggactc ccctcttggc gacaagagcc tctgcggcca aaagcccgt    480
ggataagatc cactgctgtg agcggtgcaa ccccagcacc ctggttcgat gatcattctc    540
tatggaacca gaaaatggtt ttctcaagcc ctccggtaga gaagccaaga atgtcctgaa    600
ggtaccccgc gtgcgggatc tgatcaggag accaattggc ggtgctttac actgtcactt    660
tggtttaaaa attgtcacag cttctccaaa ccaagtggtc ttggttttcc aatttttgttg  720
accgcc                                                              726

SEQ ID NO: 85            moltype = DNA  length = 549
FEATURE                  Location/Qualifiers
source                   1..549
                         mol_type = unassigned DNA
                         organism = unidentified
                         note = GLuc CK dCTG1
SEQUENCE: 85
gtggccacgc ccgggccacc gatacttccc ttcactcctt cgggactgtt ggggaggaac    60
acaacagggc tccctgtttt tcccattcct tccccctttt cccaaccccca accgccgtat   120
ctggtggcgg caagacacac gggtctttcc ctctaaagca caattgtgtg tgtgtcccag    180
gtcctcctgc gtacggtgcg ggagtgctcc cacccaactg ttgtaagcct gtccaacgcg    240
tcgtcctggc aagactatga cgtcgcatgt tccgctgcgg atgccgaccg ggtaaccggt    300
tccccagtgt gtgtagtgcg atcttccagg tcctcctggt tggcgttgtc cagaaactgc    360
ttcaggtaag tggggtgtgc ccaatcccta caaaggttga ttctttcacc accttaggaa    420
tgctccggag gtaccccagc aacagctggg atctgaccgg aggctaattg tctacggtg    480
gtgtttcctt tttcttttca cacaactcta cgtctgacaa ctcactgact atccacttgc    540
tctaaagtc                                                           549

SEQ ID NO: 86            moltype = DNA  length = 549
FEATURE                  Location/Qualifiers
source                   1..549
                         mol_type = unassigned DNA
                         organism = unidentified
                         note = GLuc CK dCTG1_2
SEQUENCE: 86
gtggccacgc ccgggccacc gatacttccc ttcactcctt cgggactgtt ggggaggaac    60
acaacagggc tccctgtttt tcccattcct tccccctttt cccaaccccca accgccgtat   120
ctggtggcgg caagacacac gggtctttcc ctctaaagca caattgtgtg tgtgtcccag    180
gtcctcctgc gtacggtgcg ggagtgctcc cacccaactg ttgtaagcct gtccaacgcg    240
tcgtcctggc aagactatga cgtcgcatgt tccgctgcgg atgccgaccg ggtaaccggt    300
tccccagtgt gtgtagtgcg atcttccagg tcctcctggt tggcgttgtc cagaaactgc    360
ttcaggtaag tggggtgtgc ccaatcccta caaaggttga ttctttcacc accttaggaa    420
tgctccggag gtaccccagc aacagctggg atctgaccgg aggctaattg tctacggtg    480
gtgtttcctt tttcttttca cacaactcta cgtcgtacaa ctcactgact atccacttgc    540
tctaaagtc                                                           549

SEQ ID NO: 87            moltype = DNA  length = 549
FEATURE                  Location/Qualifiers
source                   1..549
                         mol_type = unassigned DNA
                         organism = unidentified
                         note = GLuc CK dCTG1_2_3
SEQUENCE: 87
gtggccacgc ccgggccacc gatacttccc ttcactcctt cgggactgtt ggggaggaac    60
acaacagggc tccctgtttt tcccattcct tccccctttt cccaaccccca accgccgtat   120
ctggtggcgg caagacacac gggtctttcc ctctaaagca caattgtgtg tgtgtcccag    180
gtcctcctgc gtacggtgcg ggagtgctcc cacccaactg ttgtaagcct gtccaacgcg    240
tcgtcctggc aagactatga cgtcgcatgt tccgctgcgg atgccgaccg ggtaaccggt    300
tccccagtgt gtgtagtgcg atcttccagg tcctcctggt tggcgttgtc cagaaactgc    360
ttcaggtaag tggggtgtgc ccaatcccta caaaggttga ttctttcacc accttaggaa    420
tgctccggag gtaccccagc aacagctggg atctgaccgg aggctaattg tctacggtg    480
gtgtttcctt tttcttttca cacaactcta cgtcgtacaa ctcacgtact atccacttgc    540
tctaaagtc                                                           549

SEQ ID NO: 88            moltype = DNA  length = 549
FEATURE                  Location/Qualifiers
source                   1..549
                         mol_type = unassigned DNA
                         organism = unidentified
                         note = GLuc CK dAll
SEQUENCE: 88
gtggccacgc ccgggccacc gatacttccc ttcactcctt cgggactgtt ggggaggaac    60
acaacagggc tccctgtttt tcccattcct tccccctttt cccaaccccca accgccgtat   120
ctggtggcgg caagacacac gggtctttcc ctctaaagca caattgtgtg tgtgtcccag    180
gtcctcctgc gtacggtgcg ggagtgctcc cacccaactg ttgtaagcct gtccaacgcg    240
tcgtcctggc aagactatga cgtcgcatgt tccgctgcgg atgccgaccg ggtaaccggt    300
tccccagtgt gtgtagtgcg atcttccagg tcctcctggt tggcgttgtc cagaaactgc    360
ttcaggtaag tggggtgtgc ccaatcccta caaaggttga ttctttcacc accttaggaa    420
tgctccggag gtaccccagc aacagctggg atctgaccgg aggctaattg tctacggtg    480
```

```
gtgtttcctt tttcttttca cacaactcta cgtcgtacaa ctcacgtact actcactgtc  540
tctaaagtc                                                          549

SEQ ID NO: 89              moltype = DNA   length = 549
FEATURE                    Location/Qualifiers
source                     1..549
                           mol_type = unassigned DNA
                           organism = unidentified
                           note = CK SZ1-L1S
SEQUENCE: 89
gggggtgggg gggcctcgg  cccctcacc  ctcttttccg gtggccacgc ccgggccacc  60
gatacttccc ttcactcctt cgggactgtt ggggaggaac acaacagggc tcccctgttt 120
tccattcct  tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcg tcgtcctggc aagactatga 300
cgtcgcatgt tccgctgcgg atgccgaccg ggtaaccggt tccccagtgt gtgtagtgcg 360
atcttccagg tcctcctggt tggcgttgtc cagaaactgc ttcaggtaag tggggtgtgc 420
ccaatcccta caaaggttga accacccagg aatgccaggg aggtaccccg cttcacagcg 480
ggatctgacc ctgggctaat tgtctacggt ggttcttctt gcttccactt ctttctactg 540
ttcgccacc                                                         549

SEQ ID NO: 90              moltype = DNA   length = 553
FEATURE                    Location/Qualifiers
source                     1..553
                           mol_type = unassigned DNA
                           organism = unidentified
                           note = CK Aichi Scan (AV-S)
SEQUENCE: 90
gggggtgggg gggcctcgg  cccctcacc  ctcttttccg gtggccacgc ccgggccacc  60
gatacttccc ttcactcctt cgggactgtt ggggaggaac acaacagggc tcccctgttt 120
tccattcct  tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcg tcgtcctggc aagactatga 300
cgtcgcatgt tccgctgcgg atgccgaccg ggtaaccggt tccccagtgt gtgtagtgcg 360
atcttccagg tcctcctggt tggcgttgtc cagaaactgc ttcaggtaag tggggtgtgc 420
ccaatcccta caaaggttga ttctttcacc accttaggaa tgctccggag gtaccccagc 480
aacagctggg atctgaccgg aggctaattg tctacgggtg gtgtttcatt tccaatcctt 540
ttatgtcgga gtc                                                    553

SEQ ID NO: 91              moltype = DNA   length = 667
FEATURE                    Location/Qualifiers
source                     1..667
                           mol_type = unassigned DNA
                           organism = unidentified
                           note = CK Aichi Loop (AV-L1)
SEQUENCE: 91
gggggtgggg gggcctcgg  cccctcacc  ctcttttccg gtggccacgc ccgggccacc  60
gatacttccc ttcactcctt cgggactgtt ggggaggaac acaacagggc tcccctgttt 120
tccattcct  tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcg tcgtcctggc aagactatga 300
cgtcgcatgt tccgctgcgg atgccgaccg ggtaaccggt tccccagtgt gtgtagtgcg 360
atcttccagg tcctcctggt tggcgttgtc cagaaactgc ttcaggtaag tggggtgtgc 420
ccaatcccta caaaggttga actgcccctag gaatgccagg caggtacccc acctccgggt 480
gggatctgag cctgggctaa ttgtctacgg gtagttttcc ttttttcttt cacacaactc 540
tactgctgac aactcactga ctatccactt gctctcttgt gcctttctgc tctggttcaa 600
gttccttgat tgttttttgac tgcttttcac tgcttttctt ctcacaatcc ttgctcagtt 660
caaagtc                                                           667

SEQ ID NO: 92              moltype = DNA   length = 693
FEATURE                    Location/Qualifiers
source                     1..693
                           mol_type = unassigned DNA
                           organism = unidentified
                           note = CK SZ1-L2
SEQUENCE: 92
gggggtgggg gggcctcgg  cccctcacc  ctcttttccg gtggccacgc ccgggccacc  60
gatacttccc ttcactcctt cgggactgtt ggggaggaac acaacagggc tcccctgttt 120
tccattcct  tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcc tgatccccg  cggaagctgc 300
tcacgtggca actgtgggga cccagacagg ttatcaaagg cacccggtct ttccgccttc 360
aggagtatcc ctgctagtga attctagtag ggctctgctt gcgttgtcca gaaactgctt 420
caggtaagtg gggtgtgccc aatccctaca aaggttttca ccac cttaggaatg 480
ctccggaggt accccagcaa cagctgggat ctgaccggag gctaattgtc tacggggtggt 540
gtttcctttt tcttttcaca caactctact gctgacaact cactgactat ccacttgctc 600
tcttgtgcct ttctgctctg gttcaagttc cttgattgtt tttgactgct ttcactgct  660
tttcttctca caatccttgc tcagttcaaa gtc                               693
```

| SEQ ID NO: 93 | moltype = DNA length = 671 |
| --- | --- |
| FEATURE | Location/Qualifiers |
| source | 1..671 |
| | mol_type = unassigned DNA |
| | organism = unidentified |
| | note = CK Aichi TriLoop (AV-L2) |

SEQUENCE: 93

```
ggggtgggg gggcctcgg ccccctcacc ctcttttccg gtggccacgc ccgggccacc    60
gatacttccc ttcactcctt cgggactgtt ggggaggaac acaacagggc tccctgttt   120
tcccattcct tccccctttt cccaaccca accgccgtat ctggtggcgg caagacacac   180
gggtctttcc ctctaaagca caattgtgtg tgtgtcccag gtcctcctgc gtacggtgcg  240
ggagtgctcc cacccaactg ttgtaagcct gtccaacgca tgtgcctggc aagcatatct  300
gagaaggtgt tccgctgtgg ctgccaacct ggtgacaggt gccccagtgt gcgtaacctt  360
cttccgtctc cggacggtgc gttgtccaga aactggttca ggtaagtggg gtgtgcccaa  420
tccctacaaa ggttgattct ttcaccacct taggaatgcc ccggaggtac cccagcaaca  480
gctgggatct gaccggaggc taattgtcta cgggtggtgt ttccttttc ttttcacaca  540
actctactgc tgacaactca ctgactatcc acttgctctc ttgtgccttt ctgctctggt  600
tcaagttcct tgattgtttt tgactgcttt tcactgcttt cttctcaca atccttgctc  660
agttcaaagt c                                                      671
```

| SEQ ID NO: 94 | moltype = DNA length = 523 |
| --- | --- |
| FEATURE | Location/Qualifiers |
| source | 1..523 |
| | mol_type = unassigned DNA |
| | organism = unidentified |
| | note = CK Scan Deletion (deltaS) |

SEQUENCE: 94

```
ggggtgggg gggcctcgg ccccctcacc ctcttttccg gtggccacgc ccgggccacc    60
gatacttccc ttcactcctt cgggactgtt ggggaggaac acaacagggc tccctgttt   120
tcccattcct tccccctttt cccaaccca accgccgtat ctggtggcgg caagacacac   180
gggtctttcc ctctaaagca caattgtgtg tgtgtcccag gtcctcctgc gtacggtgcg  240
ggagtgctcc cacccaactg ttgtaagcct gtccaacgcg tcgtcctggc aagactatga  300
cgtcgcatgt tccgctgcgg atgccgaccg ggtaaccggt tccccagtgt gtgtagtgcg  360
atcttccagg tcctcctggt tggcgttgtc cagaaactgc ttcaggtaag tggggtgtgc  420
ccaatcccta caaaggttga ttctttcacc accttaggaa tgctccggag gtaccccagc  480
aacagctggg atctgaccgg aggctaattg tctacgggtg gtg                   523
```

| SEQ ID NO: 95 | moltype = DNA length = 592 |
| --- | --- |
| FEATURE | Location/Qualifiers |
| source | 1..592 |
| | mol_type = unassigned DNA |
| | organism = unidentified |
| | note = CK Loop Deletion (deltaL1) |

SEQUENCE: 95

```
ggggtgggg gggcctcgg ccccctcacc ctcttttccg gtggccacgc ccgggccacc    60
gatacttccc ttcactcctt cgggactgtt ggggaggaac acaacagggc tccctgttt   120
tcccattcct tccccctttt cccaaccca accgccgtat ctggtggcgg caagacacac   180
gggtctttcc ctctaaagca caattgtgtg tgtgtcccag gtcctcctgc gtacggtgcg  240
ggagtgctcc cacccaactg ttgtaagcct gtccaacgcg tcgtcctggc aagactatga  300
cgtcgcatgt tccgctgcgg atgccgaccg ggtaaccggt tccccagtgt gtgtagtgcg  360
atcttccagg tcctcctggt tggcgttgtc cagaaactgc ttcaggtaag tggggtgtgc  420
ccaatcccta caaaggttga tttcttttt cttttcacac aactctactg ctgacaactc  480
actgactatc cacttgctct cttgtgcctt tctgctctgg ttcaagttcc ttgattgttt  540
ttgactgctt tcactgctt ttcttctcac aatccttgct cagttcaaag tc          592
```

| SEQ ID NO: 96 | moltype = DNA length = 572 |
| --- | --- |
| FEATURE | Location/Qualifiers |
| source | 1..572 |
| | mol_type = other DNA |
| | organism = unidentified |
| | note = CK Triloop Deletion (deltaL2) |

SEQUENCE: 96

```
ggggtgggg gggcctcgg ccccctcacc ctcttttccg gtggccacgc ccgggccacc    60
gatacttccc ttcactcctt cgggactgtt ggggaggaac acaacagggc tccctgttt   120
tcccattcct tccccctttt cccaaccca accgccgtat ctggtggcgg caagacacac   180
gggtctttcc ctctaaagca caattgtgtg tgtgtcccag gtcctcctgc gtacggtgcg  240
ggagtgctcc cacccaactg ttgtaagcct gtccaacgcg cgttgtccag aaactgcttc  300
aggtaagtgg ggtgtgccca atccctacaa aggttgattc tttcaccacc ttaggaatgc  360
tccggaggta ccccagcaac agctgggatc tgaccggagg ctaattgtct acgggttgct  420
tttcctttt cttttcacac aactctactg ctgacaactc actgactatc cacttgctct  480
cttgtgcctt tctgctctgg ttcaagttcc ttgattgttt ttgactgctt tcactgctt   540
ttcttctcac aatccttgct cagttcaaag tc                               572
```

| SEQ ID NO: 97 | moltype = DNA length = 549 |
| --- | --- |
| FEATURE | Location/Qualifiers |
| source | 1..549 |
| | mol_type = unassigned DNA |
| | organism = unidentified |
| | note = GLuc CK dCTG1 |

```
SEQUENCE: 97
gtggccacgc ccgggccacc gatacttccc ttcactcctt cgggactgtt ggggaggaac    60
acaacagggc tccctgttt tccattcct tcccccttt cccaaccca accgccgtat      120
ctggtggcgg caagacacac gggtctttcc ctctaaagca caattgtgtg tgtgtcccag   180
gtcctcctgc gtacggtgcg ggagtgctcc cacccaactg ttgtaagcct gtccaacgcg   240
tcgtcctggc aagactatga cgtcgcatgt tccgctgcgg atgccgaccg ggtaaccggt   300
tccccagtgt gtgtagtgcg atcttccagg tcctcctggt tggcgttgtc cagaaactgc   360
ttcaggtaag tggggtgtgc ccaatcccta caaaggttga ttctttcacc accttaggaa   420
tgctccggag gtaccccagc aacagctggg atctgaccgg aggctaattg tctacgggtg   480
gtgtttcctt tttcttttca cacaactcta cgtctgacaa ctcactgact atccacttgc   540
tctaaagtc                                                           549

SEQ ID NO: 98           moltype = DNA  length = 549
FEATURE                 Location/Qualifiers
source                  1..549
                        mol_type = other DNA
                        organism = unidentified
                        note = GLuc CK dCTG1_2
SEQUENCE: 98
gtggccacgc ccgggccacc gatacttccc ttcactcctt cgggactgtt ggggaggaac    60
acaacagggc tccctgttt tccattcct tcccccttt cccaaccca accgccgtat      120
ctggtggcgg caagacacac gggtctttcc ctctaaagca caattgtgtg tgtgtcccag   180
gtcctcctgc gtacggtgcg ggagtgctcc cacccaactg ttgtaagcct gtccaacgcg   240
tcgtcctggc aagactatga cgtcgcatgt tccgctgcgg atgccgaccg ggtaaccggt   300
tccccagtgt gtgtagtgcg atcttccagg tcctcctggt tggcgttgtc cagaaactgc   360
ttcaggtaag tggggtgtgc ccaatcccta caaaggttga ttctttcacc accttaggaa   420
tgctccggag gtaccccagc aacagctggg atctgaccgg aggctaattg tctacgggtg   480
gtgtttcctt tttcttttca cacaactcta cgtcgtacaa ctcactgact atccacttgc   540
tctaaagtc                                                           549

SEQ ID NO: 99           moltype = DNA  length = 549
FEATURE                 Location/Qualifiers
source                  1..549
                        mol_type = unassigned DNA
                        organism = unidentified
                        note = GLuc CK dCTG1_2_3
SEQUENCE: 99
gtggccacgc ccgggccacc gatacttccc ttcactcctt cgggactgtt ggggaggaac    60
acaacagggc tccctgttt tccattcct tcccccttt cccaaccca accgccgtat      120
ctggtggcgg caagacacac gggtctttcc ctctaaagca caattgtgtg tgtgtcccag   180
gtcctcctgc gtacggtgcg ggagtgctcc cacccaactg ttgtaagcct gtccaacgcg   240
tcgtcctggc aagactatga cgtcgcatgt tccgctgcgg atgccgaccg ggtaaccggt   300
tccccagtgt gtgtagtgcg atcttccagg tcctcctggt tggcgttgtc cagaaactgc   360
ttcaggtaag tggggtgtgc ccaatcccta caaaggttga ttctttcacc accttaggaa   420
tgctccggag gtaccccagc aacagctggg atctgaccgg aggctaattg tctacgggtg   480
gtgtttcctt tttcttttca cacaactcta cgtcgtacaa ctcacgtact atccacttgc   540
tctaaagtc                                                           549

SEQ ID NO: 100          moltype = DNA  length = 167
FEATURE                 Location/Qualifiers
source                  1..167
                        mol_type = other DNA
                        organism = synthetic construct
SEQUENCE: 100
ccctgcagcc gtcaccgtaa gtttgaagtt accgcatatc agcctctgct tcccagcgcg    60
tccaattcct gttcttattg tttccctcc aggcgttacg cgtgacgacg aactgtgtcg   120
cagctaccac attattccgg agccttcatt ctcgcggctc tgatcgt                167

SEQ ID NO: 101          moltype = DNA  length = 43
FEATURE                 Location/Qualifiers
source                  1..43
                        mol_type = other DNA
                        organism = synthetic construct
SEQUENCE: 101
ggagaccgcg gccacgccga gtaggatcga gggtacagtc tcc                      43

SEQ ID NO: 102          moltype = DNA  length = 167
FEATURE                 Location/Qualifiers
source                  1..167
                        mol_type = other DNA
                        organism = synthetic construct
SEQUENCE: 102
gacaccagga tcactcttgc tctgacccgc cctgtgtaga atagactcat gcttccctaa    60
gacctggatt tcttcccagg cactttcacc cgcctgccct gctcctcag tggactgcac   120
ccagggaggc ggtctctgac tgtcctttac tttctattct ggattgc                167

SEQ ID NO: 103          moltype = DNA  length = 30
FEATURE                 Location/Qualifiers
source                  1..30
```

```
                    mol_type = other DNA
                    organism = synthetic construct
SEQUENCE: 103
aaaccccct aagccgccgc cgccgccacc                                    30

SEQ ID NO: 104      moltype = DNA  length = 18
FEATURE             Location/Qualifiers
source              1..18
                    mol_type = other DNA
                    organism = synthetic construct
SEQUENCE: 104
ccccccaac ccgtcacg                                                 18

SEQ ID NO: 105      moltype =   length =
SEQUENCE: 105
000

SEQ ID NO: 106      moltype = DNA  length = 141
FEATURE             Location/Qualifiers
source              1..141
                    mol_type = other DNA
                    organism = synthetic construct
SEQUENCE: 106
tctgcgcact cgtaatcagt actaacccc ctttgtcgga cactatgcga taatcgatcc    60
gccttttca ccgccttcgg aatttatttt acctcaactg atcctggagt ctctcttggt   120
tttcacggag gcctccgccc a                                            141

SEQ ID NO: 107      moltype = DNA  length = 43
FEATURE             Location/Qualifiers
source              1..43
                    mol_type = other DNA
                    organism = synthetic construct
SEQUENCE: 107
ggagaccgcg gccacgccga gtaggatcga gggtacagtc tcc                    43

SEQ ID NO: 108      moltype = DNA  length = 141
FEATURE             Location/Qualifiers
source              1..141
                    mol_type = other DNA
                    organism = synthetic construct
SEQUENCE: 108
ccccttgaaa ccccgcccc aggttcagtc tctcttcatc cctctgtcct gcatggtgat    60
acaaagaccc tttgtggacc ctaagccatg tagttgctgc tccctccttc cagttgtgaa   120
tattggtttc tgttaatcac a                                            141

SEQ ID NO: 109      moltype = DNA  length = 30
FEATURE             Location/Qualifiers
source              1..30
                    mol_type = other DNA
                    organism = synthetic construct
SEQUENCE: 109
aaaccccct aagccgccgc cgccgccacc                                    30

SEQ ID NO: 110      moltype = DNA  length = 18
FEATURE             Location/Qualifiers
source              1..18
                    mol_type = other DNA
                    organism = synthetic construct
SEQUENCE: 110
ccccccaac ccgtcacg                                                 18

SEQ ID NO: 111      moltype =   length =
SEQUENCE: 111
000

SEQ ID NO: 112      moltype = DNA  length = 14
FEATURE             Location/Qualifiers
source              1..14
                    mol_type = other DNA
                    organism = synthetic construct
```

-continued

| | | |
|---|---|---|
| SEQUENCE: 112 tgatagctaa ctag | | 14 |
| SEQ ID NO: 113<br>FEATURE<br>source | moltype = DNA length = 14<br>Location/Qualifiers<br>1..14<br>mol_type = other DNA<br>organism = synthetic construct | |
| SEQUENCE: 113 tagtagctaa ctag | | 14 |
| SEQ ID NO: 114<br>FEATURE<br>source | moltype = DNA length = 14<br>Location/Qualifiers<br>1..14<br>mol_type = other DNA<br>organism = synthetic construct | |
| SEQUENCE: 114 tgatgactga gtga | | 14 |
| SEQ ID NO: 115<br>FEATURE<br>source | moltype = DNA length = 14<br>Location/Qualifiers<br>1..14<br>mol_type = other DNA<br>organism = synthetic construct | |
| SEQUENCE: 115 tagtagctag gtag | | 14 |
| SEQ ID NO: 116<br>SEQUENCE: 116<br>000 | moltype = length = | |
| SEQ ID NO: 117<br>FEATURE<br>source | moltype = DNA length = 14<br>Location/Qualifiers<br>1..14<br>mol_type = other DNA<br>organism = synthetic construct | |
| SEQUENCE: 117 taatagctaa ctag | | 14 |
| SEQ ID NO: 118<br>FEATURE<br>source | moltype = DNA length = 15<br>Location/Qualifiers<br>1..15<br>mol_type = other DNA<br>organism = synthetic construct | |
| SEQUENCE: 118 taactagcta actag | | 15 |
| SEQ ID NO: 119<br>SEQUENCE: 119<br>000 | moltype = length = | |
| SEQ ID NO: 120<br>FEATURE<br>source | moltype = DNA length = 43<br>Location/Qualifiers<br>1..43<br>mol_type = other DNA<br>organism = synthetic construct | |
| SEQUENCE: 120 aataagagag aaaagaagag taagaagaaa tataagagcc acc | | 43 |
| SEQ ID NO: 121<br>FEATURE<br>source | moltype = DNA length = 49<br>Location/Qualifiers<br>1..49<br>mol_type = other DNA<br>organism = synthetic construct | |
| SEQUENCE: 121 cgaactagta ttcttctggt ccccacagac tcagagagaa cccgccacc | | 49 |
| SEQ ID NO: 122<br>SEQUENCE: 122<br>000 | moltype = length = | |
| SEQ ID NO: 123<br>FEATURE<br>source | moltype = DNA length = 30<br>Location/Qualifiers<br>1..30<br>mol_type = other DNA<br>organism = synthetic construct | |
| SEQUENCE: 123 tataattcta ccctattgag gcattgacta | | 30 |

```
SEQ ID NO: 124         moltype = AA  length = 5
FEATURE                Location/Qualifiers
source                 1..5
                       mol_type = protein
                       organism = synthetic construct
SEQUENCE: 124
GGGGS                                                              5

SEQ ID NO: 125         moltype = AA  length = 15
FEATURE                Location/Qualifiers
source                 1..15
                       mol_type = protein
                       organism = synthetic construct
SEQUENCE: 125
GGGGSGGGGS GGGGS                                                  15
```

LIPID NANOPARTICLE COMPOSITIONS FOR DELIVERING CIRCULAR POLYNUCLEOTIDES

FIELD OF THE INVENTION

The present invention generally relates to novel lipids that can be used in combination with other lipid components, such as helper lipids, structural lipids, and cholesterols, to form lipid nanoparticles for delivery of therapeutic agents, such as nucleic acids (e.g., circular polynucleotides), both in vitro and in vivo.

CROSS REFERENCE TO RELATED APPLICATIONS

This application is a continuation of PCT/US2022/049313, filed Nov. 8, 2022, which claims the benefit of, and priority to, U.S. Provisional Application No. 63/277,055, filed on Nov. 8, 2021, the contents of which are hereby incorporated by reference in their entirety for all purposes.

SEQUENCE LISTING

The instant application contains a Sequence Listing which has been submitted electronically in XML format and is hereby incorporated by reference in its entirety. Said XML copy, created on Feb. 24, 2023, is named OBS-028WO-_SL.xml and is 159,393 bytes in size.

BACKGROUND OF THE INVENTION

In the past few decades, nucleic acid therapeutics has rapidly expanded and has become the basis for treating a wide variety of diseases. Nucleic acid therapies available include, but are not limited to, the use of DNA or viral vectors for insertion of desired genetic information into the host cell, and/or RNA constructed to encode for a therapeutic protein. DNA and viral vector deliveries carry their own setbacks and challenges that make them less favorable to RNA therapeutics. For example, the introduced DNA in some cases may be unintentionally inserted into an intact gene and result in a mutation that impede or even wholly eliminate the function of the endogenous gene leading to an elimination or deleteriously reduced production of an essential enzyme or interruption of a gene critical for the regulating cell growth. Viral vector-based therapies can result in an adverse immune response. Compared to DNA or viral vectors, RNA is substantially safer and more effective gene therapy agent due to its ability to encode for the protein outside of the nucleus to perform its function. With this, the RNA does not involve the risk of being stably integrated into the genome of the transfected cell.

RNA therapeutics conventionally has consisted of engineering linear messenger RNAs (mRNA). Although more effective than DNA or viral vectors, linear mRNAs have their own set of challenges regarding the stability, immunogenicity, translation efficiency, and delivery. Some of these challenges may lead to size restraints and/or destruction of the linear mRNA due to the challenges present with linear mRNAs' caps. To overcome these limitations, circular polynucleotides or circular RNAs may be used. Due to being covalently closed continuous loops, circular RNAs are useful in the design and production of stable forms of RNA. The circularization of an RNA molecule provides an advantage to the study of RNA structure and function, especially in the case of molecules that are prone to folding in an inactive conformation (Wang and Ruffner, 1998). Circular RNA can also be particularly interesting and useful for in vivo applications, especially in the research area of RNA-based control of gene expression and therapeutics, including protein replacement therapy and vaccination.

Further to promote an effective delivery of the RNA polynucleotides, nanoparticles delivery systems can be used. This invention disclosed herein provides a robust therapeutic using engineered polynucleotides and lipid nanoparticle compositions, comprising novel lipids.

SUMMARY

The present application provides ionizable lipids and related transfer vehicles, compositions, and methods. The transfer vehicles can comprise ionizable lipid (e.g., ionizable lipids disclosed herein), PEG-modified lipid, and/or structural lipid, thereby forming lipid nanoparticles encapsulating therapeutic agents (e.g., RNA polynucleotides such as circular RNAs). Pharmaceutical compositions comprising such circular RNAs and transfer vehicles are particularly suitable for efficient protein expression in immune cells in vivo. The present application also provides precursor RNAs and materials useful in producing the precursor or circular RNAs, which have improved circularization efficiency and/or are compatible with effective circular RNA purification methods.

In one aspect, provided herein is an ionizable lipid represented by Formula (13*):

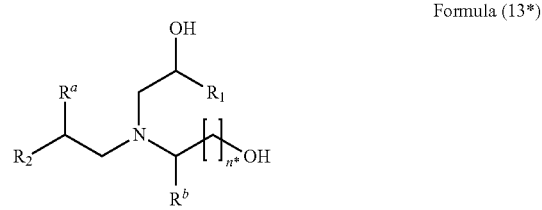

Formula (13*)

or a pharmaceutically acceptable salt thereof, wherein:

$n^*$ is an integer between 1 to 7;

$R^a$ is hydrogen or hydroxyl;

$R^b$ is hydrogen or $C_1$-$C_6$ alkyl;

$R_1$ and $R_2$ are each independently a linear or branched $C_1$-$C_{30}$ alkyl, $C_2$-$C_{30}$ alkenyl, or $C_1$-$C_{30}$ heteroalkyl, optionally substituted by one or more substituents selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, alkylcarbonyloxy, alkylcarbonate, alkenyloxycarbonyl, alkenylcarbonyloxy, alkenylcarbonate, alkynyloxycarbonyl, alkynylcarbonyloxy, alkynylcarbonate, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

with the proviso that the ionizable lipid is not

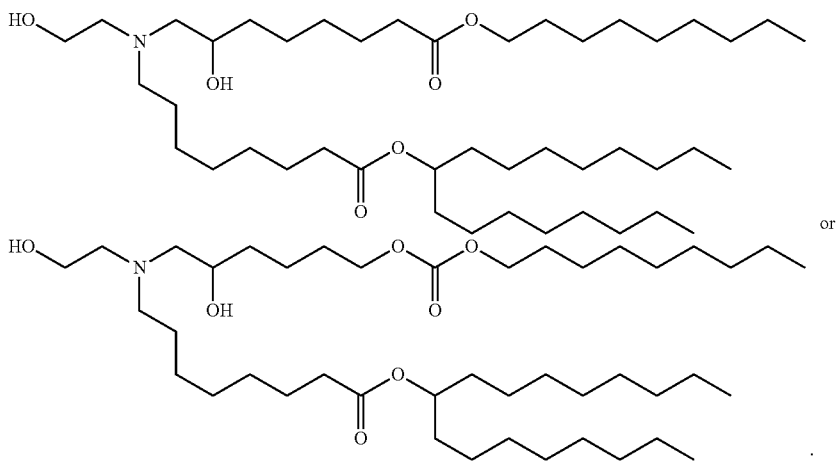

or

In some embodiments, $R^b$ is $C_1$-$C_6$ alkyl.

In some embodiments, $R^b$ is H and the ionizable lipid is represented by Formula (13):

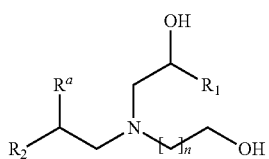

Formula (13)

wherein n is an integer between 1 to 7.

In some embodiments, n is 1, 2, 3, or 4.

In some embodiments, $R_a$ is hydrogen. In some embodiments, the ionizable lipid is represented by Formula (13a-1), Formula (13a-2), or Formula (13a-3):

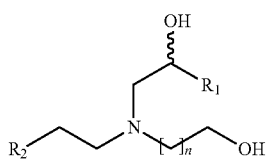

Formula (13a-1)

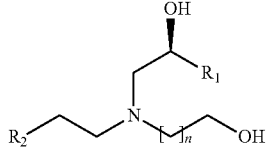

Formula (13a-2)

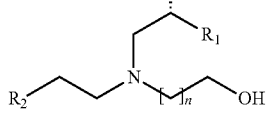

Formula (13a-3)

In some embodiments, $R_a$ is hydroxyl. In some embodiments, the ionizable lipid is represented by Formula (13b-1), Formula (13b-2), or Formula (13b-3):

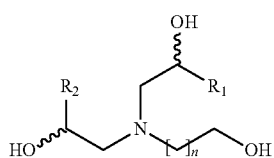

Formula (13b-1)

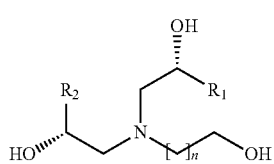

Formula (13b-2)

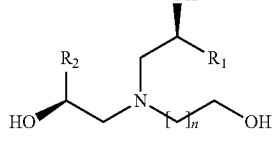

Formula (13b-3)

In some embodiments, the ionizable lipid is represented by Formula (13b-4), Formula (13b-5), Formula (13b-6), Formula (13b-7), Formula (13b-8), or Formula (13b-9):

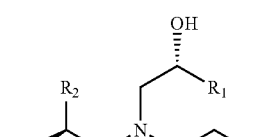

Formula (13b-4)

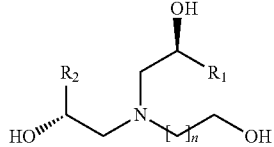

Formula (13b-5)

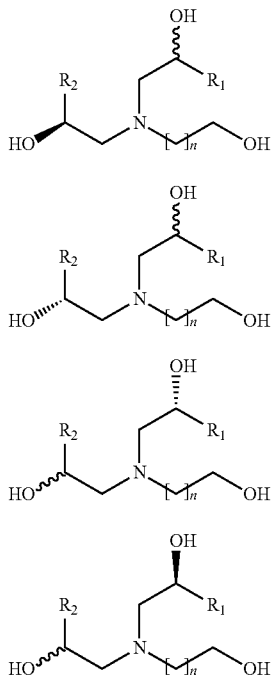

Formula (13b-6)

Formula (13b-7)

Formula (13b-8)

Formula (13b-9)

In some embodiments, $R_1$ and $R_2$ are independently a linear or branched $C_1$-$C_{20}$ alkyl, $C_2$-$C_{20}$ alkenyl, or $C_1$-$C_{20}$ heteroalkyl, optionally substituted by one or more substituents selected from $C_1$-$C_{20}$ alkoxy, $C_1$-$C_{20}$ alkyloxycarbonyl, $C_1$-$C_{20}$ alkylcarbonyloxy, $C_1$-$C_{20}$ alkylcarbonate, $C_2$-$C_{20}$ alkenyloxycarbonyl, $C_2$-$C_{20}$ alkenylcarbonyloxy, $C_2$-$C_{20}$ alkenylcarbonate, $C_2$-$C_{20}$ alkynyloxycarbonyl, $C_2$-$C_{20}$ alkynylcarbonyloxy, and $C_2$-$C_{20}$ alkynylcarbonate.

In some embodiments, at least one of $R_1$ and $R_2$ is an unsubstituted, linear or branched $C_6$-$C_{30}$ alkyl, $C_6$-$C_{30}$ alkenyl, or $C_6$-$C_{30}$ heteroalkyl. In some embodiments, at least one of $R_1$ and $R_2$ is a linear $C_1$-$C_{12}$ alkyl substituted by —OC(O)$R^6$, —C(O)O$R^6$, or —OC(O)O$R^6$, wherein each $R^6$ is independently linear or branched $C_1$-$C_{20}$ alkyl or $C_2$-$C_{20}$ alkenyl. In some embodiments, $R_1$ and $R_2$ are each independently a linear $C_1$-$C_{12}$ alkyl substituted by —OC(O)$R^6$, —C(O)O$R^6$, or —OC(O)O$R^6$, wherein each $R^6$ is independently linear or branched $C_1$-$C_{20}$ alkyl or $C_2$-$C_{20}$ alkenyl.

In some embodiments, the at least one of $R_1$ and $R_2$ is selected from:
—(CH$_2$)$_q$C(O)O(CH$_2$)$_r$CH($R^8$)($R^9$), —(CH$_2$)$_q$OC(O) (CH$_2$)$_r$CH($R^8$)($R^9$), and —(CH$_2$)$_q$OC(O)O(CH$_2$)$_r$CH ($R^8$)($R^9$), wherein:
q is an integer between 0 to 12,
r is an integer between 0 to 6,
$R^8$ is H or $R^{10}$, and
$R^9$ and $R^{10}$ are independently unsubstituted linear $C_1$-$C_{12}$ alkyl or unsubstituted linear $C_2$-$C_{12}$-alkenyl.

In some embodiments, $R_1$ and $R_2$ are each independently selected from:
—(CH$_2$)$_q$C(O)O(CH$_2$)$_r$CH($R^8$)($R^9$), —(CH$_2$)$_q$OC(O) (CH$_2$)$_r$CH($R^8$)($R^9$), and —(CH$_2$)$_q$OC(O)O(CH$_2$)$_r$CH ($R^8$)($R^9$),
wherein:
q is an integer between 0 to 12,
r is an integer between 0 to 6,
$R^8$ is H or $R^{10}$, and
$R^9$ and $R^{10}$ are independently unsubstituted linear $C_1$-$C_{12}$ alkyl or unsubstituted linear $C_2$-$C_{12}$-alkenyl.

In some embodiments, $R_1$ is unsubstituted, linear or branched $C_6$-$C_{30}$ alkyl. In some embodiments, $R_1$ is —(CH$_2$)$_q$C(O)O(CH$_2$)$_r$CH($R^8$)($R^9$). In some embodiments, $R_1$ is —(CH$_2$)$_q$OC(O)(CH$_2$)$_r$CH($R^8$)($R^9$). In some embodiments, $R_1$ is —(CH$_2$)$_q$OC(O)O(CH$_2$)$_r$CH($R^8$)($R^9$). In some embodiments, wherein $R_2$ is unsubstituted, linear or branched $C_6$-$C_{30}$ alkyl. In some embodiments, $R_2$ is —(CH$_2$)$_q$C(O)O(CH$_2$)$_r$CH($R^8$)($R^9$). In some embodiments, $R_2$ is —(CH$_2$)$_q$OC(O)(CH$_2$)$_r$CH($R^8$)($R^9$). In some embodiments, $R_2$ is —(CH$_2$)$_q$OC(O)O(CH$_2$)$_r$CH($R^8$)($R^9$).

In some embodiments, q is an integer between 1 to 6. In some embodiments, q is 3, 4, 5, or 6. In some embodiments, r is 0. In some embodiments, r is an integer between 1 to 6. In some embodiments, r is 1. In some embodiments, r is 2.

In some embodiments, $R^8$ is H. In some embodiments, $R^8$ is $R^{10}$.

In some embodiments, $R^9$ and $R^{10}$ are each independently unsubstituted linear $C_1$-$C_{12}$ alkyl. In some embodiments, $R^9$ and $R^{10}$ are each independently unsubstituted linear $C_4$-$C_8$ alkyl. In some embodiments, $R^9$ and $R^{10}$ are each independently unsubstituted linear $C_6$-$C_8$ alkyl.

In some embodiments, $R_1$ and $R_2$ are each —(CH$_2$)$_m$-L-R', wherein:
m is an integer from 0 to 10;
L is a absent, —C(H)($R^L$)—*, —OC(O)—*, or —C(O) O—*, wherein "-*" indicates the attachment point to R';
R' is selected from the group consisting of: $C_1$-$C_{30}$ alkyl, $C_2$-$C_{30}$ alkenyl, $C_1$-$C_{30}$ alkoxy, 2-30-membered heteroalkylene, and 3-12-membered heterocyclyl, wherein 2-30-membered heteroalkylene is optionally substituted with one or more R", and 3-12-membered heterocyclyl is optionally substituted with one or more $C_1$-$C_{30}$ alkyl;
$R^L$ is selected from the group consisting of: $C_1$-$C_{30}$ alkyl, $C_2$-$C_{30}$ alkenyl, $C_1$-$C_{30}$ alkoxy, 2-30-membered heteroalkylene, wherein 3-12-membered heteroalkylene is optionally substituted one or more with R",
R" is each independently selected from the group consisting of: oxo, $C_1$-$C_{30}$ alkoxy, —C(O)—$C_1$-$C_{30}$ alkyl, —C(O)—$C_1$-$C_{30}$ alkoxy, and —C(O)—$C_1$-$C_{30}$ alkylene-C(O)—$C_1$-$C_{30}$ alkoxy.

In some embodiments, $R_1$ and $R_2$ are each independently selected from the group consisting of:

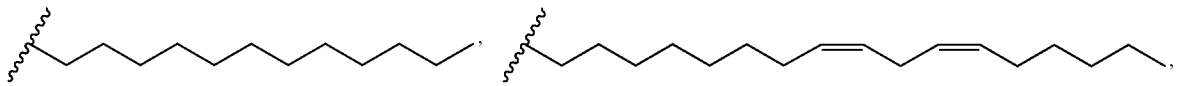

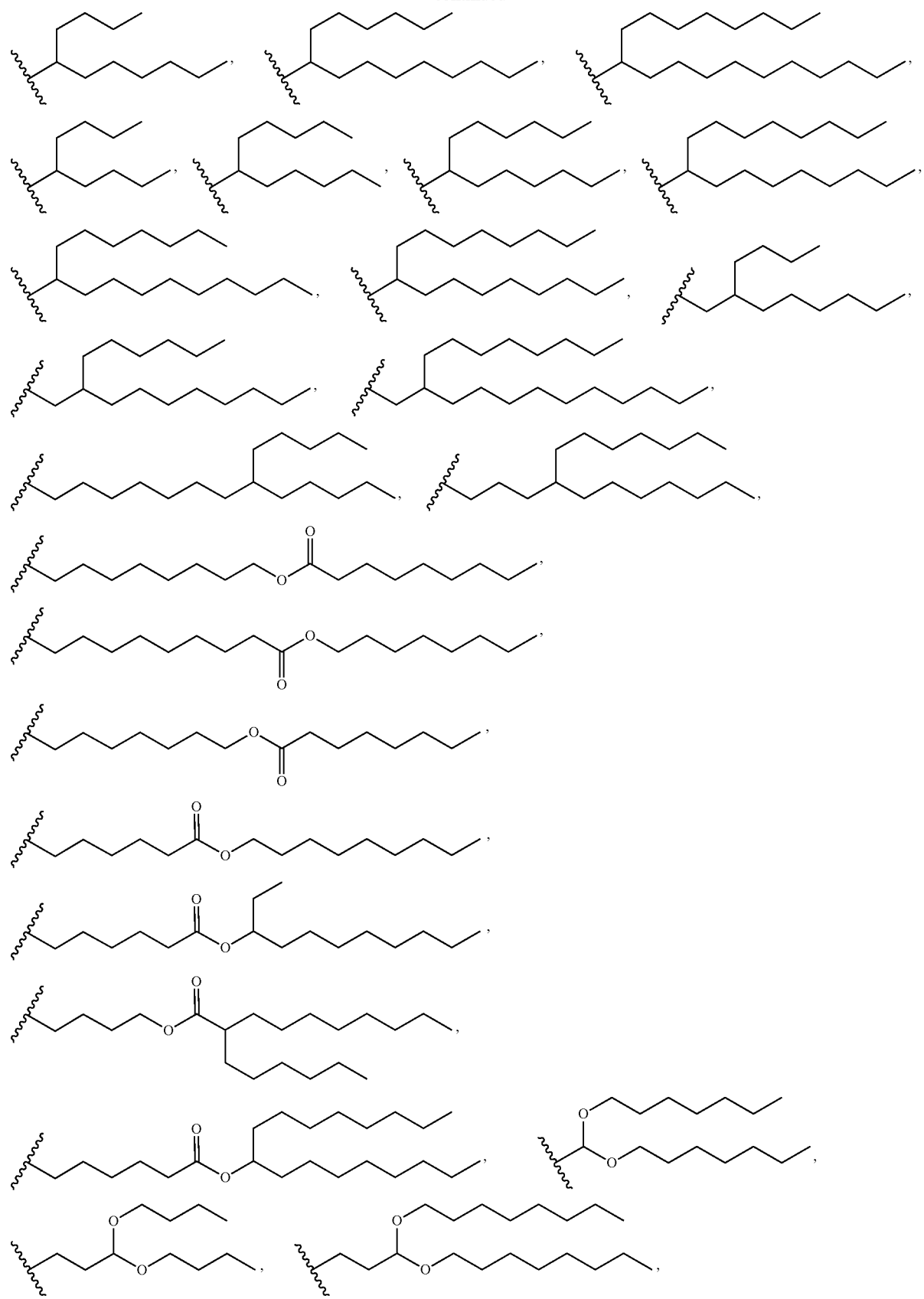

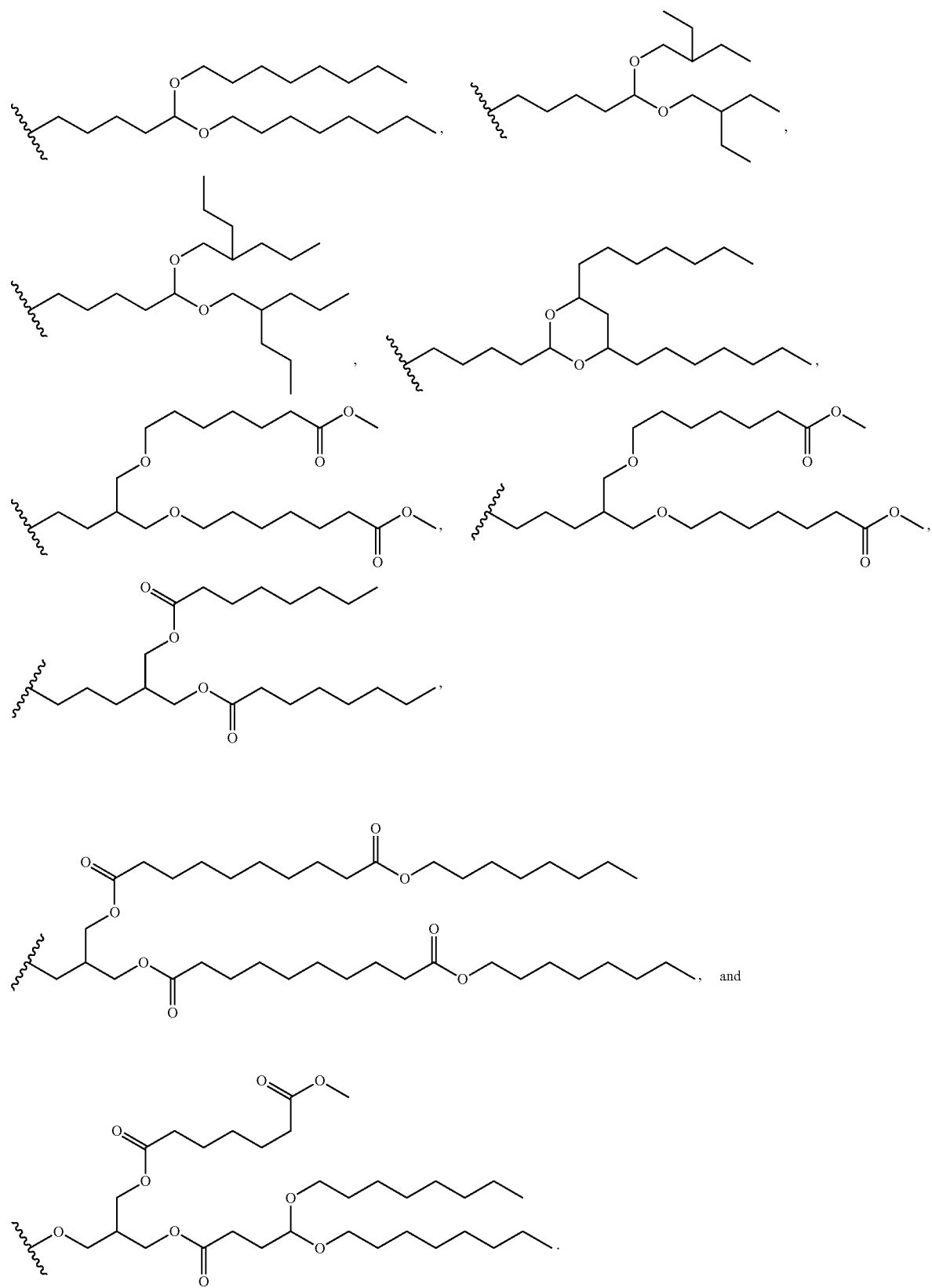

In some embodiments, $R_1$ and $R_2$ are the same. In some embodiments, $R_1$ and $R_2$ are different.
In some embodiments, the ionizable lipid is selected from the group consisting of
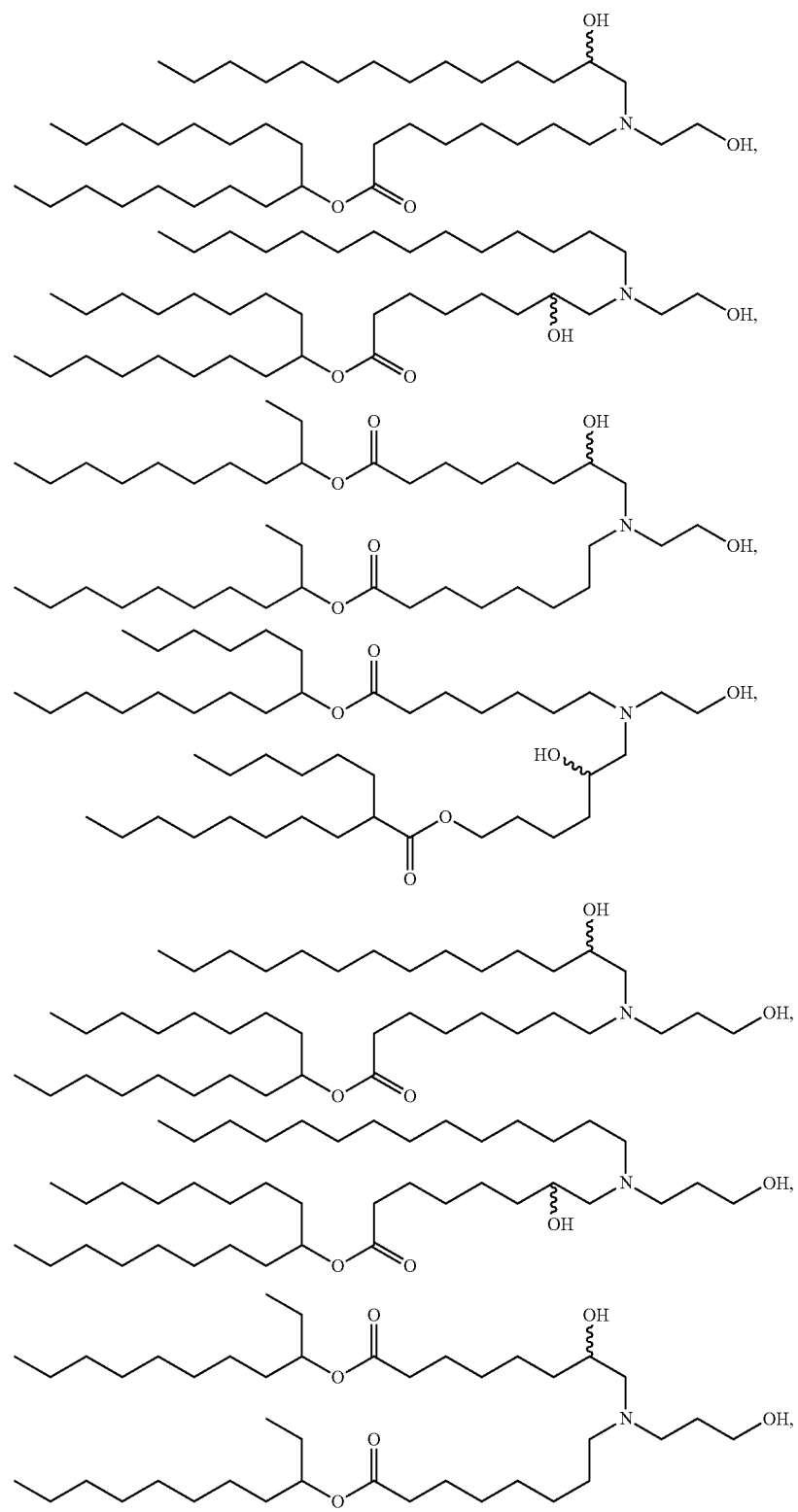

-continued

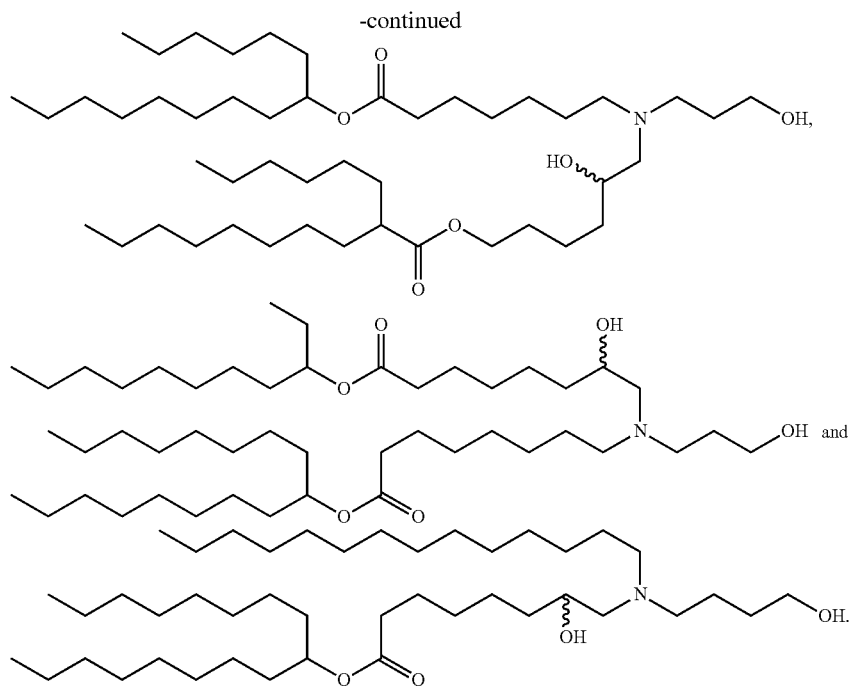

In some embodiments, the ionizable lipid is selected from the group consisting of

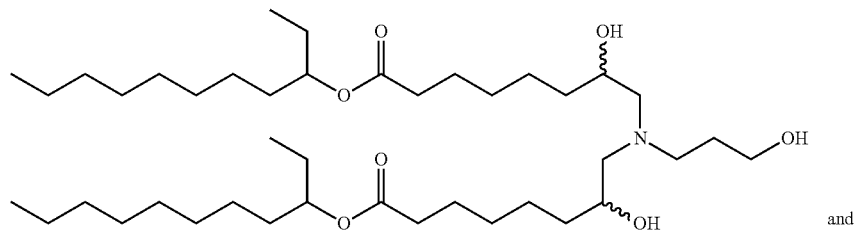

and

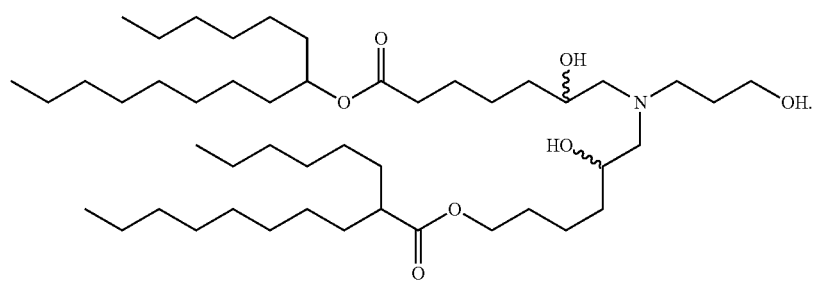

In some embodiments, the ionizable lipid is selected from Table 10e.

In another aspect, the present disclosure provides a pharmaceutical composition comprising a transfer vehicle, wherein the transfer vehicle comprises an ionizable lipid described above.

In some embodiments, the pharmaceutical composition further comprises an RNA polynucleotide. In some embodiments, the RNA polynucleotide is a linear or circular RNA polynucleotide. In some embodiments, the RNA polynucleotide is a circular RNA polynucleotide.

In another aspect, the present disclosure provides a pharmaceutical composition comprising:
a. an RNA polynucleotide, wherein the RNA polynucleotide is a circular RNA polynucleotide, and
b. a transfer vehicle comprising an ionizable lipid selected from

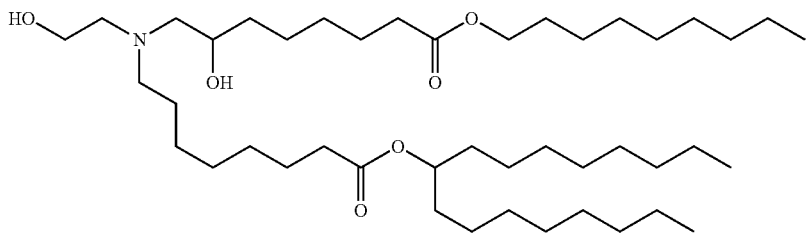

or

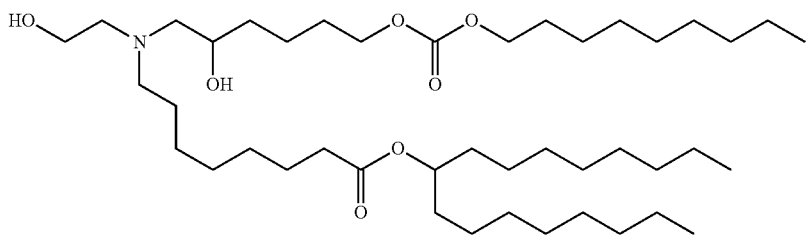

In some embodiments, the transfer vehicle comprises a nanoparticle, such as a lipid nanoparticle, a core-shell nanoparticle, a biodegradable nanoparticle, a biodegradable lipid nanoparticle, a polymer nanoparticle, or a biodegradable polymer nanoparticle.

In some embodiments, the RNA polynucleotide is encapsulated in the transfer vehicle. In some embodiments, the RNA polynucleotide is encapsulated in the transfer vehicle with an encapsulation efficiency of at least 80%.

In some embodiments, the a circular RNA polynucleotide comprises a first expression sequence. In some embodiments, the first expression sequence encodes a therapeutic protein. In some embodiments, the first expression sequence encodes a cytokine or a functional fragment thereof. In other embodiments, the first expression sequence encodes a transcription factor. In other embodiments, the first expression sequence encodes an immune checkpoint inhibitor. In other embodiments, the first expression sequence encodes a chimeric antigen receptor (CAR).

In some embodiments, the circular RNA polynucleotide comprises, in the following order: (a) a 5' enhanced exon element, (b) a core functional element, and (c) a 3' enhanced exon element. In some embodiments, the core functional element comprises a translation initiation element (TIE). In some embodiments, the TIE comprises an untranslated region (UTR) or fragment thereof. In some embodiments, the UTR or fragment thereof comprises a IRES or eukaryotic IRES. In some embodiments, the TIE comprises an aptamer complex, optionally wherein the aptamer complex comprises at least two aptamers.

In some embodiments, the core functional element comprises a coding region. In some embodiments, the coding region encodes for a therapeutic protein. In some embodiments, the therapeutic protein is a chimeric antigen receptor (CAR).

In some embodiments, the core functional element comprises a noncoding region.

In some embodiments, the RNA polynucleotide comprised in a pharmaceutical composition disclosed herein is from about 100 nt to about 10,000 nt in length. In some embodiments, the RNA polynucleotide is from about 100 nt to about 15,000 nt in length.

In some embodiments, the transfer vehicle in a pharmaceutical composition disclosed herein further comprises a structural lipid and a PEG-modified lipid.

In some embodiments, the structural lipid binds to C1q and/or promotes the binding of the transfer vehicle comprising said lipid to C1q compared to a control transfer vehicle lacking the structural lipid and/or increases uptake of C1q-bound transfer vehicle into an immune cell compared to a control transfer vehicle lacking the structural lipid. In some embodiments, wherein the immune cell is a T cell, an NK cell, an NKT cell, a macrophage, or a neutrophil. In some embodiments, the structural lipid is cholesterol. In some embodiments, the structural lipid is beta-sitosterol. In some embodiments, the structural lipid is not beta-sitosterol.

In some embodiments, the PEG-modified lipid is DSPE-PEG, DMG-PEG, PEG-DAG, PEG-S-DAG, PEG-PE, PEG-S-DMG, PEG-cer, PEG-dialkoxypropylcarbamate, PEG-OR, PEG-OH, PEG-c-DOMG, or PEG-1. In some embodiments, the PEG-modified lipid is DSPE-PEG(2000).

In some embodiments, the transfer vehicle further comprises a helper lipid. In some embodiments, the helper lipid is DSPC or DOPE.

In some embodiments, the transfer vehicle comprised in a pharmaceutical composition disclosed herein comprises DSPC, cholesterol, and DMG-PEG(2000).

In some embodiments, the transfer vehicle comprises about 0.5% to about 4% PEG-modified lipids by molar ratio. In some embodiments, the transfer vehicle comprises about 1% to about 2% PEG-modified lipids by molar ratio.

In some embodiments, the transfer vehicle comprises:
a. an ionizable lipid selected from:

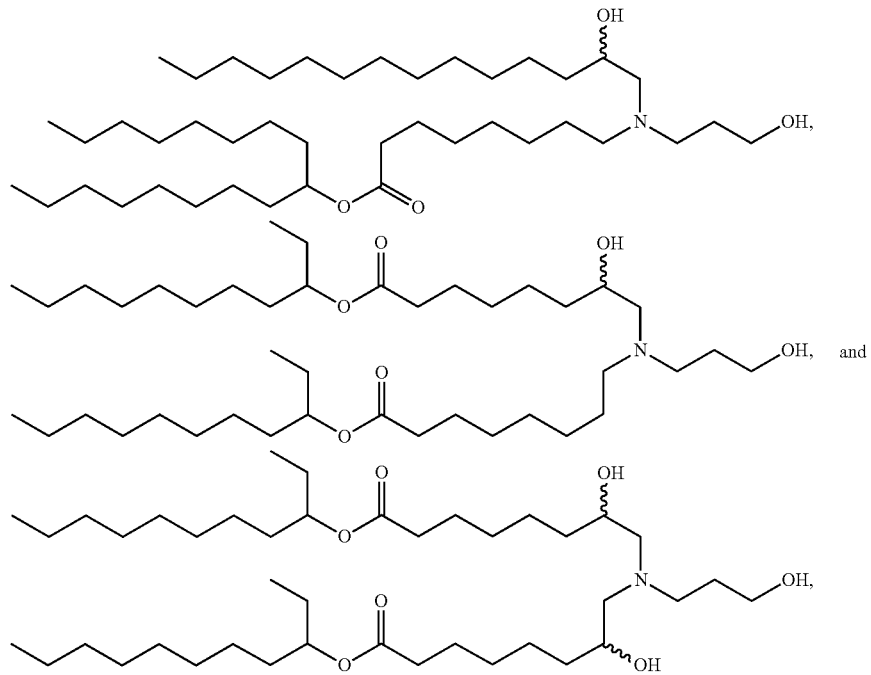

or a mixture thereof,
b. a helper lipid selected from DOPE or DSPC,
c. cholesterol, and
d. a PEG-lipid selected from DSPE-PEG(2000) or DMG-PEG(2000).

In some embodiments, the transfer vehicle comprises ionizable lipid, helper lipid, cholesterol, and PEG-lipid at the molar ratio of ionizable lipid:helper lipid:cholesterol:PEG-lipid is about 45:9:44:2, about 50:10:38.5:1.5, about 41:12:45:2, about 62:4:33:1, or about 53:5:41:1. In some embodiments, the molar ratio of each of the ionizable lipid, helper lipid, cholesterol, and PEG-lipid is within 10%, 9%, 8%, 7% 6%, 5% 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of the stated value.

In some embodiments, the transfer vehicle comprises the helper lipid of DOPE and the PEG-lipid of DMG-PEG (2000), and wherein the molar ratio of ionizable lipid:DOPE:cholesterol:DMG-PEG(2000) is about 45:9:44:2, about 50:10:38.5:1.5, about 41:12:45:2, about 62:4:33:1, or about 53:5:41:1. In some embodiments, the molar ratio of ionizable lipid:DOPE:cholesterol:DSPE-PEG(2000) is about 62:4:33:1. In some embodiments, the molar ratio of ionizable lipid:DOPE:cholesterol:DSPE-PEG(2000) is about 53:5:41:1.

In some embodiments, the transfer vehicle comprises the helper lipid of DSPC and the PEG-lipid of DMG-PEG (2000), and wherein the molar ratio of ionizable lipid:DSPC:cholesterol:DMG-PEG(2000) is about 45:9:44:2, about 50:10:38.5:1.5, about 41:12:45:2, about 62:4:33:1, or about 53:5:41:1. In some embodiments, the molar ratio of ionizable lipid:DSPC:cholesterol:DMG-PEG(2000) is about 50:10:38.5:1.5. In some embodiments, the molar ratio of ionizable lipid:DSPC:cholesterol:DMG-PEG(2000) is about 41:12:45:2. In some embodiments, the molar ratio of ionizable lipid:DSPC:cholesterol:DMG-PEG(2000) is about 45:9:44:2.

In some embodiments, the transfer vehicle comprises the helper lipid of DSPC and the PEG-lipid of DSPE-PEG (2000), and wherein the molar ratio of ionizable lipid:DSPC:cholesterol:DSPE-PEG(2000) is about 45:9:44:2, about 50:10:38.5:1.5, about 41:12:45:2, about 62:4:33:1, or about 53:5:41:1.

In some embodiments, the transfer vehicle comprises the helper lipid of DOPE and the PEG-lipid is C14-PEG(2000), and wherein the molar ratio of ionizable lipid:DOPE:cholesterol:C14-PEG(2000) is about 45:9:44:2, about 50:10:38.5:1.5, about 41:12:45:2, about 62:4:33:1, or about 53:5:41:1.

In some embodiments, the transfer vehicle comprises the helper lipid of DOPE and the PEG-lipid of DMG-PEG (2000), wherein the molar ratio of ionizable lipid:DOPE:cholesterol:DMG-PEG(2000) is about 45:9:44:2, about 50:10:38.5:1.5, about 41:12:45:2, about 62:4:33:1, or about 53:5:41:1.

In some embodiments, a pharmaceutical composition of the present disclosure has a lipid to phosphate (IL:P) molar ratio of about 3 to about 9, such as about 3, about 4, about 4.5, about 5, about 5.5, about 5.7, about 6, about 6.2, about 6.5, or about 7.

In some embodiments, the transfer vehicle is formulated for endosomal release of the RNA polynucleotide. In some embodiments, the transfer vehicle is capable of binding to apolipoprotein E (APOE) or is substantially free of APOE binding sites. In some embodiments, the transfer vehicle is capable of low density lipoprotein receptor (LDLR) dependent uptake or LDLR independent uptake into a cell.

In some embodiments, the transfer vehicle has a diameter of less than about 120 nm and/or does not form aggregates with a diameter of more than 300 nm.

In some embodiments, a pharmaceutical composition of the present disclosure is substantially free of linear RNA.

In some embodiments, further comprising a targeting moiety operably connected to the transfer vehicle. In some embodiments, the targeting moiety specifically or indirectly binds an immune cell antigen, wherein the immune cell antigen is a T cell antigen selected from the group consisting of CD2, CD3, CD5, CD7, CD8, CD4, beta7 integrin, beta2 integrin, and C1qR.

In some embodiments, the targeting moiety is a small molecule. In some embodiments, the small molecule is mannose, a lectin, acivicin, biotin, or digoxigenin. In some embodiments, the small molecule binds to an ectoenzyme on an immune cell, wherein the ectoenzyme is selected from the group consisting of CD38, CD73, adenosine 2a receptor, and adenosine 2b receptor. In some embodiments, the targeting moiety is a single chain Fv (scFv) fragment, nanobody, peptide, peptide-based macrocycle, minibody, small molecule ligand such as folate, arginylglycylaspartic acid (RGD), or phenol-soluble modulin alpha 1 peptide (PSMA1), heavy chain variable region, light chain variable region or fragment thereof.

In some embodiments, a pharmaceutical composition of the present disclosure has less than 1%, by weight, of the polynucleotides in the composition are double stranded RNA, DNA splints, or triphosphorylated RNA. In some embodiments, the pharmaceutical composition has less than 1%, by weight, of the polynucleotides and proteins in the pharmaceutical composition are double stranded RNA, DNA splints, triphosphorylated RNA, phosphatase proteins, protein ligases, or capping enzymes.

In another aspect, provided herein is a method of treating or preventing a disease, disorder, or condition, comprising administering an effective amount of a pharmaceutical composition described above and herein.

In another aspect, provided herein is a method of treating a subject in need thereof comprising administering a therapeutically effective amount of the pharmaceutical composition described above and herein.

BRIEF DESCRIPTION OF THE DRAWINGS

FIG. 32A discloses SEQ ID NO: 123.

FIG. 43A shows anti-CD19 CAR geometric mean florescence intensity, FIG. 43B shows percentage of anti-CD19 CAR expression, and FIG. 43C shows the percentage target cell lysis performed by the anti-CD19 CAR. (CK=Caprine Kobuvirus; AP=Apodemus Picornavirus; CK*=Caprine Kobuvirus with codon optimization; PV=Parabovirus; SV=Salivirus.)

FIGS. 46A, FIG. 46B, and FIG. 46G provide *Gaussia* luciferase expression in multiple donor cells. FIGS. 46C, FIG. 46D, FIG. 46E, and FIG. 46F provides firefly luciferase expression in multiple donor cells.

FIG. 48A shows Nalm6 cell lysing with an anti-CD19 CAR. FIG. 48B shows K562 cell lysing with an anti-CD19 CAR.

FIG. 49A showed the live-dead results. FIGS. 49B, FIG. 49C, FIG. 49D, and FIG. 49E provide the frequency of expression for multiple donors.

FIG. 50A shows the in vitro transcription product of the ~4.5 kb SARS-CoV2 spike-encoding circRNA. FIG. 50B shows a histogram of spike protein surface expression via flow cytometry after transfection of spike-encoding circRNA into 293 cells. Transfected 293 cells were stained 24 hours after transfection with CR3022 primary antibody and APC-labeled secondary antibody. FIG. 50C shows a flow cytometry plot of spike protein surface expression on 293 cells after transfection of spike-encoding circRNA. Transfected 293 cells were stained 24 hours after transfection with CR3022 primary antibody and APC-labeled secondary antibody.

FIG. 51 shows in vivo cytokine response to formulated circRNA generated using the indicated strategy.

FIG. 52A provides a live whole body flux post a 6 hour period and 52B provides whole body IVIS 6 hours following a 1 μg dose of the LNP-circular RNA construct. FIG. 52C provides an ex vivo expression distribution over a 24-hour period.

FIG. 53A provides hEPO titers from a single and mixed set of LNP containing circular RNA constructs, while FIG. 53B provides total flux of bioluminescence expression from single or mixed set of LNP containing circular RNA constructs.

FIG. 54A shows frequency of spike CoV2 expression;

FIG. 54B shows geometric mean fluorescence intensity (gMFI) of the spike CoV2 expression; and FIG. 54C compares gMFI expression of the construct to the frequency of expression.

FIG. 66A shows a linear RNA polynucleotide comprising an accessory element (70) at the spacer regions. FIG. 66B shows a linear RNA polynucleotide comprising an accessory element (70) located between each of the external duplex regions and the exon fragments. FIG. 66C depicts an accessory element (70) within a spacer. FIG. 66D illustrates various iterations of an accessory element (70) located within the core functional element. FIG. 66E illustrates an accessory element (70) located within an internal ribosome entry site (IRES).

FIG. 72A provides the data related to cells received from human donor 1;

FIG. 72B provides the data related to cell received from human donor 2.

In FIG. 73A circular RNA encoding for firefly luciferase and linear mRNA encoding for firefly luciferase was tested for expression. In FIG. 73B, human and mouse cells were given circular RNAs encoding for ATP7B proteins. Some of the circular RNAs tested were codon optimized. Circular RNA expressing firefly luciferase was used for comparison.

In FIG. 78, B cell aplasia was observed in blood cells. The dotted line on the figure indicates Wasabi control B cell aplasia. % B cells were normalized to the Wasabi control.

DETAILED DESCRIPTION

Figure 1A:
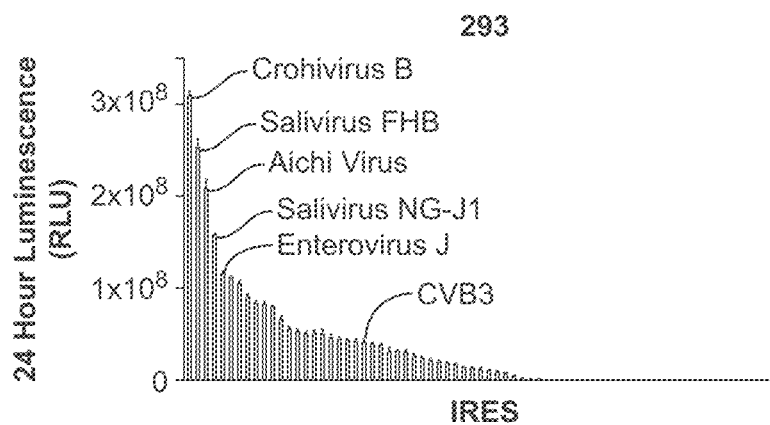
FIGS. 1A-1E depict luminescence in supernatants of HEK293, (FIGS. 1A, 1D, and 1E), HepG2 (FIG. 1B), or 1C1C7 (FIG. 1C) cells 24 hours after transfection with circular RNA comprising a *Gaussia* luciferase expression sequence and various IRES sequences.

The present invention provides, among other things, ionizable lipids and related transfer vehicles, compositions, and methods. In some embodiments, the transfer vehicles comprise ionizable lipid (e.g., ionizable lipids disclosed herein), PEG-modified lipid, and/or structural lipid, thereby forming lipid nanoparticles suitable for delivering nucleic acids. In certain embodiments, the nucleic acid may be RNA, such as siRNA, mRNA or circular RNA. The nucleic acids may encode therapeutic agents. In some embodiments, the nucleic acids are encapsulated in the transfer vehicles.

Also disclosed herein is RNA therapy, along with associated compositions and methods. In some embodiments, the RNA therapy allows for increased RNA stability, expression, and prolonged half-life, among other things.

Also disclosed herein is a DNA template (e.g., a vector) for making circular RNA. In some embodiments, the DNA template comprises a 3' enhanced intron fragment, a 3' enhanced exon fragment, a core functional element, a 5' enhanced exon fragment, and a 5' enhanced intron fragment. In some embodiments, these elements are positioned in the DNA template in the above order.

Additional embodiments include circular RNA polynucleotides, including circular RNA polynucleotides (e.g., a circular RNA comprising 3' enhanced exon element, a core functional element, and a 5' enhanced exon element) made using the DNA template provided herein, compositions comprising such circular RNA, cells comprising such circular RNA, methods of using and making such DNA template, circular RNA, compositions and cells.

In some embodiments, provided herein are methods comprising administration of circular RNA polynucleotides provided herein into cells for therapy or production of useful proteins. In some embodiments, the method is advantageous in providing the production of a desired polypeptide inside eukaryotic cells with a longer half-life than linear RNA, due to the resistance of the circular RNA to ribonucleases.

Circular RNA polynucleotides lack the free ends necessary for exonuclease-mediated degradation, causing them to be resistant to several mechanisms of RNA degradation and granting extended half-lives when compared to an equivalent linear RNA. Circularization may allow for the stabilization of RNA polynucleotides that generally suffer from short half-lives and may improve the overall efficacy of exogenous mRNA in a variety of applications. In an embodiment, the functional half-life of the circular RNA polynucleotides provided herein in eukaryotic cells (e.g., mammalian cells, such as human cells) as assessed by protein synthesis is at least 20 hours (e.g., at least 80 hours).

Various aspects of the invention are described in detail in the following sections. The use of sections is not meant to limit the invention. Each section can apply to any aspect of the invention. In this application, the use of "or" means "and/or" unless stated otherwise.

1. Definitions

As used herein, the terms "circRNA" or "circular polyribonucleotide" or "circular RNA" or "oRNA" are used interchangeably and refers to a polyribonucleotide that forms a circular structure through covalent bonds.

As used herein, the term "DNA template" refers to a DNA sequence capable of transcribing a linear RNA polynucleotide. For example, but not intending to be limiting, a DNA template may include a DNA vector, PCR product or plasmid.

As used herein, the term "3' group I intron fragment" refers to a sequence with 75% or higher similarity to the 3'-proximal end of a natural group I intron including the splice site dinucleotide.

As used herein, the term "5' group I intron fragment" refers to a sequence with 75% or higher similarity to the 5'-proximal end of a natural group I intron including the splice site dinucleotide.

As used herein, the term "permutation site" refers to the site in a group I intron where a cut is made prior to permutation of the intron. This cut generates 3' and 5' group I intron fragments that are permuted to be on either side of a stretch of precursor RNA to be circularized.

As used herein, the term "splice site" refers to a dinucleotide that is partially or fully included in a group I intron and between which a phosphodiester bond is cleaved during RNA circularization. (As used herein, "splice site" refers to the dinucleotide or dinucleotides between which cleavage of the phosphodiester bond occurs during a splicing reaction. A "5' splice site" refers to the natural 5' dinucleotide of the intron e.g., group I intron, while a "3' splice site" refers to the natural 3' dinucleotide of the intron).

As used herein, the term "expression sequence" refers to a nucleic acid sequence that encodes a product, e.g., a peptide or polypeptide, regulatory nucleic acid, or non-coding nucleic acid. An exemplary expression sequence that codes for a peptide or polypeptide can comprise a plurality of nucleotide triads, each of which can code for an amino acid and is termed as a "codon."

As used herein, "coding element" or "coding region" is region located within the expression sequence and encodings for one or more proteins or polypeptides (e.g., therapeutic protein).

As used herein, a "noncoding element" or "non-coding nucleic acid" is a region located within the expression sequence. This sequence, but itself does not encode for a protein or polypeptide, but may have other regulatory functions, including but not limited, allow the overall polynucleotide to act as a biomarker or adjuvant to a specific cell.

As used herein, the term "therapeutic protein" refers to any protein that, when administered to a subject directly or indirectly in the form of a translated nucleic acid, has a therapeutic, diagnostic, and/or prophylactic effect and/or elicits a desired biological and/or pharmacological effect.

As used herein, the term "immunogenic" refers to a potential to induce an immune response to a substance. An immune response may be induced when an immune system of an organism or a certain type of immune cells is exposed to an immunogenic substance. The term "non-immunogenic" refers to a lack of or absence of an immune response above a detectable threshold to a substance. No immune response is detected when an immune system of an organism or a certain type of immune cells is exposed to a non-immunogenic substance. In some embodiments, a non-immunogenic circular polyribonucleotide as provided herein, does not induce an immune response above a predetermined threshold when measured by an immunogenicity assay. In some embodiments, no innate immune response is detected when an immune system of an organism or a certain type of immune cells is exposed to a non-immunogenic circular polyribonucleotide as provided herein. In some embodiments, no adaptive immune response is detected when an immune system of an organism or a certain type of immune cell is exposed to a non-immunogenic circular polyribonucleotide as provided herein.

As used herein, the term "circularization efficiency" refers to a measurement of resultant circular polyribonucleotide as compared to its linear starting material.

As used herein, the term "translation efficiency" refers to a rate or amount of protein or peptide production from a ribonucleotide transcript. In some embodiments, translation efficiency can be expressed as amount of protein or peptide produced per given amount of transcript that codes for the protein or peptide.

The term "nucleotide" refers to a ribonucleotide, a deoxyribonucleotide, a modified form thereof, or an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5'-position pyrimidine modifications, 8'-position purine modifications, modifications at cytosine exocyclic amines, and substitution of 5-bromo-uracil; and 2'-position sugar modifications, including but not limited to, sugar-modified ribonucleotides in which the 2'—OH is replaced by a group such as an H, OR, R, halo, SH, SR, NH2, NHR, NR2, or CN, wherein R is an alkyl moiety as defined herein. Nucleotide analogs are also meant to include nucleotides with bases such as inosine, queuosine, xanthine; sugars such as 2'-methyl ribose; non-natural phosphodiester linkages such as methylphosphonate, phosphorothioate and peptide linkages. Nucleotide analogs include 5-methoxyuridine, 1-methylpseudouridine, and 6-methyladenosine.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, or up to about 10,000 or more bases, composed of nucleotides, e.g., deoxyribonucleotides or ribonucleotides, and may be produced enzymatically or synthetically (e.g., as described in U.S. Pat. No. 5,948,902 and the references cited therein), which can hybridize with naturally occurring nucleic acids in a sequence specific manner analogous to that of two naturally occurring nucleic acids, e.g., can participate in Watson-Crick base pairing interactions. Naturally occurring nucleic acids are comprised of nucleotides including guanine, cytosine, adenine, thymine, and uracil (G, C, A, T, and U respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

"Isolated" or "purified" generally refers to isolation of a substance (for example, in some embodiments, a compound, a polynucleotide, a protein, a polypeptide, a polynucleotide composition, or a polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90%-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is more than as it is found naturally.

The terms "duplexed," "double-stranded," or "hybridized" as used herein refer to nucleic acids formed by hybridization of two single strands of nucleic acids containing complementary sequences. In most cases, genomic DNA is double-stranded. Sequences can be fully complementary or partially complementary.

As used herein, "unstructured" with regard to RNA refers to an RNA sequence that is not predicted by the RNAFold software or similar predictive tools to form a structure (e.g., a hairpin loop) with itself or other sequences in the same RNA molecule. In some embodiments, unstructured RNA can be functionally characterized using nuclease protection assays.

As used herein, "structured" with regard to RNA refers to an RNA sequence that is predicted by the RNAFold software or similar predictive tools to form a structure (e.g., a hairpin loop) with itself or other sequences in the same RNA molecule.

As used herein, two "duplex sequences," "duplex region," "duplex regions," "homology arms," or "homology regions" may be any two regions that are thermodynamically favored to cross-pair in a sequence specific interaction. In some embodiments, two duplex sequences, duplex regions, homology arms, or homology regions, share a sufficient level of sequence identity to one another's reverse complement to act as substrates for a hybridization reaction. As used herein polynucleotide sequences have "homology" when they are either identical or share sequence identity to a reverse complement or "complementary" sequence. The percent sequence identity between a homology region and a counterpart homology region's reverse complement can be any percent of sequence identity that allows for hybridization to occur. In some embodiments, an internal duplex region of an inventive polynucleotide is capable of forming a duplex with another internal duplex region and does not form a duplex with an external duplex region.

As used herein, an "affinity sequence" or "affinity tag" is a region of polynucleotide sequences polynucleotide sequence ranging from 1 nucleotide to hundreds or thousands of nucleotides containing a repeated set of nucleotides for the purposes of aiding purification of a polynucleotide sequence. For example, an affinity sequence may comprise, but is not limited to, a polyA or polyAC sequence.

As used herein, a "spacer" refers to a region of a polynucleotide sequence ranging from 1 nucleotide to hundreds or thousands of nucleotides separating two other elements along a polynucleotide sequence. The sequences can be defined or can be random. A spacer is typically non-coding. In some embodiments, spacers include duplex regions.

Linear nucleic acid molecules are said to have a "5'-terminus" (5' end) and a "3'-terminus" (3' end) because nucleic acid phosphodiester linkages occur at the 5' carbon and 3' carbon of the sugar moieties of the substituent mononucleotides. The end nucleotide of a polynucleotide at which a new linkage would be to a 5' carbon is its 5' terminal nucleotide. The end nucleotide of a polynucleotide at which a new linkage would be to a 3' carbon is its 3' terminal nucleotide. A terminal nucleotide, as used herein, is the nucleotide at the end position of the 3'- or 5'-terminus.

As used herein, a "leading untranslated sequence" is a region of polynucleotide sequences ranging from 1 nucleotide to hundreds of nucleotides located at the upmost 5' end of a polynucleotide sequence. The sequences can be defined or can be random. An leading untranslated sequence is non-coding.

As used herein, a "leading untranslated sequence" is a region of polynucleotide sequences ranging from 1 nucleotide to hundreds of nucleotides located at the downmost 3' end of a polynucleotide sequence. The sequences can be defined or can be random. An leading untranslated sequence is non-coding.

"Transcription" means the formation or synthesis of an RNA molecule by an RNA polymerase using a DNA molecule as a template. The invention is not limited with respect to the RNA polymerase that is used for transcription. For example, in some embodiments, a T7-type RNA polymerase can be used.

"Translation" means the formation of a polypeptide molecule by a ribosome based upon an RNA template.

It is to be understood that the terminology used herein is for the purpose of describing particular embodiments only, and is not intended to be limiting. As used in this specification and the appended claims, the singular forms "a," "an," and "the" include plural referents unless the content clearly dictates otherwise. Thus, for example, reference to "a cell" includes combinations of two or more cells, or entire cultures of cells; reference to "a polynucleotide" includes, as a practical matter, many copies of that polynucleotide. Unless specifically stated or obvious from context, as used herein, the term "or" is understood to be inclusive. Unless defined herein and below in the reminder of the specification, all technical and scientific terms used herein have the same meaning as commonly understood by one of ordinary skill in the art to which the invention pertains.

Unless specifically stated or obvious from context, as used herein, the term "about," is understood as within a range of normal tolerance in the art, for example within 2 standard deviations of the mean. "About" can be understood as within 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of the stated value. Unless otherwise clear from the context, all numerical values provided herein are modified by the term "about."

As used herein, the term "encode" refers broadly to any process whereby the information in a polymeric macromolecule is used to direct the production of a second molecule that is different from the first. The second molecule may have a chemical structure that is different from the chemical nature of the first molecule.

By "co-administering" is meant administering a therapeutic agent provided herein in conjunction with one or more additional therapeutic agents sufficiently close in time such that the therapeutic agent provided herein can enhance the effect of the one or more additional therapeutic agents, or vice versa.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. The treatment or prevention provided by the method disclosed herein can include treatment or prevention of one or more conditions or symptoms of the disease. Also, for purposes herein, "prevention" can encompass delaying the onset of the disease, or a symptom or condition thereof.

As used herein, an "internal ribosome entry site" or "IRES" refers to an RNA sequence or structural element ranging in size from 10 nt to 1000 nt or more, capable of initiating translation of a polypeptide in the absence of a typical RNA cap structure. An IRES is typically about 500 nt to about 700 nt in length.

As used herein, "aptamer" refers in general to either an oligonucleotide of a single defined sequence or a mixture of said nucleotides, wherein the mixture retains the properties of binding specifically to the target molecule (e.g., eukaryotic initiation factor, 40S ribosome, polyC binding protein, polyA binding protein, polypyrimidine tract-binding protein, argonaute protein family, Heterogeneous nuclear ribonucleoprotein K and La and related RNA-binding protein). Thus, as used herein "aptamer" denotes both singular and plural sequences of nucleotides, as defined hereinabove. The term "aptamer" is meant to refer to a single- or double-stranded nucleic acid which is capable of binding to a protein or other molecule. In general, aptamers preferably comprise about 10 to about 100 nucleotides, preferably about 15 to about 40 nucleotides, more preferably about 20 to about 40 nucleotides, in that oligonucleotides of a length that falls within these ranges are readily prepared by conventional techniques. Optionally, aptamers can further comprise a minimum of approximately 6 nucleotides, preferably 10, and more preferably 14 or 15 nucleotides, that are necessary to effect specific binding.

An "eukaryotic initiation factor" or "eIF" refers to a protein or protein complex used in assembling an initiator tRNA, 40S and 60S ribosomal subunits required for initiating eukaryotic translation.

As used herein, an "internal ribosome entry site" or "IRES" refers to an RNA sequence or structural element ranging in size from 10 nt to 1000 nt or more, capable of initiating translation of a polypeptide in the absence of a typical RNA cap structure. An IRES is typically about 500 nt to about 700 nt in length.

As used herein, a "miRNA site" refers to a stretch of nucleotides within a polynucleotide that is capable of forming a duplex with at least 8 nucleotides of a natural miRNA sequence.

As used herein, an "endonuclease site" refers to a stretch of nucleotides within a polynucleotide that is capable of being recognized and cleaved by an endonuclease protein.

As used herein, "bicistronic RNA" refers to a polynucleotide that includes two expression sequences coding for two distinct proteins. These expression sequences can be separated by a nucleotide sequence encoding a cleavable peptide such as a protease cleavage site. They can also be separated by a ribosomal skipping element.

As used herein, the term "ribosomal skipping element" refers to a nucleotide sequence encoding a short peptide sequence capable of causing generation of two peptide chains from translation of one RNA molecule. While not wishing to be bound by theory, it is hypothesized that ribosomal skipping elements function by (1) terminating translation of the first peptide chain and re-initiating translation of the second peptide chain; or (2) cleavage of a peptide bond in the peptide sequence encoded by the ribosomai skipping element by an intrinsic protease activity of the encoded peptide, or by another protease in the environment (e.g., cytosol).

As used herein, the term "co-formulate" refers to a nanoparticle formulation comprising two or more nucleic acids or a nucleic acid and other active drug substance. Typically, the ratios are equimolar or defined in the ratiometric amount of the two or more nucleic acids or the nucleic acid and other active drug substance.

As used herein, "transfer vehicle" includes any of the standard pharmaceutical carriers, diluents, excipients, and the like, which are generally intended for use in connection with the administration of biologically active agents, including nucleic acids.

As used herein, the phrase "lipid nanoparticle" refers to a transfer vehicle comprising one or more lipids (e.g., in some embodiments, cationic lipids, non-cationic lipids, and PEG-modified lipids).

As used herein, the phrase "ionizable lipid" refers to any of a number of lipid species that carry a net positive charge at a selected pH, such as physiological pH 4 and a neutral charge at other pHs such as physiological pH 7.

In some embodiments, a lipid, e.g., an ionizable lipid, disclosed herein comprises one or more cleavable groups. The terms "cleave" and "cleavable" are used herein to mean that one or more chemical bonds (e.g., one or more of covalent bonds, hydrogen-bonds, van der Waals' forces and/or ionic interactions) between atoms in or adjacent to the subject functional group are broken (e.g., hydrolyzed) or are capable of being broken upon exposure to selected conditions (e.g., upon exposure to enzymatic conditions). In certain embodiments, the cleavable group is a disulfide functional group, and in particular embodiments is a disulfide group that is capable of being cleaved upon exposure to selected biological conditions (e.g., intracellular conditions). In certain embodiments, the cleavable group is an ester functional group that is capable of being cleaved upon exposure to selected biological conditions. For example, the disulfide groups may be cleaved enzymatically or by a hydrolysis, oxidation or reduction reaction. Upon cleavage of such disulfide functional group, the one or more functional moieties or groups (e.g., one or more of a head-group and/or a tail-group) that are bound thereto may be liberated. Exemplary cleavable groups may include, but are not limited to, disulfide groups, ester groups, ether groups, and any derivatives thereof (e.g., alkyl and aryl esters). In certain embodiments, the cleavable group is not an ester group or an ether group. In some embodiments, a cleavable group is bound (e.g., bound by one or more of hydrogen-bonds, van der Waals' forces, ionic interactions and covalent bonds) to one or more functional moieties or groups (e.g., at least one head-group and at least one tail-group). In certain embodiments, at least one of the functional moieties or groups is hydrophilic (e.g., a hydrophilic head-group comprising one or more of imidazole, guanidinium, amino, imine, enamine, optionally-substituted alkyl amino and pyridyl).

As used herein, the term "hydrophilic" is used to indicate in qualitative terms that a functional group is water-preferring, and typically such groups are water-soluble. For example, disclosed herein are compounds that comprise a cleavable disulfide (S—S) functional group bound to one or more hydrophilic groups (e.g., a hydrophilic head-group), wherein such hydrophilic groups comprise or are selected from the group consisting of imidazole, guanidinium, amino, imine, enamine, an optionally-substituted alkyl amino (e.g., an alkyl amino such as dimethylamino) and pyridyl.

In certain embodiments, at least one of the functional groups of moieties that comprise the compounds disclosed herein is hydrophobic in nature (e.g., a hydrophobic tail-group comprising a naturally occurring lipid such as cholesterol). As used herein, the term "hydrophobic" is used to indicate in qualitative terms that a functional group is water-avoiding, and typically such groups are not water soluble. For example, disclosed herein are compounds that comprise a cleavable functional group (e.g., a disulfide (S—S) group) bound to one or more hydrophobic groups, wherein such hydrophobic groups comprise one or more naturally occurring lipids such as cholesterol, and/or an optionally substituted, variably saturated or unsaturated C6-C20 alkyl and/or an optionally substituted, variably saturated or unsaturated C6-C20 acyl.

Compound described herein may also comprise one or more isotopic substitutions. For example, H may be in any isotopic form, including 1H, 2H (D or deuterium), and 3H (T or tritium); C may be in any isotopic form, including 12C, 13C, and 14C; O may be in any isotopic form, including 16O and 18O; F may be in any isotopic form, including 18F and 19F; and the like.

When describing the invention, which may include compounds and pharmaceutically acceptable salts thereof, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

When a range of values is listed, it is intended to encompass each value and sub-range within the range. For example, "C1-6 alkyl" is intended to encompass, C1, C2, C3, C4, C5, C6, C1-6, C1-5, C1-4, C1-3, C1-2, C2-6, C2-5, C2-4, C2-3, C3-6, C3-5, C3-4, C4-6, C4-5, and C5-6 alkyl.

In certain embodiments, the compounds disclosed herein comprise, for example, at least one hydrophilic head-group and at least one hydrophobic tail-group, each bound to at least one cleavable group, thereby rendering such compounds amphiphilic. As used herein to describe a compound or composition, the term "amphiphilic" means the ability to dissolve in both polar (e.g., water) and non-polar (e.g., lipid) environments. For example, in certain embodiments, the compounds disclosed herein comprise at least one lipophilic tail-group (e.g., cholesterol or a C6-C20 alkyl) and at least one hydrophilic head-group (e.g., imidazole), each bound to a cleavable group (e.g., disulfide).

It should be noted that the terms "head-group" and "tail-group" as used describe the compounds of the present invention, and in particular functional groups that comprise such compounds, are used for ease of reference to describe the orientation of one or more functional groups relative to other functional groups. For example, in certain embodiments a hydrophilic head-group (e.g., guanidinium) is bound (e.g., by one or more of hydrogen-bonds, van der Waals' forces, ionic interactions and covalent bonds) to a cleavable functional group (e.g., a disulfide group), which in turn is bound to a hydrophobic tail-group (e.g., cholesterol).

As used herein, the term "alkyl" refers to both straight and branched chain C1-C40 hydrocarbons (e.g., C6-C20 hydrocarbons), and include both saturated and unsaturated hydrocarbons. In certain embodiments, the alkyl may comprise one or more cyclic alkyls and/or one or more heteroatoms such as oxygen, nitrogen, or sulfur and may optionally be substituted with substituents (e.g., one or more of alkyl, halo, alkoxyl, hydroxy, amino, aryl, ether, ester or amide). In certain embodiments, a contemplated alkyl includes (9Z, 12Z)-octadeca-9, 12-dien. The use of designations such as, for example, "C6-C20" is intended to refer to an alkyl (e.g., straight or branched chain and inclusive of alkenes and alkyls) having the recited range carbon atoms. In some embodiments, an alkyl group has 1 to 10 carbon atoms ("C1-10 alkyl"). In some embodiments, an alkyl group has 1 to 9 carbon atoms ("C1-9 alkyl"). In some embodiments, an alkyl group has 1 to 8 carbon atoms ("C1-8 alkyl"). In some embodiments, an alkyl group has 1 to 7 carbon atoms ("C1-7 alkyl"). In some embodiments, an alkyl group has 1 to 6 carbon atoms ("C1-6 alkyl"). In some embodiments, an alkyl group has 1 to 5 carbon atoms ("C1-5 alkyl"). In some embodiments, an alkyl group has 1 to 4 carbon atoms ("C1-4 alkyl"). In some embodiments, an alkyl group has 1 to 3 carbon atoms ("C1-3 alkyl"). In some embodiments, an alkyl group has 1 to 2 carbon atoms ("C1-2 alkyl"). In some embodiments, an alkyl group has 1 carbon atom ("C1 alkyl"). Examples of C1-6 alkyl groups include methyl, ethyl, propyl, isopropyl, butyl, isobutyl, pentyl, hexyl, and the like.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("C2-20 alkenyl"). In certain embodiments, alkenyl does not contain any triple bonds. In some embodiments, an alkenyl group has 2 to 10 carbon atoms ("C2-10 alkenyl"). In some embodiments, an alkenyl group has 2 to 9 carbon atoms ("C2-9 alkenyl"). In some embodiments, an alkenyl group has 2 to 8 carbon atoms ("C2-8 alkenyl"). In some embodiments, an alkenyl group has 2 to 7 carbon atoms ("C2-7 alkenyl"). In some embodiments, an alkenyl group has 2 to 6 carbon atoms ("C2-6 alkenyl"). In some embodiments, an alkenyl group has 2 to 5 carbon atoms ("C2-5 alkenyl"). In some embodiments, an alkenyl group has 2 to 4 carbon atoms ("C2-4 alkenyl"). In some embodiments, an alkenyl group has 2 to 3 carbon atoms ("C2-3 alkenyl"). In some embodiments, an alkenyl group has 2 carbon atoms ("C2 alkenyl"). The one or more carbon-carbon double bonds can be internal (such as in 2-butenyl) or terminal (such as in 1-butenyl). Examples of C2-4 alkenyl groups include ethenyl (C2), 1-propenyl (C3), 2-propenyl (C3), 1-butenyl (C4), 2-butenyl (C4), butadienyl (C4), and the like. Examples of C2-6 alkenyl groups include the aforementioned C2-4 alkenyl groups as well as pentenyl (C5), pentadienyl (C5), hexenyl (C6), and the like. Additional examples of alkenyl include heptenyl (C7), octenyl (C8), octatrienyl (C8), and the like.

As used herein, "alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("C2-20 alkynyl"). In certain embodiments, alkynyl does not contain any double bonds. In some embodiments, an alkynyl group has 2 to 10 carbon atoms ("C2-10 alkynyl"). In some embodiments, an alkynyl group has 2 to 9 carbon atoms ("C2-9 alkynyl"). In some embodiments, an alkynyl group has 2 to 8 carbon atoms ("C2-8 alkynyl"). In some embodiments, an alkynyl group has 2 to 7 carbon atoms ("C2-7 alkynyl"). In some embodiments, an alkynyl group has 2 to 6 carbon atoms ("C2-6 alkynyl"). In some embodiments, an alkynyl group has 2 to 5 carbon atoms ("C2-5 alkynyl"). In some embodiments, an alkynyl group has 2 to 4 carbon atoms ("C2-4 alkynyl"). In some embodiments, an alkynyl group has 2 to 3 carbon atoms ("C2-3 alkynyl"). In some embodiments, an alkynyl group has 2 carbon atoms ("C2 alkynyl"). The one or more carbon-carbon triple bonds can be internal (such as in 2-butynyl) or terminal (such as in 1-butynyl). Examples of C2-4 alkynyl groups include, without limitation, ethynyl (C2), 1-propynyl (C3), 2-propynyl (C3), 1-butynyl (C4), 2-butynyl (C4), and the like. Examples of C2-6 alkenyl groups include the aforementioned C2-4 alkynyl groups as well as pentynyl (C5), hexynyl (C6), and the like. Additional examples of alkynyl include heptynyl (C7), octynyl (C8), and the like.

As used herein, "alkylene," "alkenylene," and "alkynylene," refer to a divalent radical of an alkyl, alkenyl, and alkynyl group respectively. When a range or number of carbons is provided for a particular "alkylene," "alkenylene," or "alkynylene," group, it is understood that the range or number refers to the range or number of carbons in the linear carbon divalent chain. "Alkylene," "alkenylene," and "alkynylene," groups may be substituted or unsubstituted with one or more substituents as described herein.

As used herein, the term "aryl" refers to aromatic groups (e.g., monocyclic, bicyclic and tricyclic structures) containing six to ten carbons in the ring portion. The aryl groups may be optionally substituted through available carbon atoms and in certain embodiments may include one or more heteroatoms such as oxygen, nitrogen or sulfur. In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl).

The term "heteroalkyl" refers to a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Exemplary heteroalkyl groups include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)$_2$, —S(O)—$CH_3$, —S(O)$_2$—$CH_2$, —$CH_2$—$CH_2$—S(O)$_2$—$CH_3$, —CH═CH—O—$CH_3$, —Si($CH_3$)$_3$, —$CH_2$—CH═N—OCH$_3$, —CH═CH—N($CH_3$)—$CH_3$, —O—$CH_3$, and —O—$CH_2$—$CH_3$. Up to two or three heteroatoms may be consecutive, such as, for example, —$CH_2$—NH—$OCH_3$ and —$CH_2$—O—Si($CH_3$)$_3$. Where "heteroalkyl" is recited, followed by recitations of specific heteroalkyl groups, such as —$CH_2$O, —NR$^B$R$^C$, or the like, it will be understood that the terms heteroalkyl and —$CH_2$O or —NR$^B$R$^C$ are not redundant or mutually exclusive. Rather, the specific heteroalkyl groups are recited to add clarity. Thus, the term "heteroalkyl" should not be interpreted herein as excluding specific heteroalkyl groups, such as —$CH_2$O, —NR$^B$R$^C$, or the like.

Similarly, the term "heteroalkylene," by itself or as part of another substituent, means, unless otherwise stated, a divalent radical derived from heteroalkyl, as exemplified, but not limited by, —$CH_2$O— and —$CH_2CH_2$O—. A heteroalkylene group may be described as, e.g., a 2-7-membered heteroalkylene, wherein the term "membered" refers to the non-hydrogen atoms within the moiety. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— may represent both —C(O)$_2$R'— and —R'C(O)$_2$—.

As used herein, "heteroaryl" refers to a radical of a 5-10 membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8cycloalkyl," derived from a cycloalkane. Exemplary cycloalkyl groups include, but are not limited to, cyclohexanes, cyclopentanes, cyclobutanes and cyclopropanes.

As used herein, "heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. The terms "heterocycle," "heterocyclyl," "heterocyclyl ring," "heterocyclic group," "heterocyclic moiety," and "heterocyclic radical," may be used interchangeably.

As used herein, "cyano" refers to —CN.

The terms "halo" and "halogen" as used herein refer to an atom selected from fluorine (fluoro, F), chlorine (chloro, Cl), bromine (bromo, Br), and iodine (iodo, I). In certain embodiments, the halo group is either fluoro or chloro.

The term "alkoxy," as used herein, refers to an alkyl group which is attached to another moiety via an oxygen atom (—O(alkyl)). Non-limiting examples include e.g., methoxy, ethoxy, propoxy, and butoxy.

As used herein, "oxo" refers to —C═O.

In general, the term "substituted", whether preceded by the term "optionally" or not, means that at least one hydrogen present on a group (e.g., a hydrogen attached to a carbon or nitrogen atom of a group) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

As used herein, "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a solvate (e.g., hydrate) of an addition salt, a tautomeric form, a polymorph, an enantiomer, a mixture of enantiomers, a stereoisomer or mixture of stereoisomers (pure or as a racemic or non-racemic mixture) of a compound described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, Stereochemistry of Carbon Compounds (McGraw-Hill, N Y, 1962); and Wilen, Tables of Resolving Agents and Optical Resolutions p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

In certain embodiments the compounds and the transfer vehicles of which such compounds are a component (e.g., lipid nanoparticles) exhibit an enhanced (e.g., increased) ability to transfect one or more target cells. Accordingly, also provided herein are methods of transfecting one or more target cells. Such methods generally comprise the step of contacting the one or more target cells with the compounds and/or pharmaceutical compositions disclosed herein such that the one or more target cells are transfected with the circular RNA encapsulated therein. As used herein, the terms "transfect" or "transfection" refer to the intracellular introduction of one or more encapsulated materials (e.g., nucleic acids and/or polynucleotides) into a cell, or preferably into a target cell. The term "transfection efficiency" refers to the relative amount of such encapsulated material (e.g., polynucleotides) up-taken by, introduced into and/or expressed by the target cell which is subject to transfection. In some embodiments, transfection efficiency may be estimated by the amount of a reporter polynucleotide product produced by the target cells following transfection. In some embodiments, a transfer vehicle has high transfection efficiency. In some embodiments, a transfer vehicle has at least about 10%, 20%, 30%, 40%, 50%, 60%, 70%, 80%, or 90% transfection efficiency.

As used herein, the term "liposome" generally refers to a vesicle composed of lipids (e.g., amphiphilic lipids) arranged in one or more spherical bilayer or bilayers. In certain embodiments, the liposome is a lipid nanoparticle (e.g., a lipid nanoparticle comprising one or more of the ionizable lipid compounds disclosed herein). Such liposomes may be unilamellar or multilamellar vesicles which have a membrane formed from a lipophilic material and an aqueous interior that contains the encapsulated circRNA to be delivered to one or more target cells, tissues and organs. In certain embodiments, the compositions described herein comprise one or more lipid nanoparticles. Examples of suitable lipids (e.g., ionizable lipids) that may be used to form the liposomes and lipid nanoparticles contemplated include one or more of the compounds disclosed herein (e.g., HGT4001, HGT4002, HGT4003, HGT4004 and/or HGT4005). Such liposomes and lipid nanoparticles may also comprise additional ionizable lipids such as C12-200, DLin-KC2-DMA, and/or HGT5001, helper lipids, structural lipids, PEG-modified lipids, MC3, DLinDMA, DLinkC2DMA, cKK-E12, ICE, HGT5000, DODAC, DDAB, DMRIE, DOSPA, DOGS, DODAP, DODMA, DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combinations thereof.

As used herein, the phrases "non-cationic lipid", "non-cationic helper lipid", and "helper lipid" are used interchangeably and refer to any neutral, zwitterionic or anionic lipid.

As used herein, the phrase "anionic lipid" refers to any of a number of lipid species that carry a net negative charge at a selected pH, such as physiological pH.

As used herein, the phrase "biodegradable lipid" or "degradable lipid" refers to any of a number of lipid species that are broken down in a host environment on the order of minutes, hours, or days ideally making them less toxic and unlikely to accumulate in a host over time. Common modifications to lipids include ester bonds, and disulfide bonds among others to increase the biodegradability of a lipid.

As used herein, the phrase "biodegradable PEG lipid" or "degradable PEG lipid" refers to any of a number of lipid species where the PEG molecules are cleaved from the lipid in a host environment on the order of minutes, hours, or days ideally making them less immunogenic. Common modifications to PEG lipids include ester bonds, and disulfide bonds among others to increase the biodegradability of a lipid.

In certain embodiments of the present invention, the transfer vehicles (e.g., lipid nanoparticles) are prepared to encapsulate one or more materials or therapeutic agents (e.g., circRNA). The process of incorporating a desired therapeutic agent (e.g., circRNA) into a transfer vehicle is referred to herein as or "loading" or "encapsulating" (Lasic, et al., FEBS Lett., 312: 255-258, 1992). The transfer vehicle-loaded or -encapsulated materials (e.g., circRNA) may be completely or partially located in the interior space of the transfer vehicle, within a bilayer membrane of the transfer vehicle, or associated with the exterior surface of the transfer vehicle.

As used herein, the term "structural lipid" refers to sterols and also to lipids containing sterol moieties.

As defined herein, "sterols" are a subgroup of steroids consisting of steroid alcohols.

As used herein, the term "PEG" means any polyethylene glycol or other polyalkylene ether polymer.

As generally defined herein, a "PEG-OH lipid" (also referred to herein as "hydroxy-PEGylated lipid") is a PEGylated lipid having one or more hydroxyl (—OH) groups on the lipid.

As used herein, a "phospholipid" is a lipid that includes a phosphate moiety and one or more carbon chains, such as unsaturated fatty acid chains.

All nucleotide sequences disclosed herein can represent an RNA sequence or a corresponding DNA sequence. It is understood that deoxythymidine (dT or T) in a DNA is transcribed into a uridine (U) in an RNA. As such, "T" and "U" are used interchangeably herein in nucleotide sequences.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

The expression sequences in the polynucleotide construct may be separated by a "cleavage site" sequence which enables polypeptides encoded by the expression sequences, once translated, to be expressed separately by the cell.

A "self-cleaving peptide" refers to a peptide which is translated without a peptide bond between two adjacent amino acids, or functions such that when the polypeptide comprising the proteins and the self-cleaving peptide is produced, it is immediately cleaved or separated into distinct and discrete first and second polypeptides without the need for any external cleavage activity.

The $\alpha$ and $\beta$ chains of $\alpha\beta$ TCR's are generally regarded as each having two domains or regions, namely variable and constant domains/regions. The variable domain consists of a concatenation of variable regions and joining regions. In the present specification and claims, the term "TCR alpha variable domain" therefore refers to the concatenation of TRAV and TRAJ regions, and the term TCR alpha constant domain refers to the extracellular TRAC region, or to a C-terminal truncated TRAC sequence. Likewise, the term "TCR beta variable domain" refers to the concatenation of TRBV and TRBD/TRBJ regions, and the term TCR beta constant domain refers to the extracellular TRBC region, or to a C-terminal truncated TRBC sequence.

The terms "duplexed," "double-stranded," or "hybridized" as used herein refer to nucleic acids formed by hybridization of two single strands of nucleic acids containing complementary sequences. In most cases, genomic DNA is double-stranded. Sequences can be fully complementary or partially complementary.

As used herein, "autoimmunity" is defined as persistent and progressive immune reactions to non-infectious self-antigens, as distinct from infectious non self-antigens from bacterial, viral, fungal, or parasitic organisms which invade and persist within mammals and humans. Autoimmune conditions include scleroderma, Grave's disease, Crohn's disease, Sjorgen's disease, multiple sclerosis, Hashimoto's disease, psoriasis, myasthenia gravis, autoimmune polyendocrinopathy syndromes, Type I diabetes mellitus (TIDM), autoimmune gastritis, autoimmune uveoretinitis, polymyositis, colitis, and thyroiditis, as well as in the generalized autoimmune diseases typified by human Lupus. "Autoantigen" or "self-antigen" as used herein refers to an antigen or epitope which is native to the mammal and which is immunogenic in said mammal.

As used herein, the phrase "cationic lipid" refers to any of a number of lipid species that carry a net positive charge at a selected pH, such as physiological pH.

The term "antibody" (Ab) includes, without limitation, a glycoprotein immunoglobulin which binds specifically to an antigen. In general, an antibody may comprise at least two heavy (H) chains and two light (L) chains interconnected by disulfide bonds, or an antigen-binding molecule thereof. Each H chain may comprise a heavy chain variable region (abbreviated herein as VH) and a heavy chain constant region. The heavy chain constant region can comprise three constant domains, CH1, CH2 and CH3. Each light chain can comprise a light chain variable region (abbreviated herein as VL) and a light chain constant region. The light chain constant region can comprise one constant domain, CL. The VH and VL regions may be further subdivided into regions of hypervariability, termed complementarity determining regions (CDRs), interspersed with regions that are more conserved, termed framework regions (FR). Each VH and VL may comprise three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component of the classical complement system. Antibodies may include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain variable fragments (scFv), camelized antibodies, affybodies, Fab fragments, F(ab')2 fragments, disulfide-linked variable fragments (sdFv), anti-idiotypic (anti-id) antibodies (including, e.g., anti-anti-Id antibodies), minibodies, domain antibodies, synthetic antibodies (sometimes referred to herein as "antibody mimetics"), and antigen-binding fragments of any of the above. In some embodiments, antibodies described herein refer to polyclonal antibody populations.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in humans. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain Ab.

An "antigen binding molecule," "antigen binding portion," or "antibody fragment" refers to any molecule that comprises the antigen binding parts (e.g., CDRs) of the antibody from which the molecule is derived. An antigen binding molecule may include the antigenic complementarity determining regions (CDRs). Examples of antibody fragments include, but are not limited to, Fab, Fab', F(ab')2, Fv fragments, dAb, linear antibodies, scFv antibodies, and multispecific antibodies formed from antigen binding molecules. Peptibodies (i.e. Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In some embodiments, the antigen binding molecule binds to BCMA. In further embodiments, the antigen binding molecule is an antibody fragment, including one or more of the complementarity determining regions (CDRs) thereof, that specifically binds to the antigen. In further embodiments, the antigen binding molecule is a single chain variable fragment (scFv). In some embodiments, the antigen binding molecule comprises or consists of avimers.

As used herein, the term "variable region" or "variable domain" is used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In some embodiments, the variable region is a human variable region. In some embodiments, the variable region comprises rodent or murine CDRs and human framework regions (FRs). In particular embodiments, the variable region is a primate (e.g., non-human primate) variable region. In some embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding molecule thereof.

The terms "VH" and "VH domain" are used interchangeably to refer to the heavy chain variable region of an antibody or an antigen-binding molecule thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures. The term "Kabat numbering" and like terms are recognized in the art and refer to a system of numbering amino acid residues in the heavy and light chain variable regions of an antibody, or an antigen-binding molecule thereof. In certain aspects, the CDRs of an antibody may be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally may include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme. In certain aspects, the CDRs of an antibody may be determined according to the Chothia numbering scheme, which refers to the location of immunoglobulin structural loops (see, e.g., Chothia C & Lesk A M, (1987), J Mol Biol 196: 901-917; Al-Lazikani B et al, (1997) J Mol Biol 273: 927-948; Chothia C et al., (1992) J Mol Biol 227: 799-817; Tramontano A et al, (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which may exhibit various effector functions, such as interaction with the Fc receptor. The constant region of an immunoglobulin molecule generally has a more conserved amino acid sequence relative to an immunoglobulin variable domain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y may generally be represented by the dissociation constant (KD or Kd). Affinity may be measured and/or expressed in a number of ways known in the art, including, but not limited to, equilibrium dissociation constant (KD), and equilibrium association constant (KA or Ka). The KD is calculated from the quotient of koff/kon, whereas KA is calculated from the quotient of kon/koff. kon refers to the association rate constant of, e.g., an antibody to an antigen, and koff refers to the dissociation of, e.g., an antibody to an antigen. The kon and koff may be determined by techniques known to one of ordinary skill in the art, such as BIACORE® or KinExA.

As used herein, a "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In some embodiments, one or more amino acid residues within a CDR(s) or within a framework region(s) of an antibody or antigen-binding molecule thereof may be replaced with an amino acid residue with a similar side chain.

As, used herein, the term "heterologous" means from any source other than naturally occurring sequences.

As used herein, an "epitope" is a term in the art and refers to a localized region of an antigen to which an antibody may specifically bind. An epitope may be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In some embodiments, the epitope to which an antibody binds may be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giege R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody: antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. Patent Publication No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323).

As used herein, an antigen binding molecule, an antibody, or an antigen binding molecule thereof "cross-competes" with a reference antibody or an antigen binding molecule thereof if the interaction between an antigen and the first binding molecule, an antibody, or an antigen binding molecule thereof blocks, limits, inhibits, or otherwise reduces the ability of the reference binding molecule, reference antibody, or an antigen binding molecule thereof to interact with the antigen. Cross competition may be complete, e.g., binding of the binding molecule to the antigen completely blocks the ability of the reference binding molecule to bind the antigen, or it may be partial, e.g., binding of the binding molecule to the antigen reduces the ability of the reference binding molecule to bind the antigen. In some embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope as the reference antigen binding molecule. Numerous types of competitive binding assays may be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137:3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE®, KinExA 3000 instrument (Sapidyne Instruments, Boise, ID), or other assays known in the art. In a specific embodiment, molecules that specifically bind to an antigen bind to the antigen with a KA that is at least 2 logs, 2.5 logs, 3 logs, 4 logs or greater than the KA when the molecules bind to another antigen.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, may serve as an antigen. An antigen may be endogenously expressed, i.e. expressed by genomic DNA, or may be recombinantly expressed. An antigen may be specific to a certain tissue, such as a cancer cell, or it may be broadly expressed. In addition, fragments of larger molecules may act as antigens. In some embodiments, antigens are tumor antigens.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" may include a tumor. The particular cancer may be responsive to chemo- or radiation therapy or the cancer may be refractory. A refractory cancer refers to a cancer that is not amenable to surgical intervention and the cancer is either initially unresponsive to chemo- or radiation therapy or the cancer becomes unresponsive over time.

An "anti-tumor effect" as used herein, refers to a biological effect that may present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect may also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. "Cytokine" as used herein is meant to refer to proteins released by one cell population that act on another cell as intercellular mediators. A cytokine may be endogenously expressed by a cell or administered to a subject. Cytokines may be released by immune cells, including macrophages, B cells, T cells, neutrophils, dendritic cells, eosinophils and mast cells to propagate an immune response. Cytokines may induce various responses in the recipient cell. Cytokines may include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines may promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, IL-23, IL-27, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), TGF-beta, IL-35, and perforin. Examples of acute phase-proteins include, but are not limited to, C-reactive protein (CRP) and serum amyloid A (SAA).

The term "lymphocyte" as used herein includes natural killer (NK) cells, T cells, or B cells. NK cells are a type of cytotoxic (cell toxic) lymphocyte that represent a major component of the innate immune system. NK cells reject tumors and cells infected by viruses. It works through the process of apoptosis or programmed cell death. They were termed "natural killers" because they do not require activation in order to kill cells. T cells play a major role in cell-mediated-immunity (no antibody involvement). T cell receptors (TCR) differentiate T cells from other lymphocyte types. The thymus, a specialized organ of the immune system, is the primary site for T cell maturation. There are numerous types of T cells, including: helper T cells (e.g., CD4+ cells), cytotoxic T cells (also known as TC, cytotoxic T lymphocytes, CTL, T-killer cells, cytolytic T cells, CD8+ T cells or killer T cells), memory T cells ((i) stem memory cells (TSCM), like naive cells, are CD45RO−, CCR7+, CD45RA+, CD62L+(L-selectin), CD27+, CD28+ and IL-7Ra+, but also express large amounts of CD95, IL-2R, CXCR3, and LFA-1, and show numerous functional attributes distinctive of memory cells); (ii) central memory cells (TCM) express L-selectin and CCR7, they secrete IL-2, but not IFNγ or IL-4, and (iii) effector memory cells (TEM), however, do not express L-selectin or CCR7 but produce effector cytokines like IFNγ and IL-4), regulatory T cells (Tregs, suppressor T cells, or CD4+CD25+ or CD4+ FoxP3+ regulatory T cells), natural killer T cells (NKT) and gamma delta T cells. B-cells, on the other hand, play a principal role in humoral immunity (with antibody involvement). B-cells make antibodies, are capable of acting as antigen-presenting cells (APCs) and turn into memory B-cells and plasma cells, both short-lived and long-lived, after activation by antigen interaction. In mammals, immature B-cells are formed in the bone marrow.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which may either be obtained from a patient or a donor. The cell may be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand," as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand may include, but is not limited to, 3/TR6, 4-IBB ligand, agonist or antibody that binds Toll-like receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) LI. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFαF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD 18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, IT GAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Lyl08), SLAMF7, SLP-76, TNF, TNFr, TNFR2, Toll ligand receptor, TRANCE/RANKL, VLA1, or VLA-6, or fragments, truncations, or combinations thereof.

As used herein, a "vaccine" refers to a composition for generating immunity for the prophylaxis and/or treatment of diseases. Accordingly, vaccines are medicaments which comprise antigens and are intended to be used in humans or animals for generating specific defense and protective substances upon administration to the human or animal.

As used herein, a "neoantigen" refers to a class of tumor antigens which arises from tumor-specific mutations in an expressed protein.

As used herein, a "fusion protein" is a protein with at least two domains that are encoded by separate genes that have been joined to transcribe for a single peptide.

2. DNA Template, Precusor RNA & Circular RNA

According to the present invention, transcription of a DNA template provided herein (e.g., comprising a 3' enhanced intron element, 3' enhanced exon element, a core functional element, a 5' enhanced exon element, and a 5' enhanced intron element) results in formation of a precursor linear RNA polynucleotide capable of circularizing. In some embodiments, this DNA template comprises a vector, PCR product, plasmid, minicircle DNA, cosmid, artificial chromosome, complementary DNA (cDNA), extrachromosomal DNA (ecDNA), or a fragment therein. In certain embodiments, the minicircle DNA may be linearized or non-linearized. In certain embodiments, the plasmid may be linearized or non-linearized. In some embodiments, the DNA template may be single-stranded. In other embodiments, the DNA template may be double-stranded. In some embodiments, the DNA template comprises in whole or in part from a viral, bacterial or eukaryotic vector.

The present invention, as provided herein, comprises a DNA template that shares the same sequence as the precursor linear RNA polynucleotide prior to splicing of the precursor linear RNA polynucleotide (e.g., a 3' enhanced intron element, a 3' enhanced exon element, a core functional element, and a 5' enhanced exon element, a 5' enhanced intron element). In some embodiments, said linear precursor RNA polynucleotide undergoes splicing leading to the removal of the 3' enhanced intron element and 5' enhanced intron element during the process of circularization. In some embodiments, the resulting circular RNA polynucleotide lacks a 3' enhanced intron fragment and a 5' enhanced intron fragment, but maintains a 3' enhanced exon fragment, a core functional element, and a 5' enhanced exon element.

In some embodiments, the precursor linear RNA polynucleotide circularizes when incubated in the presence of one or more guanosine nucleotides or nucleoside (e.g., GTP) and a divalent cation (e.g., $Mg^{2+}$). In some embodiments, the 3' enhanced exon element, 5' enhanced exon element, and/or core functional element in whole or in part promotes the circularization of the precursor linear RNA polynucleotide to form the circular RNA polynucleotide provided herein.

In certain embodiments circular RNA provided herein is produced inside a cell. In some embodiments, precursor RNA is transcribed using a DNA template (e.g., in some embodiments, using a vector provided herein) in the cytoplasm by a bacteriophage RNA polymerase, or in the nucleus by host RNA polymerase II and then circularized.

In certain embodiments, the circular RNA provided herein is injected into an animal (e.g., a human), such that a polypeptide encoded by the circular RNA molecule is expressed inside the animal.

In some embodiments, the DNA (e.g., vector), linear RNA (e.g., precursor RNA), and/or circular RNA polynucleotide provided herein is between 300 and 10000, 400 and 9000, 500 and 8000, 600 and 7000, 700 and 6000, 800 and 5000, 900 and 5000, 1000 and 5000, 1100 and 5000, 1200 and 5000, 1300 and 5000, 1400 and 5000, and/or 1500 and 5000 nucleotides in length. In some embodiments, the polynucleotide is at least 300 nt, 400 nt, 500 nt, 600 nt, 700 nt, 800 nt, 900 nt, 1000 nt, 1100 nt, 1200 nt, 1300 nt, 1400 nt, 1500 nt, 2000 nt, 2500 nt, 3000 nt, 3500 nt, 4000 nt, 4500 nt, or 5000 nt in length. In some embodiments, the polynucleotide is no more than 3000 nt, 3500 nt, 4000 nt, 4500 nt, 5000 nt, 6000 nt, 7000 nt, 8000 nt, 9000 nt, or 10000 nt in length. In some embodiments, the length of a DNA, linear RNA, and/or circular RNA polynucleotide provided herein is about 300 nt, 400 nt, 500 nt, 600 nt, 700 nt, 800 nt, 900 nt, 1000 nt, 1100 nt, 1200 nt, 1300 nt, 1400 nt, 1500 nt, 2000 nt, 2500 nt, 3000 nt, 3500 nt, 4000 nt, 4500 nt, 5000 nt, 6000 nt, 7000 nt, 8000 nt, 9000 nt, or 10000 nt.

In some embodiments, the circular RNA provided herein has higher functional stability than mRNA comprising the same expression sequence. In some embodiments, the circular RNA provided herein has higher functional stability than mRNA comprising the same expression sequence, 5moU modifications, an optimized UTR, a cap, and/or a polyA tail.

In some embodiments, the circular RNA polynucleotide provided herein has a functional half-life of at least 5 hours, 10 hours, 15 hours, 20 hours. 30 hours, 40 hours, 50 hours, 60 hours, 70 hours or 80 hours. In some embodiments, the circular RNA polynucleotide provided herein has a functional half-life of 5-80, 10-70, 15-60, and/or 20-50 hours. In some embodiments, the circular RNA polynucleotide provided herein has a functional half-life greater than (e.g., at least 1.5-fold greater than, at least 2-fold greater than) that of an equivalent linear RNA polynucleotide encoding the same protein. In some embodiments, functional half-life can be assessed through the detection of functional protein synthesis.

In some embodiments, the circular RNA polynucleotide provided herein has a half-life of at least 5 hours, 10 hours, 15 hours, 20 hours. 30 hours, 40 hours, 50 hours, 60 hours, 70 hours or 80 hours. In some embodiments, the circular RNA polynucleotide provided herein has a half-life of 5-80, 10-70, 15-60, and/or 20-50 hours. In some embodiments, the circular RNA polynucleotide provided herein has a half-life greater than (e.g., at least 1.5-fold greater than, at least 2-fold greater than) that of an equivalent linear RNA polynucleotide encoding the same protein. In some embodiments, the circular RNA polynucleotide, or pharmaceutical composition thereof, has a functional half-life in a human cell greater than or equal to that of a pre-determined threshold value. In some embodiments the functional half-life is determined by a functional protein assay. For example in some embodiments, the functional half-life is determined by an in vitro luciferase assay, wherein the activity of Gaussia luciferase (GLuc) is measured in the media of human cells (e.g. HepG2) expressing the circular RNA polynucleotide every 1, 2, 6, 12, or 24 hours over 1, 2, 3, 4, 5, 6, 7, or 14 days. In other embodiments, the functional half-life is determined by an in vivo assay, wherein levels of a protein encoded by the expression sequence of the circular RNA polynucleotide are measured in patient serum or tissue samples every 1, 2, 6, 12, or 24 hours over 1, 2, 3, 4, 5, 6, 7, or 14 days. In some embodiments, the pre-determined threshold value is the functional half-life of a reference linear RNA polynucleotide comprising the same expression sequence as the circular RNA polynucleotide.

In some embodiments, the circular RNA provided herein may have a higher magnitude of expression than equivalent linear mRNA, e.g., a higher magnitude of expression 24 hours after administration of RNA to cells. In some embodiments, the circular RNA provided herein has a higher magnitude of expression than mRNA comprising the same expression sequence, 5moU modifications, an optimized UTR, a cap, and/or a polyA tail.

In some embodiments, the circular RNA provided herein may be less immunogenic than an equivalent mRNA when exposed to an immune system of an organism or a certain type of immune cell. In some embodiments, the circular RNA provided herein is associated with modulated production of cytokines when exposed to an immune system of an organism or a certain type of immune cell. For example, in some embodiments, the circular RNA provided herein is associated with reduced production of IFN-β1, RIG-I, IL-2, IL-6, IFNγ, and/or TNFα when exposed to an immune system of an organism or a certain type of immune cell as compared to mRNA comprising the same expression sequence. In some embodiments, the circular RNA provided herein is associated with less IFN-β1, RIG-I, IL-2, IL-6, IFNγ, and/or TNFα transcript induction when exposed to an immune system of an organism or a certain type of immune cell as compared to mRNA comprising the same expression sequence. In some embodiments, the circular RNA provided herein is less immunogenic than mRNA comprising the same expression sequence. In some embodiments, the circular RNA provided herein is less immunogenic than mRNA comprising the same expression sequence, 5moU modifications, an optimized UTR, a cap, and/or a polyA tail.

In certain embodiments, the circular RNA provided herein can be transfected into a cell as is, or can be transfected in DNA vector form and transcribed in the cell. Transcription of circular RNA from a transfected DNA vector can be via added polymerases or polymerases encoded by nucleic acids transfected into the cell, or preferably via endogenous polymerases.

A. Enhanced Intron Elements & Enhanced Exon Elements

As present in the invention herein, the enhanced intron elements and enhanced exon elements may comprise spacers, duplex regions, affinity sequences, intron fragments, exon fragments and various untranslated elements. These sequences within the enhanced intron elements or enhanced exon elements are arranged to optimize circularization or protein expression.

In certain embodiments, the DNA template, precursor linear RNA polynucleotide and circular RNA provided herein comprise a first (5') and/or a second (3') spacer. In some embodiments, the DNA template or precursor linear RNA polynucleotide comprises one or more spacers in the enhanced intron elements. In some embodiments, the DNA template, precursor linear RNA polynucleotide comprises one or more spacers in the enhanced exon elements. In certain embodiments, the DNA template or linear RNA polynucleotide comprises a spacer in the 3' enhanced intron fragment and a spacer in the 5' enhanced intron fragment. In certain embodiments, DNA template, precursor linear RNA polynucleotide, or circular RNA comprises a spacer in the 3' enhanced exon fragment and another spacer in the 5' enhanced exon fragment to aid with circularization or protein expression due to symmetry created in the overall sequence.

In some embodiments, including a spacer between the 3' group I intron fragment and the core functional element may conserve secondary structures in those regions by preventing them from interacting, thus increasing splicing efficiency. In some embodiments, the first (between 3' group I intron fragment and core functional element) and second (between the two expression sequences and core functional element) spacers comprise additional base pairing regions that are predicted to base pair with each other and not to the first and second duplex regions. In other embodiments, the first (between 3' group I intron fragment and core functional element) and second (between the one of the core functional element and 5' group I intron fragment) spacers comprise additional base pairing regions that are predicted to base pair with each other and not to the first and second duplex regions. In some embodiments, such spacer base pairing brings the group I intron fragments in close proximity to each other, further increasing splicing efficiency. Additionally, in some embodiments, the combination of base pairing between the first and second duplex regions, and separately, base pairing between the first and second spacers, promotes the formation of a splicing bubble containing the group I intron fragments flanked by adjacent regions of base pairing. Typical spacers are contiguous sequences with one or more of the following qualities: 1) predicted to avoid interfering with proximal structures, for example, the IRES, expression sequence, aptamer, or intron; 2) is at least 7 nt long and no longer than 100 nt; 3) is located after and adjacent to the 3' intron fragment and/or before and adjacent to the 5' intron fragment; and 4) contains one or more of the following: a) an unstructured region at least 5 nt long, b) a region of base pairing at least 5 nt long to a distal sequence, including another spacer, and c) a structured region at least 7 nt long limited in scope to the sequence of the spacer. Spacers may have several regions, including an unstructured region, a base pairing region, a hairpin/structured region, and combinations thereof. In an embodiment, the spacer has a structured region with high GC content. In an embodiment, a region within a spacer base pairs with another region within the same spacer. In an embodiment, a region within a spacer base pairs with a region within another spacer. In an embodiment, a spacer comprises one or more hairpin structures. In an embodiment, a spacer comprises one or more hairpin structures with a stem of 4 to 12 nucleotides and a loop of 2 to 10 nucleotides. In an embodiment, there is an additional spacer between the 3' group I intron fragment and the core functional element. In an embodiment, this additional spacer prevents the structured regions of the IRES or aptamer of a TIE from interfering with the folding of the 3' group I intron fragment or reduces the extent to which this occurs. In some embodiments, the 5' spacer sequence is at least 7, 8, 9, 10, 11, 12, 13, 14, 15, 16, 17, 18, 19, 20, 25 or 30 nucleotides in length. In some embodiments, the 5' spacer sequence is no more than 100, 90, 80, 70, 60, 50, 45, 40, 35 or 30 nucleotides in length. In some embodiments the 5' spacer sequence is between 5 and 50, 10 and 50, 20 and 50, 20 and 40, and/or 25 and 35 nucleotides in length. In certain embodiments, the 5' spacer sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In one embodiment, the 5' spacer sequence is a polyA sequence. In another embodiment, the 5' spacer sequence is a polyAC sequence. In one embodiment, a spacer comprises about 10%, 20%, 30%, 40%, 50%, 60%, 70%, 80%, 90%, or 100% polyAC content. In one embodiment, a spacer comprises about 10%, 20%, 30%, 40%, 50%, 60%, 70%, 80%, 90%, or 100% polypyrimidine (C/T or C/U) content.

In some embodiments, the DNA template and precursor linear RNA polynucleotides and circular RNA polynucleotide provided herein comprise a first (5') duplex region and a second (3') duplex region. In certain embodiments, the DNA template and precursor linear RNA polynucleotide comprises a 5' external duplex region located within the 3' enhanced intron fragment and a 3' external duplex region located within the 5' enhanced intron fragment. In some embodiments, the DNA template, precursor linear RNA polynucleotide and circular RNA polynucleotide comprise a 5' internal duplex region located within the 3' enhanced exon fragment and a 3' internal duplex region located within the 5' enhanced exon fragment. In some embodiments, the DNA polynucleotide and precursor linear RNA polynucleotide comprises a 5' external duplex region, 5' internal duplex region, a 3' internal duplex region, and a 3' external duplex region.

In certain embodiments, the first and second duplex regions may form perfect or imperfect duplexes. Thus, in certain embodiments at least 75%, 80%, 85%, 90%, 91%, 92%, 93%, 94%, 95%, 96%, 97%, 98%, 99% or 100% of the first and second duplex regions may be base paired with one another. In some embodiments, the duplex regions are predicted to have less than 50% (e.g., less than 45%, less than 40%, less than 35%, less than 30%, less than 25%) base pairing with unintended sequences in the RNA (e.g., non-duplex region sequences). In some embodiments, including such duplex regions on the ends of the precursor RNA strand, and adjacent or very close to the group I intron fragment, bring the group I intron fragments in close proximity to each other, increasing splicing efficiency. In some embodiments, the duplex regions are 3 to 100 nucleotides in length (e.g., 3-75 nucleotides in length, 3-50 nucleotides in length, 20-50 nucleotides in length, 35-50 nucleotides in length, 5-25 nucleotides in length, 9-19 nucleotides in length). In some embodiments, the duplex regions are about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In some embodiments, the duplex regions have a length of about 9 to about 50 nucleotides. In one embodiment, the duplex regions have a length of about 9 to about 19 nucleotides. In some embodiments, the duplex regions have a length of about 20 to about 40 nucleotides. In certain embodiments, the duplex regions have a length of about 30 nucleotides.

In other embodiments, the DNA template, precursor linear RNA polynucleotide, or circular RNA polynucleotide does not comprise of any duplex regions to optimize translation or circularization.

As provided herein, the DNA template or precursor linear RNA polynucleotide may comprise an affinity tag. In some embodiments, the affinity tag is located in the 3' enhanced intron element. In some embodiments, the affinity tag is located in the 5' enhanced intron element. In some embodiments, both (3' and 5') enhanced intron elements each comprise an affinity tag. In one embodiment, an affinity tag of the 3' enhanced intron element is the length as an affinity tag in the 5' enhanced intron element. In some embodiments, an affinity tag of the 3' enhanced intron element is the same sequence as an affinity tag in the 5' enhanced intron element. In some embodiments, the affinity sequence is placed to optimize oligo-dT purification.

In some embodiments, an affinity tag comprises a polyA region. In some embodiments the polyA region is at least 15, 30, or 60 nucleotides long. In some embodiments, one or both polyA regions is 15-50 nucleotides long. In some embodiments, one or both polyA regions is 20-25 nucleotides long. The polyA sequence is removed upon circularization. Thus, an oligonucleotide hybridizing with the polyA sequence, such as a deoxythymine oligonucleotide (oligo (dT)) conjugated to a solid surface (e.g., a resin), can be used to separate circular RNA from its precursor RNA.

In certain embodiments, the 3' enhanced intron element comprises a leading untranslated sequence. In some embodiments, the leading untranslated sequence is a the 5' end of the 3' enhanced intron fragment. In some embodiments, the leading untranslated sequence comprises of the last nucleotide of a transcription start site (TSS). In some embodiments, the TSS is chosen from a viral, bacterial, or eukaryotic DNA template. In one embodiment, the leading untranslated sequence comprise the last nucleotide of a TSS and 0 to 100 additional nucleotides. In some embodiments, the TSS is a terminal spacer. In one embodiment, the leading untranslated sequence contains a guanosine at the 5' end upon translation of an RNA T7 polymerase.

In certain embodiments, the 5' enhanced intron element comprises a trailing untranslated sequence. In some embodiments, the 5' trailing untranslated sequence is located at the 3' end of the 5' enhanced intron element. In some embodiments, the trailing untranslated sequence is a partial restriction digest sequence. In one embodiment, the trailing untranslated sequence is in whole or in part a restriction digest site used to linearize the DNA template. In some embodiments, the restriction digest site is in whole or in part from a natural viral, bacterial or eukaryotic DNA template. In some embodiments, the trailing untranslated sequence is a terminal restriction site fragment.

a. Enhanced Intron Fragments

According to the present invention, the 3' enhanced intron element and 5' enhanced intron element each comprise an intron fragment. In certain embodiments, a 3' intron fragment is a contiguous sequence at least 75% homologous (e.g., at least 80%, 85%, 90%, 91%, 92%, 93%, 94%, 95%, 96%, 97%, 98%, 99% or 100% homologous) to a 3' proximal fragment of a natural group I intron including the 3' splice site dinucleotide. Typically, a 5' intron fragment is a contiguous sequence at least 75% homologous (e.g., at least 80%, 85%, 90%, 91%, 92%, 93%, 94%, 95%, 96%, 97%, 98%, 99% or 100% homologous) to a 5' proximal fragment of a natural group I intron including the 5' splice site dinucleotide. In some embodiments, the 3' intron fragment includes the first nucleotide of a 3' group I splice site dinucleotide. In some embodiments, the 5' intron fragment includes the first nucleotide of a 5' group I splice site dinucleotide. In other embodiments, the 3' intron fragment includes the first and second nucleotides of a 3' group I intron fragment splice site dinucleotide; and the 5' intron fragment includes the first and second nucleotides of a 3' group I intron fragment dinucleotide.

b. Enhanced Exon Fragments

In certain embodiments, as provided herein, the DNA template, linear precursor RNA polynucleotide, and circular RNA polynucleotide each comprise an enhanced exon fragment. In some embodiments, following a 5' to 3' order, the 3' enhanced exon element is located upstream to core functional element. In some embodiments, following a 5' to 3' order, the 5' enhanced intron element is located downstream to the core functional element.

According to the present invention, the 3' enhanced exon element and 5' enhanced exon element each comprise an exon fragment. In some embodiments, the 3' enhanced exon element comprises a 3' exon fragment. In some embodiments, the 5' enhanced exon element comprises a 5' exon fragment. In certain embodiments, as provided herein, the 3' exon fragment and 5' exon fragment each comprises a group I intron fragment and 1 to 100 nucleotides of an exon sequence. In certain embodiments, a 3' intron fragment is a contiguous sequence at least 75% homologous (e.g., at least 80%, 85%, 90%, 91%, 92%, 93%, 94%, 95%, 96%, 97%, 98%, 99% or 100% homologous) to a 3' proximal fragment of a natural group I intron including the 3' splice site dinucleotide. Typically, a 5' group I intron fragment is a contiguous sequence at least 75% homologous (e.g., at least 80%, 85%, 90%, 91%, 92%, 93%, 94%, 95%, 96%, 97%, 98%, 99% or 100% homologous) to a 5' proximal fragment of a natural group I intron including the 5' splice site dinucleotide. In some embodiments, the 3' exon fragment comprises a second nucleotide of a 3' group I intron splice site dinucleotide and 1 to 100 nucleotides of an exon sequence. In some embodiments, the 5' exon fragment comprises the first nucleotide of a 5' group I intron splice site dinucleotide and 1 to 100 nucleotides of an exon sequence. In some embodiments, the exon sequence comprises in part or in whole from a naturally occurring exon sequence from a virus, bacterium or eukaryotic DNA vector. In other embodiments, the exon sequence further comprises a synthetic, genetically modified (e.g., containing modified nucleotide), or other engineered exon sequence.

In one embodiment, where the 3' intron fragment comprises both nucleotides of a 3' group I splice site dinucleotide and the 5' intron fragment comprises both nucleotides of a 5' group I splice site dinucleotide, the exon fragments located within the 5' enhanced exon element and 3' enhanced exon element does not comprise of a group I splice site dinucleotide.

c. Exemplary Permutation of the Enhanced Intron Elements & Enhanced Exon Elements For means of example and not intended to be limiting, in some embodiment, a 3' enhanced intron element comprises in the following 5' to 3' order: a leading untranslated sequence, a 5' affinity tag, an optional 5' external duplex region, a 5' external spacer, and a 3' intron fragment. In same embodiments, the 3' enhanced exon element comprises in the following 5' to 3' order: a 3' exon fragment, an optional 5' internal duplex region, an optional 5' internal duplex region, and a 5' internal spacer. In the same embodiments, the 5' enhanced exon element comprises in the following 5' to 3' order: a 3' internal spacer, an optional 3' internal duplex region, and a 5' exon fragment. In still the same embodiments, the 3' enhanced intron element comprises in the following 5' to 3' order: a 5' intron fragment, a 3' external spacer, an optional 3' external duplex region, a 3' affinity tag, and a trailing untranslated sequence.

B. Core Functional Element

In some embodiments, the DNA template, linear precursor RNA polynucleotide, and circular RNA polynucleotide comprise a core functional element. In some embodiments, the core functional element comprises a coding or noncoding element. In certain embodiments, the core functional element may contain both a coding and noncoding element. In some embodiments, the core functional element further comprises translation initiation element (TIE) upstream to the coding or noncoding element. In some embodiments, the core functional element comprises a termination element. In some embodiments, the termination element is located downstream to the TIE and coding element. In some embodiments, the termination element is located downstream to the coding element but upstream to the TIE. In certain embodiments, where the coding element comprises a noncoding region, a core functional element lacks a TIE and/or a termination element.

a. Coding or Noncoding Element

In some embodiments, the polynucleotides herein comprise coding or noncoding element or a combination of both. In some embodiments, the coding element comprises an expression sequence. In some embodiments, the coding element encodes at least one therapeutic protein.

In some embodiments, the circular RNA encodes two or more polypeptides. In some embodiments, the circular RNA is a bicistronic RNA. The sequences encoding the two or more polypeptides can be separated by a ribosomal skipping element or a nucleotide sequence encoding a protease cleavage site. In certain embodiments, the ribosomai skipping element encodes thosea-asigna virus 2A peptide (T2A), porcine teschovirus-1 2 A peptide (P2A), foot-and-mouth disease virus 2 A peptide (F2A), equine rhinitis A vims 2A peptide (E2A), cytoplasmic polyhedrosis vims 2A peptide (BmCPV 2A), or flacherie vims of *B. mori* 2A peptide (BmIFV 2A).

b. Translation Initiation Element (Tie)

As provided herein in some embodiments, the core functional element comprises at least one translation initiation element (TIE). TIEs are designed to allow translation efficiency of an encoded protein. Thus, optimal core functional elements comprising only of noncoding elements lack any TIEs. In some embodiments, core functional elements comprising one or more coding element will further comprise one or more TIEs.

In some embodiments, a TIE comprises an untranslated region (UTR). In certain embodiments, the TIE provided herein comprise an internal ribosome entry site (IRES). Inclusion of an IRES permits the translation of one or more open reading frames from a circular RNA (e.g., open reading frames that form the expression sequences). The IRES element attracts a eukaryotic ribosomal translation initiation complex and promotes translation initiation. See, e.g., Kaufman et al., Nuc. Acids Res. (1991) 19:4485-4490; Gurtu et al., Biochem. Biophys. Res. Comm. (1996) 229:295-298; Rees et al., BioTechniques (1996) 20: 102-110; Kobayashi et al., BioTechniques (1996) 21:399-402; and Mosser et al., BioTechniques 1997 22 150-161.

i. Natural Ties: Viral, & Eukaryotic/Cellular Internal Ribosome Entry Site (Ires)

A multitude of IRES sequences are available and include sequences derived from a wide variety of viruses, such as from leader sequences of picornaviruses such as the encephalomyocarditis virus (EMCV) UTR (Jang et al., J. Virol. (1989) 63: 1651-1660), the polio leader sequence, the hepatitis A virus leader, the hepatitis C virus IRES, human rhinovirus type 2 IRES (Dobrikova et al., Proc. Natl. Acad. Sci. (2003) 100(25): 15125-15130), an IRES element from the foot and mouth disease virus (Ramesh et al., Nucl. Acid Res. (1996) 24:2697-2700), a giardiavirus IRES (Garlapati et al., J. Biol. Chem. (2004) 279(5):3389-3397), and the like.

For driving protein expression, the circular RNA comprises an IRES operably linked to a protein coding sequence. Modifications of IRES and accessory sequences are disclosed herein to increase or reduce IRES activities, for example, by truncating the 5' and/or 3' ends of the IRES, adding a spacer 5' to the IRES, modifying the 6 nucleotides 5' to the translation initiation site (Kozak sequence), modification of alternative translation initiation sites, and creating chimeric/hybrid IRES sequences. In some embodiments, the IRES sequence in the circular RNA disclosed herein comprises one or more of these modifications relative to a native IRES.

In some embodiments, the IRES is an IRES sequence of Taura syndrome virus, Triatoma virus, Theiler's encephalomyelitis virus, Simian Virus 40, Solenopsis invicta virus 1, Rhopalosiphum padi virus, Reticuloendotheliosis virus, Human poliovirus 1, Plautia stali intestine virus, Kashmir bee virus, Human rhinovirus 2, Homalodisca coagulata virus-1, Human Immunodeficiency Virus type 1, Himetobi P virus, Hepatitis C virus, Hepatitis A virus, Hepatitis GB virus, Foot and mouth disease virus, Human enterovirus 71, Equine rhinitis virus, Ectropis obliqua picorna-like virus, Encephalomyocarditis virus, Drosophila C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, Drosophila antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kipl, Human PDGF2/c-sis, Human p53, Human Pim-1, Mouse Rbm3, Drosophila reaper, Canine Scamper, Drosophila Ubx, Human UNR, Mouse UtrA, Human VEGF-A, Human XIAP, Drosophila hairless, *S. cerevisiae* TFIID, *S. cerevisiae* YAP1, tobacco etch virus, turnip crinkle virus, EMCV-A, EMCV-B, EMCV-Bf, EMCV-Cf, EMCV pEC9, Picobirnavirus, HCV QC64, Human Cosavirus E/D, Human Cosavirus F, Human Cosavirus JMY, Rhinovirus NAT001, HRV14, HRV89, HRVC-02, HRV-A21, Salivirus A SH1, Salivirus FHB, Salivirus NG-J1, Human Parechovirus 1, Crohivirus B, Yc-3, Rosavirus M-7, Shanbavirus A, Pasivirus A, Pasivirus A 2, Echovirus E14, Human Parechovirus 5, Aichi Virus, Hepatitis A Virus HA16, Phopivirus, CVA10, Enterovirus C, Enterovirus D, Enterovirus J, Human Pegivirus 2, GBV-C GT110, GBV-C K1737, GBV-C Iowa, Pegivirus A 1220, Pasivirus A 3, Sapelovirus, Rosavirus B, Bakunsa Virus, Tremovirus A, Swine Pasivirus 1, PLV-CHN, Pasivirus A, Sicinivirus, Hepacivirus K, Hepacivirus A, BVDV1, Border Disease Virus, BVDV2, CSFV—PK15C, SF573 Dicistrovirus, Hubei Picorna-like Virus, CRPV, Salivirus A BN5, Salivirus A BN2, Salivirus A 02394, Salivirus A GUT, Salivirus A CH, Salivirus A SZ1, Salivirus FHB, CVB3, CVB1, Echovirus 7, CVB5, EVA71, CVA3, CVA12, EV24 or an aptamer to eIF4G.

In some embodiments, the IRES comprises in whole or in part from a eukaryotic or cellular IRES. In certain embodiments, the IRES is from a human gene, where the human gene is ABCF1, ABCG1, ACAD10, ACOT7, ACSS3, ACTG2, ADCYAP1, ADK, AGTR1, AHCYL2, AHI1, AKAP8L, AKR1A1, ALDH3A1, ALDOA, ALG13, AMMECRIL, ANGPTL4, ANK3, AOC3, AP4B1, AP4E1, APAF1, APBB1, APC, APH1A, APOBEC3D, APOM, APP, AQP4, ARHGAP36, ARL13B, ARMC8, ARMCX6, ARPC1A, ARPC2, ARRDC3, ASAP1, ASB3, ASB5, ASCL1, ASMTL, ATF2, ATF3, ATG4A, ATP5B, ATP6VOA1, ATXN3, AURKA, AURKA, AURKA, AURKA, B3GALNT1, B3GNTL1, B4GALT3, BAAT, BAG1, BAIAP2, BAIAP2L2, BAZ2A, BBX, BCAR1, BCL2, BCS1 L, BET1, BID, BIRC2, BPGM, BPIFA2, BRINP2, BSG, BTN3A2, C12orf43, C14orf93, C17orf62, C1orf226, C21orf62, C2orf15, C4BPB, C4orf22, C9orf84, CACNA1A, CALCOCO2, CAPN11, CASP12, CASP8AP2, CAV1, CBX5, CCDC120, CCDC17, CCDC186, CCDC51, CCN1, CCND1, CCNT1, CD2BP2, CD9, CDC25C, CDC42, CDC7, CDCA7L, CDIP1, CDK1, CDK11A, CDKN1B, CEACAM7, CEP295NL, CFLAR, CHCHD7, CHIA, CHIC1, CHMP2A, CHRNA2, CLCN3, CLEC12A, CLEC7A, CLECL1, CLRN1, CMSS1, CNIH1, CNR1, CNTN5, COG4, COMMD1, COMMD5, CPEB1, CPS1, CRACR2B, CRBN, CREM, CRYBG1, CSDE1, CSF2RA, CSNK2A1, CSTF3, CTCFL, CTH, CTNNA3, CTNNB1, CTNNB1, CTNND1, CTSL, CUTA, CXCR5, CYB5R3, CYP24A1, CYP3A5, DAG1, DAP3, DAP5, DAXX, DCAF4, DCAF7, DCLRE1A, DCP1A, DCTN1, DCTN2, DDX19B, DDX46, DEFB123, DGKA, DGKD, DHRS4, DHX15, DIO3, DLG1, DLL4, DMD UTR, DMD ex5, DMKN, DNAH6, DNAL4, DUSP13, DUSP19, DYNC1I2, DYNLRB2, DYRK1A, ECI2, ECT2, EIF1AD, EIF2B4, EIF4G1, EIF4G2, EIF4G3, ELANE, ELOVL6, ELP5, EMCN, ENO1, EPB41, ERMN, ERVV-1, ESRRG, ETFB, ETFBKMT, ETV1, ETV4, EXD1, EXT1, EZH2, FAM111B, FAM157A, FAM213A, FBXO25, FBXO9, FBXW7, FCMR, FGF1, FGF1, FGF1A, FGF2, FGF2, FGF-9, FHL5, FMR1, FN1, FOXP1, FTH1, FUBP1, G3BP1, GABBR1, GALC, GART, GAS7, gastrin, GATA1, GATA4, GFM2, GHR, GJB2, GLI1, GLRA2, GMNN, GPAT3, GPATCH3, GPR137, GPR34, GPR55, GPR89A, GPRASP1, GRAP2, GSDMB, GSTO2, GTF2B, GTF2H4, GUCY1B2, HAX1, HCST, HIGD1A, HIGD1B, HIPK1, HISTIHIC, HIST1H3H, HK1, HLA-DRB4, HMBS, HMGA1, HNRNPC, HOPX, HOXA2, HOXA3, HPCAL1, HR, HSP90AB1, HSPA1A, HSPA4L, HSPA5, HYPK, IFFO1, IFT74, IFT81, IGF1, IGF1R, IGF1R, IGF2, IL11, IL17RE, IL1RL1, IL1RN, IL32, IL6, ILF2, ILVBL, INSR, INTS13, IP6K1, ITGA4, ITGAE, KCNE4, KERA, KIAA0355, KIAA0895L, KIAA1324, KIAA1522, KIAA1683, KIF2C, KIZ, KLHL31, KLK7, KRR1, KRT14, KRT17, KRT33A, KRT6A, KRTAP10-2, KRTAP13-3, KRTAP13-4, KRTAP5-11, KRTCAP2, LACRT, LAMB1, LAMB3, LANCL1, LBX2, LCAT, LDHA, LDHAL6A, LEF1, LINC-PINT, LMO3, LRRC4C, LRRC7, LRTOMT, LSM5, LTB4R, LYRM1, LYRM2, MAGEAI1, MAGEA8, MAGEB1, MAGEB16, MAGEB3, MAPT, MARS, MC1R, MCCC1, METTL12, METTL7A, MGC16025, MGC16025, MIA2, MIA2, MITF, MKLN1, MNT, MORF4L2, MPD6, MRFAP1, MRPL21, MRPS12, MSI2, MSLN, MSN, MT2A, MTFR1 L, MTMR2, MTRR, MTUS1, MYB, MYC, MYCL, MYCN, MYL10, MYL3, MYLK, MYO1A, MYT2, MZB1, NAP1L1, NAV1, NBAS, NCF2, NDRG1, NDST2, NDUFA7, NDUFB11, NDUFC1, NDUFS1, NEDD4L, NFAT5, NFE2L2, NFE2L2, NFIA, NHEJ1, NHP2, NIT1, NKRF, NME1NME2, NPAT, NR3C1, NRBF2, NRF1, NTRK2, NUDCD1, NXF2, NXT2, ODC1, ODF2, OPTN, OR10R2, OR11L1, OR2M2, OR2M3, OR2M5, OR2T10, OR4C15, OR4F17, OR4F5, OR5H1, OR5K1, OR6C3, OR6C75, OR6N1, OR7G2, p53, P2RY4, PAN2, PAQR6, PARP4, PARP9, PC, PCBP4, PCDHGC3, PCLAF, PDGFB, PDZRN4, PELO, PEMT, PEX2, PFKM, PGBD4, PGLYRP3, PHLDA2, PHTF1, PI4KB, PIGC, PIM1, PKD2L1, PKM, PLCB4, PLD3, PLEKHA1, PLEKHB1, PLS3, PML, PNMA5, PNN, POC1A, POC1B, POLD2, POLD4, POU5F1, PPIG, PQBP1, PRAME, PRPF4, PRR11, PRRT1, PRSS8, PSMA2, PSMA3, PSMA4, PSMD11, PSMD4, PSMD6, PSME3, PSMG3, PTBP3, PTCH1, PTHLH, PTPRD, PUS7L, PVRIG, QPRT, RAB27A, RAB7B, RABGGTB, RAETIE, RALGDS, RALYL, RARB, RCVRN, REG3G, RFC5, RGL4, RGS19, RGS3, RHD, RINL, RIPOR2, RITA1, RMDN2, RNASE1, RNASE4, RNF4, RPA2, RPL17, RPL21, RPL26L1, RPL28, RPL29, RPL41, RPL9, RPS11, RPS13, RPS14, RRBP1, RSU1, RTP2, RUNX1, RUNX1T1, RUNX1T1, RUNX2, RUSC1, RXRG, S100A13, S100A4, SAT1, SCHIP1, SCMH1, SEC14L1, SEMA4A, SERPINA1, SERPINB4, SERTAD3, SFTPD, SH3D19, SHC1, SHMT1, SHPRH, SIM1, SIRT5, SLC11A2, SLC12A4, SLC16A1, SLC25A3, SLC26A9, SLC5A11, SLC6A12, SLC6A19, SLC7A1, SLFN11, SLIRP, SMAD5, SMARCAD1, SMN1, SNCA, SNRNP200, SNRPB2, SNX12, SOD1, SOX13, SOX5, SP8, SPARCL1, SPATA12, SPATA31C2, SPN, SPOP, SQSTM1, SRBD1, SRC, SREBF1, SRPK2, SSB, SSB, SSBP1, ST3GAL6, STAB1, STAMBP, STAU1, STAU1, STAU1, STAU1, STAU1, STK16, STK24, STK38, STMN1, STX7, SULT2B1, SYK, SYNPR, TAF1C, TAGLN, TANK, TAS2R40, TBC1D15, TBXAS1, TCF4, TDGF1, TDP2, TDRD3, TDRD5, TESK2, THAP6, THBD, THTPA, TIAM2, TKFC, TKTL1, TLR10, TM9SF2, TMC6, TMCO2, TMED10, TMEM116, TMEM126A, TMEM159, TMEM208, TMEM230, TMEM67, TMPRSS13, TMUB2, TNFSF4, TNIP3, TP53, TP53, TP73, TRAF1, TRAK1, TRIM31, TRIM6, TRMT1, TRMT2B, TRPM7, TRPM8, TSPEAR, TTC39B, TTLL11, TUBB6, TXLNB, TXNIP, TXNL1, TXNRD1, TYROBP, U2AF1, UBA1, UBE2D3, UBE2I, UBE2L3, UBE2V1, UBE2V2, UMPS, UNG, UPP2, USMG5, USP18, UTP14A, UTRN, UTS2, VDR, VEGFA, VEGFA, VEPH1, VIPAS39, VPS29, VSIG10L, WDHD1, WDR12, WDR4, WDR45, WDYHV1, WRAP53, XIAP, XPNPEP3, YAP1, YWHAZ, YY1AP1, ZBTB32, ZNF146, ZNF250, ZNF385A, ZNF408, ZNF410, ZNF423, ZNF43, ZNF502, ZNF512, ZNF513, ZNF580, ZNF609, ZNF707, or ZNRD1.

ii. Synthetic Ties: Aptamer Complexes, Modified Nucleotides, Ires Variants & Other Engineered Ties As contemplated herein, in certain embodiments, a translation initiation element (TIE) comprises a synthetic TIE. In some embodiments, a synthetic TIE comprises aptamer complexes, synthetic IRES or other engineered TIES capable of initiating translation of a linear RNA or circular RNA polynucleotide.

In some embodiments, one or more aptamer sequences is capable of binding to a component of a eukaryotic initiation factor to either enhance or initiate translation. In some embodiments, aptamer may be used to enhance translation in vivo and in vitro by promoting specific eukaryotic initiation factors (eIF) (e.g., aptamer in WO2019081383A1 is capable of binding to eukaryotic initiation factor 4F (eIF4F). In some embodiments, the aptamer or a complex of aptamers may be capable of binding to EIF4G, EIF4E, EIF4A, EIF4B, EIF3, EIF2, EIF5, EIF1, EIF1A, 40S ribosome, PCBP1 (polyC binding protein), PCBP2, PCBP3, PCBP4, PABP1

(polyA binding protein), PTB, Argonaute protein family, HNRNPK (heterogeneous nuclear ribonucleoprotein K), or La protein.

c. Termination Sequence

In certain embodiments, the core functional element comprises a termination sequence. In some embodiments, the termination sequence comprises a stop codon. In one embodiment, the termination sequence comprises a stop cassette. In some embodiments, the stop cassette comprises at least 2 stop codons. In some embodiments, the stop cassette comprises at least 2 frames of stop codons. In the same embodiment, the frames of the stop codons in a stop cassette each comprise 1, 2 or more stop codons. In some embodiments, the stop cassette comprises a LoxP or a RoxStopRox, or frt-flanked stop cassette. In the same embodiment, the stop cassette comprises a lox-stop-lox stop cassette.

C. Variants

In certain embodiments, a circular RNA polynucleotide provided herein comprises modified RNA nucleotides and/or modified nucleosides. In some embodiments, the modified nucleoside is $m^5C$ (5-methylcytidine). In another embodiment, the modified nucleoside is $m^5U$ (5-methyluridine). In another embodiment, the modified nucleoside is $m^6A$ ($N^6$-methyladenosine). In another embodiment, the modified nucleoside is $s^2U$ (2-thiouridine). In another embodiment, the modified nucleoside is Ψ (pseudouridine). In another embodiment, the modified nucleoside is Um (2'-O-methyluridine). In other embodiments, the modified nucleoside is $m^1A$ (1-methyladenosine); $m^2A$ (2-methyladenosine); Am (2'-O-methyladenosine); $ms^2 m^6A$ (2-methylthio-$N^6$-methyladenosine); $i^6A$ ($N^6$-isopentenyladenosine); $ms^2i6A$ (2-methylthio-$N^6$ isopentenyladenosine); $io^6A$ ($N^6$-(cis-hydroxyisopentenyl)adenosine); $ms^2i6A$ (2-methylthio-$N^6$-(cis-hydroxyisopentenyl)adenosine); $g^6A$ ($N^6$-glycinyl-carbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$ ($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2 2G$ ($N^2,N^2$-dimethylguanosine); $m^2Gm$ ($N^2,2'$—O-dimethylguanosine); $m^2_2Gm$ ($N^2,N^2,2'$—O-trimethylguanosine); Gr(p) (2'-O-ribosylguanosine(phosphate)); yW (wybutosine); O2yW (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); preQ0 (7-cyano-7-deazaguanosine); preQ1 (7-aminomethyl-7-deazaguanosine); G+ (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5S^2U$ (5-aminomethyl-2-thiouridine); $mnm^5U$ (5-methylaminomethyluridine); $mnm^5s^2U$ (5-methylaminomethyl-2-thiouridine); $mnm^5se^2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5s^2U$ (5-carboxymethylaminomethyl-2-thiouridine); $m^6 2A$ ($N^6,N^6$-dimethyladenosine); Im (2'-O-methylinosine); $m^4C$ ($N^4$-methylcytidine); $m^4Cm$ ($N^4,2'$—O-dimethylcytidine); $hm^5C$ (5-hydroxymethylcytidine); $m^3U$ (3-methyluridine); $cm^5U$ (5-carboxymethyluridine); $m^6Am$ ($N^6,2'$—O-dimethyladenosine); $m^6 2Am$ ($N^6,N^6,O$-2'-trimethyladenosine); $m^{2,7}G$ ($N^2,7$-dimethylguanosine); $m^{2,2,7}G$ ($N^2,N^2,7$-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $τm^5U$ (5-taurinomethyluridine); $τm^5s^2U$ (5-taurinomethyl-2-thiouridine)); imG-14 (4-demethylwyosine); imG2 (isowyosine); or $ac^6A$ ($N^6$-acetyladenosine).

In some embodiments, the modified nucleoside may include a compound selected from the group of: pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-m ethoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6- thio-guanosine, and N2,N2-dimethyl-6-thio-guanosine. In another embodiment, the modifications are independently selected from the group consisting of 5-methylcytosine, pseudouridine and 1-methylpseudouridine.

In some embodiments, the modified ribonucleosides include 5-methylcytidine, 5-methoxyuridine, 1-methyl-pseudouridine, N6-methyladenosine, and/or pseudouridine. In some embodiments, such modified nucleosides provide additional stability and resistance to immune activation.

In particular embodiments, polynucleotides may be codon-optimized. A codon optimized sequence may be one in which codons in a polynucleotide encoding a polypeptide have been substituted in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, and/or (x) systematic variation of codon sets for each amino acid. In some embodiments, a codon optimized polynucleotide may minimize ribozyme collisions and/or limit structural interference between the expression sequence and the core functional element.

3. Payloads

In some embodiments, the expression sequence encodes a therapeutic protein. In some embodiments, the therapeutic protein is selected from the proteins listed in the following table.

| Payload | Sequence | Target cell/organ | Preferred delivery formulation |
|---|---|---|---|
| CD19 CAR | Any of sequences 309-314 | T cells | 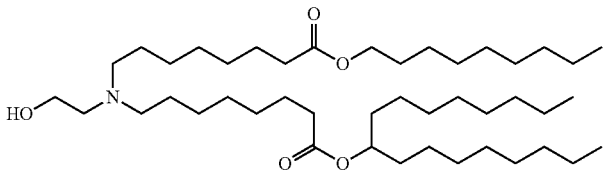<br>(50 mol %)<br>DSPC (10 mol %)<br>Beta-sitosterol (28.5% mol %)<br>Cholesterol (10 mol %)<br>PEG DMG (1.5 mol %) |
| BCMA CAR | MALPVTALLLPLALLLH AARPDIVLTQSPASLAVS LGERATINCRASESVSVI GAHLIHWYQQKPGQPPK LLIYLASNLETGVPARFS GSGSGTDFTLTISSLQAE DAAIYYCLQSRIFPRTFG QGTKLEIKGSTSGSGKPG SGEGSTKGQVQLVQSGS ELKKPGASVKVSCKASG YTFTDYSINWVRQAPGQ GLEWMGWINTETREPA YAYDFRGRFVFSLDTSV STAYLQISSLKAEDTAVY YCARDYSYAMDYWGQ GTLVTVSSAAATTTPAP RPPTPAPTIASQPLSLRPE ACRPAAGGAVHTRGLDF ACDIYIWAPLAGTCGVL LLSLVITLYCKRGRKKLL YIFKQPFMRPVQTTQEE DGCSCRFPEEEEGGCELR VKFSRSADAPAYQQGQN QLYNELNLGRREEYDVL DKRRGRDPEMGGKPRR KNPQEGLYNELQKDKM AEAYSEIGMKGERRRGK GHDGLYQGLSTATKDTY DALHMQALPPR (SEQ ID NO: 1) | T cells | 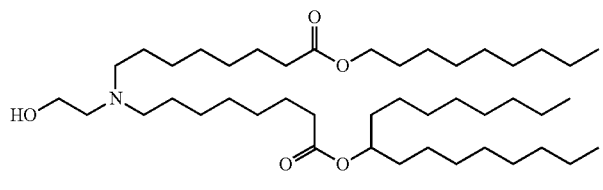<br>(50 mol %)<br>DSPC (10 mol %)<br>Beta-sitosterol (28.5% mol %)<br>Cholesterol (10 mol %)<br>PEG DMG (1.5 mol %) |

| Payload | Sequence | Target cell/organ | Preferred delivery formulation |
|---|---|---|---|
| MAGE-A4 TCR | TCR alpha chain: KNQVEQSPQSLIILEGKN CTLQCNYTVSPFSNLRW YKQDTGRGPVSLTIMTF SENTKSNGRYTATLDAD TKQSSLHITASQLSDSAS YICVVNHSGGSYIPTFGR GTSLIVHPYIQKPDPAVY QLRDSKSSDKSVCLFTDF DSQTNVSQSKDSDVYIT DKTVLDMRSMDFKSNS AVAWSNKSDFACANAF NNSIIPEDTFFFPSPESS (SEQ ID NO: 2) TCR beta chain: DVKVTQSSRYLVKRTGE KVFLECVQDMDHENMF WYRQDPGLGLRLIYFSY DVKMKEKGDIPEGYSVS REKKERFSLILESASTNQ TSMYLCASSFLMTSGDP YEQYFGPGTRLTVTEDL KNVFPPEVAVFEPSEAEI SHTQKATLVCLATGFYP DHVELSWWVNGKEVHS GVSTDPQPLKEQPALND SRYCLSSRLRVSATFWQ NPRNHFRCQVQFYGLSE NDEWTQDRAKPVTQIVS AEAWGRAD (SEQ ID NO: 3) | T cells | 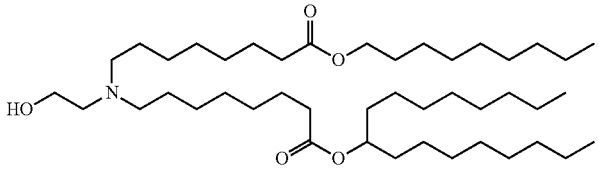<br>(50 mol %)<br>DSPC (10 mol %)<br>Beta-sitosterol (28.5% mol %)<br>Cholesterol (10 mol %)<br>PEG DMG (1.5 mol %) |
| NY-ESO TCR | TCR alpha extracellular sequence (SEQ ID NO: 4) MQEVTQIPAALSVPEGE NLVLNCSFTDSAIYNLQ WFRQDPGKGLTSLLLIQS SQREQTSGRLNASLDKS SGRSTLYIAASQPGDSAT YLCAVRPTSGGSYIPTFG RGTSLIVHPY TCR beta extracellular sequence MGVTQTPKFQVLKTGQS (SEQ ID NO: 5) MTLQCAQDMNHEYMS WYRQDPGMGLRLIHYS VGAGITDQGEVPNGYNV SRSTTEDFPLRLLSAAPS QTSVYFCASSYVGNTGE LFFGEGSRLTVL | T cells | 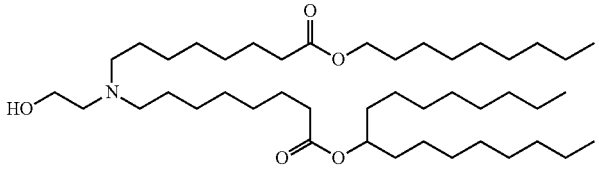<br>(50 mol %)<br>DSPC (10 mol %)<br>Beta-sitosterol (28.5% mol %)<br>Cholesterol (10 mol %)<br>PEG DMG (1.5 mol %) |
| EPO | APPRLICDSRVLERYLLE AKEAENITTGCAEHCSL NENITVPDTKVNFYAWK RMEVGQQAVEVWQGLA LLSEAVLRGQALLVNSS QPWEPLQLHVDKAVSGL RSLTTLLRALGAQKEAIS PPDAASAAPLRTITADTF RKLFRVYSNFLRGKLKL YTGEACRTGDR (SEQ ID NO: 6) | Kidney or bone marrow | |

| Payload | Sequence | Target cell/organ | Preferred delivery formulation |
|---|---|---|---|
| PAH | MSTAVLENPGLGRKLSD FGQETSYIEDNCNQNGAI SLIFSLKEEVGALAKVLR LFEENDVNLTHIESRPSR LKKDEYEFFTHLDKRSL PALTNIIKILRHDIGATVH ELSRDKKKDTVPWFPRT IQELDRFANQILSYGAEL DADHPGFKDPVYRARR KQFADIAYNYRHGQPIP RVEYMEEEKKTWGTVF KTLKSLYKTHACYEYNH IFPLLEKYCGFHEDNIPQ LEDVSQFLQTCTGFRLRP VAGLLSSRDFLGGLAFR VFHCTQYIRHGSKPMYT PEPDICHELLGHVPLFSD RSFAQFSQEIGLASLGAP DEYIEKLATIYWFTVEFG LCKQGDSIKAYGAGLLS SFGELQYCLSEKPKLLPL ELEKTAIQNYTVTEFQPL YYVAESFNDAKEKVRNF AATIPRPFSVRYDPYTQR IEVLDNTQQLKILADSIN SEIGILCSALQKIK (SEQ ID NO: 7) | Hepatic cells | (50 mol %)<br>DSPC (10 mol %)<br>Cholesterol (38.5% mol %)<br>PEG-DMG (1.5%)<br>OR<br>MC3 (50 mol %)<br>DSPC (10 mol %)<br>Cholesterol (38.5% mol %)<br>PEG-DMG (1.5%) |
| CPS1 | LSVKAQTAHIVLEDGTK MKGYSFGHPSSVAGEVV FNTGLGGYPEAITDPAY KGQILTMANPIIGNGGAP DTTALDELGLSKYLESN GIKVSGLLVLDYSKDYN HWLATKSLGQWLQEEK VPAIYGVDTRMLTKIIRD KGTMLGKIEFEGQPVDF VDPNKQNLIAEVSTKDV KVYGKGNPTKVVAVDC GIKNNVIRLLVKRGAEV HLVPWNHDFTKMEYDG ILIAGGPGNPALAEPLIQ NVRKILESDRKEPLFGIS TGNLITGLAAGAKTYKM SMANRGQNQPVLNITNK QAFITAQNHGYALDNTL PAGWKPLFVNVNDQTN EGIMHESKPFFAVQFHPE VTPGPIDTEYLFDSFFSLI KKGKATTITSVLPKPALV ASRVEVSKVLILGSGGLS IGQAGEFDYSGSQAVKA MKEENVKTVLMNPNIAS VQTNEVGLKQADTVYFL PITPQFVTEVIKAEQPDG LILGMGGQTALNCGVEL FKRGVLKEYGVKVLGTS VESIMATEDRQLFSDKL NEINEKIAPSFAVESIEDA LKAADTIGYPVMIRSAY ALGGLGSGICPNRETLM DLSTKAFAMTNQILVEK SVTGWKEIEYEVVRDAD DNCVTVCNMENVDAMG VHTGDSVVVAPAQTLSN AEFQMLRRTSINVVRHL GIVGECNIQFALHPTSME YCIIEVNARLSRSSALAS KATGYPLAFIAAKIALGI PLPEIKNVVSGKTSACFE PSLDYMVTKIPRWDLDR FHGTSSRIGSSMKSVGEV MAIGRTFEESFQKALRM | Hepatic cells | (50 mol %)<br>DSPC (10 mol %)<br>Cholesterol (38.5% mol %)<br>PEG-DMG (1.5%)<br>OR<br>MC3 (50 mol %)<br>DSPC (10 mol %)<br>Cholesterol (38.5% mol %)<br>PEG-DMG (1.5%) |

-continued

| Payload | Sequence | Target cell/ organ | Preferred delivery formulation |
|---|---|---|---|
| | CHPSIEGFTPRLPMNKE WPSNLDLRKELSEPSSTR IYAIAKAIDDNMSLDEIE KLTYIDKWFLYKMRDIL NMEKTLKGLNSESMTEE TLKRAKEIGFSDKQISKC LGLTEAQTRELRLKKNI HPWVKQIDTLAAEYPSV TNYLYVTYNGQEHDVN FDDHGMMVLGCGPYHI GSSVEFDWCAVSSIRTLR QLGKKTVVVNCNPETVS TDFDECDKLYFEELSLER ILDIYHQEACGGCIISVG GQIPNNLAVPLYKNGVK IMGTSPLQIDRAEDRSIFS AVLDELKVAQAPWKAV NTLNEALEFAKSVDYPC LLRPSYVLSGSAMNVVF SEDEMKKFLEEATRVSQ EHPVVLTKFVEGAREVE MDAVGKDGRVISHAISE HVEDAGVHSGDATLML PTQTISQGAIEKVKDATR KAIKAFAISGPFNVQFLV KGNDVLVIECNLRASRS FPFVSKTLGVDFIDVATK VMIGENVDEKHLPTLDH PIIPADYVAIKAPMFSWP RLRDADPILRCEMSATG EVACFGEGIHTAFLKAM LSTGFKIPQKGILIGIQQS FRPRFLGVAEQLHNEGF KLFATEATSDWLNANN VPATPVAWPSQEGQNPS LSSIRKLIRDGSIDLVINL PNNNTKFVHDNYVIRRT AVDSGIPLLTNFQVTKLF AEAVQKSRKVDSKSLFH YRQYSAGKAA (SEQ ID NO: 8) | | |

-continued

| Payload | Sequence | Target cell/ organ | Preferred delivery formulation |
|---|---|---|---|
| Cas9 | MKRNYILGLDIGITSVGY GIIDYETRDVIDAGVRLF KEANVENNEGRRSKRG ARRLKRRRRHRIQRVKK LLFDYNLLTDHSELSGIN PYEARVKGLSQKLSEEE FSAALLHLAKRRGVHNV NEVEEDTGNELSTKEQIS RNSKALEEKYVAELQLE RLKKDGEVRGSINRFKT SDYVKEAKQLLKVQKA YHQLDQSFIDTYIDLLET RRTYYEGPGEGSPFGWK DIKEWYEMLMGHCTYF PEELRSVKYAYNADLYN ALNDLNNLVITRDENEK LEYYEKFQIIENVFKQKK KPTLKQIAKEILVNEEDI KGYRVTSTGKPEFTNLK VYHDIKDITARKEIIENA ELLDQIAKILTIYQSSEDI QEELTNLNSELTQEEIEQI SNLKGYTGTHNLSLKAI NLILDELWHTNDNQIAIF NRLKLVPKKVDLSQQKE IPTTLVDDFILSPVVKRSF IQSIKVINAIIKKYGLPND IIIELAREKNSKDAQKMI NEMQKRNRQTNERIEEII RTTGKENAKYLIEKIKLH DMQEGKCLYSLEAIPLE DLLNNPFNYEVDHIIPRS VSFDNSFNNKVLVKQEE NSKKGNRTPFQYLSSSDS KISYETFKKHILNLAKGK GRISKTKKEYLLEERDIN RFSVQKDFINRNLVDTR YATRGLMNLLRSYFRVN NLDVKVKSINGGFTSFLR RKWKFKKERNKGYKHH AEDALIIANADFIFKEWK KLDKAKKVMENQMFEE KQAESMPEIETEQEYKEI FITPHQIKHIKDFKDYKY SHRVDKKPNRELINDTL YSTRKDDKGNTLIVNNL NGLYDKDNDKLKKLINK SPEKLLMYHHDPQTYQK LKLIMEQYGDEKNPLYK YYEETGNYLTKYSKKDN GPVIKKIKYYGNKLNAH LDITDDYPNSRNKVVKL SLKPYRFDVYLDNGVYK FVTVKNLDVIKKENYYE VNSKCYEEAKKLKKISN QAEFIASFYNNDLIKING ELYRVIGVNNDLLNRIEV NMIDITYREYLENMNDK RPPRIIKTIASKTQSIKKY STDILGNLYEVKSKKHP QIIKKG (SEQ ID NO: 9) | Immune cells | 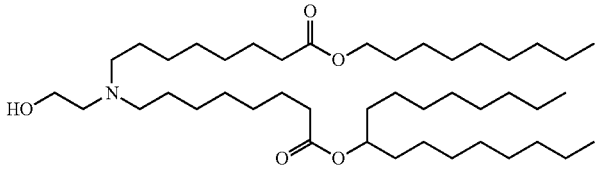<br>(50 mol %)<br>DSPC (10 mol %)<br>Beta-sitosterol (28.5% mol %)<br>Cholesterol (10 mol %)<br>PEG DMG (1.5 mol %) |

-continued

| Payload | Sequence | Target cell/organ | Preferred delivery formulation |
|---|---|---|---|
| ADAMTS13 | AAGGILHLELLVAVGPD VFQAHQEDTERYVLTNL NIGAELLRDPSLGAQFRV HLVKMVILTEPEGAPNIT ANLTSSLLSVCGWSQTIN PEDDTDPGHADLVLYIT RFDLELPDGNRQVRGVT QLGGACSPTWSCLITEDT GFDLGVTIAHEIGHSFGL EHDGAPGSGCGPSGHV MASDGAAPRAGLA -continued

| Payload | Sequence | Target cell/organ | Preferred delivery formulation |
|---|---|---|---|
| | TFYRECMQLFGPWGEI VSPSLSPATSNAGGCRLF INVAPHARIAIHALATNM GAGTEGANASYILIRDTH SLRTTAFHGQQVLYWES ESSQAEMEFSEGFLKAQ ASLRGQYWTLQSWVPE MQDPQSWKGKEGT (SEQ ID NO: 10) | | |
| FOXP3 | MPNPRPGKPSAPSLALGP SPGASPSWRAAPKASDL LGARGPGGTFQGRDLRG GAHASSSSLNPMPPSQL QLPTLPLVMVAPSGARL GPLPHLQALLQDRPHFM HQLSTVDAHARTPVLQV HPLESPAMISLTPPTTAT GVFSLKARPGLPPGINVA SLEWVSREPALLCTFPNP SAPRKDSTLSAVPQSSYP LLANGVCKWPGCEKVF EEPEDFLKHCQADHLLD EKGRAQCLLQREMVQSL EQQLVLEKEKLSAMQA HLAGKMALTKASSVASS DKGSCCIVAAGSQGPVV PAWSGPREAPDSLFAVR RHLWGSHGNSTFPEFLH NMDYFKFHNMRPPFTY ATLIRWAILEAPEKQRTL NEIYHWFTRMFAFFRNH PATWKNAIRHNLSLHKC FVRVESEKGAVWTVDEL EFRKKRSQRPSRCSNPTP GP (SEQ ID NO: 11) | Immune cells | 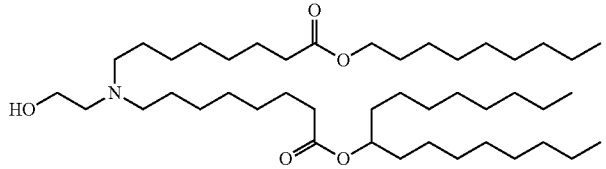<br>(50 mol %)<br>DSPC (10 mol %)<br>Beta-sitosterol (28.5% mol %)<br>Cholesterol (10 mol %)<br>PEG DMG (1.5 mol %) |
| IL-10 | SPGQGTQSENSCTHFPG NLPNMLRDLRDAFSRVK TFFQMKDQLDNLLLKES LLEDFKGYLGCQALSEM IQFYLEEVMPQAENQDP DIKAHVNSLGENLKTLR LRLRRCHRFLPCENKSK AVEQVKNAFNKLQEKGI YKAMSEFDIFINYIEAYM TMKIRN (SEQ ID NO: 12) | Immune cells | 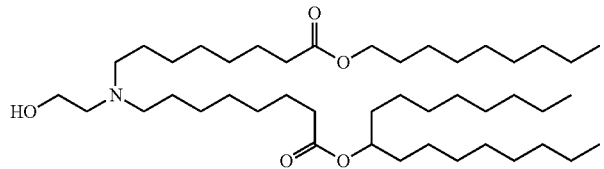<br>(50 mol %)<br>DSPC (10 mol %)<br>Beta-sitosterol (28.5% mol %)<br>Cholesterol (10 mol %)<br>PEG DMG (1.5 mol %) |
| IL-2 | APTSSSTKKTQLQLEHLL LDLQMILNGINNYKNPK LTRMLTFKFYMPKKATE LKHLQCLEEELKPLEEVL NLAQSKNFHLRPRDLISN INVIVLELKGSETTFMCE YADETATIVEFLNRWITF CQSIISTLT (SEQ ID NO: 13) | Immune cells | 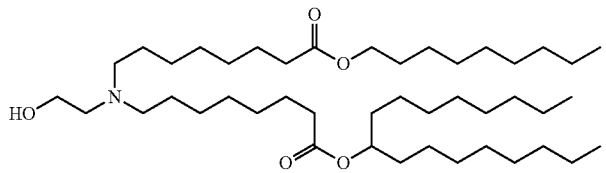<br>(50 mol %)<br>DSPC (10 mol %)<br>Beta-sitosterol (28.5% mol %)<br>Cholesterol (10 mol %)<br>PEG DMG (1.5 mol %) |

-continued

| Payload | Sequence | Target cell/ organ | Preferred delivery formulation |
|---|---|---|---|
| BCSP31 (BCSP_ BRUME) | MKFGSKIRRLAVAAVAG AIALGASFAVAQAPTFFR IGTGGTAGTYYPIGGLIA NAISGAGEKGVPGLVAT AVSSNGSVANINAIKSGA LESGFTQSDVAYWAYN GTGLYDGKGKVEDLRLL ATLYPETIHIVARKDANI KSVADLKGKRVSLDEPG SGTIVDARIVLEAYGLTE DDIKAE HLKPGPAGERLKDGALD AYFFVGGYPTGAISELAI SNGISLVPISGPEADKILE KYSFFSKDVVPAGAYKD VAETPTLAVAAQWVTS AKQPDDLIYNITKVLWN EDTRKALDAGHAKGKLI KLDSATSSLGIPLHPGAE RFYKEAGVLK (SEQ ID NO: 14) | Immune cells | |
| MOMP (MOMP6_ CHLP6) | MKKLLKSALLFAATGSA LSLQALPVGNPAEPSLLI DGTMWEGASGDPCDPC ATWCDAISIRAGYYGDY VFDRVLKVDVNKTFSG MAATPTQATGNASNTN QPEANGRPNIAYGRHMQ DAEWFSNAAFLALNIWD RFDIFCTLGASNGYFKAS SAAFNLVGLIGFSAASSIS TDLPMQLPNVGITQGVV EFYTDTSFSWSVGARGA LWECGCATLGAEFQYA QSNPKIEMLNVTSSPAQF VIHKPRGYKGASSNFPLP ITAGTTEATDTKSATIKY HEWQVGLALSYRLNML VPYIGVNWSRATFDADT IRIAQPKLKSEILNITTWN PSLIGSTTALPNNSGKDV LSDVLQIASIQINKM KSRKACGVAVGATLIDA DKWSITGEARLINEARAA HMNAQFRF (SEQ ID NO: 15) | Immune cell | |
| FomA | MKKLALVLGLLLVVGS VASAKEVMPAPTPAPEK VVEYVEKPVIVYRDREV APAWRPNGSVDVQYRW YGEVEKKNPKDDKDEN WATGKVNAGRLQTLTK VNFTEKQTLEVRTRNHH TLNDT DANNKKSNGAADEYRL RHFYNFGKLGSSKVNAT SRVEFKQKTNDGEKSLG ASVLFDFADYIYSNNFFK VDKLGLRPGYKYVWKG HGNGEEGTPTVHNEYHL AFESDFTLPFNFALNLEY DLSYNRYREKFETTDGL KKAEWYGELTAVLSNY TPLYKAGAFELGNAEG GYDTYNMHQYKRIGGE DGTSVDRRDYELYLEPT LQVSYKPTDFVKLYAAA GADYRNRITGESEVKRW RWQP TASAGMKVTF (SEQ ID NO: 16) | Immune cell | |

-continued

| Payload | Sequence | Target cell/ organ | Preferred delivery formulation |
|---|---|---|---|
| MymA | MNQHFDVLIIGAGLSGIG TACHVTAEFPDKTIALLE RRERLGGTWDLFRYPGV RSDSDMFTFGYKFRPWR DVKVLADGASIRQYIAD TATEFGVDEKIHYGLKV NTAEWSSRQCRWTVAG VHEATGETRTYTCDYLIS CTGYYNYDAGYLPDFPG VHRFGGRCVHPQHWPE DLDYSGKKVVVIGSGAT AVTLVPAMAGSNPGSAA HVTMLQRSPSYIFSLPAV DKISEVLGRFLPDRWVY EFGRRRNIAIQRKLYQAC RRWPKLMRRLLLWEVR RRLGRSVDMSNFTPNYL PWDERLCAV PNGDLFKTLASGAASVV TDQIETFTEKGILCKSGR EIEADIIVTATGLNIQML GGMRLIVDGAEYQLPEK MTYKGVLLENAPNLAWI IGYTNASWTLKSDIAGA YLCRLLRHMADNGYTV ATPRDAQDCALDVGMF DQLNSGYVKRGQDIMPR QGSKHPWRVLMHYEKD AKILLEDPIDDGVLHFAA AAQDHAAA (SEQ ID NO: 17) | Immune cell | |
| ESAT6 | MTEQQWNFAGIEAAAS AIQGNVTSIHSLLDEGKQ SLTKLAAAWGGSGSEAY QGVQQKWDATATELNN ALQNLARTISEAGQAMA STEGNVTGMFA (SEQ ID NO: 18) | Immune cell | |
| PorB | MKKSLIALTLAALPVAA MADVTLYGTIKAGVETY RFVAHNGAQASGVETAT EIADLGSKIGFKGQEDLG NGLKAIWQLEQKAYVS GTNTGWGNRQSFIGLKG GFGKVRVGRLNSVLKDT GGFNPWEGKSEYLSLSNI ARPEERPISVRYDSPEFA GFSGSVQYVPNDNSGEN KSESYHAGFNYKNSGFF VQYAGSYKRHNYTTEK HQIHRLVGGYDHDALY ASVAVQQQDAKLAWPD DNSHNSQTEVATTVAYR FGNVTPRVSYAHGFKGS VYEANHDNTYDQVVVG AEYDFSKRTSALVSAGW LQEGKGA (SEQ ID NO: 19) | Immune cell | |
| PVL (Panton Valentine leukocidin) | FVGYKPYSQNPRDYFVP DNELPPLVHSGFNPSFIA TVSHEKGSGDTSEFEITY GRNMDVTHATRRTTHY GNSYLEGSRIHNAFVNR NYTVKYEVNWKTHEIK VKGHN (SEQ ID NO: 20) | Immune cell | |
| Porin | EVKLSGDARMGVMYNG DDWNFSSRSRVLFTMSG TTDSGLEFGASFKAHES VGAETGEDGTVFLSGAF GKIEMGDALGASEALFG DLYEVGYTDLDDRGGN DIPYLTGDERLTAEDNPV | Immune cell | |

-continued

| Payload | Sequence | Target cell/ organ | Preferred delivery formulation |
|---|---|---|---|
| | LLYTYSAGAFSVAASMS DGKVGETSEDDAQEMA VAAAYTFGNYTVGLGY EKIDSPDTALMADMEQL ELAAIAKFGATNVKAYY ADGELDRDFARAVFDLT PVAAAATAVDHKAYGL SVDSTFGATTVGGYVQV LDIDTIDDVTYYGLGAS YDLGGGASIVGGIADND LPNSDMVADLGVKFKF (SEQ ID NO: 21) | | |
| OmpA | MKKTAIAIAVALAGFAT VAQAAPKDNTWYTGAK LGWSQYHDTGFINNNGP THENQLGAGAFGGYQV NPYVGFEMGYDWLGRM PYKGSVENGAYKAQGV QLTAKLGYPITDDLDIYT RLGGMVWRADTKSNVY GKNHDTGVSPVFAGGVE YAITPEIATRLEYQWTNN IGDAHTIGTRPDNGMLSL GVSYRFGQGEAAPVVAP APAPAPEVQTKHFTLKS DVLFNFNKATLKPEGQA ALDQLYSQLSNLDPKDG SVVVLGYTDRIGSDAYN QGLSERRAQSVVDYLIS KGIPADKISARGM GESNPVTGNTCDNVKQR AALIDCLAPDRRVEIEVK GIKDVVTQPQA (SEQ ID NO: 22) | Immune cell | |
| MOMP | AGVATATGTKSATINYH EWQVGASLSYRLNSLVP YIGVQWSRATFDADNIRI AQPKLPTAVLNLTAWNP SLLGNATALSTTDSFSDF (SEQ ID NO: 23) | Immune cell | |
| PepO | MTTYQDDFYQAVNGKW AETAVIPDDKPRTGGFSD LADEIEALMLDTTDAWL AGENIPDDAILKNFVKFH RLVADYAKRDEVGVSPI LPLIEEYQSLKSFSEFVA NIAKYELAGLPNEFPFSV APDFMNAQLNVLWAEA PSILLPDTTYYEEGNEKA EELRGIWRQSQEKLLPQF GFSTEEIKDLLDKVIELD KQLAKYVLSREEGSEYA KLYHPYVWADFKKLAP ELPLDSIFEKILGQVPDK VIVPEERFWTEFAATYYS EANWDLLKANLIVDAA NAYNAYLTDDIRVESGA YSRALSGTPQAMDKQK AAFYLAQGPFSQALGLW YAGQKFSPEAKADVESK VARMIEVYKSRLETADW LAPATREKAITKLNVITP HIGYPEKLPETYAKKVID ESLSLVENAQNLAKITIA HTWSKWNKPVDRSEWH MPAHLVNAYYDPQQNQ IVFPAAILQEPFYSLDQSS SANYGGIGAVIAHEISHA FDTNGASFDEHGSLNDW WTQEDYAAFKERTDKIV AQFDGLESHGAKVNGK LTVSENVADLGGVACAL EAAQSEEDFSARDFFINF | Immune cell | |

| Payload | Sequence | Target cell/organ | Preferred delivery formulation |
|---|---|---|---|
| | ATIWRMKAREEYMQML ASIDVHAPGELRTNVTLT NFDAFHETFDIKEGDAM WRAPKDRVIIW (SEQ ID NO: 24) | | |
| OmpU | MNKTLIALAVSAAAVAT GAYADGINQSGDKAGST VYSAKGTSLEVGGRAEA RLSLKDGKAQDNSRVRL NFLGKAEINDSLYGVGF YEGEFTTNDQGKNASNN SLDNRYTYAGIGGTYGE VTYGKNDGALGVITDFT DIMSYHGNTAAEKIAVA DRVDNMLAYKGQFGDL GVKASYRFADRNAVDA MGNVVTETNAAKYSDN GEDGYSLSAIYTFGDTGF NVGAGYADQDDQNEY MLAASYRMENLYFAGL FTDGELAKDVDYTGYEL AAGYKLGQAAFTATYN NAETAKETSADNFAIDA TYYFKPNFRSYISYQFNL LDSDKVGKVASEDELAI GLRYDF (SEQ ID NO: 25) | Immune cell | |
| Lumazine synthase | MKGGAGVPDLPSLDASG VRLAIVASSWHGKICDA LLDGARKVAAGCGLDD PTVVRVLGAIEPVVAQE LARNHDAVVALGVVIRG QTPHFDYVCDAVTQGLT RVSLDSSTPIANGVLTTN TEEQALDRAGLPTSAED KGAQATVAALATALTLR ELRAHS (SEQ ID NO: 26) | Immune cell | |
| Omp16 | MKKLTKVLLVAGSVAV LAACGSSKKDESAGQMF GGYSVQDLQQRYNTVY FGFDKYNIEGEYVQILDA HAAFLNATPATKVVVEG NTDERGTPEYNIALGQR RADAVKHYLSAKGVQA GQVSTVSYGEEKPAVLG HDEAAYSKNRRAVLAY (SEQ ID NO: 27) | Immune cell | |
| Omp19 | MGISKASLLSLAAAGIVL AGCQSSRLGNLDNVSPP PPPAPVNAVPAGTVQKG NLDSPTQFPNAPSTDMS AQSGTQVASLPPASAPD LTPGAVAGVWNASLGG QSCKIATPQTKYGQGYR AGPLRCPGELANLASWA VNGKQLVLYDANGGTV ASLYSSGQGRFDGQTTG GQAVTLSR (SEQ ID NO: 28) | Immune cell | |
| CobT | MQILADLLNTIPAIDSTA MSRAQRHIDGLLKPVGS LGKLEVLAIQLAGMPGL NGIPHVGKKAVLVMCA DHGVWEEGVAISPKEVT AIQAENMTRGTTGVCVL AEQAGANVHVIDVGIDT AEPIPGLINMRVARGSGN IASAPAMSRRQAEKLLL DVICYTQELAKNGVTLF GVGELGMANTTPAAAIV STITGRDPEEVVGIGANL PTDKLANKIDVVRRAITL | Immune cell | |

| Payload | Sequence | Target cell/organ | Preferred delivery formulation |
|---|---|---|---|
| | NQPNPQDGVDVLAKVG<br>GFDLVGIAGVMLGAASC<br>GLPVLLDGFLSYAAALA<br>ACQMSPAIKPYLIPSHLS<br>AEKGARIALSHLGLEPYL<br>NMEMRLGEGSGAALAM<br>PIIEAACAIYNNMGELAA<br>SNIVLPGNTTSDLNS<br>(SEQ ID NO: 29) | | |
| RpfE | MKNARTTLIAAAIAGTL<br>VTTSPAGIANADDAGLD<br>PNAAAGPDAVGFDPNLP<br>PAPDAAPVDTPPAPEDA<br>GFDPNLPPPLAPDFLSPP<br>AEEAPPVPVAYSVNWD<br>AIAQCESGGNWSINTGN<br>GYYGGLRFTAGTWRAN<br>GGSGSAANASREEQIRV<br>AENVLRSQGIRAWWPVCG<br>RRG (SEQ ID NO: 30) | Immune cell | |
| Rv0652 | MAKLSTDELLDAFKEMT<br>LLELSDFVKKFEETFEVT<br>AAAPVAVAAAGAAPAG<br>AAVEAAEEQSEFDVILE<br>AAGDKKIGVIKVVREIVS<br>GLGLKEAKDLVDGAPKP<br>LLEKVAKEAADEAKAK<br>LEAAGATVTVK<br>(SEQ ID NO: 31) | Immune cell | |
| HBHA | MAENSNIDDIKAPLLAA<br>LGAADLALATVNELITN<br>LRERAEETRTDTRSRVEE<br>SRARLTKLQEDLPEQLTE<br>LREKFTAEELRKAAEGY<br>LEAATSRYNELVERGEA<br>ALERLRSQQSFEEVSAR<br>AEGYVDQAVELTQEAL<br>GTVASQTRAVGERAAKL<br>VGIELPKKAAPAKKAAP<br>AKKAAPAAKKAAAKKAP<br>AKKAAAKKVTQK<br>(SEQ ID NO: 32) | Immune cell | |
| NhhA | MNKIYRIIWNSALNAWV<br>AVSELTRNHTKRASATV<br>ATAVLATLLFATVQAST<br>TDDDDLYLEPVQRTAVV<br>LSFRSDKEGTGEKEVTE<br>DSNWGVYFDKKGVLTA<br>GTITLKAGDNLKIKQNT<br>NENTNASSFTYSLKKDL<br>TDLTSVGTEKLSFSANSN<br>KVNITSDTKGLNFAKKT<br>AETNGDTTVHLNGIGST<br>LTDTLLNTGATTNVTND<br>NVTDDEKKRAASVKDV<br>LNAGWNIKGVKPGTTAS<br>DNVDFVRTYDTVEFLSA<br>DTKTTTVNVESKDNGKR<br>TEVKIGAKTSVIKEKDG<br>KLVTGKDKGENDSSTDK<br>GEGLVTAKEVIDAVNKA<br>GWRMKTTTANGQTGQA<br>DKFETVTSGTNVTFASG<br>KGTTATVSKDDQGNITV<br>MYDVNVGDALNVNQLQ<br>NSGWNLDSKAVAGSSG<br>KVISGNVSPSKGKMDET<br>VNINAGNNIEITRNGKNI<br>DIATSMTPQFSSVSLGAG<br>ADAPTLSVDDEGALNVG<br>SKDNAKPVRITNVAPGV<br>KEGDVTNVAQLKGVAQ | Immune cell | |

-continued

| Payload | Sequence | Target cell/ organ | Preferred delivery formulation |
|---|---|---|---|
| | NLNNHIDNVDGNARAGI AQAIATAGLVQAYLPGK SMMAIGGGTYRGEAGY AIGYSSISDGGNWIIKGT ASGNSRGHFGASASVGY QW (SEQ ID NO: 33) | | |
| DnaJ | MAKQDYYEILGVSKTAE EREIRKAYKRLAMKYHP DRNQGDKEAEAKFKEIK EAYEVLTDSQKRAAYD QYGHAAFEQGGMGGGG FGGGADGSDIFGDVFGDI FGGGRGRQRAARGADL RYNMELTLEEAVRGVTK EIRIPTLEECDVCHGSGA KPGTQPQTCPTCHGSGQ VQMRQGFFAVQQTCPH CQGRGTLIKDPCNKCHG HGRVERSKTLSVKIPAG VDTGDRIRLAGEGEAGE HGAPAGDLYVQVQVKQ HPIFEREGNNLYCEVPIN FAMAALGGEIEVPTLDG RVKLKVPGETQTGKLFR MRGKGVKSVRGGAQGD LLCRVVVETPVGLNERQ KQLLQELQESFGGPTGE HNSPRSKSFFDGVKKFF DDLTR (SEQ ID NO: 34) | Immune cell | |
| Pneumo-lysin | MANKAVNDFILAMNYD KKKLLTHQGESIENRFIK EGNQLPDEFVVIERKKRS LSTNTSDISVTATNDSRL YPGALLVVDETLLENNP TLLAVDRAPMTYSIDLP GLASSDSFLQVEDPSNSS VRGAVNDLLAKWHQDY GQVNNVPARMQYEKIT AHSMEQLKVKFGSDFEK TGNSLDIDFNSVHSGEK QIQIVNFKQIYYTVSVDA VKNPGDVFQDTVTVEDL KQRGISAERPLVYISSVA YGRQVYLKLETTSKSDE VEAAFEALIKGVKVAPQ TEWKQILDNTEVKAVIL GGDPSSGARVVTGKVD MVEDLIQEGSRFTADHP GLPISYTTSFLRDNVVAT FQNSTDYVETKVTAYRN GDLLLDHSGAYVAQYYI TWDELSYDHQGEVLTP KAWDRNGQDLTAHFTT SIPLKGNVRNLSVKIREC TGLAWEWWRTVYEKTD LPLVRKRTISIWGTTLYP QVEDKVEND (SEQ ID NO: 35) | Immune cell | |
| *Flagellin* (FLIC_ *ECOLI Flagellin* OS = *Escherichia coli* (strain K12)) | MAQVINTNSLSLITQNNI NKNQSALSSSIERLSSGL RINSAKDDAAGQAIANR FTSNIKGLTQAARNAND GISVAQTTEGALSEINNN LQRVRELTVQATTGTNS ESDLSSIQDEIKSRLDEID RVSGQTQFNGVNVLAK NGSMKIQVGANDNQTIT IDLKQIDAKTLGLDGFSV KNNDTVTTSAPVTAFGA TTTNNIKLTGITLSTEAA TDTGGTNPASIEGVYTD NGNDYYAKITGGDNDG KYYAVTVANDGTVTMA | Immune cell | |

-continued

| Payload | Sequence | Target cell/organ | Preferred delivery formulation |
|---|---|---|---|
| | TGATANATVTDANTTK ATTITSGGTPVQIDNTAG SATANLGAVSLVKLQDS KGNDTDTYALKDTNGN LYAADVNETTGAVSVKT ITYTDSSGAASSPTVAVKL GGDDGKTEVVDIDGKTY DSADLNGGNLQTGLTAG GEALTAVANGKTTDPLK ALDDAIASVDKFRSSLG AVQNRLDSAVTNLNNTT TNLSEAQSRIQDADYAT EVSNMSKAQIIQQAGNS VLAKANQVPQQVLSLLQ G (SEQ ID NO: 36) | | |
| IFN-alpha (IFNA1_HUMAN Interferon alpha-1/13) | MASPFALLMVLVVLSCK SSCSLGCDLPETHSLDNR RTLMLLAQMSRISPSSCL MDRHDFGFPQEEFDGNQ FQKAPAISVLHELIQQFN LFTTKDSSAAWDEDLLD KFCTELYQQLNDLEACV MQEERVGETPLMNADSI LAVKKYFRRITLYLTEK KYSPCAWEVVRAEIMRS LSLSTNLQERLRRKE (SEQ ID NO: 37) | Immune cell | |
| IFN-gamma (IFNG_HUMAN Interferon gamma) | MKYTSYILAFQLCIVLGS LGCYCQDPYVKEAENLK KYFNAGHSDVADNGTLF LGILKNWKEESDRKIMQ SQIVSFYFKLFKNFKDDQ SIQKSVETIKEDMNVKFF NSNKKKRDDFEKLTNYS VTDLNVQRKAIHELIQV MAELSPAAKTGKRKRSQ MLFRGRRASQ (SEQ ID NO: 38) | | |
| IL-2 (IL2_HUMAN Interleukin-2) | MYRMQLLSCIALSLALV TNSAPTSSSTKKTQLQLE HLLLDLQMILNGINNYK NPKLTRMLTFKFYMPKK ATELKHLQCLEEELKPLE EVLNLAQSKNFHLRPRD LISNINVIVLELKGSETTF MCEYADETATIVEFLNR WITFCQSIISTLT (SEQ ID NO: 39) | Immune cell | |
| Interleukin-12 p35 subunit | MWPPGSASQPPPSPAAA TGLHPAARPVSLQCRLS MCPAR (SEQ ID NO: 40) | Immune cell | |
| p40 | MGKKQNRKTGNSKTQS ASPPPKERSSSPATEQSW MENDFDELREEGFRRSN YSELREDIQTKGKEVENF EKNLEECITRISNTEKCL KELMELKTKTRELREEC RSLRSRCDQLEERVSAM EDEMNEMKREGKFREK RIKRNEQTLQEIWDYVK RPNLRLIGVPESDVENGT KLENTLQDIIQENFPNLA RQANVQIQEIQRTPQRYS SRRATPRHIIVRFTKVEM KEKMLRAAREKGRVTL KGKPIRLTADLLAETLQ | Immune cell | |

-continued

| Payload | Sequence | Target cell/organ | Preferred delivery formulation |
|---|---|---|---|
| | ARREWGPIFNILKGKNF<br>QPRISYPAKLSFISEGEIK<br>YFIDKQMLRDFVTTRPA<br>LKELLKEALNMERNNRY<br>QLLQNHAKM<br>(SEQ ID NO: 41) | | |
| IL-15<br>(1L15_<br>HUMAN<br>Interleukin-<br>15) | MRISKPHLRSISIQCYLCL<br>LLNSHFLTEAGIHVFILG<br>CFSAGLPKTEANWVNVI<br>SDLKKIEDLIQSMHIDAT<br>LYTESDVHPSCKVTAMK<br>CFLLELQVISLESGDASIH<br>DTVENLIILANNSLSSNG<br>NVTESGCKECEELEEKNI<br>KEFLQSFVHIVQMFINTS<br>(SEQ ID NO: 42) | Immune<br>cell | |
| IL-18<br>(IL18_<br>HUMAN<br>Interleukin-<br>18) | MAAEPVEDNCINFVAM<br>KFIDNTLYFIAEDDENLE<br>SDYFGKLESKLSVIRNLN<br>DQVLFIDQGNRPLFEDM<br>TDSDCRDNAPRTIFIISM<br>YKDSQPRGMAVTISVKC<br>EKISTLSCENKIISFKEMN<br>PPDNIKDTKSDIIFFQRSV<br>PGHDNKMQFESSSYEGY<br>FLACEKERDLFKLILKKE<br>DELGDRSIMFTVQNED<br>(SEQ ID NO: 43) | | |
| IL-21 | MRSSPGNMERIVICLMVI<br>FLGTLVHKSSSQGQDRH<br>MIRMRQLIDIVDQLKNY<br>VNDLVPEFLPAPEDVET<br>NCEWSAFSCFQKAQLKS<br>ANTGNNERIINVSIKKLK<br>RKPPSTNAGRRQKHRLT<br>CPSCDSYEKKPPKEFLER<br>FKSLLQKMIHQHLSSRT<br>HGSEDS<br>(SEQ ID NO: 44) | Immune<br>cell | |
| GM-CSF | MWLQSLLLLGTVACSIS<br>APARSPSPSTQPWEHVN<br>AIQEARRLLNLSRDTAA<br>EMNETVEVISEMFDLQE<br>PTCLQTRLELYKQGLRG<br>SLTKLKGPLTMMASHYK<br>QHCPPTPETSCATQIITFE<br>SFKENLKDFLLVIPFDCW<br>EPVQE (SEQ ID NO: 45) | Immune<br>cell | |
| IL-1beta | MAEVPELASEMMAYYS<br>GNEDDLFFEADGPKQM<br>KCSFQDLDLCPLDGGIQL<br>RISDHHYSKGFRQAASV<br>VVAMDKLRKMLVPCPQ<br>TFQENDLSTFFPFIFEEEPI<br>FFDTWDNEAYVHDAPV<br>RSLNCTLRDSQQKLSVM<br>SGPYELKALHLQGQDME<br>QQVVFSMSFVQGEESND<br>KIPVALGLKEKNLYLSC<br>VLKDDKPTLQLESVDPK<br>NYPKKKMEKRFVFNKIE<br>INNKLEFESAQFPNWYIS<br>TSQAENMPVFLGGTKGG<br>QDITDFTMQFVSS<br>(SEQ ID NO: 46) | Immune<br>cell | |
| IL-6 | MNSFSTSAFGPVAFSLGL<br>LLVLPAAFPAPVPPGEDS<br>KDVAAPHRQPLTSSERID<br>KQIRYILDGISALRKETC<br>NKSNMCESSKEALAENN | Immune<br>cell | |

-continued

| Payload | Sequence | Target cell/organ | Preferred delivery formulation |
|---|---|---|---|
| | LNLPKMAEKDGCFQSGF NEETCLVKIITGLLEFEV YLEYLQNRFESSEEQAR AVQMSTKVLIQFLQKKA KNLDAITTPDPTTNASLL TKLQAQNQWLQDMTTH LILRSFKEFLQSSLRALR QM (SEQ ID NO: 47) | | |
| TNF-a | MSTESMIRDVELAEEAL PKKTGGPQGSRRCLFLSL FSFLIVAGATTLFCLLHF GVIGPQREEFPRDLSLISP LAQAVRSSSRTPSDKPV AHVVANPQAEGQLQWL NRRANALLANGVELRD NQLVVPSEGLYIYSQVL FKGQGCPSTHVLLTHTIS RIAVSYQTKVNLLSAIKS PCQRETPEGAEAKPWYE PIYLGGVFQLEKGDRLS AEINRPDYLDFAESGQV YFGIIAL (SEQ ID NO: 48) | Immune cell | |
| IL-7 | MFHVSFRYIFGLPPLILV LLPVASSDCDIEGKDGK QYESVLMVSIDQLLDSM KEIGSNCLNNEFNFFKRH ICDANKEGMFLFRAARK LRQFLKMNSTGDFDLHL LKVSEGTTILLNCTGQV KGRKPAALGEAQPTKSL EENKSLKEQKKLNDLCF LKRLLQEIKTCWNKILM GTKEH (SEQ ID NO: 49) | Immune cell | |
| IL-17a | MTPGKTSLVSLLLLLSLE AIVKAGITIPRNPGCPNSE DKNFPRTVMVNLNIHNR NTNTNPKRSSDYYNRST SPQNLHRNEDPERYPSVI WEAKCRHLGCINADGN VDYHMNSVPIQQEILVL RREPPHCPNSFRLEKILV SVGCTCVTPIVHHVA (SEQ ID NO: 50) | Immune cell | |
| FLt3-ligand | MTVLAPAWSPTTYLLLL LLLSSGLSGTQDCSFQHS PISSDFAVKIRELSDYLL QDYPVTVASNLQDEELC GGLWRLVLAQRWMERL KTVAGSKMQGLLERVN TEIHFVTKCAFQPPPSCL RFVQTNISRLLQETSEQL VALKPWITRQNFSRCLE LQCQPDSSTLPPPWSPRP LEATAPTAPQPPLLLLL LPVGLLLLAAAWCLHW QRTRRRTPRPGEQVPPVP SPQDLLLVEH (SEQ ID NO: 51) | Immune cell | |
| anti-CTLA4 (ipilumi-mab) | QVQLVESGGGVVQPGRS LRLSCAASGFTFSSYTM HWVRQAPGKGLEWVTF ISYDGNNKYYADSVKGR FTISRDNSKNTLYLQMN SLRAEDTAIYYCARTGW LGPFDYWGQGTLVTVSS AS TKGPSVFPLAPSSKSTSG GTAALGCLVKDYFPEPV TVSWNSGALTSGVHTFP AVLQSSGLYSLSSVVTVP | Immune cell | |

| Payload | Sequence | Target cell/organ | Preferred delivery formulation |
|---|---|---|---|
| | SSSLGTQTYICNVNHKPS<br>NTKVDKRVEPKSCDKTH<br>TCPPCPAPELLGGPSVFL<br>FPPKPKDTLMISRTPEVT<br>CVVVDVSHEDPEVKFN<br>WYVDGVEVHNAKTKPR<br>EEQYNST<br>YRVVSVLTVLHQDWLN<br>GKEYKCKVSNKALPAPI<br>EKTISKAKGQPREPQVY<br>TLPPSRDELTKNQVSLTC<br>LVKGFYPSDIAVEWESN<br>GQPENNYKTTPPVLDSD<br>GSFFLYSKLTVDKSRWQ<br>QGNVFSCSVMHEALHN<br>HYTQKSLSLSPGK<br>(SEQ ID NO: 52) | | |
| anti-PD1<br>(nivo) | QVQLVESGGGVVQPGRS<br>LRLDCKASGITFSNSGM<br>HWVRQAPGKGLEWVAV<br>IWYDGSKRYYADSVKG<br>RFTISRDNSKNTLFLQMN<br>SLRAEDTAVYYCATNDD<br>YWGQGTLVTVSSASTKG<br>PSVFPLAPCSRSTSESTA<br>ALGCLVKDYFPEPVTVS<br>WNSGALTSGVHTFPAVL<br>QSSGLYSLSSVVTVPSSS<br>LGTKTYTCNVDHKPSNT<br>KVDKRVESKYGPPCPPC<br>PAPEFLGGPSVFLFPPKP<br>KDTLMISRTPEVTCVVV<br>DVSQEDPEVQFNWYVD<br>GVEVHNAKTKPREEQFN<br>STYRVVSVLTVLHQDWL<br>NGKEYKCKVSNKGLPSS<br>IEKTISKAKGQPREPQVY<br>TLPPSQEEMTKNQVSLT<br>CLVKGFYPSDIAVEWES<br>NGQPENNYKTTPPVLDS<br>DGSFFLYSRLTVDKSRW<br>QEGNVFSCSVMHEALHN<br>HYTQKSLSLSLGK<br>(SEQ ID NO: 53) | Immune cell | |
| anti-41BB<br>(utomilumab) | EVQLVQSGAEVKKPGES<br>LRISCKGSGYSFSTYWIS<br>WVRQMPGKGLEWMGKI<br>YPGDSYTNYSPSFQGQV<br>TISADKSISTAYLQWSSL<br>KASDTAMYYCARGYGIF<br>DYWGQGTLVTVSSADTK<br>GPSVFPLAPCSRSTSEST<br>AALGCLVKDYFPEPVTV<br>SWNSGALTSGVHTFPAV<br>LQSSGLYSLSSVVTVPSS<br>NFGTQTYTCNVDHKPSN<br>TKVDKTVERKCCVECPP<br>CPAPPVAGPSVFLFPPKP<br>KDTLMISRTPEVTCVVV<br>DVSHEDPEVQFNWYVD<br>GVEVHNAKTKPREEQFN<br>STFRVVSVLTVVHQDWL<br>NGKEYKCKVSNKGLPAP<br>IEKTISKTKGQPREPQVY<br>TLPPSREEMTKNQVSLT<br>CLVKGFYPSDIAVEWES<br>NGQPENNYKTTPPMLDS<br>DGSFFLYSKLTVDKSRW<br>QQGNVFSCSVMHEALH<br>NHYTQKSLSLSPGK<br>(SEQ ID NO: 54) | Immune cell | |

In some embodiments, the expression sequence encodes a therapeutic protein. In some embodiments, the expression sequence encodes a cytokine, e.g., IL-12p70, IL-15, IL-2, IL-18, IL-21, IFN-α, IFN-β, IL-10, TGF-beta, IL-4, or IL-35, or a functional fragment thereof. In some embodiments, the expression sequence encodes an immune checkpoint inhibitor. In some embodiments, the expression sequence encodes an agonist (e.g., a TNFR family member such as CD137L, OX40L, ICOSL, LIGHT, or CD70). In some embodiments, the expression sequence encodes a chimeric antigen receptor. In some embodiments, the expression sequence encodes an inhibitory receptor agonist (e.g., PDL1, PDL2, Galectin-9, VISTA, B37H4, or MHCII) or inhibitory receptor (e.g., PD1, CTLA4, TIGIT, LAG3, or TTM3). In some embodiments, the expression sequence encodes an inhibitory receptor antagonist. In some embodiments, the expression sequence encodes one or more TCR chains (alpha and beta chains or gamma and delta chains). In some embodiments, the expression sequence encodes a secreted T cell or immune cell engager (e.g., a bispecific antibody such as BiTE, targeting, e.g., CD3, CD137, or CD28 and a tumor-expressed protein e.g., CD19, CD20, or BCMA etc.). In some embodiments, the expression sequence encodes a transcription factor (e.g., FOXP3, HELIOS, TOX1, or TOX2). In some embodiments, the expression sequence encodes an immunosuppressive enzyme (e.g., IDO or CD39/CD73). In some embodiments, the expression sequence encodes a GvHD (e.g., anti-HLA-A2 CAR-Tregs).

In some embodiments, a polynucleotide encodes a protein that is made up of subunits that are encoded by more than one gene. For example, the protein may be a heterodimer, wherein each chain or subunit of the protein is encoded by a separate gene. It is possible that more than one circRNA molecule is delivered in the transfer vehicle and each circRNA encodes a separate subunit of the protein. Alternatively, a single circRNA may be engineered to encode more than one subunit. In certain embodiments, separate circRNA molecules encoding the individual subunits may be administered in separate transfer vehicles.

A. Antigen-Recognition Receptors
a. Chimeric Antigen Receptors (Cars)

Chimeric antigen receptors (CARs or CAR-Ts) are genetically-engineered receptors. These engineered receptors may be inserted into and expressed by immune cells, including T cells via circular RNA as described herein. With a CAR, a single receptor may be programmed to both recognize a specific antigen and, when bound to that antigen, activate the immune cell to attack and destroy the cell bearing that antigen. When these antigens exist on tumor cells, an immune cell that expresses the CAR may target and kill the tumor cell. In some embodiments, the CAR encoded by the polynucleotide comprises (i) an antigen-binding molecule that specifically binds to a target antigen, (ii) a hinge domain, a transmembrane domain, and an intracellular domain, and (iii) an activating domain.

In some embodiments, an orientation of the CARs in accordance with the disclosure comprises an antigen binding domain (such as an scFv) in tandem with a costimulatory domain and an activating domain. The costimulatory domain may comprise one or more of an extracellular portion, a transmembrane portion, and an intracellular portion. In other embodiments, multiple costimulatory domains may be utilized in tandem.

i. Antigen Binding Domain

CARs may be engineered to bind to an antigen (such as a cell-surface antigen) by incorporating an antigen binding molecule that interacts with that targeted antigen. In some embodiments, the antigen binding molecule is an antibody fragment thereof, e.g., one or more single chain antibody fragment (scFv). An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45: 131-136. An scFv retains the parent antibody's ability to specifically interact with target antigen. scFvs are useful in chimeric antigen receptors because they may be engineered to be expressed as part of a single chain along with the other CAR components. Id. See also Krause et al., J. Exp. Med., Volume 188, No. 4, 1998 (619-626); Finney et al., Journal of Immunology, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the invention, with specificity to more than one target of interest.

In some embodiments, the antigen binding molecule comprises a single chain, wherein the heavy chain variable region and the light chain variable region are connected by a linker. In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids.

In some embodiments, the antigen binding molecule comprises a nanobody. In some embodiments, the antigen binding molecule comprises a DARPin. In some embodiments, the antigen binding molecule comprises an anticalin or other synthetic protein capable of specific binding to target protein.

In some embodiments, the CAR comprises an antigen binding domain specific for an antigen selected from the group CD19, CD123, CD22, CD30, CD171, CS-1, C-type lectin-like molecule-1, CD33, epidermal growth factor receptor variant III (EGFRvIII), ganglioside G2 (GD2), ganglioside GD3, TNF receptor family member B cell maturation (BCMA), Tn antigen ((Tn Ag) or (GaINAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EP-CAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, HER2, HER3, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), thyroid stimulating hormone receptor (TSHR), G protein-coupled receptor class C group 5, member D (GPRC5D), chromosome X open reading frame 61 (CXORF61), CD97, CD179a, anaplastic lymphoma kinase (ALK), Polysialic acid, placenta-specific 1 (PLAC1), hexasaccharide portion of globoH glycoceramide (GloboH), mammary gland differentiation antigen (NY—BR-1), uroplakin 2 (UPK2), Hepatitis A virus cellular receptor 1 (HAVCR1), adrenoceptor beta 3 (ADRB3), pannexin 3 (PANX3), G protein-coupled receptor 20 (GPR20), lymphocyte antigen 6 complex, locus K 9 (LY6K), Olfactory receptor 51E2 (OR51E2), TCR Gamma Alternate Reading Frame Protein (TARP), Wilms tumor protein (WTi), Cancer/testis antigen 1 (NY-ESO1), Cancer/testis antigen 2 (LAGE-1a), MAGE family members (including MAGE-A1, MAGE-A3 and MAGE-A4), ETS translocation-variant gene 6, located on chromosome 12p (ETV6-AML), sperm protein 17 (SPA17), X Antigen Family, Member 1A (XAGE1), angiopoietin-binding cell surface receptor 2 (Tie 2), melanoma cancer testis antigen-1 (MAD-CT-1), melanoma cancer testis antigen-2 (MAD-CT-2), Fos-related antigen 1, tumor protein p53 (p53), p53 mutant, prostein, surviving, telomerase, prostate carcinoma tumor antigen-1, melanoma antigen recognized by T cells 1, Rat sarcoma (Ras) mutant, human Telomerase reverse transcriptase (hTERT), sarcoma translocation breakpoints, melanoma inhibitor of apoptosis (ML-IAP), ERG (transmembrane protease, serine 2 (TMPRSS2) ETS fusion gene), N-Acetyl glucosaminyl-transferase V (NA17), paired box protein Pax-3 (PAX3), Androgen receptor, Cyclin B1, v-myc avian myelocytomatosis viral oncogene neuroblastoma derived homolog (MYCN), Ras Homolog Family Member C (RhoC), Tyrosinase-related protein 2 (TRP-2), Cytochrome P450 1B1 (CYP1B1), CCCTC-Binding Factor (Zinc Finger Protein)-Like, Squamous Cell Carcinoma Antigen Recognized By T Cells 3 (SART3), Paired box protein Pax-5 (PAX5), proacrosin binding protein sp32 (OY-TES1), lymphocyte-specific protein tyrosine kinase (LCK), A kinase anchor protein 4 (AKAP-4), synovial sarcoma, X breakpoint 2 (SSX2), Receptor for Advanced Glycation Endproducts (RAGE-1), renal ubiquitous 1 (RU1), renal ubiquitous 2 (RU2), legumain, human papilloma virus E6 (HPV E6), human papilloma virus E7 (HPV E7), intestinal carboxyl esterase, heat shock protein 70-2 mutated (mut hsp70-2), CD79a, CD79b, CD72, Leukocyte-associated immunoglobulin-like receptor 1 (LAIR1), Fc fragment of IgA receptor (FCAR or CD89), Leukocyte immunoglobulin-like receptor subfamily A member 2 (LILRA2), CD300 molecule-like family member f (CD300LF), C-type lectin domain family 12 member A (CLECi2A), bone marrow stromal cell antigen 2 (BST2), EGF-like module-containing mucin-like hormone receptor-like 2 (EMR2), lymphocyte antigen 75 (LY75), Glypican-3 (GPC3), Fc receptor-like 5 (FCRL5), MUC16, 5T4, 8H9, avpE) integrin, avR6 integrin, alphafetoprotein (AFP), B7-H6, ca-125, CA9, CD44, CD44v7/8, CD52, E-cadherin, EMA (epithelial membrane antigen), epithelial glycoprotein-2 (EGP-2), epithelial glycoprotein-40 (EGP-40), ErbB4, epithelial tumor antigen (ETA), folate binding protein (FBP), kinase insert domain receptor (KDR), k-light chain, L1 cell adhesion molecule, MUC18, NKG2D, oncofetal antigen (h5T4), tumor/testis-antigen 1B, GAGE, GAGE-1, BAGE, SCP-1, CTZ9, SAGE, CAGE, CT10, MART-1, immunoglobulin lambda-like polypeptide 1 (IGLL1), Hepatitis B Surface Antigen Binding Protein (HBsAg), viral capsid antigen (VCA), early antigen (EA), EBV nuclear antigen (EBNA), HHV-6 p41 early antigen, HHV-6B U94 latent antigen, HHV-6B p98 late antigen, cytomegalovirus (CMV) antigen, large T antigen, small T antigen, adenovirus antigen, respiratory syncytial virus (RSV) antigen, haemagglutinin (HA), neuraminidase (NA), parainfluenza type 1 antigen, parainfluenza type 2 antigen, parainfluenza type 3 antigen, parainfluenza type 4 antigen, Human Metapneumovirus (HMPV) antigen, hepatitis C virus (HCV) core antigen, HIV p24 antigen, human T-cell lympotrophic virus (HTLV-1) antigen, Merkel cell polyoma virus small T antigen, Merkel cell polyoma virus large T antigen, Kaposi sarcoma-associated herpesvirus (KSHV) lytic nuclear antigen and KSHV latent nuclear antigen.

ii. Hinge Spacer Domain

In some embodiments, a CAR of the instant disclosure comprises a hinge or spacer domain. In some embodiments, the hinge/spacer domain may comprise a truncated hinge/spacer domain (THD) the THD domain is a truncated version of a complete hinge/spacer domain ("CHD"). In some embodiments, an extracellular domain is from or derived from (e.g., comprises all or a fragment of) ErbB2, glycophorin A (GpA), CD2, CD3 delta, CD3 epsilon, CD3 gamma, CD4, CD7, CD8a, CD8[T CD11a (IT GAL), CD11b (IT GAM), CD11c (ITGAX), CD11d (IT GAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-11B), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRT AM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof. A hinge or spacer domain may be derived either from a natural or from a synthetic source.

In some embodiments, a hinge or spacer domain is positioned between an antigen binding molecule (e.g., an scFv) and a transmembrane domain. In this orientation, the hinge/spacer domain provides distance between the antigen binding molecule and the surface of a cell membrane on which the CAR is expressed. In some embodiments, a hinge or spacer domain is from or derived from an immunoglobulin. In some embodiments, a hinge or spacer domain is selected from the hinge/spacer regions of IgG1, IgG2, IgG3, IgG4, IgA, IgD, IgE, IgM, or a fragment thereof. In some embodiments, a hinge or spacer domain comprises, is from, or is derived from the hinge/spacer region of CD8 alpha. In some embodiments, a hinge or spacer domain comprises, is from, or is derived from the hinge/spacer region of CD28. In some embodiments, a hinge or spacer domain comprises a fragment of the hinge/spacer region of CD8 alpha or a fragment of the hinge/spacer region of CD28, wherein the fragment is anything less than the whole hinge/spacer region. In some embodiments, the fragment of the CD8 alpha hinge/spacer region or the fragment of the CD28 hinge/spacer region comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of the CD8 alpha hinge/spacer region, or of the CD28 hinge/spacer region.

iii. Transmembrane Domain

The CAR of the present disclosure may further comprise a transmembrane domain and/or an intracellular signaling domain. The transmembrane domain may be designed to be fused to the extracellular domain of the CAR. It may similarly be fused to the intracellular domain of the CAR. In some embodiments, the transmembrane domain that naturally is associated with one of the domains in a CAR is used. In some instances, the transmembrane domain may be selected or modified (e.g., by an amino acid substitution) to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein.

Transmembrane regions may be derived from (i.e. comprise) a receptor tyrosine kinase (e.g., ErbB2), glycophorin A (GpA), 4-1BB/CD137, activating NK cell receptors, an immunoglobulin protein, B7-H3, BAFFR, BFAME (SEAMF8), BTEA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (EIGHTR), IA4, ICAM-1, ICAM-1, Ig alpha (CD79a), IE-2R beta, IE-2R gamma, IE-7R alpha, inducible T cell costimulator (ICOS), integrins, ITGA4, ITGA4, ITGA6, IT GAD, ITGAE, ITGAE, IT GAM, ITGAX, ITGB2, ITGB7, ITGB1, KIRDS2, EAT, LFA-1, LFA-1, a ligand that specifically binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Lyl08), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

In some embodiments, suitable intracellular signaling domain include, but are not limited to, activating Macrophage/Myeloid cell receptors CSFR1, MYD88, CD14, TIE2, TLR4, CR3, CD64, TREM2, DAP10, DAP12, CD169, DECTIN 1, CD206, CD47, CD163, CD36, MARCO, TIM4, MERTK, F4/80, CD91, CIQR, LOX-1, CD68, SRA, BAI-1, ABCA7, CD36, CD31, Lactoferrin, or a fragment, truncation, or combination thereof.

In some embodiments, a receptor tyrosine kinase may be derived from (e.g., comprise) Insulin receptor (InsR), Insulin-like growth factor I receptor (IGF1R), Insulin receptor-related receptor (IRR), platelet derived growth factor receptor alpha (PDGFRa), platelet derived growth factor receptor beta (PDGFRfi). KIT proto-oncogene receptor tyrosine kinase (Kit), colony stimulating factor 1 receptor (CSFR), fms related tyrosine kinase 3 (FLT3), fms related tyrosine kinase 1 (VEGFR-1), kinase insert domain receptor (VEGFR-2), fms related tyrosine kinase 4 (VEGFR-3), fibroblast growth factor receptor 1 (FGFR1), fibroblast growth factor receptor 2 (FGFR2), fibroblast growth factor receptor 3 (FGFR3), fibroblast growth factor receptor 4 (FGFR4), protein tyrosine kinase 7 (CCK4), neurotrophic receptor tyrosine kinase 1 (trkA), neurotrophic receptor tyrosine kinase 2 (trkB), neurotrophic receptor tyrosine kinase 3 (trkC), receptor tyrosine kinase like orphan receptor 1 (ROR1), receptor tyrosine kinase like orphan receptor 2 (ROR2), muscle associated receptor tyrosine kinase (MuSK), MET proto-oncogene, receptor tyrosine kinase (MET), macrophage stimulating 1 receptor (Ron), AXL receptor tyrosine kinase (Axl), TYR03 protein tyrosine kinase (Tyro3), MER proto-oncogene, tyrosine kinase (Mer), tyrosine kinase with immunoglobulin like and EGF like domains 1 (TIE1), TEK receptor tyrosine kinase (TIE2), EPH receptor A1 (EphA1), EPH receptor A2 (EphA2), (EPH receptor A3) EphA3, EPH receptor A4 (EphA4), EPH receptor A5 (EphA5), EPH receptor A6 (EphA6), EPH receptor A7 (EphA7), EPH receptor A8 (EphA8), EPH receptor A10 (EphA10), EPH receptor B1 (EphB1), EPH receptor B2 (EphB2), EPH receptor B3 (EphB3), EPH receptor B4 (EphB4), EPH receptor B6 (EphB6), ret proto oncogene (Ret), receptor-like tyrosine kinase (RYK), discoidin domain receptor tyrosine kinase 1 (DDR1), discoidin domain receptor tyrosine kinase 2 (DDR2), c-ros oncogene 1, receptor tyrosine kinase (ROS), apoptosis associated tyrosine kinase (Lmr1), lemur tyrosine kinase 2 (Lmr2), lemur tyrosine kinase 3 (Lmr3), leukocyte receptor tyrosine kinase (LTK), ALK receptor tyrosine kinase (ALK), or serine/threonine/tyrosine kinase 1 (STYK1).

iv. Costimulatory Domain

In certain embodiments, the CAR comprises a costimulatory domain. In some embodiments, the costimulatory domain comprises 4-1BB (CD137), CD28, or both, and/or an intracellular T cell signaling domain. In a preferred embodiment, the costimulatory domain is human CD28, human 4-1BB, or both, and the intracellular T cell signaling domain is human CD3 zeta (ζ). 4-1BB, CD28, CD3 zeta may comprise less than the whole 4-1BB, CD28 or CD3 zeta, respectively. Chimeric antigen receptors may incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Amur. Rev. Pharmacol. Toxicol. 56:59-83 (2016).

v. Intracellular Signalling Domain

The intracellular (signaling) domain of the engineered T cells disclosed herein may provide signaling to an activating domain, which then activates at least one of the normal effector functions of the immune cell. Effector function of a T cell, for example, may be cytolytic activity or helper activity including the secretion of cytokines.

In some embodiments, suitable intracellular signaling domain include (e.g., comprise), but are not limited to 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD 19a, CD2, CD247, CD27, CD276 (B7-H3), CD28, CD29, CD3 elta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), integrins, ITGA4, ITGA6, ITGAD, ITGAE, ITGAL, ITGAM, ITGAX, ITGB2, ITGB7, ITGB1, KIRDS2, LAT, LFA-1, ligand that specifically binds with CD83, LIGHT, LTBR, Ly9 (CD229), Ly108, lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

CD3 is an element of the T cell receptor on native T cells, and has been shown to be an important intracellular activating element in CARs. In some embodiments, the CD3 is CD3 zeta.

b. T-Cell Receptors (TCR)

TCRs are described using the International Immunogenetics (IMGT) TCR nomenclature, and links to the IMGT public database of TCR sequences. Native alpha-beta heterodimeric TCRs have an alpha chain and a beta chain. Broadly, each chain may comprise variable, joining and constant regions, and the beta chain also usually contains a short diversity region between the variable and joining regions, but this diversity region is often considered as part of the joining region. Each variable region may comprise three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number. Thus "TRAV21" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. In the same way, "TRBV5-1" defines a TCR Vβ region having unique framework and CDR1 and CDR2 sequences, but with only a partly defined CDR3 sequence.

The joining regions of the TCR are similarly defined by the unique IMGT TRAJ and TRBJ nomenclature, and the constant regions by the IMGT TRAC and TRBC nomenclature.

The beta chain diversity region is referred to in IMGT nomenclature by the abbreviation TRBD, and, as mentioned, the concatenated TRBD/TRBJ regions are often considered together as the joining region.

The unique sequences defined by the IMGT nomenclature are widely known and accessible to those working in the TCR field. For example, they can be found in the IMGT public database. The "T cell Receptor Factsbook", (2001) LeFranc and LeFranc, Academic Press, ISBN 0-12-441352-8 also discloses sequences defined by the IMGT nomenclature, but because of its publication date and consequent time-lag, the information therein sometimes needs to be confirmed by reference to the IMGT database.

Native TCRs exist in heterodimeric αβ or γδ forms. However, recombinant TCRs consisting of αα or ββ homodimers have previously been shown to bind to peptide MHC molecules. Therefore, the TCR of the invention may be a heterodimeric αβ TCR or may be an αα or ββ homodimeric TCR.

For use in adoptive therapy, an αβ heterodimeric TCR may, for example, be transfected as full length chains having both cytoplasmic and transmembrane domains. In certain embodiments TCRs of the invention may have an introduced disulfide bond between residues of the respective constant domains, as described, for example, in WO 2006/000830.

TCRs of the invention, particularly alpha-beta heterodimeric TCRs, may comprise an alpha chain TRAC constant domain sequence and/or a beta chain TRBC1 or TRBC2 constant domain sequence. The alpha and beta chain constant domain sequences may be modified by truncation or substitution to delete the native disulfide bond between Cys4 of exon 2 of TRAC and Cys2 of exon 2 of TRBC1 or TRBC2. The alpha and/or beta chain constant domain sequence(s) may also be modified by substitution of cysteine residues for Thr 48 of TRAC and Ser 57 of TRBC1 or TRBC2, the said cysteines forming a disulfide bond between the alpha and beta constant domains of the TCR.

Binding affinity (inversely proportional to the equilibrium constant $K_D$) and binding half-life (expressed as T ½) can be determined by any appropriate method. It will be appreciated that doubling the affinity of a TCR results in halving the $K_D$. T ½ is calculated as ln 2 divided by the off-rate (koff). So doubling of T ½ results in a halving in koff. $K_D$ and koff values for TCRs are usually measured for soluble forms of the TCR, i.e. those forms which are truncated to remove cytoplasmic and transmembrane domain residues. Therefore it is to be understood that a given TCR has an improved binding affinity for, and/or a binding half-life for the parental TCR if a soluble form of that TCR has the said characteristics. Preferably the binding affinity or binding half-life of a given TCR is measured several times, for example 3 or more times, using the same assay protocol, and an average of the results is taken.

Since the TCRs of the invention have utility in adoptive therapy, the invention includes a non-naturally occurring and/or purified and/or or engineered cell, especially a T-cell, presenting a TCR of the invention. There are a number of methods suitable for the transfection of T cells with nucleic acid (such as DNA, cDNA or RNA) encoding the TCRs of the invention (see for example Robbins et al., (2008) J Immunol. 180: 6116-6131). T cells expressing the TCRs of the invention will be suitable for use in adoptive therapy-based treatment of cancers such as those of the pancreas and liver. As will be known to those skilled in the art, there are a number of suitable methods by which adoptive therapy can be carried out (see for example Rosenberg et al., (2008) Nat Rev Cancer 8(4): 299-308).

As is well-known in the art TCRs of the invention may be subject to post-translational modifications when expressed by transfected cells. Glycosylation is one such modification, which may comprise the covalent attachment of oligosaccharide moieties to defined amino acids in the TCR chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e oligosaccharide type, covalent linkage and total number of attachments) can influence protein function. Therefore, when producing recombinant proteins, controlling glycosylation is often desirable. Glycosylation of transfected TCRs may be controlled by mutations of the transfected gene (Kuball J et al. (2009), J Exp Med 206(2):463-475). Such mutations are also encompassed in this invention.

A TCR may be specific for an antigen in the group MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (AGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1, CT-7, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RARa fusion protein, PTPRK, K-ras, N-ras, Triosephosphate isomeras, GnTV, Herv-K-mel, Lage-1, Mage-C2, NA-88, Lage-2, SP17, and TRP2-Int2, (MART-I), gp100 (Pmel 17), TRP-1, TRP-2, MAGE-1, MAGE-3, p15(58), CEA, NY-ESO (LAGE), SCP-1, Hom/Mel-40, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, beta-catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\170K, NY—CO-1, RCAS1, SDCCAG16, TA-90 (Mac-2 binding protein\cyclophilin C-associated protein), TAAL6, TAG72, TLP, and TPS.

c. B-Cell Receptors (BCR)

B-cell receptors (BCRs) or B-cell antigen receptors are immunoglobulin molecules that form a type I transmembrane protein on the surface of a B cell. A BCR is capable of transmitting activatory signal into a B cell following recognition of a specific antigen. Prior to binding of a B cell to an antigen, the BCR will remain in an unstimulated or "resting" stage. Binding of an antigen to a BCR leads to signaling that initiates a humoral immune response.

A BCR is expressed by mature B cells. These B cells work with immunoglobulins (Igs) in recognizing and tagging pathogens. The typical BCR comprises a membrane-bound immunoglobulin (e.g., mIgA, mIgD, mIgE, mIgG, and mIgM), along with associated and Igα/Igβ (CD79a/CD79b) heterodimers (α/β). These membrane-bound immunoglobulins are tetramers consisting of two identical heavy and two light chains. Within the BCR, the membrane bound immunoglobulins is capable of responding to antigen binding by signal transmission across the plasma membrane leading to B cell activation and consequently clonal expansion and specific antibody production (Friess M et al. (2018), Front. Immunol. 2947(9)). The Igα/Igβ heterodimers is responsible for transducing signals to the cell interior.

A Igα/Igβ heterodimer signaling relies on the presence of immunoreceptor tyrosine-based activation motifs (ITAMs) located on each of the cytosolic tails of the heterodimers. ITAMs comprise two tyrosine residues separated by 9-12 amino acids (e.g., tyrosine, leucine, and/or valine). Upon binding of an antigen, the tyrosine of the BCR's ITAMs become phosphorylated by Src-family tyrosine kinases Blk, Fyn, or Lyn (Janeway C et al., Immunobiology: The Immune System in Health and Disease (Garland Science, 5th ed. 2001)).

d. Other Chimeric Proteins

In addition to the chimeric proteins provided above, the circular RNA polynucleotide may encode for a various number of other chimeric proteins available in the art. The chimeric proteins may include recombinant fusion proteins, chimeric mutant protein, or other fusion proteins.

B. Immune Modulatory Ligands

In some embodiments, the circular RNA polynucleotide encodes for an immune modulatory ligand. In certain embodiments, the immune modulatory ligand may be immunostimulatory; while in other embodiments, the immune modulatory ligand may be immunosuppressive.

1. Cytokines: Interferon, Chemokines, Interleukins, Growth Factor & Others

In some embodiments, the circular RNA polynucleotide encodes for a cytokine. In some embodiments, the cytokine comprises a chemokine, interferon, interleukin, lymphokine, and tumor necrosis factor. Chemokines are chemotactic cytokine produced by a variety of cell types in acute and chronic inflammation that mobilizes and activates white blood cells. An interferon comprises a family of secreted α-helical cytokines induced in response to specific extracellular molecules through stimulation of TLRs (Borden, Molecular Basis of Cancer (Fourth Edition) 2015). Interleukins are cytokines expressed by leukocytes.

Descriptions and/or amino acid sequences of IL-2, IL-7, IL-10, IL-12, IL-15, IL-18, IL-270, IFNγ, and/or TGFβ1 are provided herein and at the www.uniprot.org database at accession numbers: P60568 (IL-2), P29459 (IL-12A), P29460 (IL-12B), P13232 (IL-7), P22301 (IL-10), P40933 (IL-15), Q14116 (IL-18), Q14213 (IL-270), P01579 (IFNγ), and/or P01137 (TGFβ1).

C. Transcription Factors

Regulatory T cells (Treg) are important in maintaining homeostasis, controlling the magnitude and duration of the inflammatory response, and in preventing autoimmune and allergic responses.

In general, Tregs are thought to be mainly involved in suppressing immune responses, functioning in part as a "self-check" for the immune system to prevent excessive reactions. In particular, Tregs are involved in maintaining tolerance to self-antigens, harmless agents such as pollen or food, and abrogating autoimmune disease.

Tregs are found throughout the body including, without limitation, the gut, skin, lung, and liver. Additionally, Treg cells may also be found in certain compartments of the body that are not directly exposed to the external environment such as the spleen, lymph nodes, and even adipose tissue. Each of these Treg cell populations is known or suspected to have one or more unique features and additional information may be found in Lehtimaki and Lahesmaa, Regulatory T cells control immune responses through their non-redundant tissue specific features, 2013, FRONTIERS IN IMMUNOL., 4(294): 1-10, the disclosure of which is hereby incorporated in its entirety.

Typically, Tregs are known to require TGF-β and IL-2 for proper activation and development. Tregs, expressing abundant amounts of the IL-2 receptor (IL-2R), are reliant on IL-2 produced by activated T cells. Tregs are known to produce both IL-10 and TGF-β, both potent immune suppressive cytokines. Additionally, Tregs are known to inhibit the ability of antigen presenting cells (APCs) to stimulate T cells. One proposed mechanism for APC inhibition is via CTLA-4, which is expressed by Foxp3+ Tregs. It is thought that CTLA-4 may bind to B7 molecules on APCs and either block these molecules or remove them by causing internalization resulting in reduced availability of B7 and an inability to provide adequate co-stimulation for immune responses. Additional discussion regarding the origin, differentiation and function of Tregs may be found in Dhamne et al., Peripheral and thymic Foxp3+ regulatory T cells in search of origin, distinction, and function, 2013, Frontiers in Immunol., 4 (253): 1-11, the disclosure of which is hereby incorporated in its entirety.

D. Checkpoint Inhibitors & Agonists

As provided herein, in certain embodiments, the coding element of the circular RNA encodes for one or more checkpoint inhibitors or agonists.

In some embodiments, the immune checkpoint inhibitor is an inhibitor of Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GAL9, GITR, HAVCR2, HVEM, IDO1, IDO2, ICOS (inducible T cell costimulator), KIR, LAIR1, LIGHT, MARCO (macrophage receptor with collageneous structure), PS (phosphatidylserine), OX-40, SLAM, TIGHT, VISTA, VTCN1, or any combinations thereof. In some embodiments, the immune checkpoint inhibitor is an inhibitor of IDO1, CTLA4, PD-1, LAG3, PD-L1, TIM3, or combinations thereof. In some embodiments, the immune checkpoint inhibitor is an inhibitor of PD-L1. In some embodiments, the immune checkpoint inhibitor is an inhibitor of PD-1. In some embodiments, the immune checkpoint inhibitor is an inhibitor of CTLA-4. In some embodiments, the immune checkpoint inhibitor is an inhibitor of LAG3. In some embodiments, the immune checkpoint inhibitor is an inhibitor of TIM3. In some embodiments, the immune checkpoint inhibitor is an inhibitor of IDO1.

As described herein, at least in one aspect, the invention encompasses the use of immune checkpoint antagonists. Such immune checkpoint antagonists include antagonists of immune checkpoint molecules such as Cytotoxic T-Lymphocyte Antigen 4 (CTLA-4), Programmed Cell Death Protein 1 (PD-1), Programmed Death-Ligand 1 (PDL-1), Lymphocyte-activation gene 3 (LAG-3), and T-cell immunoglobulin and mucin domain 3 (TIM-3). An antagonist of CTLA-4, PD-1, PDL-1, LAG-3, or TIM-3 interferes with CTLA-4, PD-1, PDL-1, LAG-3, or TIM-3 function, respectively. Such antagonists of CTLA-4, PD-1, PDL-1, LAG-3, and TIM-3 can include antibodies which specifically bind to CTLA-4, PD-1, PDL-1, LAG-3, and TIM-3, respectively and inhibit and/or block biological activity and function.

E. Others

In some embodiments, the payload encoded within one or more of the coding elements is a hormone, FC fusion protein, anticoagulant, blood clotting factor, protein associated with deficiencies and genetic disease, a chaperone protein, an antimicrobial protein, an enzyme (e.g., metabolic enzyme), a structural protein (e.g., a channel or nuclear pore protein), protein variant, small molecule, antibody, nanobody, an engineered non-body antibody, or a combination thereof.

4. Additional Accessory Elements (Sequence Elements)

As described in this invention, the circular RNA polynucleotide, linear RNA polynucleotide, and/or DNA template may further comprise of accessory elements. In certain embodiments, these accessory elements may be included within the sequences of the circular RNA, linear RNA polynucleotide and/or DNA template for enhancing circularization, translation or both. Accessory elements are sequences, in certain embodiments that are located with specificity between or within the enhanced intron elements, enhanced exon elements, or core functional element of the respective polynucleotide. As an example, but not intended to be limiting, an accessory element includes, a IRES transacting factor region, a miRNA binding site, a restriction site, an RNA editing region, a structural or sequence element, a granule site, a zip code element, an RNA trafficking element or another specialized sequence as found in the art that enhances promotes circularization and/or translation of the protein encoded within the circular RNA polynucleotide.

A. Ires Transacting Factors

In certain embodiments, the accessory element comprises an IRES transacting factor (ITAF) region. In some embodiments, the IRES transacting factor region modulates the initiation of translation through binding to PCBP1-PCBP4 (polyC binding protein), PABP1 (polyA binding protein), PTB (polyprimidine tract binding), Argonaute protein family, HNRNPK (Heterogeneous nuclear ribonucleoprotein K protein), or La protein. In some embodiments, the IRES transacting factor region comprises a polyA, polyC, polyAC, or polyprimidine track.

In some embodiments, the ITAF region is located within the core functional element. In some embodiments, the ITAF region is located within the TIE.

B. MiRNA Binding Sites

In certain embodiments, the accessory element comprises a miRNA binding site. In some embodiments the miRNA binding site is located within the 5' enhanced intron element, 5' enhanced exon element, core functional element, 3' enhanced exon element, and/or 3' enhanced intron element.

In some embodiments, wherein the miRNA binding site is located within the spacer within the enhanced intron element or enhanced exon element. In certain embodiments, the miRNA binding site comprises the entire spacer regions.

In some embodiments, the 5' enhanced intron element and 3' enhanced intron elements each comprise identical miRNA binding sites. In another embodiment, the miRNA binding site of the 5' enhanced intron element comprises a different, in length or nucleotides, miRNA binding site than the 3' enhanced intron element. In one embodiment, the 5' enhanced exon element and 3' enhanced exon element comprise identical miRNA binding sites. In other embodiments, the 5' enhanced exon element and 3' enhanced exon element comprises different, in length or nucleotides, miRNA binding sites.

In some embodiments, the miRNA binding sites are located adjacent to each other within the circular RNA polynucleotide, linear RNA polynucleotide precursor, and/or DNA template. In certain embodiments, the first nucleotide of one of the miRNA binding sites follows the first nucleotide last nucleotide of the second miRNA binding site.

In some embodiments, the miRNA binding site is located within a translation initiation element (TIE) of a core functional element. In one embodiment, the miRNA binding site is located before, trailing or within an internal ribosome entry site (IRES). In another embodiment, the miRNA binding site is located before, trailing, or within an aptamer complex.

The unique sequences defined by the miRNA nomenclature are widely known and accessible to those working in the microRNA field. For example, they can be found in the miRDB public database.

5. Production of Polynucleotides

The DNA templates provided herein can be made using standard techniques of molecular biology. For example, the various elements of the vectors provided herein can be obtained using recombinant methods, such as by screening cDNA and genomic libraries from cells, or by deriving the polynucleotides from a DNA template known to include the same.

The various elements of the DNA template provided herein can also be produced synthetically, rather than cloned, based on the known sequences. The complete sequence can be assembled from overlapping oligonucleotides prepared by standard methods and assembled into the complete sequence. See, e.g., Edge, Nature (1981) 292:756; Nambair et al., Science (1984) 223: 1299; and Jay et al., J. Biol. Chem. (1984) 259:631 1.

Thus, particular nucleotide sequences can be obtained from DNA template harboring the desired sequences or synthesized completely, or in part, using various oligonucleotide synthesis techniques known in the art, such as site-directed mutagenesis and polymerase chain reaction (PCR) techniques where appropriate. One method of obtaining nucleotide sequences encoding the desired DNA template elements is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al., Proc. Natl. Acad. Sci. USA (1991) 88:4084-4088. Additionally, oligonucleotide-directed synthesis (Jones et al., Nature (1986) 54:75-82), oligonucleotide directed mutagenesis of preexisting nucleotide regions (Riechmann et al., Nature (1988) 332:323-327 and Verhoeyen et al., Science (1988) 239: 1534-1536), and enzymatic filling-in of gapped oligonucleotides using T4 DNA polymerase (Queen et al., Proc. Natl. Acad. Sci. USA (1989) 86: 10029-10033) can be used.

The precursor RNA provided herein can be generated by incubating a DNA template provided herein under conditions permissive of transcription of the precursor RNA encoded by the DNA template. For example, in some embodiments a precursor RNA is synthesized by incubating a DNA template provided herein that comprises an RNA polymerase promoter upstream of its 5' duplex sequence and/or expression sequences with a compatible RNA polymerase enzyme under conditions permissive of in vitro transcription. In some embodiments, the DNA template is incubated inside of a cell by a bacteriophage RNA polymerase or in the nucleus of a cell by host RNA polymerase II.

In certain embodiments, provided herein is a method of generating precursor RNA by performing in vitro transcription using a DNA template provided herein as a template (e.g., a vector provided herein with an RNA polymerase promoter positioned upstream of the 5' duplex region).

In certain embodiments, the resulting precursor RNA can be used to generate circular RNA (e.g., a circular RNA polynucleotide provided herein) by incubating it in the presence of magnesium ions and guanosine nucleotide or nucleoside at a temperature at which RNA circularization occurs (e.g., between 20° C. and 60° C.).

Thus, in certain embodiments provided herein is a method of making circular RNA. In certain embodiments, the method comprises synthesizing precursor RNA by transcription (e.g., run-off transcription) using a vector provided herein (e.g., a 5' enhanced intron element, a 5' enhanced exon element, a core functional element, a 3' enhanced exon element, and a 3' enhanced intron element) as a template, and incubating the resulting precursor RNA in the presence of divalent cations (e.g., magnesium ions) and GTP such that it circularizes to form circular RNA. In some embodiments, the precursor RNA disclosed herein is capable of circularizing in the absence of magnesium ions and GTP and/or without the step of incubation with magnesium ions and GTP. It has been discovered that circular RNA has reduced immunogenicity relative to a corresponding mRNA, at least partially because the mRNA contains an immunogenic 5' cap. When transcribing a DNA vector from certain promoters (e.g., a T7 promoter) to produce a precursor RNA, it is understood that the 5' end of the precursor RNA is G. To reduce the immunogenicity of a circular RNA composition that contains a low level of contaminant linear mRNA, an excess of GMP relative to GTP can be provided during transcription such that most transcripts contain a 5' GMP, which cannot be capped. Therefore, in some embodiments, transcription is carried out in the presence of an excess of GMP. In some embodiments, transcription is carried out where the ratio of GMP concentration to GTP concentration is within the range of about 3:1 to about 15:1, for example, about 3:1 to about 10:1, about 3:1 to about 5:1, about 3:1, about 4:1, or about 5:1.

In some embodiments, a composition comprising circular RNA has been purified. Circular RNA may be purified by any known method commonly used in the art, such as column chromatography, gel filtration chromatography, and size exclusion chromatography. In some embodiments, purification comprises one or more of the following steps: phosphatase treatment, HPLC size exclusion purification, and RNase R digestion. In some embodiments, purification comprises the following steps in order: RNase R digestion, phosphatase treatment, and HPLC size exclusion purification. In some embodiments, purification comprises reverse phase HPLC. In some embodiments, a purified composition contains less double stranded RNA, DNA splints, triphosphorylated RNA, phosphatase proteins, protein ligases, capping enzymes and/or nicked RNA than unpurified RNA. In some embodiments, a purified composition is less immunogenic than an unpurified composition. In some embodiments, immune cells exposed to a purified composition produce less TNFα, RIG-I, IL-2, IL-6, IFNγ, and/or a type 1 interferon, e.g., IFN-β1, than immune cells exposed to an unpurified composition.

6. Overview of Transfer Vehicle & Other Delivery Mechanisms

A. Ionizable Lipids

In certain embodiments disclosed herein are ionizable lipids that may be used as a component of a transfer vehicle to facilitate or enhance the delivery and release of circular RNA to one or more target cells (e.g., by permeating or fusing with the lipid membranes of such target cells). In certain embodiments, an ionizable lipid comprises one or more cleavable functional groups (e.g., a disulfide) that allow, for example, a hydrophilic functional head-group to dissociate from a lipophilic functional tail-group of the compound (e.g., upon exposure to oxidative, reducing or acidic conditions), thereby facilitating a phase transition in the lipid bilayer of the one or more target cells.

In various embodiments, an ionizable lipid of the disclosure is a compound of Formula (13*):

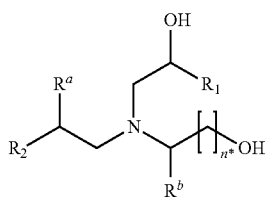

Formula (13*)

wherein:

n* is an integer between 1 to 7, $R^a$ is hydrogen or hydroxyl, $R^b$ is hydrogen or $C_1$-$C_6$ alkyl, $R_1$ and $R_2$ are each independently a linear or branched $C_1$-$C_{30}$ alkyl, $C_2$-$C_{30}$ alkenyl, or $C_1$-$C_{30}$ heteroalkyl, optionally substituted by one or more substituents selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, alkylcarbonyloxy, alkylcarbonate, alkenyloxycarbonyl, alkenylcarbonyloxy, alkenylcarbonate, alkynyloxycarbonyl, alkynylcarbonyloxy, alkynylcarbonate, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl.

In some embodiments of Formula (13*), $R^b$ is $C_1$-$C_6$ alkyl. In some embodiments of Formula (13*), $R^b$ is methyl. In some embodiments of Formula (13*), $R^b$ is ethyl.

In some embodiments of Formula (13*), $R^b$ is H and the ionizable lipid is of Formula (13):

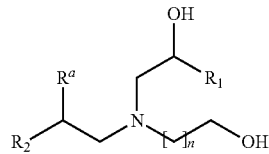

Formula (13)

wherein n is an integer between 1 to 7. In some embodiments of Formula (13), n is an integer between 1 to 4.

In some embodiments of Formula (13*) and Formula (13), $R_1$ and $R_2$ are the same. In some embodiments of Formula (13*) and Formula (13), $R_1$ and $R_2$ are different.

In some embodiments of Formula (13*) and Formula (13), $R_1$ and $R_2$ are each independently an optionally substituted linear or branched alkyl, alkenyl, or heteroalkyl, where the total number of carbon atoms present in the optionally substituted linear or branched group is 30 carbons or less, such as 6-30 carbon atoms, or 6-20 carbon atoms.

In some embodiments of Formula (13*) and Formula (13), at least one of $R_1$ and $R_2$ is an unsubstituted, linear or branched $C_6$-$C_{30}$ alkyl, $C_6$-$C_{30}$ alkenyl, or $C_6$-$C_{30}$ heteroalkyl.

In some embodiments of Formula (13*) and Formula (13), $R_1$ and $R_2$ are each independently a linear or branched $C_6$-$C_{30}$ alkyl, $C_6$-$C_{30}$ alkenyl, or $C_9$-$C_{20}$ heteroalkyl, optionally substituted by one or more substituents (e.g., as described above). In some embodiments of Formula (13*) and Formula (13), $R_1$ and $R_2$ are independently selected from a linear or branched $C_6$-$C_{30}$ alkyl, $C_6$-$C_{30}$ alkenyl, or $C_9$-$C_{20}$ heteroalkyl, substituted with alkyloxycarbonyl, alkylcarbonyloxy, alkylcarbonate, alkenyloxycarbonyl, alkenylcarbonyloxy, alkenylcarbonate.

In some embodiments of Formula (13*) and Formula (13), $R_1$ and $R_2$ are each independently a linear or branched $C_1$-$C_{20}$ alkyl, $C_2$-$C_{20}$ alkenyl, or $C_1$-$C_2M$ heteroalkyl, optionally substituted by one or more substituents each independently selected from linear or branched $C_1$-$C_2M$ alkoxy, linear or branched $C_1$-$C_{20}$ alkyloxycarbonyl, linear or branched $C_1$-$C_{20}$ alkylcarbonyloxy, linear or branched $C_1$-$C_{20}$ alkylcarbonate, linear or branched $C_2$-$C_{20}$ alkenyloxycarbonyl, linear or branched $C_2$-$C_{20}$ alkenylcarbonyloxy, linear or branched $C_2$-$C_{20}$ alkenylcarbonate, linear or branched $C_2$-$C_{20}$ alkynyloxycarbonyl, linear or branched $C_2$-$C_{20}$ alkynylcarbonyloxy, and linear or branched $C_2$-$C_{20}$ alkynylcarbonate.

In some embodiments of Formula (13*) and Formula (13), at least one of $R_1$ and $R_2$ is a linear $C_1$-$C_{12}$ alkyl substituted by —O(CO)$R^6$, —C(O)O$R^6$, or —O(CO)O$R^6$, wherein each $R^6$ is independently linear or branched $C_1$-$C_{20}$ alkyl or $C_2$-$C_{20}$ alkenyl. In some embodiments of Formula (13*) and Formula (13), $R_1$ and $R_2$ are each independently a linear $C_1$-$C_{12}$ alkyl substituted by —O(CO)$R^6$, —C(O)O$R^6$, or —O(CO)O$R^6$, wherein each $R^6$ is independently linear or branched $C_1$-$C_{20}$ alkyl or $C_2$-$C_{20}$ alkenyl.

In some embodiments, at least one of $R_1$ and $R_2$ is substituted with an alkyloxycarbonyl. In some embodiments, the alkyloxycarbonyl is of the formula —C(O)O$R^{6'}$, wherein $R^{6'}$ is unsubstituted $C_6$-$C_{30}$ alkyl or $C_6$-$C_{30}$ alkenyl.

In some embodiments, at least one of $R_1$ and $R_2$ is substituted with an alkylcarbonyloxy. In some embodiments, the alkylcarbonyloxy is of the formula —OC(O)$R^{6'}$, wherein $R^{6'}$ is unsubstituted $C_6$-$C_{30}$ alkyl or $C_6$-$C_{30}$ alkenyl.

In some embodiments, at least one of $R_1$ and $R_2$ is substituted with an alkylcarbonate. In some embodiments, the alkylcarbonate is of the formula —O(CO)OR$^{6'}$, wherein R$^{6'}$ is unsubstituted C$_6$-C$_{30}$ alkyl or C$_6$-C$_{30}$ alkenyl.

In some embodiments, R$_1$ and R$_2$ are each independently C$_1$-C$_{12}$ alkyl substituted by —O(CO)R$^{6'}$, —C(O)OR$^{6'}$, or —O(CO)OR$^{6'}$, wherein R$^{6'}$ is unsubstituted C$_6$-C$_{30}$ alkyl or C$_6$-C$_{30}$ alkenyl. In some embodiments, R$_1$ and R$_2$ are each C$_1$-C$_{12}$ alkyl substituted by —O(CO)R$^{6'}$. In some embodiments, R$_1$ and R$_2$ are each C$_1$-C$_{12}$ alkyl substituted by —C(O)OR$^{6'}$. In some embodiments, R$_1$ and R$_2$ are each C$_1$-C$_{12}$ alkyl substituted by —O(CO)OR$^{6'}$. In some embodiments, R$_1$ is —C(O)OR$^{6'}$ or —O(CO)R$^{6'}$ and R$_2$ is —O(CO)OR$^{6'}$. In some embodiments, R$_1$ is —O(CO)OR$^6$ and R$_2$ is —C(O)R$^6$ or —O(CO)R$^6$.

In some embodiments, at least one of R$_1$ and R$_2$ is selected from the following formulae:

—(CH$_2$)$_q$C(O)O(CH$_2$)$_r$CH(R$^8$)(R$^9$), (i)

—(CH$_2$)$_q$OC(O)(CH$_2$)$_r$CH(R$^8$)(R$^9$), and (ii)

—(CH$_2$)$_q$OC(O)O(CH$_2$)$_r$CH(R$^8$)(R$^9$), (iii)

wherein:
q is an integer between 0 to 12,
r is an integer between 0 to 6,
R$^8$ is H or R$^{10}$, and
R$^9$ and R$^{10}$ are independently unsubstituted linear C$_1$-C$_{12}$ alkyl or unsubstituted linear C$_2$-C$_{12}$-alkenyl.

In some embodiments, each of R$_1$ and R$_2$ is independently selected from one of the following formulae:

—(CH$_2$)$_q$C(O)O(CH$_2$)$_r$CH(R$^8$)(R$^9$), (i)

—(CH$_2$)$_q$OC(O)(CH$_2$)$_r$CH(R$^8$)(R$^9$), and (ii)

—(CH$_2$)$_q$OC(O)O(CH$_2$)$_r$CH(R$^8$)(R$^9$), (iii)

wherein:
q is an integer between 0 to 12,
r is an integer between 0 to 6,
R$^8$ is H or R$^{10}$, and
R$^9$ and R$^{10}$ are independently unsubstituted linear C$_1$-C$_{12}$ alkyl or unsubstituted linear C$_2$-C$_{12}$-alkenyl.

In some embodiments, of any one of formulae (i)-(iii), q is an integer between 1 to 6. In some embodiments of any one of formulae (i)-(iii), q is 0. In some embodiments, of any one of formulae (i)-(iii), q is 1. In some embodiments of any one of formulae (i)-(iii), q is 2. In some embodiments, of any one of formulae (i)-(iii), q is an integer between 3 to 12. In some embodiments, of any one of formulae (i)-(iii), q is an integer between 3 to 6.

In some embodiments of any one of formulae (i)-(iii), r is 0. In some embodiments of any one of formulae (i)-(iii), r is an integer between 1 to 6. In some embodiments of any one of formulae (i)-(iii), r is 1. In some embodiments of any one of formulae (i)-(iii), r is 2.

In some embodiments of formulae (i)-(iii), R$^8$ is H. In some embodiments of formulae (i)-(iii), R$^8$ is R$^{10}$. In some embodiments of formulae (i)-(iii), R$^9$ and R$^{10}$ are different. In some embodiments of formulae (i)-(iii), R$^9$ and R$^{10}$ are the same.

In some embodiments of formulae (i)-(iii), R$^8$ is H, and R$^9$ is unsubstituted linear C$_1$-C$_{12}$ alkyl or unsubstituted linear C$_1$-C$_{12}$-alkenyl. In some embodiments of formulae (i)-(iii), R$^8$ is H, and R$^9$ is unsubstituted linear C$_2$-C$_{12}$ alkyl. In some embodiments of formulae (i)-(iii), R$^8$ is H, and R$^9$ is unsubstituted linear C$_2$-C$_8$ alkyl. In some embodiments of formulae (i)-(iii), R$^8$ is H, and R$^9$ is unsubstituted linear C$_4$-C$_8$ alkyl. In some embodiments of formulae (i)-(iii), R$^8$ is H, and R$^9$ is unsubstituted linear C$_5$-C$_8$ alkyl. In some embodiments of formulae (i)-(iii), R$^8$ is H, and R$^9$ is unsubstituted linear C$_6$-C$_8$ alkyl.

In some embodiments of formulae (i)-(iii), R$^8$ and R$^9$ are each independently unsubstituted linear C$_1$-C$_{12}$ alkyl or unsubstituted linear C$_1$-C$_{12}$-alkenyl. In some embodiments of formulae (i)-(iii), R$^8$ and R$^9$ are each independently unsubstituted linear C$_2$-C$_{12}$ alkyl. In some embodiments of formulae (i)-(iii), R$^8$ and R$^9$ are each independently unsubstituted linear C$_2$-C$_8$ alkyl. In some embodiments of formulae (i)-(iii), R$^8$ and R$^9$ are each independently unsubstituted linear C$_4$-C$_8$ alkyl. In some embodiments of formulae (i)-(iii), R$^8$ and R$^9$ are each independently unsubstituted linear C$_6$-C$_8$ alkyl.

In some embodiments, at least one of R$_1$ and R$_2$ is —(CH$_2$)$_q$C(O)O(CH$_2$)$_r$CH(R$^8$)(R$^9$), where q, r, R$^8$ and R$^9$ are as defined above. In some embodiments, at least one of R$^1$ and R$^2$ is —(CH$_2$)$_q$OC(O)(CH$_2$)$_r$CH(R$^8$)(R$^9$), where q, r, R$^8$ and R$^9$ are as defined above. In some embodiments, at least one of R$_1$ and R$_2$ is —(CH$_2$)$_q$OC(O)O(CH$_2$)$_r$CH(R$^8$)(R$^9$), where q, r, R$^8$ and R$^9$ are as defined above.

In certain embodiments, at least one of R$_1$ and R$_2$ is —(CH$_2$)$_q$C(O)O(CH$_2$)$_r$CH(R$^8$)(R$^9$) or —(CH$_2$)$_q$OC(O)(CH$_2$)$_r$CH(R$^8$)(R$^9$), where q, r, R$^8$ and R$^9$ are as defined above. In other embodiments, at least one of R$_1$ and R$_2$ is —(CH$_2$)$_q$OC(O)(CH$_2$)$_r$CH(R$^8$)(R$^9$) or —(CH$_2$)$_q$OC(O)O(CH$_2$)$_r$CH(R$^8$)(R$^9$), where q, r, R$^8$ and R$^9$ are as defined above. In some embodiments, at least one of R$_1$ and R$_2$ is —(CH$_2$)$_q$C(O)O(CH$_2$)$_r$CH(R$^8$)(R$^9$) or —(CH$_2$)$_q$OC(O)O(CH$_2$)$_r$CH(R$^8$)(R$^9$), where q, r, R$^8$ and R$^9$ are as defined above.

In certain embodiments, R$_1$ is —(CH$_2$)$_q$C(O)O(CH$_2$)$_r$CH(R$^8$)(R$^9$), and R$_2$ is —(CH$_2$)$_q$C(O)O(CH$_2$)$_r$CH(R$^8$)(R$^9$), where q, r, R$^8$ and R$^9$ are as defined above. In certain embodiments, R$_1$ is —(CH$_2$)$_q$C(O)O(CH$_2$)$_r$CH(R$^8$)(R$^9$), and R$_2$ is —(CH$_2$)$_q$OC(O)(CH$_2$)$_r$CH(R$^8$)(R$^9$), where q, r, R$^8$ and R$^9$ are as defined above. In certain embodiments, R$_1$ is —(CH$_2$)$_q$C(O)O(CH$_2$)$_r$CH(R$^8$)(R$^9$), and R$_2$ is —(CH$_2$)$_q$OC(O)O(CH$_2$)$_r$CH(R$^8$)(R$^9$), where q, r, R$^8$ and R$^9$ are as defined above.

In certain embodiments, R$^1$ is —(CH$_2$)$_q$OC(O)(CH$_2$)$_r$CH(R$^8$)(R$^9$), and R$_2$ is —(CH$_2$)$_q$C(O)O(CH$_2$)$_r$CH(R$^8$)(R$^9$), where q, r, R$^8$ and R$^9$ are as defined above. In certain embodiments, R$_1$ is —(CH$_2$)$_q$OC(O)(CH$_2$)$_r$CH(R$^8$)(R$^9$), and R$_2$ is —(CH$_2$)$_q$OC(O)(CH$_2$)$_r$CH(R$^8$)(R$^9$), where q, r, R$^8$ and R$^9$ are as defined above. In certain embodiments, R$_1$ is —(CH$_2$)$_q$OC(O)(CH$_2$)$_r$CH(R$^8$)(R$^9$), and R$_2$ is —(CH$_2$)$_q$OC(O)O(CH$_2$)$_r$CH(R$^8$)(R$^9$), where q, r, R$^8$ and R$^9$ are as defined above.

In certain embodiments, R$_1$ is —(CH$_2$)$_q$OC(O)O(CH$_2$)$_r$CH(R$^8$)(R$^9$), and R$_2$ is —(CH$_2$)$_q$C(O)O(CH$_2$)$_r$CH(R$^8$)(R$^9$), where q, r, R$^8$ and R$^9$ are as defined above. In certain embodiments, R$_1$ is —(CH$_2$)$_q$OC(O)O(CH$_2$)$_r$CH(R$^8$)(R$^9$), and R$_2$ is —(CH$_2$)$_q$OC(O)(CH$_2$)$_r$CH(R$^8$)(R$^9$), where q, r, R$^8$ and R$^9$ are as defined above. In certain embodiments, R$_1$ is —(CH$_2$)$_q$OC(O)O(CH$_2$)$_r$CH(R$^8$)(R$^9$), and R$_2$ is —(CH$_2$)$_q$OC(O)O(CH$_2$)$_r$CH(R$^8$)(R$^9$), where q, r, R$^8$ and R$^9$ are as defined above.

In some embodiments, R$_1$ and R$_2$ are each independently selected from the group consisting of:

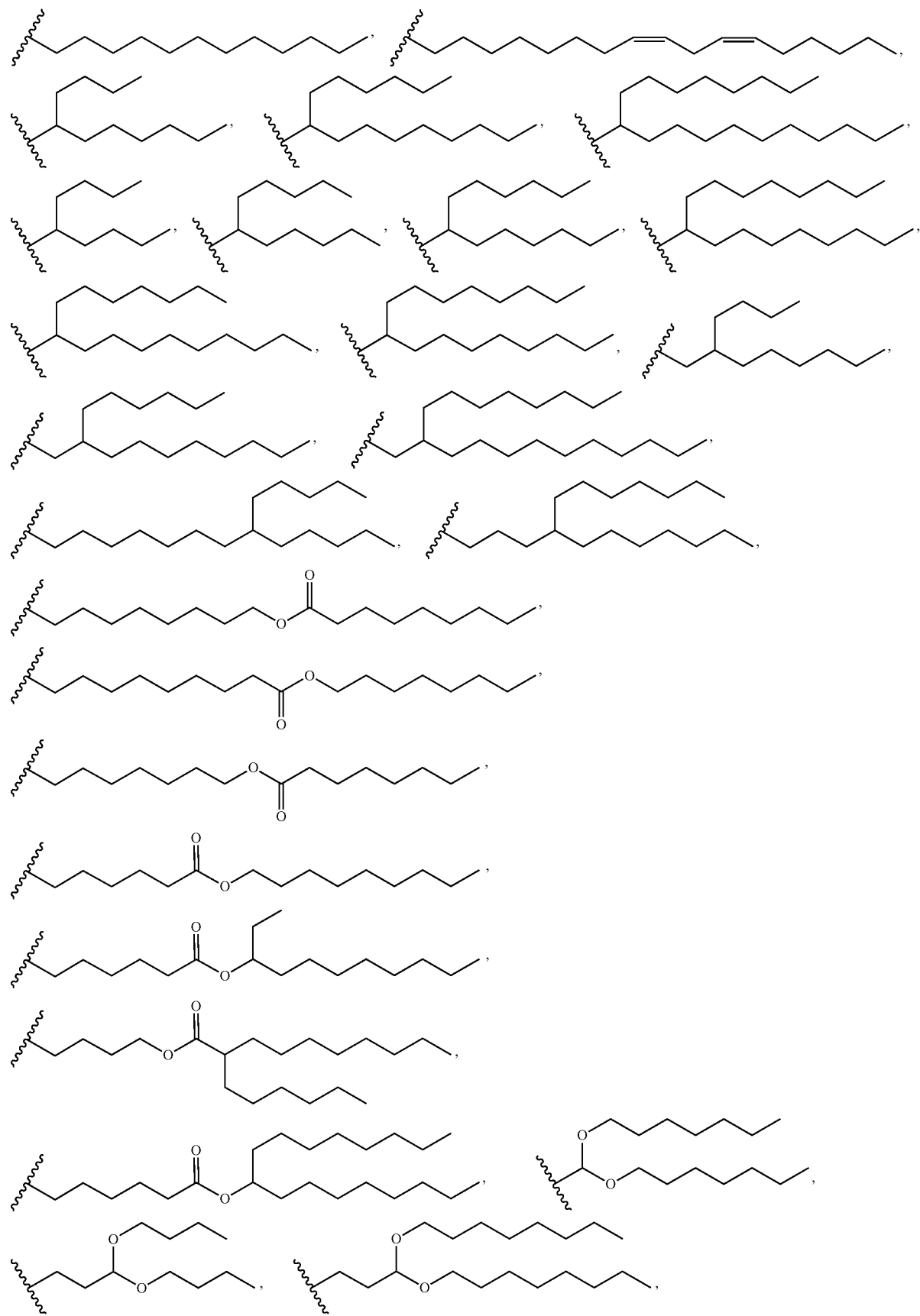

115                                    116
-continued
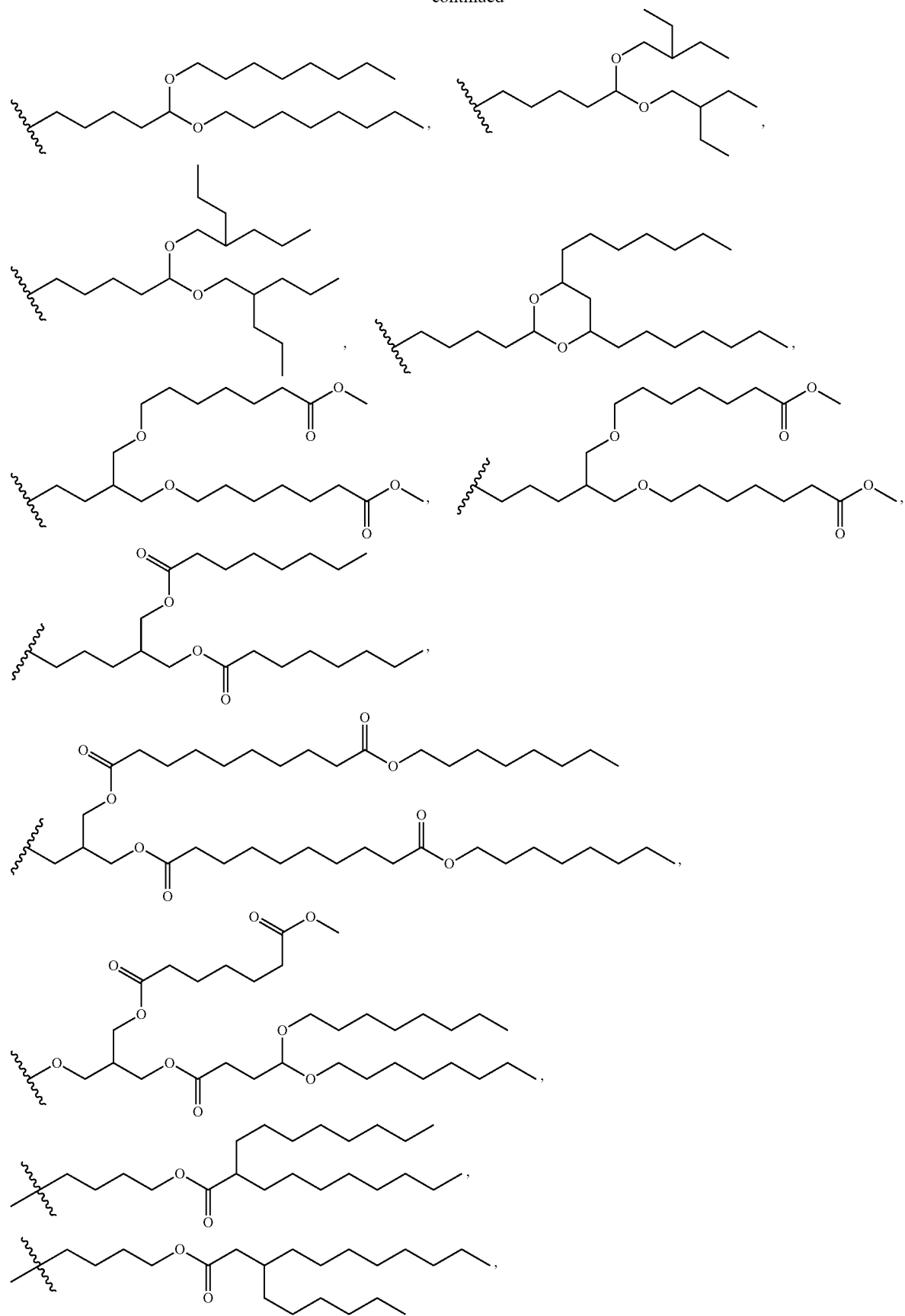

-continued

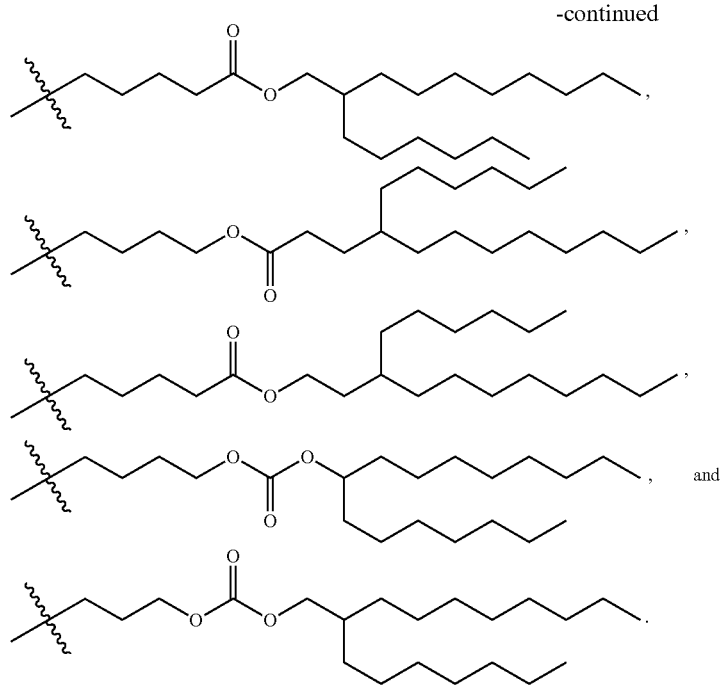

In some embodiments, the ionizable lipid of Formula (13) is represented by Formula (13a-1), Formula (13a-2), or Formula (13a-3):

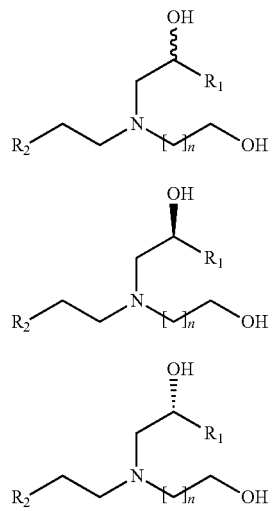

Formula (13a-1)

Formula (13a-2)

Formula (13a-3)

In some embodiments, the ionizable lipid is represented by Formula (13b-1), Formula (13b-2), or Formula (13b-3):

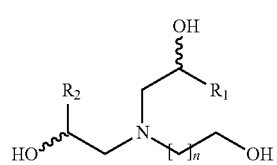

Formula (13b-1)

Formula (13b-2)

Formula (13b-3)

In some embodiments, the ionizable lipid is represented by Formula (13b-4), Formula (13b-5), Formula (13b-6), Formula (13b-7), Formula (13b-8), or Formula (13b-9):

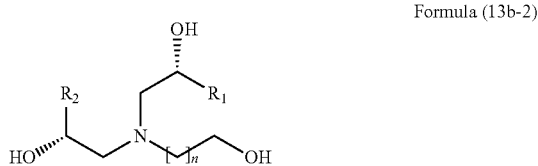

Formula (13b-4)

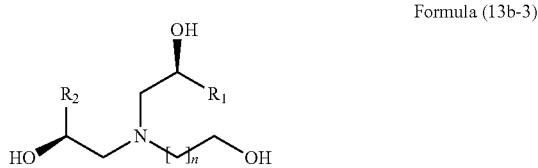

Formula (13b-5)

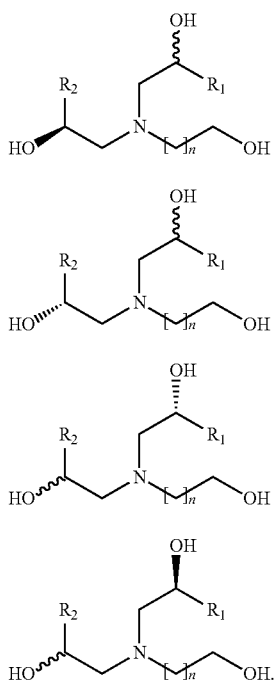

Formula (13b-6)

Formula (13b-7)

Formula (13b-8)

Formula (13b-9)

In some embodiments of Formula (13a-1) to (13b-9), $R^1$ and $R^2$ are independently $C_1$-$C_{12}$ alkyl optionally substituted by —O(CO)$R^6$, —C(O)O$R^6$, or —O(CO)O$R^6$, wherein $R^6$ is unsubstituted linear or branched $C_1$-$C_{20}$ alkyl or $C_2$-$C_{20}$ alkenyl. In some embodiments, $R^6$ is unsubstituted linear $C_1$-$C_{20}$ alkyl. In some embodiments, $R^6$ is unsubstituted branched $C_6$—$C_{20}$ alkyl. In some embodiments, $R^6$ is unsubstituted linear $C_6$-$C_{20}$ alkyl. In some embodiments, $R^6$ is unsubstituted branched $C_6$-$C_{20}$ alkyl.

In some embodiments of Formula (13a-1) to (13b-9), $R^1$ and $R^2$ are independently selected from linear or branched $C_6$-$C_{30}$ alkyl, linear or branched $C_6$-$C_{30}$ alkenyl, linear or branched $C_6$-$C_{30}$ heteroalkyl, —(CH$_2$)$_q$C(O)O(CH$_2$)$_r$CH(R$^8$)(R$^9$), —(CH$_2$)$_q$OC(O)(CH$_2$)$_r$CH(R$^8$)(R$^9$), and —(CH$_2$)$_q$OC(O)O(CH$_2$)$_r$CH(R$^8$)(R$^9$), wherein q is 0 to 12, r is 0 to 6, $R^8$ is H or $R^{10}$, and $R^9$ and $R^{10}$ are independently unsubstituted linear $C_1$-$C_{20}$ alkyl or $C_2$-$C_{20}$ alkenyl. In some embodiments, q is 1 to 8, such as 1 to 6, or 2 to 6. In some embodiments, r is 0. In some embodiments, r is 1 to 6, such as 1 to 3. In some embodiments, r is 1. In some embodiments, r is 2.

In some embodiments of Formula (13a-1) to (13b-9), $R^1$ and $R^2$ are different groups. In some embodiments of Formula (13a-1) to (13b-9), $R^1$ and $R^2$ are the same. In some embodiments of Formula (13a-1) to (13b-9), one of $R^1$ and $R^2$ is a linear group, and the other of $R^1$ and $R^2$ includes a branched group.

In some embodiments of Formula (13a-1) to (13b-9), at least one of $R^1$ and $R^2$ is selected from the following formulae:

—(CH$_2$)$_q$C(O)O(CH$_2$)$_r$CH(R$^8$)(R$^9$), (i)

—(CH$_2$)$_q$OC(O)(CH$_2$)$_r$CH(R$^8$)(R$^9$), and (ii)

—(CH$_2$)$_q$OC(O)O(CH$_2$)$_r$CH(R$^8$)(R$^9$), (iii)

wherein:
q is an integer between 0 to 12,
r is an integer between 0 to 6,
$R^8$ is H or $R^{10}$, and
$R^9$ and $R^{10}$ are independently unsubstituted linear $C_1$-$C_{12}$ alkyl or unsubstituted linear $C_2$-$C_{12}$-alkenyl.

In some embodiments of Formula (13a-1) to (13b-9), each of $R^1$ and $R^2$ is independently selected from one of the following formulae:

—(CH$_2$)$_q$C(O)O(CH$_2$)$_r$CH(R$^8$)(R$^9$), (i)

—(CH$_2$)$_q$OC(O)(CH$_2$)$_r$CH(R$^8$)(R$^9$), and (ii)

—(CH$_2$)$_q$OC(O)O(CH$_2$)$_r$CH(R$^8$)(R$^9$), (iii)

wherein:
q is an integer between 0 to 12,
r is an integer between 0 to 6,
$R^8$ is H or $R^{10}$, and
$R^9$ and $R^{10}$ are independently unsubstituted linear $C_1$-$C_{12}$ alkyl or unsubstituted linear $C_2$-$C_{12}$-alkenyl.

In some embodiments, of any one of formulae (i)-(iii), q is an integer between 1 to 6. In some embodiments of any one of formulae (i)-(iii), q is 1. In some embodiments of any one of formulae (i)-(iii), q is 2. In some embodiments, of any one of formulae (i)-(iii), q is an integer between 3 to 12. In some embodiments, of any one of formulae (i)-(iii), q is an integer between 3 to 6.

In some embodiments of any one of formulae (i)-(iii), r is 0. In some embodiments of any one of formulae (i)-(iii), r is an integer between 1 to 6. In some embodiments of any one of formulae (i)-(iii), r is 1. In some embodiments of any one of formulae (i)-(iii), r is 2.

In some embodiments of formulae (i)-(iii), $R^8$ is H. In some embodiments of formulae (i)-(iii), $R^8$ is $R^{10}$. In some embodiments of formulae (i)-(iii), $R^9$ and $R^{10}$ are different. In some embodiments of formulae (i)-(iii), $R^9$ and $R^{10}$ are the same.

In some embodiments of formulae (i)-(iii), $R^8$ is H, and $R^9$ is unsubstituted linear $C_1$-$C_{12}$ alkyl or unsubstituted linear $C_1$-$C_{12}$-alkenyl. In some embodiments of formulae (i)-(iii), $R^8$ is H, and $R^9$ is unsubstituted linear $C_2$-$C_{12}$ alkyl. In some embodiments of formulae (i)-(iii), $R^8$ is H, and $R^9$ is unsubstituted linear $C_2$-$C_8$ alkyl. In some embodiments of formulae (i)-(iii), $R^8$ is H, and $R^9$ is unsubstituted linear $C_4$-$C_8$ alkyl. In some embodiments of formulae (i)-(iii), $R^8$ is H, and $R^9$ is unsubstituted linear $C_6$-$C_8$ alkyl.

In some embodiments of formulae (i)-(iii), $R^8$ and $R^9$ are each independently unsubstituted linear $C_1$-$C_{12}$ alkyl or unsubstituted linear $C_1$-$C_{12}$-alkenyl. In some embodiments of formulae (i)-(iii), $R^8$ and $R^9$ are each independently unsubstituted linear $C_2$-$C_{12}$ alkyl. In some embodiments of formulae (i)-(iii), $R^8$ and $R^9$ are each independently unsubstituted linear $C_2$-$C_8$ alkyl. In some embodiments of formulae (i)-(iii), $R^8$ and $R^9$ are each independently unsubstituted linear $C_4$-$C_8$ alkyl. In some embodiments of formulae (i)-(iii), $R^8$ and $R^9$ are each independently unsubstituted linear $C_6$-$C_8$ alkyl.

In some embodiments of Formula (13a-1) to (13b-9), at least one of $R^1$ and $R^2$ is —(CH$_2$)$_q$C(O)O(CH$_2$)$_r$CH(R$^8$)(R$^9$), where q, r, $R^8$ and $R^9$ are as defined above. In some embodiments of Formula (13a-1) to (13b-9), at least one of $R^1$ and $R^2$ is —(CH$_2$)$_q$OC(O)(CH$_2$)$_r$CH(R$^8$)(R$^9$), where q, r, $R^8$ and $R^9$ are as defined above. In some embodiments of Formula (13a-1) to (13b-9), at least one of $R^1$ and $R^2$ is —(CH$_2$)$_q$OC(O)O(CH$_2$)$_r$CH(R$^8$)(R$^9$), where q, r, $R^8$ and $R^9$ are as defined above.

In certain embodiments of Formula (13a-1) to (13b-9), at least one of $R^1$ and $R^2$ is —(CH$_2$)$_q$C(O)O(CH$_2$)$_r$CH(R$^8$)(R$^9$)

or —$(CH_2)_qOC(O)(CH_2)_rCH(R^8)(R^9)$, where q, r, $R^8$ and $R^9$ are as defined above. In some embodiments of Formula (13a-1) to (13b-9), at least one of $R^1$ and $R^2$ is —$(CH_2)_qOC(O)(CH_2)_rCH(R^8)(R^9)$ or —$(CH_2)_qOC(O)O(CH_2)_rCH(R^8)(R^9)$, where q, r, $R^8$ and $R^9$ are as defined above. In some embodiments of Formula (13a-1) to (13b-9), at least one of $R^1$ and $R^2$ is —$(CH_2)_qC(O)O(CH_2)_rCH(R^8)(R^9)$ or —$(CH_2)_qOC(O)O(CH_2)_rCH(R^8)(R^9)$, where q, r, $R^8$ and $R^9$ are as defined above.

In other embodiments of Formula (13a-1) to (13b-9), at least one of $R^1$ and $R^2$ is —$(CH_2)_qOC(O)(CH_2)_rCH(R^8)(R^9)$ where q, r, $R^8$ and $R^9$ are as defined above. In some embodiments of Formula (13a-1) to (13b-9), at least one of $R^1$ and $R^2$ is —$(CH_2)_qC(O)O(CH_2)_rCH(R^8)(R^9)$ or —$(CH_2)_qOC(O)O(CH_2)_rCH(R^8)(R^9)$, where q, r, $R^1$ and $R^9$ are as defined above.

In certain embodiments of Formula (13a-1) to (13b-9), $R^1$ is —$(CH_2)_qC(O)O(CH_2)_rCH(R^8)(R^9)$, and $R^2$ is —$(CH_2)_qC(O)O(CH_2)_rCH(R^8)(R^9)$, where q, r, $R^1$ and $R^9$ are as defined above. In certain embodiments of Formula (13a-1) to (13b-9), $R^1$ is —$(CH_2)_qC(O)O(CH_2)_rCH(R^8)(R^9)$, and $R^2$ is —$(CH_2)_qOC(O)(CH_2)_rCH(R^8)(R^9)$, where q, r, $R^1$ and $R^9$ are as defined above. In certain embodiments of Formula (13a-1) to (13b-9), $R^1$ is —$(CH_2)_qC(O)O(CH_2)_rCH(R^8)(R^9)$, and $R^2$ is —$(CH_2)_qOC(O)O(CH_2)_rCH(R^8)(R^9)$, where q, r, $R^8$ and $R^9$ are as defined above.

In certain embodiments of Formula (13a-1) to (13b-9), $R^1$ is —$(CH_2)_qOC(O)(CH_2)_rCH(R^8)(R^9)$, and $R^2$ is —$(CH_2)_qC(O)O(CH_2)_rCH(R^8)(R^9)$, where q, r, $R^1$ and $R^9$ are as defined above. In certain embodiments of Formula (13a-1) to (13b-9), $R^1$ is —$(CH_2)_qOC(O)(CH_2)_rCH(R^8)(R^9)$, and $R^2$ is —$(CH_2)_qOC(O)(CH_2)_rCH(R^8)(R^9)$, where q, r, $R^8$ and $R^9$ are as defined above. In certain embodiments of Formula (13a-1) to (13b-9), $R^1$ is —$(CH_2)_qOC(O)(CH_2)_rCH(R^8)(R^9)$, and $R^2$ is —$(CH_2)_qOC(O)O(CH_2)_rCH(R^8)(R^9)$, where q, r, $R^8$ and $R^9$ are as defined above.

In certain embodiments of Formula (13a-1) to (13b-9), $R^1$ is —$(CH_2)_qOC(O)O(CH_2)_rCH(R^8)(R^9)$, and $R^2$ is —$(CH_2)_qC(O)O(CH_2)_rCH(R^8)(R^9)$, where q, r, $R^8$ and $R^9$ are as defined above. In certain embodiments of Formula (13a-1) to (13b-9), $R^1$ is —$(CH_2)_qOC(O)O(CH_2)_rCH(R^8)(R^9)$, and $R^2$ is —$(CH_2)_qOC(O)(CH_2)_rCH(R^8)(R^9)$, where q, r, $R^8$ and $R^9$ are as defined above. In certain embodiments of Formula (13a-1) to (13b-9), $R^1$ is —$(CH_2)_qOC(O)O(CH_2)_rCH(R^8)(R^9)$, and $R^2$ is —$(CH_2)_qOC(O)O(CH_2)_rCH(R^8)(R^9)$, where q, r, $R^8$ and $R^9$ are as defined above.

In some embodiments of Formula (13a-1) to (13b-9), n is 1. In some embodiments of Formula (13a-1) to (13b-9), n is and integer between 2 to 7. In some embodiments of Formula (13a-1) to (13b-9), n is 2. In some embodiments of Formula (13a-1) to (13b-9), n is and integer between 3 to 7. In some embodiments of Formula (13a-1) to (13b-9), n is 3. In some embodiments of Formula (13a-1) to (13b-9), n is and integer between 4 to 7. In some embodiments of Formula (13a-1) to (13b-9), n is 4. In some embodiments of Formula (13a-1) to (13b-9), n is 5. In some embodiments of Formula (13a-1) to (13b-9), n is 6. In some embodiments of Formula (13a-1) to (13b-9), n is 7.

In some embodiments of Formula (13*), the ionizable lipid is of Formula (13c-1) or (13c-2):

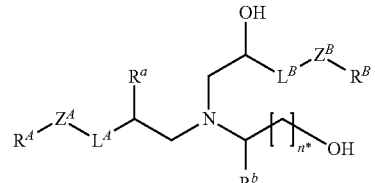

Formula (13c-1)

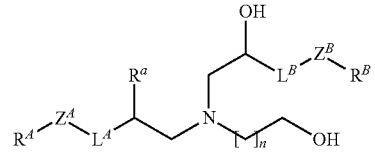

Formula (13c-2)

wherein:
n* and n are each an integer between 1 to 7;
$R^a$ is hydrogen or hydroxyl,
$R^b$ is hydrogen or $C_1$-$C_6$ alkyl,
$L^A$ and $L^B$ are each independently linear $C_1$-$C_{12}$ alkyl;
$Z^A$ and $Z^B$ are each independently absent or selected from —C(O)O—, —OC(O)—, and —OC(O)O—; and
$R^A$ and $R^B$ are independently linear or branched $C_1$-$C_{20}$ alkyl or $C_2$-$C_{20}$ alkenyl.

In some embodiments of Formula (13c-1) and (13c-2), $Z^A$ is selected from —C(O)O—, —OC(O)—, and —OC(O)O—, and $Z^B$ is absent. In some embodiments of Formula (13c-1) and (13c-2), $Z^B$ is selected from —C(O)O—, —OC(O)—, and —OC(O)O—, and $Z^A$ is absent.

In some embodiments of Formula (13c-2), the ionizable lipid is of Formula (13d-2):

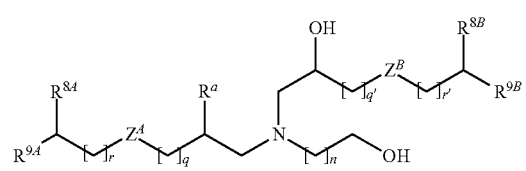

Formula (13d-2)

wherein:
q and q' are each independently an integer between 1 to 12,
r and r' are each independently an integer between 0 to 6,
$R^{8A}$ is H or $R^{10A}$,
$R^{8B}$ is H or $R^{10B}$, and
$R^{9A}$, $R^{9B}$, $R^{10A}$, and $R_{10A}$ are each independently unsubstituted linear $C_1$-$C_{12}$ alkyl or unsubstituted linear $C_2$-$C_{12}$-alkenyl.

In some embodiments of Formula (13d-2), $R^{9A}$, $R^{9B}$, $R_{10A}$, and $R_{10A}$ are each independently unsubstituted linear $C_1$-$C_{12}$ alkyl or unsubstituted linear $C_2$-$C_{12}$-alkenyl.

In some embodiments, of Formula (13d-2), q is an integer between 1 to 6. In some embodiments of Formula (13d-2), q is 0. In some embodiments of Formula (13d-2), q is 1. In some embodiments of Formula (13d-2), q is 2. In some embodiments of Formula (13d-2), q is 3 to 12. In some embodiments of Formula (13d-2), q is 3 to 6.

In some embodiments of Formula (13d-2), r is 0. In some embodiments of Formula (13d-2), r is an integer between 1 to 6. In some embodiments of Formula (13d-2), r is 1. In some embodiments of Formula (13d-2), r is 2.

In some embodiments of Formula (13d-2), $R^a$ is hydrogen, $Z^A$ is selected from —C(O)O—, —OC(O)—, and —OC(O)O—, and $Z^B$ is absent. In some embodiments of Formula (13d-2), $R^a$ is hydrogen, $Z^B$ is a linking group selected from —C(O)O—, —OC(O)—, and —OC(O)O—, and $Z^A$ is absent.

In some embodiments of Formula (13d-2), $R^a$ is hydroxyl, $Z^A$ is selected from —C(O)O—, —OC(O)—, and —OC(O)O—, and $Z^B$ is absent. In some embodiments of Formula (13d-2), $R^a$ is hydroxyl, $Z^B$ is selected from —C(O)O—, —OC(O)—, and —OC(O)O—, and $Z^A$ is absent.

In some embodiments, the ionizable lipid of the disclosure is of Formula (13d-2) as described in the compounds of the Table 1 below, where any undefined variables are as described above.

TABLE 1

Exemplary ionizable lipids of Formula (13d-2). In some embodiments of the exemplary lipids of Table 1, n is 1 or 2.

Formula (13d-2)

| Cmpd # | $R^{9A}$ | $R^{8A}$ | r | $Z^A$ | q | $R^a$ | q' | $Z^B$ | r' | $R^{8B}$ | $R^{9B}$ |
|---|---|---|---|---|---|---|---|---|---|---|---|
| 1 | $C_4$-$C_8$ alkyl | $C_4$-$CH_8$ alkyl | 0 | —C(O)O— | 3-6 | H | 3-6 | —OC(O)— | 0 | $C_4$-$C_8$ alkyl | $C_4$-$C_8$ alkyl |
| 2 | $C_4$-$C_8$ alkyl | $C_4$-$C_8$ alkyl | 1 | —C(O)O— | 3-6 | H | 3-6 | —OC(O)— | 1 | $C_4$-$C_8$ alkyl | $C_4$-$C_8$ alkyl |
| 3 | $C_4$-$C_8$ alkyl | $C_4$-$C_8$ alkyl | 2 | —C(O)O— | 3-6 | H | 3-6 | —OC(O)— | 2 | $C_4$-$C_8$ alkyl | $C_4$-$C_8$ alkyl |
| 4 | $C_4$-$C_8$ alkyl | $C_4$-$C_8$ alkyl | 0 | —OC(O)— | 3-6 | H | 3-6 | —C(O)O— | 0 | $C_4$-$C_8$ alkyl | $C_4$-$C_8$ alkyl |
| 5 | $C_4$-$C_8$ alkyl | $C_4$-$C_8$ alkyl | 1 | —OC(O)— | 3-6 | H | 3-6 | —C(O)O— | 1 | $C_4$-$C_8$ alkyl | $C_4$-$C_8$ alkyl |
| 6 | $C_4$-$C_8$ alkyl | $C_4$-$C_8$ alkyl | 2 | —OC(O)— | 3-6 | H | 3-6 | —C(O)O— | 2 | $C_4$-$C_8$ alkyl | $C_4$-$C_8$ alkyl |
| 7 | $C_4$-$C_8$ alkyl | $C_4$-$C_8$ alkyl | 0 | —OC(O)O— | 3-6 | H | 3-6 | —OC(O)O— | 0 | $C_4$-$C_8$ alkyl | $C_4$-$C_8$ alkyl |
| 8 | $C_4$-$C_8$ alkyl | $C_4$-$C_8$ alkyl | 1 | —OC(O)O— | 3-6 | H | 3-6 | —OC(O)O— | 1 | $C_4$-$C_8$ alkyl | $C_4$-$C_8$ alkyl |
| 9 | $C_4$-$C_8$ alkyl | $C_4$-$C_8$ alkyl | 0 | —OC(O)— | 3-6 | H | 1-12 | absent | 0 | H | $C_1$-$C_{12}$ alkyl |
| 10 | $C_4$-$C_8$ alkyl | $C_4$-$C_8$ alkyl | 0 | —OC(O)— | 3-6 | H | 3-6 | —C(O)O— | 0 | H | $C_4$-$C_{12}$ alkyl |
| 11 | $C_1$-$C_{12}$ alkyl | H | 0 | absent | 3-6 | H | 3-6 | —C(O)O— | 0 | $C_4$-$C_8$ alkyl | $C_4$-$C_8$ alkyl |
| 12 | $C_4$-$C_8$ alkyl | $C_4$-$C_8$ alkyl | 0 | —OC(O)— | 3-6 | OH | 1-12 | absent | 0 | H | $C_1$-$C_{12}$ alkyl |
| 13 | $C_4$-$C_8$ alkyl | $C_4$-$C_8$ alkyl | 0 | —OC(O)— | 3-6 | OH | 3-6 | —C(O)O— | 0 | H | $C_4$-$C_{12}$ alkyl |
| 14 | $C_4$-$C_8$ alkyl | $C_4$-$C_8$ alkyl | 0 | —OC(O)O— | 3-6 | H | 3-6 | —C(O)O— | 0 | H | $C_4$-$C_{12}$ alkyl |
| 15 | $C_4$-$C_8$ alkyl | $C_4$-$C_8$ alkyl | 0 | —OC(O)— | 3-6 | H | 3-6 | —OC(O)O— | 0 | H | $C_4$-$C_{12}$ alkyl |
| 16 | $C_4$-$C_8$ alkyl | $C_4$-$C_8$ alkyl | 0 | —OC(O)O— | 3-6 | H | 3-6 | —OC(O)O— | 0 | H | $C_4$-$C_{12}$ alkyl |
| 17 | $C_4$-$C_8$ alkyl | H | 0 | —OC(O)— | 3-6 | H | 3-6 | —OC(O)O— | 0 | $C_4$-$C_8$ alkyl | $C_4$-$C_8$ alkyl |
| 18 | $C_4$-$C_8$ alkyl | H | 0 | —OC(O)O— | 3-6 | H | 3-6 | —C(O)O | 0 | $C_4$-$C_8$ alkyl | $C_4$-$C_8$ alkyl |
| 19 | $C_4$-$C_8$ alkyl | H | 0 | —OC(O)O— | 3-6 | H | 3-6 | —OC(O)O— | 0 | $C_4$-$C_8$ alkyl | $C_4$-$C_8$ alkyl |
| 20 | $C_4$-$C_8$ alkyl | H | 0 | —OC(O)— | 3-6 | OH | 3-6 | —OC(O)O— | 0 | $C_4$-$C_8$ alkyl | $C_4$-$C_8$ alkyl |
| 21 | $C_4$-$C_8$ alkyl | H | 0 | —OC(O)O— | 3-6 | OH | 3-6 | —C(O)O | 0 | $C_4$-$C_8$ alkyl | $C_4$-$C_8$ alkyl |
| 22 | $C_4$-$C_8$ alkyl | H | 0 | —OC(O)O— | 3-6 | OH | 3-6 | —OC(O)O— | 0 | $C_4$-$C_8$ alkyl | $C_4$-$C_8$ alkyl |
| 23 | $C_4$-$C_8$ alkyl | $C_4$-$C_8$ alkyl | 0 | —OC(O)O— | 3-6 | H | 3-6 | —C(O)O— | 0 | $C_1$-$C_4$ alkyl | $C_4$-$C_{12}$ alkyl |
| 24 | $C_4$-$C_8$ alkyl | $C_4$-$C_8$ alkyl | 0 | —OC(O)O— | 3-6 | H | 3-6 | —C(O)O— | 0 | $C_1$-$C_5$ alkyl | $C_6$-$C_{12}$ alkyl |

In some embodiments, the ionizable lipid of the disclosure is selected from the group consisting of:
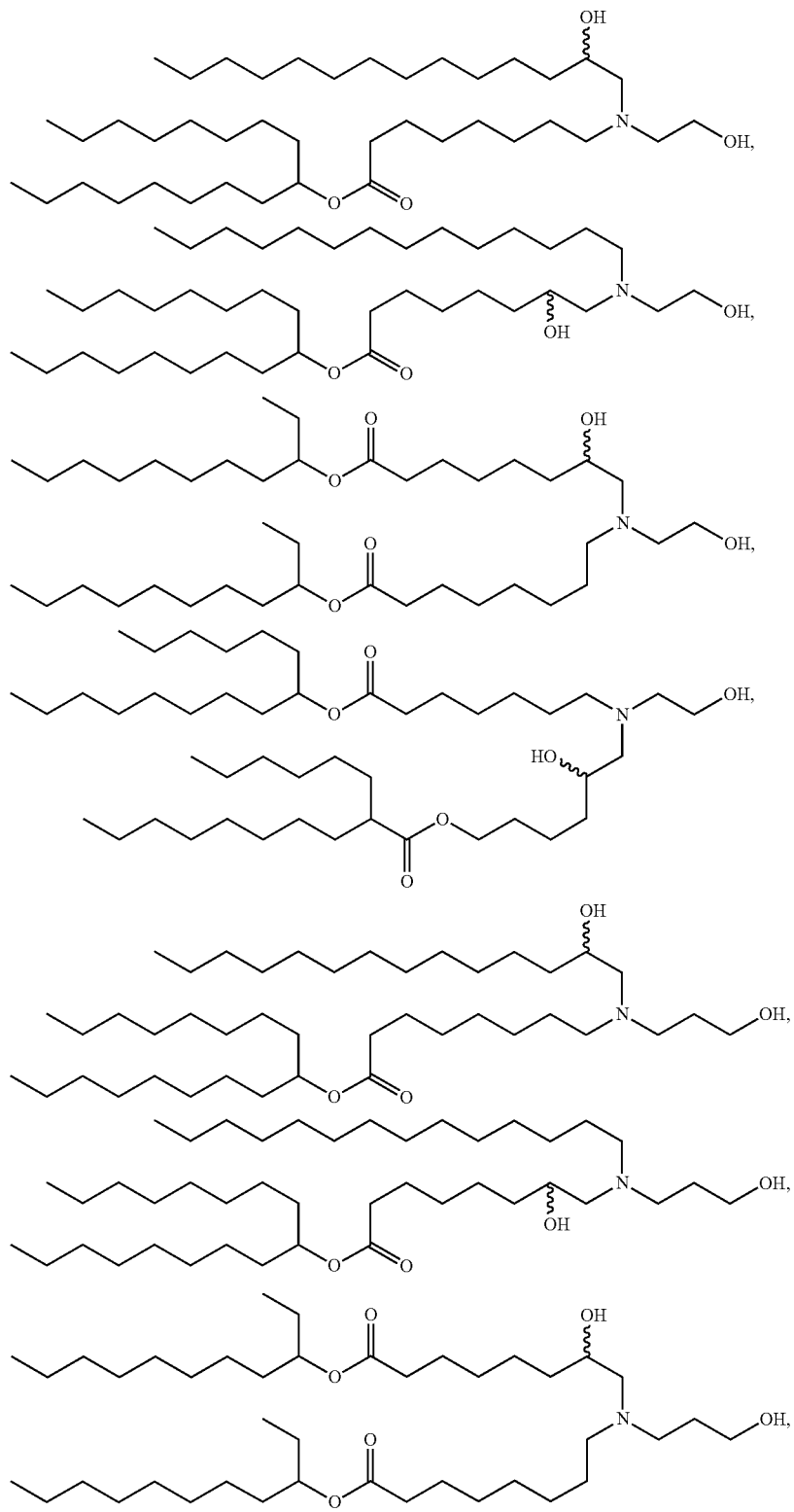

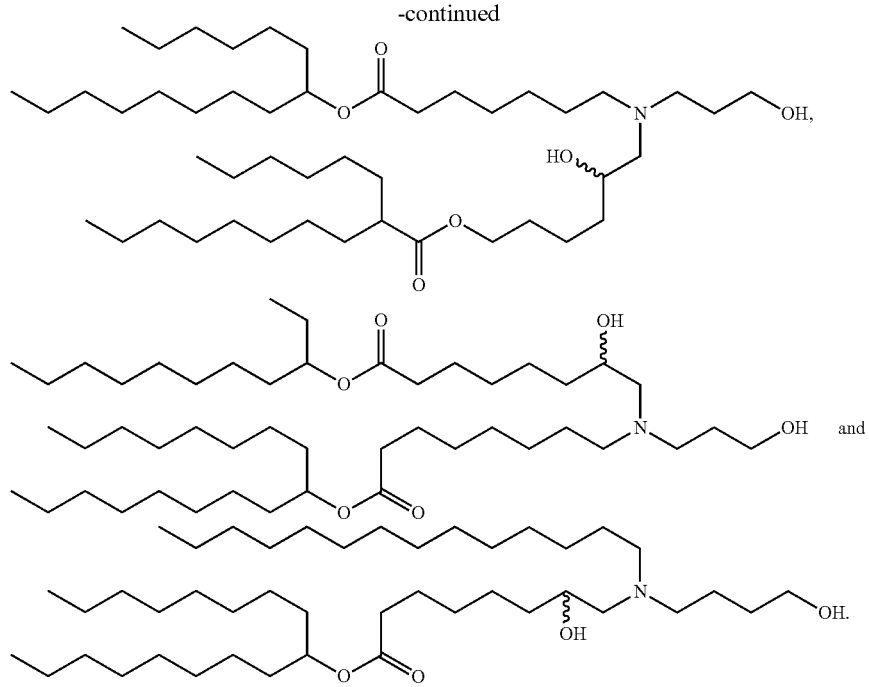
In some embodiments, the ionizable lipid is selected from the group consisting of
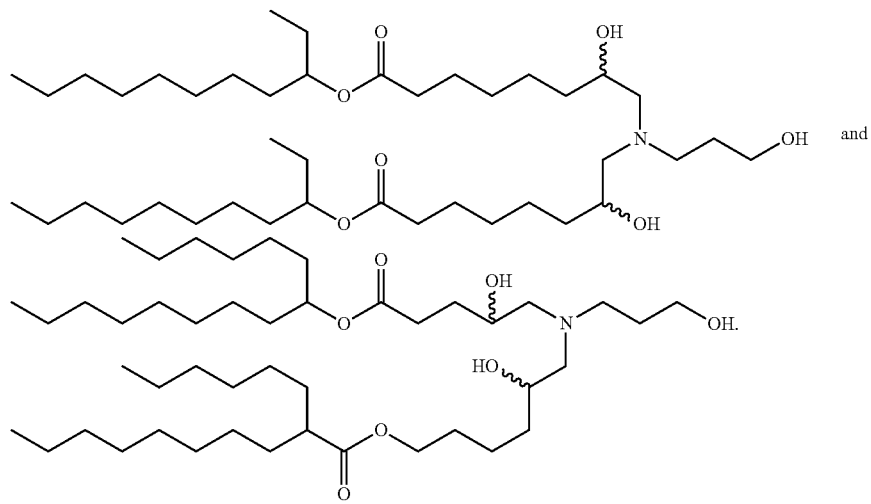
In some embodiments, the ionizable lipid is not
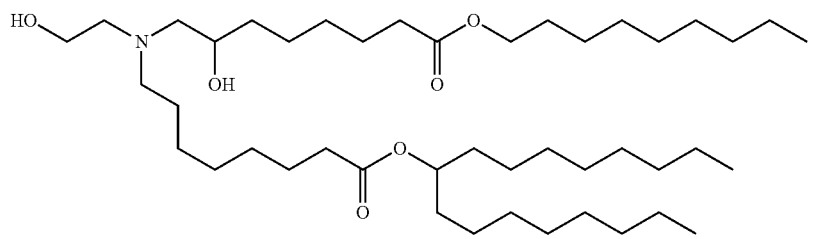
or -continued

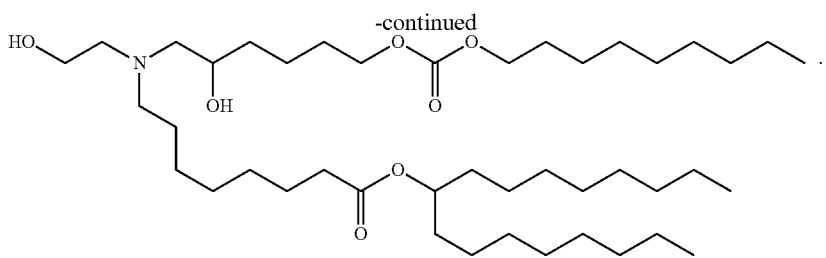

In some embodiments of Formula (13c-1) and/or (13c-2), each $R^b$ is hydrogen.

In some embodiments of Formula (13c-1) and/or to (13c-2), one and only one $R^b$ is $C_1$-$C_6$ alkyl, and the other $R^b$ group(s), if present, are hydrogen. In some embodiments of Formula (13c-1) and/or (13c-2), one and only one $R^b$ is methyl or ethyl. In some embodiments, the one and only one $R^b$ that is $C_1$-$C_6$ alkyl is attached to the carbon atom adjacent to the nitrogen atom of the ionizable lipid. In some embodiments of Formula (13c-1) and/or (13c-2), n is 2 to 7, one and only one $R^b$ is $C_1$-$C_6$ alkyl, and the other $R^b$ group(s), if present, are hydrogen.

In some embodiments, an ionizable lipid of the disclosure is a lipid selected from Table 10e-Table 10 h.

In some embodiments, an ionizable lipid of the disclosure has a beta-hydroxyl amine head group. In some embodiments, the ionizable lipid has a gamma-hydroxyl amine head group.

In an embodiment, the ionizable lipid is described in US patent publication number US20170210697A1. In an embodiment, the ionizable lipid is described in US patent publication number US20170119904A1.

TABLE 10e

| Ionizable lipid number | Structure |
|---|---|
| 1 | 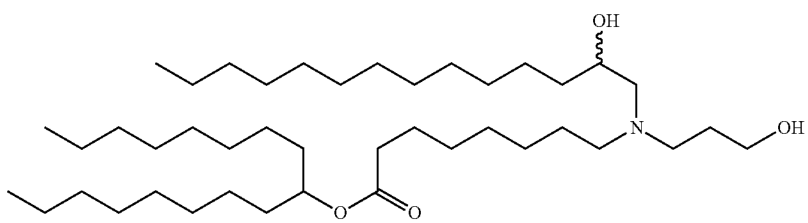 [SMILES: CCCCCCCCCCCCC(O)CN(CCCO)CCCCCCCC(=O)OC(CCCCCCCC)CCCCCCCC] |
| 2 | 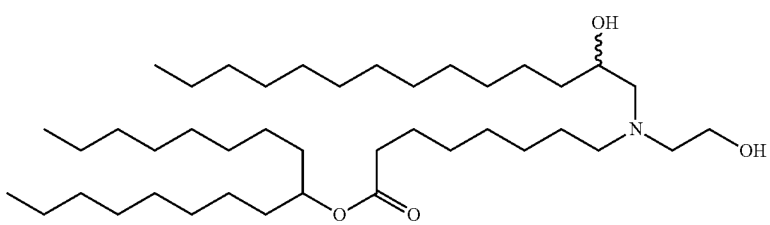 [SMILES: CCCCCCCCCCCCC(O)CN(CCO)CCCCCCCC(=O)OC(CCCCCCCC)CCCCCCCC] |
| 3 | 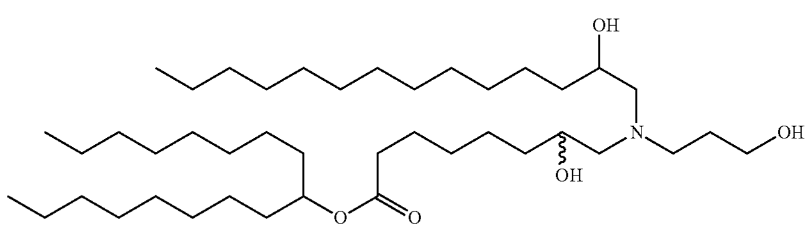 [SMILES: CCCCCCCCCCCCC(O)CN(CCCO)CC(O)CCCCCC(=O)OC(CCCCCCCC)CCCCCCCC] |
| 4 | 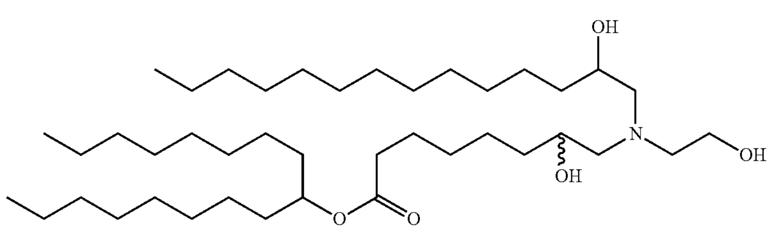 [SMILES: CCCCCCCCCCCCC(O)CN(CCO)CC(O)CCCCCC(=O)OC(CCCCCCCC)CCCCCCCC] |

TABLE 10e-continued
| Ionizable lipid number | Structure |
|---|---|
| 5 | 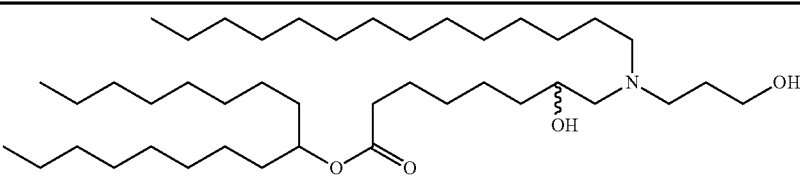 |
| 6 | 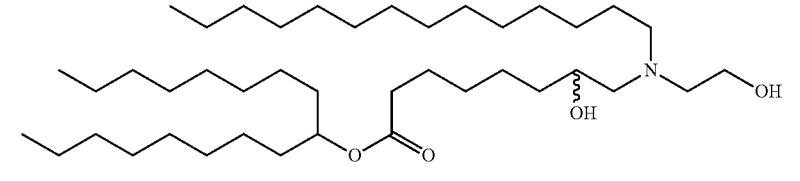 [SMILES: CCCCCCCCCCCCCCN(CCO)CC(O)CCCCCC(=O)OC(CCCCCCCC)CCCCCCCC] |
| 7 | 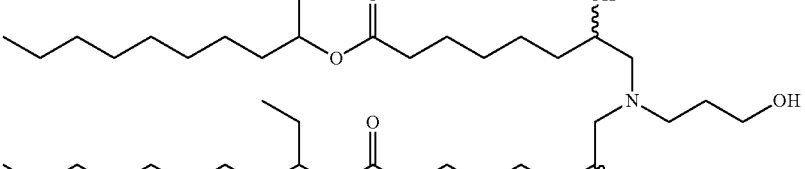 |
| 8 | 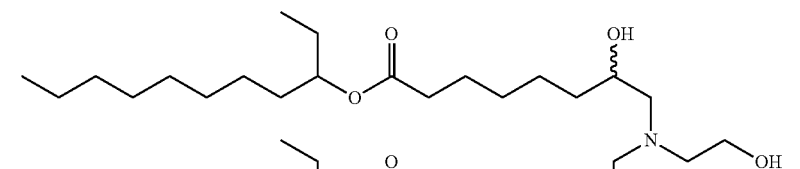 |
| 9 | 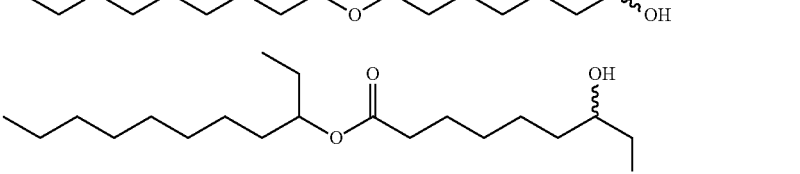 |
| 10 | 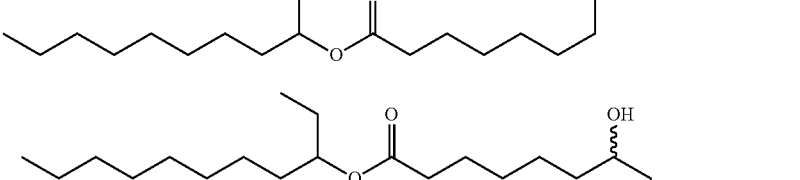 |
| 11 | 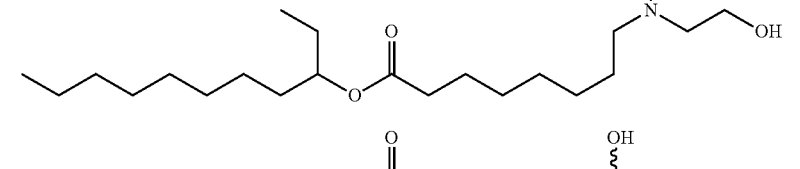 |

TABLE 10e-continued
| Ionizable lipid number | Structure |
|---|---|
| 12 | 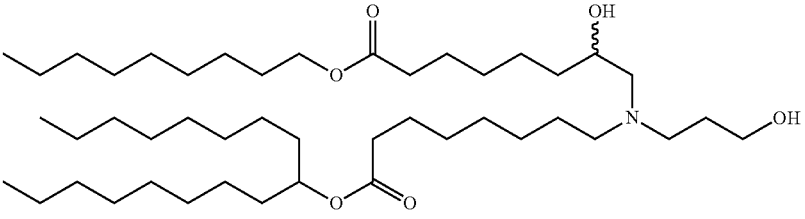 [SMILES: CCCCCCCCCOC(=O)CCCCCC(O)CN(CCCO)CCCCCCCC(=O)OC(CCCCCCCC)CCCCCCCC] |
| 13 | 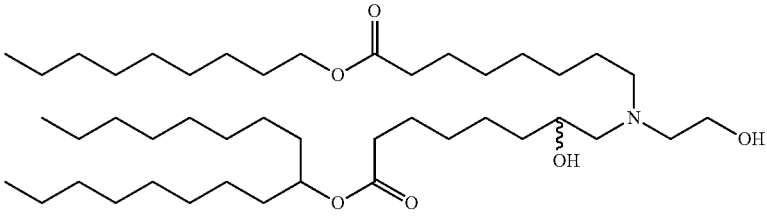 [SMILES: CCCCCCCCCOC(=O)CCCCCCCN(CCO)CC(O)CCCCCC(=O)OC(CCCCCCCC)CCCCCCCC] |
| 14 | 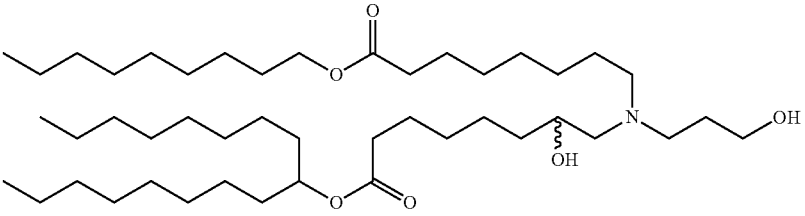 [SMILES: CCCCCCCCCOC(=O)CCCCCCCN(CCCO)CC(O)CCCCCC(=O)OC(CCCCCCCC)CCCCCCCC] |
| 15 | 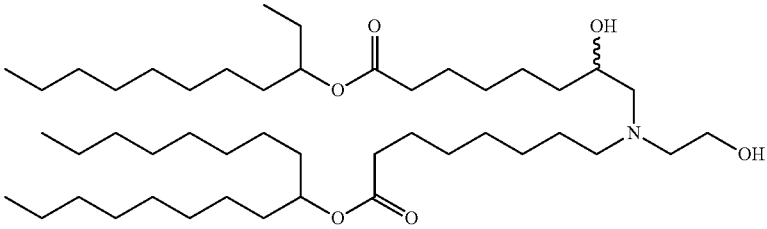 [SMILES: CCCCCCCCC(CC)OC(=O)CCCCCC(O)CN(CCO)CCCCCCCC(=O)OC(CCCCCCCC)CCCCCCCC] |
| 16 | 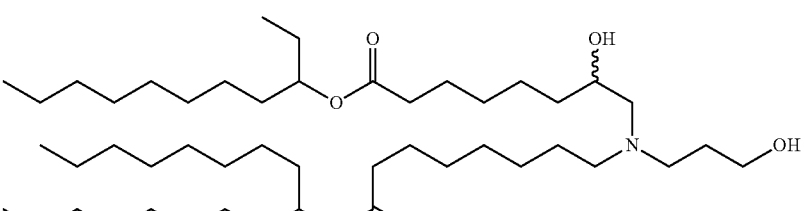 |
| 17 | 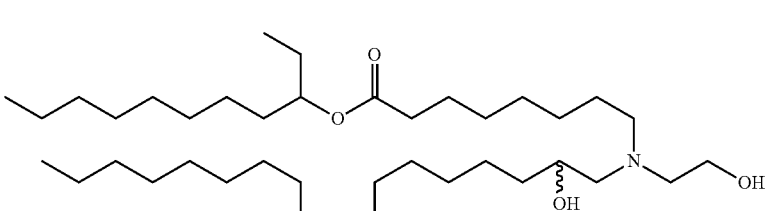 |

TABLE 10e-continued
| Ionizable lipid number | Structure |
|---|---|
| 18 | 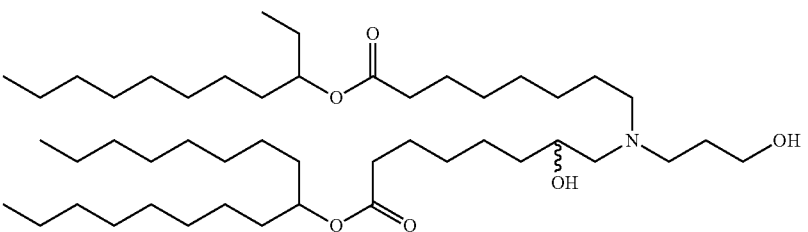 [SMILES: CCCCCCCCC(CC)OC(=O)CCCCCCCN(CCCO)CC(O)CCCCCC(=O)OC(CCCCCCCC)CCCCCCCC] |
| 19 | 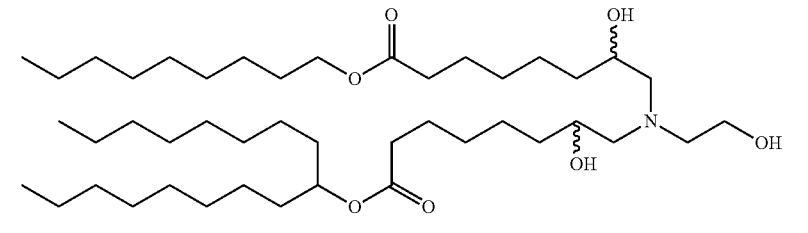 [SMILES: CCCCCCCCCOC(=O)CCCCCC(O)CN(CCO)CC(O)CCCCCC(=O)OC(CCCCCCCC)CCCCCCCC] |
| 20 | 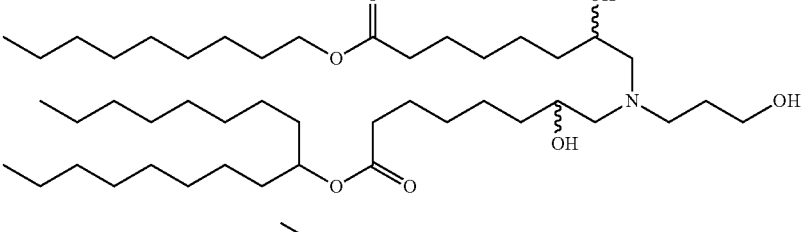 |
| 21 | 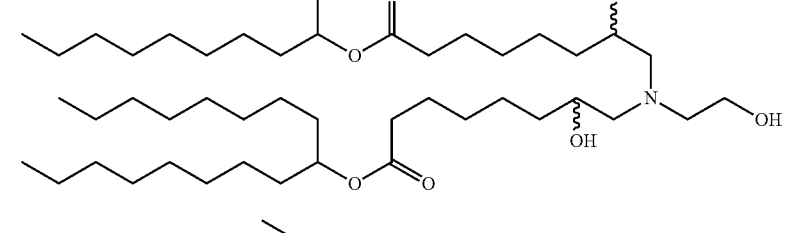 |
| 22 | 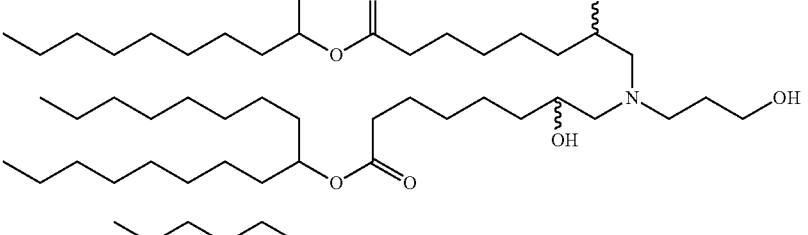 |
| 23 | 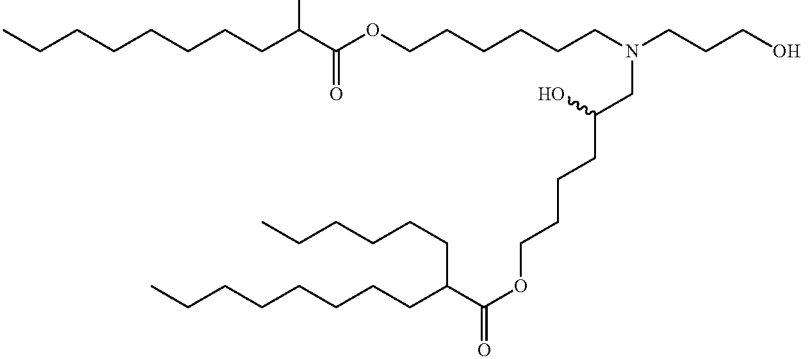 |

TABLE 10e-continued
| Ionizable lipid number | Structure |
| --- | --- |
| 24 | 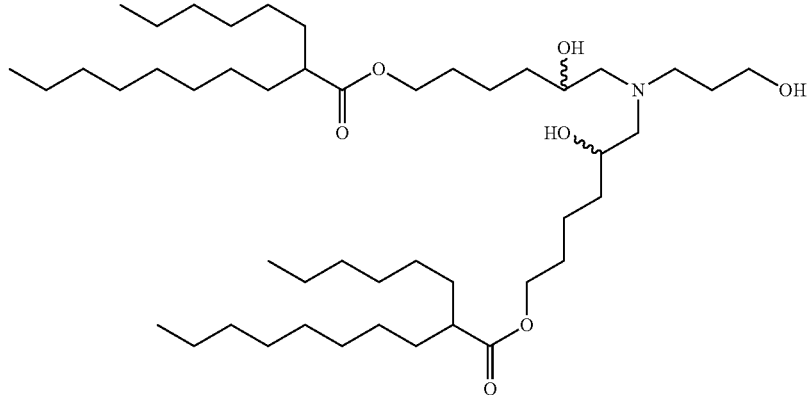 [SMILES: CCCCCCCCC(CCCCCC)C(=O)OCCCCC(O)CN(CCCO)CC(O)CCCCOC(=O)C(CCCCCC)CCCCCCCC] |
| 25 | 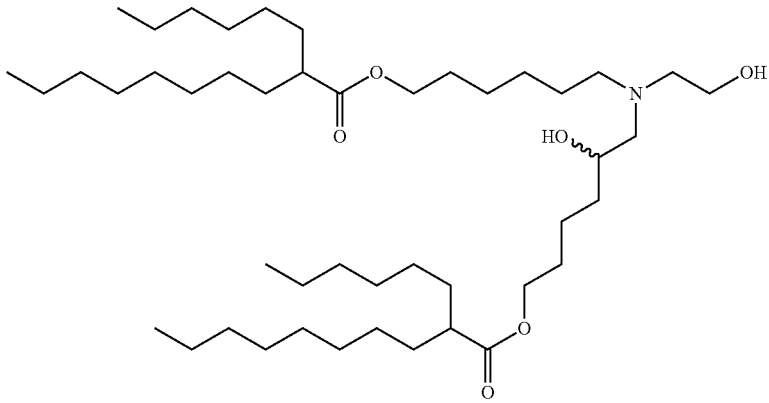 |
| 26 | 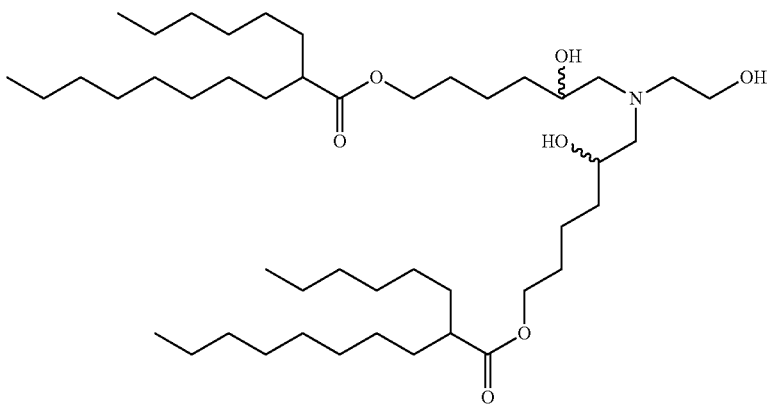 [SMILES: CCCCCCCCC(CCCCCC)C(=O)OCCCCC(O)CN(CCO)CC(O)CCCCOC(=O)C(CCCCCC)CCCCCCCC] |
| 27 | 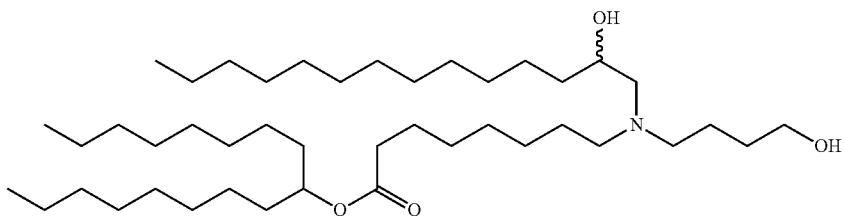 [SMILES: CCCCCCCCCCCCC(O)CN(CCCCO)CCCCCCCC(=O)OC(CCCCCCCC)CCCCCCCC] |

TABLE 10e-continued
| Ionizable lipid number | Structure |
|---|---|
| 28 | 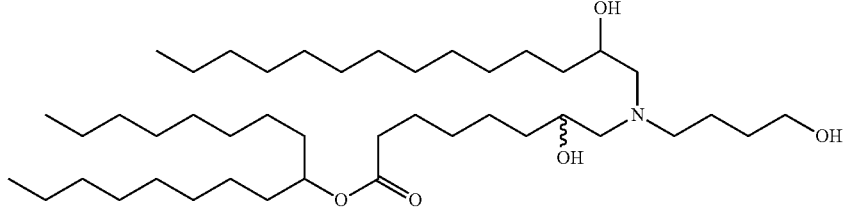 [SMILES: CCCCCCCCCCCCC(O)CN(CCCCO)CC(O)CCCCCC(=O)OC(CCCCCCCC)CCCCCCCC] |
| 29 | 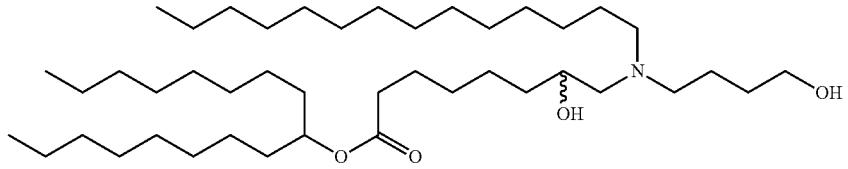 [SMILES: CCCCCCCCCCCCCCN(CCCCO)CC(O)CCCCCC(=O)OC(CCCCCCCC)CCCCCCCC] |
| 30 | 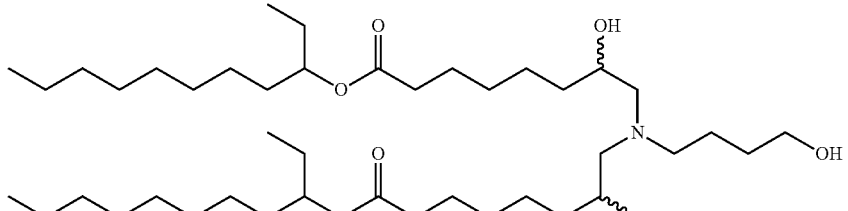 |
| 31 | 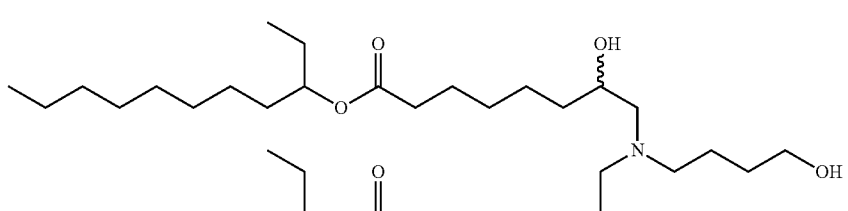 |
| 32 | 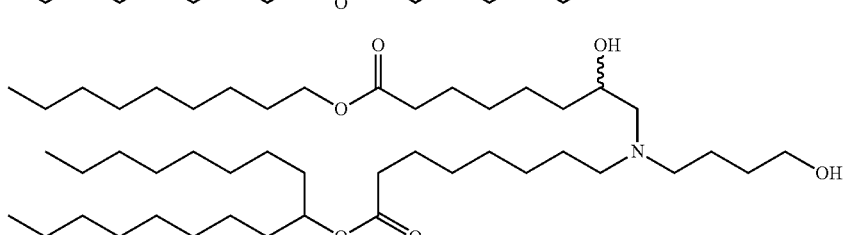 |
| 33 | 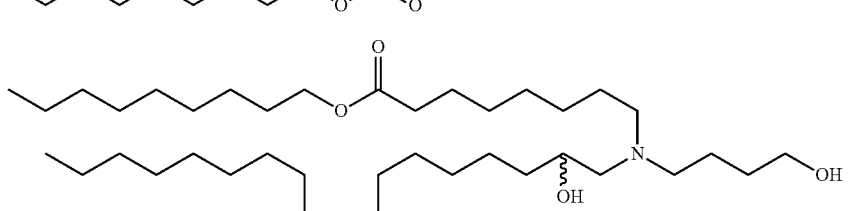 |
| 34 | 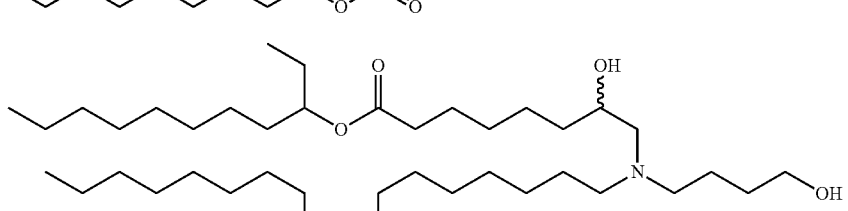 |

TABLE 10e-continued
| Ionizable lipid number | Structure |
|---|---|
| 35 | 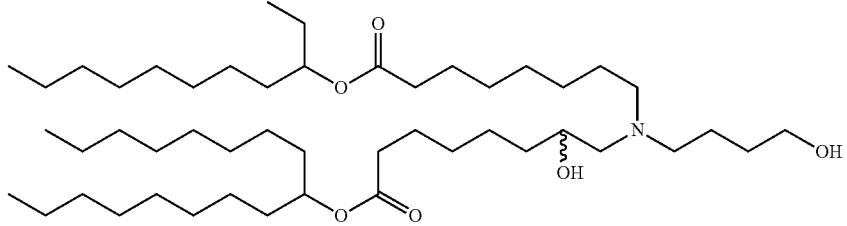 [SMILES: CCCCCCCCC(CC)OC(=O)CCCCCCCN(CCCCO)CC(O)CCCCCC(=O)OC(CCCCCCCC)CCCCCCCC] |
| 36 | 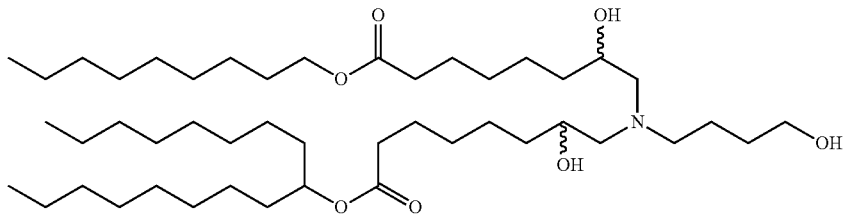 [SMILES: CCCCCCCCCOC(=O)CCCCCC(O)CN(CCCCO)CC(O)CCCCCC(=O)OC(CCCCCCCC)CCCCCCCC] |
| 37 | 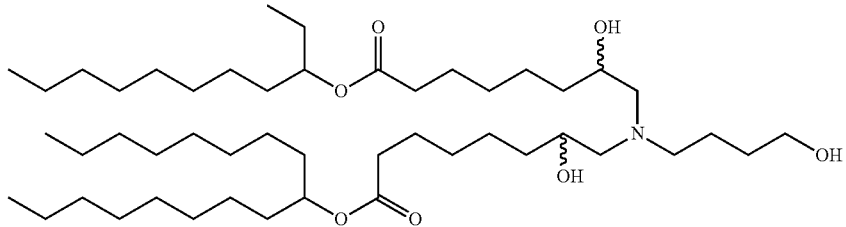 [SMILES: CCCCCCCCC(CC)OC(=O)CCCCCC(O)CN(CCCCO)CC(O)CCCCCC(=O)OC(CCCCCCCC)CCCCCCCC] |
| 38 | 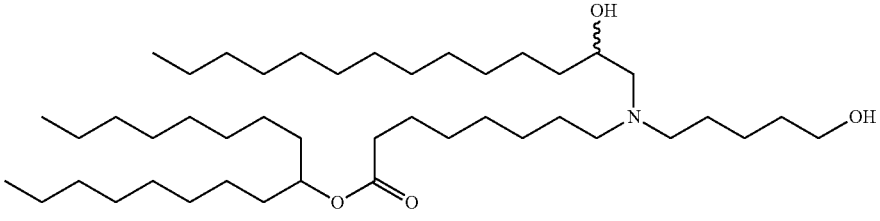 [SMILES: CCCCCCCCCCCCC(O)CN(CCCCCO)CCCCCCCC(=O)OC(CCCCCCCC)CCCCCCCC] |
| 39 | 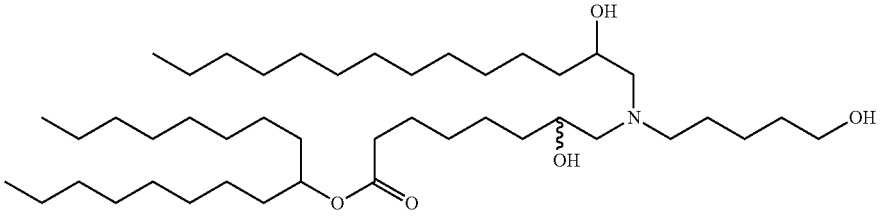 [SMILES: CCCCCCCCCCCCC(O)CN(CCCCCO)CC(O)CCCCCC(=O)OC(CCCCCCCC)CCCCCCCC] |
| 40 | 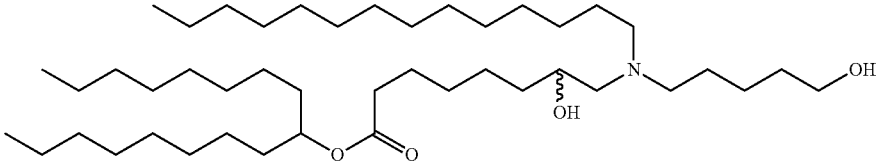 [SMILES: CCCCCCCCCCCCCCN(CCCCCO)CC(O)CCCCCC(=O)OC(CCCCCCCC)CCCCCCCC] |

TABLE 10e-continued
| Ionizable lipid number | Structure |
|---|---|
| 41 | 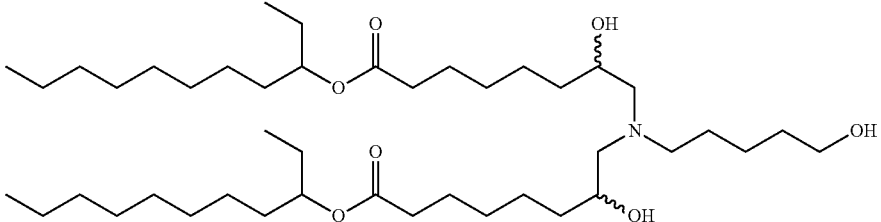 [SMILES: CCCCCCCCC(CC)OC(=O)CCCCCC(O)CN(CCCCCO)CC(O)CCCCCC(=O)OC(CC)CCCCCCCC] |
| 42 | 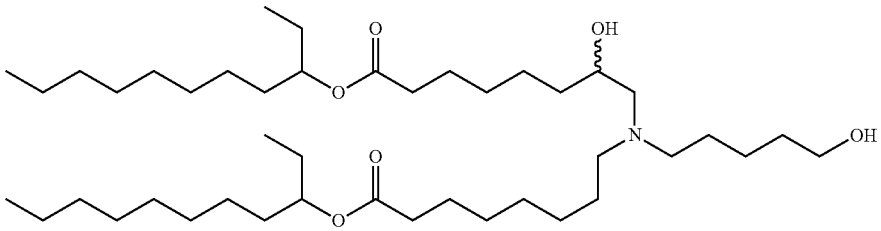 [SMILES: CCCCCCCCC(CC)OC(=O)CCCCCCCN(CCCCCO)CC(O)CCCCCC(=O)OC(CC)CCCCCCCC] |
| 43 | 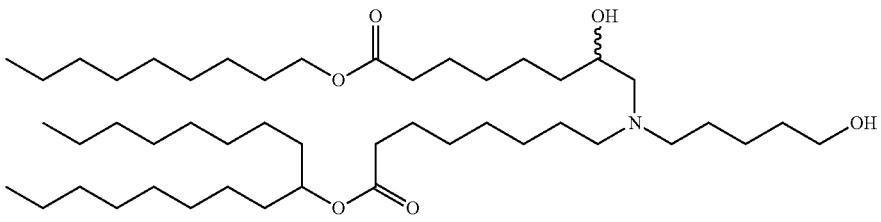 [SMILES: CCCCCCCCCOC(=O)CCCCCC(O)CN(CCCCCO)CCCCCCCC(=O)OC(CCCCCCCC)CCCCCCCC] |
| 44 | 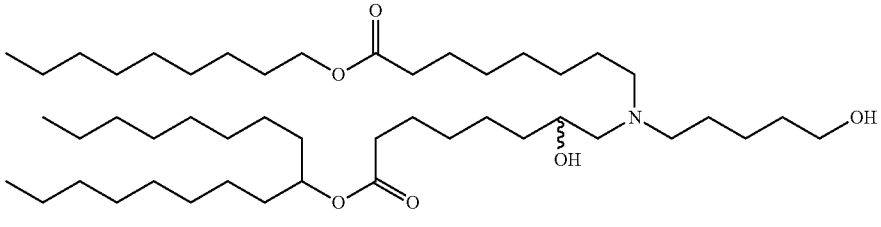 [SMILES: CCCCCCCCCOC(=O)CCCCCCCN(CCCCCO)CC(O)CCCCCC(=O)OC(CCCCCCCC)CCCCCCCC] |
| 45 | 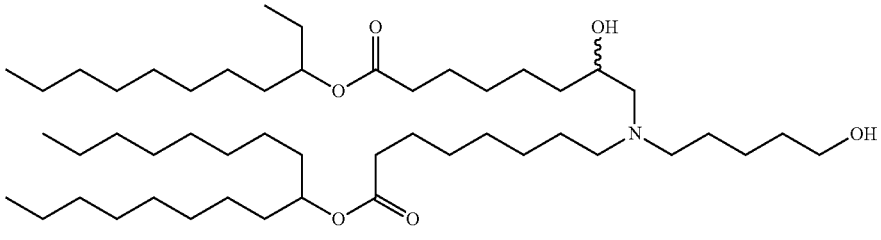 [SMILES: CCCCCCCCC(CC)OC(=O)CCCCCC(O)CN(CCCCCO)CCCCCCCC(=O)OC(CCCCCCCC)CCCCCCCC] |
| 46 | 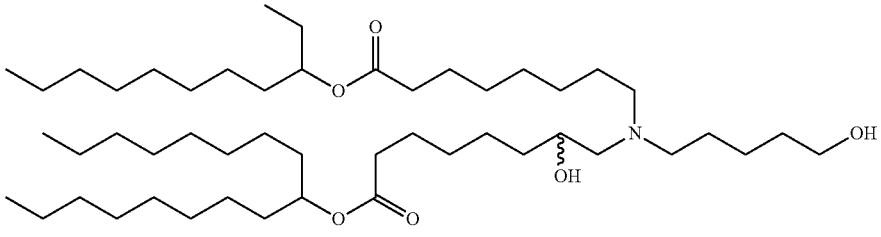 [SMILES: CCCCCCCCC(CC)OC(=O)CCCCCCCN(CCCCCO)CC(O)CCCCCC(=O)OC(CCCCCCCC)CCCCCCCC] |

TABLE 10e-continued
| Ionizable lipid number | Structure |
|---|---|
| 47 | 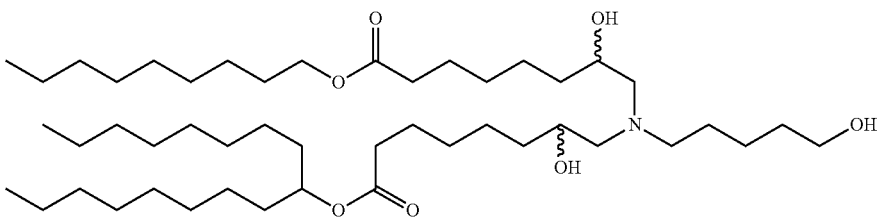 [SMILES: CCCCCCCCCOC(=O)CCCCCC(O)CN(CCCCCO)CC(O)CCCCCC(=O)OC(CCCCCCCC)CCCCCCCC] |
| 48 | 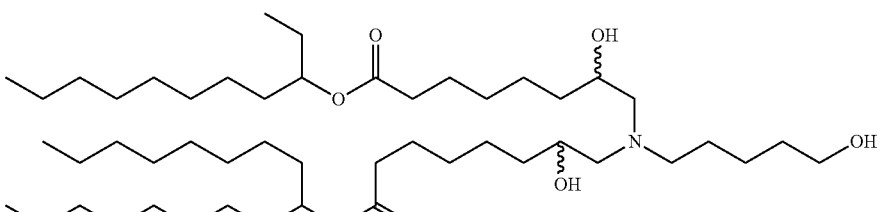 |
| 49 | 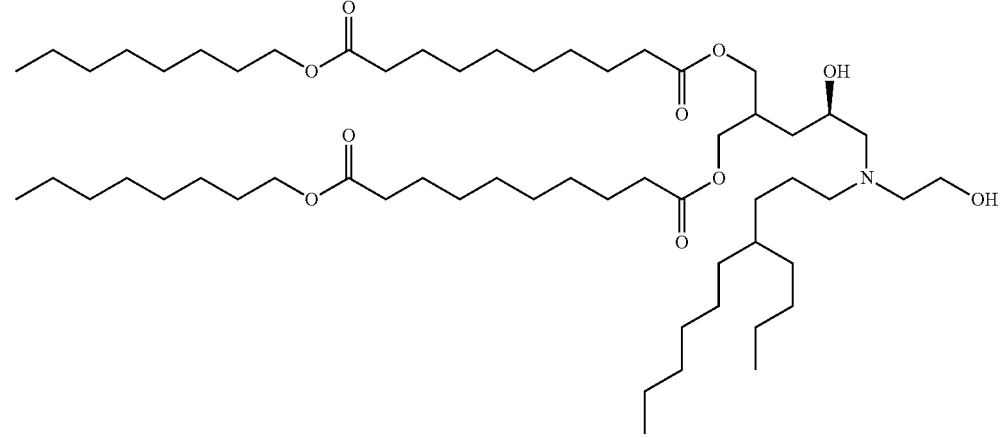 [SMILES: CCCCCCCCOC(=O)CCCCCCCCC(=O)OCC(COC(=O)CCCCCCCCC(=O)OCCCCCCCC)C[C@@H](O)CN(CCO)CCCC(CCCC)CCCCCC] |
| 50 | 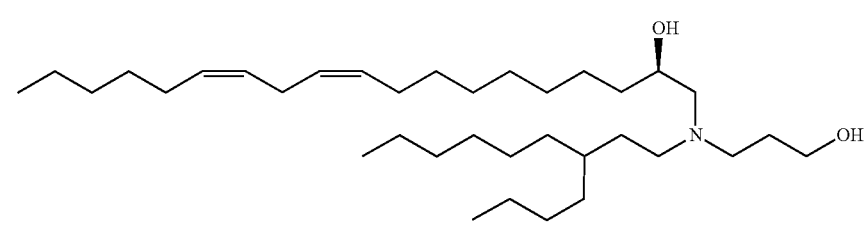 [SMILES: CCCCC/C=C\C/C=C\CCCCCCC[C@@H](O)CN(CCCO)CCC(CCCC)CCCCCC] |
| 51 | 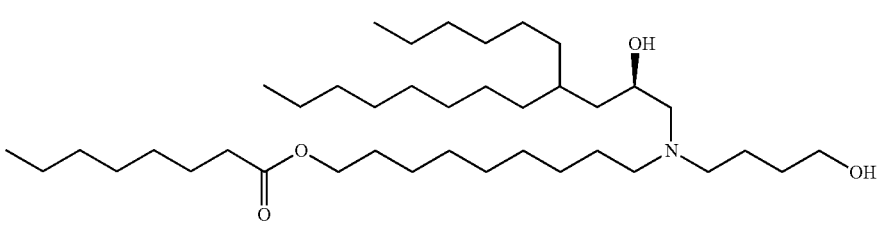 [SMILES: CCCCCCCCC(CCCCCC)C[C@@H](O)CN(CCCCO)CCCCCCCCCOC(=O)CCCCCCC] |
| 52 | 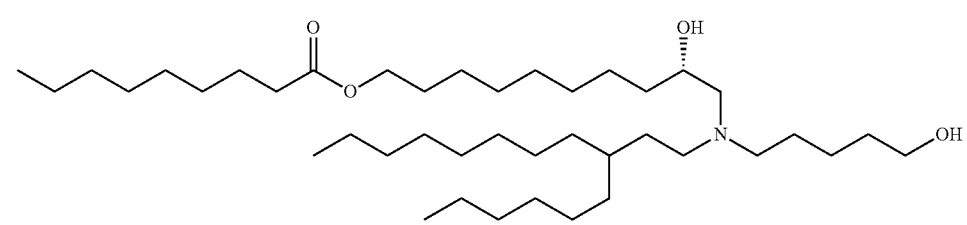 [SMILES: CCCCCCCCC(=O)OCCCCCCCC[C@H](O)CN(CCCCCO)CCC(CCCCCC)CCCCCCCC] |

TABLE 10e-continued
| Ionizable lipid number | Structure |
|---|---|
| 53 | 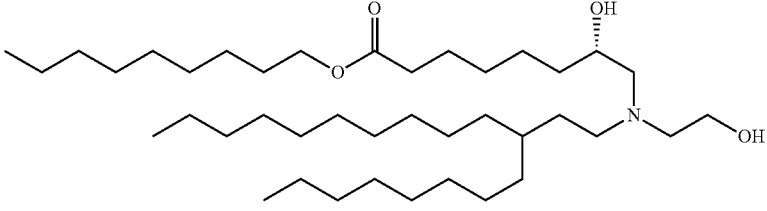 [SMILES: CCCCCCCCCCC(CCCCCCCC)CCN(CCO)C[C@@H](O)CCCCCC(=O)OCCCCCCCCC] |
| 54 | 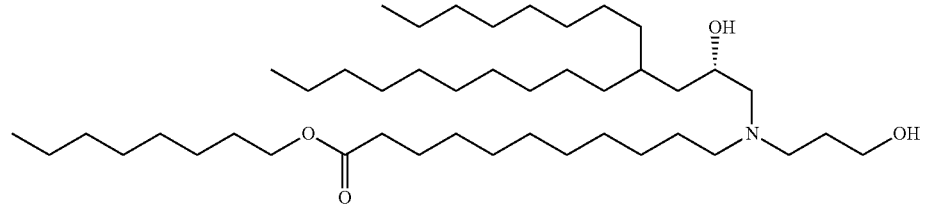 [SMILES: CCCCCCCCCCC(CCCCCCCC)C[C@H](O)CN(CCCO)CCCCCCCCCCC(=O)OCCCCCCCC] |
| 55 | 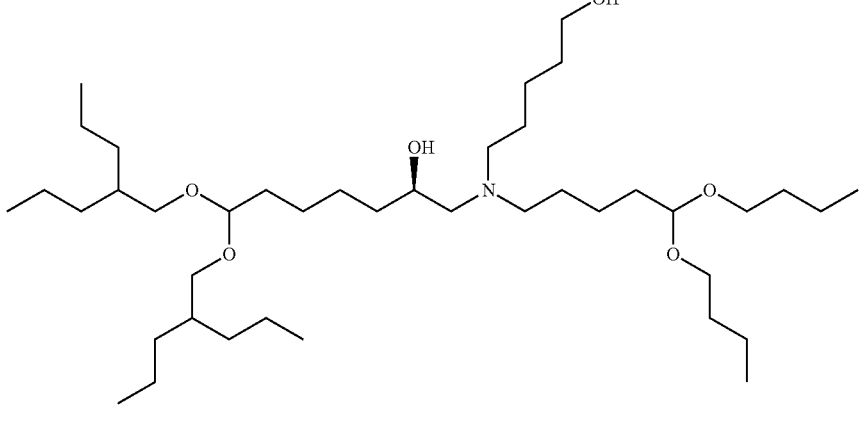 |
| 56 | 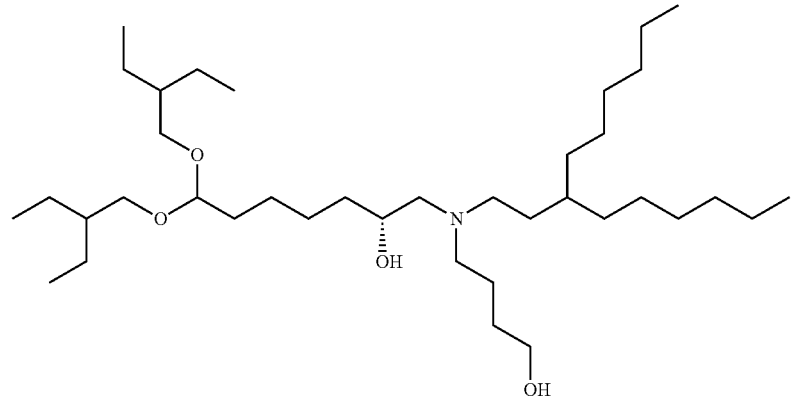 [SMILES: CCCCCCC(CCCCCC)CCN(CCCCO)C[C@H](O)CCCCC(OCC(CC)CC)OCC(CC)CC] |

TABLE 10e-continued
| Ionizable lipid number | Structure |
| --- | --- |
| 57 | 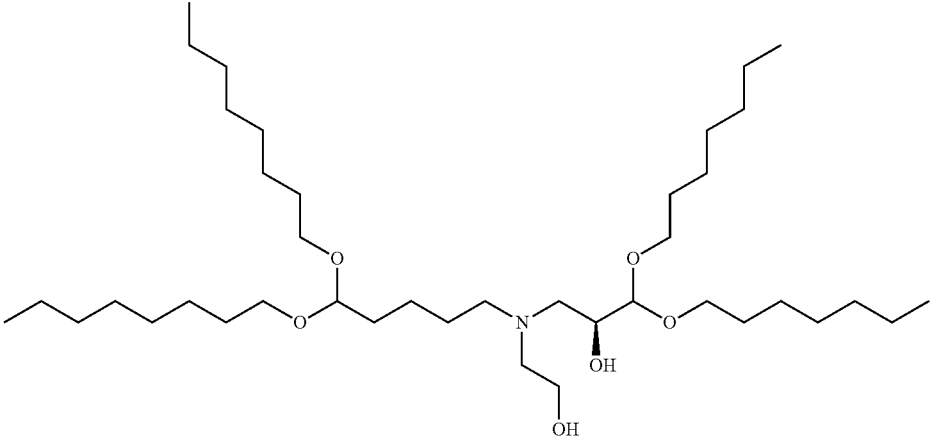 [SMILES: CCCCCCCCOC(CCCCN(CCO)C[C@H](O)C(OCCCCCCC)OCCCCCCC)OCCCCCCCC] |
| 58 | 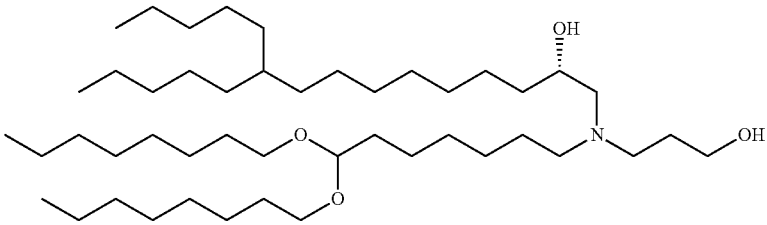 [SMILES: CCCCCCCCOC(CCCCCCN(CCCO)C[C@@H](O)CCCCCCCC(CCCCC)CCCCC)OCCCCCCCC] |
| 59 | 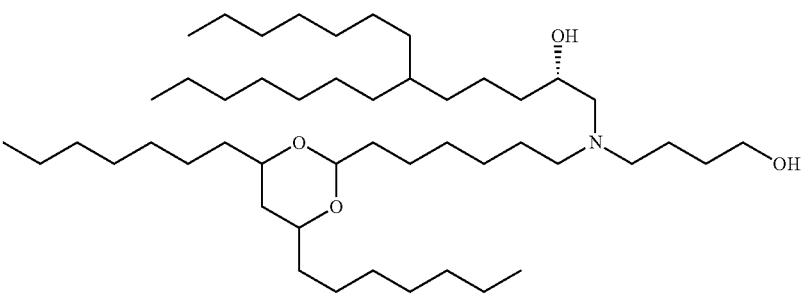 [SMILES: CCCCCCCC(CCCCCCC)CCC[C@H](O)CN(CCCCO)CCCCCCC1OC(CCCCCCC)CC(CCCCCCC)O1] |
| 60 | 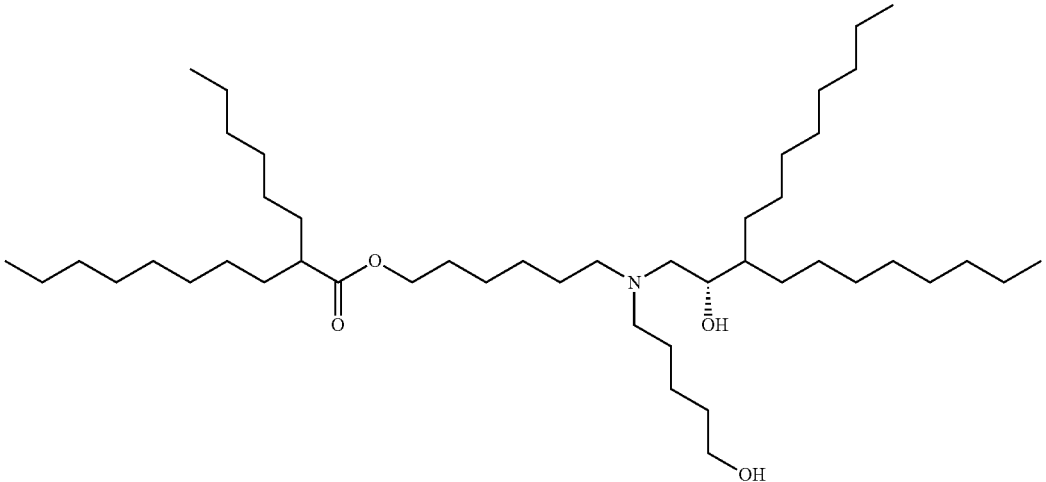 [SMILES: CCCCCCCCC(CCCCCC)C(=O)OCCCCCCN(CCCCCO)C[C@@H](O)C(CCCCCCCC)CCCCCCCC] |

TABLE 10e-continued
| Ionizable lipid number | Structure |
|---|---|
| 61 | 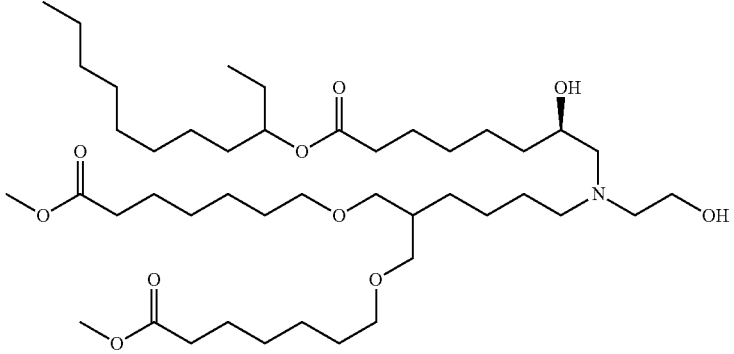 [SMILES: CCCCCCCCC(CC)OC(=O)CCCCC[C@@H](O)CN(CCO)CCCCC(COCCCCCCC(=O)OC)COCCCCCCC(=O)OC] |
| 62 | 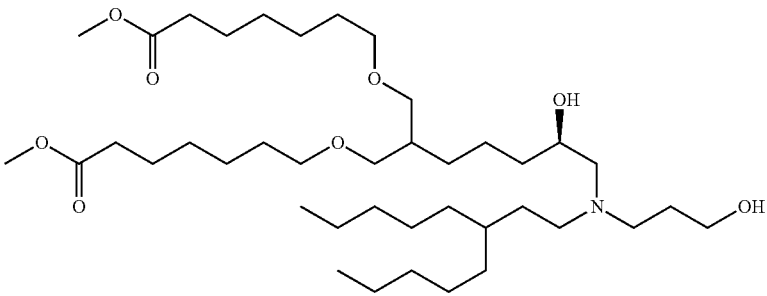 [SMILES: CCCCCC(CCCCC)CCN(CCCO)C[C@H](O)CCCC(COCCCCCCC(=O)OC)COCCCCCCC(=O)OC] |
| 63 | 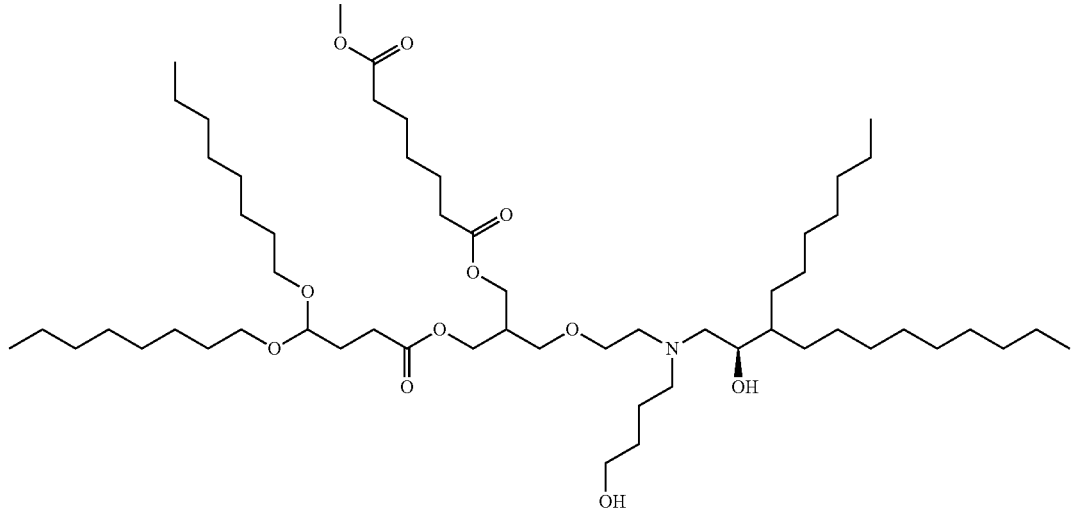 [SMILES: CCCCCCCCCC(CCCCCCC)[C@@H](O)CN(CCCCO)CCOCC(COC(=O)CCCCCC(=O)OC)COC(=O)CCC(OCCCCCCCC)OCCCCCCCC] |

TABLE 10e-continued
| Ionizable lipid number | Structure |
|---|---|
| 64 | 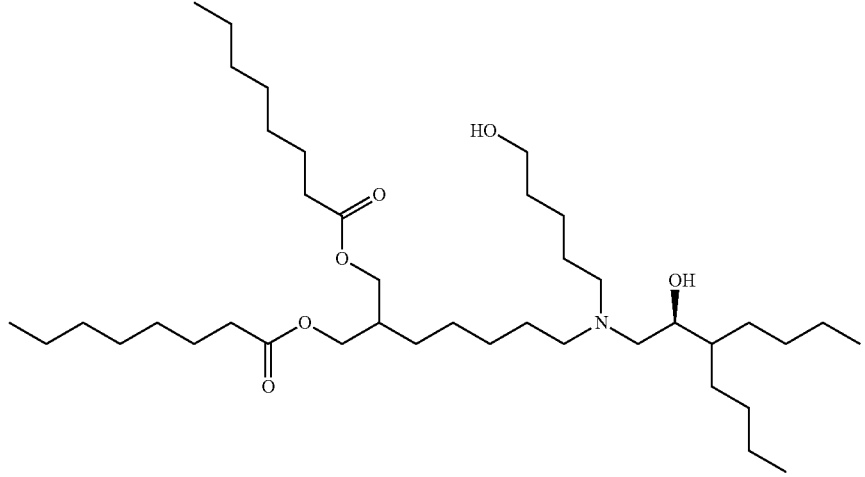 [SMILES: CCCCCCCC(=O)OCC(CCCCCN(CCCCCO)C[C@@H](O)C(CCCC)CCCC)COC(=O)CCCCCCC] |
| 65 | 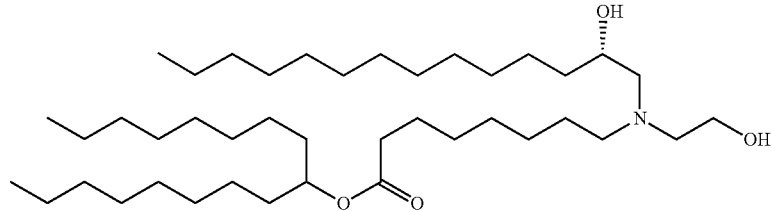 [SMILES: CCCCCCCCCCCC[C@H](O)CN(CCO)CCCCCCCC(=O)OC(CCCCCCCC)CCCCCCCC] |
| 66 | 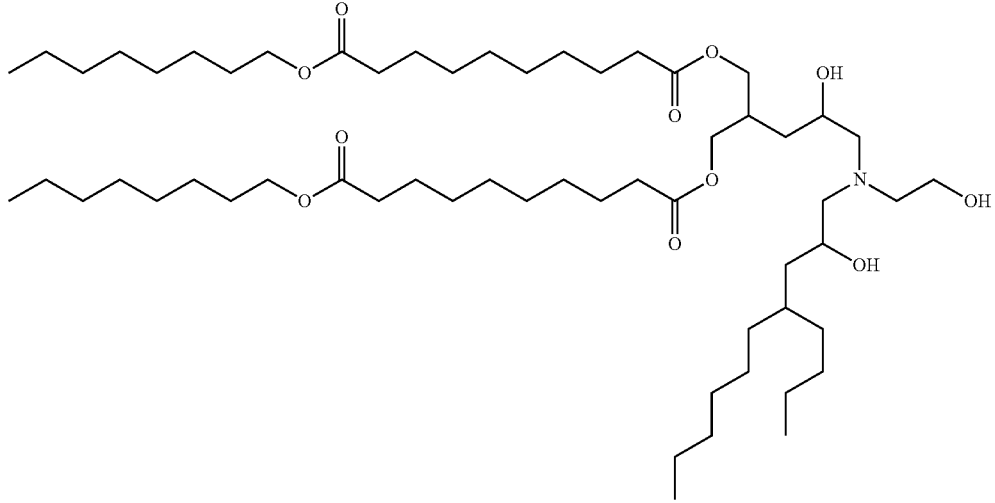 [SMILES: CCCCCCCCOC(=O)CCCCCCCCC(=O)OCC(COC(=O)CCCCCCCCC(=O)OCCCCCCCC)CC(O)CN(CCO)CC(O)CC(CCCC)CCCCCC] |
| 67 | 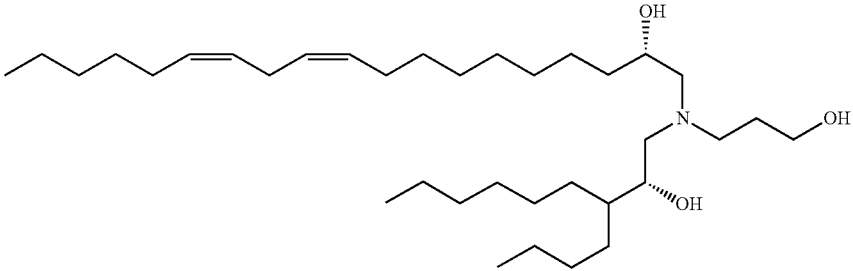 [SMILES: CCCCC/C=C\C/C=C\CCCCCCC[C@H](O)CN(CCCO)C[C@H](O)C(CCCC)CCCCCC] |

TABLE 10e-continued
| Ionizable lipid number | Structure |
|---|---|
| 68 | 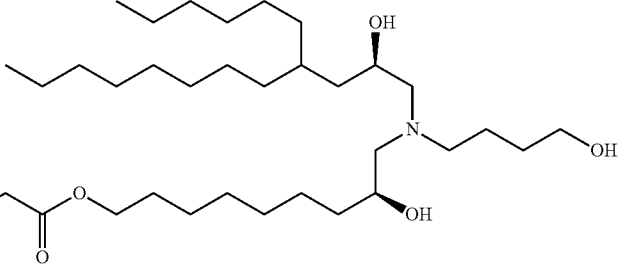 |
| 69 | 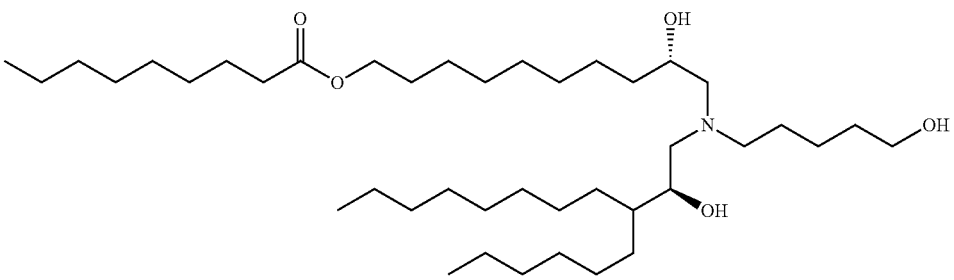 [SMILES: CCCCCCCCC(=O)OCCCCCCCC[C@H](O)CN(CCCCCO)C[C@@H](O)C(CCCCCC)CCCCCCCC] |
| 70 | 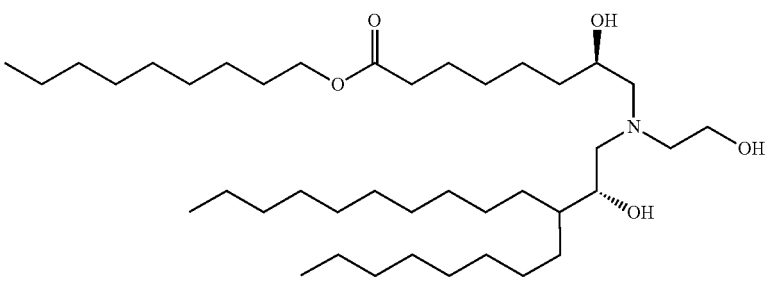 [SMILES: CCCCCCCCCCC(CCCCCCCC)[C@@H](O)CN(CCO)C[C@H](O)CCCCCC(=O)OCCCCCCCCC] |
| 71 | 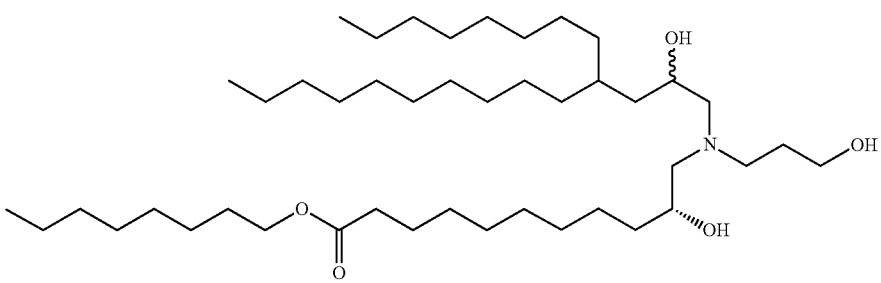 [SMILES: CCCCCCCCCCC(CCCCCCCC)CC(O)CN(CCCO)C[C@H](O)CCCCCCCCC(=O)OCCCCCCCC] |
| 72 | 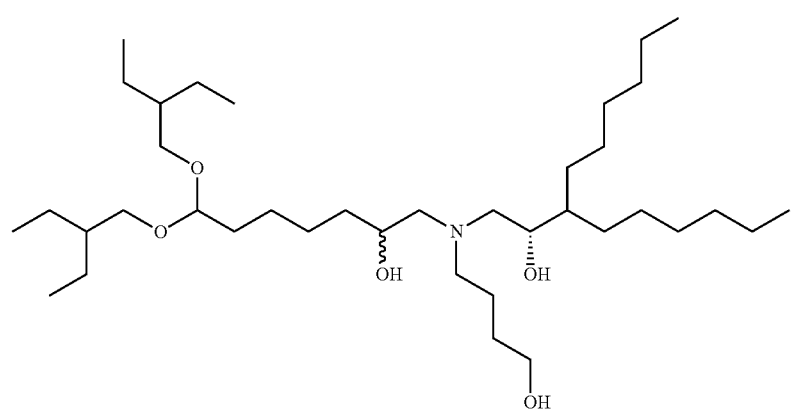 [SMILES: CCCCCCC(CCCCCC)[C@H](O)CN(CCCCO)CC(O)CCCCC(OCC(CC)CC)OCC(CC)CC] |

TABLE 10e-continued
| Ionizable lipid number | Structure |
|---|---|
| 73 | 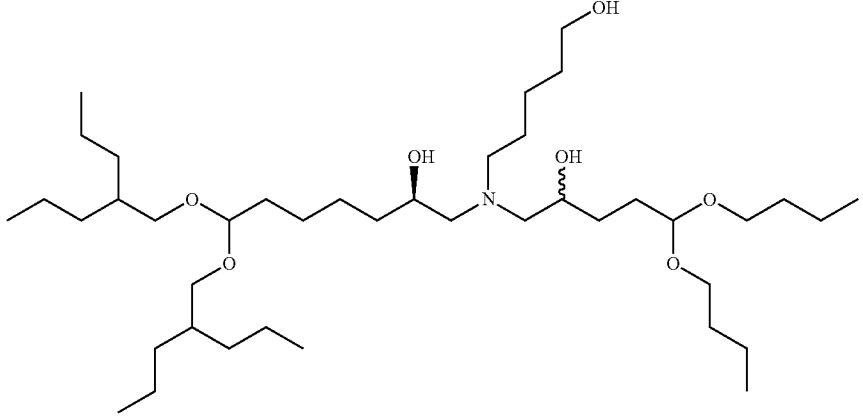 [SMILES: CCCCOC(CCC(O)CN(CCCCCO)C[C@H](O)CCCCC(OCC(CCC)CCC)OCC(CCC)CCC)OCCCC] |
| 74 | 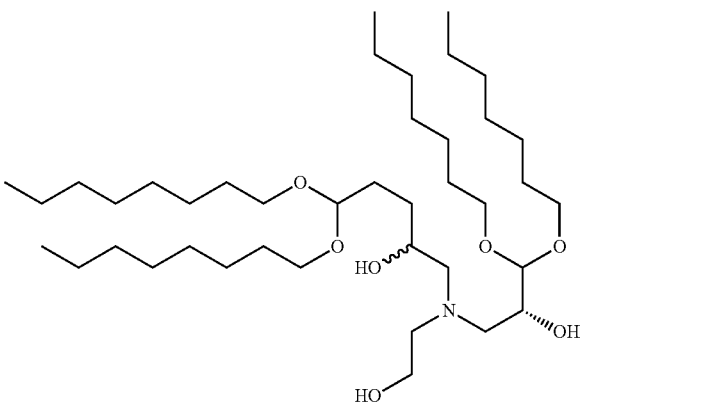 [SMILES: CCCCCCCCOC(CCC(O)CN(CCO)C[C@@H](O)C(OCCCCCCC)OCCCCCCC)OCCCCCCCC] |
| 75 | 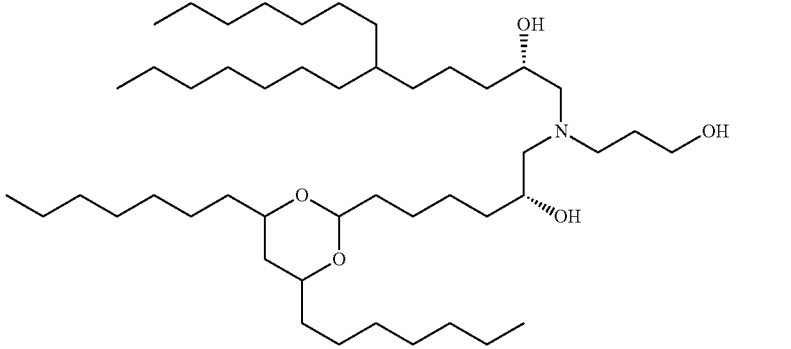 [SMILES: CCCCCCCC(CCCCCCC)CCC[C@H](O)CN(CCCO)C[C@H](O)CCCCC1OC(CCCCCCC)CC(CCCCCCC)O1] |
| 76 | 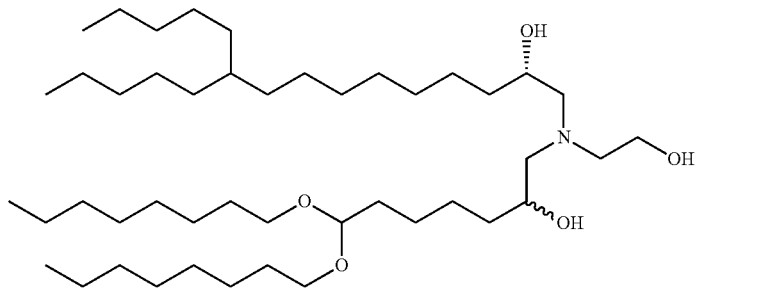 [SMILES: CCCCCCCCOC(CCCCC(O)CN(CCO)C[C@@H](O)CCCCCCCC(CCCCC)CCCCC)OCCCCCCCC] |

TABLE 10e-continued
| Ionizable lipid number | Structure |
|---|---|
| 77 | 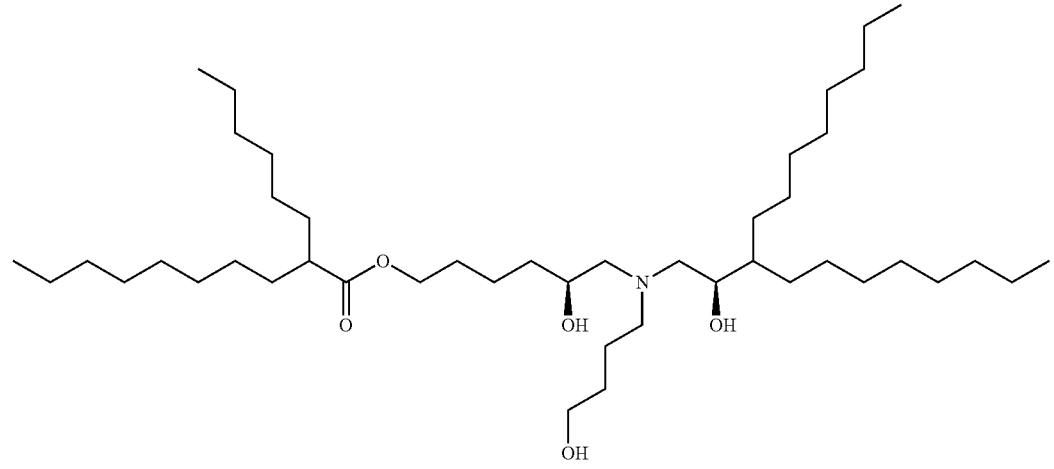 [SMILES: CCCCCCCCC(CCCCCC)C(=O)OCCCC[C@H](O)CN(CCCCO)C[C@H](O)C(CCCCCCCC)CCCCCCCC] |
| 78 | 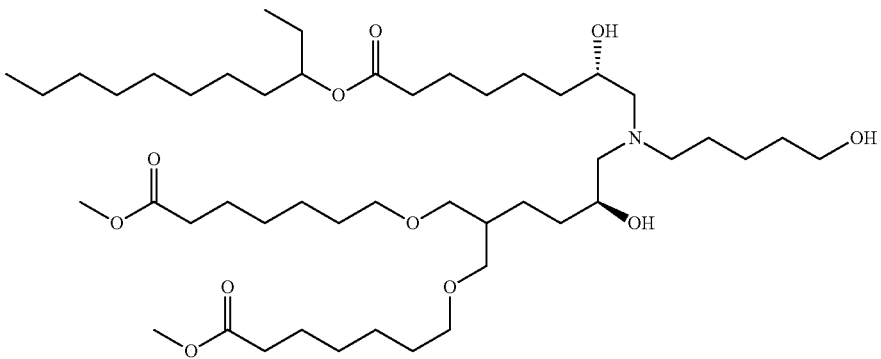 [SMILES: CCCCCCCCC(CC)OC(=O)CCCCC[C@H](O)CN(CCCCCO)C[C@@H](O)CCC(COCCCCCCC(=O)OC)COCCCCCCC(=O)OC] |
| 79 | 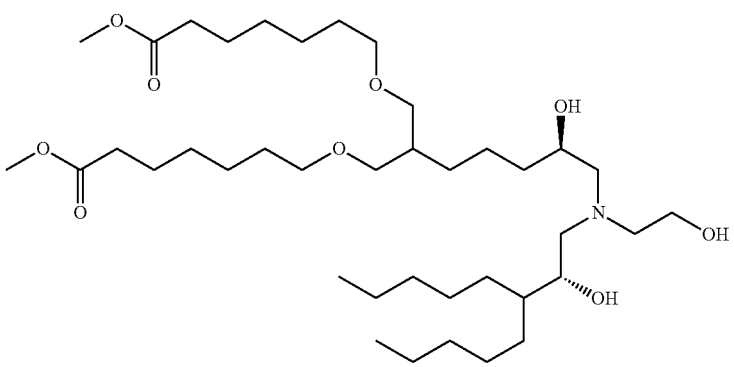 [SMILES: CCCCCC(CCCCC)[C@@H](O)CN(CCO)C[C@H](O)CCCC(COCCCCCCC(=O)OC)COCCCCCCC(=O)OC] |

TABLE 10e-continued
| Ionizable lipid number | Structure |
|---|---|
| 80 | 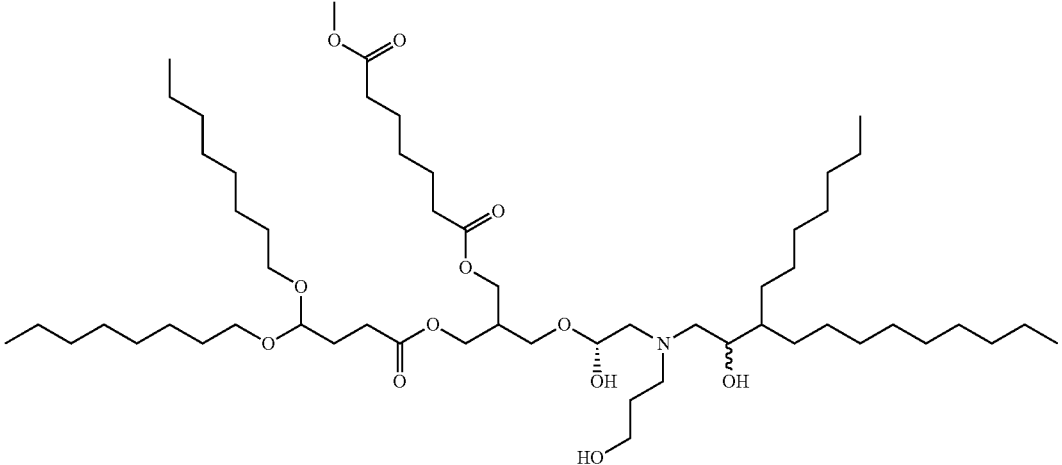 [SMILES: CCCCCCCCCC(CCCCCCC)C(O)CN(CCCO)C[C@H](O)OCC(COC(=O)CCCCCC(=O)OC)COC(=O)CCC(OCCCCCCCC)OCCCCCCCC] |
| 81 | 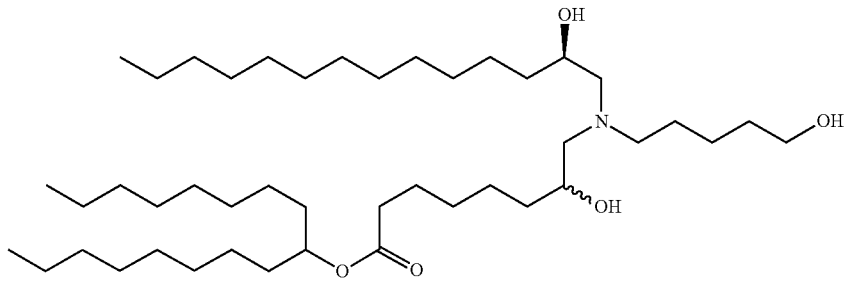 [SMILES: CCCCCCCCCCCC[C@@H](O)CN(CCCCCO)CC(O)CCCCCC(=O)OC(CCCCCCCC)CCCCCCCC] |
| 82 | 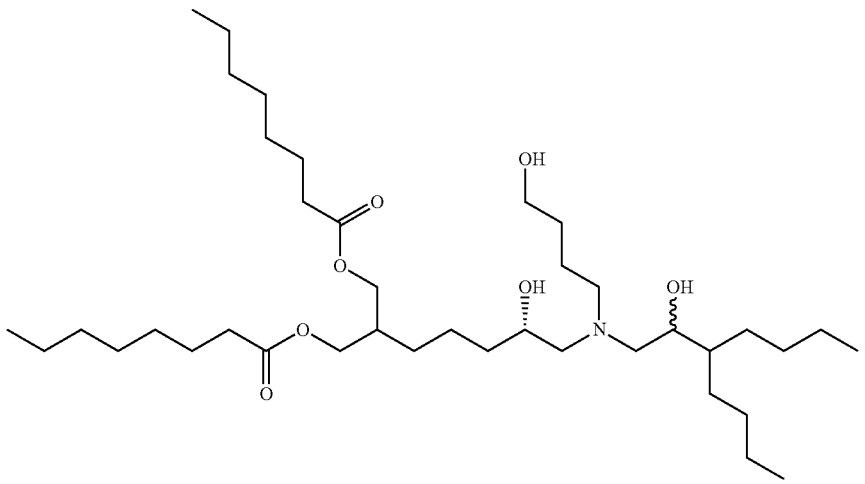 [SMILES: CCCCCCCC(=O)OCC(CCC[C@H](O)CN(CCCCO)CC(O)C(CCCC)CCCC)COC(=O)CCCCCCC] |

TABLE 10e-continued
| Ionizable lipid number | Structure |
|---|---|
| 83 | 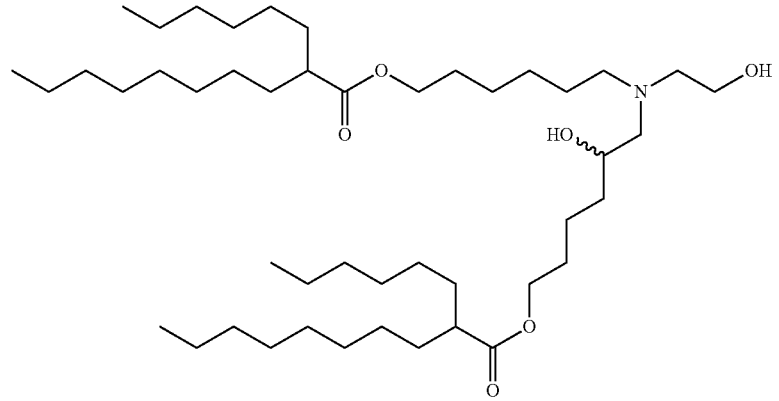 [SMILES: CCCCCCCCC(CCCCCC)C(=O)OCCCCCCN(CCO)CC(O)CCCCOC(=O)C(CCCCCC)CCCCCCCC] |
| 84 | 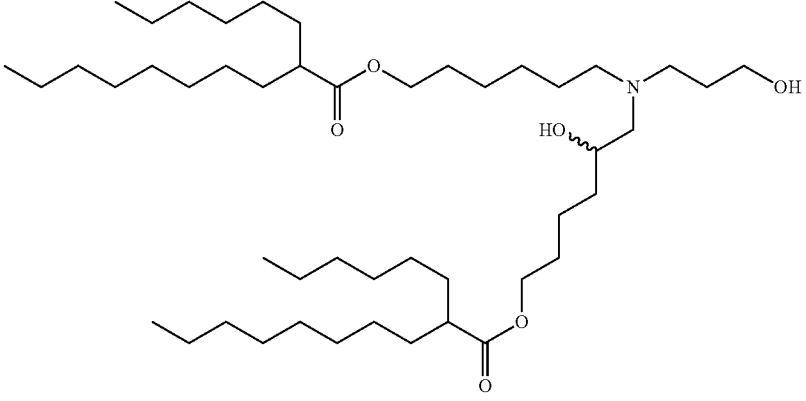 [SMILES: CCCCCCCCC(CCCCCC)C(=O)OCCCCCCN(CCCO)CC(O)CCCCOC(=O)C(CCCCCC)CCCCCCCC] |
| 85 | 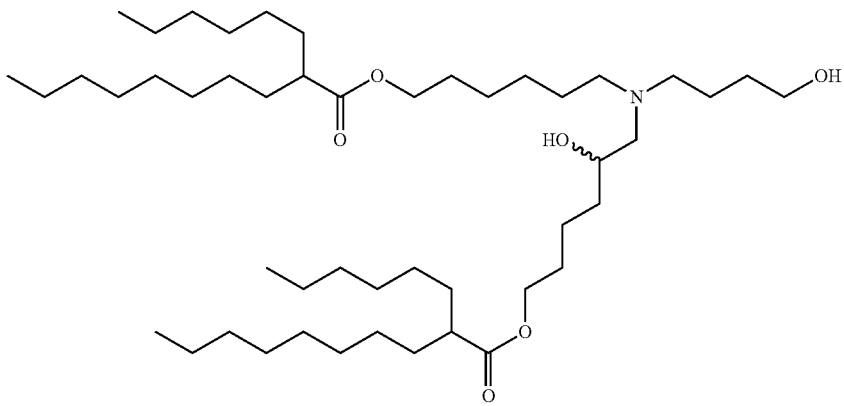 [SMILES: CCCCCCCCC(CCCCCC)C(=O)OCCCCCCN(CCCCO)CC(O)CCCCOC(=O)C(CCCCCC)CCCCCCCC] |

TABLE 10e-continued

| Ionizable lipid number | Structure |
|---|---|
| 86 | 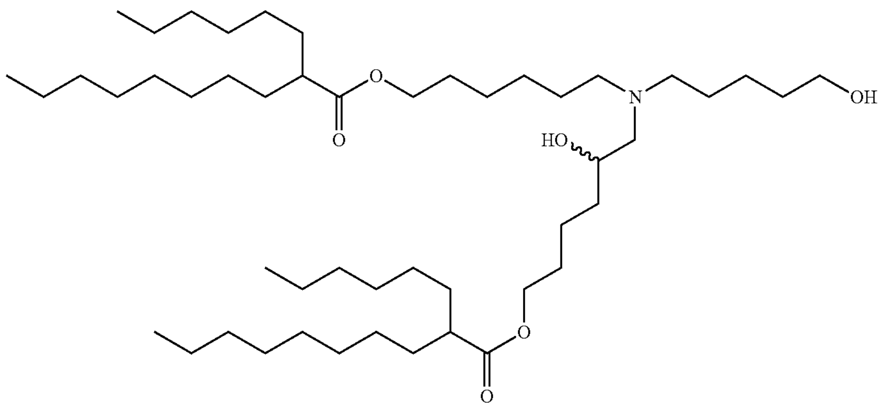 [SMILES: CCCCCCCCC(CCCCCC)C(=O)OCCCCCCN(CCCCCO)CC(O)CCCCOC(=O)C(CCCCCC)CCCCCCCC] |
| 87 | 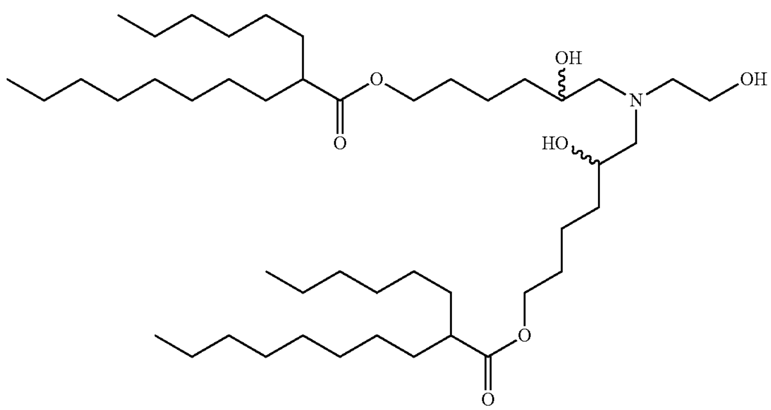 [SMILES: CCCCCCCCC(CCCCCC)C(=O)OCCCCC(O)CN(CCO)CC(O)CCCCOC(=O)C(CCCCCC)CCCCCCCC] |
| 88 | 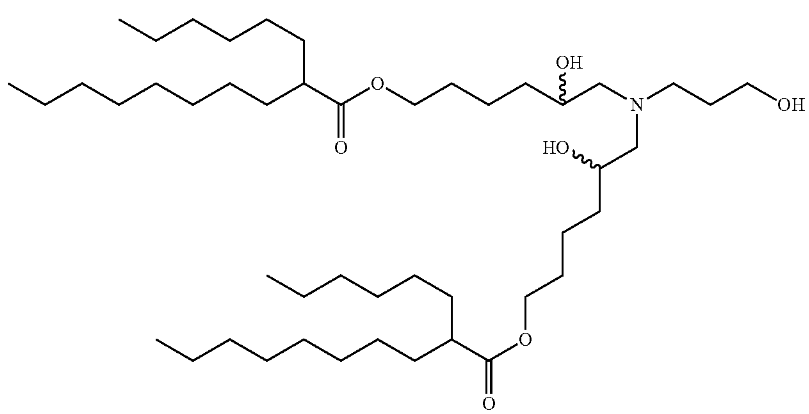 [SMILES: CCCCCCCCC(CCCCCC)C(=O)OCCCCC(O)CN(CCCO)CC(O)CCCCOC(=O)C(CCCCCC)CCCCCCCC] |

TABLE 10e-continued
| Ionizable lipid number | Structure |
| --- | --- |
| 89 | 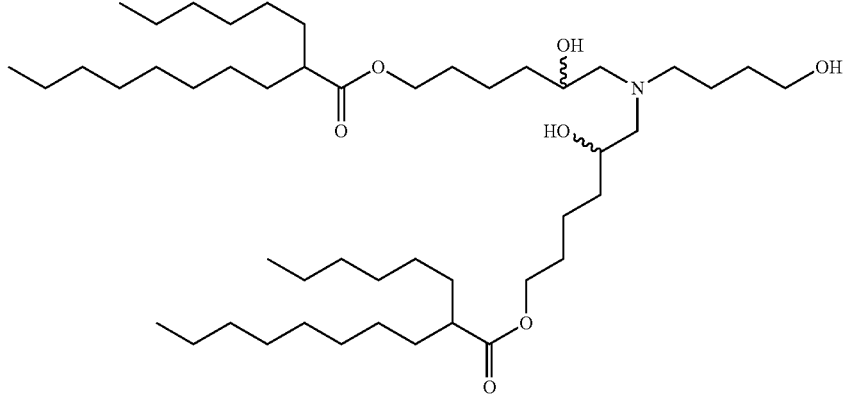 [SMILES: CCCCCCCCC(CCCCCC)C(=O)OCCCCC(O)CN(CCCCO)CC(O)CCCCOC(=O)C(CCCCCC)CCCCCCCC] |
| 90 | 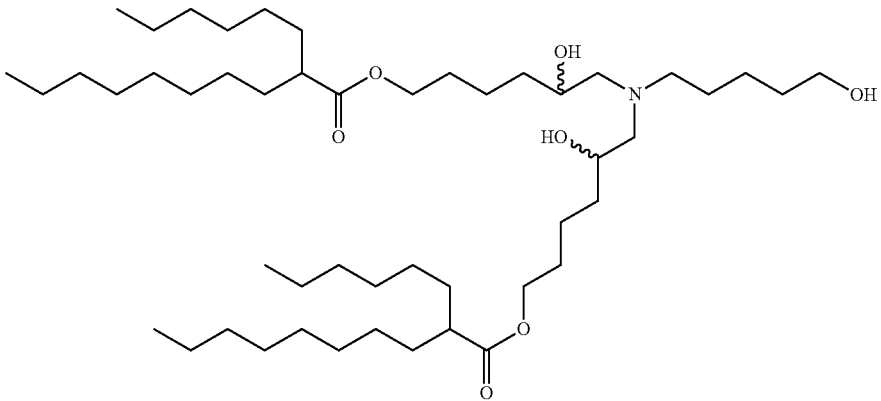 [SMILES: CCCCCCCCC(CCCCCC)C(=O)OCCCCC(O)CN(CCCCCO)CC(O)CCCCOC(=O)C(CCCCCC)CCCCCCCC] |
| 91 | 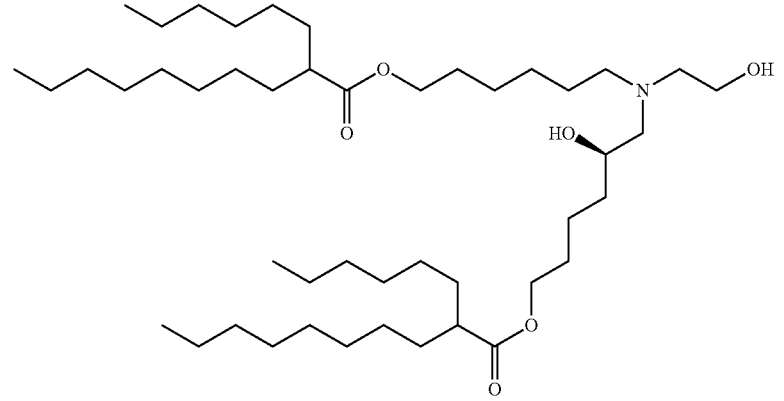 [SMILES: CCCCCCCCC(CCCCCC)C(=O)OCCCCCCN(CCO)C[C@H](O)CCCCOC(=O)C(CCCCCC)CCCCCCCC] |

TABLE 10e-continued
| Ionizable lipid number | Structure |
|---|---|
| 92 | 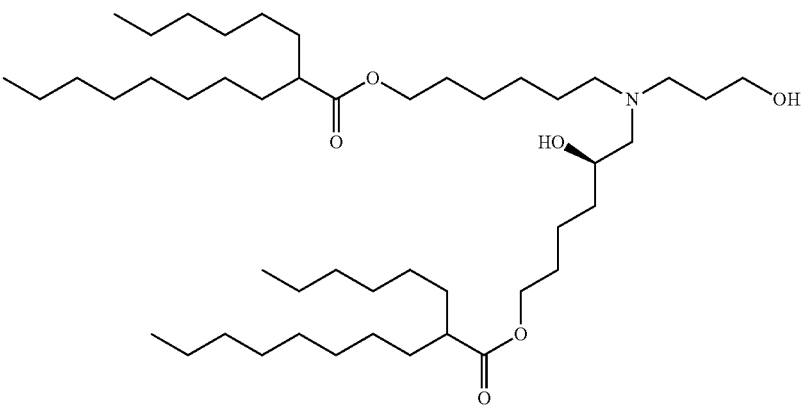 |
| 93 | 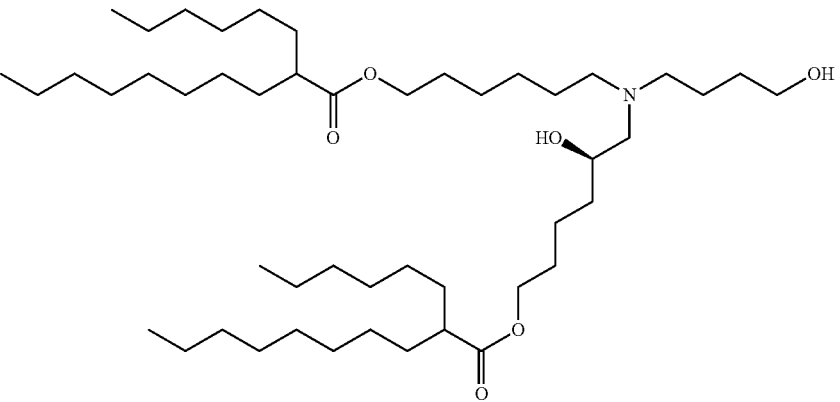 |
| 94 | 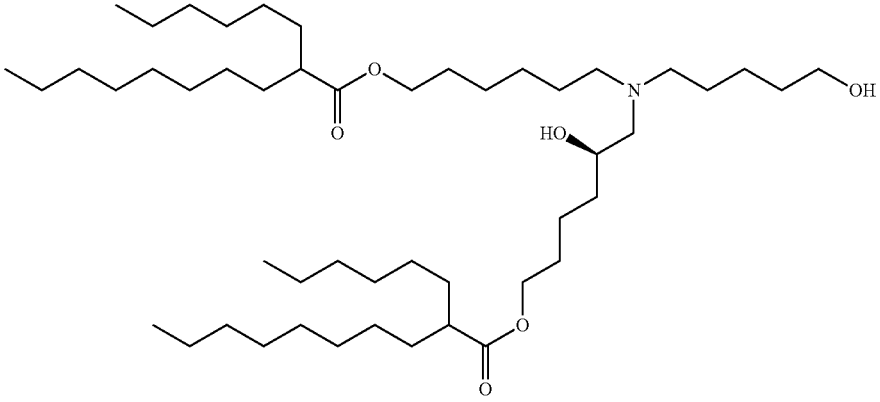 [SMILES: CCCCCCCCC(CCCCCC)C(=O)OCCCCCCN(CCCCCO)C[C@H](O)CCCCOC(=O)C(CCCCCC)CCCCCCCC] |

TABLE 10e-continued
| Ionizable lipid number | Structure |
|---|---|
| 95 | 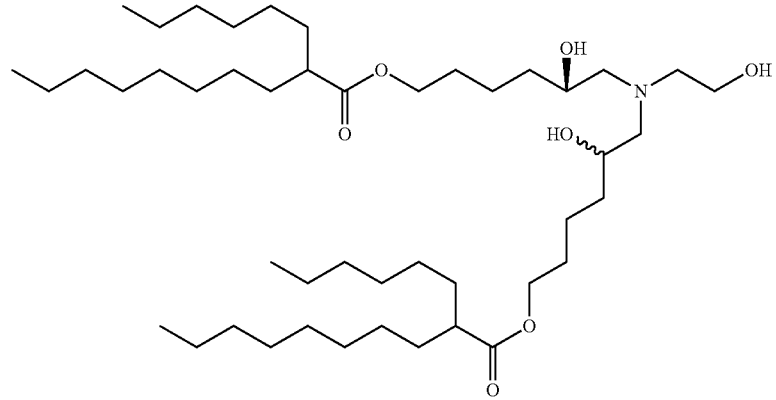 |
| 96 | 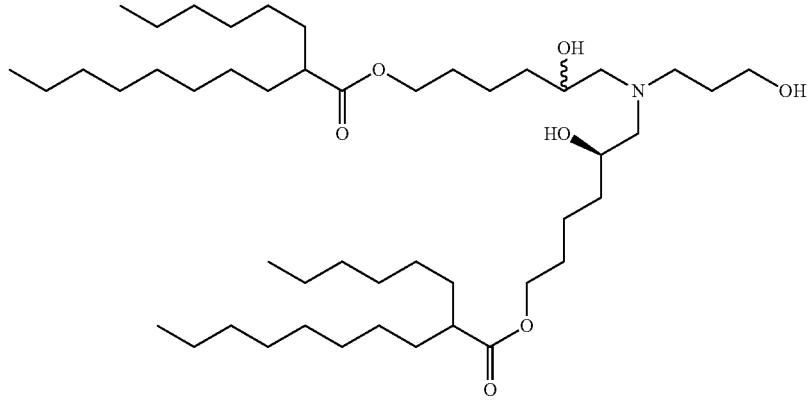 [SMILES: CCCCCCCCC(CCCCCC)C(=O)OCCCCC(O)CN(CCCO)C[C@H](O)CCCCOC(=O)C(CCCCCC)CCCCCCCC] |
| 97 | 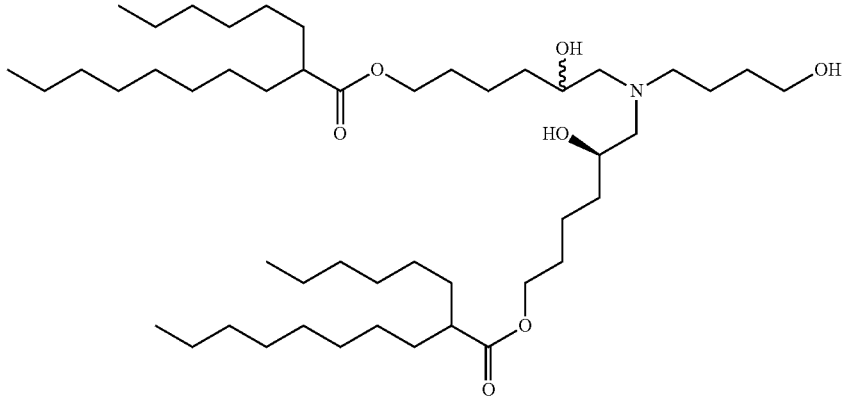 |

TABLE 10e-continued

| Ionizable lipid number | Structure |
|---|---|
| 98 | 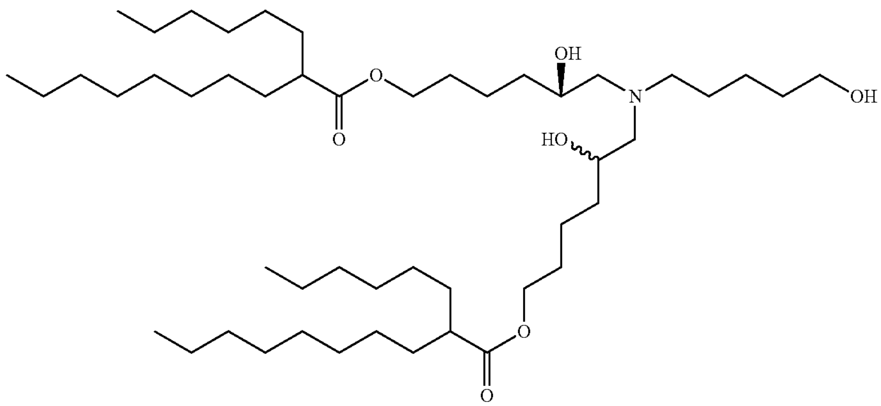 |
| 99 | 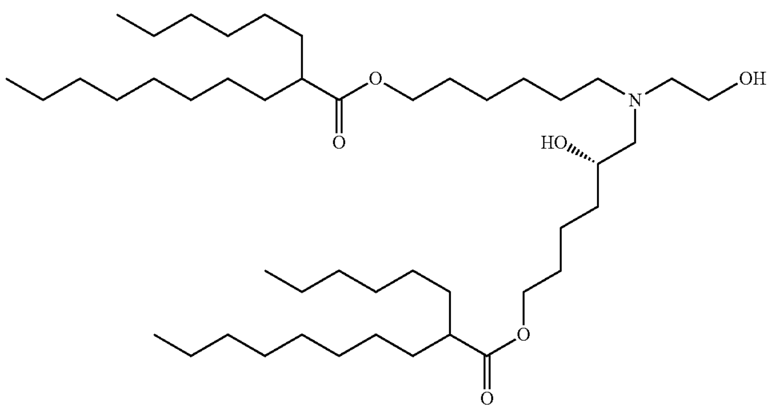 [SMILES: CCCCCCCCC(CCCCCC)C(=O)OCCCCCCN(CCO)C[C@@H](O)CCCCOC(=O)C(CCCCCC)CCCCCCCC] |
| 100 | 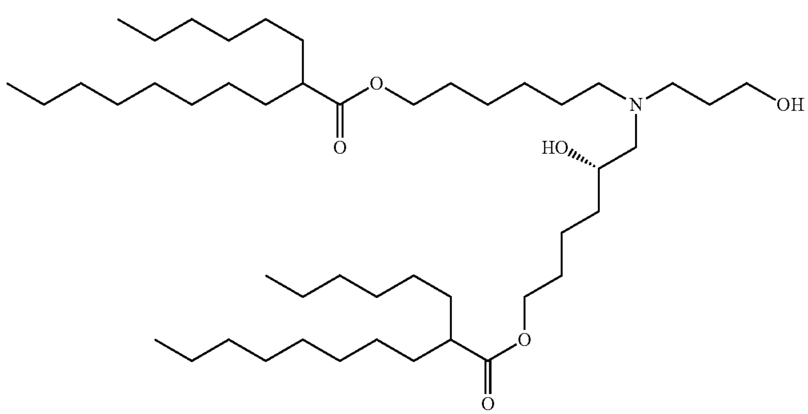 [SMILES: CCCCCCCCC(CCCCCC)C(=O)OCCCCCCN(CCCO)C[C@@H](O)CCCCOC(=O)C(CCCCCC)CCCCCCCC] |

TABLE 10e-continued
| Ionizable lipid number | Structure |
|---|---|
| 101 | 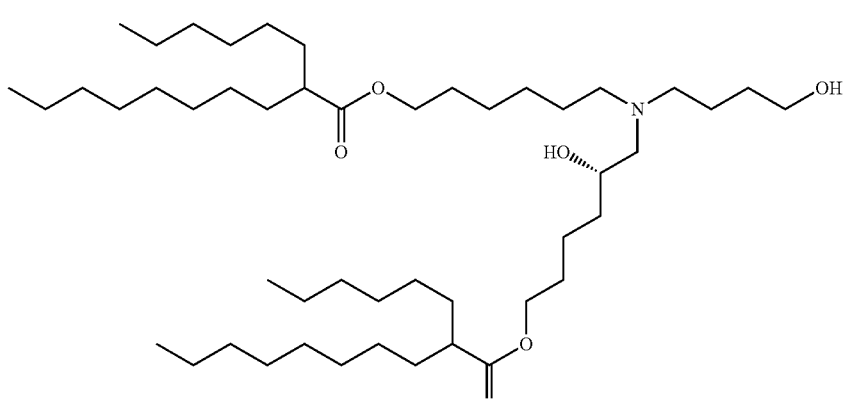 |
| 102 | 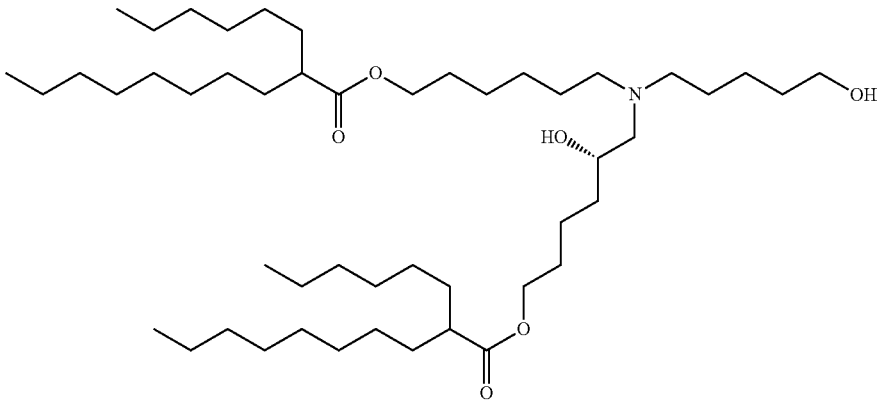 [SMILES: CCCCCCCCC(CCCCCC)C(=O)OCCCCCCN(CCCCCO)C[C@@H](O)CCCCOC(=O)C(CCCCCC)CCCCCCCC] |
| 103 | 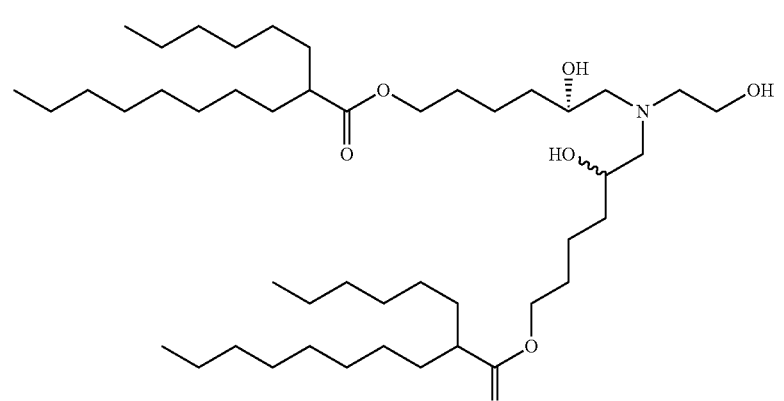 |

TABLE 10e-continued
| Ionizable lipid number | Structure |
|---|---|
| 104 | 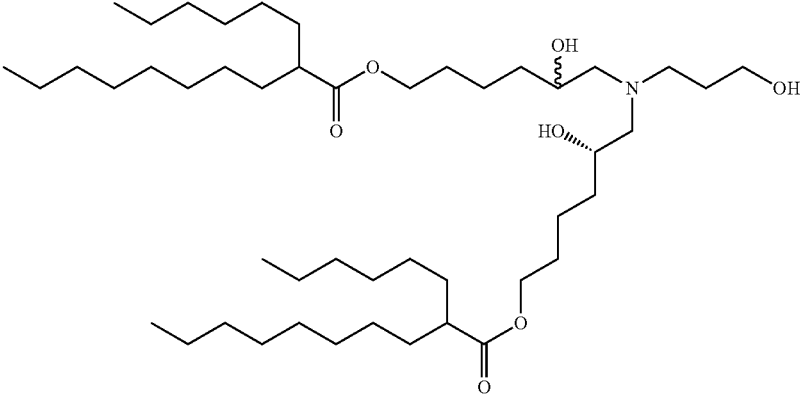 [SMILES: CCCCCCCCC(CCCCCC)C(=O)OCCCCC(O)CN(CCCO)C[C@@H](O)CCCCOC(=O)C(CCCCCC)CCCCCCCC] |
| 105 | 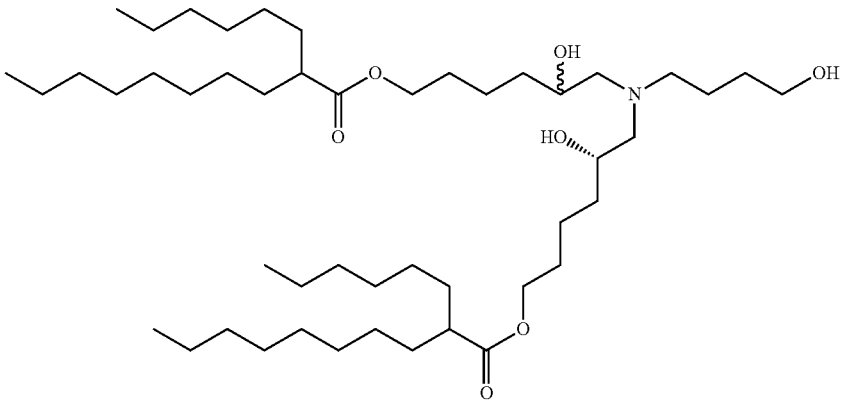 [SMILES: CCCCCCCCC(CCCCCC)C(=O)OCCCCC(O)CN(CCCCO)C[C@@H](O)CCCCOC(=O)C(CCCCCC)CCCCCCCC] |
| 106 | 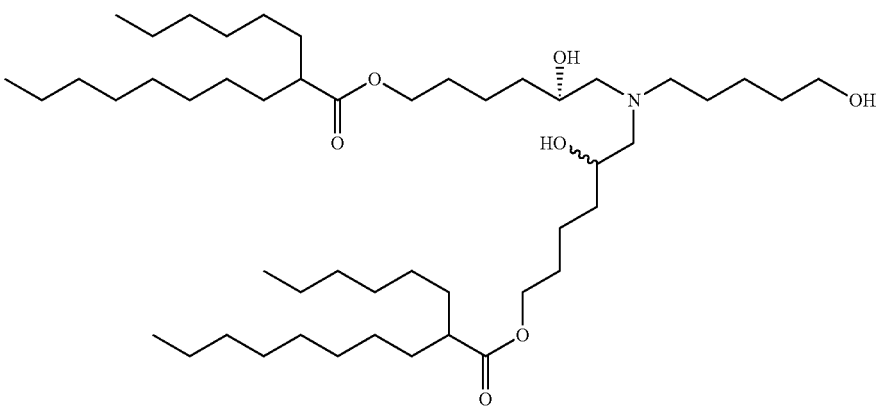 [SMILES: CCCCCCCCC(CCCCCC)C(=O)OCCCCC(O)CN(CCCCCO)C[C@H](O)CCCCOC(=O)C(CCCCCC)CCCCCCCC] |

TABLE 10e-continued

| Ionizable lipid number | Structure |
| --- | --- |
| 107 | 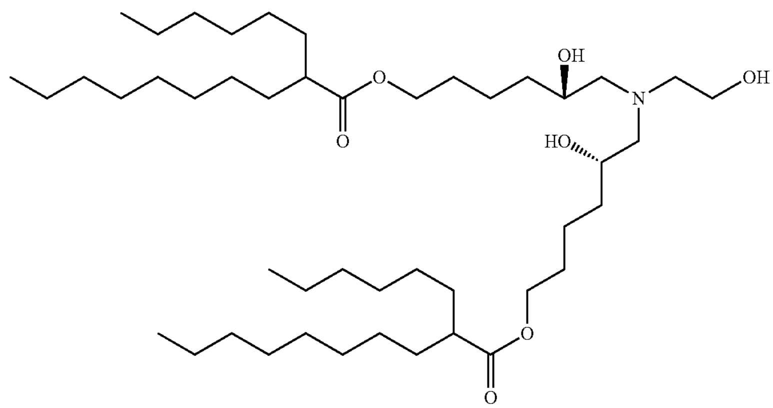 [SMILES: CCCCCCCCC(CCCCCC)C(=O)OCCCC[C@H](O)CN(CCO)C[C@@H](O)CCCCOC(=O)C(CCCCCC)CCCCCCCC] |
| 108 | 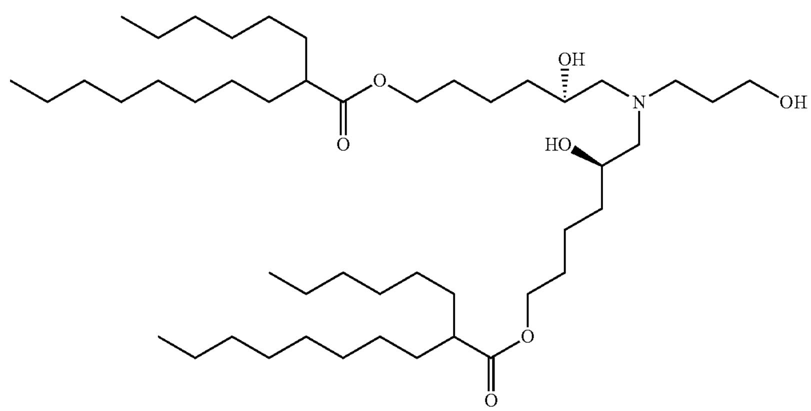 [SMILES: CCCCCCCCC(CCCCCC)C(=O)OCCCC[C@@H](O)CN(CCCO)C[C@H](O)CCCCOC(=O)C(CCCCCC)CCCCCCCC] |
| 109 | 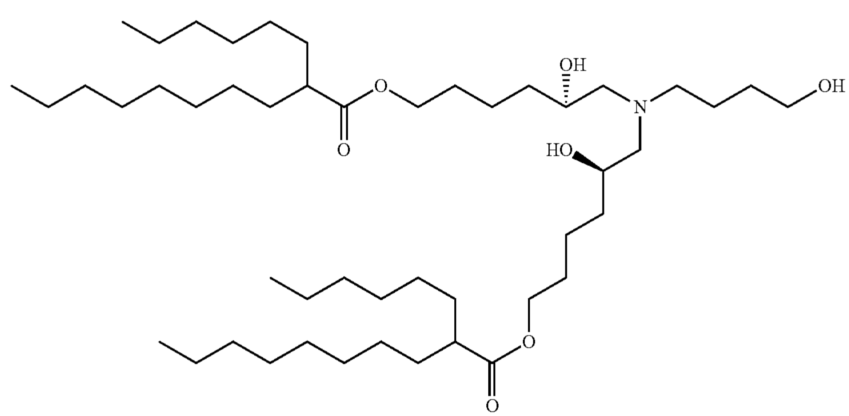 [SMILES: CCCCCCCCC(CCCCCC)C(=O)OCCCC[C@@H](O)CN(CCCCO)C[C@H](O)CCCCOC(=O)C(CCCCCC)CCCCCCCC] |

TABLE 10e-continued

| Ionizable lipid number | Structure |
| --- | --- |
| 110 | 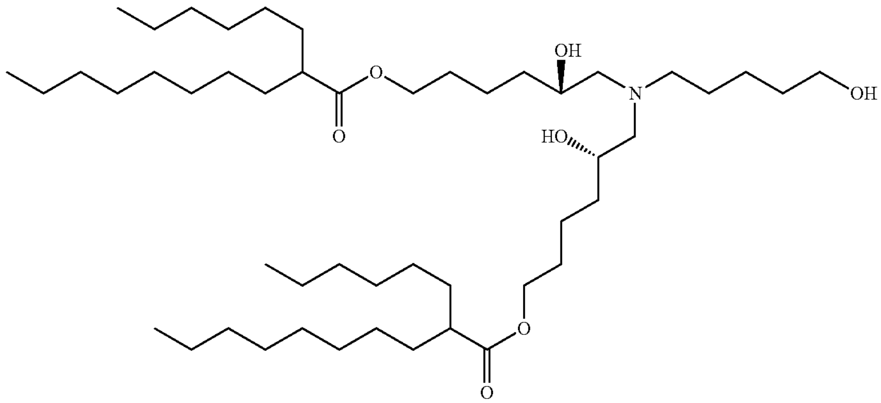 [SMILES: CCCCCCCCC(CCCCCC)C(=O)OCCCC[C@H](O)CN(CCCCCO)C[C@@H](O)CCCCOC(=O)C(CCCCCC)CCCCCCCC] |
| 111 | 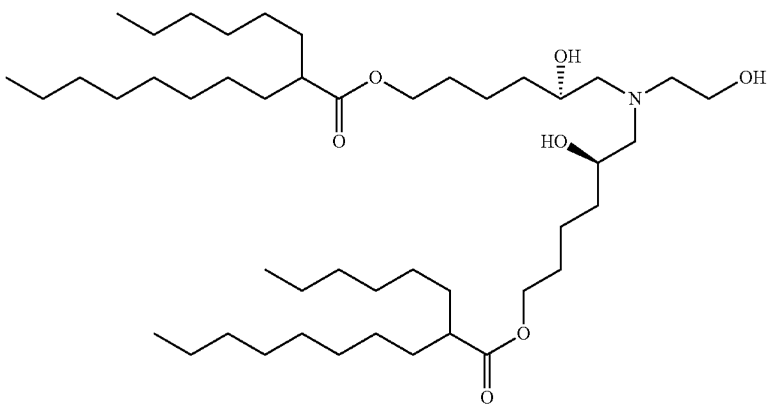 [SMILES: CCCCCCCCC(CCCCCC)C(=O)OCCCC[C@@H](O)CN(CCO)C[C@H](O)CCCCOC(=O)C(CCCCCC)CCCCCCCC] |
| 112 | 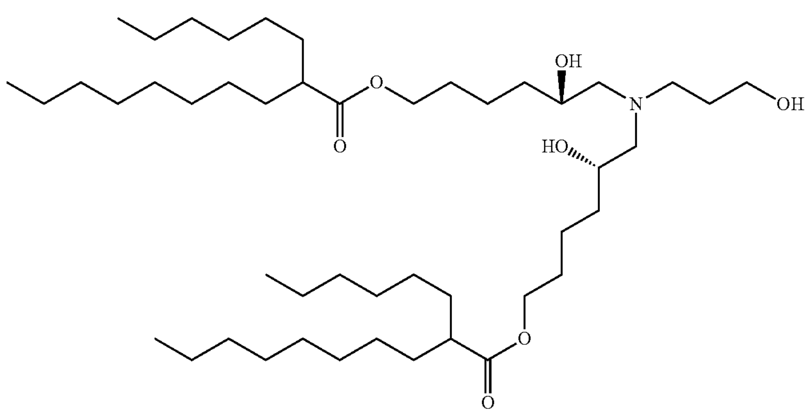 |

TABLE 10e-continued

| Ionizable lipid number | Structure |
| --- | --- |
| 113 | (structure) |
| 114 | (structure) |
| 115 | (structure) |

TABLE 10e-continued

| Ionizable lipid number | Structure |
|---|---|
| 116 | 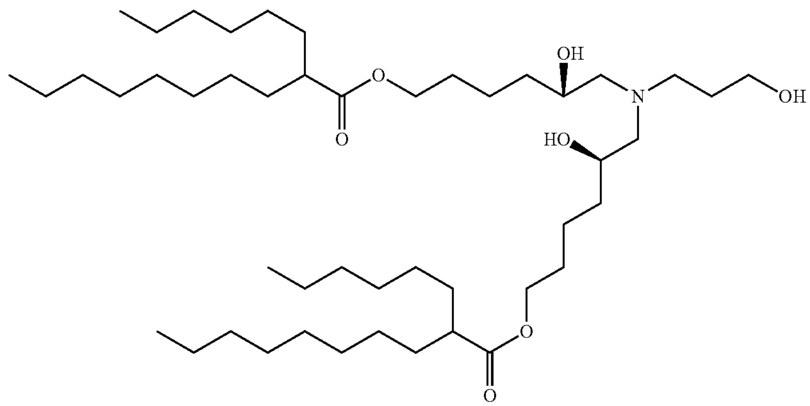 [SMILES: CCCCCCCCC(CCCCCC)C(=O)OCCCC[C@@H](O)CN(CCCO)C[C@@H](O)CCCCOC(=O)C(CCCCCC)CCCCCCCC] |
| 117 | 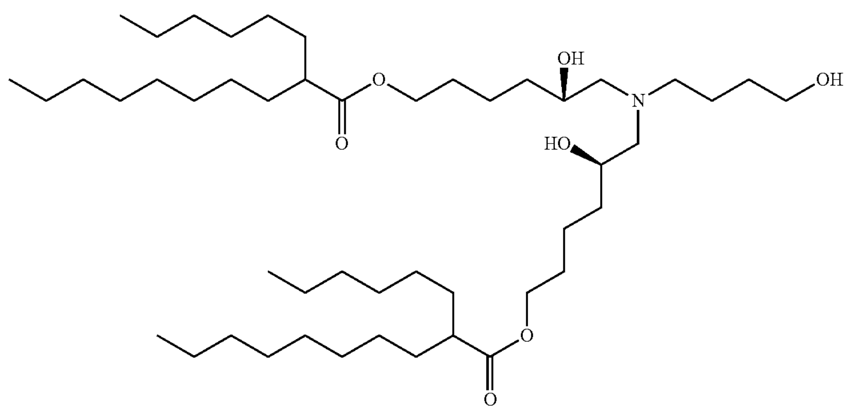 [SMILES: CCCCCCCCC(CCCCCC)C(=O)OCCCC[C@@H](O)CN(CCCCO)C[C@@H](O)CCCCOC(=O)C(CCCCCC)CCCCCCCC] |
| 118 | 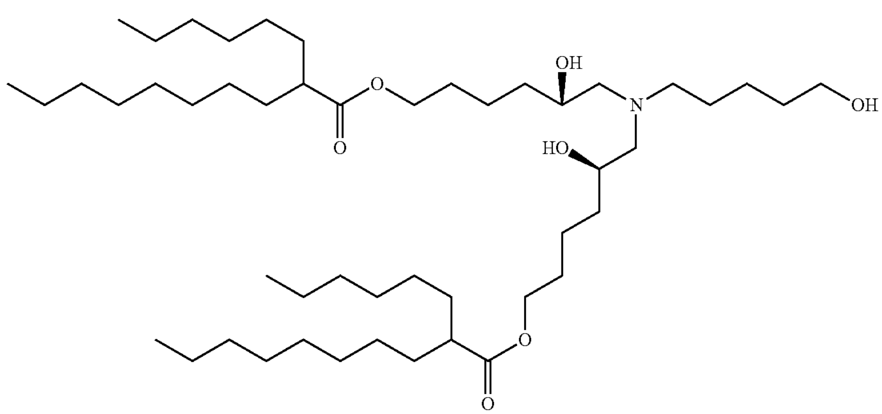 [SMILES: CCCCCCCCC(CCCCCC)C(=O)OCCCC[C@@H](O)CN(CCCCCO)C[C@@H](O)CCCCOC(=O)C(CCCCCC)CCCCCCCC] |

TABLE 10e-continued
| Ionizable lipid number | Structure |
|---|---|
| 119 | 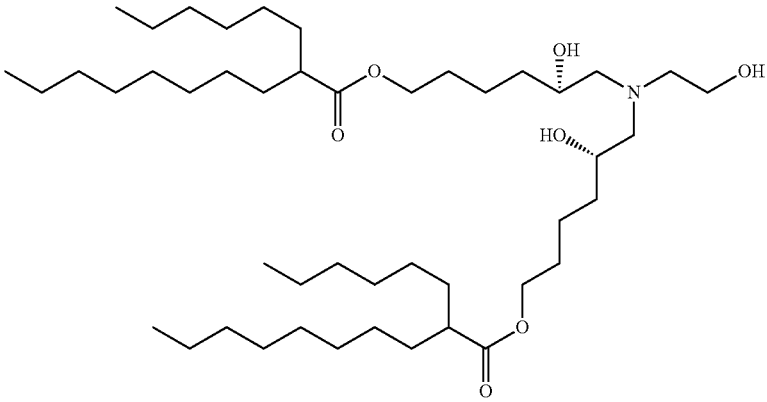 [SMILES: CCCCCCCCC(CCCCCC)C(=O)OCCCC[C@@H](O)CN(CCO)C[C@@H](O)CCCCOC(=O)C(CCCCCC)CCCCCCCC] |
| 120 | 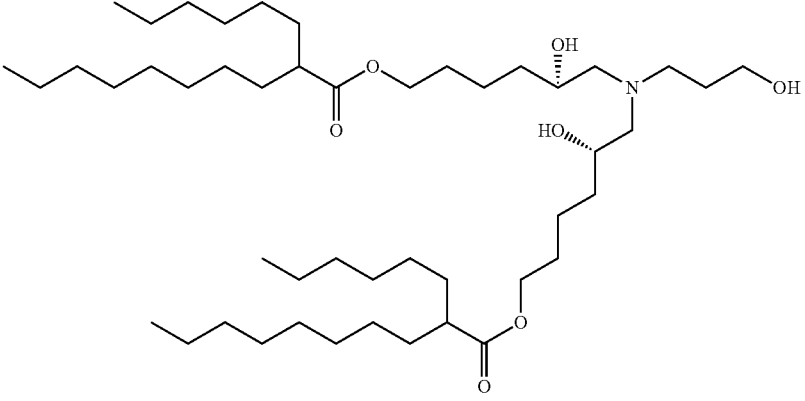 [SMILES: CCCCCCCCC(CCCCCC)C(=O)OCCCC[C@@H](O)CN(CCCO)C[C@@H](O)CCCCOC(=O)C(CCCCCC)CCCCCCCC] |
| 121 | 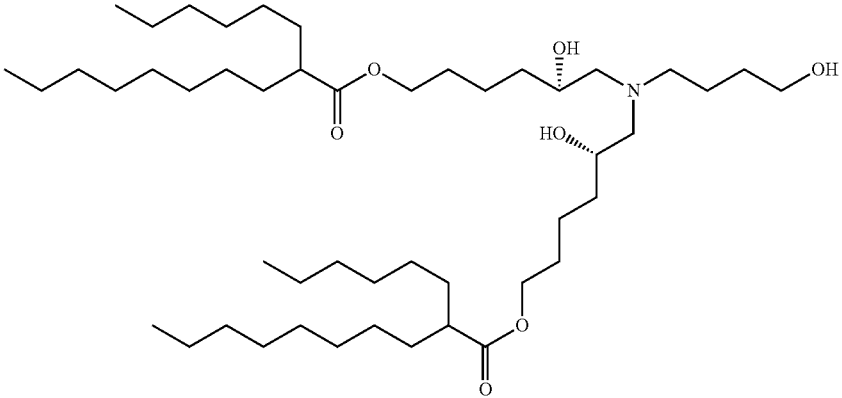 [SMILES: CCCCCCCCC(CCCCCC)C(=O)OCCCC[C@@H](O)CN(CCCCO)C[C@@H](O)CCCCOC(=O)C(CCCCCC)CCCCCCCC] |

TABLE 10e-continued
| Ionizable lipid number | Structure |
|---|---|
| 122 | 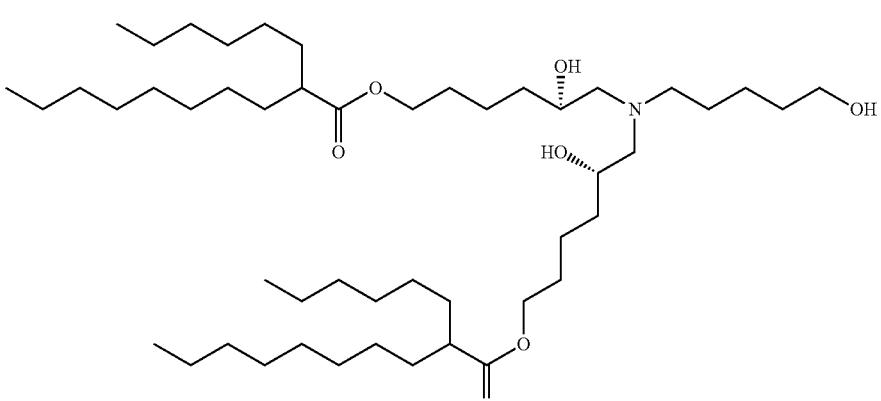 |
TABLE 10f
| Ionizable lipid number | Structure |
|---|---|
| 1 | 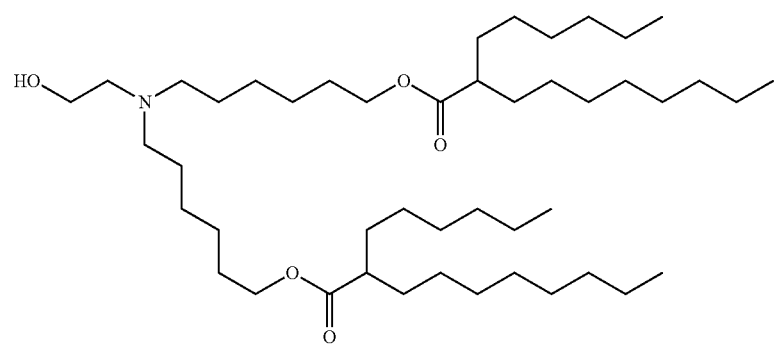 [SMILES: CCCCCCCCC(CCCCCC)C(=O)OCCCCCCN(CCO)CCCCCCOC(=O)C(CCCCCC)CCCCCCCC] |
| 2 | 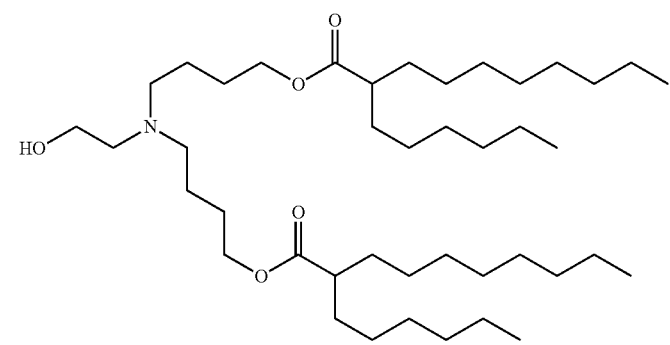 [SMILES: CCCCCCCCC(CCCCCC)C(=O)OCCCCN(CCO)CCCCOC(=O)C(CCCCCC)CCCCCCCC] |

TABLE 10f-continued
| Ionizable lipid number | Structure |
|---|---|
| 3 | 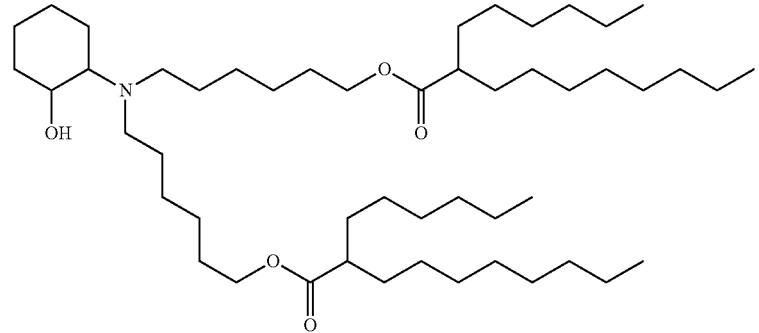 [SMILES: CCCCCCCCC(CCCCCC)C(=O)OCCCCCCN(CCCCCCOC(=O)C(CCCCCC)CCCCCCCC)C1CCCCC1O] |
| 4 | 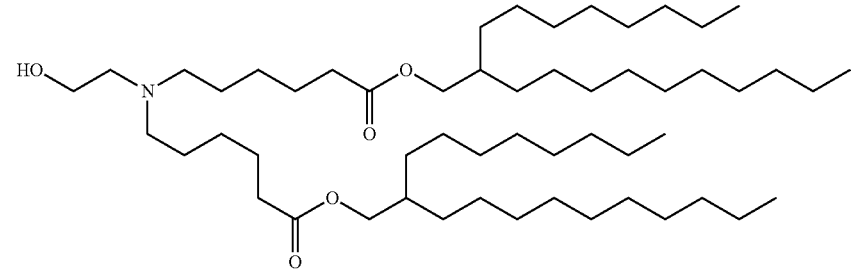 [SMILES: CCCCCCCCCCC(CCCCCCCC)COC(=O)CCCCCN(CCO)CCCCCC(=O)OCC(CCCCCCCC)CCCCCCCCCC] |
| 5 | 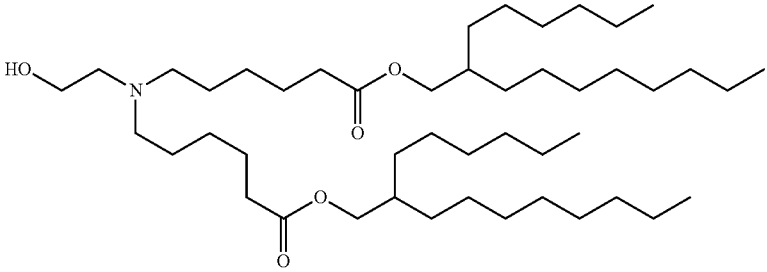 [SMILES: CCCCCCCCC(CCCCCC)COC(=O)CCCCCN(CCO)CCCCCC(=O)OCC(CCCCCC)CCCCCCCC] |
| 6 | 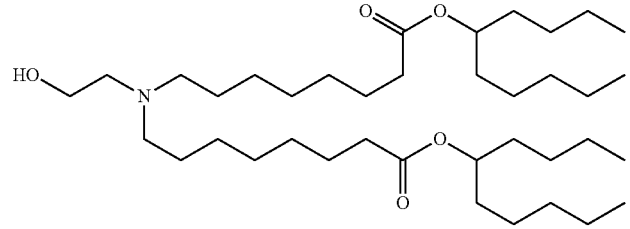 [SMILES: CCCCCC(CCCC)OC(=O)CCCCCCCN(CCO)CCCCCCCC(=O)OC(CCCC)CCCCC] |
| 7 | 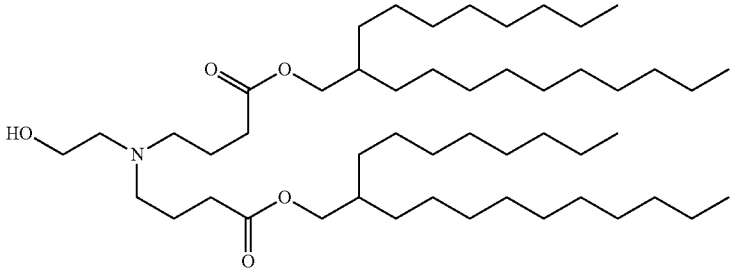 [SMILES: CCCCCCCCCCC(CCCCCCCC)COC(=O)CCCN(CCO)CCCC(=O)OCC(CCCCCCCC)CCCCCCCCCC] |

TABLE 10f-continued

| Ionizable lipid number | Structure |
|---|---|
| 8 | 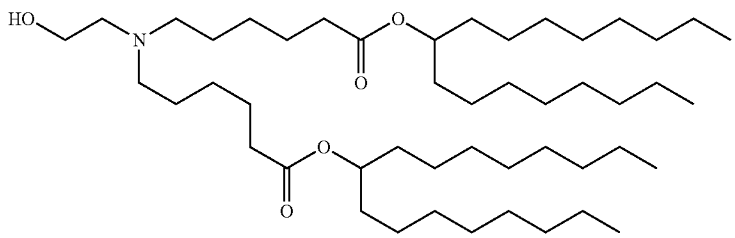 [SMILES: CCCCCCCCC(CCCCCCCC)OC(=O)CCCCCN(CCO)CCCCCC(=O)OC(CCCCCCCC)CCCCCCCC] |
| 9 | 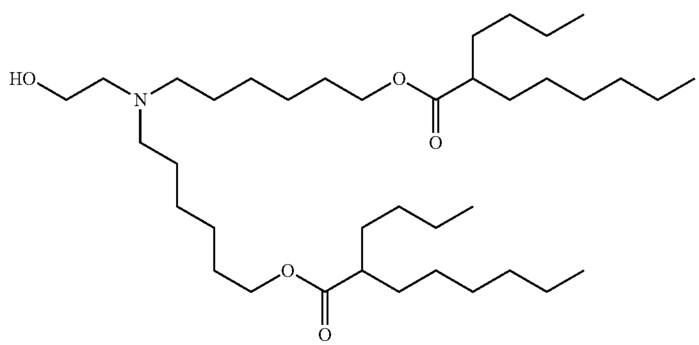 [SMILES: CCCCCCC(CCCC)C(=O)OCCCCCCN(CCO)CCCCCCOC(=O)C(CCCC)CCCCCC] |
| 10 | 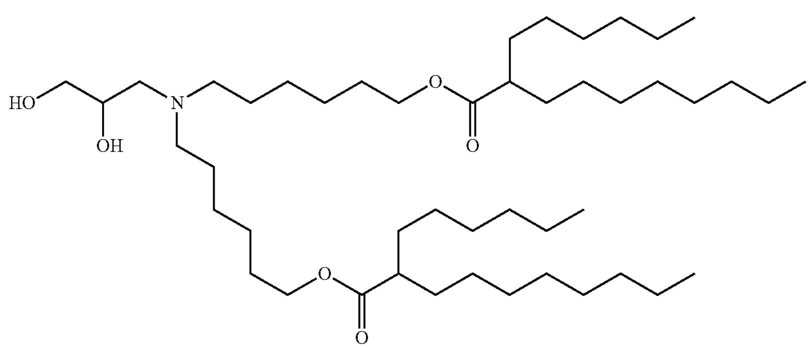 [SMILES: CCCCCCCCC(CCCCCC)C(=O)OCCCCCCN(CCCCCCOC(=O)C(CCCCCC)CCCCCCCC)CC(O)CO] |
| 11 | 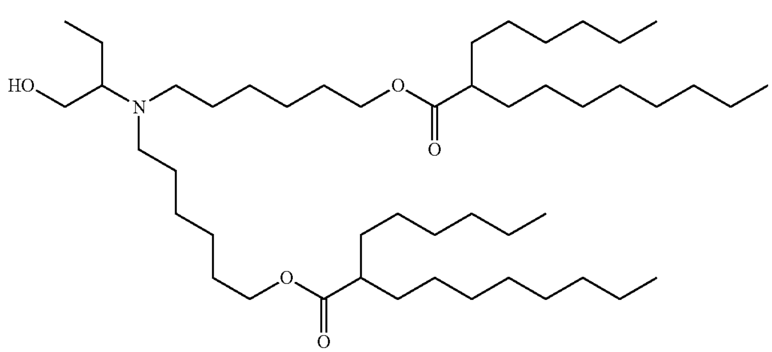 [SMILES: CCCCCCCCC(CCCCCC)C(=O)OCCCCCCN(CCCCCCOC(=O)C(CCCCCC)CCCCCCCC)C(CC)CO] |

TABLE 10f-continued
| Ionizable lipid number | Structure |
| --- | --- |
| 12 | 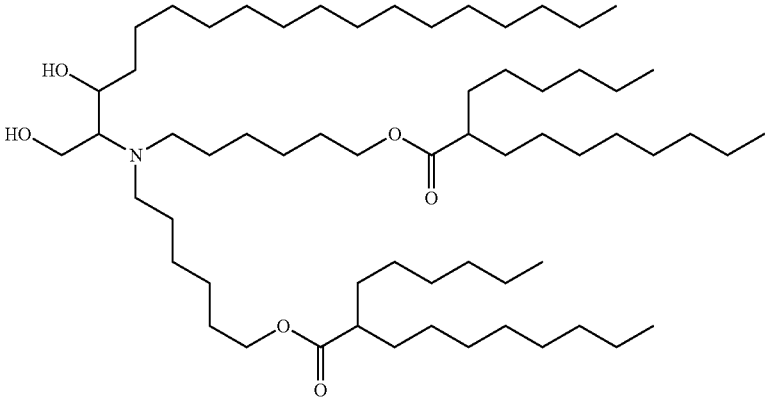 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] |
| 13 | 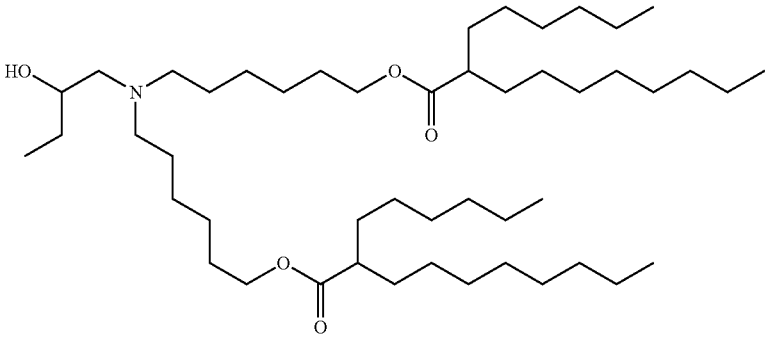 [SMILES: CCCCCCCCC(CCCCCC)C(=O)OCCCCCCN(CCCCCCOC(=O)C(CCCCCC)CCCCCCCC)CC(O)CC] |
| 14 | 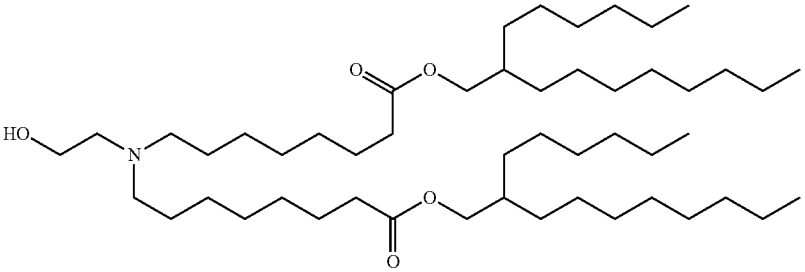 [SMILES: CCCCCCCCC(CCCCCC)COC(=O)CCCCCCCN(CCO)CCCCCCCC(=O)OCC(CCCCCC)CCCCCCCC] |
| 15 | 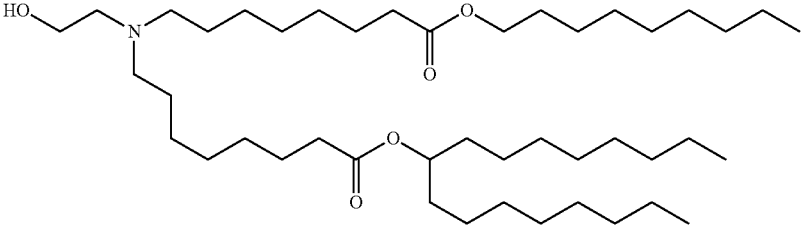 [SMILES: CCCCCCCCCOC(=O)CCCCCCCN(CCO)CCCCCCCC(=O)OC(CCCCCCCC)CCCCCCCC] |

TABLE 10f-continued
| Ionizable lipid number | Structure |
| --- | --- |
| 16 | 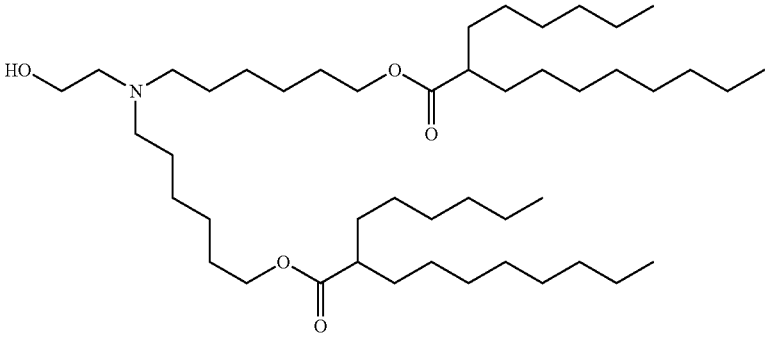 [SMILES: CCCCCCCCC(CCCCCC)C(=O)OCCCCCCN(CCO)CCCCCCOC(=O)C(CCCCCC)CCCCCCCC] |
| 17 | 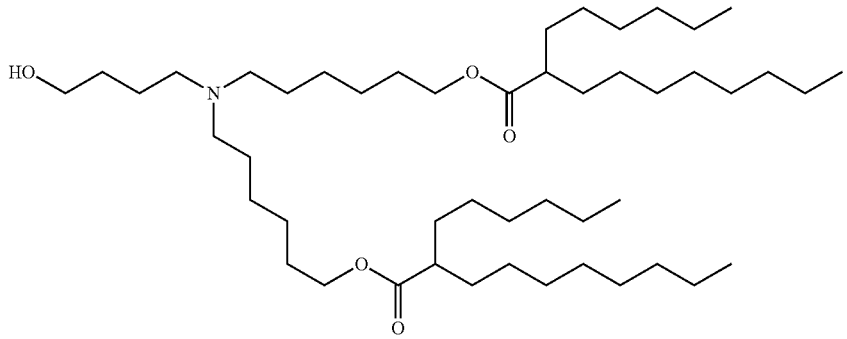 [SMILES: CCCCCCCCC(CCCCCC)C(=O)OCCCCCCN(CCCCO)CCCCCCOC(=O)C(CCCCCC)CCCCCCCC] |
| 18 | 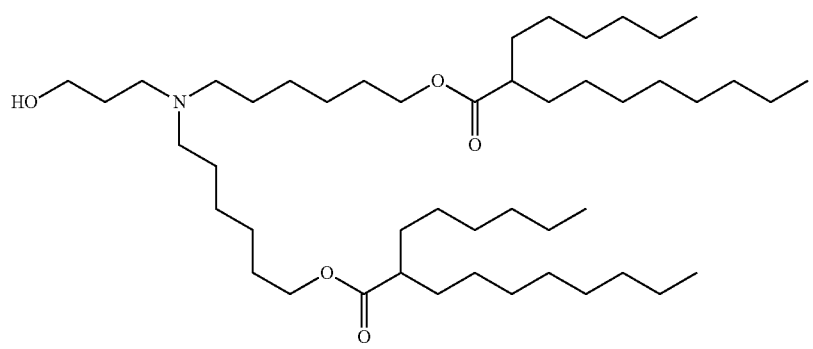 [SMILES: CCCCCCCCC(CCCCCC)C(=O)OCCCCCCN(CCCO)CCCCCCOC(=O)C(CCCCCC)CCCCCCCC] |
| 19 | 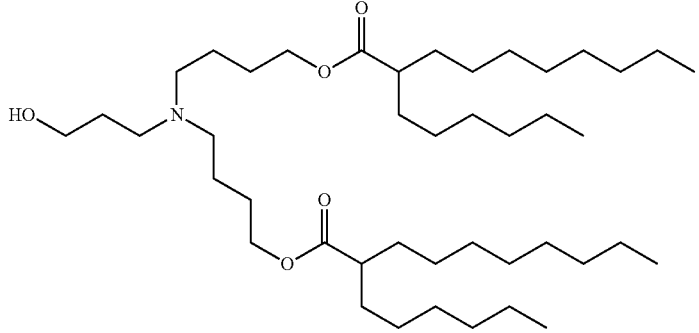 [SMILES: CCCCCCCCC(CCCCCC)C(=O)OCCCCN(CCCO)CCCCOC(=O)C(CCCCCC)CCCCCCCC] |

TABLE 10f-continued
| Ionizable lipid number | Structure |
|---|---|
| 20 | 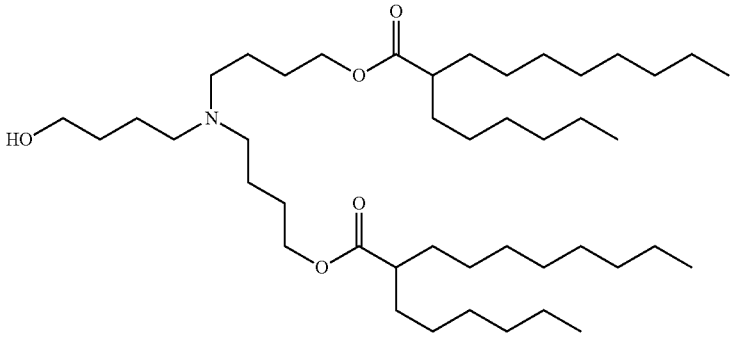 [SMILES: CCCCCCCCC(CCCCCC)C(=O)OCCCCN(CCCCO)CCCCOC(=O)C(CCCCCC)CCCCCCCC] |
| 21 | 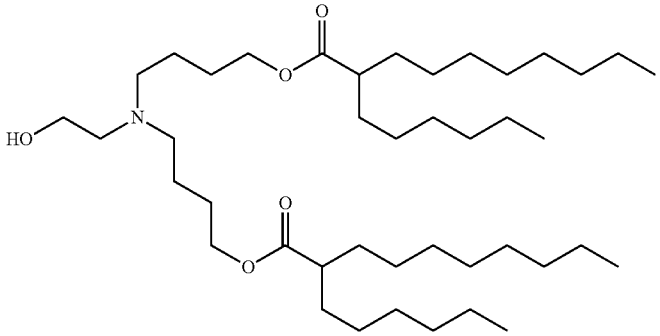 [SMILES: CCCCCCCCC(CCCCCC)C(=O)OCCCCN(CCO)CCCCOC(=O)C(CCCCCC)CCCCCCCC] |
| 22 | 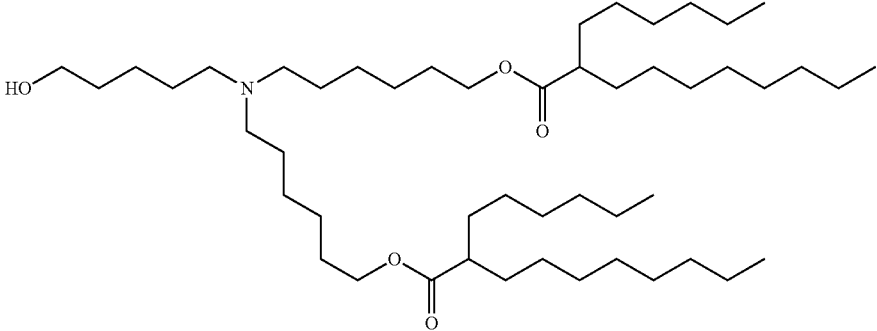 [SMILES: CCCCCCCCC(CCCCCC)C(=O)OCCCCCCN(CCCCCO)CCCCCCOC(=O)C(CCCCCC)CCCCCCCC] |
| 23 | 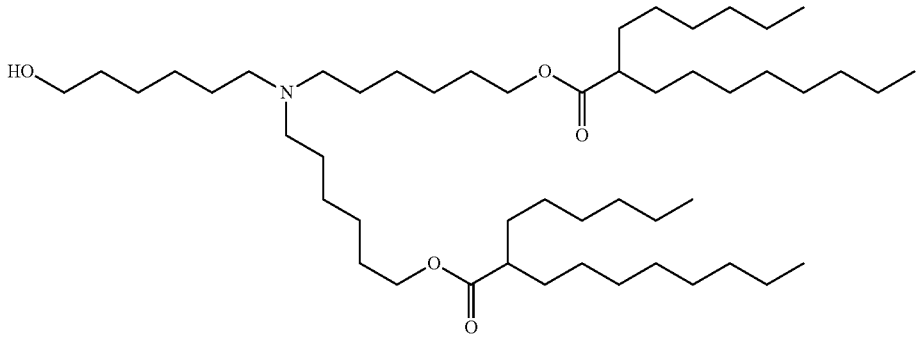 [SMILES: CCCCCCCCC(CCCCCC)C(=O)OCCCCCCN(CCCCCCO)CCCCCCOC(=O)C(CCCCCC)CCCCCCCC] |

TABLE 10f-continued
| Ionizable lipid number | Structure |
|---|---|
| 24 | 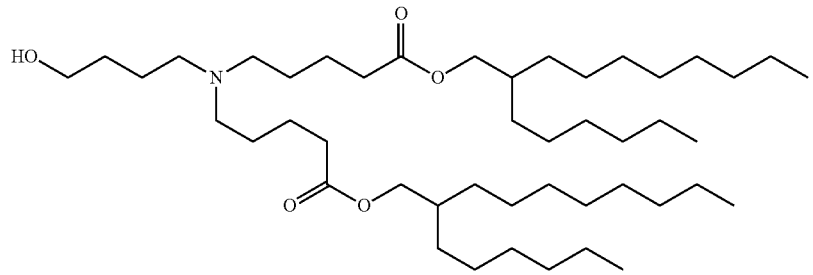 [SMILES: CCCCCCCCC(CCCCCC)COC(=O)CCCCN(CCCCO)CCCCC(=O)OCC(CCCCCC)CCCCCCCC] |
| 25 | 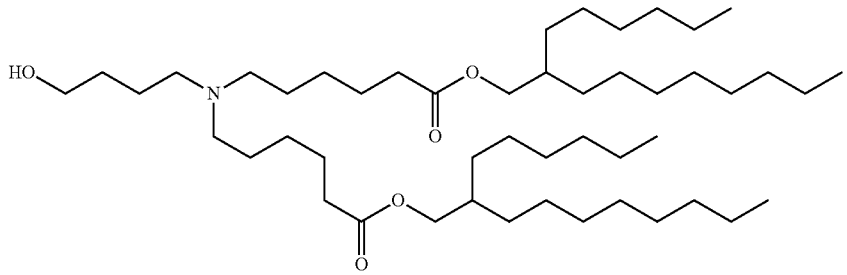 [SMILES: CCCCCCCCC(CCCCCC)COC(=O)CCCCCN(CCCCO)CCCCCC(=O)OCC(CCCCCC)CCCCCCCC] |
| 26 | 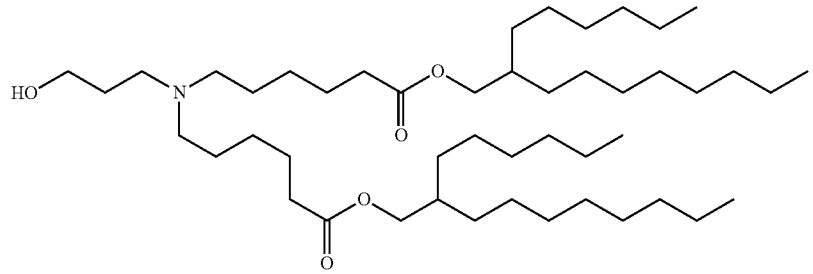 [SMILES: CCCCCCCCC(CCCCCC)COC(=O)CCCCCN(CCCO)CCCCCC(=O)OCC(CCCCCC)CCCCCCCC] |
| 27 | 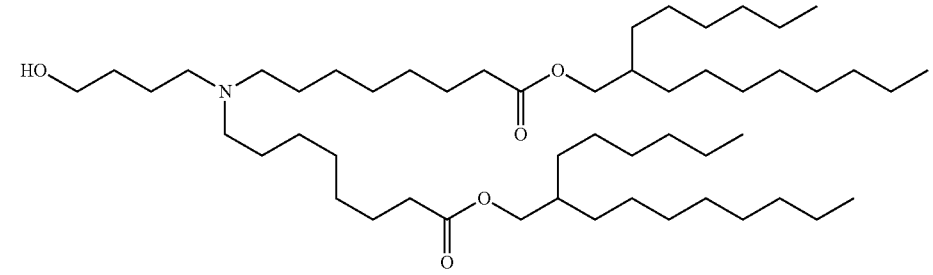 [SMILES: CCCCCCCCC(CCCCCC)COC(=O)CCCCCCCN(CCCCO)CCCCCCCC(=O)OCC(CCCCCC)CCCCCCCC] |
| 28 | 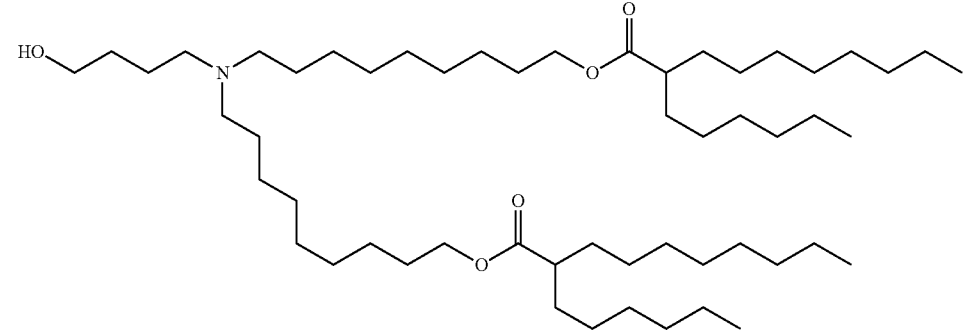 [SMILES: CCCCCCCCC(CCCCCC)C(=O)OCCCCCCCCCN(CCCCO)CCCCCCCCCOC(=O)C(CCCCCC)CCCCCCCC] |

TABLE 10f-continued
| Ionizable lipid number | Structure |
|---|---|
| 29 | 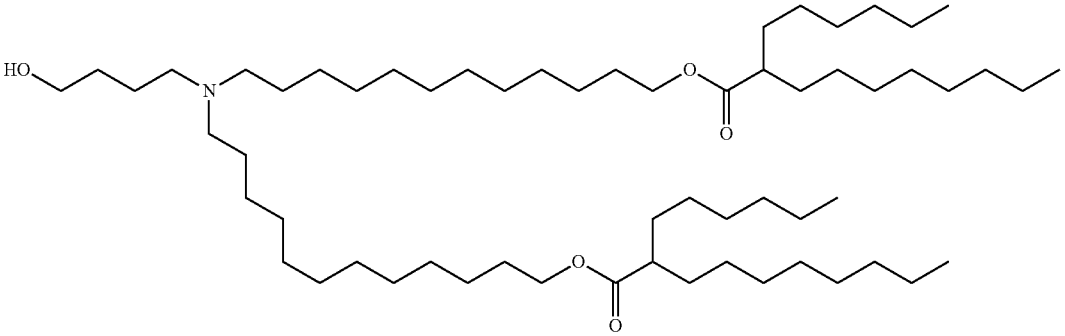 [SMILES: CCCCCCCCC(CCCCCC)C(=O)OCCCCCCCCCCCCN(CCCCO)CCCCCCCCCCCCOC(=O)C(CCCCCC)CCCCCCCC] |
| 30 | 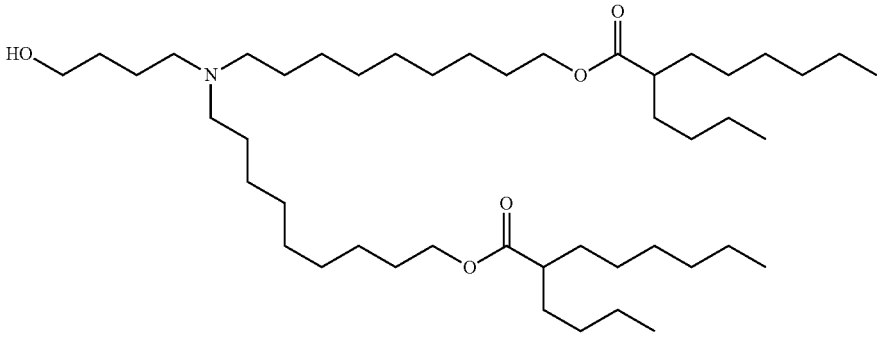 [SMILES: CCCCCCC(CCCC)C(=O)OCCCCCCCCCN(CCCCO)CCCCCCCCCOC(=O)C(CCCC)CCCCCC] |
| 31 | 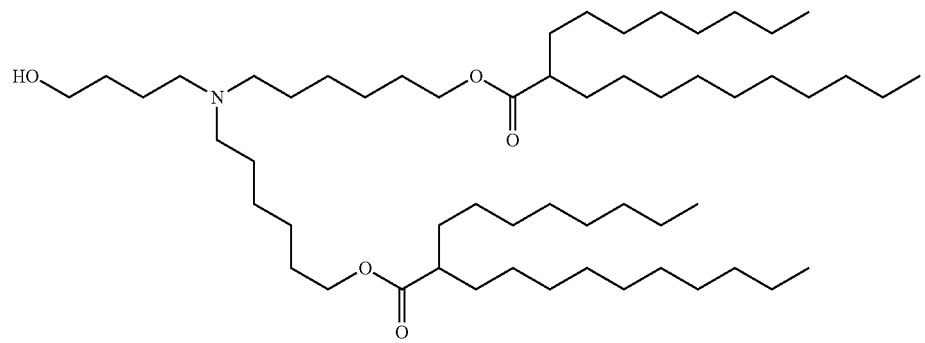 [SMILES: CCCCCCCCCCC(CCCCCCCC)C(=O)OCCCCCCN(CCCCO)CCCCCCOC(=O)C(CCCCCCCC)CCCCCCCCCC] |
| 32 | 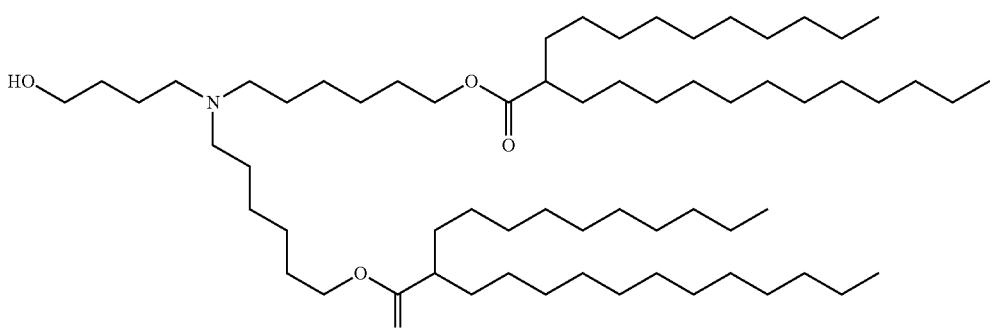 |

TABLE 10f-continued
| Ionizable lipid number | Structure |
|---|---|
| 33 | 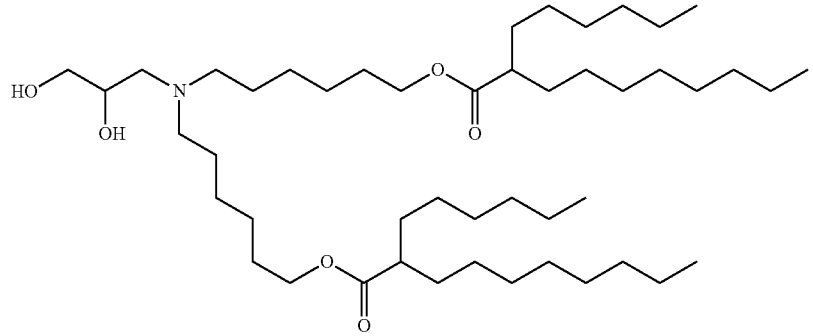 [SMILES: CCCCCCCCC(CCCCCC)C(=O)OCCCCCCN(CCCCCCOC(=O)C(CCCCCC)CCCCCCCC)CC(O)CO] |
| 34 | 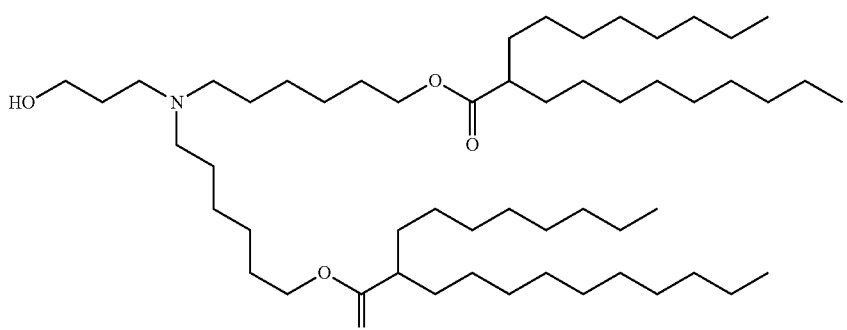 |
| 35 | 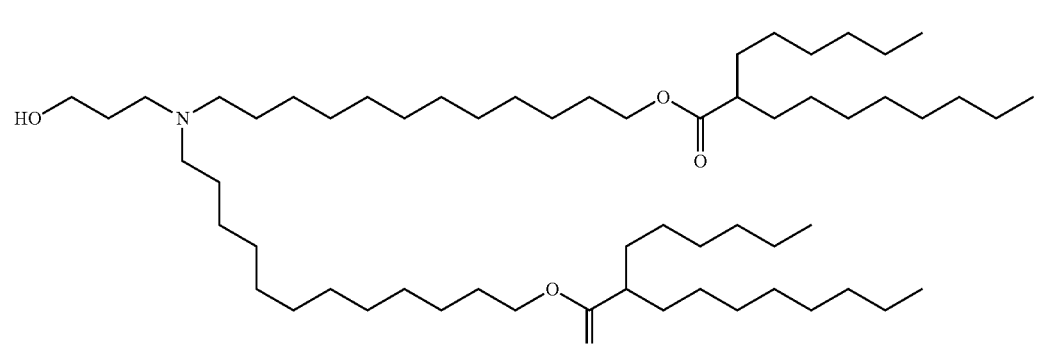 |
| 36 | 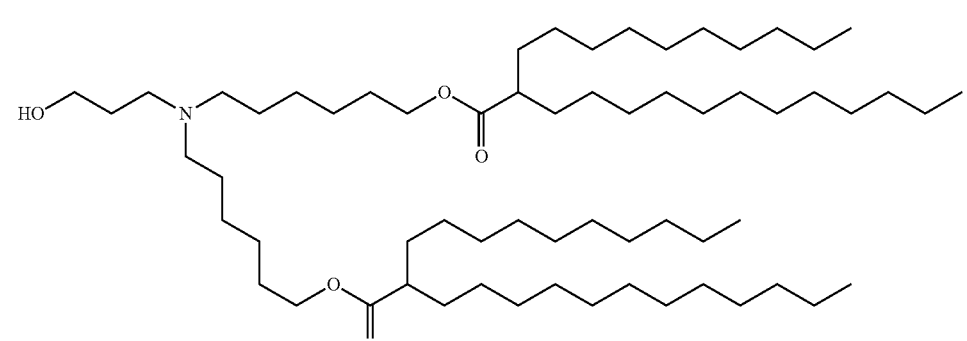 |

TABLE 10f-continued

| Ionizable lipid number | Structure |
|---|---|
| 37 | (structure) |
| 38 | (structure) |

In some embodiments, an ionizable lipid has one of the structures set forth in Table 10 below.

TABLE 10g

| Number | Structure |
|---|---|
| 1 | (structure) |
| 2 | (structure) |

TABLE 10g-continued

| Number | Structure |
|---|---|
| 3 | 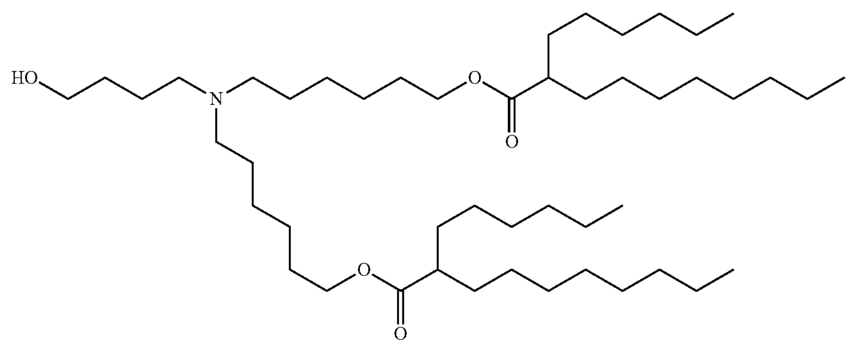 [SMILES: CCCCCCCCC(CCCCCC)C(=O)OCCCCCCN(CCCCO)CCCCCCOC(=O)C(CCCCCC)CCCCCCCC] |
| 4 | 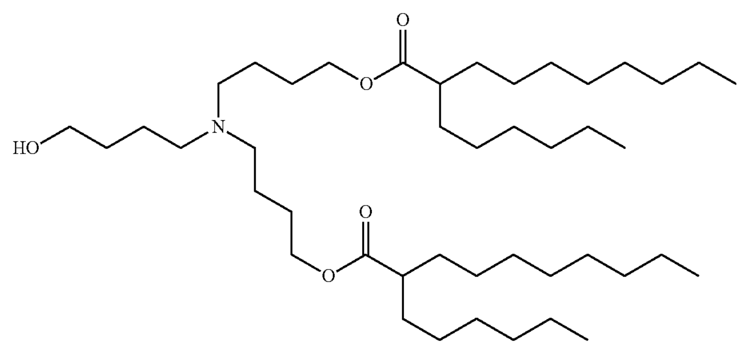 [SMILES: CCCCCCCCC(CCCCCC)C(=O)OCCCCN(CCCCO)CCCCOC(=O)C(CCCCCC)CCCCCCCC] |
| 5 | 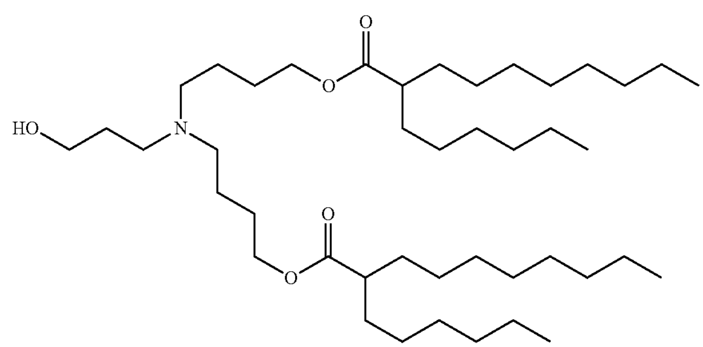 [SMILES: CCCCCCCCC(CCCCCC)C(=O)OCCCCN(CCCO)CCCCOC(=O)C(CCCCCC)CCCCCCCC] |
| 6 | 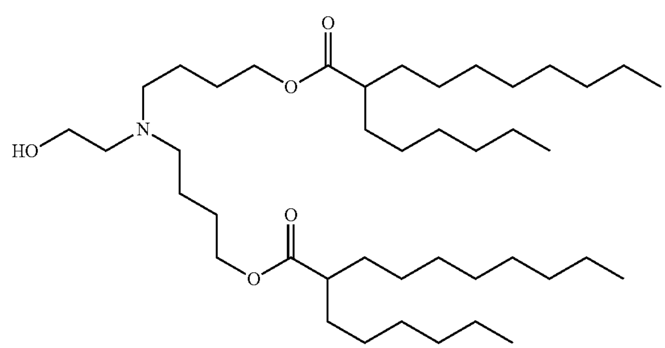 [SMILES: CCCCCCCCC(CCCCCC)C(=O)OCCCCN(CCO)CCCCOC(=O)C(CCCCCC)CCCCCCCC] |

TABLE 10g-continued
| Number | Structure |
|---|---|
| 7 | 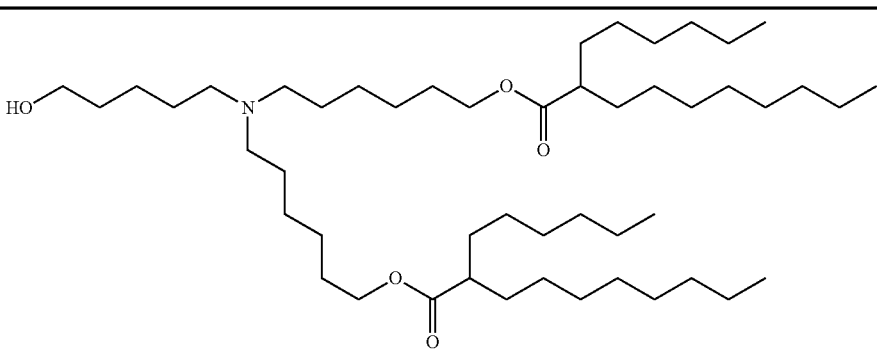 |
| 8 | 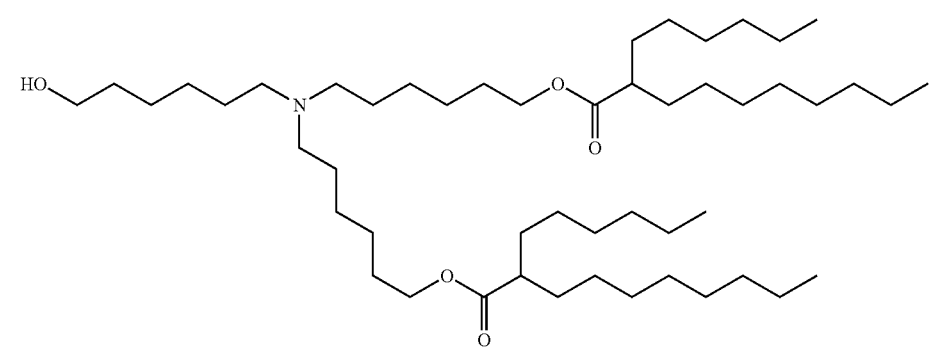 [SMILES: CCCCCCCCC(CCCCCC)C(=O)OCCCCCCN(CCCCCCO)CCCCCCOC(=O)C(CCCCCC)CCCCCCCC] |
| 9 | 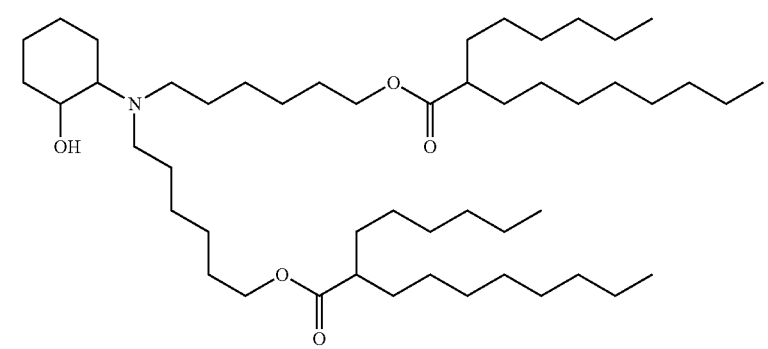 [SMILES: CCCCCCCCC(CCCCCC)C(=O)OCCCCCCN(CCCCCCOC(=O)C(CCCCCC)CCCCCCCC)C1CCCCC1O] |
| 10 | 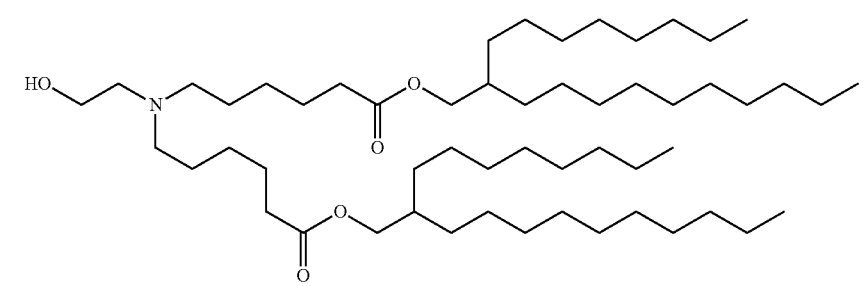 [SMILES: CCCCCCCCCCC(CCCCCCCC)COC(=O)CCCCCN(CCO)CCCCCC(=O)OCC(CCCCCCCC)CCCCCCCCCC] |
| 11 | 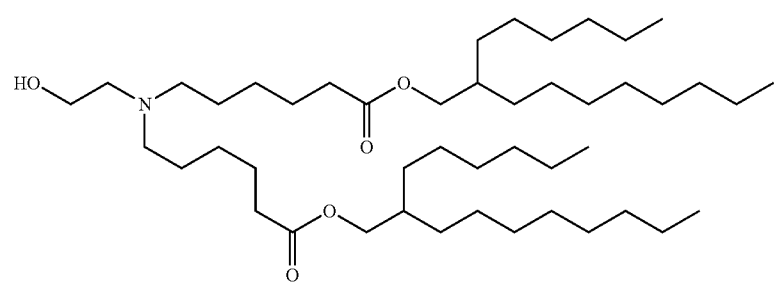 [SMILES: CCCCCCCCC(CCCCCC)COC(=O)CCCCCN(CCO)CCCCCC(=O)OCC(CCCCCC)CCCCCCCC] |

TABLE 10g-continued

| Number | Structure |
|---|---|
| 12 | 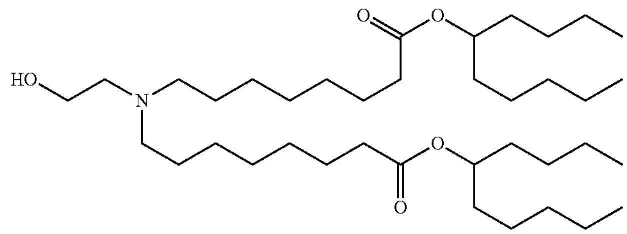 [SMILES: CCCCCC(CCCC)OC(=O)CCCCCCCN(CCO)CCCCCCCC(=O)OC(CCCC)CCCCC] |
| 13 | 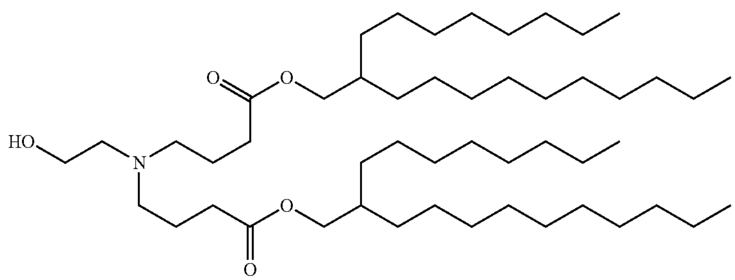 [SMILES: CCCCCCCCCCC(CCCCCCCC)COC(=O)CCCN(CCO)CCCC(=O)OCC(CCCCCCCC)CCCCCCCCCC] |
| 14 | 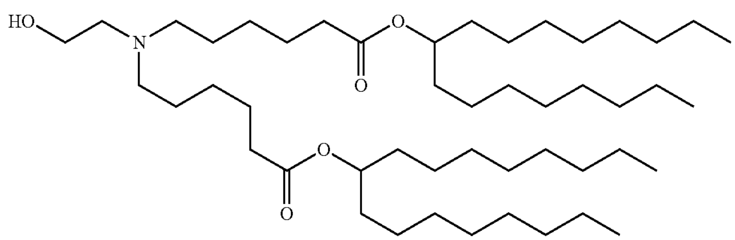 [SMILES: CCCCCCCCC(CCCCCCCC)OC(=O)CCCCCN(CCO)CCCCCC(=O)OC(CCCCCCCC)CCCCCCCC] |
| 15 | 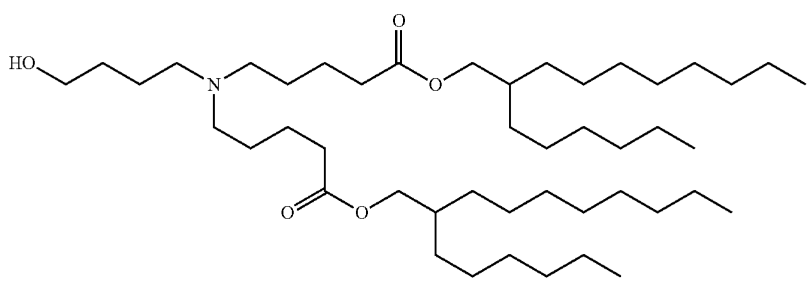 [SMILES: CCCCCCCCC(CCCCCC)COC(=O)CCCCN(CCCCO)CCCCC(=O)OCC(CCCCCC)CCCCCCCC] |
| 16 | 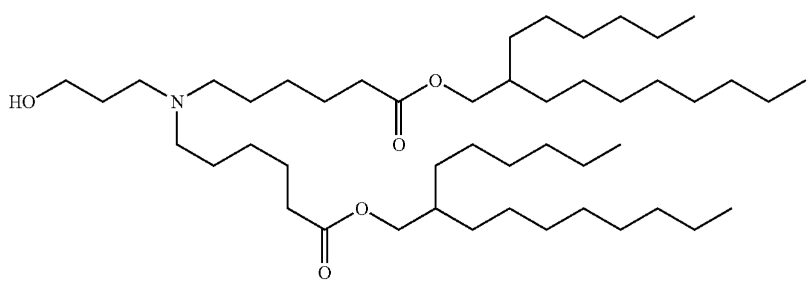 [SMILES: CCCCCCCCC(CCCCCC)COC(=O)CCCCCN(CCCO)CCCCCC(=O)OCC(CCCCCC)CCCCCCCC] |
| 17 | 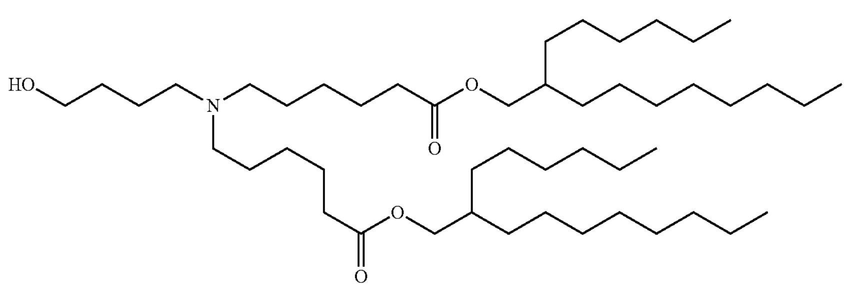 [SMILES: CCCCCCCCC(CCCCCC)COC(=O)CCCCCN(CCCCO)CCCCCC(=O)OCC(CCCCCC)CCCCCCCC] |

TABLE 10g-continued

| Number | Structure |
|---|---|
| 18 | 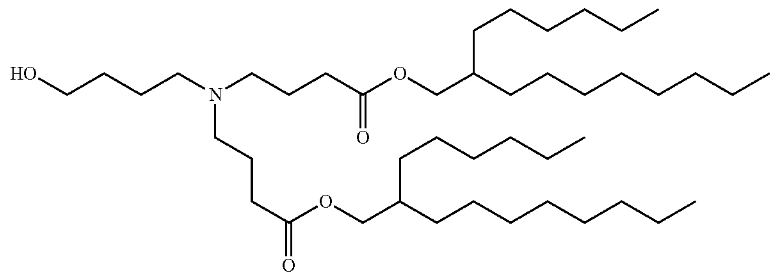 [SMILES: CCCCCCCCC(CCCCCC)COC(=O)CCCN(CCCCO)CCCC(=O)OCC(CCCCCC)CCCCCCCC] |
| 19 | 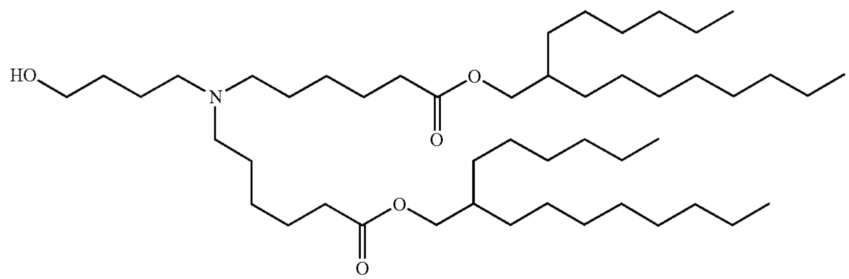 [SMILES: CCCCCCCCC(CCCCCC)COC(=O)CCCCCN(CCCCO)CCCCCC(=O)OCC(CCCCCC)CCCCCCCC] |
| 20 | 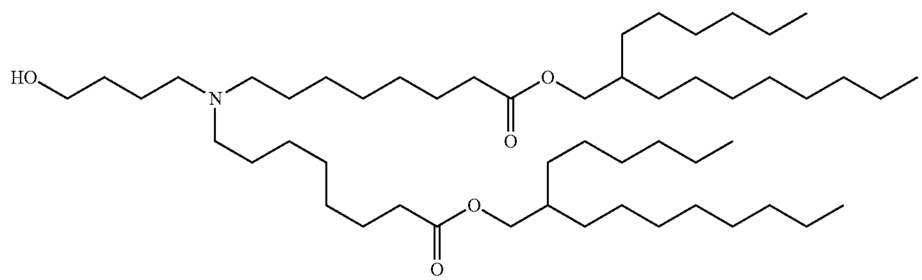 [SMILES: CCCCCCCCC(CCCCCC)COC(=O)CCCCCCCN(CCCCO)CCCCCCCC(=O)OCC(CCCCCC)CCCCCCCC] |
| 21 | 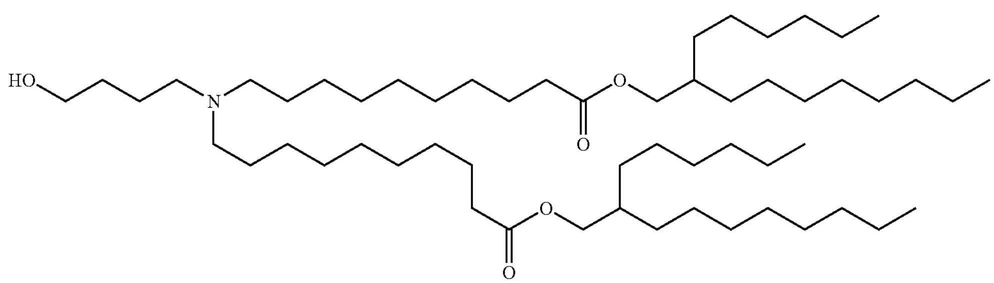 [SMILES: CCCCCCCCC(CCCCCC)COC(=O)CCCCCCCCCN(CCCCO)CCCCCCCCCC(=O)OCC(CCCCCC)CCCCCCCC] |
| 22 | 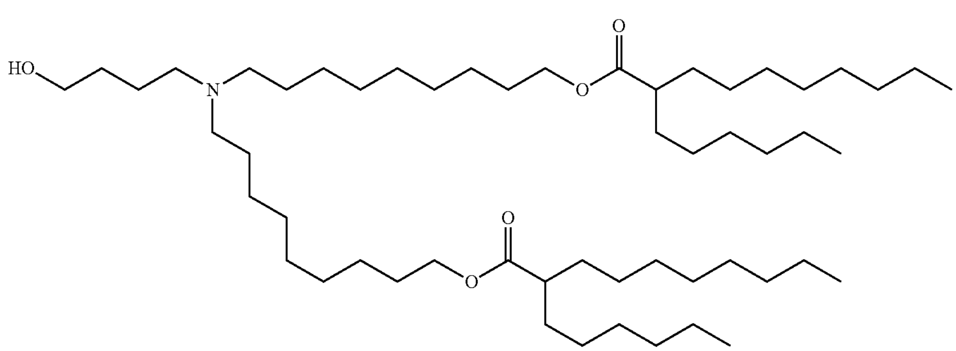 [SMILES: CCCCCCCCC(CCCCCC)C(=O)OCCCCCCCCCN(CCCCO)CCCCCCCCCOC(=O)C(CCCCCC)CCCCCCCC] |

TABLE 10g-continued

| Number | Structure |
|---|---|
| 23 | 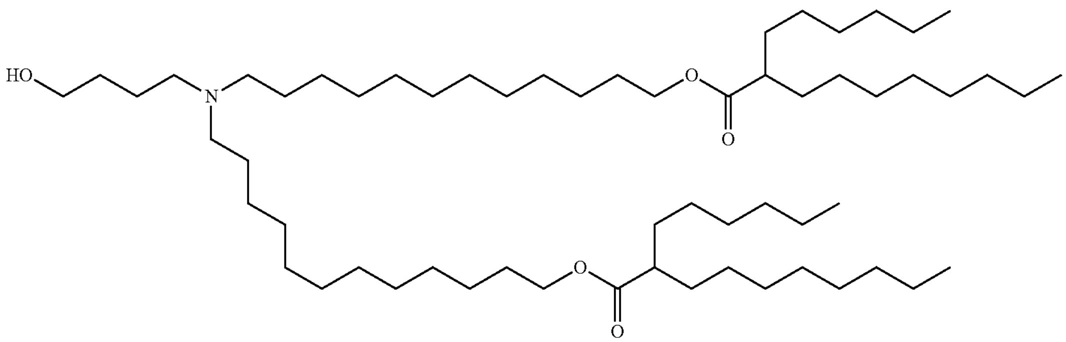 [SMILES: CCCCCCCCC(CCCCCC)C(=O)OCCCCCCCCCCCCN(CCCCO)CCCCCCCCCCCCOC(=O)C(CCCCCC)CCCCCCCC] |
| 24 | 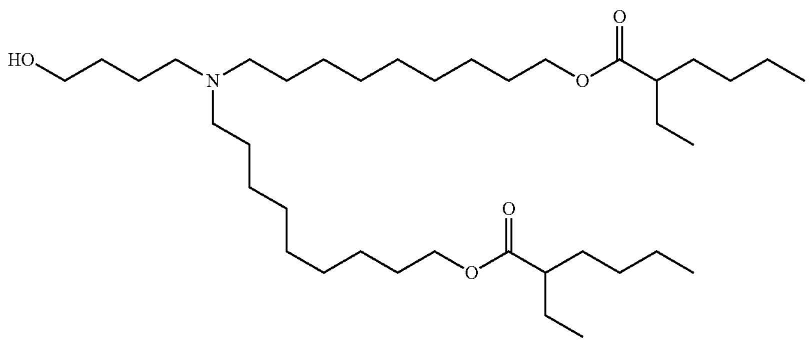 [SMILES: CCCCC(CC)C(=O)OCCCCCCCCCN(CCCCO)CCCCCCCCCOC(=O)C(CC)CCCC] |
| 25 | 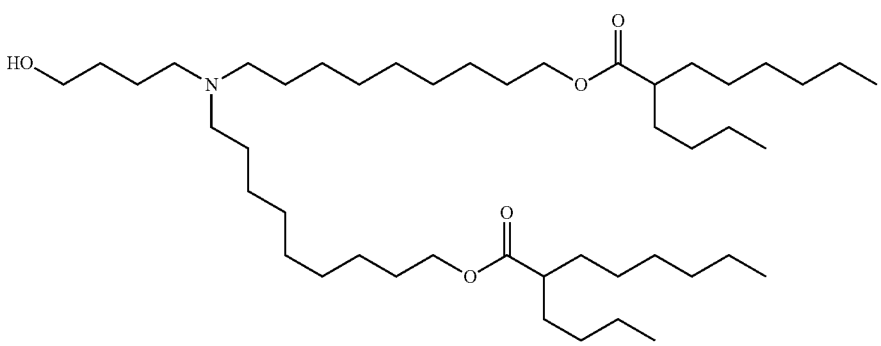 [SMILES: CCCCCCC(CCCC)C(=O)OCCCCCCCCCN(CCCCO)CCCCCCCCCOC(=O)C(CCCC)CCCCCC] |
| 26 | 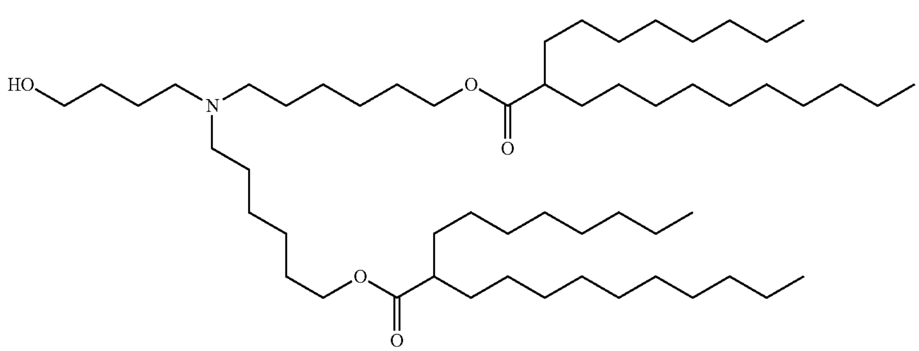 [SMILES: CCCCCCCCCCC(CCCCCCCC)C(=O)OCCCCCCN(CCCCO)CCCCCCOC(=O)C(CCCCCCCC)CCCCCCCCCC] |

TABLE 10g-continued

| Number | Structure |
|---|---|
| 27 | 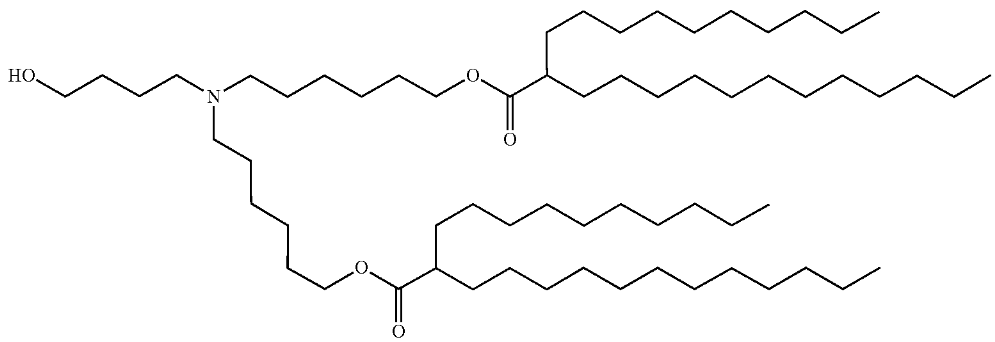 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] |
| 28 | 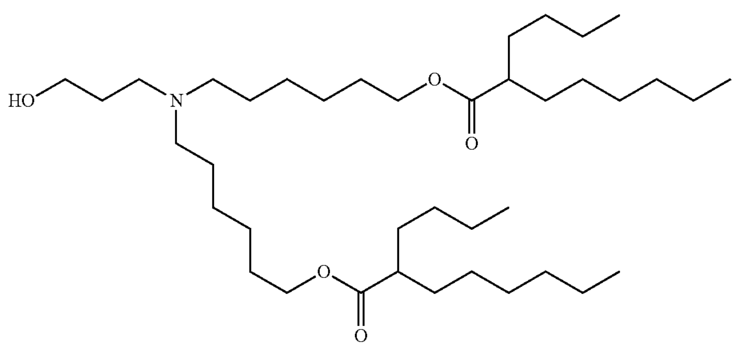 [SMILES: CCCCCCC(CCCC)C(=O)OCCCCCCN(CCCO)CCCCCCOC(=O)C(CCCC)CCCCCC] |
| 29 | 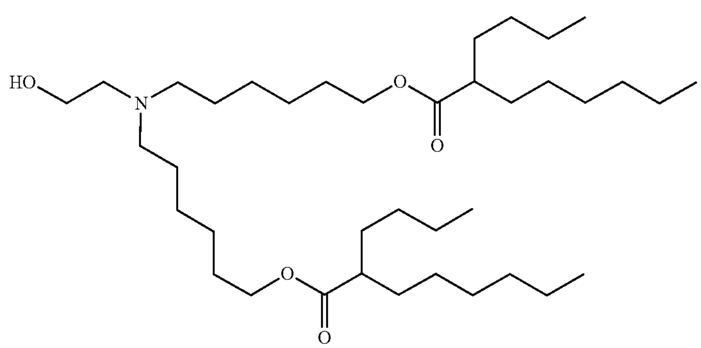 [SMILES: CCCCCCC(CCCC)C(=O)OCCCCCCN(CCO)CCCCCCOC(=O)C(CCCC)CCCCCC] |
| 30 | 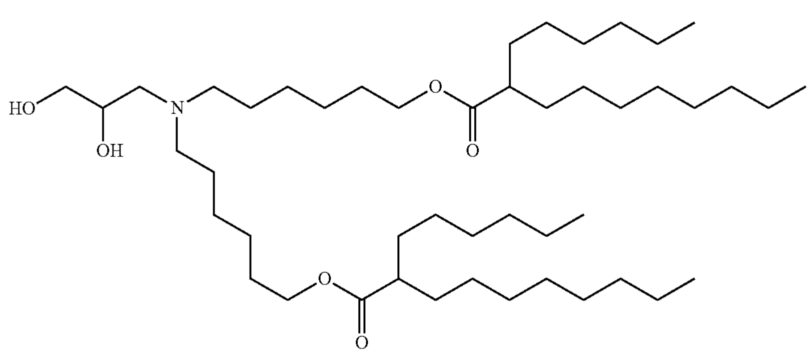 [SMILES: CCCCCCCCC(CCCCCC)C(=O)OCCCCCCN(CCCCCCOC(=O)C(CCCCCC)CCCCCCCC)CC(O)CO] |

TABLE 10g-continued

| Number | Structure |
| --- | --- |
| 31 | 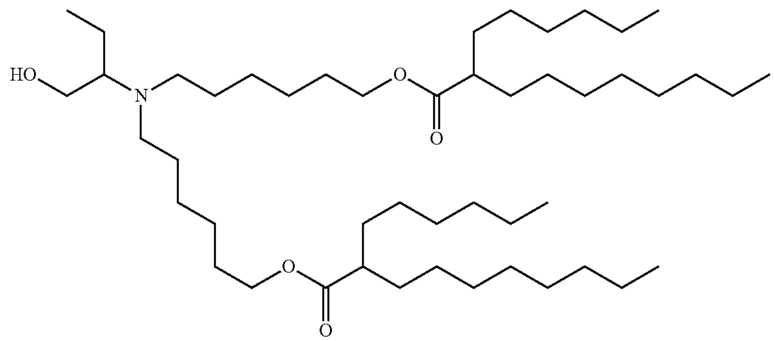 [SMILES: CCCCCCCCC(CCCCCC)C(=O)OCCCCCCN(CCCCCCOC(=O)C(CCCCCC)CCCCCCCC)C(CC)CO] |
| 32 | 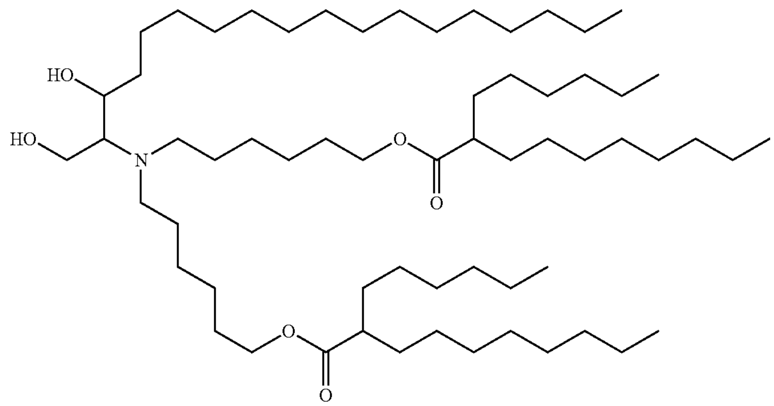 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] |
| 33 | 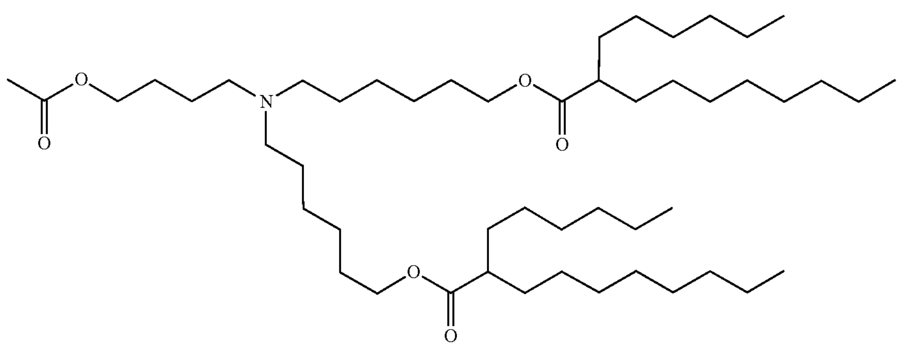 [SMILES: CCCCCCCCC(CCCCCC)C(=O)OCCCCCCN(CCCCCCOC(=O)C(CCCCCC)CCCCCCCC)CCCCOC(C)=O] |
| 34 | 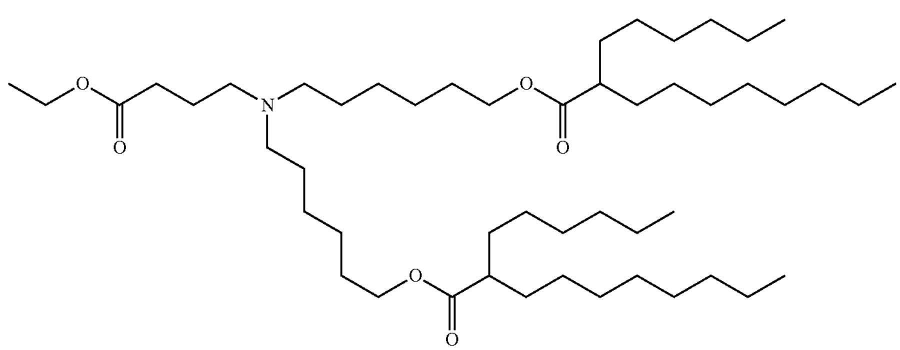 [SMILES: CCCCCCCCC(CCCCCC)C(=O)OCCCCCCN(CCCCCCOC(=O)C(CCCCCC)CCCCCCCC)CCCC(=O)OCC] |

TABLE 10g-continued

| Number | Structure |
|---|---|
| 35 | 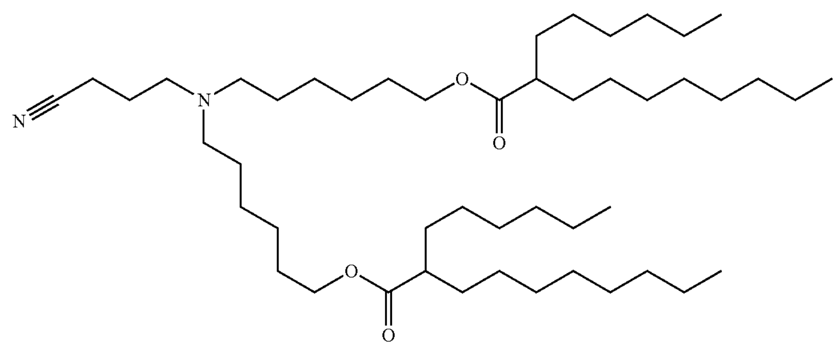 [SMILES: CCCCCCCCC(CCCCCC)C(=O)OCCCCCCN(CCCC#N)CCCCCCOC(=O)C(CCCCCC)CCCCCCCC] |
| 36 | 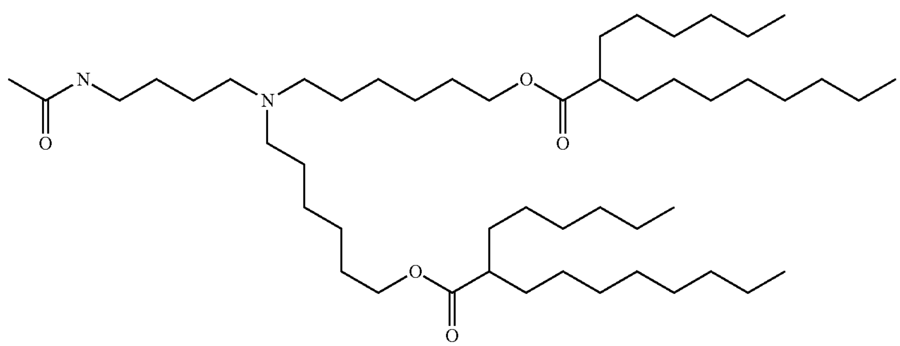 |
| 37 | 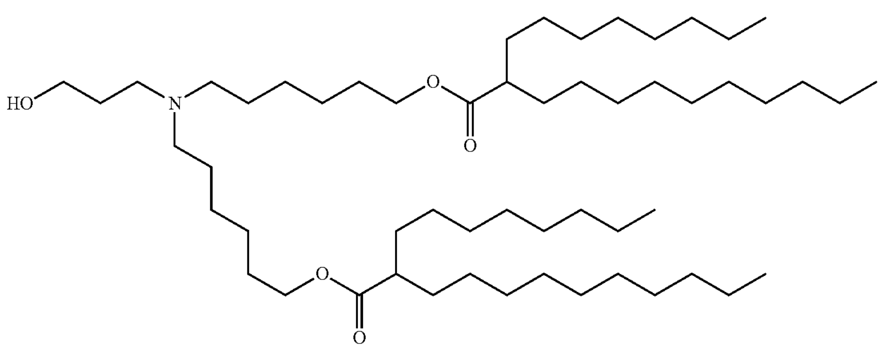 [SMILES: CCCCCCCCCCC(CCCCCCCC)C(=O)OCCCCCCN(CCCO)CCCCCCOC(=O)C(CCCCCCCC)CCCCCCCCCC] |
| 38 | 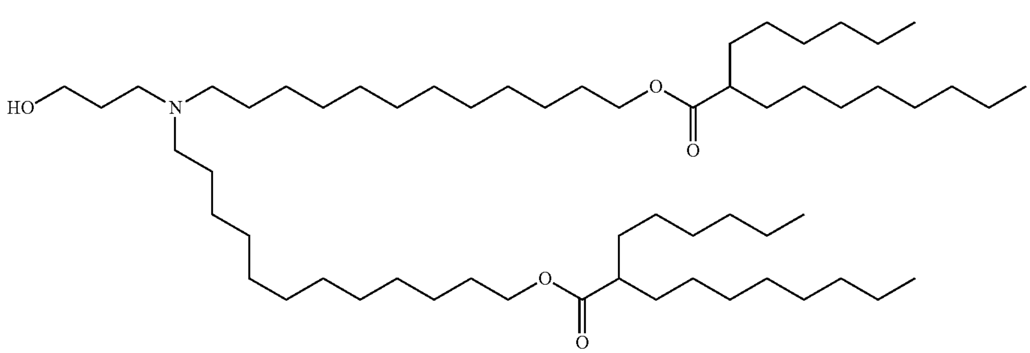 [SMILES: CCCCCCCCC(CCCCCC)C(=O)OCCCCCCCCCCCCN(CCCO)CCCCCCCCCCCCOC(=O)C(CCCCCC)CCCCCCCC] |

TABLE 10g-continued

| Number | Structure |
|---|---|
| 39 | 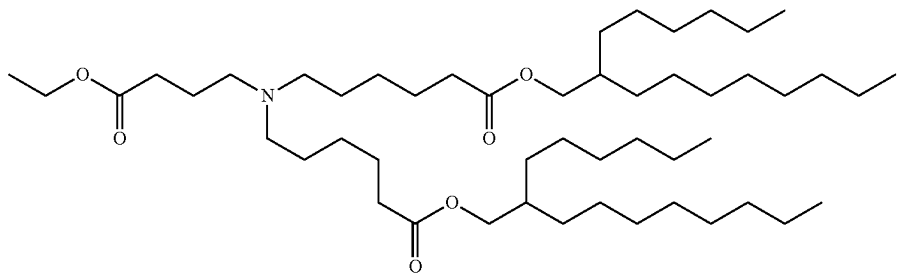 [SMILES: CCCCCCCCC(CCCCCC)COC(=O)CCCCCN(CCCCCC(=O)OCC(CCCCCC)CCCCCCCC)CCCC(=O)OCC] |
| 40 | 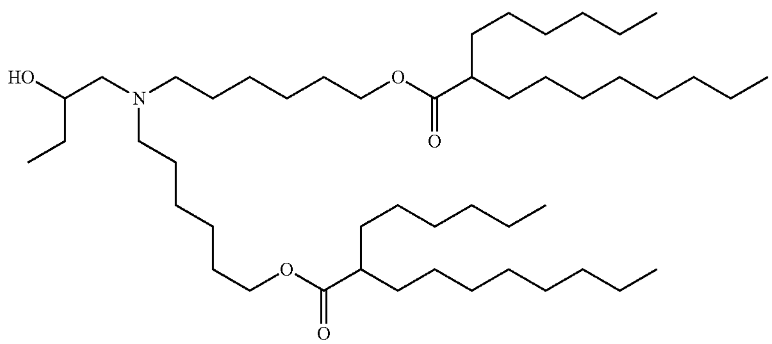 [SMILES: CCCCCCCCC(CCCCCC)C(=O)OCCCCCCN(CCCCCCOC(=O)C(CCCCCC)CCCCCCCC)CC(O)CC] |
| 41 | 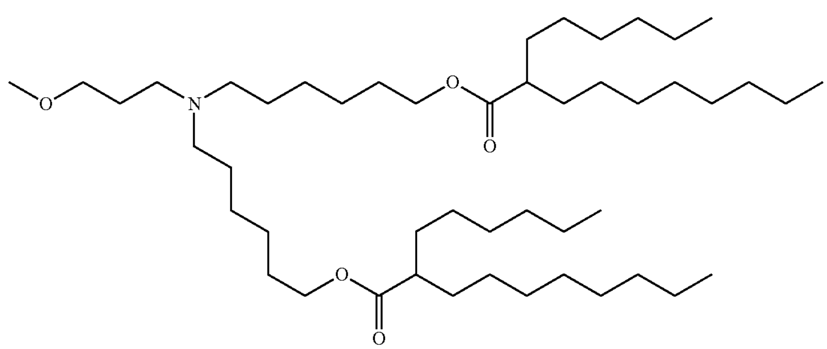 [SMILES: CCCCCCCCC(CCCCCC)C(=O)OCCCCCCN(CCCCCCOC(=O)C(CCCCCC)CCCCCCCC)CCCOC] |
| 42 | 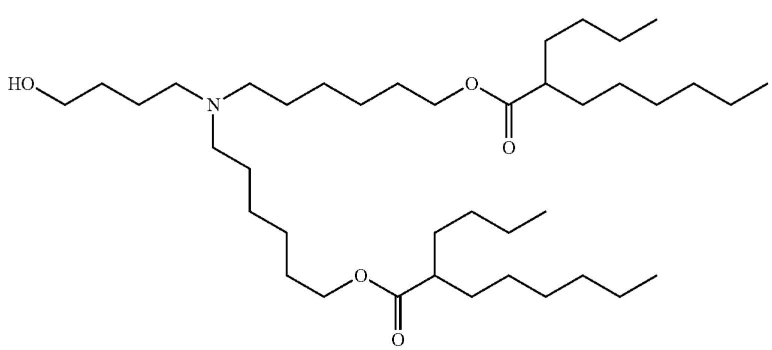 [SMILES: CCCCCCC(CCCC)C(=O)OCCCCCCN(CCCCO)CCCCCCOC(=O)C(CCCC)CCCCCC] |

TABLE 10g-continued

| Number | Structure |
|---|---|
| 43 | 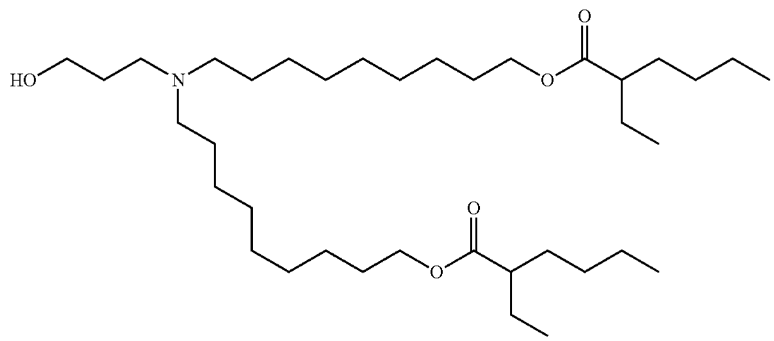 [SMILES: CCCCC(CC)C(=O)OCCCCCCCCCN(CCCO)CCCCCCCCCOC(=O)C(CC)CCCC] |
| 44 | 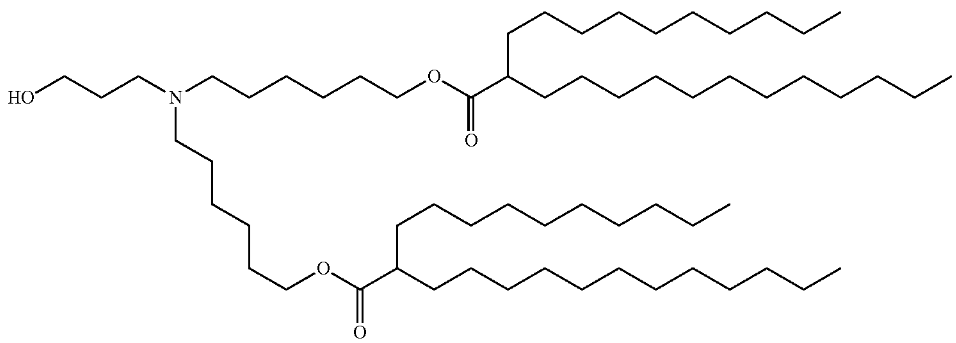 [SMILES: CCCCCCCCCCCCC(CCCCCCCCCC)C(=O)OCCCCCCN(CCCO)CCCCCCOC(=O)C(CCCCCCCCCC)CCCCCCCCCCCC] |
| 45 | 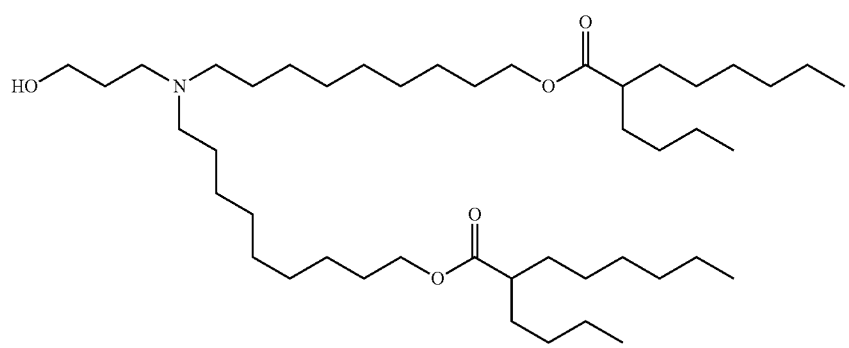 [SMILES: CCCCCCC(CCCC)C(=O)OCCCCCCCCCN(CCCO)CCCCCCCCCOC(=O)C(CCCC)CCCCCC] |
| 46 | 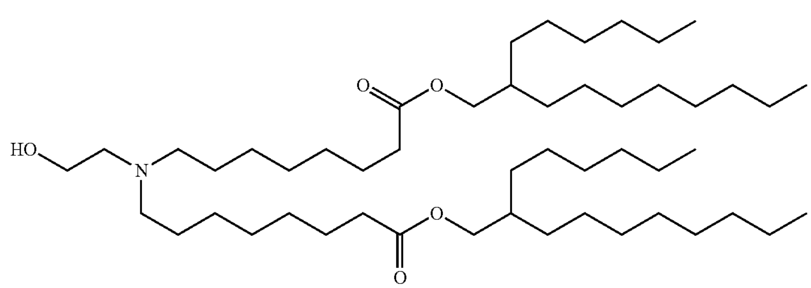 [SMILES: CCCCCCCCC(CCCCCC)COC(=O)CCCCCCCN(CCO)CCCCCCCC(=O)OCC(CCCCCC)CCCCCCCC] |

TABLE 10g-continued

| Number | Structure |
|---|---|
| 47 | 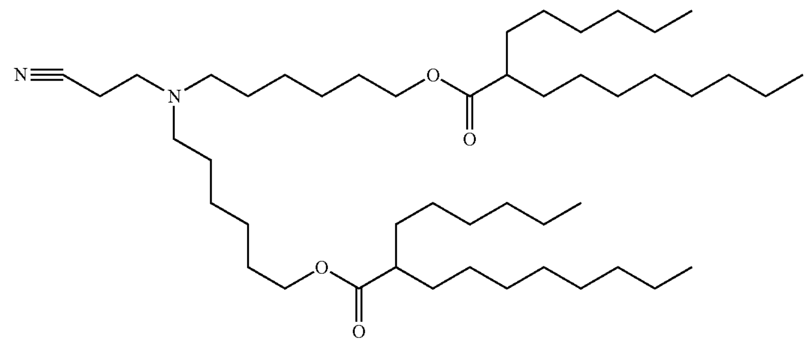 [SMILES: CCCCCCCCC(CCCCCC)C(=O)OCCCCCCN(CCC#N)CCCCCCOC(=O)C(CCCCCC)CCCCCCCC] |
| 48 | 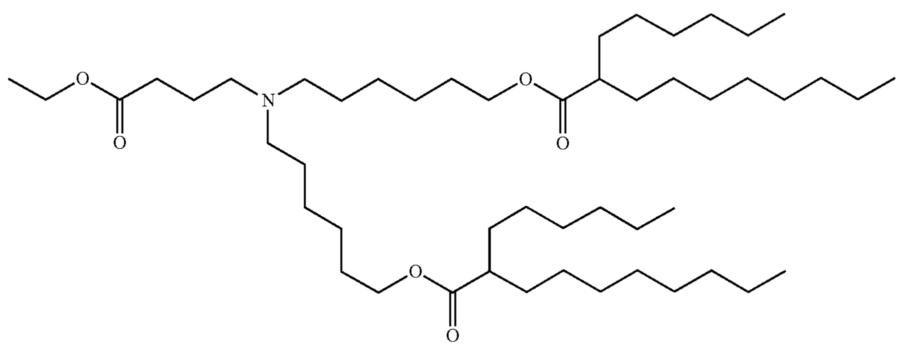 [SMILES: CCCCCCCCC(CCCCCC)C(=O)OCCCCCCN(CCCCCCOC(=O)C(CCCCCC)CCCCCCCC)CCCC(=O)OCC] |
| 49 | 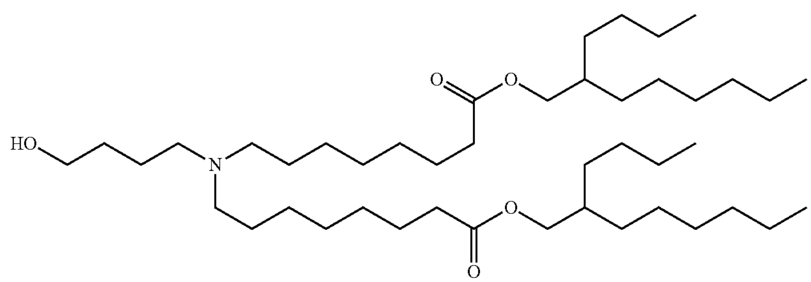 [SMILES: CCCCCCC(CCCC)COC(=O)CCCCCCCN(CCCCO)CCCCCCCC(=O)OCC(CCCC)CCCCCC] |

In some embodiments, an ionizable lipid is as described in international patent application PCT/US2020/038678.

In some embodiments, the ionizable lipid is represented by Formula (14*):

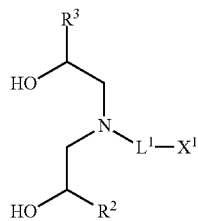

Formula (14*)

or a pharmaceutically acceptable salt thereof, wherein
$L^1$ is $C_2$-$C_{11}$ alkylene, $C_4$-$C_{10}$-alkenylene, or $C_4$-$C_{10}$-alkynylene;
$X^1$ is $OR^1$, $SR^1$, or $N(R^1)_2$, where $R^1$ is independently H or unsubstituted $C_1$-$C_6$ alkyl; and
$R_2$ and $R_3$ are each independently a linear or branched $C_1$-$C_{30}$ alkyl, $C_2$-$C_{30}$ alkenyl, or $C_1$-$C_{30}$ heteroalkyl, optionally substituted by one or more substituents selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, alkylcarbonyloxy, alkylcarbonate, alkenyloxycarbonyl, alkenylcarbonyloxy, alkenylcarbonate, alkynyloxycarbonyl, alkynylcarbonyloxy, alkynylcarbonate, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl.

In some embodiments, the ionizable lipid is represented by Formula (14):

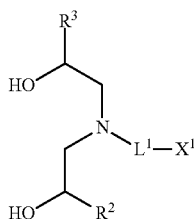

Formula (14)

or a pharmaceutically acceptable salt thereof, wherein $L^1$ is $C_2$-$C_{11}$ alkylene, $C_4$-$C_{10}$-alkenylene, or $C_4$-$C_{10}$-alkynylene;

$X^1$ is $OR^1$, $SR^1$, or $N(R^1)_2$, where $R^1$ is independently H or unsubstituted $C_1$-$C_6$ alkyl; and $R_2$ and $R_3$ are each independently $C_6$-$C_{30}$-alkyl, $C_6$-$C_{30}$-alkenyl, or $C_6$-$C_{30}$-alkynyl.

In some embodiments, $X^1$ is $OR^1$. In some embodiments, $X^1$ is OH. In some embodiments, $X^1$ is $SR^1$. In some embodiments, $X^1$ is SH. In some embodiments, $X^1$ is $N(R^1)_2$. In some embodiments, $X^1$ is $NH_2$.

In some embodiments, $L^1$ is $C_2$-$C_{10}$ alkylene. In some embodiments, $L^1$ is unsubstituted $C_2$-$C_{10}$ alkylene. In some embodiments, $L^1$ is $C_4$-$C_{10}$ alkenylene. In some embodiments, $L^1$ is unsubstituted $C_4$-$C_{10}$ alkenylene. In some embodiments, $L^1$ is $C_4$-$C_{10}$ alkynylene. In some embodiments, $L^1$ is unsubstituted $C_4$-$C_{10}$ alkynylene.

In some embodiments of Formula (14), a lipid has a structure according to Formula (14-2),

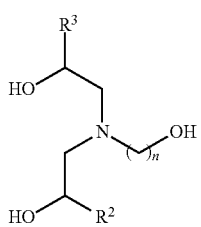

Formula (14-2)

or a pharmaceutically acceptable salt thereof, wherein n is an integer of 2-10.

In some embodiments, n is 2, 3, 4, or 5. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments of Formula (14*) or Formula (14-2), $R_2$ and $R_3$ are independently a linear or branched $C_1$-$C_{20}$ alkyl, $C_2$-$C_{20}$ alkenyl, or $C_1$-$C_{20}$ heteroalkyl, optionally substituted by one or more substituents each independently selected from linear or branched $C_1$-$C_{20}$ alkoxy, linear or branched $C_1$-$C_{20}$ alkyloxycarbonyl, linear or branched $C_1$-$C_{20}$ alkylcarbonyloxy, linear or branched $C_1$-$C_{20}$ alkylcarbonate, linear or branched $C_2$-$C_{20}$ alkenyloxycarbonyl, linear or branched $C_2$-$C_{20}$ alkenylcarbonyloxy, linear or branched $C_2$-$C_{20}$ alkenylcarbonate, linear or branched $C_2$-$C_{20}$ alkynyloxycarbonyl, linear or branched $C_2$-$C_{20}$ alkynylcarbonyloxy, and linear or branched $C_2$-$C_{20}$ alkynylcarbonate.

In certain embodiments of Formula (14*) or Formula (14-2), one or each of $R^2$ and $R^3$ is unsubstituted $C_6$-$C_{30}$-alkyl, unsubstituted $C_6$-$C_{30}$-alkenyl, or unsubstituted $C_6$-$C_{30}$-alkynyl. In certain embodiments, each of $R^2$ and $R^3$ is unsubstituted $C_6$-$C_{30}$-alkyl. In certain embodiments, each of $R^2$ and $R_3$ is unsubstituted $C_6$-$C_{30}$-alkenyl. In certain embodiments, each of $R^2$ and $R^3$ is unsubstituted $C_6$-$C_{30}$-alkynyl.

In some embodiments of Formula (14*), the alkyloxycarbonyl substituent is of the formula —C(O)OR$^6$, wherein $R^6$ is unsubstituted $C_6$-$C_{30}$ alkyl or $C_6$-$C_{30}$ alkenyl. In some embodiments of Formula (14*) or Formula (14-2), at least one of $R_2$ and $R_3$ is substituted with an alkylcarbonyloxy. In some embodiments, the alkylcarbonyloxy is of the formula —OC(O)R$^6$, wherein $R^6$ is unsubstituted $C_6$-$C_{30}$ alkyl or $C_6$-$C_{30}$ alkenyl. In some embodiments, at least one of $R_2$ and $R_3$ is substituted with an alkylcarbonate. In some embodiments, the alkylcarbonate is of the formula —O(CO)OR$^6$, wherein $R^6$ is unsubstituted $C_6$-$C_{30}$ alkyl or $C_6$-$C_{30}$ alkenyl. In some embodiments, $R_2$ and $R_3$ are independently $C_1$-$C_{12}$ alkyl substituted by —O(CO)R$^6$, —C(O)OR$^6$, or —O(CO)OR$^6$, wherein $R^6$ is unsubstituted $C_6$-$C_{30}$ alkyl or $C_6$-$C_{30}$ alkenyl. In some embodiments, $R_2$ and $R_3$ are each $C_1$-$C_{12}$ alkyl substituted by —O(CO)R$^6$. In some embodiments, $R_2$ and $R_3$ are each $C_1$-$C_{12}$ alkyl substituted by —C(O)OR$^6$. In some embodiments, $R_2$ and $R_3$ are each $C_1$-$C_{12}$ alkyl substituted by —O(CO)OR$^6$. In some embodiments $R_2$ is —C(O)OR$^6$ or —O(CO)R$^6$ and $R_3$ is —O(CO)OR$^6$. In some embodiments, $R_2$ is —O(CO)OR$^6$ and $R_3$ is —C(O)OR$^6$ or —O(CO)R$^6$.

In some embodiments of Formula (14*) or Formula (14-2), at least one of $R_2$ and $R_3$ is selected from the following formulae:

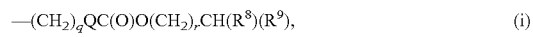 (i)

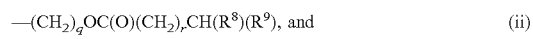 (ii)

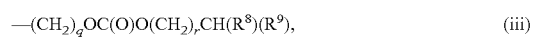 (iii)

wherein:
q is 0 to 12,
r is 0 to 6,
$R^8$ is H or $R^{10}$, and
$R^9$ and $R^{10}$ are independently unsubstituted linear $C_1$-$C_{12}$ alkyl or unsubstituted linear $C_2$-$C_{12}$-alkenyl.

In some embodiments of Formula (14*) or Formula (14-2), each of $R_2$ and $R_3$ is independently selected from one of the following formulae:

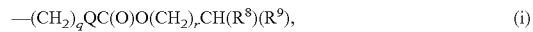 (i)

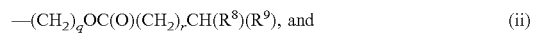 (ii)

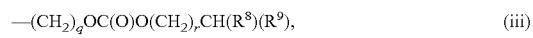 (iii)

wherein:
q is 0 to 12,
r is 0 to 6,
$R^8$ is H or $R^{10}$, and
$R^9$ and $R^{10}$ are independently unsubstituted linear $C_1$-$C_{12}$ alkyl or unsubstituted linear $C_2$-$C_{12}$-alkenyl.

In some embodiments, of any one of formulae (i)-(iii), q is 1 to 6. In some embodiments of any one of formulae (i)-(iii), q is 0. In some embodiments, of any one of formulae (i)-(iii), q is 1. In some embodiments of any one of formulae (i)-(iii), q is 2. In some embodiments of any one of formulae (i)-(iii), q is 3 to 12. In some embodiments, of any one of formulae (i)-(iii), q is 3 to 6.

In some embodiments of any one of formulae (i)-(iii), r is 0. In some embodiments of any one of formulae (i)-(iii), r is 1 to 6. In some embodiments of any one of formulae (i)-(iii), r is 1. In some embodiments of any one of formulae (i)-(iii), r is 2. In some embodiments of any one of formulae (i)-(iii), r is 3. In some embodiments of any one of formulae (i)-(iii), r is 4.

In some embodiments of formulae (i)-(iii), $R^8$ is H. In some embodiments of formulae (i)-(iii), $R^8$ is $R^{10}$. In some embodiments of formulae (i)-(iii), $R^9$ and $R^{10}$ are different. In some embodiments of formulae (i)-(iii), $R^9$ and $R^{10}$ are the same.

In some embodiments of formulae (i)-(iii), $R^8$ is H, and $R^9$ is unsubstituted linear $C_1$-$C_{12}$ alkyl or unsubstituted linear $C_1$-$C_{12}$-alkenyl. In some embodiments of formulae (i)-(iii), $R^8$ is H, and $R^9$ is unsubstituted linear $C_2$-$C_{12}$ alkyl. In some embodiments of formulae (i)-(iii), $R^8$ is H, and $R^9$ is unsubstituted linear $C_2$-$C_8$ alkyl. In some embodiments of formulae (i)-(iii), $R^8$ is H, and $R^9$ is unsubstituted linear $C_4$-$C_8$ alkyl. In some embodiments of formulae (i)-(iii), $R^8$ is H, and $R^9$ is unsubstituted linear $C_5$-$C_8$ alkyl. In some embodiments of formulae (i)-(iii), $R^8$ is H, and $R^9$ is unsubstituted linear $C_6$-$C_8$ alkyl.

In some embodiments of formulae (i)-(iii), $R^8$ and $R^9$ are each independently unsubstituted linear $C_1$-$C_{12}$ alkyl or unsubstituted linear $C_1$-$C_{12}$-alkenyl. In some embodiments of formulae (i)-(iii), $R^8$ and $R^9$ are each independently unsubstituted linear $C_2$-$C_{12}$ alkyl. In some embodiments of formulae (i)-(iii), $R^8$ and $R^9$ are each independently unsubstituted linear $C_2$-$C_8$ alkyl. In some embodiments of formulae (i)-(iii), $R^8$ and $R^9$ are each independently unsubstituted linear $C_4$-$C_8$ alkyl. In some embodiments of formulae (i)-(iii), $R^8$ and $R^9$ are each independently unsubstituted linear $C_6$-$C_8$ alkyl.

In some embodiments of Formula (14*) or Formula (14-2), at least one of $R_2$ and $R_3$ is —$(CH_2)_qC(O)O(CH_2)_rCH(R^8)(R^9)$, where q, r, $R^8$ and $R^9$ are as defined above. In some embodiments at least one of $R_2$ and $R_3$ is —$(CH_2)_qOC(O)(CH_2)_rCH(R^8)(R^9)$, where q, r, $R^8$ and $R^9$ are as defined above. In some embodiments at least one of $R_2$ and $R_3$ is —$(CH_2)_qOC(O)O(CH_2)_rCH(R^8)(R^9)$, where q, r, $R^8$ and $R^9$ are as defined above. In some embodiments of Formula (14*) or Formula (14-2), at least one of $R_2$ and $R_3$ is —$(CH_2)_qQC(O)O(CH_2)_rCH(R^8)(R^9)$, where q is 3 to 12 (e.g., 6 to 12), r is 1 to 6 (e.g., 1, 2 or 3), and $R^8$ and $R^9$ are each independently unsubstituted linear $C_4$-$C_8$ alkyl.

In certain embodiments of Formula (14*) or Formula (14-2), at least one of $R_2$ and $R_3$ is —$(CH_2)_qC(O)O(CH_2)_rCH(R^8)(R^9)$ or —$(CH_2)_qOC(O)(CH_2)_rCH(R^8)(R^9)$, where q, r, $R^8$ and $R^9$ are as defined above. In other embodiments, at least one of $R_2$ and $R_3$ is —$(CH_2)_qOC(O)(CH_2)_rCH(R^8)(R^9)$ or —$(CH_2)_qOC(O)O(CH_2)_rCH(R^8)(R^9)$, where q, r, $R^8$ and $R^9$ are as defined above. In some embodiments, at least one of $R_2$ and $R_3$ is —$(CH_2)_qQC(O)O(CH_2)_rCH(R^8)(R^9)$ or —$(CH_2)_qOC(O)O(CH_2)_rCH(R^8)(R^9)$, where q, r, $R^8$ and $R^9$ are as defined above.

In other embodiments of Formula (14*) or Formula (14-2), at least one of $R_2$ and $R_3$ is —$(CH_2)_qOC(O)(CH_2)_rCH(R^8)(R^9)$ where q, r, $R^8$ and $R^9$ are as defined above. In some embodiments, at least one of $R_2$ and $R_3$ is —$(CH_2)_qQC(O)O(CH_2)_rCH(R^8)(R^9)$ or —$(CH_2)_qOC(O)O(CH_2)_rCH(R^8)(R^9)$, where q, r, $R^8$ and $R^9$ are as defined above.

In certain embodiments of Formula (14*) or Formula (14-2), $R_2$ is —$(CH_2)_qQC(O)O(CH_2)_rCH(R^8)(R^9)$, and $R_3$ is —$(CH_2)_qQC(O)O(CH_2)_rCH(R^8)(R^9)$, where q, r, $R^8$ and $R^9$ are as defined above. In certain embodiments, $R_2$ is —$(CH_2)_qQC(O)O(CH_2)_rCH(R^8)(R^9)$, and $R_3$ is —$(CH_2)_qOC(O)(CH_2)_rCH(R^8)(R^9)$, where q, r, $R^8$ and $R^9$ are as defined above. In certain embodiments, R is —$(CH_2)_qQC(O)O(CH_2)_rCH(R^8)(R^9)$, and $R_3$ is —$(CH_2)_qOC(O)O(CH_2)_rCH(R^8)(R^9)$, where q, r, $R^8$ and $R^9$ are as defined above.

In certain embodiments of Formula (14*) or Formula (14-2), $R_2$ is —$(CH_2)_qOC(O)(CH_2)_rCH(R^8)(R^9)$, and $R_3$ is —$(CH_2)_qQC(O)O(CH_2)_rCH(R^8)(R^9)$, where q, r, $R^8$ and $R^9$ are as defined above. In certain embodiments, $R_2$ is —$(CH_2)_qOC(O)(CH_2)_rCH(R^8)(R^9)$, and $R_3$ is —$(CH_2)_qOC(O)(CH_2)_rCH(R^8)(R^9)$, where q, r, $R^8$ and $R^9$ are as defined above. In certain embodiments, $R_2$ is —$(CH_2)_qOC(O)(CH_2)_rCH(R^8)(R^9)$, and $R_3$ is —$(CH_2)_qOC(O)O(CH_2)_rCH(R^8)(R^9)$, where q, r, $R^8$ and $R^9$ are as defined above.

In certain embodiments of Formula (14*) or Formula (14-2), $R_2$ is —$(CH_2)_qOC(O)O(CH_2)_rCH(R^8)(R^9)$, and $R_3$ is —$(CH_2)_qQC(O)O(CH_2)_rCH(R^8)(R^9)$, where q, r, $R^8$ and $R^9$ are as defined above. In certain embodiments, $R_2$ is —$(CH_2)_qOC(O)O(CH_2)_rCH(R^8)(R^9)$, and $R_3$ is —$(CH_2)_qOC(O)(CH_2)_rCH(R^8)(R^9)$, where q, r, $R^8$ and $R^9$ are as defined above. In certain embodiments, $R_2$ is —$(CH_2)_qOC(O)O(CH_2)_rCH(R^8)(R^9)$, and $R_3$ is —$(CH_2)_qOC(O)O(CH_2)_rCH(R^8)(R^9)$, where q, r, $R^8$ and $R^9$ are as defined above.

In certain embodiments of Formula (14*) or Formula (14-2), one or each of $R_2$ and $R_3$ is unsubstituted $C_6$-$C_{22}$-alkyl, or one or each of $R^2$ and $R^3$ is unsubstituted $C_6$-$C_{22}$-alkenyl. In certain embodiments, each of $R^2$ and $R^3$ is unsubstituted $C_6$-$C_{22}$-alkyl. In certain embodiments, each of $R_2$ and $R_3$ is unsubstituted $C_6$-$C_{22}$-alkenyl.

In certain embodiments, one or each of $R_2$ and $R_3$ is —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$, —$C_{18}H_{37}$, —$C_{19}H_{39}$, —$C_{20}H_{41}$, —$C_{21}H_{43}$, —$C_{22}H_{45}$, —$C_{23}C_{47}$, —$C_{24}H_{49}$, —$C_{25}H_{51}$.

In certain embodiments, one or each of $R_2$ and $R_3$ is —$(CH_2)_4CH=CH_2$, —$(CH_2)_5CH=CH_2$, —$(CH_2)_6CH=CH_2$, —$(CH_2)_7CH=CH_2$, —$(CH_2)_8CH=CH_2$, —$(CH_2)_9CH=CH_2$, —$(CH_2)_{10}CH=CH_2$, —$(CH_2)_{11}CH=CH_2$, —$(CH_2)_{12}CH=CH_2$, —$(CH_2)_{13}CH=CH_2$, —$(CH_2)_{14}CH=CH_2$, —$(CH_2)_{15}CH=CH_2$, —$(CH_2)_{16}CH=CH_2$, —$(CH_2)_{17}CH=CH_2$, —$(CH_2)_{18}CH=CH_2$, —$(CH_2)_7CH=CH(CH_2)_3CH_3$, —$(CH_2)_7CH=CH(CH_2)_5CH_3$, —$(CH_2)_4CH=CH(CH_2)_8CH_3$, —$(CH_2)_7CH=CH(CH_2)_7CH_3$, —$(CH_2)_6CH=CHCH_2CH=CH(CH_2)_4CH_3$, —$(CH_2)_7CH=CHCH_2CH=CH(CH_2)_4CH_3$, —$(CH_2)_7CH=CHCH_2CH=CHCH_2CH=CHCH_2CH_3$, —$(CH_2)_3CH=CHCH_2CH=CHCH_2CH=CHCH_2CH=CH(CH_2)_4CH_3$, —$(CH_2)_3CH=CHCH_2CH=CHCH_2CH=CHCH_2CH=CHCH_2CH_3$, —$(CH_2)IICH=CH(CH_2)_7CH_3$, or —$(CH_2)_2CH=CHCH_2CH=CHCH_2CH=CHCH_2CH=CHCH_2CH=CHCH_2CH_3$.

In certain embodiments, one or each of $R_2$ and $R_3$ is $C_6$-$C_{12}$ alkyl substituted by —O(CO)$R^6$ or —C(O)O$R^6$, wherein $R^6$ is unsubstituted $C_6$-$C_{14}$ alkyl. In certain embodiments, $R^6$ is unsubstituted linear $C_6$-$C_{14}$ alkyl. In certain embodiments, $R^6$ is unsubstituted branched $C_6$-$C_{14}$ alkyl.

In certain embodiments, one or each of $R_2$ and $R_3$ is $(CH_2)_7C(O)O(CH_2)_2CH(C_5H_{11})_2$ or $(CH_2)_8C(O)O(CH_2)_2CH(C_5H_{11})_2$. In certain embodiments, one or each of $R^2$ and $R^3$ is

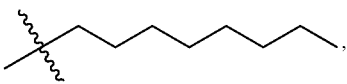

-continued

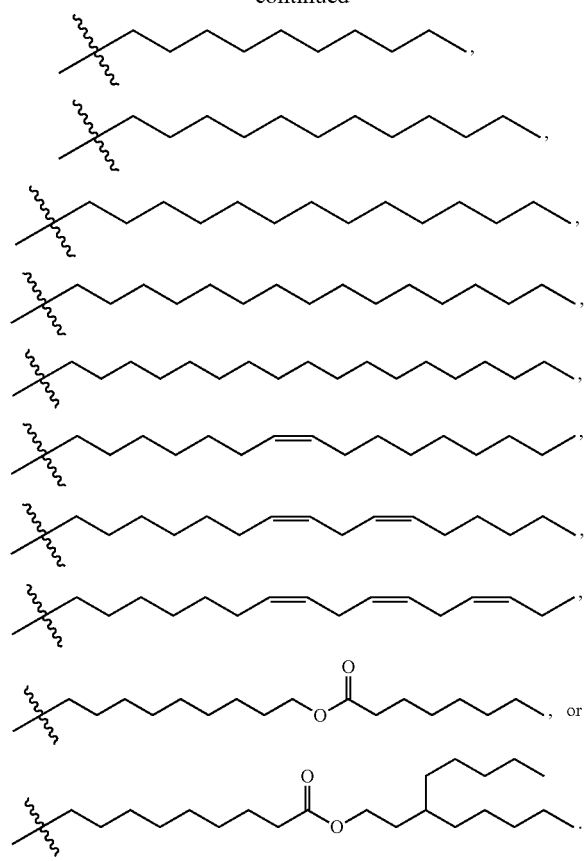

In certain embodiments, one of each of $R^2$ and $R^3$ is

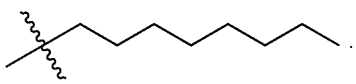 [SMILES: *CCCCCCCC]

In certain embodiments, one or each of $R^2$ and $R^3$ is

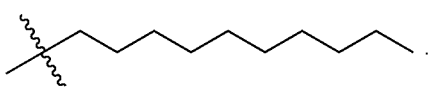 [SMILES: *CCCCCCCCCC]

In certain embodiments, one or each of $R^2$ and $R^3$ is

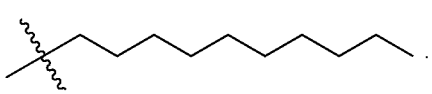 [SMILES: *CCCCCCCCCC]

In certain embodiments, one or each of $R^2$ and $R_3$ is

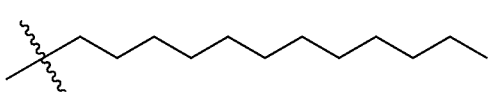

In certain embodiments, one or each of $R^2$ and $R^3$ is

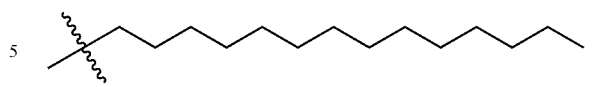

In certain embodiments, one or each of $R^2$ and $R^3$ is

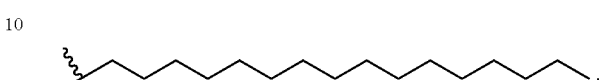

In certain embodiments, one or each of $R^2$ and $R^3$ is

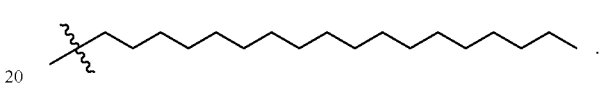

In certain embodiments, one or each of $R^2$ and $R^3$ is

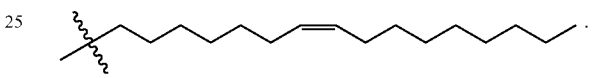

In certain embodiments, one or each of $R^2$ and $R^3$ is

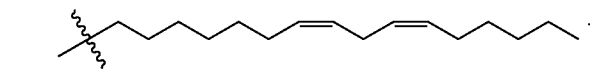 [SMILES: *CCCCCC/C=C\C/C=C\CCCCC]

In certain embodiments, one or each of $R^2$ and $R^3$ is

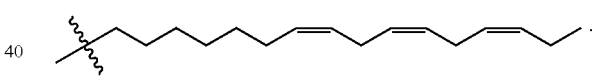

In certain embodiments, one or each of $R_2$ and $R^3$ is

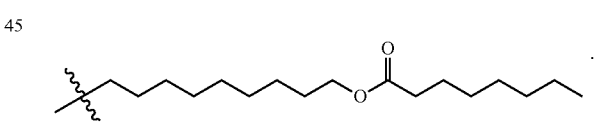

In certain embodiments, one or each of $R^2$ and $R^3$ is

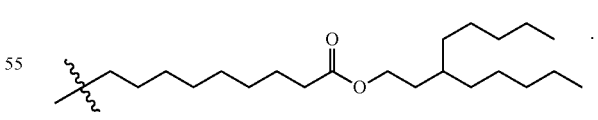

In certain embodiments, one or each of $R^2$ and $R^3$ is

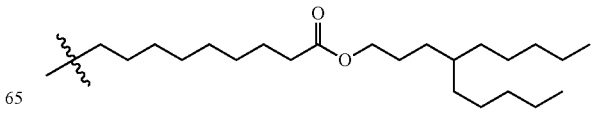

In some embodiments, an ionizable lipid is described in Table 10 h.
TABLE 10h
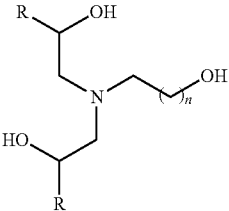
| Compound | n | R | Structure |
|---|---|---|---|
| 1 | 1 | $C_8H_{17}$ | 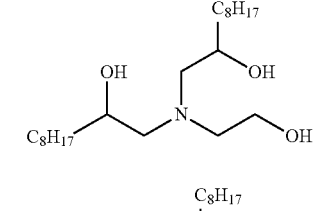 |
| 2 | 2 | $C_8H_{17}$ | 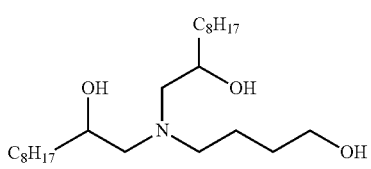 |
| 3 | 3 | $C_8H_{17}$ | 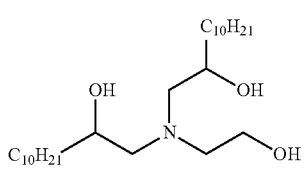 |
| 4 | 1 | $C_{10}H_{21}$ | 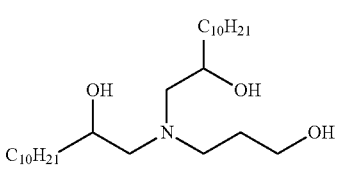 |
| 5 | 2 | $C_{10}H_{21}$ | 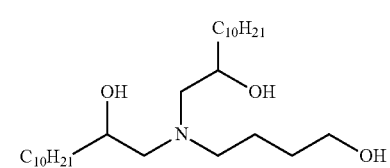 |
| 6 | 3 | $C_{10}H_{21}$ | 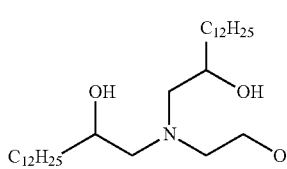 |
| 7 | 1 | $C_{12}H_{25}$ | 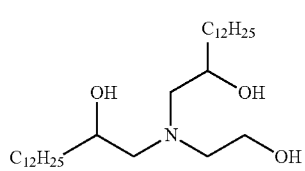 |

TABLE 10h-continued

[Structure: R-CH(OH)-CH2-N(CH2-CH(OH)-R)(-(CH2)n-OH)]

| Compound | n | R | Structure |
|---|---|---|---|
| 8 | 2 | C₁₂H₂₅ | 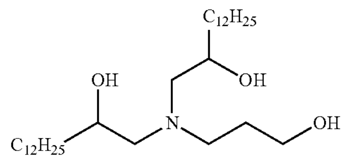 |
| 9 | 3 | C₁₂H₂₅ | 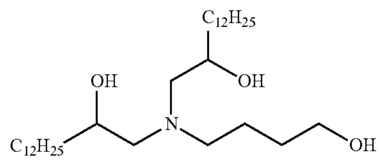 |
| 10 | 1 | C₁₄H₂₉ | 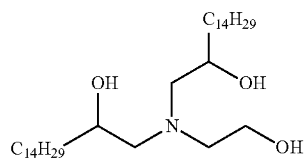 |
| 11 | 2 | C₁₄H₂₉ | 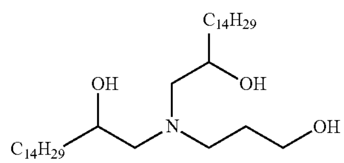 |
| 12 | 3 | C₁₄H₂₉ | 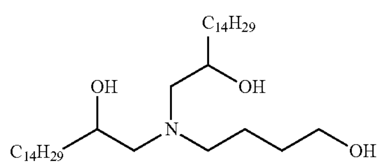 |
| 13 | 1 | C₁₆H₃₃ | 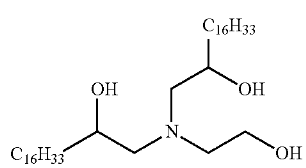 |
| 14 | 2 | C₁₆H₃₃ | 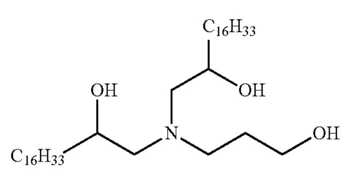 |
| 15 | 3 | C₁₆H₃₃ | 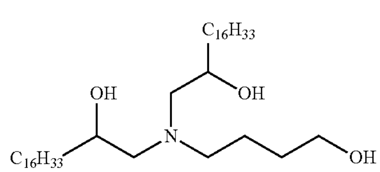 |

TABLE 10h-continued
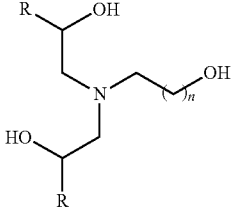
| Compound | n | R | Structure |
|---|---|---|---|
| 16 | 1 | C$_{18}$H$_{37}$ | 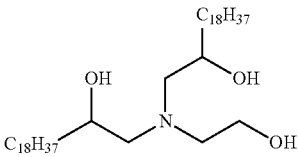 |
| 17 | 2 | C$_{18}$H$_{37}$ | 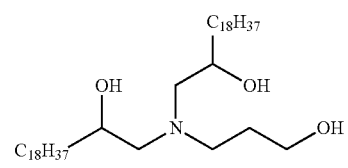 |
| 18 | 3 | C$_{18}$H$_{37}$ | 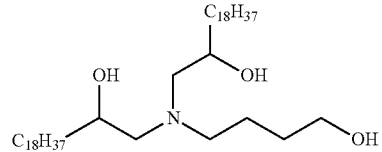 |
| 19 | 1 | C$_6$H$_{12}$CH=CHC$_8$H$_{17}$ | 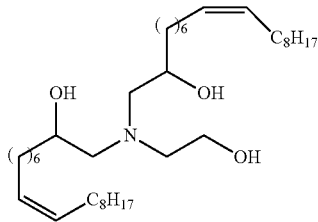 |
| 20 | 2 | C$_6$H$_{12}$CH=CHC$_8$H$_{17}$ | 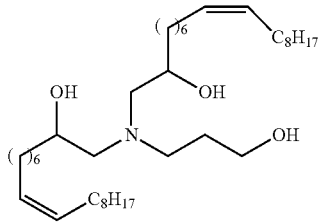 |
| 21 | 3 | C$_6$H$_{12}$CH=CHC$_8$H$_{17}$ | 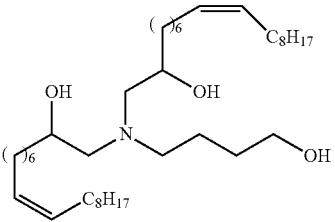 |

TABLE 10h-continued
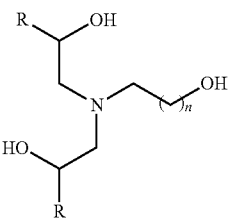
| Compound | n | R | Structure |
|---|---|---|---|
| 22 | 1 | C$_6$H$_{12}$CH=CHCH$_2$CH=CHC$_5$H$_{11}$ | 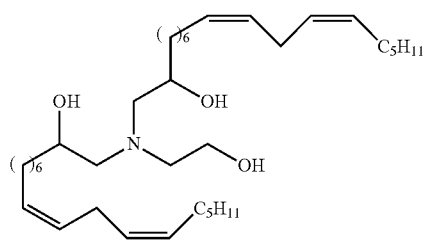 |
| 23 | 2 | C$_6$H$_{12}$CH=CHCH$_2$CH=CHC$_5$H$_{11}$ | 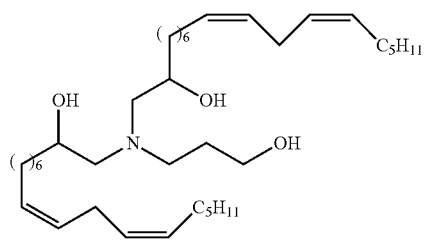 |
| 24 | 3 | C$_6$H$_{12}$CH=CHCH$_2$CH=CHC$_5$H$_{11}$ | 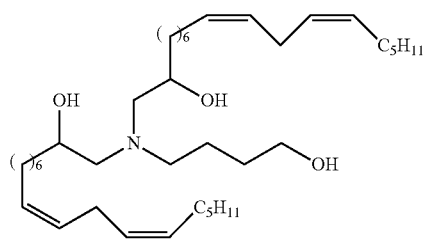 |
| 25 | 1 | (CH$_2$)$_6$CH=CH(CH$_2$)CH=CH(CH$_2$)CH=CHC$_2$H$_5$ | 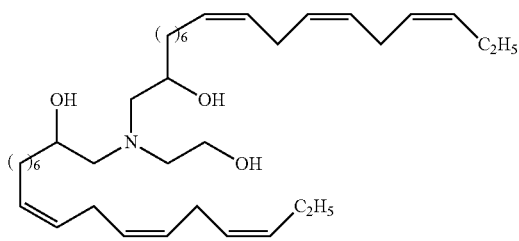 |
| 26 | 2 | (CH$_2$)$_6$CH=CH(CH$_2$)CH=CH(CH$_2$)CH=CHC$_2$H$_5$ | 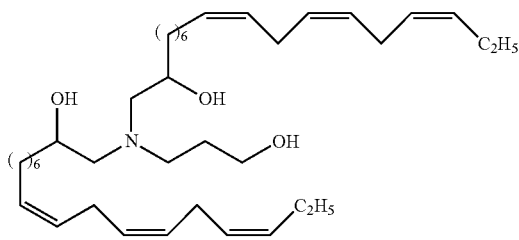 |

TABLE 10h-continued
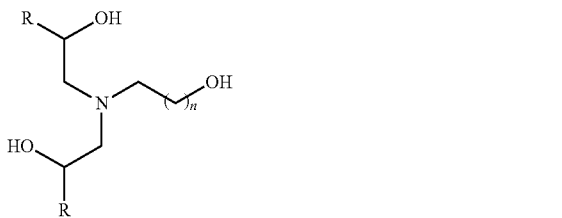
| Compound | n | R | Structure |
|---|---|---|---|
| 27 | 3 | (CH$_2$)$_6$CH=CH(CH$_2$)CH=CH(CH$_2$)CH=CHC$_2$H$_5$ | 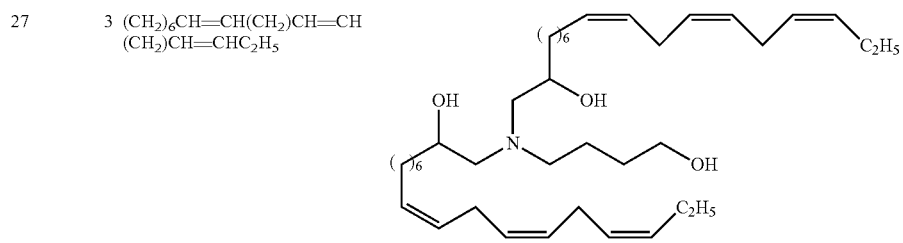 |
| 28 | 1 | C$_7$H$_{14}$O(CO)C$_7$H$_{15}$ | 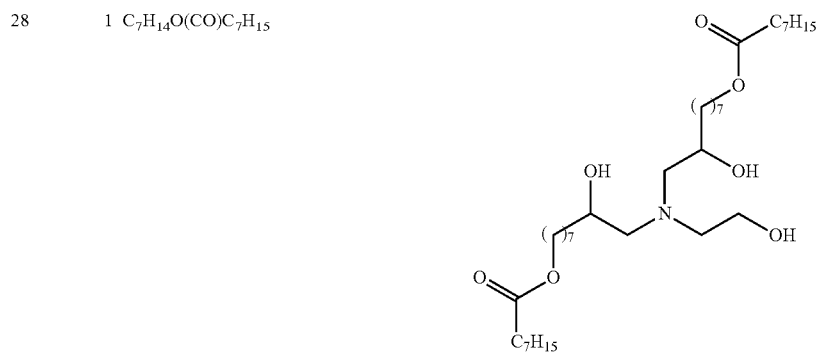 |
| 29 | 2 | C$_7$H$_{14}$O(CO)C$_7$H$_{15}$ | 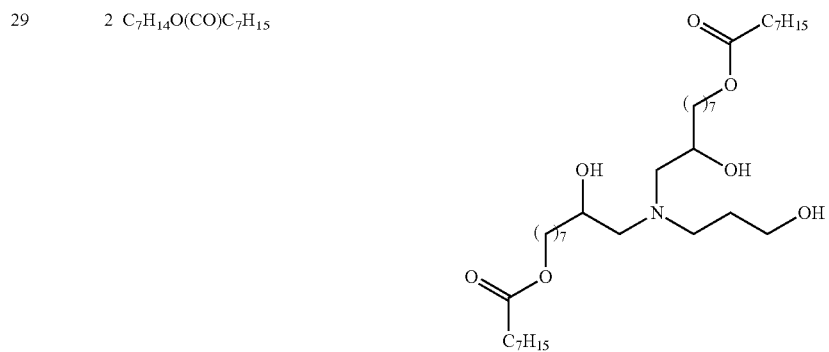 |
| 30 | 3 | C$_7$H$_{14}$O(CO)C$_7$H$_{15}$ | 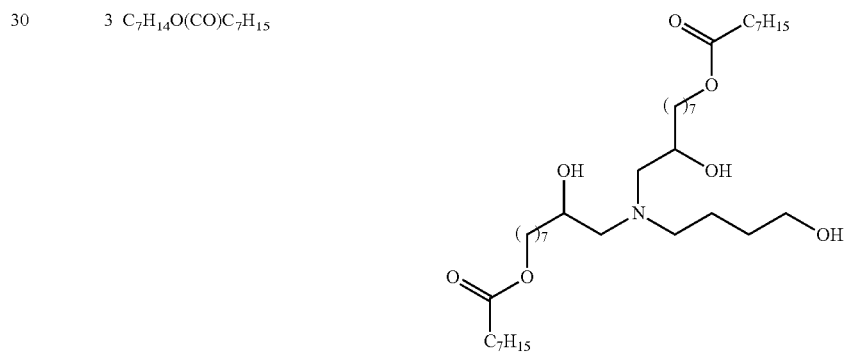 |

TABLE 10h-continued
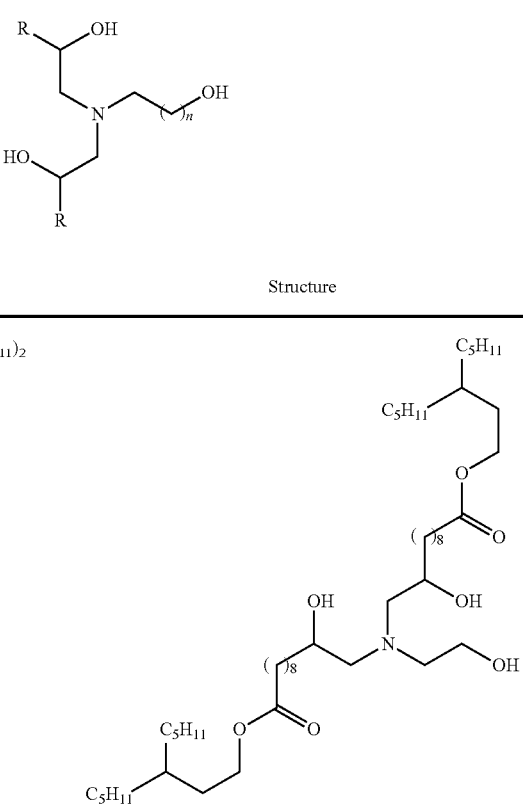
| Compound | n | R | Structure |
|---|---|---|---|
| 31 | 1 | C$_8$H$_{16}$C(O)O(CH$_2$)$_2$CH(C$_5$H$_{11}$)$_2$ | 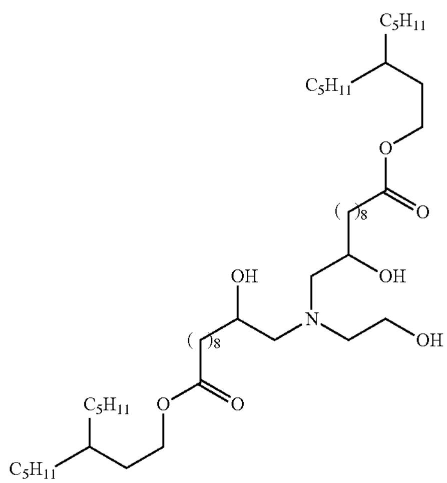 |
| 32 | 2 | C$_8$H$_{16}$C(O)O(CH$_2$)$_2$CH(C$_5$H$_{11}$)$_2$ | 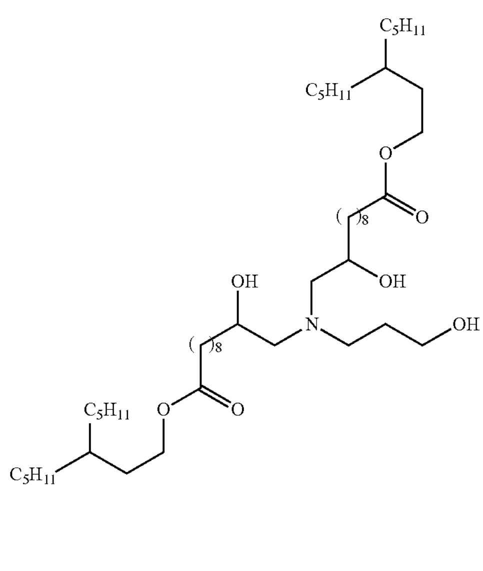 |
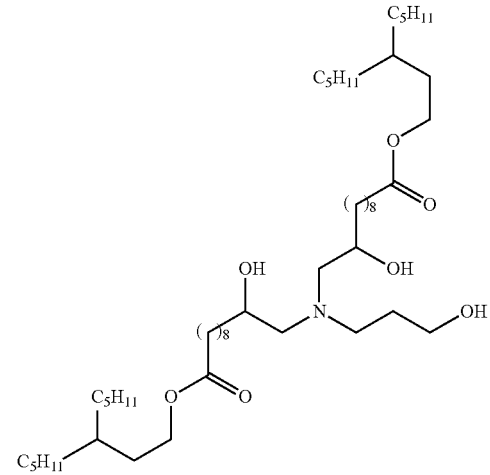

TABLE 10h-continued

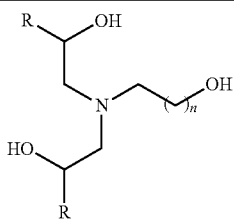

| Compound | n | R | Structure |
|---|---|---|---|
| 33 | 3 | C8H16C(O)O(CH2)2CH(C5H11)2 | 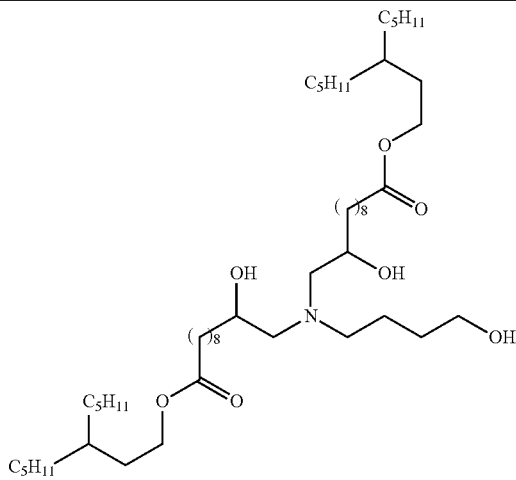 |

5.1 Other Ionizable Lipids

In some embodiments, one or more (e.g., two or more, or three or more) ionizable lipids are utilized in the transfer vehicles of this disclosure. In some embodiments, the transfer vehicle includes a first ionizable lipid (e.g., as described herein, such as a lipid of Formula (13*) or (14*)), and one or more additional ionizable lipids.

Lipids of interest, including ionizable lipids that can be used in combination with a first ionizable lipid as described herein, such as by being incorporated into the transfer vehicles of this disclosure, include, but are not limited to, lipids as described in: international application PCT/US2018/058555, international application PCT/US2020/038678, US publication US2019/0314524, WO2019/152848, international application PCT/US2010/061058, international application PCT/US2017/028981, WO2015/095340, WO2014/136086, US2019/0321489, WO2010/053572, U.S. provisional patent application 61/617,468, international patent application PCT/US2019/025246, US patent publications 2017/0190661 and 2017/0114010, US publication 20190314284, WO2015/095340, WO2019/152557, WO2019/152848, international application PCT/US2019/015913, U.S. Pat. Nos. 9,708,628, 9,765,022; Wang et al., ACS Synthetic Biology, 1, 403-07 (2012); WO 2008/042973, U.S. Pat. No. 8,071,082, the disclosures of which are incorporated herein by reference in their entirety.

In some embodiments, tail groups as used in the lipids may be as described in. WO2015/095340, WO2019/152557, and WO2019/152848, the disclosures of which are incorporated herein by reference in their entirety.

The lipid-like compounds can be prepared by methods well known in the art. See

In some embodiments, the ionizable lipid N-[1-(2,3-dioleyloxy)propyl]-N,N,N-trimethylammonium chloride or "DOTMA" is used. (Felgner et al. Proc. Nat'l Acad. Sci. 84, 7413 (1987); U.S. Pat. No. 4,897,355). DOTMA can be formulated with an ionizable lipid (e.g., as described herein), and/or can be combined with a neutral lipid, dioleoylphosphatidylethanolamine or "DOPE" or other cationic or non-cationic lipids into a lipid nanoparticle.

Other suitable lipids include, for example, ionizable cationic lipids, such as, e.g., (15Z,18Z)—N,N-dimethyl-6-(9Z,12Z)-octadeca-9,12-dien-1-yl)tetracosa-15,18-dien-1-amine (HGT5000), (15Z,18Z)—N,N-dimethyl-6-((9Z,12Z)-octadeca-9,12-dien-1-yl)tetracosa-4,15,18-trien-1-amine (HGT5001), and (15Z,18Z)—N,N-dimethyl-6-((9Z,12Z)-octadeca-9,12-dien-1-yl)tetracosa-5,15,18-trien-1-amine (HGT5002), C12-200 (described in WO 2010/053572), 2-(2,2-di((9Z,12Z)-octadeca-9,12-dien-1-yl)-1,3-dioxolan-4-yl)-N,N-dimethylethanamine (DLinKC2-DMA)) (See, WO 2010/042877; Semple et al., Nature Biotech. 28:172-176 (2010)), 2-(2,2-di((9Z,2Z)-octadeca-9,12-dien-1-yl)-1,3-dioxolan-4-yl)-N,N-dimethylethanamine (DLin-KC2-DMA), (3S,10R,13R,17R)-10,13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate (ICE), (15Z,18Z)—N,N-dimethyl-6-(9Z,12Z)-octadeca-9,12-dien-1-yl)tetracosa-15,18-dien-1-amine (HGT5000), (15Z,18Z)—N,N-dimethyl-6-((9Z,12Z)-octadeca-9,12-dien-1-yl)tetracosa-4,15,18-trien-1-amine (HGT5001), (15Z,18 Z)—N,N-dimethyl-6-((9Z,12Z)-octadeca-9,12-dien-1-yl)tetracosa-5,15,18-trien-1-amine (HGT5002), 5-carboxyspermylglycine-dioctadecylamide (DOGS), 2,3-dioleyloxy-N-[2(spermine-carboxamido)ethyl]-N,N-dimethyl-1-propanaminium (DOSPA) (Behr et al. Proc. Nat.'l Acad. Sci. 86, 6982 (1989); U.S. Pat. Nos. 5,171,678; 5,334,761), 1,2-Dioleyl-3-Dimethylammonium-Propane (DODAP), 1,2-Dioleoyl-3-

Trimethylammonium-Propane or (DOTAP). Contemplated ionizable lipids also include 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA), N-dioleyl-N,N-dimethylammonium chloride (DODAC), N,N-distearyl-N,N-dimethylammonium bromide (DDAB), N-(1,2-dimyristyloxyprop-3-yl)-N,N-dimethyl-N-hydroxyethyl ammonium bromide (DMRIE), 3-dimethylamino-2-(cholest-5-end-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylamninopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA) or GL67, or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). The use of cholesterol-based ionizable lipids to formulate the transfer vehicles (e.g., lipid nanoparticles) is also contemplated by the present invention. Such cholesterol-based ionizable lipids can be used, either alone or in combination with other lipids. Suitable cholesterol-based ionizable lipids include, for example, DC-Cholesterol (N,N-dimethyl-N-ethylcarboxamidocholesterol), and 1,4-bis(3-N-oleylamino-propyl)piperazine (Gao, et al., Biochem. Biophys. Res. Comm. 179, 280 (1991); Wolf et al. BioTechniques 23, 139 (1997); U.S. Pat. No. 5,744,335).

Also contemplated are cationic lipids such as dialkylamino-based, imidazole-based, and guanidinium-based lipids. For example, also contemplated is the use of the ionizable lipid (3S,10R, 13R, 17R)-10,13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate (ICE), as disclosed in International Application No. PCT/US2010/058457, incorporated herein by reference.

Also contemplated are ionizable lipids such as the dialkylamino-based, imidazole-based, and guanidinium-based lipids. For example, certain embodiments are directed to a composition comprising one or more imidazole-based ionizable lipids, for example, the imidazole cholesterol ester or "ICE" lipid, (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate.

Without wishing to be bound by a particular theory, it is believed that the fusogenicity of the imidazole-based cationic lipid ICE is related to the endosomal disruption which is facilitated by the imidazole group, which has a lower pKa relative to traditional ionizable lipids. The endosomal disruption in turn promotes osmotic swelling and the disruption of the liposomal membrane, followed by the transfection or intracellular release of the nucleic acid(s) contents loaded therein into the target cell.

The imidazole-based ionizable lipids are also characterized by their reduced toxicity relative to other ionizable lipids.

In certain embodiments, transfer vehicle compositions for the delivery of circular RNA comprise an amine lipid. In certain embodiments, an ionizable lipid is an amine lipid. In some embodiments, an amine lipid is described in international patent application PCT/US2018/053569.

In some embodiments, the amine lipid is Lipid E, which is (9Z, 12Z)-3-((4,4-bis(octyloxy)butanoyl)oxy)-2-((((3-(diethylamino)propoxy)carbonyl)oxy)methyl)propyl octadeca-9, 12-dienoate.

In certain embodiments, an amine lipid is an analog of Lipid E. In certain embodiments, a Lipid E analog is an acetal analog of Lipid E. In particular transfer vehicle compositions, the acetal analog is a C4-C12 acetal analog. In some embodiments, the acetal analog is a C5-C12 acetal analog. In additional embodiments, the acetal analog is a C5-C10 acetal analog. In further embodiments, the acetal analog is chosen from a C4, C5, C6, C7, C9, C10, C11 and C12 acetal analog.

Amine lipids and other biodegradable lipids suitable for use in the transfer vehicles, e.g., lipid nanoparticles, described herein are biodegradable in vivo. The amine lipids described herein have low toxicity (e.g., are tolerated in animal models without adverse effect in amounts of greater than or equal to 10 mg/kg). In certain embodiments, transfer vehicles composing an amine lipid include those where at least 75% of the amine lipid is cleared from the plasma within 8, 10, 12, 24, or 48 hours, or 3, 4, 5, 6, 7, or 10 days.

Biodegradable lipids include, for example, the biodegradable lipids of WO2017/173054, WO2015/095340, and WO2014/136086.

Lipid clearance may be measured by methods known by persons of skill in the art. See, for example, Maier, M. A., et al. Biodegradable Lipids Enabling Rapidly Eliminated Lipid Nanoparticles for Systemic Delivery of RNAi Therapeutics. Mol. Ther. 2013, 21(8), 1570-78.

Transfer vehicle compositions comprising an amine lipid can lead to an increased clearance rate. In some embodiments, the clearance rate is a lipid clearance rate, for example the rate at which a lipid is cleared from the blood, serum, or plasma. In some embodiments, the clearance rate is an RNA clearance rate, for example the rate at which an circRNA is cleared from the blood, serum, or plasma. In some embodiments, the clearance rate is the rate at which transfer vehicles are cleared from the blood, serum, or plasma. In some embodiments, the clearance rate is the rate at which transfer vehicles are cleared from a tissue, such as liver tissue or spleen tissue. In certain embodiments, a high rate of clearance leads to a safety profile with no substantial adverse effects. The amine lipids and biodegradable lipids may reduce transfer vehicle accumulation in circulation and in tissues. In some embodiments, a reduction in transfer vehicle accumulation in circulation and in tissues leads to a safety profile with no substantial adverse effects.

Lipids may be ionizable depending upon the pH of the medium they are in. For example, in a slightly acidic medium, the lipid, such as an amine lipid, may be protonated and thus bear a positive charge. Conversely, in a slightly basic medium, such as, for example, blood, where pH is approximately 7.35, the lipid, such as an amine lipid, may not be protonated and thus bear no charge.

The ability of a lipid to bear a charge is related to its intrinsic pKa. In some embodiments, the amine lipids of the present disclosure may each, independently, have a pKa in the range of from about 5.1 to about 7.4. In some embodiments, the bioavailable lipids of the present disclosure may each, independently, have a pKa in the range of from about 5.1 to about 7.4. For example, the amine lipids of the present disclosure may each, independently, have a pKa in the range of from about 5.8 to about 6.5. Lipids with a pKa ranging from about 5.1 to about 7.4 are effective for delivery of cargo in vivo, e.g., to the liver. Further, it has been found that lipids with a pKa ranging from about 5.3 to about 6.4 are effective for delivery in vivo, e.g., into tumors. See, e.g., WO2014/136086.

A lipid of the present disclosure may have an —S—S (disulfide) bond.

Lipid-like compounds of this disclosure can be prepared using suitable starting materials through synthetic route known in the art. The method can include an additional step(s) to add or remove suitable protecting groups in order to ultimately allow synthesis of the lipid-like compounds. In addition, various synthetic steps can be performed in an alternate sequence or order to give the desired material. Synthetic chemistry transformations and protecting group methodologies (protection and deprotection) useful in synthesizing applicable lipid-like compounds are known in the art, including, for example, R. Larock, Comprehensive Organic Transformations (2nd Ed., VCH Publishers 1999); P. G. M. Wuts and T. W. Greene, Greene's Protective Groups in Organic Synthesis (4th Ed., John Wiley and Sons 2007); L. Fieser and M. Fieser, Fieser and Fieser's Reagents for Organic Synthesis (John Wiley and Sons 1994); and L. Paquette, ed., Encyclopedia of Reagents for Organic Synthesis (2nd ed., John Wiley and Sons 2009) and subsequent editions thereof. Certain lipid-like compounds may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Preparation methods for the above compounds and compositions are described herein below and/or known in the art.

It will be appreciated by those skilled in the art that in the process described herein the functional groups of intermediate compounds may need to be protected by suitable protecting groups. Such functional groups include, e.g., hydroxyl, amino, mercapto, and carboxylic acid. Suitable protecting groups for hydroxyl include, e.g., trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino, and guanidino include, e.g., t-butoxycarbonyl, benzyloxycarbonyl, and the like. Suitable protecting groups for mercapto include, e.g., —C(O)—R" (where R" is alkyl, aryl, or arylalkyl), p-methoxybenzyl, trityl, and the like. Suitable protecting groups for carboxylic acid include, e.g., alkyl, aryl, or arylalkyl esters. Protecting groups may be added or removed in accordance with standard techniques, which are known to one skilled in the art and as described herein. The use of protecting groups is described in detail in, e.g., Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin, or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as prodrugs. All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can also be converted to their free base or acid form by standard techniques.

It is understood that one skilled in the art may be able to make these compounds by similar methods or by combining other methods known to one skilled in the art. It is also understood that one skilled in the art would be able to make other compounds of Formula (1) not specifically illustrated herein by using the appropriate starting materials and modifying the parameters of the synthesis. In general, starting materials may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention.

As mentioned above, these lipid-like compounds are useful for delivery of pharmaceutical agents. They can be preliminarily screened for their efficacy in delivering pharmaceutical agents by an in vitro assay and then confirmed by animal experiments and clinic trials. Other methods will also be apparent to those of ordinary skill in the art.

Not to be bound by any theory, the lipid-like compounds of this disclosure can facilitate delivery of pharmaceutical agents by forming complexes, e.g., nanocomplexes and microparticles. The hydrophilic head of such a lipid-like compound, positively or negatively charged, binds to a moiety of a pharmaceutical agent that is oppositely charged and its hydrophobic moiety binds to a hydrophobic moiety of the pharmaceutical agent. Either binding can be covalent or non-covalent.

The above described complexes can be prepared using procedures described in publications such as Wang et al., ACS Synthetic Biology, 1, 403-07 (2012). Generally, they are obtained by incubating a lipid-like compound and a pharmaceutical agent in a buffer such as a sodium acetate buffer or a phosphate buffered saline ("PBS").

5.2 Hydrophilic Groups

In certain embodiments, the selected hydrophilic functional group or moiety may alter or otherwise impart properties to the compound or to the transfer vehicle of which such compound is a component (e.g., by improving the transfection efficiencies of a lipid nanoparticle of which the compound is a component). For example, the incorporation of guanidinium as a hydrophilic head-group in the compounds disclosed herein may promote the fusogenicity of such compounds (or of the transfer vehicle of which such compounds are a component) with the cell membrane of one or more target cells, thereby enhancing, for example, the transfection efficiencies of such compounds. It has been hypothesized that the nitrogen from the hydrophilic guanidinium moiety forms a six-membered ring transition state which grants stability to the interaction and thus allows for cellular uptake of encapsulated materials. (Wender, et al., Adv. Drug Del. Rev. (2008) 60: 452-472.) Similarly, the incorporation of one or more amino groups or moieties into the disclosed compounds (e.g., as a head-group) may further promote disruption of the endosomal/lysosomal membrane of the target cell by exploiting the fusogenicity of such amino groups. This is based not only on the pKa of the amino group of the composition, but also on the ability of the amino group to undergo a hexagonal phase transition and fuse with the target cell surface, i.e. the vesicle membrane. (Koltover, et al. Science (1998) 281: 78-81.) The result is believed to promote the disruption of the vesicle membrane and release of the lipid nanoparticle contents into the target cell.

Similarly, in certain embodiments the incorporation of, for example, imidazole as a hydrophilic head-group in the compounds disclosed herein may serve to promote endosomal or lysosomal release of, for example, contents that are encapsulated in a transfer vehicle (e.g., lipid nanoparticle) of the invention. Such enhanced release may be achieved by one or both of a proton-sponge mediated disruption mechanism and/or an enhanced fusogenicity mechanism. The proton-sponge mechanism is based on the ability of a compound, and in particular a functional moiety or group of the compound, to buffer the acidification of the endosome. This may be manipulated or otherwise controlled by the pKa of the compound or of one or more of the functional groups comprising such compound (e.g., imidazole). Accordingly, in certain embodiments the fusogenicity of, for example, the imidazole-based compounds disclosed herein (e.g., HGT4001 and HGT4004) are related to the endosomal disruption properties, which are facilitated by such imidazole groups, which have a lower pKa relative to other traditional ionizable lipids. Such endosomal disruption properties in turn promote osmotic swelling and the disruption of the liposomal membrane, followed by the transfection or intracellular release of the polynucleotide materials loaded or encapsulated therein into the target cell. This phenomenon can be applicable to a variety of compounds with desirable pKa profiles in addition to an imidazole moiety. Such embodiments also include multi-nitrogen based functionalities such as polyamines, poly-peptide (histidine), and nitrogen-based dendritic structures.

Exemplary ionizable and/or cationic lipids are described in International PCT patent publications WO2015/095340, WO2015/199952, WO2018/011633, WO2017/049245, WO2015/061467, WO2012/040184, WO2012/000104, WO2015/074085, WO2016/081029, WO2017/004 143, WO2017/075531, WO2017/117528, WO2011/022460, WO2013/148541, WO2013/116126, WO2011/153120, WO2012/044638, WO2012/054365, WO2011/090965, WO2013/016058, WO2012/162210, WO2008/042973, WO2010/129709, WO2010/144740, WO2012/099755, WO2013/049328, WO2013/086322, WO2013/086373, WO2011/071860, WO2009/132131, WO2010/048536, WO2010/088537, WO2010/054401, WO2010/054406, WO2010/054405, WO2010/054384, WO2012/016184, WO2009/086558, WO2010/042877, WO2011/000106, WO2011/000107, WO2005/120152, WO2011/141705, WO2013/126803, WO2006/007712, WO2011/038160, WO2005/121348, WO2011/066651, WO2009/127060, WO2011/141704, WO2006/069782, WO2012/031043, WO2013/006825, WO2013/033563, WO2013/089151, WO2017/099823, WO2015/095346, and WO2013/086354, and US patent publications US2016/0311759, US2015/0376115, US2016/0151284, US2017/0210697, US2015/0140070, US2013/0178541, US2013/0303587, US2015/0141678, US2015/0239926, US2016/0376224, US2017/0119904, US2012/0149894, US2015/0057373, US2013/0090372, US2013/0274523, US2013/0274504, US2013/0274504, US2009/0023673, US2012/0128760, US2010/0324120, US2014/0200257, US2015/0203446, US2018/0005363, US2014/0308304, US2013/0338210, US2012/0101148, US2012/0027796, US2012/0058144, US2013/0323269, US2011/0117125, US2011/0256175, US2012/0202871, US2011/0076335, US2006/0083780, US2013/0123338, US2015/0064242, US2006/0051405, US2013/0065939, US2006/0008910, US2003/0022649, US2010/0130588, US2013/0116307, US2010/0062967, US2013/0202684, US2014/0141070, US2014/0255472, US2014/0039032, US2018/0028664, US2016/0317458, and US2013/0195920, the contents of all of which are incorporated herein by reference in their entirety. International patent application WO 2019/131770 is also incorporated herein by reference in its entirety.

B. Peg Lipids

The use and inclusion of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) in the liposomal and pharmaceutical compositions described herein is contemplated, preferably in combination with one or more of the compounds and lipids disclosed herein. Contemplated PEG-modified lipids include, but are not limited to, a polyethylene glycol chain of up to 5 kDa in length covalently attached to a lipid with alkyl chain(s) of C6-C20 length. In some embodiments, the PEG-modified lipid employed in the compositions and methods of the invention is 1,2-dimyristoyl-sn-glycerol, methoxypolyethylene Glycol (2000 MW PEG) "DMG-PEG2000." The addition of PEG-modified lipids to the lipid delivery vehicle may prevent complex aggregation and may also provide a means for increasing circulation lifetime and increasing the delivery of the lipid-polynucleotide composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in a liposomal lipid nanoparticle.

In an embodiment, a PEG-modified lipid is described in International Pat. Appl. No. PCT/US2019/015913 or PCT/US2020/046407, which are incorporated herein by reference in their entirety. In an embodiment, a transfer vehicle comprises one or more PEG-modified lipids.

Non-limiting examples of PEG-modified lipids include PEG-modified phosphatidylethanolamines and phosphatidic acids, PEG-ceramide conjugates (e.g., PEG-CerC14 or PEG-CerC20), PEG-modified dialkylamines and PEG-modified 1,2-diacyloxypropan-3-amines. In some further embodiments, a PEG-modified lipid may be, e.g., PEG-c-DOMG, PEG-DMG, PEG-DLPE, PEG-DMPE, PEG-DPPC, or a PEG-DSPE.

In some still further embodiments, the PEG-modified lipid includes, but is not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), PEG-1,2-dimyristyloxlpropyl-3-amine (PEG-c-DMA).

In some still further embodiments, the PEG-modified lipid is DSPE-PEG, DMG-PEG, PEG-DAG, PEG-S-DAG, PEG-PE, PEG-S-DMG, PEG-cer, PEG-dialkoxypropylcarbamate, PEG-OR, PEG-OH, PEG-c-DOMG, or PEG-1. In some embodiments, the PEG-modified lipid is DSPE-PEG (2000).

In some embodiments, the PEG-modified lipid comprises a PEG moiety comprising 10-70 (e.g., 30-60) oxyethylene ($-O-CH_2-CH_2-$) units or portions thereof. In some embodiments, the PEG-modified lipid comprises (OCH$_2$CH$_2$)$_v$—OR$_w$, and v is an integer between 0 and 70 (inclusive) (e.g., an integer between 30 and 60), w is hydrogen or alkyl.

In various embodiments, a PEG-modified lipid may also be referred to as "PEGylated lipid" or "PEG-lipid."

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about C$_{14}$ to about C$_{22}$, such as from about C$_{14}$ to about C$_{16}$. In some embodiments, a PEG moiety, for example a mPEG-NH$_2$, has a size of about 1000, about 2000, about 5000, about 10,000, about 15,000 or about 20,000 daltons. In one embodiment, the PEG-lipid is PEG2k-DMG.

In one embodiment, the lipid nanoparticles described herein can comprise a lipid modified with a non-diffusible PEG. Non-limiting examples of non-diffusible PEGs include PEG-DSG and PEG-DSPE.

PEG-lipids are known in the art, such as those described in U.S. Pat. No. 8,158,601 and International Pat. Publ. No. WO2015/130584 A2, which are incorporated herein by reference in their entirety.

In various embodiments, lipids (e.g., PEG-lipids), described herein may be synthesized as described International Pat. Publ. No. PCT/US2016/000129, which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG-DMG. PEG-DMG has the following structure:

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In some embodiments, the PEG lipid is a compound of Formula (P1):

(P1)

or a salt or isomer thereof, wherein:
r is an integer between 1 and 100;
R is C$_{10-40}$ alkyl, C$_{10-40}$ alkenyl, or C$_{10-40}$ alkynyl; and optionally one or more methylene groups of R are independently replaced with C$_{3-10}$ carbocyclylene, 4 to 10 membered heterocyclylene, C$_{6-10}$ arylene, 4 to 10 membered heteroarylene, —N(R$^N$)—, —O—, —S—, —C(O)—, —C(O)N(R$^N$)—, —NR$^N$C(O)—, —NR$^N$C(O)N(R$^N$)—, —C(O)O—, —OC(O)O—, —OC(O)N(R$^N$)—, —NR$^N$C(O)O—, —C(O)S—, —SC(O)—, —C(=NR$^N$)—, —C(=NR$^N$)N(R$^N$)—, —NR$^N$C(=NR$^N$)—, —NR$^N$C(=NR$^N$)N(R$^N$)—, —C(S)—, —C(S)N(R$^N$)—, —NR$^N$C(S)—NR$^N$C(S)N(R$^N$)—, —S(O)—, —OS(O)—, —S(O)O—, —OS(O)O—, —OS(O)$_2$—, —S(O)$_2$O—, —OS(O)$_2$O—, —N(R$^N$)S(O)—, —S(O)N(R$^N$)—, —N(R$^N$)S(O)N(R$^N$)—, —OS(O)N(R$^N$)—, —N(R$^N$)S(O)O—, —S(O)$_2$—, —N(R$^N$)S(O)$_2$—, —S(O)$_2$N(R$^N$)—, —N(R$^N$)S(O)$_2$N(R$^N$)—, —OS(O)$_2$N(R$^N$)—, or —N(R$^N$)S(O)$_2$O—; and each instance of R$^N$ is independently hydrogen, C$_{1-6}$ alkyl, or a nitrogen protecting group.

For example, R is C17 alkyl. For example, the PEG lipid is a compound of Formula (P1-a):

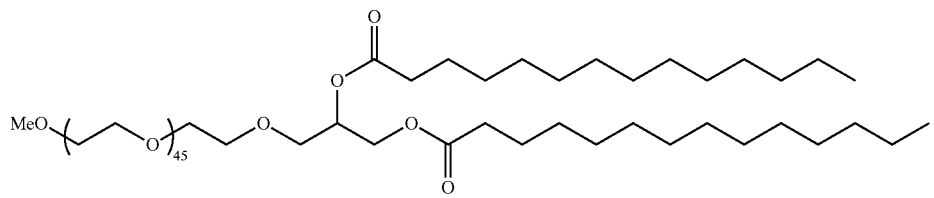

In some embodiments the PEG-modified lipids are a modified form of PEG-C18, or PEG-1. PEG-1 has the following structure

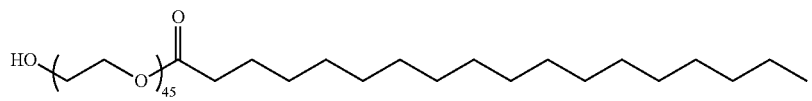

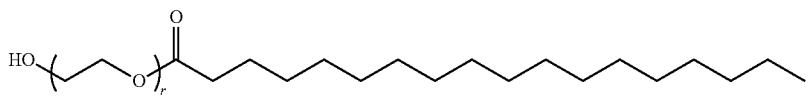

or a salt or isomer thereof, wherein r is an integer between 1 and 100.

For example, the PEG lipid is a compound of the following formula:

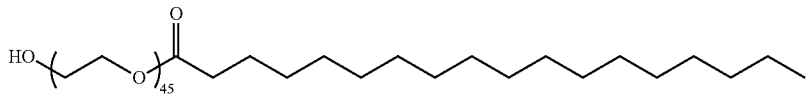

C. Helper Lipids

In some embodiments, the transfer vehicle (e.g., LNP) described herein comprises one or more non-cationic helper lipids. In some embodiments, the helper lipid is a phospholipid. In some embodiments, the helper lipid is a phospholipid substitute or replacement. In some embodiments, the phospholipid or phospholipid substitute can be, for example, one or more saturated or (poly)unsaturated phospholipids, or phospholipid substitutes, or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, the helper lipid is a 1,2-distearoyl-177-glycero-3-phosphocholine (DSPC) analog, a DSPC substitute, oleic acid, or an oleic acid analog.

In some embodiments, a helper lipid is a non-phosphatidyl choline (PC) zwitterionic lipid, a DSPC analog, oleic acid, an oleic acid analog, or a DSPC substitute.

In some embodiments, a helper lipid is described in PCT/US2018/053569. Helper lipids suitable for use in a lipid composition of the disclosure include, for example, a variety of neutral, uncharged or zwitterionic lipids. Such helper lipids are preferably used in combination with one or more of the compounds and lipids disclosed herein. Examples of helper lipids include, but are not limited to, 5-heptadecylbenzene-1,3-diol (resorcinol), dipalmitoylphosphatidylcholine (DPPC), distearoylphosphatidylcholine (DSPC), dioleoylphosphatidylcholine (DOPC), dimyristoylphosphatidylcholine (DMPC), phosphatidylcholine (PLPC), 1,2-distearoylsn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-paimitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), paimitoyioieoyl phosphatidylcholine (POPC), lysophosphatidyl choline, dioleoyl phosphatidylethanol amine (DOPE) dilinoleoylphosphatidylcholine distearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lyso-phosphatidylethanolamine and combinations thereof. In one embodiment, the helper lipid may be distearoylphosphatidylcholine (DSPC) or dimyristoyl phosphatidyl ethanolamine (DMPE). In another embodiment, the helper lipid may be distearoylphosphatidylcholine (DSPC). Helper lipids function to stabilize and improve processing of the transfer vehicles. Such helper lipids are preferably used in combination with other excipients, for example, one or more of the ionizable lipids disclosed herein. In some embodiments, when used in combination with an ionizable lipid, the helper lipid may comprise a molar ratio of 5% to about 90%, or about 10% to about 70% of the total lipid present in the lipid nanoparticle.

D. Structural Lipids

In an embodiment, a structural lipid is described in international patent application PCT/US2019/015913.

The transfer vehicles described herein comprise one or more structural lipids. Incorporation of structural lipids in the lipid nanoparticle may help mitigate aggregation of other lipids in the particle. Structural lipids can include, but are not limited to, cholesterol, fecosterol, ergosterol, bassicasterol, tomatidine, tomatine, ursolic, alpha-tocopherol, and mixtures thereof. In certain embodiments, the structural lipid is cholesterol. In certain embodiments, the structural lipid includes cholesterol and a corticosteroid (such as, for example, prednisolone, dexamethasone, prednisone, and hydrocortisone), or a combination thereof.

In some embodiments, the structural lipid is a sterol. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

The transfer vehicles described herein comprise one or more structural lipids. Incorporation of structural lipids in a transfer vehicle, e.g., a lipid nanoparticle, may help mitigate aggregation of other lipids in the particle. In certain embodiments, the structural lipid includes cholesterol and a corticosteroid (such as, for example, prednisolone, dexamethasone, prednisone, and hydrocortisone), or a combination thereof.

In some embodiments, the structural lipid is a sterol. Structural lipids can include, but are not limited to, sterols (e.g., phytosterols or zoosterols).

In certain embodiments, the structural lipid is a steroid. For example, sterols can include, but are not limited to, cholesterol, β-sitosterol, fecosterol, ergosterol, sitosterol, campesterol, stigmasterol, brassicasterol, ergosterol, tomatidine, tomatine, ursolic acid, or alpha-tocopherol.

In some embodiments, a transfer vehicle includes an effective amount of an immune cell delivery potentiating lipid, e.g., a cholesterol analog or an amino lipid or combination thereof, that, when present in a transfer vehicle, e.g., an lipid nanoparticle, may function by enhancing cellular association and/or uptake, internalization, intracellular trafficking and/or processing, and/or endosomal escape and/or may enhance recognition by and/or binding to immune cells, relative to a transfer vehicle lacking the immune cell delivery potentiating lipid. Accordingly, while not intending to be bound by any particular mechanism or theory, in one embodiment, a structural lipid or other immune cell delivery potentiating lipid of the disclosure binds to C1q or promotes the binding of a transfer vehicle comprising such lipid to C1q. Thus, for in vitro use of the transfer vehicles of the disclosure for delivery of a nucleic acid molecule to an immune cell, culture conditions that include C1q are used (e.g., use of culture media that includes serum or addition of exogenous C1q to serum-free media). For in vivo use of the transfer vehicles of the disclosure, the requirement for C1q is supplied by endogenous C1q.

In certain embodiments, the structural lipid is cholesterol. In certain embodiments, the structural lipid is an analog of cholesterol. In some embodiments, the structural lipid is a lipid

TABLE 16

| CMPD No. S- | Structure |
|---|---|
| 1 | 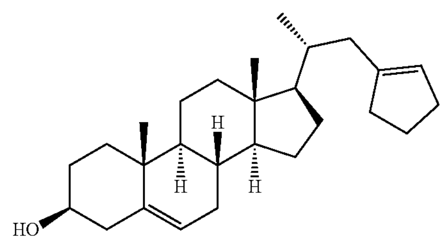 |
| 22 | 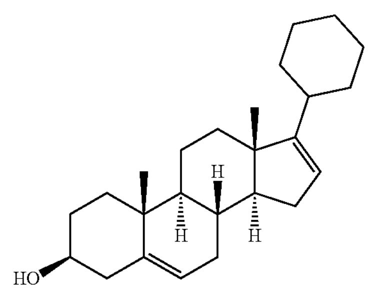 |
| 2 | 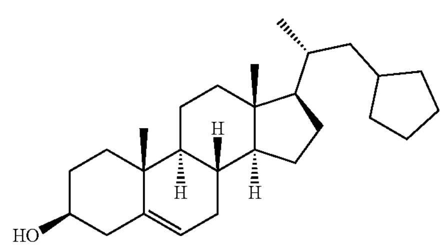 |
| 3 | 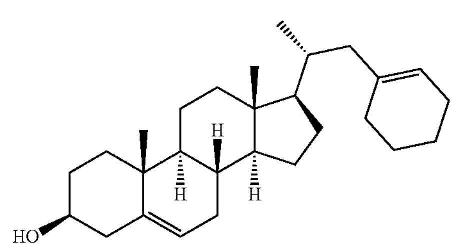 |

TABLE 16-continued
4
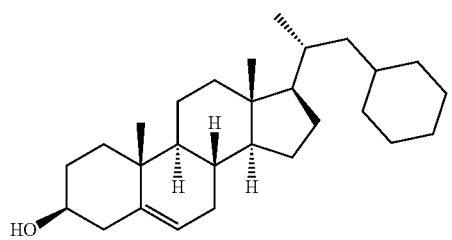
5
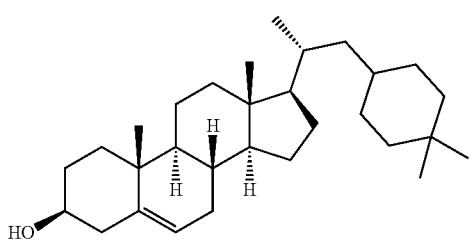
6
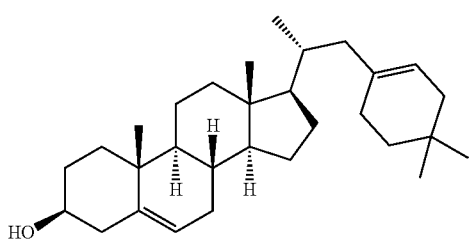
7
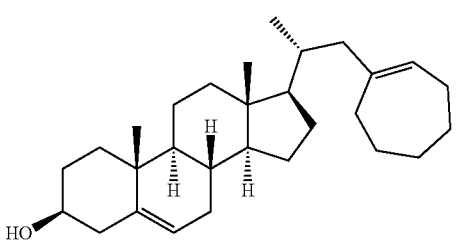
23
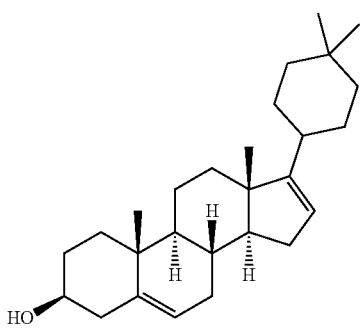
24
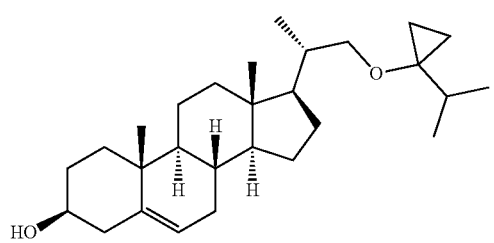

TABLE 16-continued
25 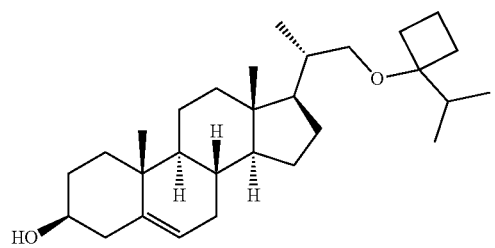
26 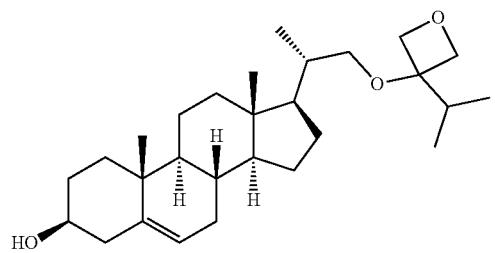
27 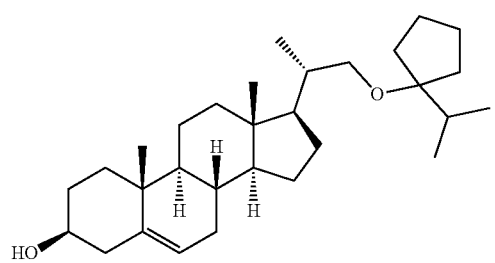
28 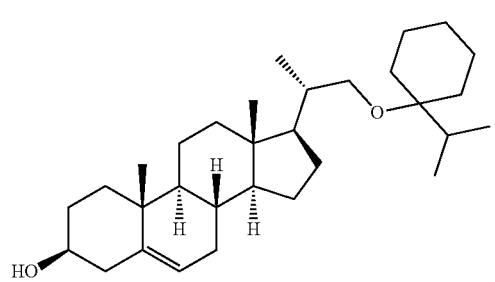
8 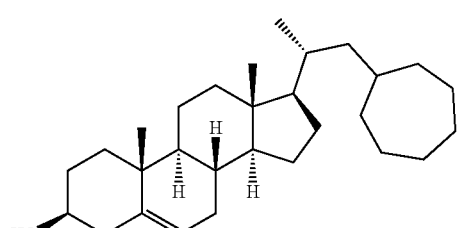
9 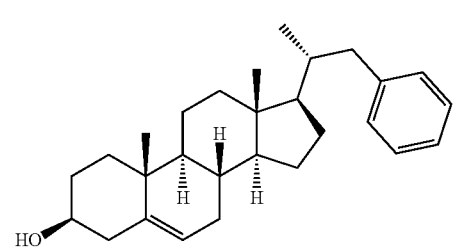

TABLE 16-continued
10
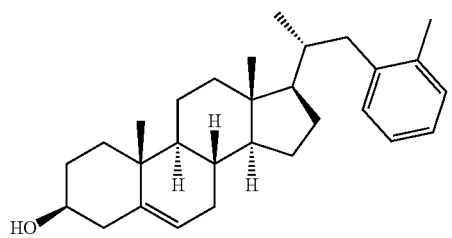
11
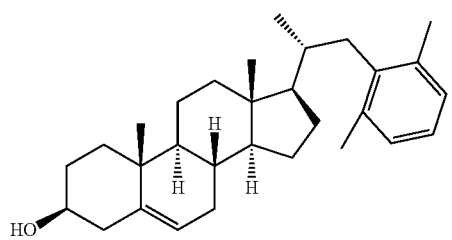
12
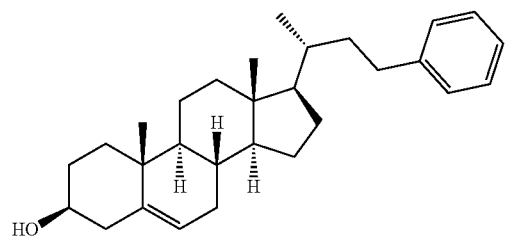
13
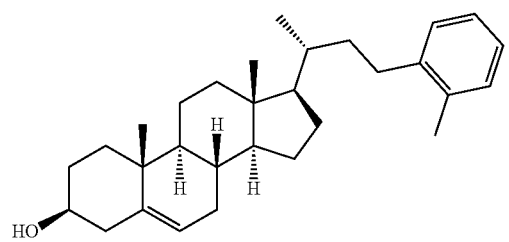
29
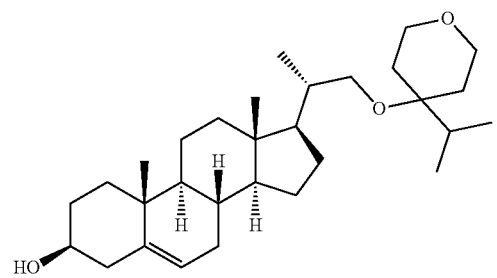
30
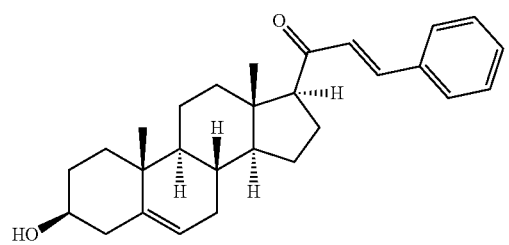

TABLE 16-continued
31 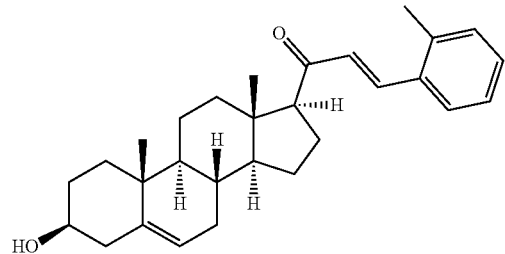
32 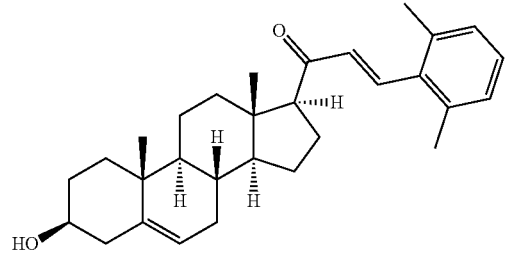
33 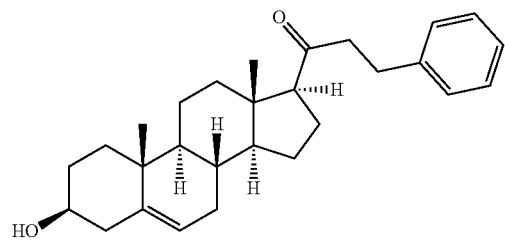
34 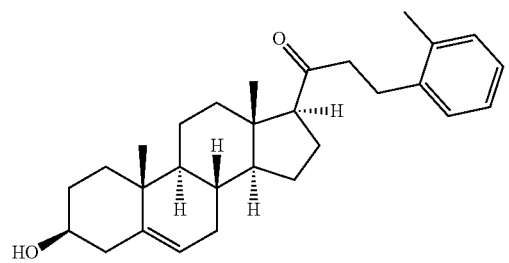
14 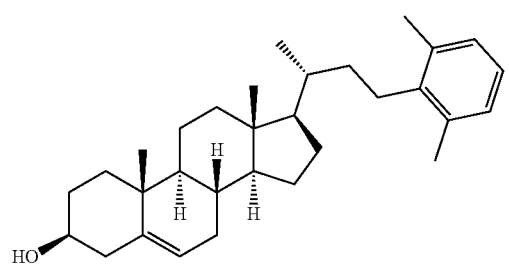
15 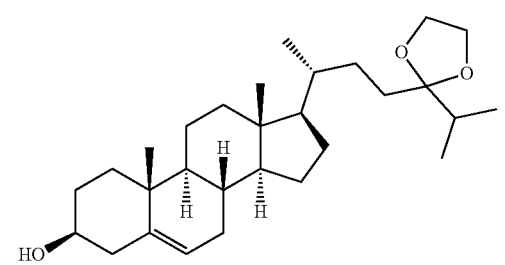

TABLE 16-continued
16 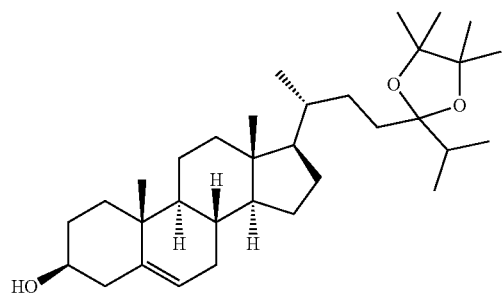
17 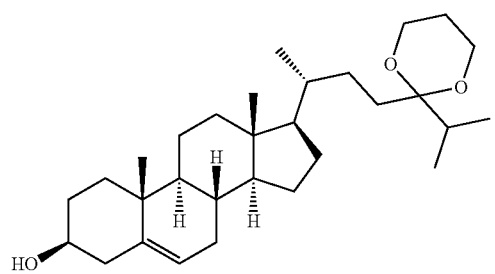
18 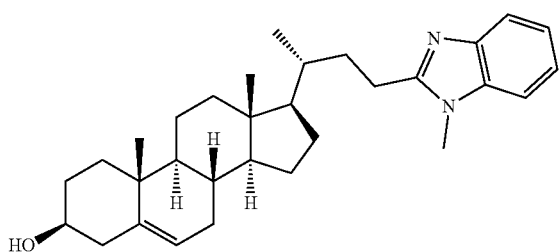
19 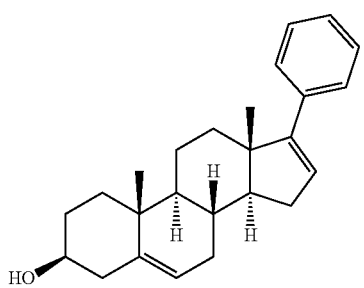
35 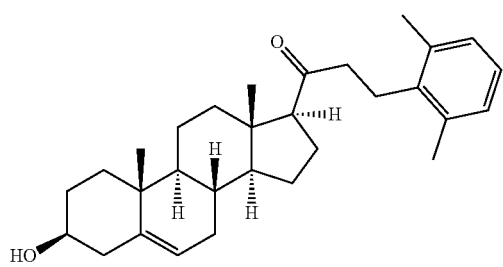
36 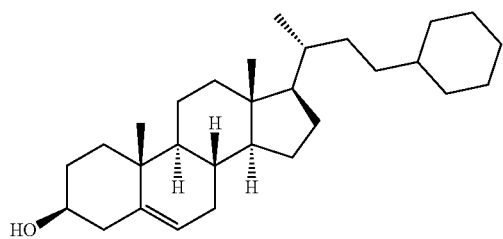

TABLE 16-continued
37
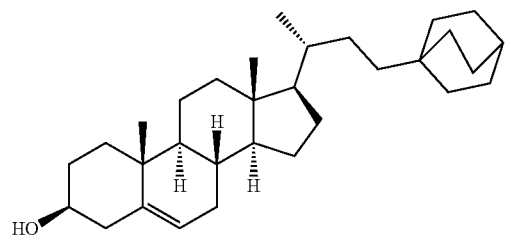
38
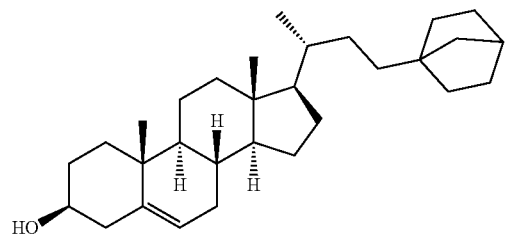
39
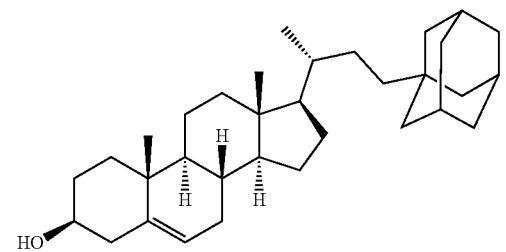
40
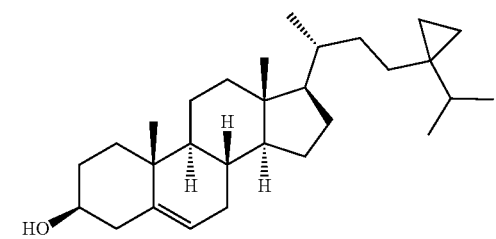
20
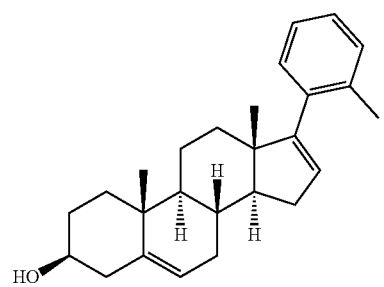
21
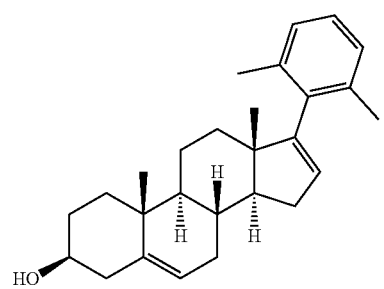

TABLE 16-continued
150
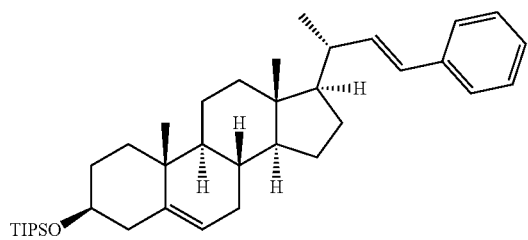
154
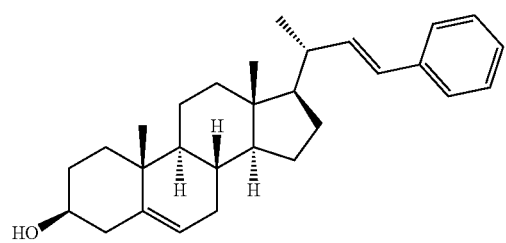
162
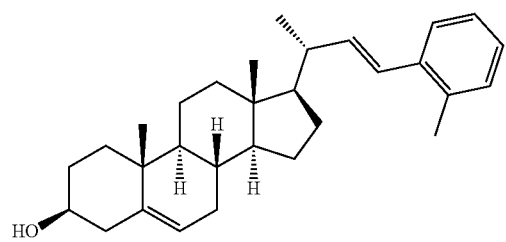
41
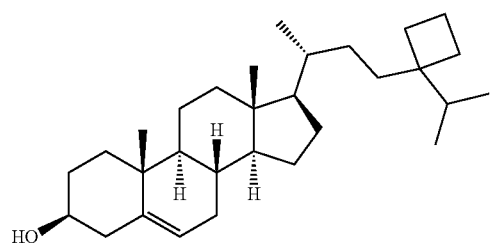
42
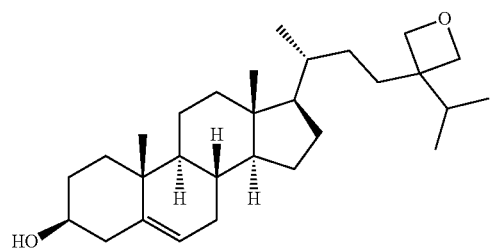
165
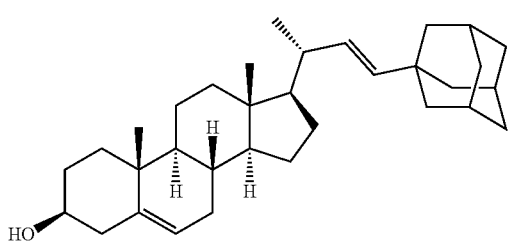

TABLE 16-continued
169 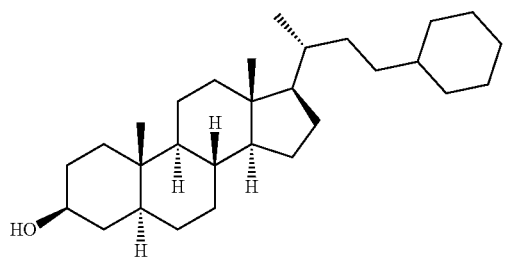
170 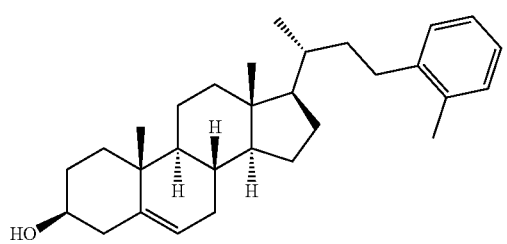
163 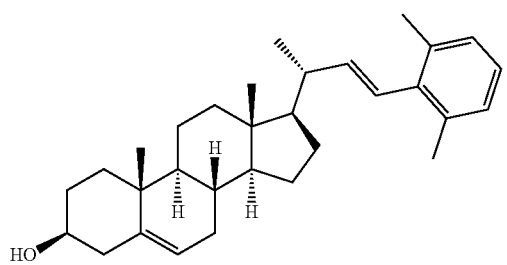
164 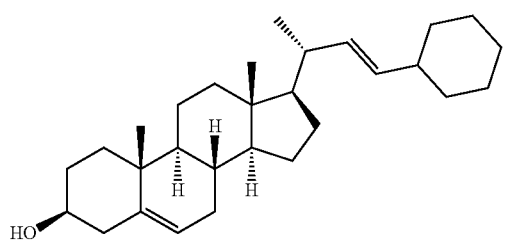
184 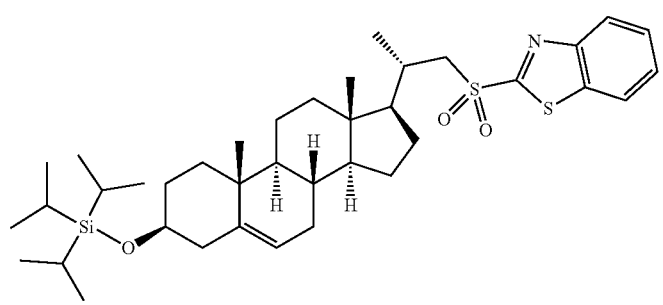
171 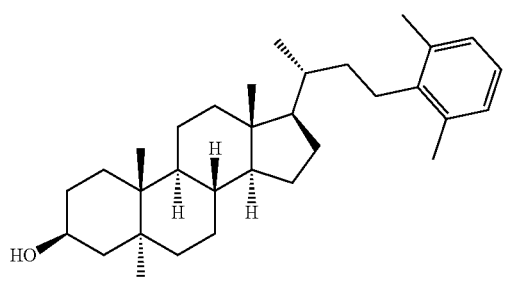

TABLE 16-continued
172
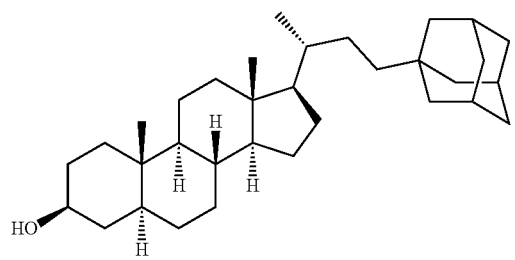
43
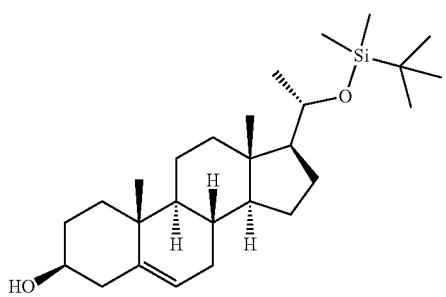
47
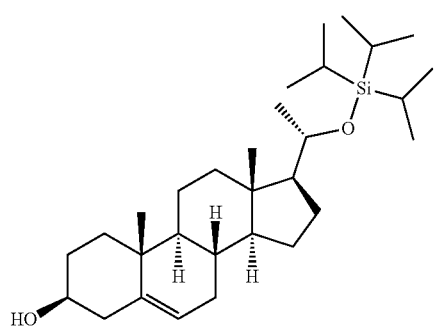
44
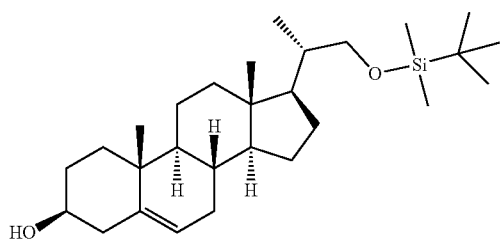
45
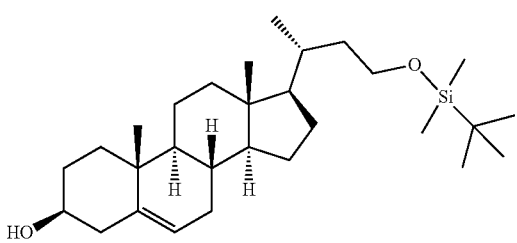
46
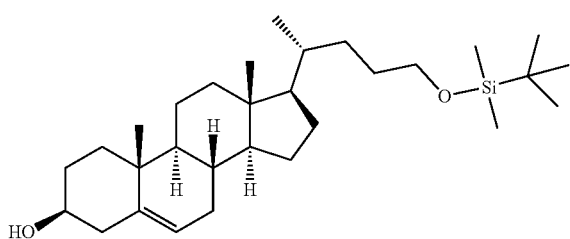

TABLE 16-continued
175 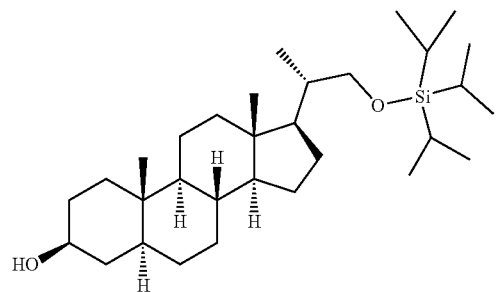
176 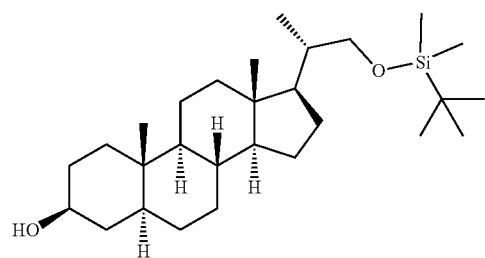
48 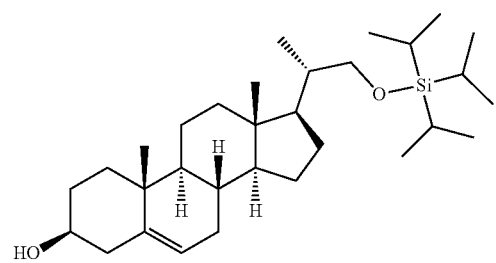
49 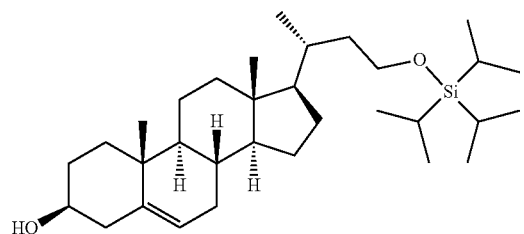
50 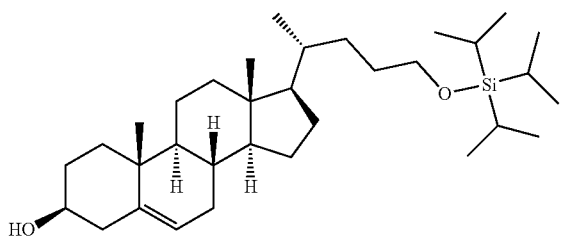
177 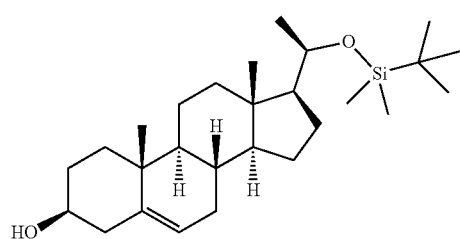

TABLE 16-continued
178
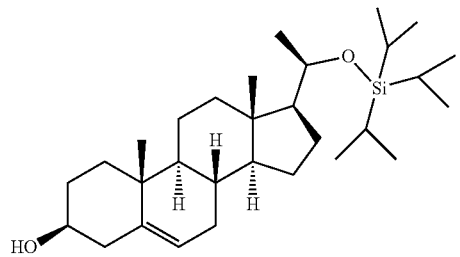
51
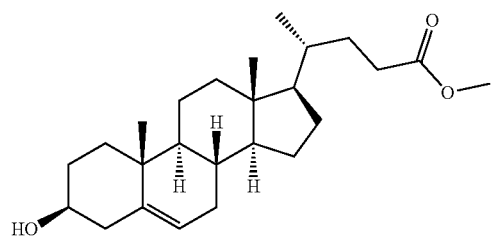
52
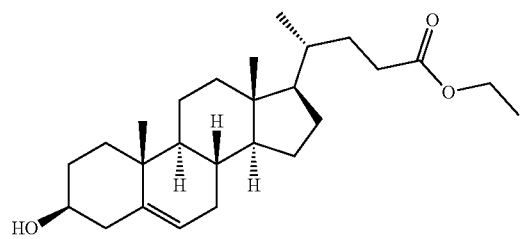
53
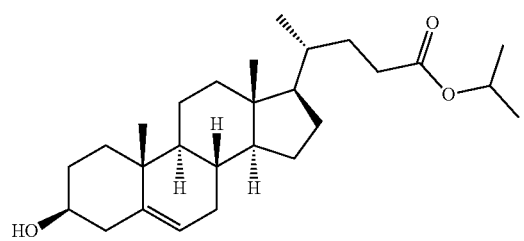
54
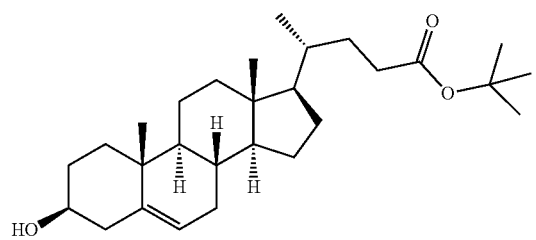
55
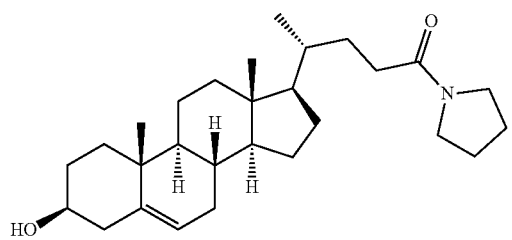

TABLE 16-continued
56 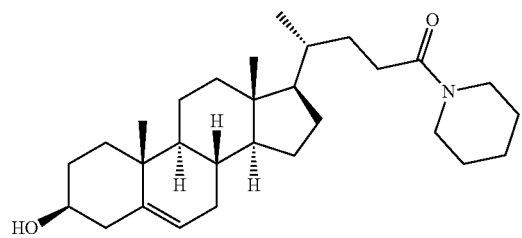
57 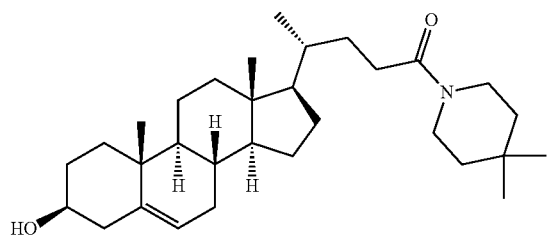
60 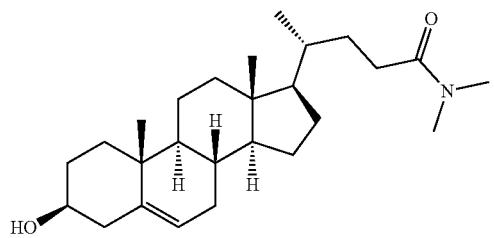
61 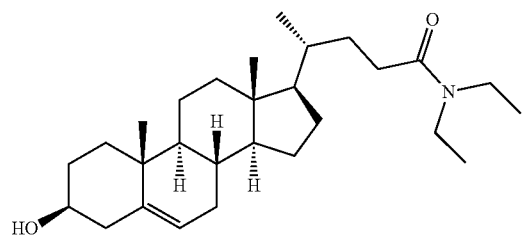
62 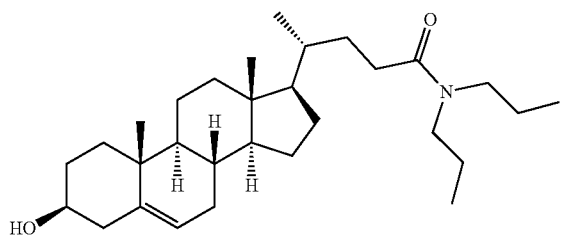
63 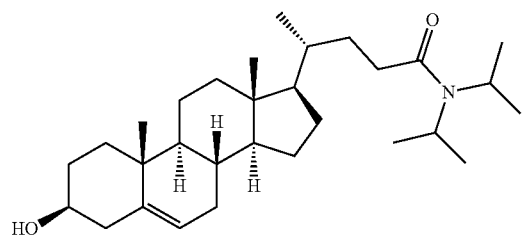

TABLE 16-continued
64
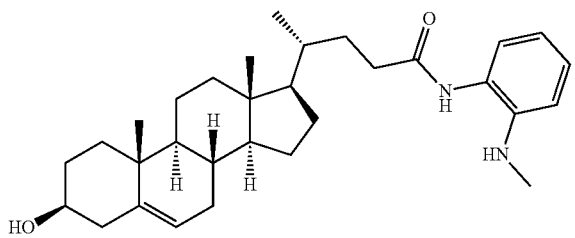
65
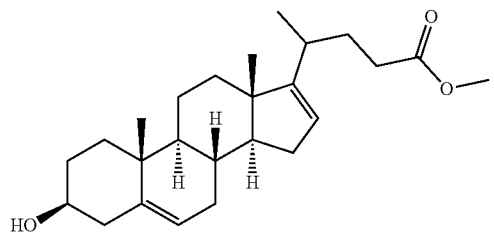
66
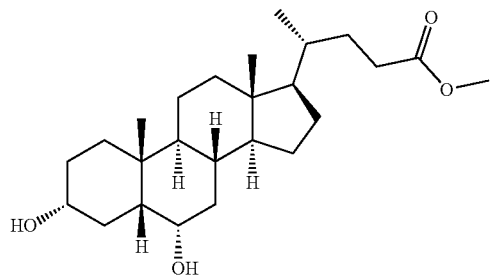
58
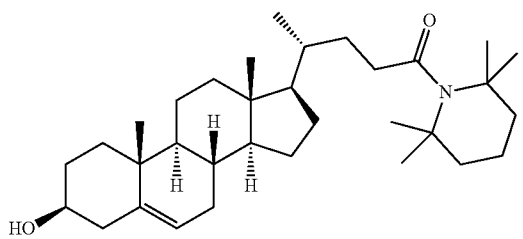
59
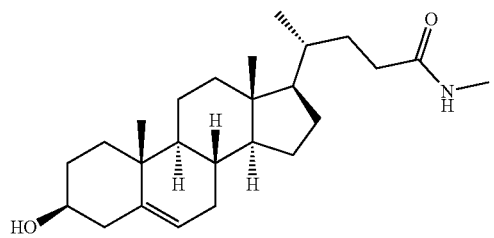
153
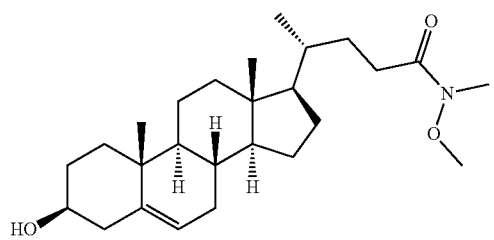

TABLE 16-continued
67
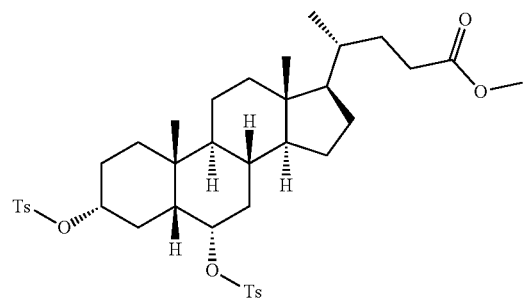
149
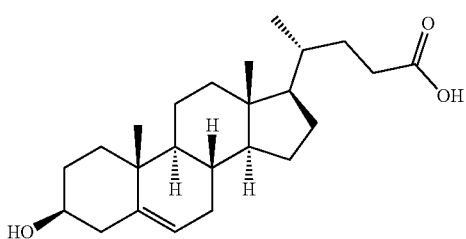
68
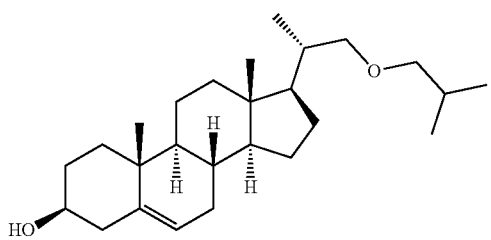
69
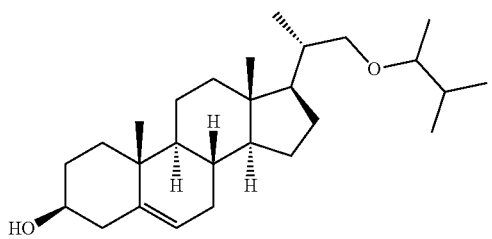
71
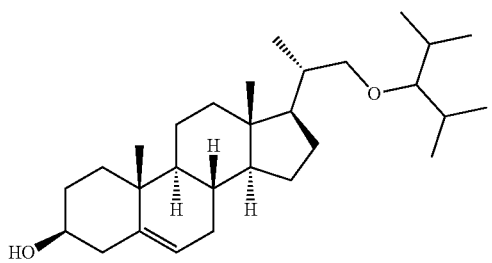
72
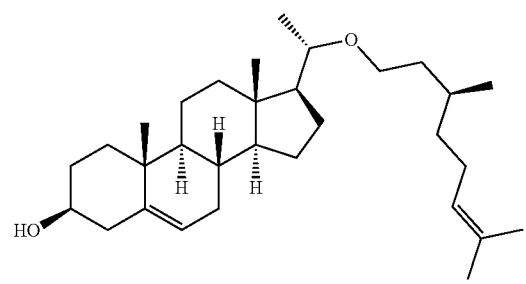

TABLE 16-continued
70 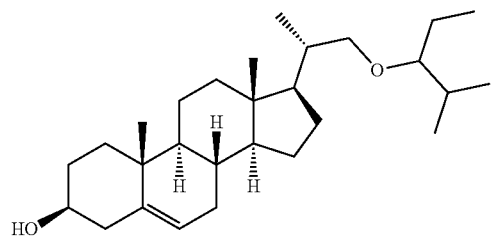
73 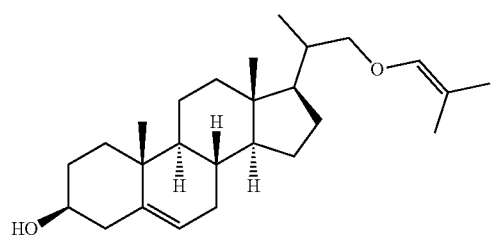
74 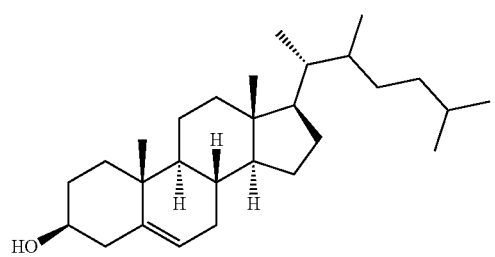
75 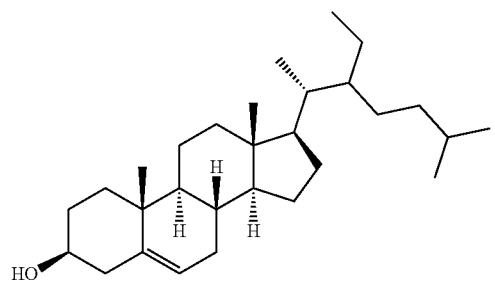
76 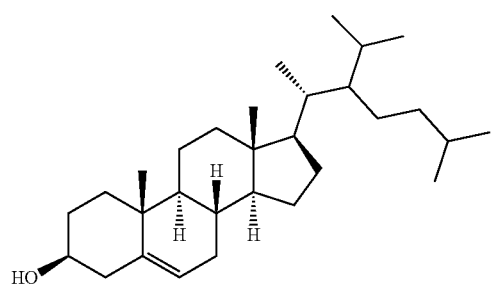
77 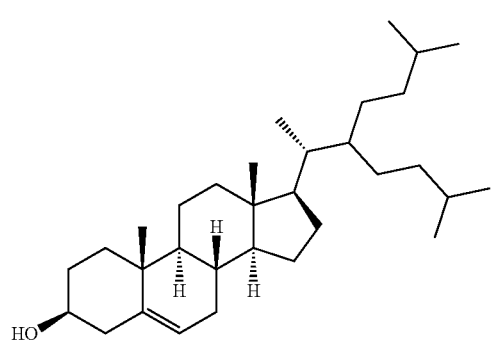

TABLE 16-continued
78 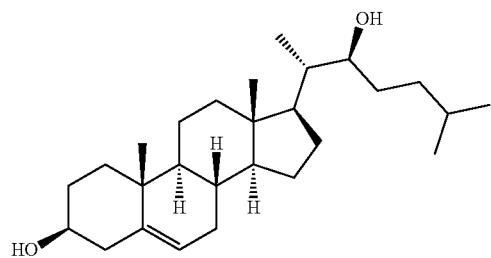
79 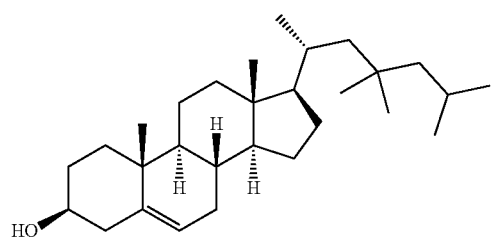
80 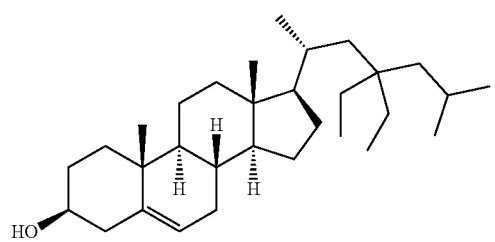
81 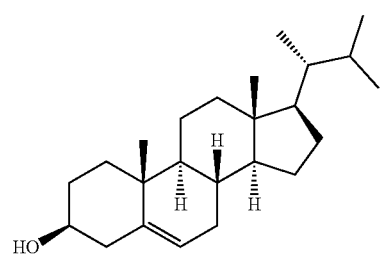
82 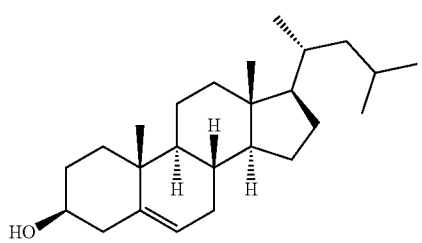
83 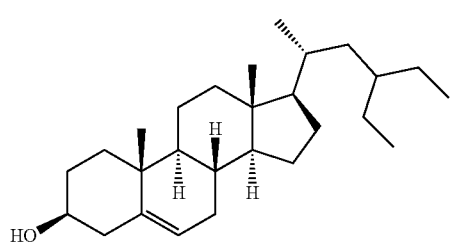

TABLE 16-continued
84 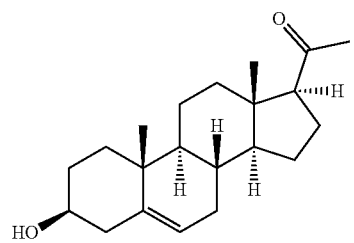
85 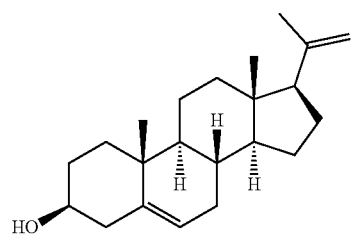
86 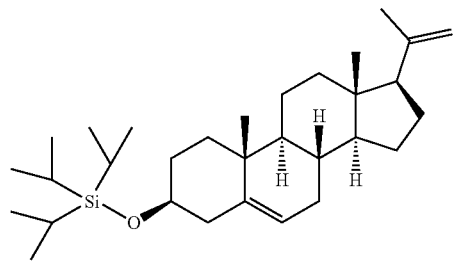
87 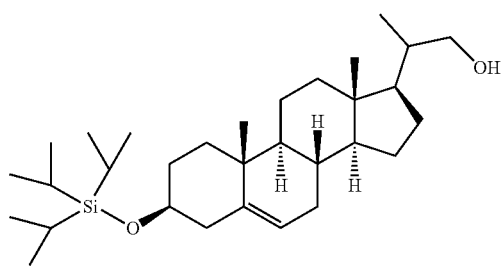
152 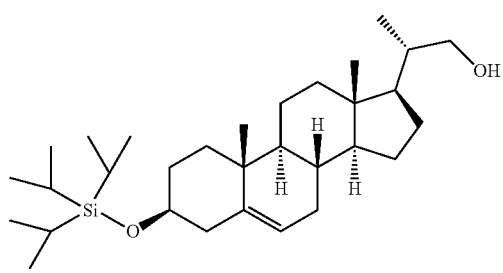
157 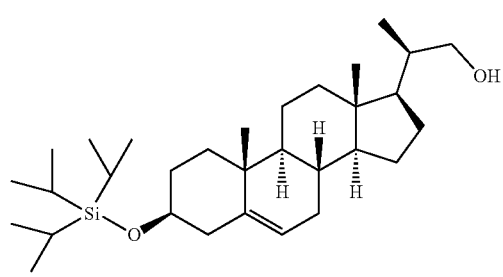

TABLE 16-continued
88
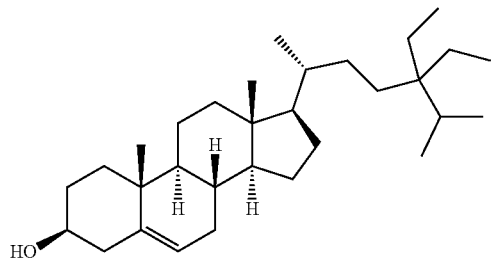
89
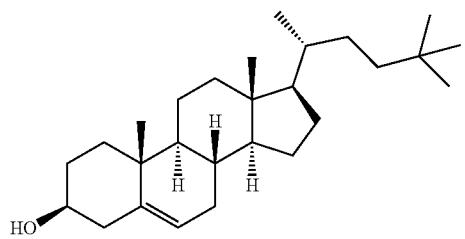
90
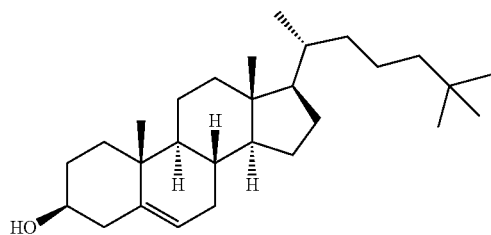
91
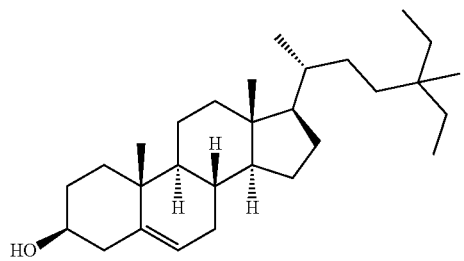
93
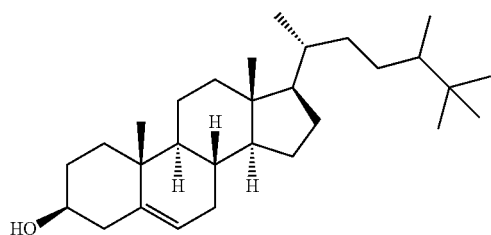
94
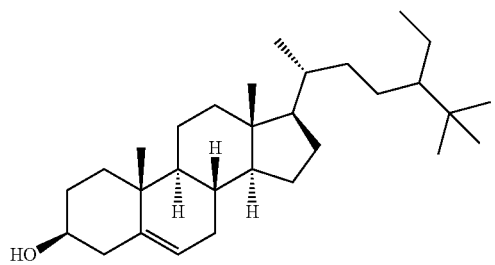

TABLE 16-continued
95
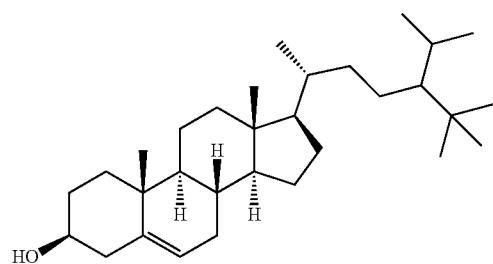
96
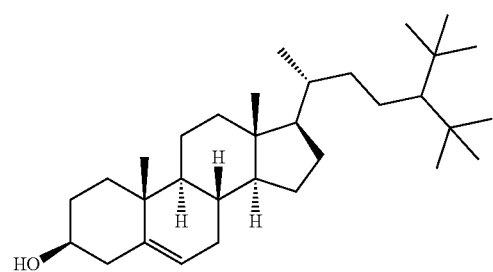
92
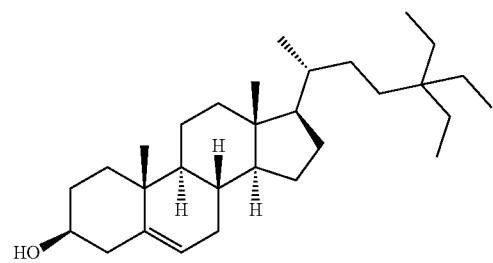
97
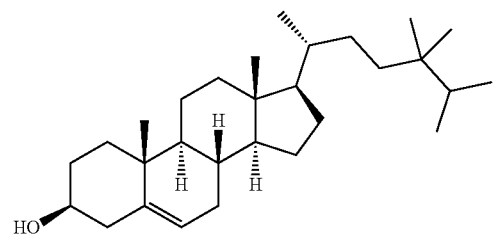
98
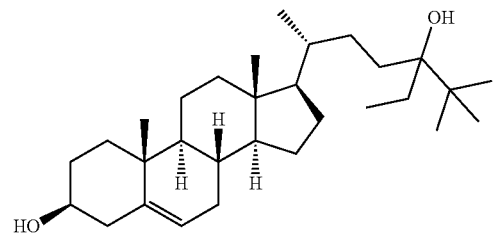
99
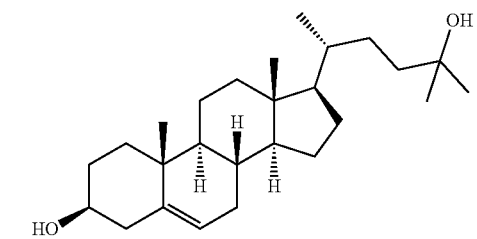

TABLE 16-continued
100 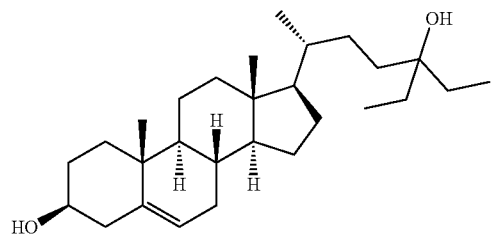
101 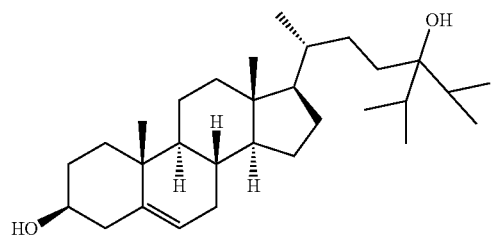
102 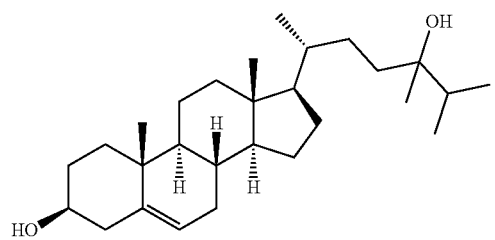
103 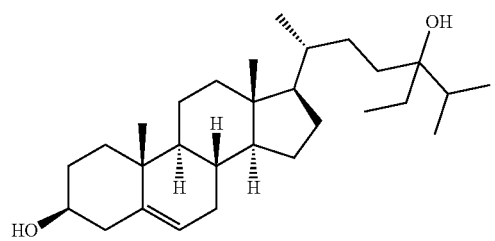
104 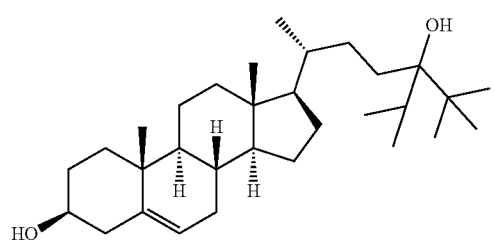
105 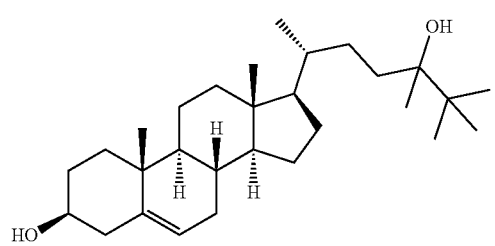

TABLE 16-continued
180
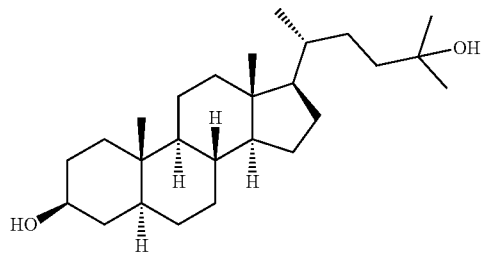
181
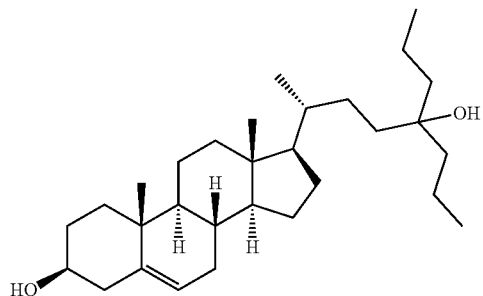
182
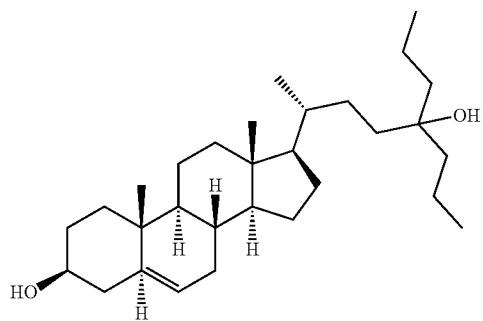
106
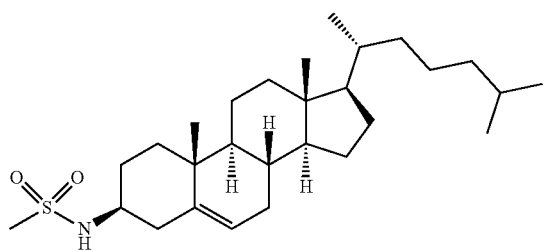
107
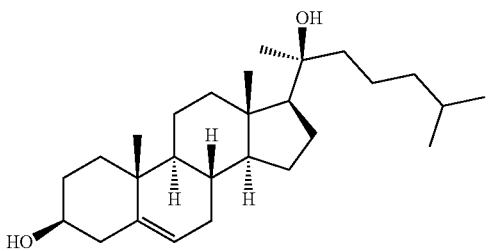
108
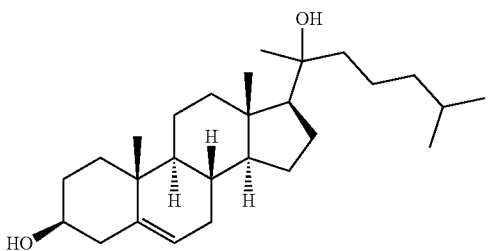

TABLE 16-continued
109
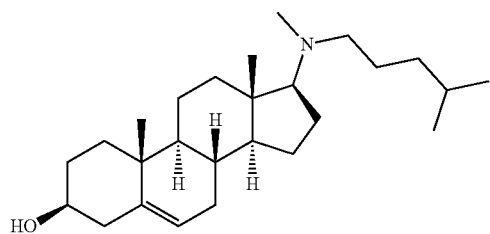
110
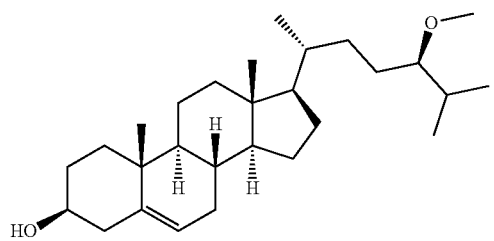
121
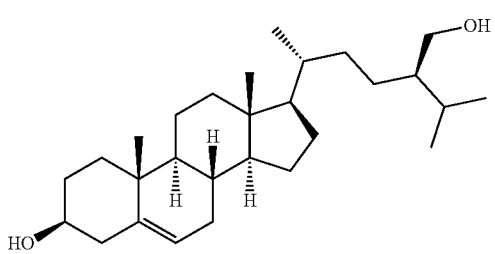
111
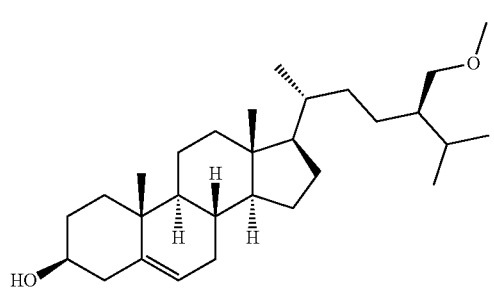
112
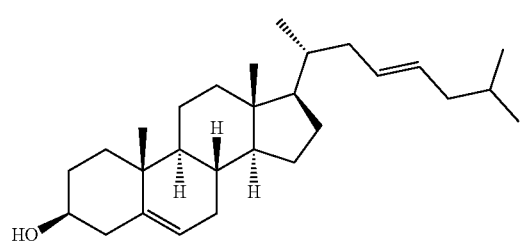
113
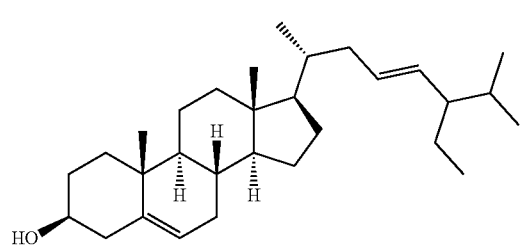

TABLE 16-continued
114
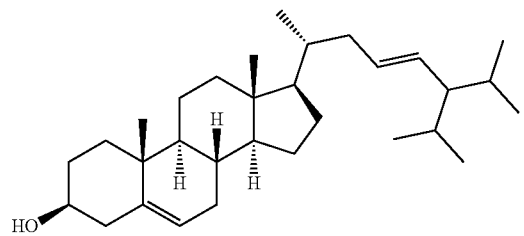
115
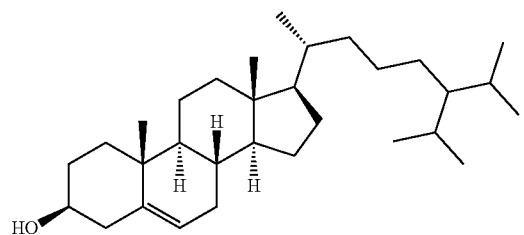
116
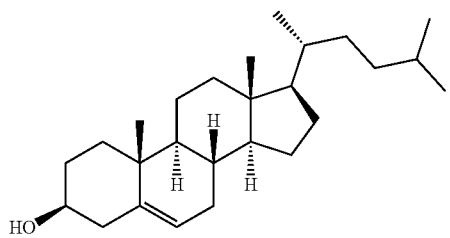
117
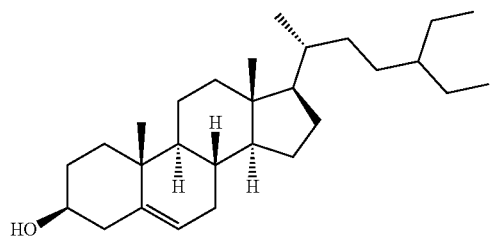
122
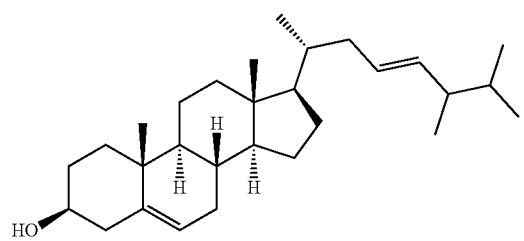
123
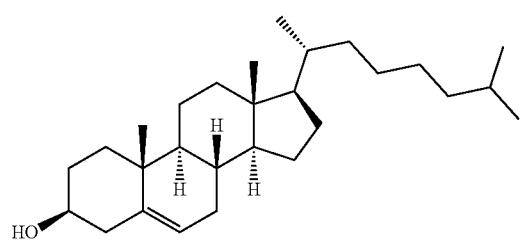

TABLE 16-continued
124
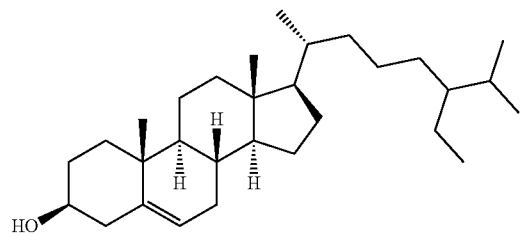
125
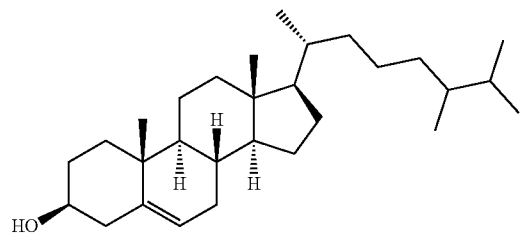
126
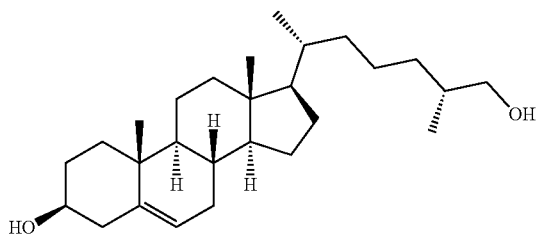
127
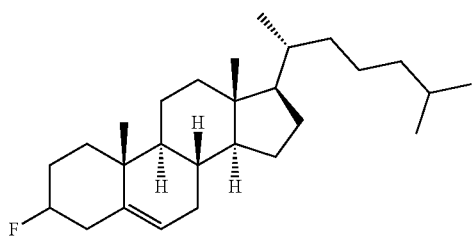
128
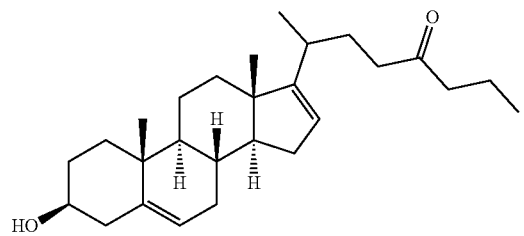
118
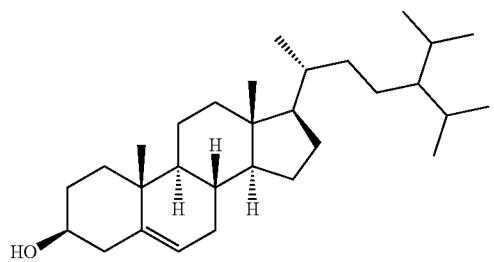

TABLE 16-continued
119
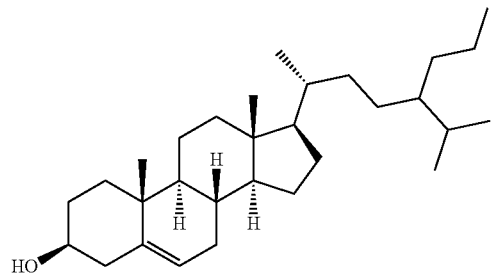
120
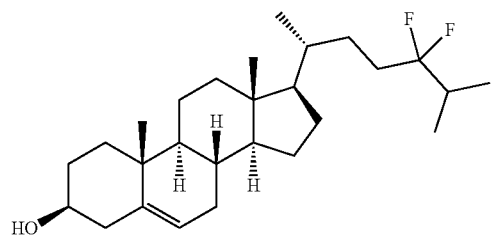
156
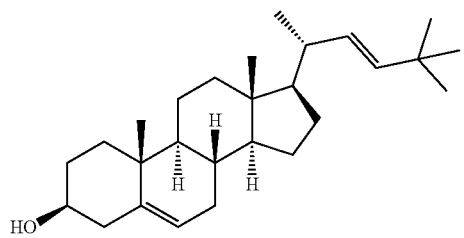
158
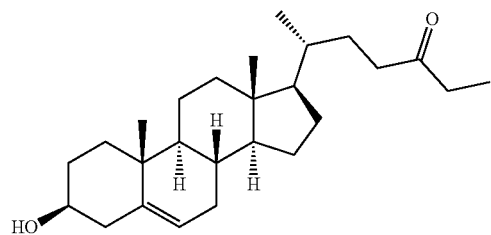
160
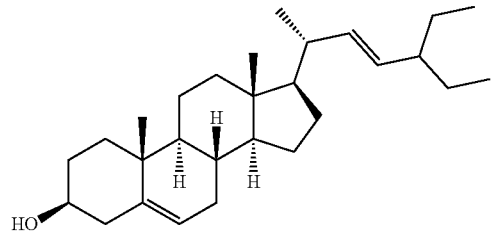
129
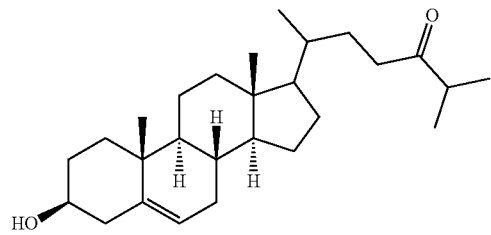

TABLE 16-continued
130 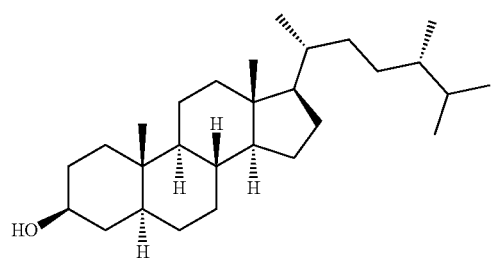
155 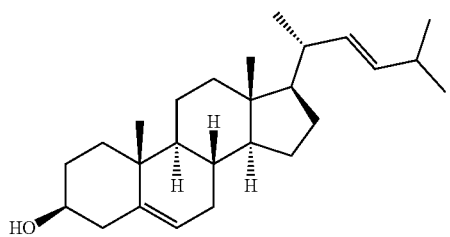
167 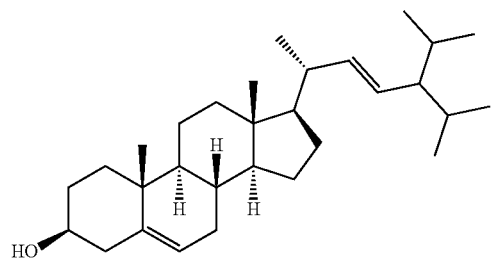
168 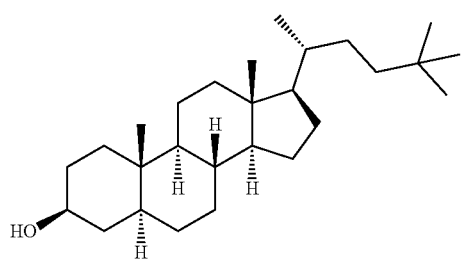
173 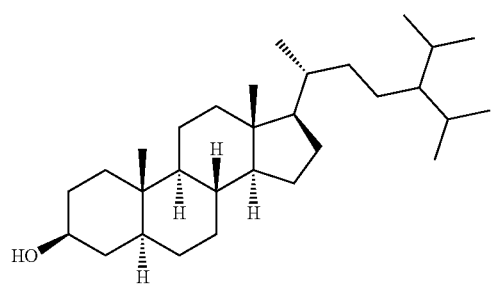
161 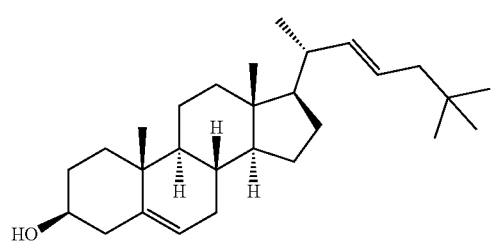

TABLE 16-continued
166 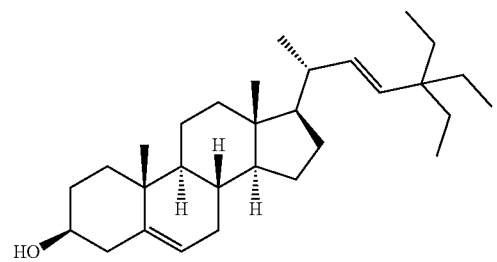
174 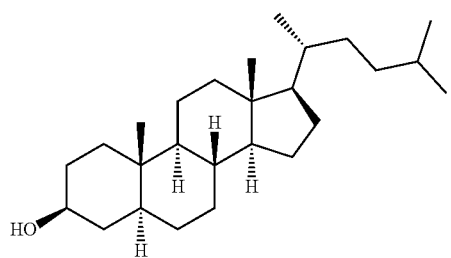
179 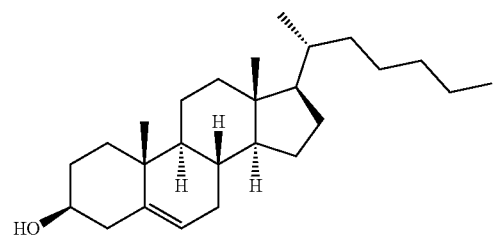
131 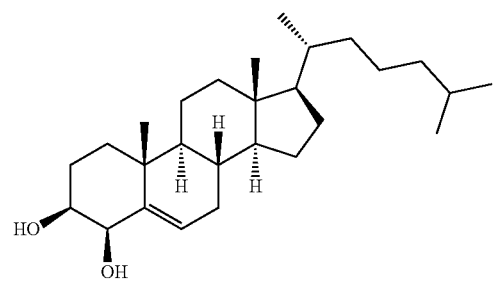
132 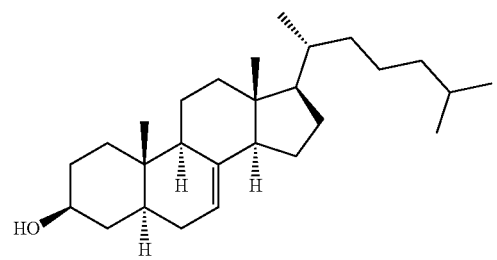
133 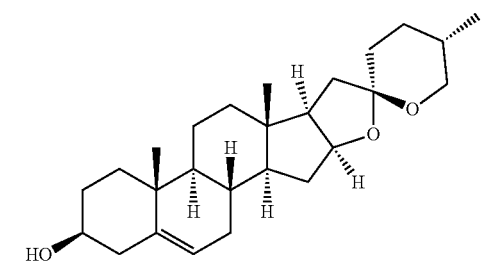

TABLE 16-continued
134
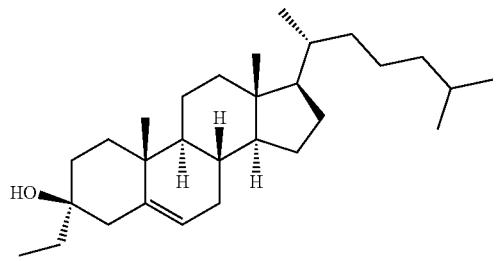
135
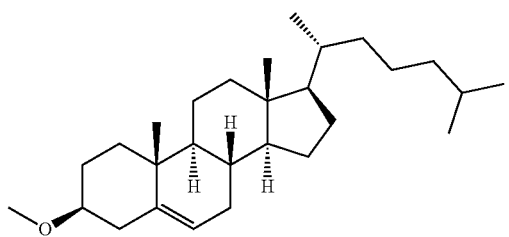
136
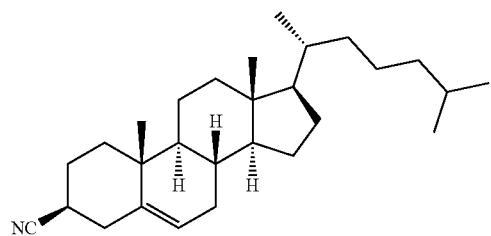
137
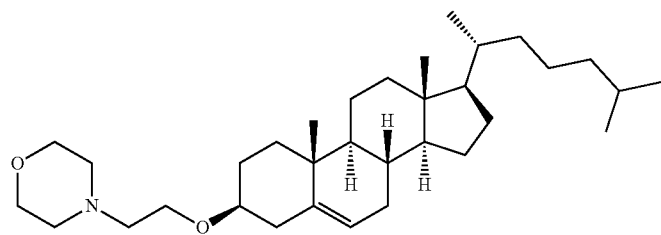
138
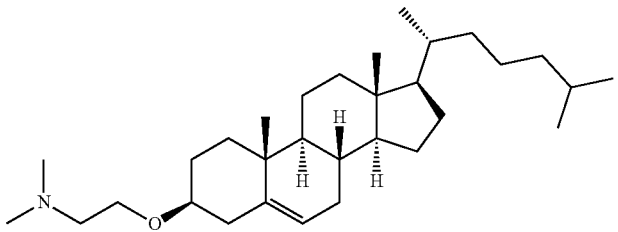
139
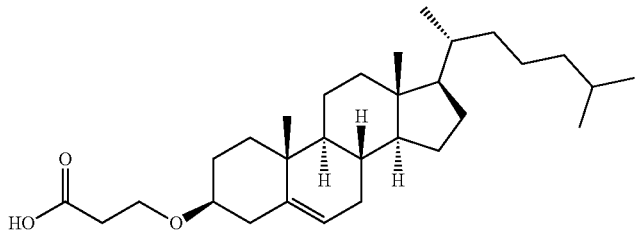

TABLE 16-continued
140
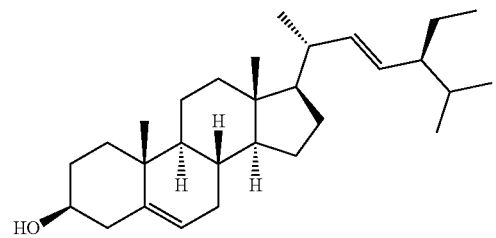
142
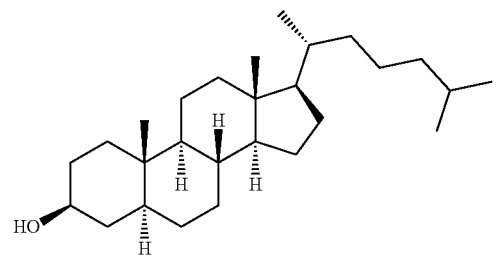
143
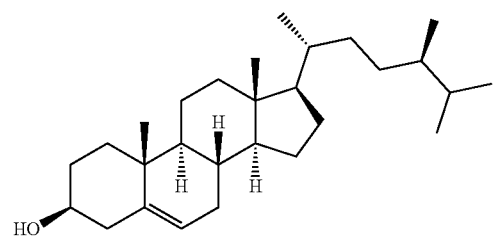
144
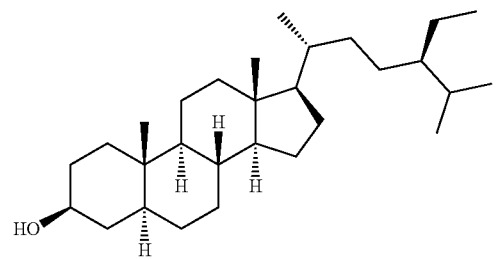
145
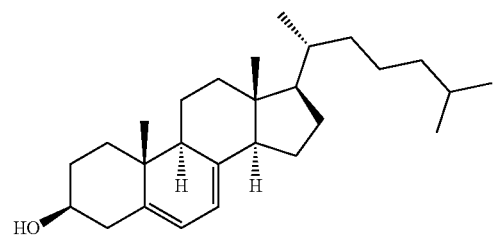
146
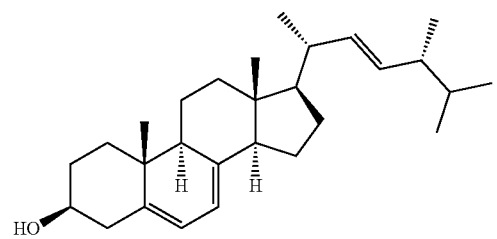

TABLE 16-continued
147
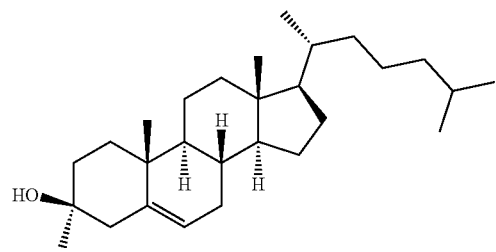
148
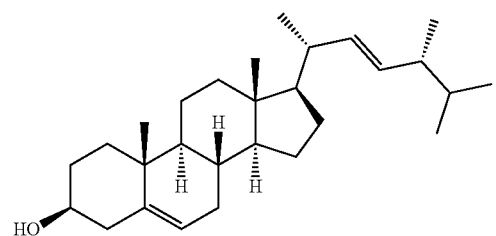
141
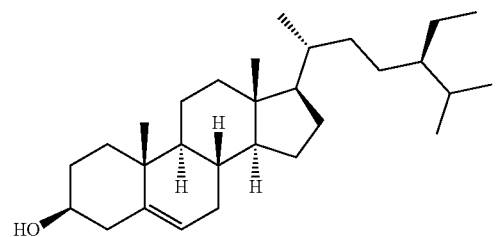
159
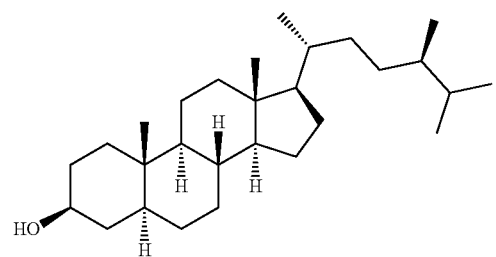
151
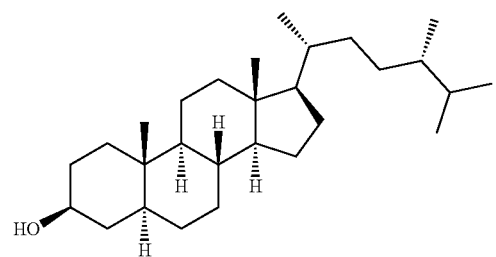
| Composition S- No. | Structure |
|---|---|
183
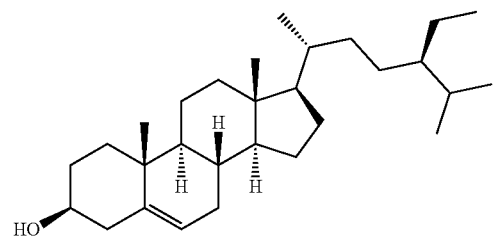
Compound 141

TABLE 16-continued

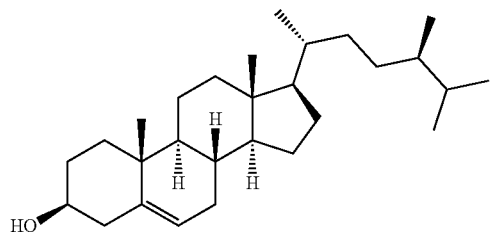

Compund 143

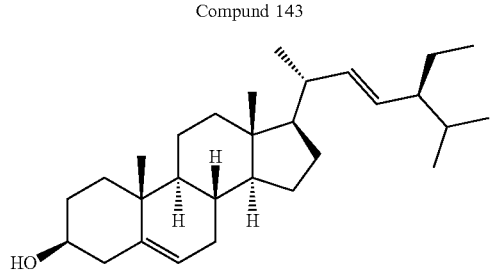

compound 140

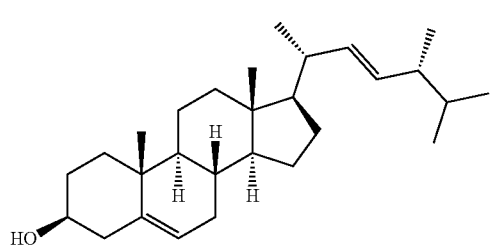

Compound 148

E. Lipid Nanoparticle (LNP) Formulations

The formation of a lipid nanoparticle (LNP) described herein may be accomplished by any methods known in the art. For example, as described in U.S. Pat. Pub. No. US2012/0178702 A1, which is incorporated herein by reference in its entirety. Non-limiting examples of lipid nanoparticle compositions and methods of making them are described, for example, in Semple et al. (2010) Nat. Biotechnol. 28:172-176; Jayarama et al. (2012), Angew. Chem. Int. Ed., 51:8529-8533; and Maier et al. (2013) Molecular Therapy 21, 1570-1578 (the contents of each of which are incorporated herein by reference in their entirety).

In one embodiment, the LNP formulation may be prepared by, e.g., the methods described in International Pat. Pub. No. WO 2011/127255 or WO 2008/103276, the contents of each of which are herein incorporated by reference in their entirety.

In one embodiment, LNP formulations described herein may comprise a polycationic composition. As a non-limiting example, the polycationic composition may be a composition selected from Formulae 1-60 of U.S. Pat. Pub. No. US2005/0222064 A1, the content of which is herein incorporated by reference in its entirety.

In one embodiment, the lipid nanoparticle may be formulated by the methods described in U.S. Pat. Pub. No. US2013/0156845 A1, and International Pat. Pub. No. WO2013/093648 A2 or WO2012/024526 A2, each of which is herein incorporated by reference in its entirety.

In one embodiment, the lipid nanoparticles described herein may be made in a sterile environment by the system and/or methods described in U.S. Pat. Pub. No. US2013/0164400 A1, which is incorporated herein by reference in its entirety.

In one embodiment, the LNP formulation may be formulated in a nanoparticle such as a nucleic acid-lipid particle described in U.S. Pat. No. 8,492,359, which is incorporated herein by reference in its entirety.

A nanoparticle composition may optionally comprise one or more coatings. For example, a nanoparticle composition may be formulated in a capsule, film, or tablet having a coating. A capsule, film, or tablet including a composition described herein may have any useful size, tensile strength, hardness, or density.

In some embodiments, the lipid nanoparticles described herein may be synthesized using methods comprising microfluidic mixers. Exemplary microfluidic mixers may include, but are not limited to, a slit interdigitial micromixer including, but not limited to, those manufactured by Precision Nanosystems (Vancouver, BC, Canada), Microinnova (Allerheiligen bei Wildon, Austria) and/or a staggered herringbone micromixer (SHM) (Zhigaltsev, I. V. et al. (2012) Langmuir. 28:3633-40; Belliveau, N. M. et al. Mol. Ther. Nucleic. Acids. (2012) 1:e37; Chen, D. et al. J. Am. Chem. Soc. (2012) 134(16):6948-51; each of which is herein incorporated by reference in its entirety).

In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Pat. Pub. Nos. US2004/0262223 A1 and US2012/0276209 A1, each of which is incorporated herein by reference in their entirety.

In one embodiment, the lipid nanoparticles may be formulated using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut fur Mikrotechnik Mainz GmbH, Mainz Germany). In one embodiment, the lipid nanoparticles are created using microfluidic technology (see, Whitesides (2006) Nature. 442: 368-373; and Abraham et al. (2002) Science. 295: 647-651; each of which is herein incorporated by reference in its entirety). As a non-limiting example, controlled microfluidic formulation includes a passive method for mixing streams of steady pressure-driven flows in micro channels at a low Reynolds number (see, e.g., Abraham et al. (2002) Science. 295: 647651; which is herein incorporated by reference in its entirety).

In one embodiment, the circRNA of the present invention may be formulated in lipid nanoparticles created using a micromixer chip such as, but not limited to, those from Harvard Apparatus (Holliston, MA), Dolomite Microfluidics (Royston, UK), or Precision Nanosystems (Van Couver, BC, Canada). A micromixer chip can be used for rapid mixing of two or more fluid streams with a split and recombine mechanism.

In some embodiments, the LNP of the present disclosure comprises a molar ratio of between about 40% and about 60% ionizable lipid, a molar ratio of between about 3.5% and about 14% helper lipid, a molar ratio of between about 28% and about 50% structural lipid, and a molar ratio of between about 0.5% and about 5% PEG-lipid, inclusive of all endpoints. In some embodiments, the total molar percentage of the ionizable lipid, the helper lipid, the structural lipid, and the PEG-lipid is 100% in the LNP.

In some embodiments, the molar ratio of the ionizable lipid in the LNP is from about 40 to about 60% of the total lipid present in the LNP. In some embodiments, the molar ratio of the ionizable lipid in the LNP is about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the total lipid present in the LNP. In some embodiments, the ionizable lipid is represented by Formula (7). In some embodiments, the ionizable lipid is represented by Formula (8). All values are inclusive of all endpoints.

In some embodiments, the molar ratio of the helper lipid in the LNP is from about 3.5% to about 14% of the total lipid present in the LNP. In some embodiments, the molar ratio of the helper lipid in the LNP is about 3, about 4%, about 5%, about 6%, about 7%, about 8%, about 9%, about 10%, about 11%, about 12%, about 13%, or about 14% of the total lipid present in the LNP. In some embodiments, the helper lipid is DSPC. In some embodiments, the helper lipid is DOPE. All values are inclusive of all endpoints.

In some embodiments, the molar ratio of the structural lipid in the LNP is from about 28% to about 50% of the total lipid present in the LNP. In some embodiments, the molar ratio of the structural lipid in the LNP is about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% of the total lipid present in the LNP. In some embodiments, the structural lipid is cholesterol. All values are inclusive of all endpoints.

In some embodiments, the molar ratio of the PEG-lipid in the LNP is from about 0.5% to about 5% of the total lipid present in the LNP. In some embodiments, the molar ratio of the PEG-lipid in the LNP is about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, 3.4%, about 3.5%, about 4.0%, about 4.5%, or about 5% of the total lipid present in the LNP. In some embodiments, the PEG-lipid is DSPE-PEG(2000). In some embodiments, the PEG-lipid is DMG-PEG(2000). All values are inclusive of all endpoints.

In some embodiments, the molar ratio of ionizable lipid: helper lipid: structural lipid:PEG-lipid in the LNP is about 45:9:44:2. In some embodiments, the molar ratio of ionizable lipid:helper lipid:structural lipid:PEG-lipid in the LNP is about 50:10:38.5:1.5. In some embodiments, the molar ratio of ionizable lipid:helper lipid:structural lipid:PEG-lipid in the LNP is about 41:12:45:2. In some embodiments, the molar ratio of ionizable lipid:helper lipid:structural lipid: PEG-lipid in the LNP is about 62:4:33:1. In some embodiments, the molar ratio of ionizable lipid:helper lipid:structural lipid:PEG-lipid in the LNP is about 53:5:41:1. In some embodiments, the molar ratio of each of the ionizable lipid, helper lipid, structural lipid, and PEG-lipid is within 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of the stated value.

In one embodiment, the lipid nanoparticles may have a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm. In one embodiment, the lipid nanoparticles may have a diameter from about 10 to 500 nm. In one embodiment, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm. Each possibility represents a separate embodiment of the present invention.

In some embodiments, a nanoparticle (e.g., a lipid nanoparticle) has a mean diameter of 10-500 nm, 20-400 nm, 30-300 nm, or 40-200 nm. In some embodiments, a nanoparticle (e.g., a lipid nanoparticle) has a mean diameter of 50-150 nm, 50-200 nm, 80-100 nm, or 80-200 nm.

In some embodiments, the lipid nanoparticles described herein can have a diameter from below 0.1 µm to up to 1 mm such as, but not limited to, less than 0.1 µm, less than 1.0 µm, less than 5 µm, less than 10 µm, less than 15 µm, less than 20 µm, less than 25 µm, less than 30 µm, less than 35 µm, less than 40 µm, less than 50 µm, less than 55 µm, less than 60 µm, less than 65 µm, less than 70 µm, less than 75 µm, less than 80 µm, less than 85 µm, less than 90 µm, less than 95 µm, less than 100 µm, less than 125 µm, less than 150 µm, less than 175 µm, less than 200 µm, less than 225 µm, less than 250 µm, less than 275 µm, less than 300 µm, less than 325 µm, less than 350 µm, less than 375 µm, less than 400 µm, less than 425 µm, less than 450 µm, less than 475 µm, less than 500 µm, less than 525 µm, less than 550 µm, less than 575 µm, less than 600 µm, less than 625 µm, less than 650 µm, less than 675 µm, less than 700 µm, less than 725 µm, less than 750 µm, less than 775 µm, less than 800 µm, less than 825 µm, less than 850 µm, less than 875 µm, less than 900 µm, less than 925 µm, less than 950 µm, less than 975 µm.

In another embodiment, LNPs may have a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm. Each possibility represents a separate embodiment of the present invention.

A nanoparticle composition may be relatively homogenous. A polydispersity index may be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition may be from about 0.10 to about 0.20. Each possibility represents a separate embodiment of the present invention.

The zeta potential of a nanoparticle composition may be used to indicate the electrokinetic potential of the composition. For example, the zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the zeta potential of a nanoparticle composition may be from about −20 mV to about +20 mV, from about −20 mV to about +15 mV, from about −20 mV to about +10 mV, from about −20 mV to about +5 mV, from about −20 mV to about 0 mV, from about −20 mV to about −5 mV, from about −20 mV to about −10 mV, from about −20 mV to about −15 mV from about −20 mV to about +20 mV, from about −20 mV to about +15 mV, from about −20 mV to about +10 mV, from about −20 mV to about +5 mV, from about −20 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV. Each possibility represents a separate embodiment of the present invention.

The efficiency of encapsulation of a therapeutic agent describes the amount of therapeutic agent that is encapsulated or otherwise associated with a nanoparticle composition after preparation, relative to the initial amount provided. The encapsulation efficiency is desirably high (e.g., close to 100%). The encapsulation efficiency may be measured, for example, by comparing the amount of therapeutic agent in a solution containing the nanoparticle composition before and after breaking up the nanoparticle composition with one or more organic solvents or detergents. Fluorescence may be used to measure the amount of free therapeutic agent (e.g., nucleic acids) in a solution. For the nanoparticle compositions described herein, the encapsulation efficiency of a therapeutic agent may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%. Each possibility represents a separate embodiment of the present invention. In some embodiments, the lipid nanoparticle has a polydiversity value of less than 0.4. In some embodiments, the lipid nanoparticle has a net neutral charge at a neutral pH. In some embodiments, the lipid nanoparticle has a mean diameter of 50-200 nm.

The properties of a lipid nanoparticle formulation may be influenced by factors including, but not limited to, the selection of the cationic lipid component, the degree of cationic lipid saturation, the selection of the non-cationic lipid component, the degree of noncationic lipid saturation, the selection of the structural lipid component, the nature of the PEGylation, ratio of all components and biophysical parameters such as size. As described herein, the purity of a PEG lipid component is also important to an LNP's properties and performance.

F. Methods for Lipid Nanoparticles (LNP)

In one embodiment, a lipid nanoparticle formulation may be prepared by the methods described in International Publication Nos. WO2011127255 or WO2008103276, each of which is herein incorporated by reference in their entirety. In some embodiments, lipid nanoparticle formulations may be as described in International Publication No. WO2019131770, which is herein incorporated by reference in its entirety.

In some embodiments, circular RNA is formulated according to a process described in U.S. patent application Ser. No. 15/809,680. In some embodiments, the present invention provides a process of encapsulating circular RNA in transfer vehicles comprising the steps of forming lipids into pre-formed transfer vehicles (i.e. formed in the absence of RNA) and then combining the pre-formed transfer vehicles with RNA. In some embodiments, the novel formulation process results in an RNA formulation with higher potency (peptide or protein expression) and higher efficacy (improvement of a biologically relevant endpoint) both in vitro and in vivo with potentially better tolerability as compared to the same RNA formulation prepared without the step of preforming the lipid nanoparticles (e.g., combining the lipids directly with the RNA).

For certain cationic lipid nanoparticle formulations of RNA, in order to achieve high encapsulation of RNA, the RNA in buffer (e.g., citrate buffer) has to be heated. In those processes or methods, the heating is required to occur before the formulation process (i.e. heating the separate components) as heating post-formulation (post-formation of nanoparticles) does not increase the encapsulation efficiency of the RNA in the lipid nanoparticles. In contrast, in some embodiments of the novel processes of the present invention, the order of heating of RNA does not appear to affect the RNA encapsulation percentage. In some embodiments, no heating (i.e. maintaining at ambient temperature) of one or more of the solutions comprising the pre-formed lipid nanoparticles, the solution comprising the RNA and the mixed solution comprising the lipid nanoparticle encapsulated RNA is required to occur before or after the formulation process.

RNA may be provided in a solution to be mixed with a lipid solution such that the RNA may be encapsulated in lipid nanoparticles. A suitable RNA solution may be any aqueous solution containing RNA to be encapsulated at various concentrations. For example, a suitable RNA solution may contain an RNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In some embodiments, a suitable RNA solution may contain an RNA at a concentration in a range from about 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml.

Typically, a suitable RNA solution may also contain a buffering agent and/or salt. Generally, buffering agents can include HEPES, Tris, ammonium sulfate, sodium bicarbonate, sodium citrate, sodium acetate, potassium phosphate or sodium phosphate. In some embodiments, suitable concentration of the buffering agent may be in a range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM.

Exemplary salts can include sodium chloride, magnesium chloride, and potassium chloride. In some embodiments, suitable concentration of salts in an RNA solution may be in a range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM.

In some embodiments, a suitable RNA solution may have a pH in a range from about 3.5-6.5, 3.5-6.0, 3.5-5.5, 3.5-5.0, 3.5-4.5, 4.0-5.5, 4.0-5.0, 4.0-4.9, 4.0-4.8, 4.0-4.7, 4.0-4.6, or 4.0-4.5.

Various methods may be used to prepare an RNA solution suitable for the present invention. In some embodiments, RNA may be directly dissolved in a buffer solution described herein. In some embodiments, an RNA solution may be generated by mixing an RNA stock solution with a buffer solution prior to mixing with a lipid solution for encapsulation. In some embodiments, an RNA solution may be generated by mixing an RNA stock solution with a buffer solution immediately before mixing with a lipid solution for encapsulation.

According to the present invention, a lipid solution contains a mixture of lipids suitable to form transfer vehicles for encapsulation of RNA. In some embodiments, a suitable lipid solution is ethanol based. For example, a suitable lipid solution may contain a mixture of desired lipids dissolved in pure ethanol (i.e. 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. In some embodiments, a suitable lipid solution may contain a mixture of desired lipids at a total concentration in a range from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9 mg/ml, 1.0-8 mg/ml, 1.0-7 mg/ml, 1.0-6 mg/ml, or 1.0-5 mg/ml.

G. Liposomes

In certain embodiments, liposomes or other lipid bilayer vesicles are disclosed herein and may be used as a component or as the whole transfer vehicle to facilitate or enhance the delivery and release of circular RAN to one or more target cells. Liposomes are usually characterized by having an interior space sequestered from an outer medium by a membrane of one or more bilayers forming a microscopic sack or vesicle. Bilayer membranes of liposomes are typically formed by lipids, i.e. amphiphilic molecules of synthetic or natural origin that comprise spatially separated hydrophobic or hydrophilic domains (Lasic, D, and Papahadjopoulos, D., eds. Medical Applications of Liposomes. Elsevier, Amsterdam, 1998).

In some embodiments, the circular RNA is encapsulated, or the liposome can be prepared using various methods, including but not limited to mechanical dispersion, solvent dispersion, and or detergent removal. Each of these methods include the steps of drying the lipids from organic solvents, dispersing the lipid in aqueous media, resizing the liposomes and purifying the/liposome suspension (Gomez et al., ACS Omega. 2019. 4(6): 10866-10876). Various other methods of liposome preparation can be found in Akbarzadeh et al., Nanoscale Res Lett. 2013; 8(1): 102. In some embodiments, the circular RNA may be loaded passively (i.e. the circular RNA is encapsulated during liposome formation) or actively (i.e. after liposome formation).

In some embodiments, the liposome disclosed herein may comprise one or more bilayers. In certain embodiments, the liposome may comprise a multilamellar vesicle or a unilamellar vesicle.

In certain embodiments, the liposome as described herein comprises of naturally derived or engineered phospholipids. In some embodiments, the liposomes may further comprise PEG-lipids that aid with stability of the overall liposome structure. Other improvements, including but not limited to corticosteroid and other steroids may be used to help with maintaining structure and stability of the liposome.

H. Dendrimer

In certain embodiments, the transfer vehicle for transporting the circular RNA comprises a dendrimer. Use of "dendrimer" describes the architectural motif of the transfer vehicle. In some embodiments, the dendrimer includes but is not limited to containing an interior core and one or more layers (i.e. generations) that extend or attach out from the interior core. In some of the embodiments, the generations may contain one or more branching points and an exterior surface of terminal groups that attach to the outermost generation. The branching points, in certain embodiments, may be mostly monodispersed and contain symmetric branching units built around the interior core.

Synthesis of the dendrimer may comprise the divergent method, convergent growth, hypercore and branched monomer growth, double exponential growth, lego chemistry, click chemistry and other methods as available in the art (Mendes L. et al., Molecules. 2017. 22 (9): 1401 further describes these methods).

I. Polymer-Based Delivery

In certain embodiments, as described herein, the transfer vehicle for the circular RNA polynucleotide comprises a polymer nanoparticle. In some embodiments, the polymer nanoparticle includes nanocapsules and nanospheres. Nanocapsules, in some embodiments, are composed of an oily core surrounded by a polymeric shell. In some embodiments, the circular RNA is contained within the core and the polymeric shell controls the release of the circular RNA. On the other hand, nanospheres comprise a continuous polymeric network in which the circular RNA is retained or absorbed onto the surface. In some embodiments, cationic polymers is used to encapsulate the circular RNA due to the favorable electrostatic interaction of the cations to the negatively charged nucleic acids and cell membrane.

The polymer nanoparticle may be prepared by various methods. In some embodiments, the polymer nanoparticle may be prepared by nanoprecipitation, emulsion techniques, solvent evaporation, solvent diffusion, reverse salting-out or other methods available in the art.

J. Polymer-Lipid Hybrids

In certain embodiments, as described herein, the transfer vehicle for the circular RNA polynucleotide comprises a polymer-lipid hybrid nanoparticle (LPHNP). In some embodiments, the LPHNP comprises a polymer core enveloped within a lipid bilayer. In some embodiments, the polymer core encapsulates the circular RNA polynucleotide. In some embodiments, the LPHNP further comprises an outer lipid bilayer. In certain embodiments this outer lipid bilayer comprises a PEG-lipid, helper lipid, cholesterol or other molecule as known in the art to help with stability in a lipid-based nanoparticle. The lipid bilayer closest to the polymer core mitigates the loss of the entrapped circular RNA during LPHNP formation and protects from degradation of the polymer core by preventing diffusion of water from outside of the transfer vehicle into the polymer core (Mukherjee et al., In J. Nanomedicine. 2019; 14: 1937-1952).

There are various methods of developing and formulating a LPHNP. In certain embodiments, the LPHNP is developed using a one-step or a two-step method available in the art. In some embodiments, the one-step method for forming an LPHNP is through nanoprecipitation or emulsification-solvent evaporation. In certain embodiments, the two-step method includes nanoprecipitation, emulsification-solvent evaporation, high-pressure homogenization, or other method available in the art.

K. Peptide-Based Delivery

In certain embodiments, the circular RNA can be transported using a peptide-based delivery mechanism. In some embodiments, the peptide-based delivery mechanism comprises a lipoprotein. Based on the size of the drug to be delivered, the lipoprotein may be either a low-density (LDL) or high-density lipoprotein (HDL). As seen in U.S. Pat. No. 8,734,853B2, high-density lipoproteins are capable of transporting a nucleic acid in vivo and in vitro.

In particular embodiments, the lipid component includes cholesterol. In more particular embodiments, the lipid component includes a combination of cholesterol and cholesterol oleate.

The HDL-nucleic acid particle can be of any size, but in particular embodiments the particle has a molecular size of from about 100 Angstroms to about 500 Angstroms. In more particular embodiments, the particle has a molecular size of from about 100 Angstroms to about 300 Angstroms. The size may be dependent on the size of the nucleic acid component incorporated into the particle.

The HDL-nucleic acid particle can have a broad range in molecular weight. The weight is dependent on the size of the nucleic acid incorporated into the particle. For example, in some embodiments, the particle has a molecular weight of between about 100,000 Daltons to about 1,000,000 Daltons. In more particular embodiments, the particle has a molecular weight of between about 100,000 Daltons to about 500,000 Daltons. In specific embodiments, the particle has a molecular weight of between about 100,000 Daltons to about 300,000 Daltons.

The HDL-nucleic acid particles of the present invention can be made by different methods. For example, a nucleic acid (e.g., siRNA) may be neutralized by combining the nucleic acid with peptides or polypeptides composed of contiguous positively-charged amino acids. For example, as discussed above, amino acid sequences may include 2 or more contiguous lysine residues. The positive charge of the amino acid sequences neutralizes the negatively charged nucleic acid molecule. The nucleic acid can then be encapsulated in an HDL particle using a method as described in Lacko et al. (2002).

L. Carbohydrate Carrier

In certain embodiments, the circular RNA polynucleotide can be transported using a carbohydrate carrier or a sugar-nanocapsule. In certain embodiments, the carbohydrate carrier comprises a sugar-decorated nanoparticle, peptide- and saccharide-conjugated dendrimer, nanoparticles based on polysaccharides, and other carbohydrate-based carriers available in the art. As described herein, the incorporation of carbohydrate molecules may be through synthetic means.

In some embodiments, the carbohydrate carrier comprises polysaccharides. These polysaccharides may be made from the microbial cell wall of the target cell. For example, carbohydrate carriers comprise of mannan carbohydrates have been shown to successfully deliver mRNA (Son et al., Nano Lett. 2020. 20(3): 1499-1509).

M. Glycan-Decorated Nanoparticles/Glyconanoparticles

In certain embodiments, as provided herein, the transfer vehicle for the circular RNA is a glyconanoparticle (GlycoNP). As known in the art, glyconanoparticles comprise a core comprising gold, iron oxide, semiconductor nanoparticles or a combination thereof. In some embodiments, the glyconanoparticle is functionalized using carbohydrates. In certain embodiments, the glyconanoparticle comprises a carbon nanotube or graphene. In one embodiment the glyconanoparticle comprises a polysaccharide-based GlycoNP (e.g., chitosan-based GlycoNP). In certain embodiments, the glyconanoparticle is a glycodendrimer.

7. Combinations of Proteins and Ires

In certain embodiments, as provided herein, the payload encoded by the circular RNA polynucleotide may be optimized through use of a specific internal ribosome entry sites (IRES) within the translation initiation element (TIE). In some embodiments, IRES specificity within a circular RNA can significantly enhance expression of specific proteins encoded within the coding element.

8. Targeting

A. Targeting Methods

The present invention also contemplates the discriminatory targeting of target cells and tissues by both passive and active targeting means. The phenomenon of passive targeting exploits the natural distributions patterns of a transfer vehicle in vivo without relying upon the use of additional excipients or means to enhance recognition of the transfer vehicle by target cells. For example, transfer vehicles which are subject to phagocytosis by the cells of the reticuloendothelial system are likely to accumulate in the liver or spleen, and accordingly may provide a means to passively direct the delivery of the compositions to such target cells.

Alternatively, the present invention contemplates active targeting, which involves the use of targeting moieties that may be bound (either covalently or non-covalently) to the transfer vehicle to encourage localization of such transfer vehicle at certain target cells or target tissues. For example, targeting may be mediated by the inclusion of one or more endogenous targeting moieties in or on the transfer vehicle to encourage distribution to the target cells or tissues. Recognition of the targeting moiety by the target tissues actively facilitates tissue distribution and cellular uptake of the transfer vehicle and/or its contents in the target cells and tissues (e.g., the inclusion of an apolipoprotein-E targeting ligand in or on the transfer vehicle encourages recognition and binding of the transfer vehicle to endogenous low density lipoprotein receptors expressed by hepatocytes). As provided herein, the composition can comprise a moiety capable of enhancing affinity of the composition to the target cell. Targeting moieties may be linked to the outer bilayer of the lipid particle during formulation or post-formulation. These methods are well known in the art. In addition, some lipid particle formulations may employ fusogenic polymers such as PEAA, hemagluttinin, other lipopeptides (see U.S. patent application Ser. No. 08/835,281, and 60/083,294, which are incorporated herein by reference) and other features useful for in vivo and/or intracellular delivery. In other some embodiments, the compositions of the present invention demonstrate improved transfection efficacies, and/or demonstrate enhanced selectivity towards target cells or tissues of interest. Contemplated therefore are compositions which comprise one or more moieties (e.g., peptides, aptamers, oligonucleotides, a vitamin or other molecules) that are capable of enhancing the affinity of the compositions and their nucleic acid contents for the target cells or tissues. Suitable moieties may optionally be bound or linked to the surface of the transfer vehicle. In some embodiments, the targeting moiety may span the surface of a transfer vehicle or be encapsulated within the transfer vehicle. Suitable moieties and are selected based upon their physical, chemical or biological properties (e.g., selective affinity and/or recognition of target cell surface markers or features). Cell-specific target sites and their corresponding targeting ligand can vary widely. Suitable targeting moieties are selected such that the unique characteristics of a target cell are exploited, thus allowing the composition to discriminate between target and non-target cells. For example, compositions of the invention may include surface markers (e.g., apolipoprotein-B or apolipoprotein-E) that selectively enhance recognition of, or affinity to hepatocytes (e.g., by receptor-mediated recognition of and binding to such surface markers). As an example, the use of galactose as a targeting moiety would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting moieties that have been conjugated to moieties present in the transfer vehicle (e.g., a lipid nanoparticle) therefore facilitate recognition and uptake of the compositions of the present invention in target cells and tissues. Examples of suitable targeting moieties include one or more peptides, proteins, aptamers, vitamins and oligonucleotides.

In particular embodiments, a transfer vehicle comprises a targeting moiety. In some embodiments, the targeting moiety mediates receptor-mediated endocytosis selectively into a specific population of cells. In some embodiments, the targeting moiety is capable of binding to a T cell antigen. In some embodiments, the targeting moiety is capable of binding to a NK, NKT, or macrophage antigen. In some embodiments, the targeting moiety is capable of binding to a protein selected from the group CD3, CD4, CD8, PD-1, 4-1BB, and CD2. In some embodiments, the targeting moiety is an single chain Fv (scFv) fragment, nanobody, peptide, peptide-based macrocycle, minibody, heavy chain variable region, light chain variable region or fragment thereof. In some embodiments, the targeting moiety is selected from T-cell receptor motif antibodies, T-cell α chain antibodies, T-cell β chain antibodies, T-cell γ chain antibodies, T-cell δ chain antibodies, CCR7 antibodies, CD3 antibodies, CD4 antibodies, CD5 antibodies, CD7 antibodies, CD8 antibodies, CD11b antibodies, CD11c antibodies, CD16 antibodies, CD19 antibodies, CD20 antibodies, CD21 antibodies, CD22 antibodies, CD25 antibodies, CD28 antibodies, CD34 antibodies, CD35 antibodies, CD40 antibodies, CD45RA antibodies, CD45RO antibodies, CD52 antibodies, CD56 antibodies, CD62L antibodies, CD68 antibodies, CD80 antibodies, CD95 antibodies, CD117 antibodies, CD127 antibodies, CD133 antibodies, CD137 (4-1BB) antibodies, CD163 antibodies, F4/80 antibodies, IL-4Rα antibodies, Sca-1 antibodies, CTLA-4 antibodies, GITR antibodies GARP antibodies, LAP antibodies, granzyme B antibodies, LFA-1 antibodies, transferrin receptor antibodies, and fragments thereof. In some embodiments, the targeting moiety is a small molecule binder of an ectoenzyme on lymphocytes. Small molecule binders of ectoenzymes include A2A inhibitors CD73 inhibitors, CD39 or adesines receptors A2aR and A2bR. Potential small molecules include AB928.

In some embodiments, transfer vehicles are formulated and/or targeted as described in Shobaki N, Sato Y, Harashima H. Mixing lipids to manipulate the ionization status of lipid nanoparticles for specific tissue targeting. Int J Nanomedicine. 2018; 13:8395-8410. Published 2018 Dec. 10. In some embodiments, a transfer vehicle is made up of 3 lipid types. In some embodiments, a transfer vehicle is made up of 4 lipid types. In some embodiments, a transfer vehicle is made up of 5 lipid types. In some embodiments, a transfer vehicle is made up of 6 lipid types.

B. Target Cells

Where it is desired to deliver a nucleic acid to an immune cell, the immune cell represents the target cell. In some embodiments, the compositions of the invention transfect the target cells on a discriminatory basis (i.e., do not transfect non-target cells). The compositions of the invention may also be prepared to preferentially target a variety of target cells, which include, but are not limited to, T cells, B cells, macrophages, and dentritic cells.

In some embodiments, the target cells are deficient in a protein or enzyme of interest. For example, where it is desired to deliver a nucleic acid to a hepatocyte, the hepatocyte represents the target cell. In some embodiments, the compositions of the invention transfect the target cells on a discriminatory basis (i.e., do not transfect non-target cells). The compositions of the invention may also be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

The compositions of the invention may be prepared to preferentially distribute to target cells such as in the heart, lungs, kidneys, liver, and spleen. In some embodiments, the compositions of the invention distribute into the cells of the liver or spleen to facilitate the delivery and the subsequent expression of the circRNA comprised therein by the cells of the liver (e.g., hepatocytes) or the cells of spleen (e.g., immune cells). The targeted cells may function as a biological "reservoir" or "depot" capable of producing, and systemically excreting a functional protein or enzyme. Accordingly, in one embodiment of the invention the transfer vehicle may target hepatocytes or immune cells and/or preferentially distribute to the cells of the liver or spleen upon delivery. In an embodiment, following transfection of the target hepatocytes or immune cells, the circRNA loaded in the vehicle are translated and a functional protein product is produced, excreted and systemically distributed. In other embodiments, cells other than hepatocytes (e.g., lung, spleen, heart, ocular, or cells of the central nervous system) can serve as a depot location for protein production.

In one embodiment, the compositions of the invention facilitate a subject's endogenous production of one or more functional proteins and/or enzymes. In an embodiment of the present invention, the transfer vehicles comprise circRNA which encode a deficient protein or enzyme. Upon distribution of such compositions to the target tissues and the subsequent transfection of such target cells, the exogenous circRNA loaded into the transfer vehicle (e.g., a lipid nanoparticle) may be translated in vivo to produce a functional protein or enzyme encoded by the exogenously administered circRNA (e.g., a protein or enzyme in which the subject is deficient). Accordingly, the compositions of the present invention exploit a subject's ability to translate exogenously- or recombinantly-prepared circRNA to produce an endogenously-translated protein or enzyme, and thereby produce (and where applicable excrete) a functional protein or enzyme. The expressed or translated proteins or enzymes may also be characterized by the in vivo inclusion of native post-translational modifications which may often be absent in recombinantly-prepared proteins or enzymes, thereby further reducing the immunogenicity of the translated protein or enzyme.

The administration of circRNA encoding a deficient protein or enzyme avoids the need to deliver the nucleic acids to specific organelles within a target cell. Rather, upon transfection of a target cell and delivery of the nucleic acids to the cytoplasm of the target cell, the circRNA contents of a transfer vehicle may be translated and a functional protein or enzyme expressed.

In some embodiments, a circular RNA comprises one or more miRNA binding sites. In some embodiments, a circular RNA comprises one or more miRNA binding sites recognized by miRNA present in one or more non-target cells or non-target cell types (e.g., Kupffer cells or hepatic cells) and not present in one or more target cells or target cell types (e.g., hepatocytes or T cells). In some embodiments, a circular RNA comprises one or more miRNA binding sites recognized by miRNA present in an increased concentration in one or more non-target cells or non-target cell types (e.g., Kupffer cells or hepatic cells) compared to one or more target cells or target cell types (e.g., hepatocytes or T cells). miRNAs are thought to function by pairing with complementary sequences within RNA molecules, resulting in gene silencing.

In some embodiments, the compositions of the invention transfect or distribute to target cells on a discriminatory basis (i.e. do not transfect non-target cells). The compositions of the invention may also be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

9. Pharmaceutical Compositions

In certain embodiments, provided herein are compositions (e.g., pharmaceutical compositions) comprising a therapeutic agent provided herein. In some embodiments, the therapeutic agent is a circular RNA polynucleotide provided herein. In some embodiments the therapeutic agent is a vector provided herein. In some embodiments, the therapeutic agent is a cell comprising a circular RNA or vector provided herein (e.g., a human cell, such as a human T cell). In certain embodiments, the composition further comprises a pharmaceutically acceptable carrier. In some embodiments, the compositions provided herein comprise a therapeutic agent provided herein in combination with other pharmaceutically active agents or drugs, such as anti-inflammatory drugs or antibodies capable of targeting B cell antigens, e.g., anti-CD20 antibodies, e.g., rituximab.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the therapeutic agent(s) and one which has no detrimental side effects or toxicity under the conditions of use.

The choice of carrier will be determined in part by the particular therapeutic agent, as well as by the particular method used to administer the therapeutic agent. Accordingly, there are a variety of suitable formulations of the pharmaceutical compositions provided herein.

In certain embodiments, the pharmaceutical composition comprises a preservative. In certain embodiments, suitable preservatives may include, for example, methylparaben, propylparaben, sodium benzoate, and benzalkonium chloride. Optionally, a mixture of two or more preservatives may be used. The preservative or mixtures thereof are typically present in an amount of about 0.0001% to about 2% by weight of the total composition.

In some embodiments, the pharmaceutical composition comprises a buffering agent. In some embodiments, suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

In some embodiments, the concentration of therapeutic agent in the pharmaceutical composition can vary, e.g., less than about 1%, or at least about 1%, 2%, 3%, 4%, 5%, 6%, 7%, 8%, 9% 10%, 15%, 20%, 25%, 30%, 35%, 40%, 45%, or about 50% or more by weight, and can be selected primarily by fluid volumes, and viscosities, in accordance with the particular mode of administration selected.

The following formulations for oral, aerosol, parenteral (e.g., subcutaneous, intravenous, intraarterial, intramuscular, intradermal, intraperitoneal, and intrathecal), and topical administration are merely exemplary and are in no way limiting. More than one route can be used to administer the therapeutic agents provided herein, and in certain instances, a particular route can provide a more immediate and more effective response than another route.

Formulations suitable for oral administration can comprise or consist of (a) liquid solutions, such as an effective amount of the therapeutic agent dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol and the polyethylene alcohols, either with or without the addition of a pharmaceutically acceptable surfactant. Capsule forms can be of the ordinary hard or soft shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the therapeutic agent with a flavorant, usually sucrose, acacia or tragacanth. Pastilles can comprise the therapeutic agent with an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In some embodiments, the therapeutic agents provided herein can be administered in a physiologically acceptable diluent in a pharmaceutical carrier, such as a sterile liquid or mixture of liquids including water, saline, aqueous dextrose and related sugar solutions, an alcohol such as ethanol or hexadecyl alcohol, a glycol such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agents and other pharmaceutical adjuvants.

Oils, which can be used in parenteral formulations in some embodiments, include petroleum, animal oils, vegetable oils, or synthetic oils. Specific examples of oils include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in certain embodiments of parenteral formulations include fatty alkali metal, ammonium, and triethanolamine salts, and suitable detergents include (a) cationic detergents such as, for example, dimethyl dialkyl ammonium halides. and alkyl pyridinium halides, (b) anionic detergents such as, for example, alkyl, aryl, and olefin sulfonates, alky, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

In some embodiments, the parenteral formulations will contain, for example, from about 0.5% to about 25% by weight of the therapeutic agent in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol, sorbitan, fatty acid esters such as sorbitan monooleate, and high molecular weight adducts of ethylene oxide with a hydrophobic base formed by the condensation of propylene oxide with propylene glycol. The parenteral formulations can be presented in unit-dose or multi-dose sealed containers, such as ampoules or vials, and can be stored in a freeze-dried (lyophilized) condition requiring only the addition of a sterile liquid excipient, for example, water for injections, immediately prior to use. Extemporaneous injection solutions and suspensions can be prepared from sterile powders, granules, and tablets of the kind previously described.

In certain embodiments, injectable formulations are provided herein. The requirements for effective pharmaceutical carriers for injectable compositions are well-known to those of ordinary skill in the art (see, e.g., Pharmaceutics and Pharmacy Practice, J. B. Lippincott Company, Philadelphia, PA, Banker and Chalmers, eds., pages 238-250 (1982), and ASHP Handbook on Injectable Drugs, Toissel, 4th ed, pages 622-630 (1986)).

In some embodiments, topical formulations are provided herein. Topical formulations, including those that are useful for transdermal drug release, are suitable in the context of certain embodiments provided herein for application to skin. In some embodiments, the therapeutic agent alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

In certain embodiments, the therapeutic agents provided herein can be formulated as inclusion complexes, such as cyclodextrin inclusion complexes, or liposomes. Liposomes can serve to target the therapeutic agents to a particular tissue. Liposomes also can be used to increase the half-life of the therapeutic agents. Many methods are available for preparing liposomes, as described in, for example, Szoka et al., Ann. Rev. Biophys. Bioeng., 9, 467 (1980) and U.S. Pat. Nos. 4,235,871, 4,501,728, 4,837,028, and 5,019,369.

In some embodiments, the therapeutic agents provided herein are formulated in time-released, delayed release, or sustained release delivery systems such that the delivery of the composition occurs prior to, and with sufficient time to, cause sensitization of the site to be treated. Such systems can avoid repeated administrations of the therapeutic agent, thereby increasing convenience to the subject and the physician, and may be particularly suitable for certain composition embodiments provided herein. In one embodiment, the compositions of the invention are formulated such that they are suitable for extended-release of the circRNA contained therein. Such extended-release compositions may be conveniently administered to a subject at extended dosing intervals. For example, in one embodiment, the compositions of the present invention are administered to a subject twice a day, daily or every other day. In an embodiment, the compositions of the present invention are administered to a subject twice a week, once a week, every ten days, every two weeks, every three weeks, every four weeks, once a month, every six weeks, every eight weeks, every three months, every four months, every six months, every eight months, every nine months or annually.

In some embodiments, a protein encoded by an inventive polynucleotide is produced by a target cell for sustained amounts of time. For example, the protein may be produced for more than one hour, more than four, more than six, more than 12, more than 24, more than 48 hours, or more than 72 hours after administration. In some embodiments the polypeptide is expressed at a peak level about six hours after administration. In some embodiments the expression of the polypeptide is sustained at least at a therapeutic level. In some embodiments, the polypeptide is expressed at least at a therapeutic level for more than one, more than four, more than six, more than 12, more than 24, more than 48, or more than 72 hours after administration. In some embodiments, the polypeptide is detectable at a therapeutic level in patient tissue (e.g., liver or lung). In some embodiments, the level of detectable polypeptide is from continuous expression from the circRNA composition over periods of time of more than one, more than four, more than six, more than 12, more than 24, more than 48, or more than 72 hours after administration.

In certain embodiments, a protein encoded by an inventive polynucleotide is produced at levels above normal physiological levels. The level of protein may be increased as compared to a control. In some embodiments, the control is the baseline physiological level of the polypeptide in a normal individual or in a population of normal individuals. In other embodiments, the control is the baseline physiological level of the polypeptide in an individual having a deficiency in the relevant protein or polypeptide or in a population of individuals having a deficiency in the relevant protein or polypeptide. In some embodiments, the control can be the normal level of the relevant protein or polypeptide in the individual to whom the composition is administered. In other embodiments, the control is the expression level of the polypeptide upon other therapeutic intervention, e.g., upon direct injection of the corresponding polypeptide, at one or more comparable time points.

In certain embodiments, the levels of a protein encoded by an inventive polynucleotide are detectable at 3 days, 4 days, 5 days, or 1 week or more after administration. Increased levels of protein may be observed in a tissue (e.g., liver or lung).

In some embodiments, the method yields a sustained circulation half-life of a protein encoded by an inventive polynucleotide. For example, the protein may be detected for hours or days longer than the half-life observed via subcutaneous injection of the protein or mRNA encoding the protein. In some embodiments, the half-life of the protein is 1 day, 2 days, 3 days, 4 days, 5 days, or 1 week or more.

Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems: wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

In some embodiments, the therapeutic agent can be conjugated either directly or indirectly through a linking moiety to a targeting moiety. Methods for conjugating therapeutic agents to targeting moieties is known in the art. See, for instance, Wadwa et al., J, Drug Targeting 3:111 (1995) and U.S. Pat. No. 5,087,616.

In some embodiments, the therapeutic agents provided herein are formulated into a depot form, such that the manner in which the therapeutic agent is released into the body to which it is administered is controlled with respect to time and location within the body (see, for example, U.S. Pat. No. 4,450,150). Depot forms of therapeutic agents can be, for example, an implantable composition comprising the therapeutic agents and a porous or non-porous material, such as a polymer, wherein the therapeutic agents are encapsulated by or diffused throughout the material and/or degradation of the non-porous material. The depot is then implanted into the desired location within the body and the therapeutic agents are released from the implant at a predetermined rate.

10. Therapeutic Methods

A. Areas for Treatment & Relevant Diseases/Disorders

In certain aspects, provided herein is a method of treating and/or preventing a condition, e.g., an autoimmune disorder or cancer.

In certain embodiments, the therapeutic agents provided herein are co-administered with one or more additional therapeutic agents (e.g., in the same pharmaceutical composition or in separate pharmaceutical compositions). In some embodiments, the therapeutic agent provided herein can be administered first and the one or more additional therapeutic agents can be administered second, or vice versa. Alternatively, the therapeutic agent provided herein and the one or more additional therapeutic agents can be administered simultaneously.

In some embodiments, the subject is a mammal. In some embodiments, the mammal referred to herein can be any mammal, including, but not limited to, mammals of the order Rodentia, such as mice and hamsters, or mammals of the order Logomorpha, such as rabbits. The mammals may be from the order Carnivora, including Felines (cats) and Canines (dogs). The mammals may be from the order Artiodactyla, including Bovines (cows) and Swines (pigs), or of the order Perssodactyla, including Equines (horses). The mammals may be of the order Primates, Ceboids, or Simoids (monkeys) or of the order Anthropoids (humans and apes). Preferably, the mammal is a human.

11. Additional Embodiments

The invention is further described by the following non-limiting exemplary embodiments:

Embodiment 1. A pharmaceutical composition comprising:
a. an RNA polynucleotide, and
b. a transfer vehicle comprising an ionizable lipid represented by Formula (13):

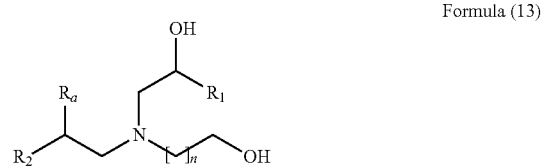

Formula (13)

wherein:
n is an integer between 1 and 4;
$R_a$ is hydrogen or hydroxyl;
$R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;
with the proviso that the ionizable lipid is not

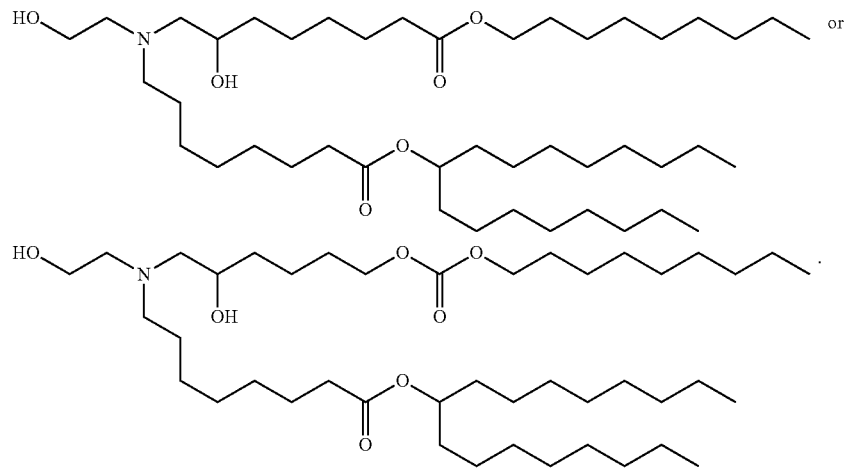

Embodiment 2. The pharmaceutical composition of embodiment 1, wherein $R_a$ is hydrogen.

Embodiment 3. The pharmaceutical composition of embodiment 2, wherein the ionizable lipid is represented by Formula (13a-1), Formula (13a-2), or Formula (13a-3):

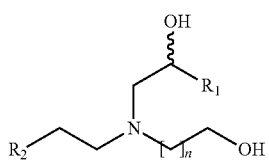

Formula (13a-1)

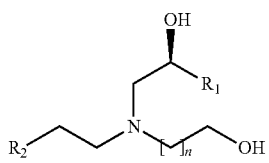

Formula (13a-2)

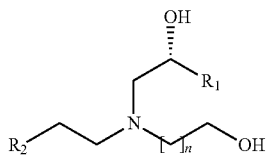

Formula (13a-3)

Embodiment 4. The pharmaceutical composition of embodiment 1, wherein $R_a$ is hydroxyl.

Embodiment 5. The pharmaceutical composition of embodiment 4, wherein the ionizable lipid is represented by Formula (13b-1), Formula (13b-2), or Formula (13b-3):

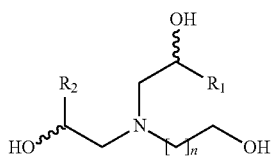

Formula (13b-1)

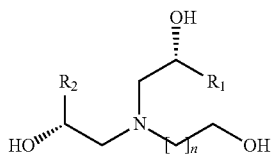

Formula (13b-2)

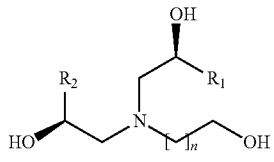

Formula (13b-3)

Embodiment 6. The pharmaceutical composition of embodiment 4, wherein the ionizable lipid is represented by Formula (13b-4), Formula (13b-5), Formula (13b-6), Formula (13b-7), Formula (13b-8), or Formula (13b-9):

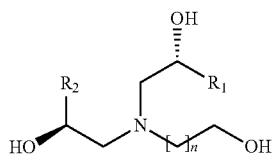

Formula (13b-4)

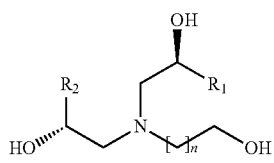

Formula (13b-5)

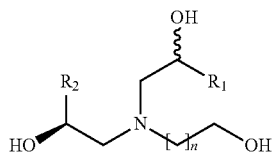

Formula (13b-6)

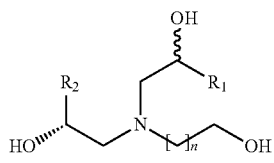

Formula (13b-7)

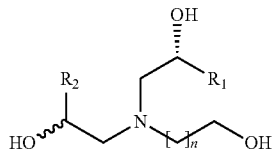

Formula (13b-8)

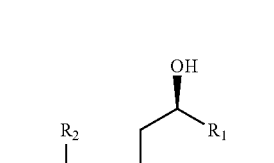

Formula (13b-9)

Embodiment 7. The pharmaceutical composition of any one of embodiments 1-6, wherein $R_1$ and $R_2$ are each independently selected from the group consisting of:

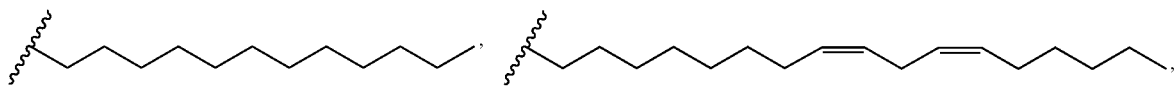

-continued
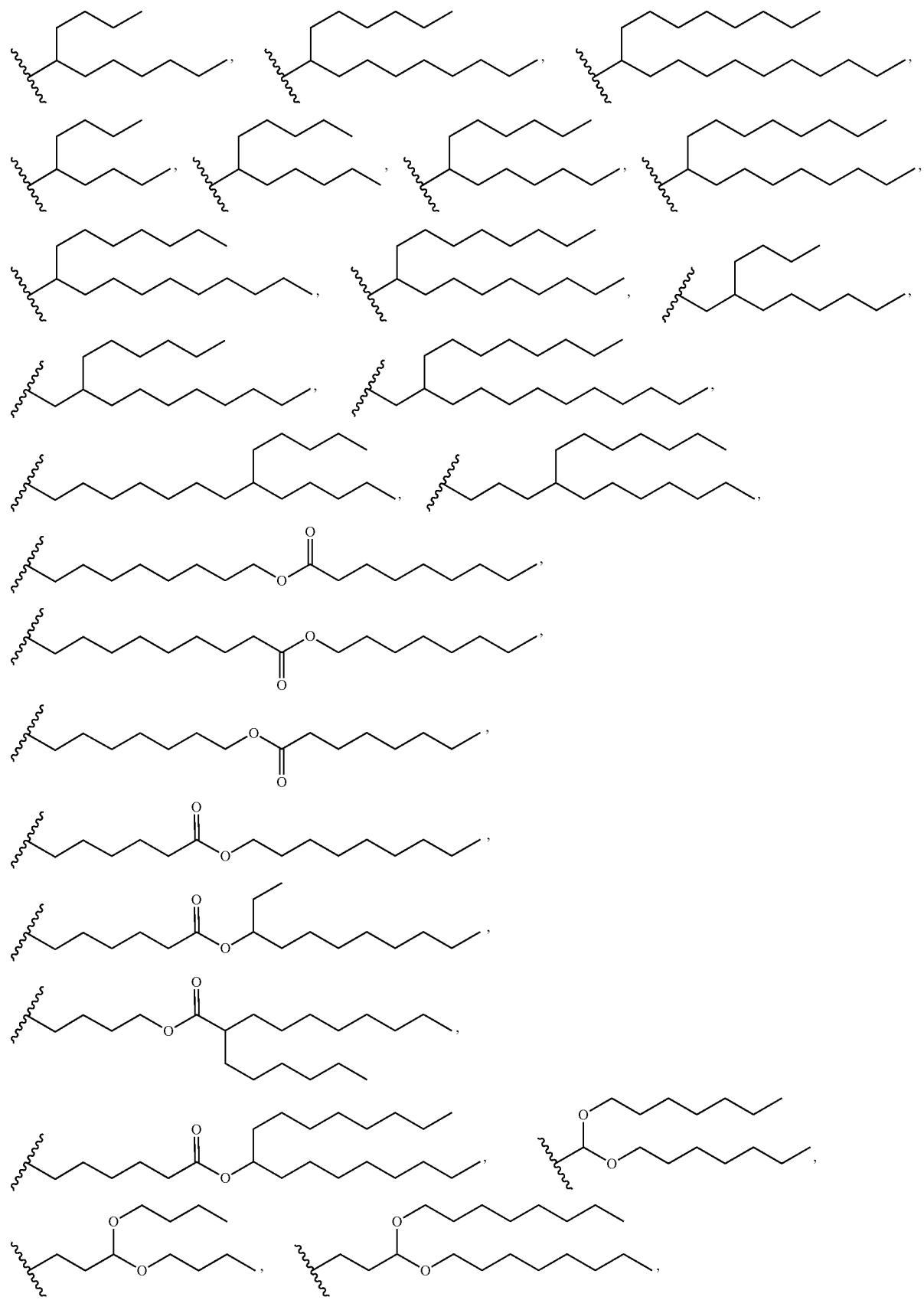

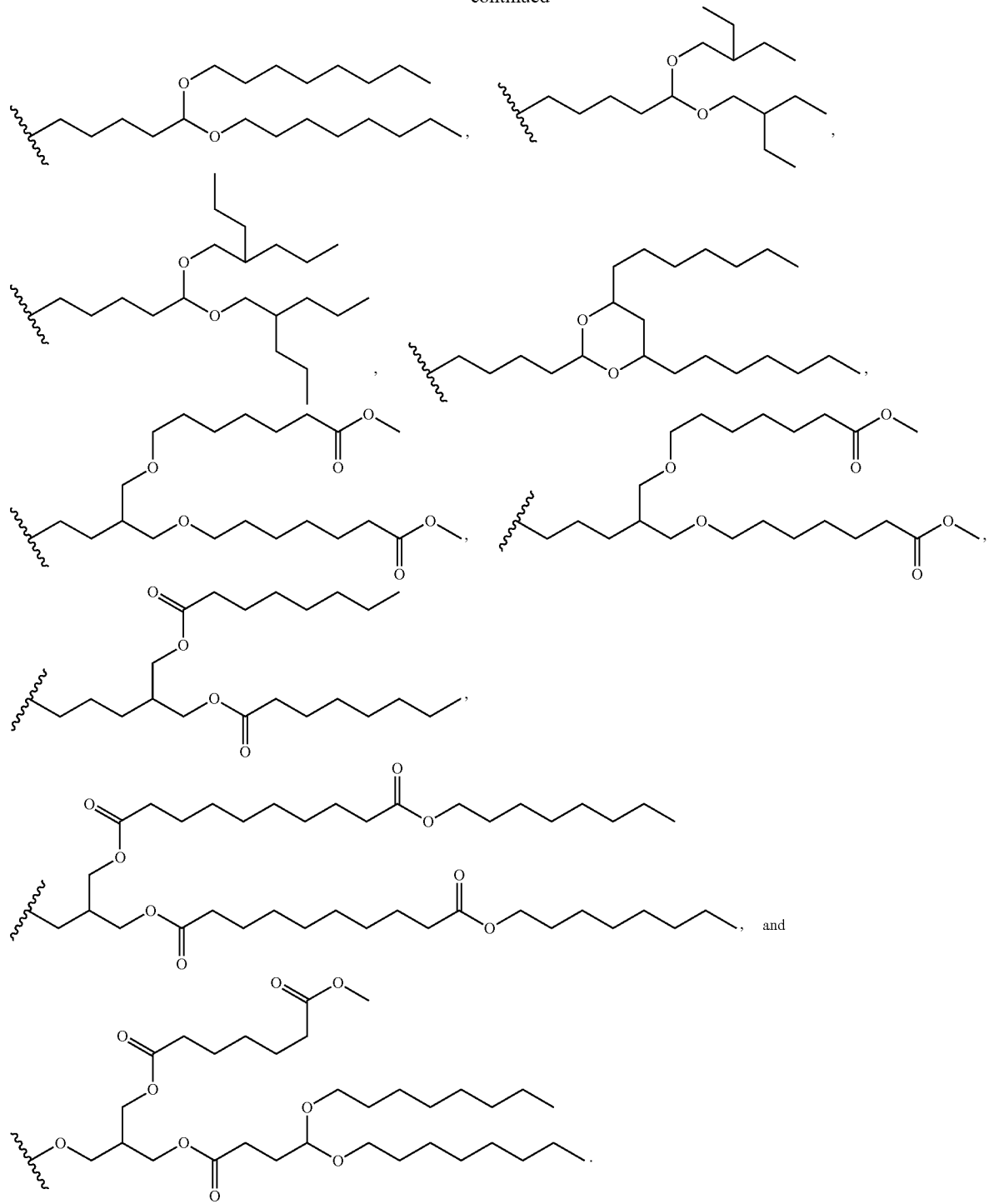
Embodiment 8. The pharmaceutical composition of any one of embodiments 1-7, wherein $R_1$ and $R_2$ are the same.
Embodiment 9. The pharmaceutical composition of any one of embodiments 1-7, wherein $R_1$ and $R_2$ are different.
Embodiment 10. The pharmaceutical composition of any one of embodiments 1-9, wherein the ionizable lipid is selected from the group consisting of

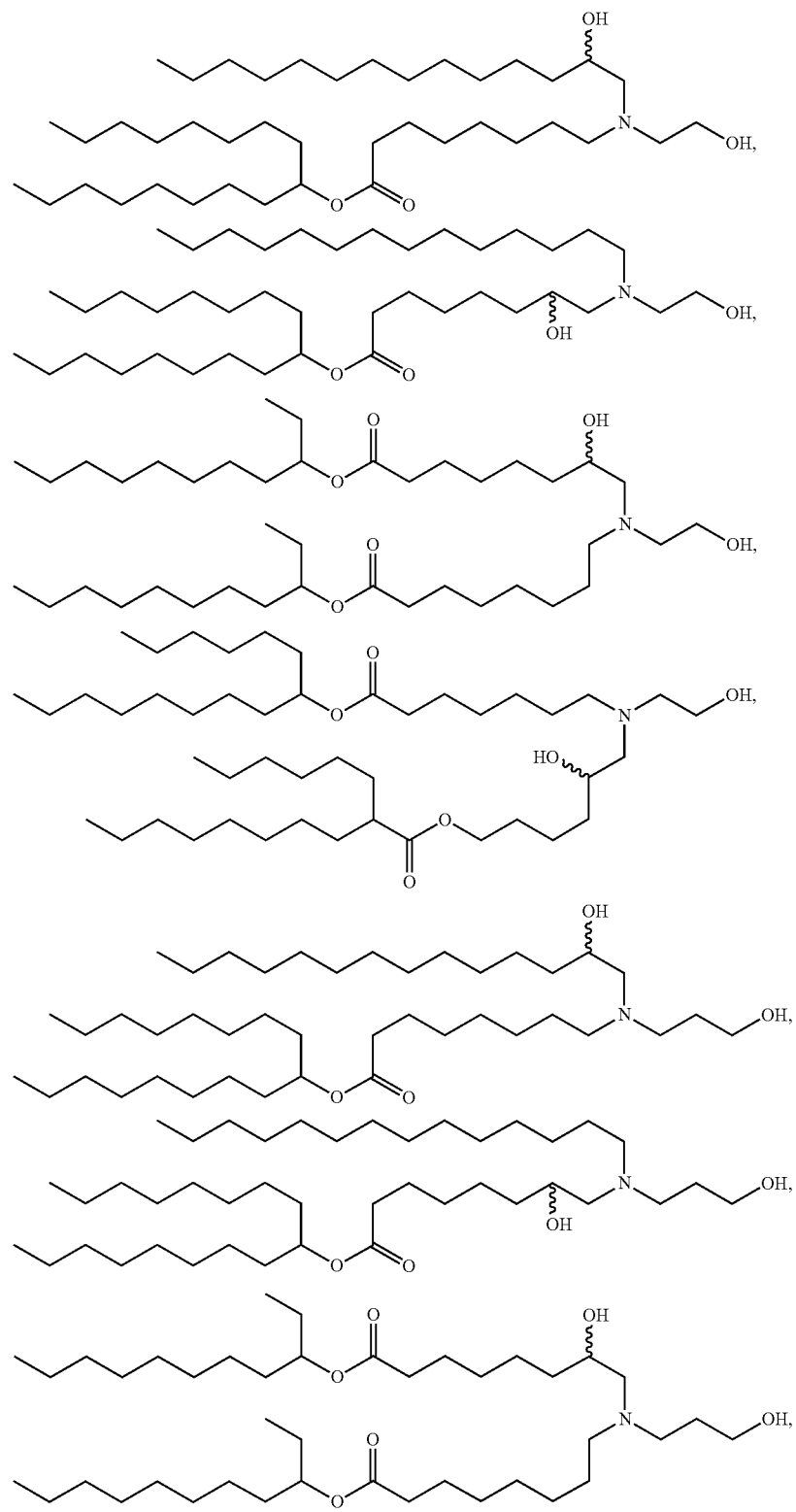

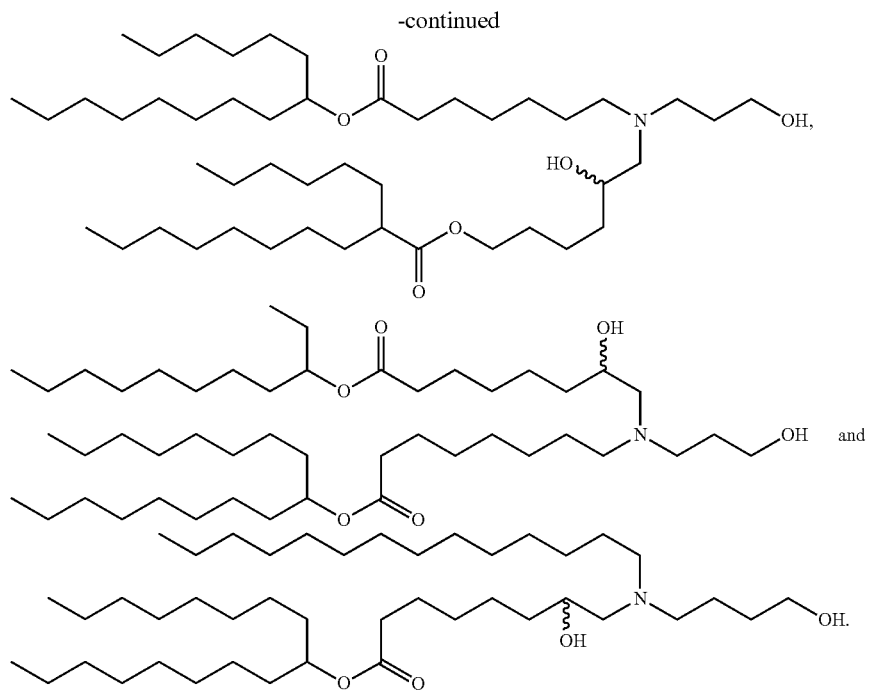

Embodiment 11. The pharmaceutical composition of any one of embodiments 1-9, wherein the ionizable lipid is selected from the group consisting of

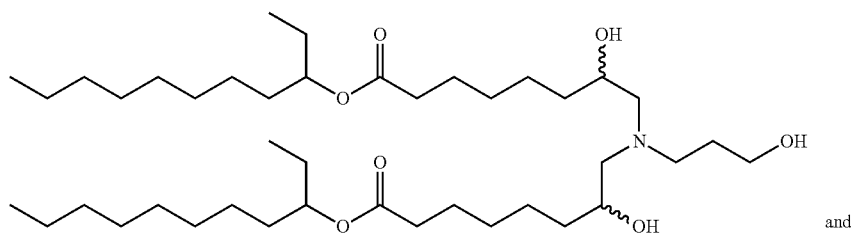

Embodiment 12. The pharmaceutical composition of any one of embodiments 1-9, wherein the ionizable lipid is selected from Table 10e.

Embodiment 13. The pharmaceutical composition of any one of embodiments 1-12, wherein the RNA polynucleotide is a linear or circular RNA polynucleotide.

Embodiment 14. The pharmaceutical composition of any one of embodiments 1-13, wherein the RNA polynucleotide is a circular RNA polynucleotide.

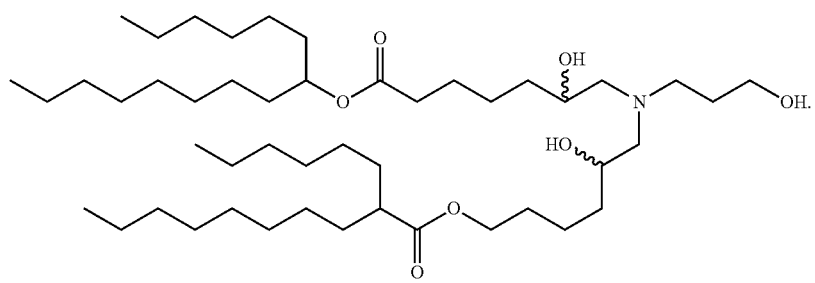

Embodiment 15. A pharmaceutical composition comprising:
a. an RNA polynucleotide, wherein the RNA polynucleotide is a circular RNA polynucleotide, and
b. a transfer vehicle comprising an ionizable lipid selected from

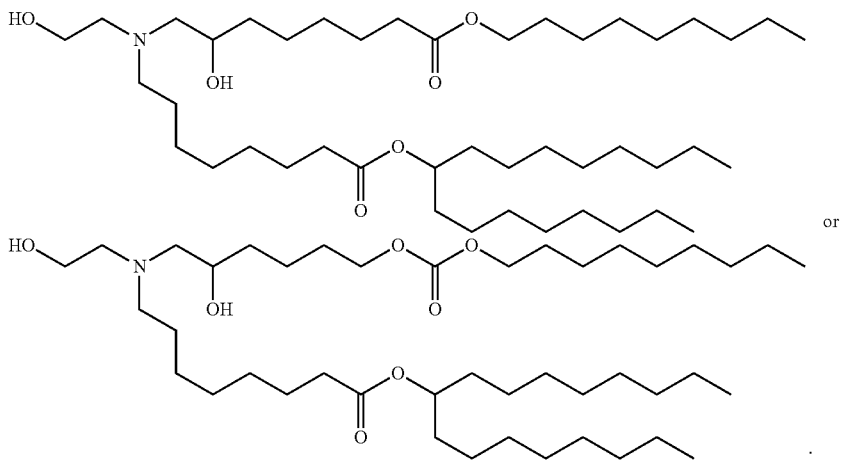

or

Embodiment 16. The pharmaceutical composition of any one of embodiments 1-15, wherein the RNA polynucleotide is encapsulated in the transfer vehicle.

Embodiment 17. The pharmaceutical composition of any one of embodiments 1-16, wherein the RNA polynucleotide is encapsulated in the transfer vehicle with an encapsulation efficiency of at least 80%.

Embodiment 18. The pharmaceutical composition of any one of embodiments 1-14, wherein the RNA comprises a first expression sequence.

Embodiment 19. The pharmaceutical composition of embodiment 18, wherein the first expression sequence encodes a therapeutic protein.

Embodiment 20. The pharmaceutical composition of embodiment 19, wherein the first expression sequence encodes a cytokine or a functional fragment thereof.

Embodiment 21. The pharmaceutical composition of embodiment 19, wherein the first expression sequence encodes a transcription factor.

Embodiment 22. The pharmaceutical composition of embodiment 19, wherein the first expression sequence encodes an immune checkpoint inhibitor.

Embodiment 23. The pharmaceutical composition of embodiment 19, wherein the first expression sequence encodes a chimeric antigen receptor (CAR).

Embodiment 24. The pharmaceutical composition of any one of embodiments 1-23, wherein the RNA polynucleotide further comprises a second expression sequence.

Embodiment 25. The pharmaceutical composition of embodiment 24, wherein the RNA polynucleotide further comprises an internal ribosome entry site (IRES).

Embodiment 26. The pharmaceutical composition of embodiment 25, wherein the first and second expression sequences are separated by a ribosomal skipping element or a nucleotide sequence encoding a protease cleavage site.

Embodiment 27. The pharmaceutical composition of any one of embodiments 24 or 26, wherein the first expression sequence encodes a first T-cell receptor (TCR) chain, and the second expression sequence encodes a second TCR chain.

Embodiment 28. The pharmaceutical composition of any one of embodiments 1-27, wherein the RNA polynucleotide comprises one or more microRNA binding sites.

Embodiment 29. The pharmaceutical composition of embodiment 28, wherein the microRNA binding site is recognized by a microRNA expressed in the liver.

Embodiment 30. The pharmaceutical composition of embodiment 28 or 29, wherein the microRNA binding site is recognized by miR-122.

Embodiment 31. The pharmaceutical composition of any one of embodiments 1-30, wherein the RNA polynucleotide comprises a first IRES associated with greater protein expression in a human immune cell than in a reference human cell.

Embodiment 32. The pharmaceutical composition of embodiment 31, wherein the human immune cell is a T cell, an NK cell, an NKT cell, a macrophage, or a neutrophil.

Embodiment 33. The pharmaceutical composition of embodiment 31 or 32, wherein the reference human cell is a hepatic cell.

Embodiment 34. The pharmaceutical composition of any one of embodiments 1-33, wherein the RNA polynucleotide comprises, in the following order:
a. a 5' enhanced exon element,
b. a core functional element, and
c. a 3' enhanced exon element.

Embodiment 35. The pharmaceutical composition of any one of embodiments 1-34, further comprising a post-splicing intron fragment.

Embodiment 36. The pharmaceutical composition of embodiment 34 or 35, wherein the 5' enhanced exon element comprises a 3' exon fragment.

Embodiment 37. The pharmaceutical composition of any one of embodiments 34-36, wherein the 5' enhanced exon element comprises a 5' internal duplex region located downstream to the 3' exon fragment.

Embodiment 38. The pharmaceutical composition of any one of embodiments 34-37, wherein the 5' enhanced exon element comprises a 5' internal spacer located downstream to the 3' exon fragment.

Embodiment 39. The pharmaceutical composition of embodiment 38, wherein the 5' internal spacer has a length of about 10 to about 60 nucleotides.

Embodiment 40. The pharmaceutical composition of embodiment 38 or 39, wherein the 5' internal spacer comprises a polyA or polyA-C sequence.

Embodiment 41. The pharmaceutical composition of embodiment 40, wherein the polyA or polyA-C sequence comprises a length of about 10-50 nucleotides.

Embodiment 42. The pharmaceutical composition of any one of embodiments 34-41, wherein the core functional element comprises a translation initiation element (TIE).

Embodiment 43. The pharmaceutical composition of any one of embodiments 42, wherein the translation initiation element (TIE) comprises an untranslated region (UTR) or fragment thereof.

Embodiment 44. The pharmaceutical composition of embodiment 43, wherein the UTR or fragment thereof comprises a viral internal ribosome entry site (IRES) or eukaryotic IRES.

Embodiment 45. The pharmaceutical composition of embodiment 44, wherein the IRES is selected from Table 17, or is a functional fragment or variant thereof.

Embodiment 46. The pharmaceutical composition of embodiment 44 or 45, wherein the IRES has a sequence in whole or in part from a Taura syndrome virus, Triatoma virus, Theiler's encephalomyelitis virus, Simian Virus 40, Solenopsis invicta virus 1, Rhopalosiphum padi virus, Reticuloendotheliosis virus, Human poliovirus 1, Plautia stali intestine virus, Kashmir bee virus, Human rhinovirus 2, Homalodisca coagulata virus-1, Human Immunodeficiency Virus type 1, Homalodisca coagulata virus-1, Himetobi P virus, Hepatitis C virus, Hepatitis A virus, Hepatitis GB virus, Foot and mouth disease virus, Human enterovirus 71, Equine rhinitis virus, Ectropis obliqua picorna-like virus, Encephalomyocarditis virus, Drosophila C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, Drosophila antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kipl, Human PDGF2/c-sis, Human p53, Human Pim-1, Mouse Rbm3, Drosophila reaper, Canine Scamper, Drosophila Ubx, Human UNR, Mouse UtrA, Human VEGF-A, Human XIAP, Drosophila hairless, S. cerevisiae TFIID, S. cerevisiae YAP1, tobacco etch virus, turnip crinkle virus, EMCV-A, EMCV-B, EMCV-Bf, EMCV-Cf, EMCV pEC9, Picobirnavirus, HCV QC64, Human Cosavirus E/D, Human Cosavirus F, Human Cosavirus JMY, Rhinovirus NAT001, HRV14, HRV89, HRVC-02, HRV-A21, Salivirus A SH1, Salivirus FHB, Salivirus NG-J1, Human Parechovirus 1, Crohivirus B, Yc-3, Rosavirus M-7, Shanbavirus A, Pasivirus A, Pasivirus A 2, Echovirus E14, Human Parechovirus 5, Aichi Virus, Hepatitis A Virus HA16, Phopivirus, CVA10, Enterovirus C, Enterovirus D, Enterovirus J, Human Pegivirus 2, GBV-C GT110, GBV-C K1737, GBV-C Iowa, Pegivirus A 1220, Pasivirus A 3, Sapelovirus, Rosavirus B, Bakunsa Virus, Tremovirus A, Swine Pasivirus 1, PLV-CHN, Pasivirus A, Sicinivirus, Hepacivirus K, Hepacivirus A, BVDV1, Border Disease Virus, BVDV2, CSFV—PK15C, SF573 Dicistrovirus, Hubei Picorna-like Virus, CRPV, Apodemus Agrarius Picornavirus, Caprine Koburvirus, Parabovirus, Salivirus A BN5, Salivirus A BN2, Salivirus A 02394, Salivirus A GUT, Salivirus A CH, Salivirus A SZ1, Salivirus FHB, CVB3, CVB1, Echovirus 7, CVB5, EVA71, CVA3, CVA12, EV24, or an aptamer to eIF4G.

Embodiment 47. The pharmaceutical composition of any one of embodiments 42-46, wherein the translation initiation element (TIE) comprises an aptamer complex.

Embodiment 48. The pharmaceutical composition of embodiment 42, wherein the aptamer complex comprises at least two aptamers.

Embodiment 49. The pharmaceutical composition of any one of embodiments 34-48, wherein the core functional element comprises a coding region.

Embodiment 50. The pharmaceutical composition of embodiment 49, wherein the coding region encodes for a therapeutic protein.

Embodiment 51. The pharmaceutical composition of embodiment 50, wherein the therapeutic protein is a chimeric antigen receptor (CAR), a cytokine, a transcription factor, a T cell receptor (TCR), B-cell receptor (BCR), ligand, immune cell activation or inhibitory receptor, recombinant fusion protein, chimeric mutant protein, or fusion protein or a functional fragment thereof.

Embodiment 52. The pharmaceutical composition of embodiment 51, wherein the therapeutic protein is an antigen.

Embodiment 53. The pharmaceutical composition of embodiment 52, wherein the antigen is a viral polypeptide from an adenovirus; Herpes simplex, type 1; Herpes simplex, type 2; encephalitis virus, papillomavirus, Varicella-zoster virus; Epstein-barr virus; Human cytomegalovirus; Human herpes virus, type 8; Human papillomavirus; BK virus; JC virus; Smallpox; polio virus; Hepatitis B virus; Human bocavirus; Parvovirus B19; Human astrovirus; Norwalk virus; coxsackievirus; hepatitis A virus; poliovirus; rhinovirus; Severe acute respiratory syndrome virus; Hepatitis C virus; Yellow Fever virus; Dengue virus; West Nile virus; Rubella virus; Hepatitis E virus; Human Immunodeficiency virus (HIV); Influenza virus; Guanarito virus; Junin virus; Lassa virus; Machupo virus; Sabia virus; Crimean-Congo hemorrhagic fever virus; Ebola virus; Marburg virus; Measles virus; Mumps virus; Parainfluenza virus; Respiratory syncytial virus; Human metapneumo virus; Hendra virus; Nipah virus; Rabies virus; Hepatitis D; Rotavirus; Orbivirus; Coltivirus; Banna virus; Human Enterovirus; Hanta virus; West Nile virus; Middle East Respiratory Syndrome Corona Virus; Japanese encephalitis virus; Vesicular exanthernavirus; SARS-CoV-2; Eastern equine encephalitis, or a combination of any two or more of the foregoing.

Embodiment 54. The pharmaceutical composition of any one of embodiments 34-53, wherein the core functional element comprises a stop codon or a stop cassette.

Embodiment 55. The pharmaceutical composition of any one of embodiment 34-53, wherein the core functional element comprises a noncoding region.

Embodiment 56. The pharmaceutical composition of any one of embodiment 34-53, wherein the core functional element comprises an accessory or modulatory element.

Embodiment 57. The pharmaceutical composition of embodiment 56, wherein the accessory or modulatory element comprises a miRNA binding site or a fragment thereof, a restriction site or a fragment thereof, a RNA editing motif or a fragment thereof, a zip code element or a fragment thereof, a RNA trafficking element or fragment thereof, or a combination thereof.

Embodiment 58. The pharmaceutical composition of embodiment 56, wherein the accessory or modulatory element comprises a binding domain to an IRES transacting factor (ITAF).

Embodiment 59. The pharmaceutical composition of any one of embodiments 34-58, wherein the 3' enhanced exon element comprises a 5' exon fragment.

Embodiment 60. The pharmaceutical composition of embodiments 59, wherein the 3' enhanced exon element comprises a 3' internal spacer located upstream to the 5' exon fragment.

Embodiment 61. The pharmaceutical composition of embodiment 60, wherein the 3' internal spacer is a polyA or polyA-C sequence.

Embodiment 62. The pharmaceutical composition of embodiment 60 or 61, wherein the 3' internal spacer has a length of about 10 to about 60 nucleotides.

Embodiment 63. The pharmaceutical composition of any one of embodiments 59-62, wherein the 3' enhanced exon element comprises a 3' internal duplex element located upstream to the 5' exon fragment.

Embodiment 64. The pharmaceutical composition of any one of embodiments 1-63, wherein the RNA polynucleotide is made via circularization of a RNA polynucleotide comprising, in the following order:
  a. a 5' enhanced intron element,
  b. a 5' enhanced exon element,
  c. a core functional element,
  d. a 3' enhanced exon element, and
  e. a 3' enhanced intron element.

Embodiment 65. The pharmaceutical composition of embodiment 64, wherein the 5' enhanced intron element comprises a 3' intron fragment.

Embodiment 66. The pharmaceutical composition of embodiment 65, wherein the 3' intron fragment comprises a first or a first and second nucleotide of a 3' group I intron splice site dinucleotide.

Embodiment 67. The pharmaceutical composition of embodiment 64 or 65, wherein the 5' enhanced intron element comprises a 5' affinity tag located upstream to the 3' intron fragment.

Embodiment 68. The pharmaceutical composition of any one of embodiments 65-67, wherein the 5' enhanced intron element comprises a 5' external spacer located upstream to the 3' intron fragment.

Embodiment 69. The pharmaceutical composition of any one of embodiments 64-68, wherein the 5' enhanced intron element comprises a leading untranslated sequence located at the 5' end of said 5' enhanced intron element.

Embodiment 70. The pharmaceutical composition of any one of embodiments 64-69, wherein the 3' enhanced intron element comprises a 5' intron fragment.

Embodiment 71. The pharmaceutical composition of any one of embodiments 64-70, wherein the 3' enhanced intron element comprises a 3' external spacer located downstream to the 5' intron fragment.

Embodiment 72. The pharmaceutical composition of any one of embodiments 64-71, wherein the 3' enhanced intron element comprises a 3' affinity tag located downstream to the 5' intron fragment.

Embodiment 73. The pharmaceutical composition of any one of embodiments 64-72, wherein the 3' enhanced intron element comprises a 3' terminal untranslated sequence at the 3' end of the said 5' enhanced intron element.

Embodiment 74. The pharmaceutical composition of any one of embodiments 64-73, wherein the 5' enhanced intron element comprises a 5' external duplex region upstream to the 3' intron fragment, and the 3' enhanced intron element comprises a 3' external duplex region downstream to the 5' intron fragment.

Embodiment 75. The pharmaceutical composition of embodiment 74, wherein the 5' external duplex region and the 3' external duplex region are the same.

Embodiment 76. The pharmaceutical composition of embodiment 74, wherein the 5' external duplex region and the 3' external duplex region are different.

Embodiment 77. The pharmaceutical composition of any one of embodiments 66-76, wherein the group I intron comprises in part or in whole from a bacterial phage, viral vector, organelle genome, or a nuclear rDNA gene.

Embodiment 78. The pharmaceutical composition of embodiment 77, wherein the nuclear rDNA gene comprises a nuclear rDNA gene derived from a fungi, plant, or algae, or a fragment thereof.

Embodiment 79. The pharmaceutical composition of any one of embodiments 1-78, wherein the RNA polynucleotide contains at least about 80%, at least about 90%, at least about 95%, or at least about 99% naturally occurring nucleotides.

Embodiment 80. The pharmaceutical composition of any one of embodiments 1-79, wherein the RNA polynucleotide consists of naturally occurring nucleotides.

Embodiment 81. The pharmaceutical composition of any one of embodiments 34-80, wherein the expression sequence is codon optimized.

Embodiment 82. The pharmaceutical composition of any one of embodiments 1-81, wherein the RNA polynucleotide is optimized to lack at least one microRNA binding site present in an equivalent pre-optimized polynucleotide.

Embodiment 83. The pharmaceutical composition of any one of embodiments 1-82, wherein the RNA polynucleotide is optimized to lack at least one microRNA binding site capable of binding to a microRNA present in a cell within which the RNA polynucleotide is expressed.

Embodiment 84. The pharmaceutical composition of any one of embodiments 1-83, wherein the RNA polynucleotide is optimized to lack at least one endonuclease susceptible site present in an equivalent pre-optimized polynucleotide.

Embodiment 85. The pharmaceutical composition of any one of embodiments 1-84, wherein the RNA polynucleotide is optimized to lack at least one endonuclease susceptible site capable of being cleaved by an endonuclease present in a cell within which the endonuclease is expressed.

Embodiment 86. The pharmaceutical composition of any one of embodiments 1-85, wherein the RNA polynucleotide is optimized to lack at least one RNA editing susceptible site present in an equivalent pre-optimized polynucleotide.

Embodiment 87. The pharmaceutical composition of any one of embodiments 1-86, wherein the RNA polynucleotide is from about 100 nt to about 10,000 nt in length.

Embodiment 88. The pharmaceutical composition of any one of embodiments 1-87, wherein the RNA polynucleotide is from about 100 nt to about 15,000 nt in length.

Embodiment 89. The pharmaceutical composition of any one of embodiments 1-88, wherein the RNA polynucleotide is a circular RNA polynucleotide, and wherein the circular RNA polynucleotide is more compact than a reference linear RNA polynucleotide having the same expression sequence as the circular RNA polynucleotide.

Embodiment 90. The pharmaceutical composition of any one of embodiments 1-89, wherein the RNA polynucleotide is a circular RNA polynucleotide, and wherein the composition has a duration of therapeutic effect in a human cell greater than or equal to that of a composition comprising a reference linear RNA polynucleotide having the same expression sequence as the circular RNA polynucleotide.

Embodiment 91. The pharmaceutical composition of embodiment 90, wherein the reference linear RNA polynucleotide is a linear, unmodified or nucleoside-modified, fully-processed mRNA comprising a cap1 structure and a polyA tail at least 80 nt in length.

Embodiment 92. The pharmaceutical composition of any one of embodiments 1-91, wherein the RNA polynucleotide is a circular RNA polynucleotide, and wherein the composition has a duration of therapeutic effect in vivo in humans greater than that of a composition comprising a reference linear RNA polynucleotide having the same expression sequence as the circular RNA polynucleotide.

Embodiment 93. The pharmaceutical composition of any one of embodiments 1-92, wherein the composition has a duration of therapeutic effect in vivo in humans of at least about 10, at least about 20, at least about 30, at least about 40, at least about 50, at least about 60, at least about 70, at least about 80, at least about 90, or at least about 100 hours.

Embodiment 94. The pharmaceutical composition of any one of embodiments 1-93, wherein the composition has a functional half-life in a human cell greater than or equal to that of a pre-determined threshold value.

Embodiment 95. The pharmaceutical composition of any one of embodiments 1-94, wherein the composition has a functional half-life in vivo in humans greater than that of a pre-determined threshold value.

Embodiment 96. The pharmaceutical composition of embodiment 94 or 95, wherein the functional half-life is determined by a functional protein assay.

Embodiment 97. The pharmaceutical composition of embodiment 96, wherein the functional protein assay is an in vitro luciferase assay.

Embodiment 98. The pharmaceutical composition of embodiment 96, wherein the functional protein assay comprises measuring levels of protein encoded by the expression sequence of the RNA polynucleotide in a patient serum or tissue sample.

Embodiment 99. The pharmaceutical composition of any one of embodiments 94-98, wherein the pre-determined threshold value is the functional half-life of a reference linear RNA polynucleotide comprising the same expression sequence as the RNA polynucleotide.

Embodiment 100. The pharmaceutical composition of any one of embodiments 1-99, wherein the composition has a functional half-life of at least about 20 hours.

Embodiment 101. The pharmaceutic composition of any one of embodiments 1-100, further comprising a structural lipid and a PEG-modified lipid.

Embodiment 102. The pharmaceutical composition of any one of embodiment 101, wherein the structural lipid binds to C1q and/or promotes the binding of the transfer vehicle comprising said lipid to C1q compared to a control transfer vehicle lacking the structural lipid and/or increases uptake of C1q-bound transfer vehicle into an immune cell compared to a control transfer vehicle lacking the structural lipid.

Embodiment 103. The pharmaceutical composition of any one of embodiment 97-102, wherein the immune cell is a T cell, an NK cell, an NKT cell, a macrophage, or a neutrophil.

Embodiment 104. The pharmaceutical composition of any one of embodiments 101-103, wherein the structural lipid is cholesterol.

Embodiment 105. The pharmaceutical composition of embodiment 102, wherein the structural lipid is beta-sitosterol.

Embodiment 106. The pharmaceutical composition of embodiment 102, wherein the structural lipid is not beta-sitosterol.

Embodiment 107. The pharmaceutical composition of any one of embodiments 101-106, wherein the PEG-modified lipid is DSPE-PEG, DMG-PEG, PEG-DAG, PEG-S-DAG, PEG-PE, PEG-S-DMG, PEG-cer, PEG-dialkoxypropylcarbamate, PEG-OR, PEG-OH, PEG-c-DOMG, or PEG-1.

Embodiment 108. The pharmaceutical composition of embodiment 107, wherein the PEG-modified lipid is DSPE-PEG(2000).

Embodiment 109. The pharmaceutical composition of any one of embodiments 1-108, further comprising a helper lipid.

Embodiment 110. The pharmaceutical composition of embodiment 109, wherein the helper lipid is DSPC or DOPE.

Embodiment 111. The pharmaceutical composition of any one of embodiments 1-110, further comprising DSPC, cholesterol, and DMG-PEG(2000).

Embodiment 112. The pharmaceutical composition of any one of embodiments 102-111, wherein the transfer vehicle comprises about 0.5% to about 4% PEG-modified lipids by molar ratio.

Embodiment 113. The pharmaceutical composition of any one of embodiments 102-112, wherein the transfer vehicle comprises about 1% to about 2% PEG-modified lipids by molar ratio.

Embodiment 114. The pharmaceutical composition of any one of embodiments 1-113, wherein the transfer vehicle comprises:

a. an ionizable lipid selected from:

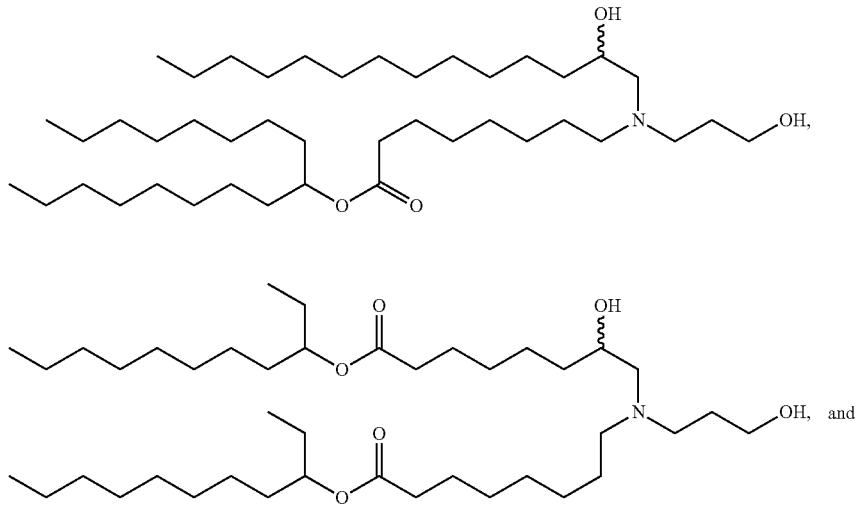

-continued

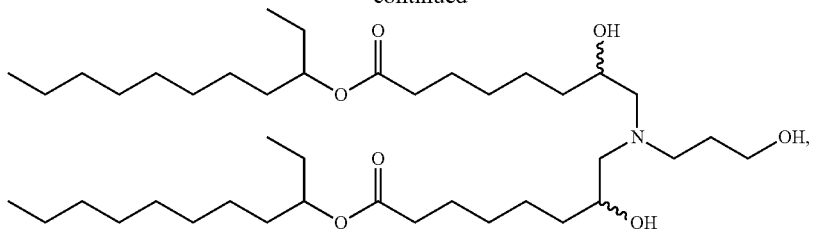

or a mixture thereof,
b. a helper lipid selected from DOPE or DSPC,
c. cholesterol, and
d. a PEG-lipid selected from DSPE-PEG(2000) or DMG-PEG(2000).

Embodiment 115. The pharmaceutical composition of embodiment 114, wherein the molar ratio of ionizable lipid:helper lipid:cholesterol:PEG-lipid is 45:9:44:2, 50:10:38.5:1.5, 41:12:45:2, 62:4:33:1, or 53:5:41:1.

Embodiment 116. The pharmaceutical composition of embodiment 114, wherein the transfer vehicle comprises the helper lipid of DOPE and the PEG-lipid of DMG-PEG (2000), and wherein the molar ratio of ionizable lipid:DOPE:cholesterol:DMG-PEG(2000) is 45:9:44:2, 50:10:38.5:1.5, 41:12:45:2, 62:4:33:1, or 53:5:41:1.

Embodiment 117. The pharmaceutical composition of embodiment 117, wherein the transfer vehicle comprises the helper lipid of DOPE and the PEG-lipid of DSPE-PEG (2000), and wherein the molar ratio of ionizable lipid:DOPE:cholesterol:DSPE-PEG(2000) is 45:9:44:2, 50:10:38.5:1.5, 41:12:45:2, 62:4:33:1, or 53:5:41:1.

Embodiment 118. The pharmaceutical composition of embodiment 117, wherein the transfer vehicle comprises the helper lipid of DOPE and the PEG-lipid of DSPE-PEG (2000), and wherein the molar ratio of ionizable lipid:DOPE:cholesterol:DSPE-PEG(2000) is 62:4:33:1.

Embodiment 119. The pharmaceutical composition of embodiment 114, wherein the transfer vehicle comprises the helper lipid of DOPE and the PEG-lipid of DSPE-PEG (2000), and wherein the molar ratio of ionizable lipid:DOPE:cholesterol:DSPE-PEG(2000) is 53:5:41:1.

Embodiment 120. The pharmaceutical composition of embodiment 114, wherein the transfer vehicle comprises the helper lipid of DSPC and the PEG-lipid of DMG-PEG (2000), and wherein the molar ratio of ionizable lipid:DSPC:cholesterol:DMG-PEG(2000) is 45:9:44:2, 50:10:38.5:1.5, 41:12:45:2, 62:4:33:1, or 53:5:41:1.

Embodiment 121. The pharmaceutical composition of embodiment 120, wherein the transfer vehicle comprises the helper lipid of DSPC and the PEG-lipid of DMG-PEG (2000), and wherein the molar ratio of ionizable lipid:DSPC:cholesterol:DMG-PEG(2000) is 50:10:38.5:1.5.

Embodiment 122. The pharmaceutical composition of embodiment 120, wherein the transfer vehicle comprises the helper lipid of DSPC and the PEG-lipid of DMG-PEG (2000), and wherein the molar ratio of ionizable lipid:DSPC:cholesterol:DMG-PEG(2000) is 41:12:45:2.

Embodiment 123. The pharmaceutical composition of embodiment 120, wherein the transfer vehicle comprises the helper lipid of DSPC and the PEG-lipid of DMG-PEG (2000), and wherein the molar ratio of ionizable lipid:DSPC:cholesterol:DMG-PEG(2000) is 45:9:44:2.

Embodiment 124. The pharmaceutical composition of embodiment 114, wherein the transfer vehicle comprises the helper lipid of DSPC and the PEG-lipid of DSPE-PEG (2000), and wherein the molar ratio of ionizable lipid:DSPC:cholesterol:DSPE-PEG(2000) is 45:9:44:2, 50:10:38.5:1.5, 41:12:45:2, 62:4:33:1, or 53:5:41:1.

Embodiment 125. The pharmaceutical composition of embodiment 114, wherein the transfer vehicle comprises the helper lipid of DOPE and the PEG-lipid is C14-PEG(2000), and wherein the molar ratio of ionizable lipid:DOPE:cholesterol:C14-PEG(2000) is 45:9:44:2, 50:10:38.5:1.5, 41:12:45:2, 62:4:33:1, or 53:5:41:1.

Embodiment 126. The pharmaceutical composition of embodiment 114, wherein the transfer vehicle comprises the helper lipid of DOPE and the PEG-lipid of DMG-PEG (2000), wherein the molar ratio of ionizable lipid:DOPE:cholesterol:DMG-PEG(2000) is 45:9:44:2, 50:10:38.5:1.5, 41:12:45:2, 62:4:33:1, or 53:5:41:1.

Embodiment 127. The pharmaceutical composition of any one of embodiments 1-126, having a lipid to phosphate (IL:P) molar ratio of about 3 to about 9.

Embodiment 128. The pharmaceutical composition of any one of embodiments 1-127, having a lipid to phosphate (IL:P) molar ratio of about 3, about 4, about 4.5, about 5, about 5.5, about 5.7, about 6, about 6.2, about 6.5, or about 7.

Embodiment 129. The pharmaceutical composition of any one of embodiments 1-128, wherein the transfer vehicle is formulated for endosomal release of the RNA polynucleotide.

Embodiment 130. The pharmaceutical composition of any one of embodiments 1-129, wherein the transfer vehicle is capable of binding to APOE.

Embodiment 131. The pharmaceutical composition of any one of embodiments 1-130, wherein the transfer vehicle interacts with apolipoprotein E (APOE) less than an equivalent transfer vehicle loaded with a reference linear RNA having the same expression sequence as the RNA polynucleotide.

Embodiment 132. The pharmaceutical composition of any one of embodiments 1-131, wherein the exterior surface of the transfer vehicle is substantially free of APOE binding sites.

Embodiment 133. The pharmaceutical composition of any one of embodiments 1-132, wherein the transfer vehicle has a diameter of less than about 120 nm.

Embodiment 134. The pharmaceutical composition of any one of embodiments 1-133, wherein the transfer vehicle does not form aggregates with a diameter of more than 300 nm.

Embodiment 135. The pharmaceutical composition of any one of embodiments 1-134, wherein the transfer vehicle has an in vivo half-life of less than about 30 hours.

Embodiment 136. The pharmaceutical composition of any one of embodiments 1-135, wherein the transfer vehicle is capable of low density lipoprotein receptor (LDLR) dependent uptake into a cell.

Embodiment 137. The pharmaceutical composition of any one of embodiments 1-136, wherein the transfer vehicle is capable of LDLR independent uptake into a cell.

Embodiment 138. The pharmaceutical composition of any one of embodiments 1-137, wherein the pharmaceutical composition is substantially free of linear RNA.

Embodiment 139. The pharmaceutical composition of any one of embodiments 1-138, further comprising a targeting moiety operably connected to the transfer vehicle.

Embodiment 140. The pharmaceutical composition of embodiment 139, wherein the targeting moiety specifically binds an immune cell antigen or indirectly.

Embodiment 141. The pharmaceutical composition of embodiment 140, wherein the immune cell antigen is a T cell antigen.

Embodiment 142. The pharmaceutical composition of embodiment 141, wherein the T cell antigen is selected from the group consisting of CD2, CD3, CD5, CD7, CD8, CD4, beta7 integrin, beta2 integrin, and C1qR.

Embodiment 143. The pharmaceutical composition of embodiment 142, further comprising an adapter molecule comprising a transfer vehicle binding moiety and a cell binding moiety, wherein the targeting moiety specifically binds the transfer vehicle binding moiety and the cell binding moiety specifically binds a target cell antigen.

Embodiment 144. The pharmaceutical composition of embodiment 143, wherein the target cell antigen is an immune cell antigen.

Embodiment 145. The pharmaceutical composition of embodiment 144, wherein the immune cell antigen is a T cell antigen, an NK cell, an NKT cell, a macrophage, or a neutrophil.

Embodiment 146. The pharmaceutical composition of embodiment 145, wherein the T cell antigen is selected from the group consisting of CD2, CD3, CD5, CD7, CD8, CD4, beta7 integrin, beta2 integrin, CD25, CD39, CD73, A2a Receptor, A2b Receptor, and C1qR.

Embodiment 147. The pharmaceutical composition of embodiment 140 or 143, wherein the immune cell antigen is a macrophage antigen.

Embodiment 148. The pharmaceutical composition of embodiment 147, wherein the macrophage antigen is selected from the group consisting of mannose receptor, CD206, and C1q.

Embodiment 149. The pharmaceutical composition of any one of embodiments 139-148, wherein the targeting moiety is a small molecule.

Embodiment 150. The pharmaceutical composition of embodiment 149, wherein the small molecule is mannose, a lectin, acivicin, biotin, or digoxigenin.

Embodiment 151. The pharmaceutical composition of embodiment 149, wherein the small molecule binds to an ectoenzyme on an immune cell, wherein the ectoenzyme is selected from the group consisting of CD38, CD73, adenosine 2a receptor, and adenosine 2b receptor.

Embodiment 152. The pharmaceutical composition of any one of embodiments 139-148, wherein the targeting moiety is a single chain Fv (scFv) fragment, nanobody, peptide, peptide-based macrocycle, minibody, small molecule ligand such as folate, arginylglycylaspartic acid (RGD), or phenol-soluble modulin alpha 1 peptide (PSMA1), heavy chain variable region, light chain variable region or fragment thereof.

Embodiment 153. The pharmaceutical composition of any one of embodiments 1-152, wherein the ionizable lipid has a half-life in a cell membrane less than about 2 weeks.

Embodiment 154. The pharmaceutical composition of any one of embodiments 1-153, wherein the ionizable lipid has a half-life in a cell membrane less than about 1 week.

Embodiment 155. The pharmaceutical composition of any one of embodiments 1-154, wherein the ionizable lipid has a half-life in a cell membrane less than about 30 hours.

Embodiment 156. The pharmaceutical composition of any one of embodiments 1-155, wherein the ionizable lipid has a half-life in a cell membrane less than the functional half-life of the RNA polynucleotide.

Embodiment 157. A method of treating or preventing a disease, disorder, or condition, comprising administering an effective amount of a pharmaceutical composition of any one of embodiments 1-156.

Embodiment 158. The method of embodiment 157, wherein the disease, disorder, or condition is associated with aberrant expression, activity, or localization of a polypeptide selected from ASCII Tables L and M.

Embodiment 159. The method of embodiment 157 or 158, wherein the RNA polynucleotide encodes a therapeutic protein.

Embodiment 160. The method of embodiment 159, wherein therapeutic protein expression in the spleen is higher than therapeutic protein expression in the liver.

Embodiment 161. The method of embodiment 160, wherein therapeutic protein expression in the spleen is at least about 2.9× therapeutic protein expression in the liver.

Embodiment 162. The method of embodiment 160, wherein the therapeutic protein is not expressed at functional levels in the liver.

Embodiment 163. The method of embodiment 160, wherein the therapeutic protein is not expressed at detectable levels in the liver.

Embodiment 164. The method of embodiment 160, wherein therapeutic protein expression in the spleen is at least about 50% of total therapeutic protein expression.

Embodiment 165. The method of embodiment 160, wherein therapeutic protein expression in the spleen is at least about 63% of total therapeutic protein expression.

Embodiment 166. A pharmaceutical composition of any one of embodiments 1-156, wherein the transfer vehicle comprises a nanoparticle, and optionally, a targeting moiety operably connected to the nanoparticle.

Embodiment 167. The pharmaceutical composition of embodiment 166, wherein the nanoparticle is a lipid nanoparticle, a core-shell nanoparticle, a biodegradable nanoparticle, a biodegradable lipid nanoparticle, a polymer nanoparticle, or a biodegradable polymer nanoparticle.

Embodiment 168. The pharmaceutical composition of embodiment 166 or 167, comprising a targeting moiety, wherein the targeting moiety mediates receptor-mediated endocytosis or direct fusion selectively into cells of a selected cell population or tissue in the absence of cell isolation or purification.

Embodiment 169. The pharmaceutical composition of any one of embodiments 166-168, wherein the targeting moiety is a scfv, nanobody, peptide, minibody, polynucleotide aptamer, heavy chain variable region, light chain variable region or fragment thereof.

Embodiment 170. The pharmaceutical composition of any one of embodiments 166-169, wherein less than 1%, by weight, of the polynucleotides in the composition are double stranded RNA, DNA splints, or triphosphorylated RNA.

Embodiment 171. The pharmaceutical composition of any one of embodiments 166-170, wherein less than 1%, by weight, of the polynucleotides and proteins in the pharmaceutical composition are double stranded RNA, DNA splints, triphosphorylated RNA, phosphatase proteins, protein ligases, and capping enzymes.

Embodiment 172. A method of treating a subject in need thereof comprising administering a therapeutically effective amount of the pharmaceutical composition of any one of embodiments 166-171.

Embodiment 173. The method of embodiment 172, wherein the targeting moiety is a scfv, nanobody, peptide, minibody, heavy chain variable region, light chain variable region, an extracellular domain of a TCR, or a fragment thereof.

Embodiment 174. The method of embodiment 172 or 173, wherein the nanoparticle comprises one or more cationic lipids, ionizable lipids, or poly 3-amino esters.

Embodiment 175. The method of any one of embodiments 172-174, wherein the nanoparticle comprises one or more non-cationic lipids.

Embodiment 176. The method of any one of embodiments 172-175, wherein the nanoparticle comprises one or more PEG-modified lipids, polyglutamic acid lipids, or Hyaluronic acid lipids.

Embodiment 177. The method of any one of embodiments 172-176, wherein the nanoparticle comprises cholesterol.

Embodiment 178. The method of any one of embodiments 172-177, wherein the nanoparticle comprises arachidonic acid or oleic acid.

Embodiment 179. The method of any one of embodiments 172-178, wherein the pharmaceutical composition comprises a targeting moiety, wherein the targeting moiety mediates receptor-mediated endocytosis selectively into cells of a selected cell population in the absence of cell selection or purification.

Embodiment 180. The method of any one of embodiments 172-179, wherein the nanoparticle comprises more than one circular RNA polynucleotide.

Embodiment 181. A DNA vector encoding the RNA polynucleotide of any one of embodiments 64-78.

Embodiment 182. The DNA vector of embodiment 181, further comprising a transcription regulatory sequence.

Embodiment 183. The DNA vector of embodiment 182, wherein the transcription regulatory sequence comprises a promoter and/or an enhancer.

Embodiment 184. The DNA vector of embodiment 183, wherein the promoter comprises a T7 promoter.

Embodiment 185. The DNA vector of any one of embodiments 181-184, wherein the DNA vector comprises a circular DNA.

Embodiment 186. The DNA vector of any one of embodiments 181-185, wherein the DNA vector comprises a linear DNA.

Embodiment 187. A prokaryotic cell comprising the DNA vector according to any one of embodiments 181-186.

Embodiment 188. A eukaryotic cell comprising the RNA polynucleotide according to any one of embodiments 1-187.

Embodiment 189. The eukaryotic cell of embodiment 189, wherein the eukaryotic cell is a human cell.

Embodiment 190. A method of producing a circular RNA polynucleotide, the method comprising incubating the RNA polynucleotide of any one of embodiments 64-78 under suitable conditions for circularization.

Embodiment 191. A method of producing a circular RNA polynucleotide, the method comprising incubating DNA of any one of embodiments 181-186 under suitable conditions for transcription.

Embodiment 192. The method of embodiment 191, wherein the DNA is transcribed in vitro.

Embodiment 193. The method of embodiment 191, wherein the suitable conditions comprises adenosine triphosphate (ATP), guanine triphosphate (GTP), cytosine triphosphate (CTP), uridine triphosphate (UTP), and an RNA polymerase.

Embodiment 194. The method of embodiment 191, wherein the suitable conditions further comprises guanine monophosphate (GMP).

Embodiment 195. The method of embodiment 194, wherein the ratio of GMP concentration to GTP concentration is within the range of about 3:1 to about 15:1, optionally about 4:1, 5:1, or 6:1.

Embodiment 196. A method of producing a circular RNA polynucleotide, the method comprising culturing the prokaryotic cell of embodiment 187 under suitable conditions for transcribing the DNA in the cell.

Embodiment 197. The method of any one of embodiments 190-196, further comprising purifying a circular RNA polynucleotide.

Embodiment 198. The method of embodiment 197, wherein the circular RNA polynucleotide is purified by negative selection using an affinity oligonucleotide that hybridizes with the first or second spacer conjugated to a solid surface.

Embodiment 199. The method of embodiment 198, wherein the first or second spacer comprises a polyA sequence, and wherein the affinity oligonucleotide is a deoxythymine oligonucleotide.

EXAMPLES

Wesselhoeft et al., (2019) RNA Circularization Diminishes Immunogenicity and Can Extend Translation Duration In vivo. Molecular Cell. 74(3), 508-520 and Wesselhoeft et al., (2018) Engineering circular RNA for Potent and Stable Translation in Eukaryotic Cells. Nature Communications. 9, 2629 are incorporated by reference in their entirety.

The invention is further described in detail by reference to the following examples but are not intended to be limited to the following examples. These examples encompass any and all variations of the illustrations with the intention of providing those of ordinary skill in the art with complete disclosure and description of how to make and use the subject invention and are not intended to limit the scope of what is regarded as the invention.

Example 1

Example 1A: External Duplex Regions Allow for Circularization of Long Precursor RNA Using the Permuted Intron Exon (PIE) Circularization Strategy A 1.1 kb sequence containing a full-length encephalomyocarditis virus (EMCV) IRES, a *Gaussia* luciferase (GLuc) expression sequence, and two short exon fragments of the permuted intron-exon (PIE) construct were inserted between the 3' and 5' introns of the permuted group I catalytic intron in the thymidylate synthase (Td) gene of the T4 phage. Precursor RNA was synthesized by run-off transcription. Circularization was attempted by heating the precursor RNA in the presence of magnesium ions and GTP, but splicing products were not obtained.

Perfectly complementary 9 nucleotide and 19 nucleotide long duplex regions were designed and added at the 5' and 3' ends of the precursor RNA. Addition of these homology arms increased splicing efficiency from 0 to 16% for 9 nucleotide duplex regions and to 48% for 19 nucleotide duplex regions as assessed by disappearance of the precursor RNA band.

The splicing product was treated with RNase R. Sequencing across the putative splice junction of RNase R-treated splicing reactions revealed ligated exons, and digestion of the RNase R-treated splicing reaction with oligonucleotide-targeted RNase H produced a single band in contrast to two bands yielded by RNase H-digested linear precursor. This shows that circular RNA is a major product of the splicing reactions of precursor RNA containing the 9 or 19 nucleotide long external duplex regions Example 1B: Spacers that Conserve Secondary Structures of IRES and PIE Splice Sites Increase Circularization Efficiency A series of spacers was designed and inserted between the 3' PIE splice site and the IRES. These spacers were designed to either conserve or disrupt secondary structures within intron sequences in the IRES, 3' PIE splice site, and/or 5' splice site. The addition of spacer sequences designed to conserve secondary structures resulted in 87% splicing efficiency, while the addition of a disruptive spacer sequences resulted in no detectable splicing.

Example 2

Example 2A: Internal Duplex Regions in Addition to External Duplex Regions Create a Splicing Bubble and Allows for Translation of Several Expression Sequences Spacers were designed to be unstructured, non-homologous to the intron and IRES sequences, and to contain spacer-spacer duplex regions. These were inserted between the 5' exon and IRES and between the 3' exon and expression sequence in constructs containing external duplex regions, EMCV IRES, and expression sequences for *Gaussia* luciferase (total length: 1289 nt), Firefly luciferase (2384 nt), eGFP (1451 nt), human erythropoietin (1313 nt), and Cas9 endonuclease (4934 nt). Circularization of all 5 constructs was achieved. Circularization of constructs utilizing T4 phage and Anabaena introns were roughly equal. Circularization efficiency was higher for shorter sequences. To measure translation, each construct was transfected into HEK293 cells. *Gaussia* and Firefly luciferase transfected cells produced a robust response as measured by luminescence, human erythropoietin was detectable in the media of cells transfected with erythropoietin circRNA, and EGFP fluorescence was observed from cells transfected with EGFP circRNA. Co-transfection of Cas9 circRNA with sgRNA directed against GFP into cells constitutively expressing GFP resulted in ablated fluorescence in up to 97% of cells in comparison to an sgRNA-only control.

Example 2B: Use of CVB3 IRES Increases Protein Production

Constructs with internal and external duplex regions and differing IRES containing either *Gaussia* luciferase or Firefly luciferase expression sequences were made. Protein production was measured by luminescence in the supernatant of HEK293 cells 24 hours after transfection. The Coxsackievirus B3 (CVB3) IRES construct produced the most protein in both cases.

Example 2C: Use of polyA or polyAC Spacers Increases Protein Production

Thirty nucleotide long polyA or polyAC spacers were added between the IRES and splice junction in a construct with each TRES that produced protein in example 2B. *Gaussia* luciferase activity was measured by luminescence in the supernatant of HEK293 cells 24 hours after transfection. Both spacers improved expression in every construct over control constructs without spacers.

Example 3

HEK293 or HeLa Cells Transfected with Circular RNA Produce More Protein than Those Transfected with Comparable Unmodified or Modified Linear RNA HPLC-purified *Gaussia* luciferase-coding circRNA (CVB3-GLuc-pAC) was compared with a canonical unmodified 5' methylguanosine-capped and 3' polyA-tailed linear GLuc mRNA, and a commercially available nucleoside-modified (pseudouridine, 5-methylcytosine) linear GLuc mRNA (from Trilink). Luminescence was measured 24 h post-transfection, revealing that circRNA produced 811.2% more protein than the unmodified linear mRNA in HEK293 cells and 54.5% more protein than the modified mRNA. Similar results were obtained in HeLa cells and a comparison of optimized circRNA coding for human erythropoietin with linear mRNA modified with 5-methoxyuridine.

Luminescence data was collected over 6 days. In HEK293 cells, circRNA transfection resulted in a protein production half-life of 80 hours, in comparison with the 43 hours of unmodified linear mRNA and 45 hours of modified linear mRNA. In HeLa cells, circRNA transfection resulted in a protein production half-life of 116 hours, in comparison with the 44 hours of unmodified linear mRNA and 49 hours of modified linear mRNA. CircRNA produced substantially more protein than both the unmodified and modified linear mRNAs over its lifetime in both cell types.

Example 4

Example 4A: Purification of circRNA by RNase Digestion, HPLC Purification, and Phosphatase Treatment Decreases Immunogenicity. Completely Purified Circular RNA is Significantly Less Immunogenic than Unpurified or Partially Purified Circular RNA. Protein Expression Stability and Cell Viability are Dependent on Cell Type and Circular RNA Purity Human Embryonic Kidney 293 (HEK293) and Human Lung Carcinoma A549 Cells were transfected with:
  a. products of an unpurified GLuc circular RNA splicing reaction,
  b. products of RNase R digestion of the splicing reaction,
  c. products of RNase R digestion and HPLC purification of the splicing reaction, or
  d. products of RNase digestion, HPLC purification, and phosphatase treatment of the splicing reaction.

RNase R digestion of splicing reactions was insufficient to prevent cytokine release in A549 cells in comparison to untransfected controls.

The addition of HPLC purification was also insufficient to prevent cytokine release, although there was a significant reduction in interleukin-6 (IL-6) and a significant increase in interferon-α1 (IFNα1) compared to the unpurified splicing reaction.

The addition of a phosphatase treatment after HPLC purification and before RNase R digestion dramatically reduced the expression of all upregulated cytokines assessed in A549 cells. Secreted monocyte chemoattractant protein 1 (MCP1), IL-6, IFNα1, tumor necrosis factor α (TNFα), and IFNγ inducible protein-10 (IP-10) fell to undetectable or un-transfected baseline levels.

There was no substantial cytokine release in HEK293 cells. A549 cells had increased GLuc expression stability and cell viability when transfected with higher purity circular RNA. Completely purified circular RNA had a stability phenotype similar to that of transfected 293 cells.

Example 4B: Circular RNA does not Cause Significant Immunogenicity and is not a RIG-I Ligand A549 cells were transfected with:
a. unpurified circular RNA,
b. high molecular weight (linear and circular concatenations) RNA,
c. circular (nicked) RNA,
d. an early fraction of purified circular RNA (more overlap with nicked RNA peak),
e. a late fraction of purified circular RNA (less overlap with nicked RNA peak),
f. introns excised during circularization, or
g. vehicle (i.e. untransfected control).

Precursor RNA was separately synthesized and purified in the form of the splice site deletion mutant (DS) due to difficulties in obtaining suitably pure linear precursor RNA from the splicing reaction. Cytokine release and cell viability was measured in each case.

Robust IL-6, RANTES, and IP-10 release was observed in response to most of the species present within the splicing reaction, as well as precursor RNA. Early circRNA fractions elicited cytokine responses comparable to other non-circRNA fractions, indicating that even relatively small quantities of linear RNA contaminants are able to induce a substantial cellular immune response in A549 cells. Late circRNA fractions elicited no cytokine response in excess of that from untransfected controls. A549 cell viability 36 hours post-transfection was significantly greater for late circRNA fractions compared with all of the other fractions.

RIG-I and IFN-j1 transcript induction upon transfection of A549 cells with late circRNA HPLC fractions, precursor RNA or unpurified splicing reactions were analyzed. Induction of both RIG-I and IFN-β1 transcripts were weaker for late circRNA fractions than precursor RNA and unpurified splicing reactions. RNase R treatment of splicing reactions alone was not sufficient to ablate this effect. Addition of very small quantities of the RIG-I ligand 3p-hpRNA to circular RNA induced substantial RIG-I transcription. In HeLa cells, transfection of RNase R-digested splicing reactions induced RIG-I and IFN-β1, but purified circRNA did not. Overall, HeLa cells were less sensitive to contaminating RNA species than A549 cells.

A time course experiment monitoring RIG-I, IFN-β1, IL-6, and RANTES transcript induction within the first 8 hours after transfection of A549 cells with splicing reactions or fully purified circRNA did not reveal a transient response to circRNA. Purified circRNA similarly failed to induce pro-inflammatory transcripts in RAW264.7 murine macrophages.

A549 cells were transfected with purified circRNA containing an EMCV IRES and EGFP expression sequence. This failed to produce substantial induction of pro-inflammatory transcripts. These data demonstrate that non-circular components of the splicing reaction are responsible for the immunogenicity observed in previous studies and that circRNA is not a natural ligand for RIG-I.

Example 5

Circular RNA Avoids Detection by TLRs.

TLR 3, 7, and 8 reporter cell lines were transfected with multiple linear or circular RNA constructs and secreted embryonic alkaline phosphatase (SEAP) was measured.

Linearized RNA was constructed by deleting the intron and homology arm sequences. The linear RNA constructs were then treated with phosphatase (in the case of capped RNAs, after capping) and purified by HPLC.

None of the attempted transfections produced a response in TLR7 reporter cells. TLR3 and TLR8 reporter cells were activated by capped linearized RNA, polyadenylated linearized RNA, the nicked circRNA HPLC fraction, and the early circRNA fraction. The late circRNA fraction and m1ψ-mRNA did not provoke TLR-mediated response in any cell line.

In a second experiment, circRNA was linearized using two methods: treatment of circRNA with heat in the presence of magnesium ions and DNA oligonucleotide-guided RNase H digestion. Both methods yielded a majority of full-length linear RNA with small amounts of intact circRNA. TLR3, 7, and 8 reporter cells were transfected with circular RNA, circular RNA degraded by heat, or circular RNA degraded by RNase H, and SEAP secretion was measured 36 hours after transfection. TLR8 reporter cells secreted SEAP in response to both forms of degraded circular RNA, but did not produce a greater response to circular RNA transfection than mock transfection. No activation was observed in TLR3 and TLR7 reporter cells for degraded or intact conditions, despite the activation of TLR3 by in vitro transcribed linearized RNA.

Example 6

Unmodified Circular RNA Produces Increased Sustained In Vivo Protein Expression than Linear RNA.

Mice were injected and HEK293 cells were transfected with unmodified and m1ψ-modified human erythropoietin (hEpo) linear mRNAs and circRNAs. Equimolar transfection of m1ψ-mRNA and unmodified circRNA resulted in robust protein expression in HEK293 cells. hEpo linear mRNA and circRNA displayed similar relative protein expression patterns and cell viabilities in comparison to GLuc linear mRNA and circRNA upon equal weight transfection of HEK293 and A549 cells.

In mice, hEpo was detected in serum after the injection of hEpo circRNA or linear mRNA into visceral adipose. hEpo detected after the injection of unmodified circRNA decayed more slowly than that from unmodified or m1ψ-mRNA and was still present 42 hours post-injection. Serum hEpo rapidly declined upon the injection of unpurified circRNA splicing reactions or unmodified linear mRNA. Injection of unpurified splicing reactions produced a cytokine response detectable in serum that was not observed for the other RNAs, including purified circRNA.

Example 7

Circular RNA can be Effectively Delivered In Vivo or In Vitro Via Lipid Nanoparticles Purified circular RNA was formulated into lipid nanoparticles (LNPs) with the ionizable lipidoid cKK-E12 (Dong et al., 2014; Kauffman et al., 2015). The particles formed uniform multilamellar structures with an average size, polydispersity index, and encapsulation efficiency similar to that of particles containing commercially available control linear mRNA modified with 5moU.

Purified hEpo circRNA displayed greater expression than 5moU-mRNA when encapsulated in LNPs and added to HEK293 cells. Expression stability from LNP-RNA in HEK293 cells was similar to that of RNA delivered by transfection reagent, with the exception of a slight delay in decay for both 5moU-mRNA and circRNA. Both unmodified circRNA and 5moU-mRNA failed to activate RIG-I/IFN-β1 in vitro.

In mice, LNP-RNA was delivered by local injection into visceral adipose tissue or intravenous delivery to the liver. Serum hEpo expression from circRNA was lower but comparable with that from 5moU-mRNA 6 hours after delivery in both cases. Serum hEpo detected after adipose injection of unmodified LNP-circRNA decayed more slowly than that from LNP-5moU-mRNA, with a delay in expression decay present in serum that was similar to that noted in vitro, but serum hEpo after intravenous injection of LNP-circRNA or LNP-5moU-mRNA decayed at approximately the same rate. There was no increase in serum cytokines or local RIG-I, TNFα, or IL-6 transcript induction in any of these cases.

Example 8

Expression and Functional Stability by IRES in HEK293, HepG2, and IC1C7 Cells.

Figure 1B:
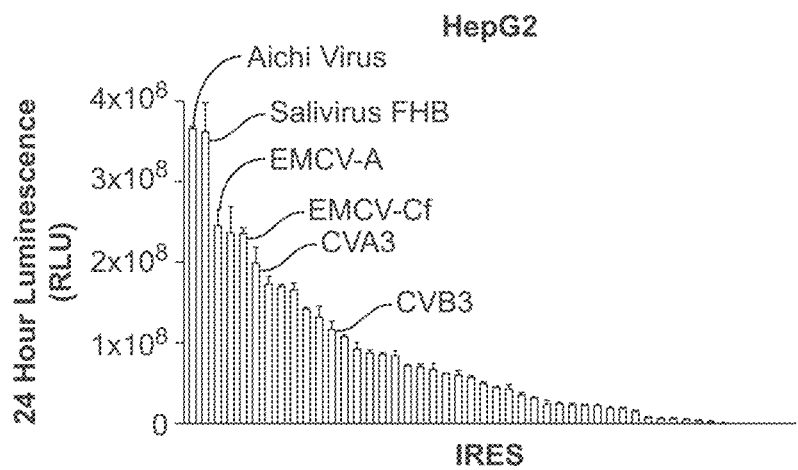
Figure 1C:
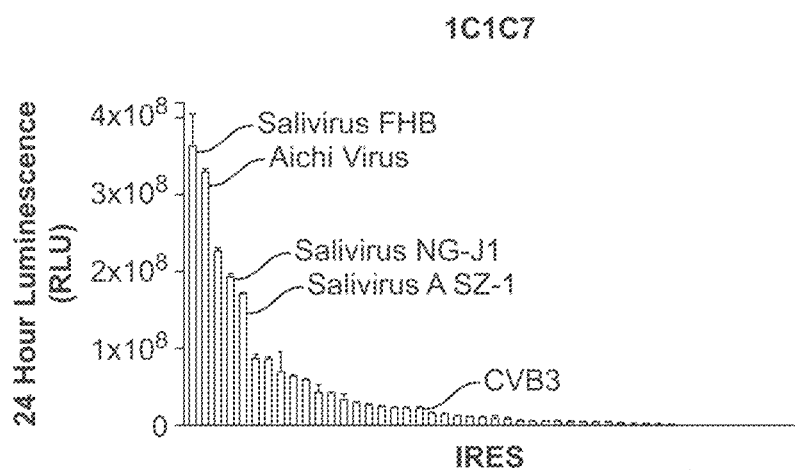
Figure 1D:
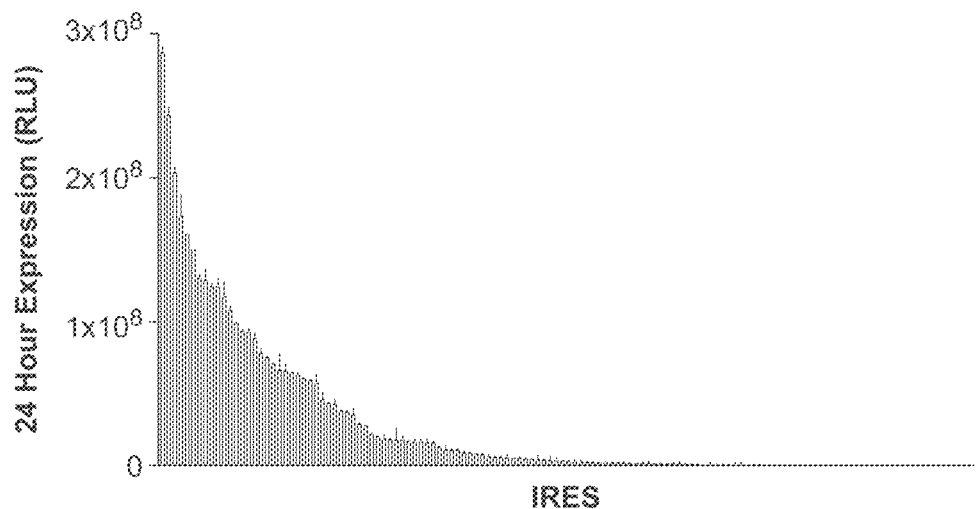
Figure 1E:
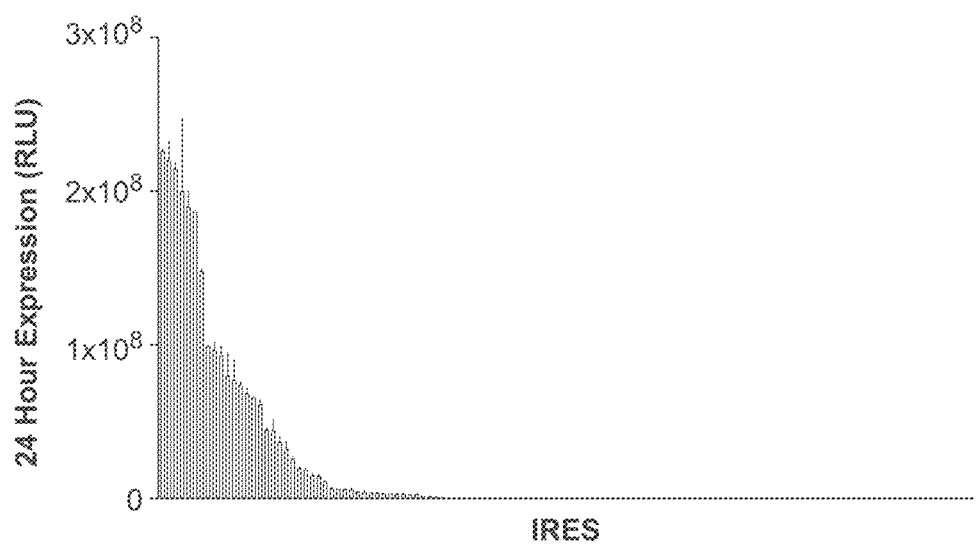

Constructs including anabaena intron/exon regions, a *Gaussia* luciferase expression sequence, and varying IRES were circularized. 100 ng of each circularization reaction was separately transfected into 20,000 HEK293 cells, HepG2 cells, and 1C1C7 cells using Lipofectamine MessengerMax. Luminescence in each supernatant was assessed after 24 hours as a measure of protein expression. In HEK293 cells, constructs including Crohivirus B, Salivirus FHB, Aichi Virus, Salivirus HG-J1, and Enterovirus J IRES produced the most luminescence at 24 hours (FIG. 1A). In HepG2 cells, constructs including Aichi Virus, Salivirus FHB, EMCV-Cf, and CVA3 IRES produced high luminescence at 24 hours (FIG. 1B). In 1C1C7 cells, constructs including Salivirus FHB, Aichi Virus, Salivirus NG-J1, and Salivirus A SZ-1 TRES produced high luminescence at 24 hours (FIG. 1C).

Figure 2A:
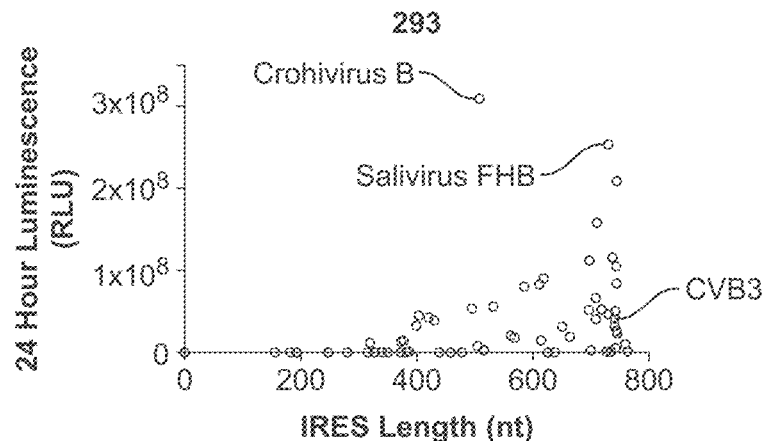
FIG. 2A-2C depict luminescence in supernatants of HEK293 (FIG. 2A), HepG2 (FIG. 2B), or 1C1C7 (FIG. 2C) cells 24 hours after transfection with circular RNA comprising a *Gaussia* luciferase expression sequence and various IRES sequences having different lengths.
Figure 2B:
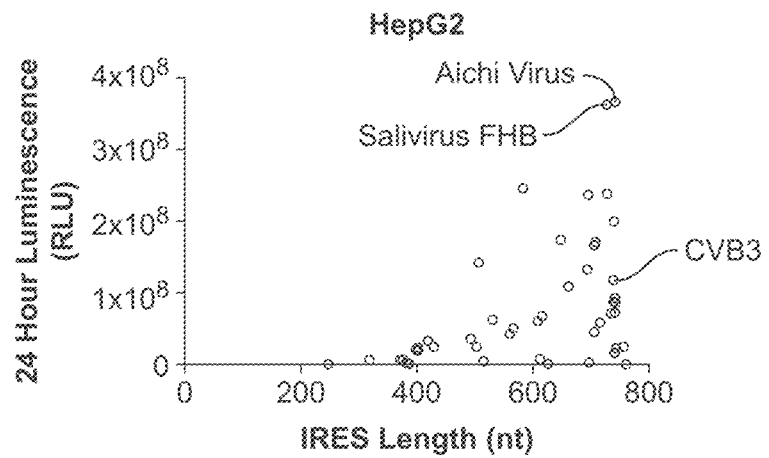
Figure 2C:
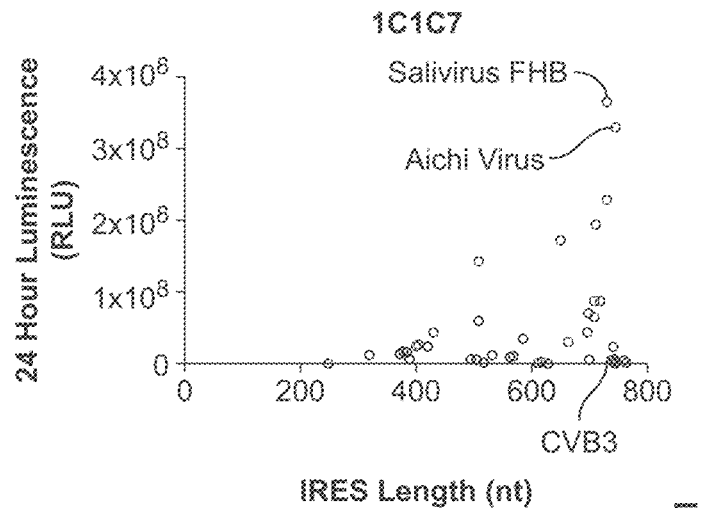

A trend of larger IRES producing greater luminescence at 24 hours was observed. Shorter total sequence length tends to increase circularization efficiency, so selecting a high expression and relatively short IRES may result in an improved construct. In HEK293 cells, a construct using the Crohivirus B IRES produced the highest luminescence, especially in comparison to other IRES of similar length (FIG. 2A). Expression from IRES constructs in HepG2 and 1C1C7 cells plotted against IRES size are in FIGS. 2B and 2C.

Figure 3A:
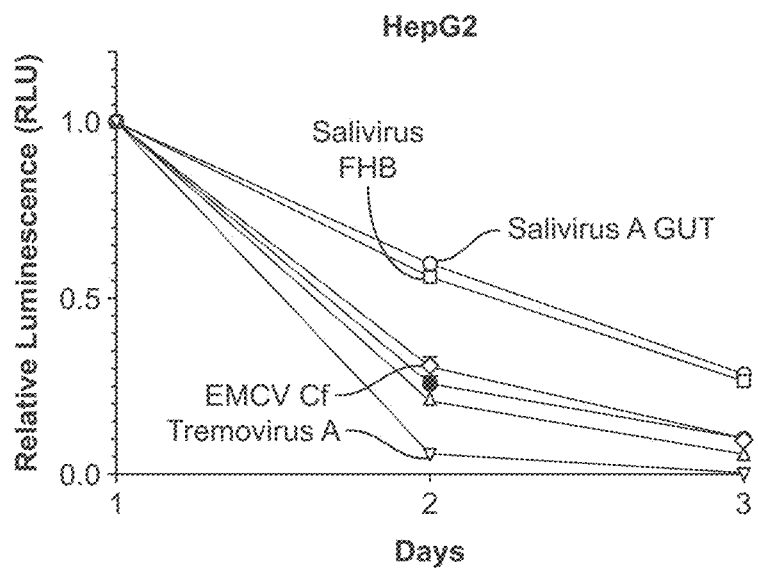
FIG. 3A and FIG. 3B depict stability of select IRES constructs in HepG2 (FIG. 3A) or 1C1C7 (FIG. 3B) cells over 3 days as measured by luminescence.
Figure 3B:
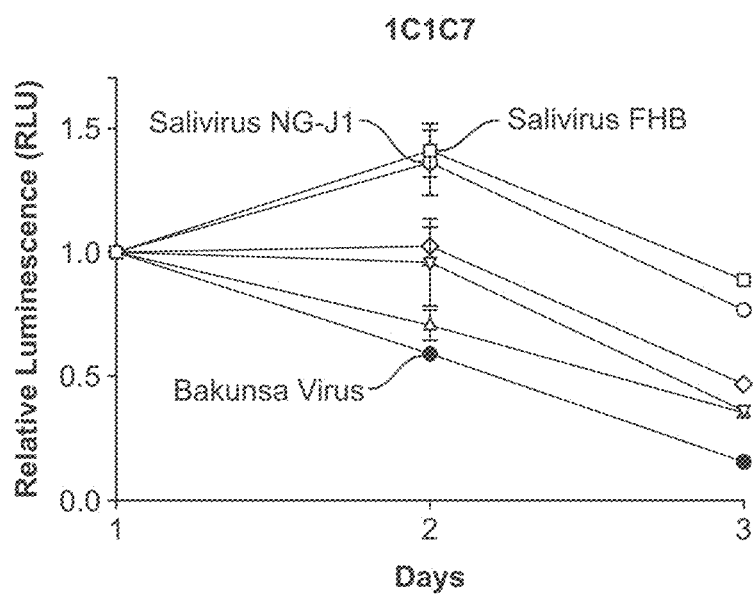

Functional stability of select IRES constructs in HepG2 and 1C1C7 cells were measured over 3 days. Luminescence from secreted *Gaussia* luciferase in supernatant was measured every 24 hours after transfection of 20,000 cells with 100 ng of each circularization reaction, followed by complete media replacement. Salivirus A GUT and Salivirus FHB exhibited the highest functional stability in HepG2 cells, and Salivirus N-J1 and Salivirus FHB produced the most stable expression in 1C1C7 cells (FIGS. 3A and 3B).

Example 9

Figure 4A:
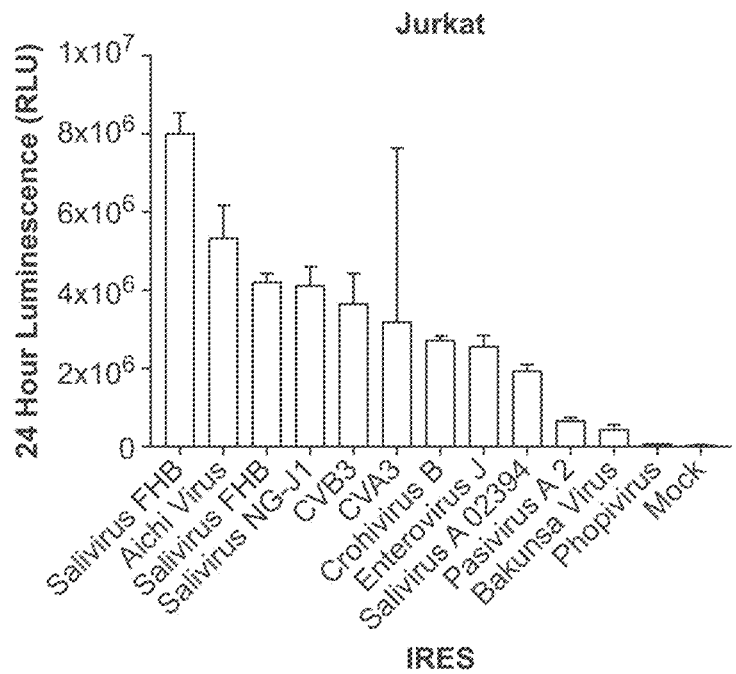
FIG. 4A and FIG. 4B depict protein expression from select IRES constructs in Jurkat cells, as measured by luminescence from secreted *Gaussia* luciferase in cell supernatants.
Figure 4B:
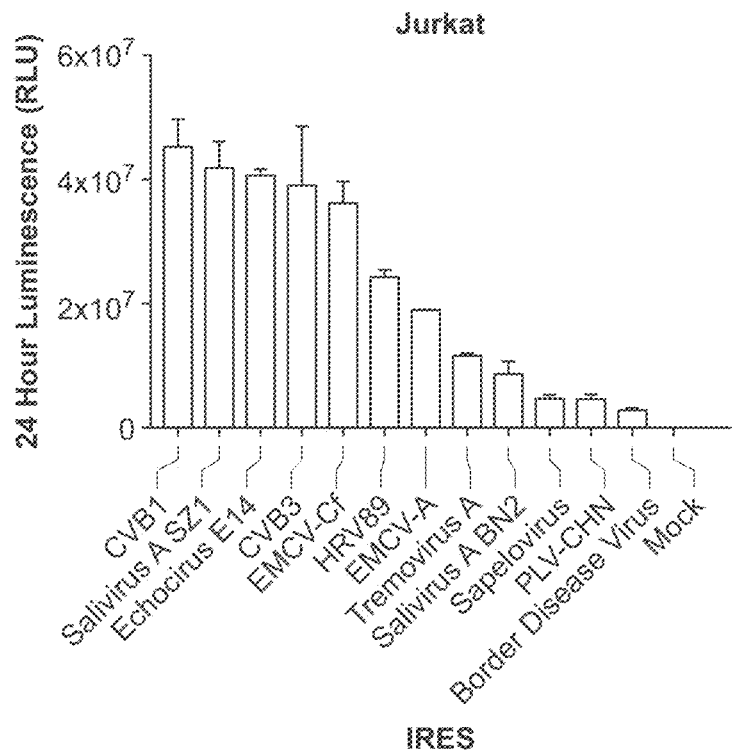

Expression and Functional Stability by IRES in Jurkat Cells 2 sets of constructs including anabaena intron/exon regions, a *Gaussia* luciferase expression sequence, and a subset of previously tested IRES were circularized. 60,000 Jurkat cells were electroporated with 1 µg of each circularization reaction. Luminescence from secreted *Gaussia* luciferase in supernatant was measured 24 hours after electroporation. A CVB3 IRES construct was included in both sets for comparison between sets and to previously defined IRES efficacy. CVB1 and Salivirus A SZ1 IRES constructs produced the most expression at 24 h. Data can be found in FIGS. 4A and 4B.

Figure 5A:
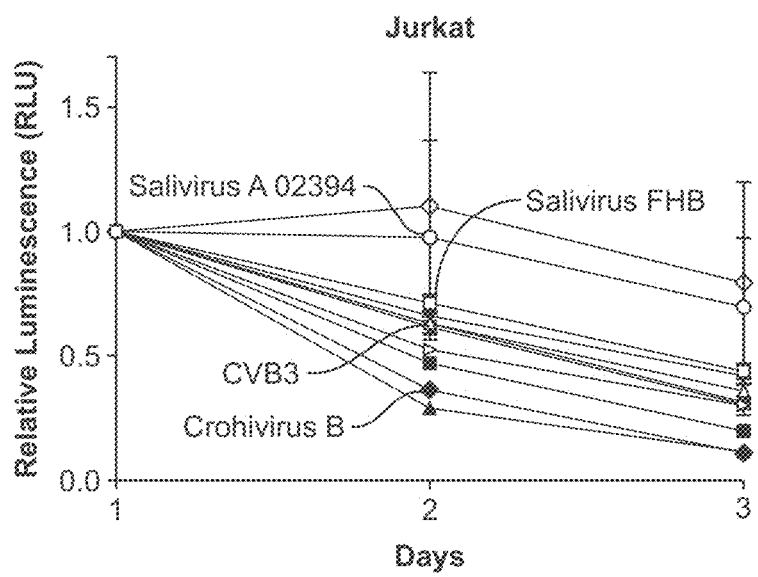
FIG. 5A and FIG. 5B stability of select IRES constructs in Jurkat cells over 3 days as measured by luminescence.
Figure 5B:
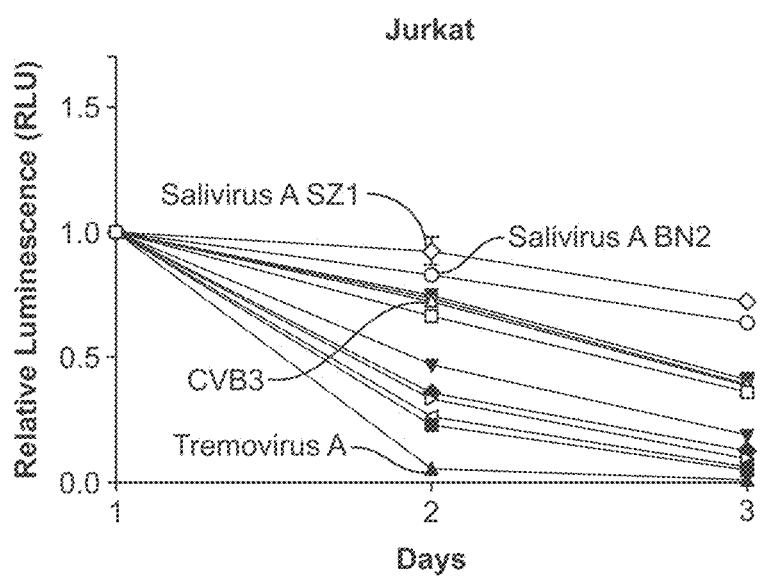

Functional stability of the IRES constructs in each round of electroporated Jurkat cells was measured over 3 days. Luminescence from secreted *Gaussia* luciferase in supernatant was measured every 24 hours after electroporation of 60,000 cells with 1 µg of each circularization reaction, followed by complete media replacement (FIGS. 5A and 5B).

Salivirus A SZ1 and Salivirus A BN2 IRES constructs had high functional stability compared to other constructs.

Example 10

Figure 6A:
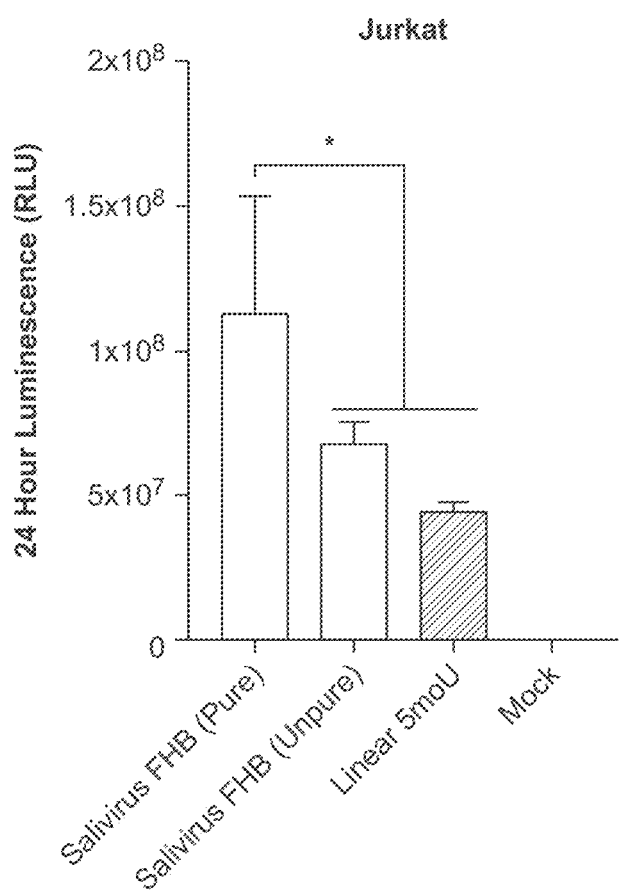
FIG. 6A and FIG. 6B depict comparisons of 24 hour luminescence (FIG. 6A) or relative luminescence over 3 days (FIG. 6B) of modified linear, unpurified circular, or purified circular RNA encoding *Gaussia* luciferase.

Expression, Functional Stability, and Cytokine Release of Circular and Linear RNA in Jurkat Cells A construct including anabaena intron/exon regions, a *Gaussia* luciferase expression sequence, and a Salivirus FHB IRES was circularized. mRNA including a *Gaussia* luciferase expression sequence and a ~150 nt polyA tail, and modified to replace 100% of uridine with 5-methoxy uridine (5moU) is commercially available and was purchased from Trilink. 5moU nucleotide modifications have been shown to improve mRNA stability and expression (Bioconjug Chem. 2016 Mar. 16; 27(3):849-53). Expression of modified mRNA, circularization reactions (unpure), and circRNA purified by size exclusion HPLC (pure) in Jurkat cells were measured and compared (FIG. 6A). Luminescence from secreted *Gaussia* luciferase in supernatant was measured 24 hours after electroporation of 60,000 cells with 1 µg of each RNA species.

Figure 6B:
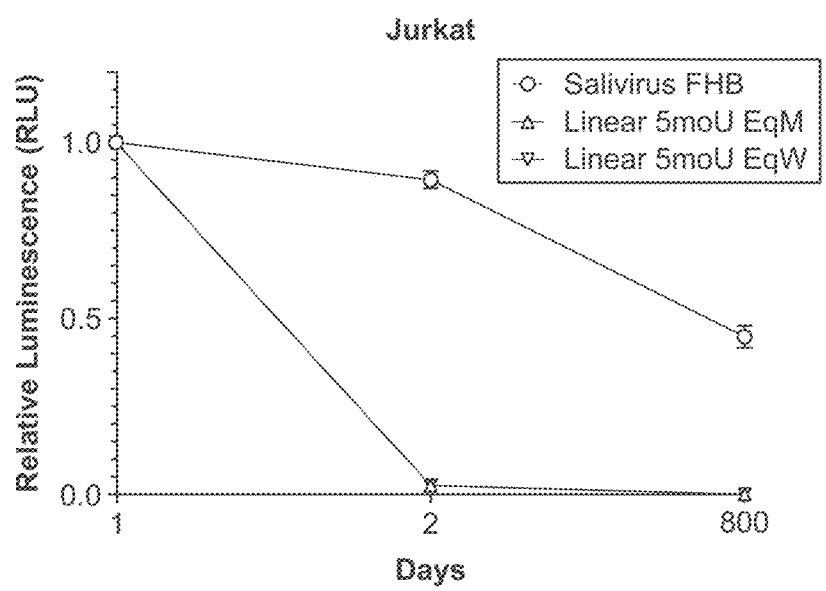

Luminescence from secreted *Gaussia* luciferase in supernatant was measured every 24 hours after electroporation of 60,000 cells with 1 ug of each RNA species, followed by complete media replacement. A comparison of functional stability data of modified mRNA and circRNA in Jurkat cells over 3 days is in FIG. 6B.

Figure 7A:
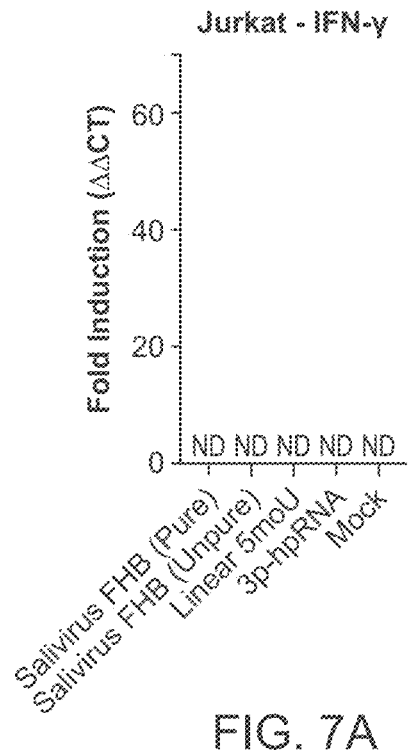
FIGS. 7A-7F depict transcript induction of IFNγ (FIG. 7A), IL-6 (FIG. 7B), IL-2 (FIG. 7C), RIG-I (FIG. 7D), IFN-β1 (FIG. 7E), and TNFα (FIG. 7F) after electroporation of Jurkat cells with modified linear, unpurified circular, or purified circular RNA.
Figure 7B:
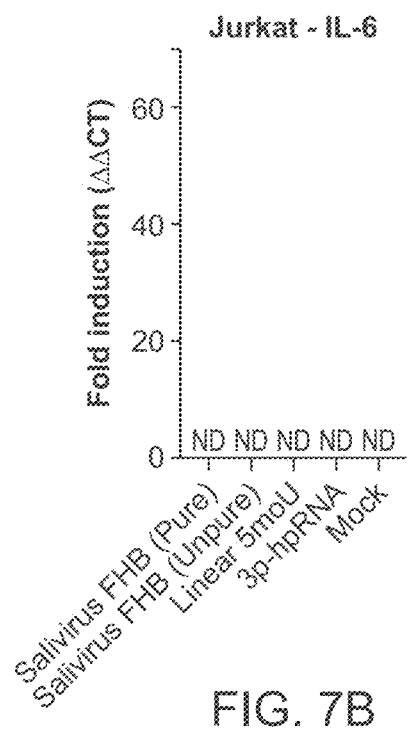
Figure 7C:
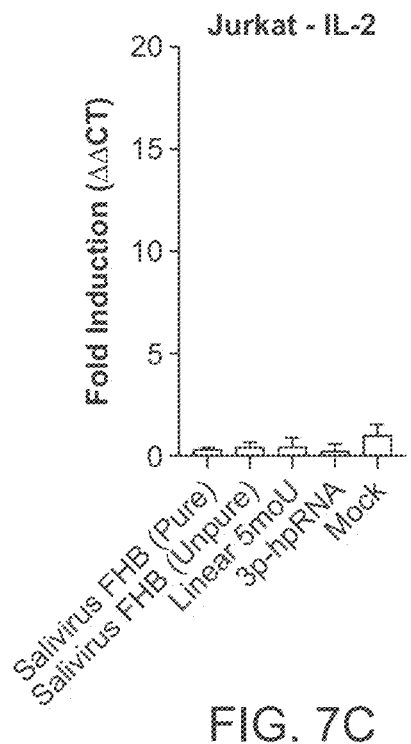
Figure 7D:
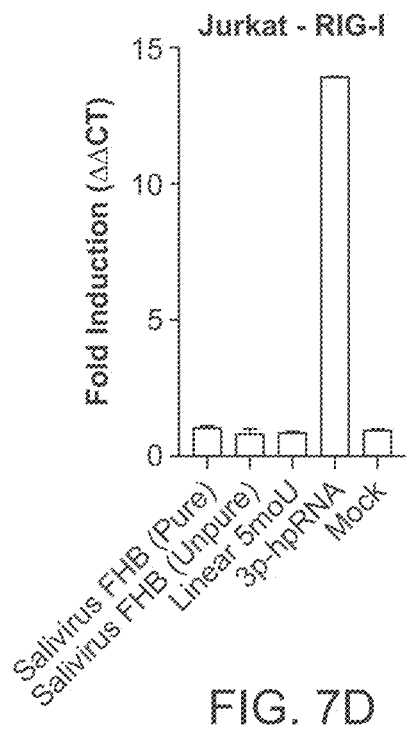
Figure 7E:
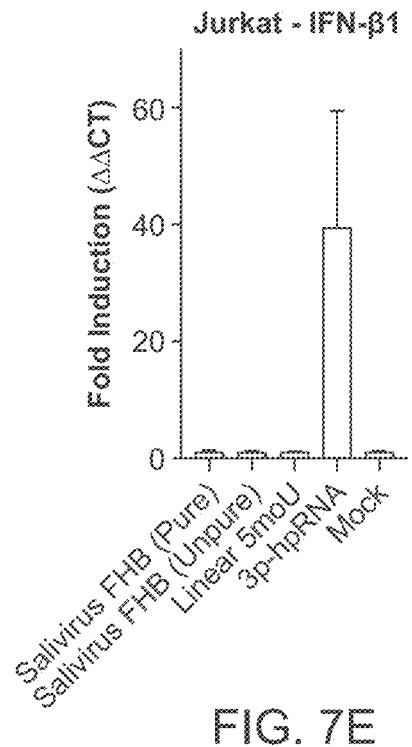
Figure 7F:
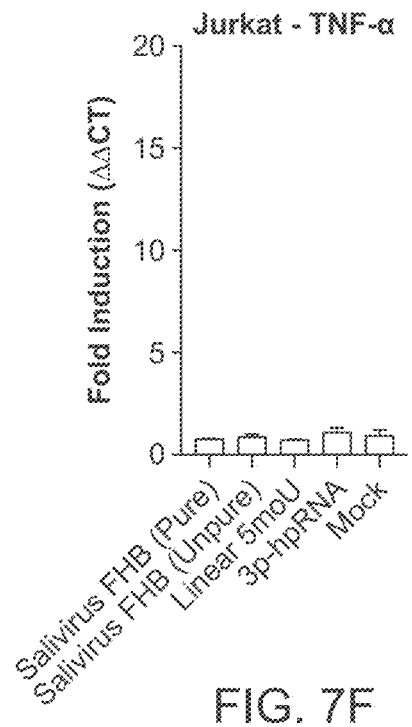

IFNγ (FIG. 7A), IL-6 (FIG. 7B), IL-2 (FIG. 7C), RIG-I (FIG. 7D), IFN-β1 (FIG. 7E), and TNFα (FIG. 7F) transcript induction was measured 18 hours after electroporation of 60,000 Jurkat cells with 1 µg of each RNA species described above and 3p-hpRNA (5' triphosphate hairpin RNA, which is a known RIG-I agonist).

Example 11

Expression of Circular and Linear RNA in Monocytes and Macrophages

Figure 8A:
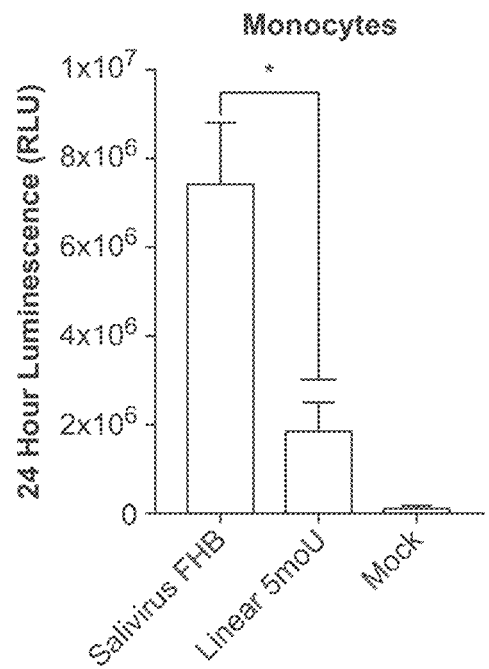
FIGS. 8A-8C depict a comparison of luminescence of circular RNA and modified linear RNA encoding *Gaussia* luciferase in human primary monocytes (FIG. 8A) and macrophages (FIG. 8B and FIG. 8C).
Figure 8B:
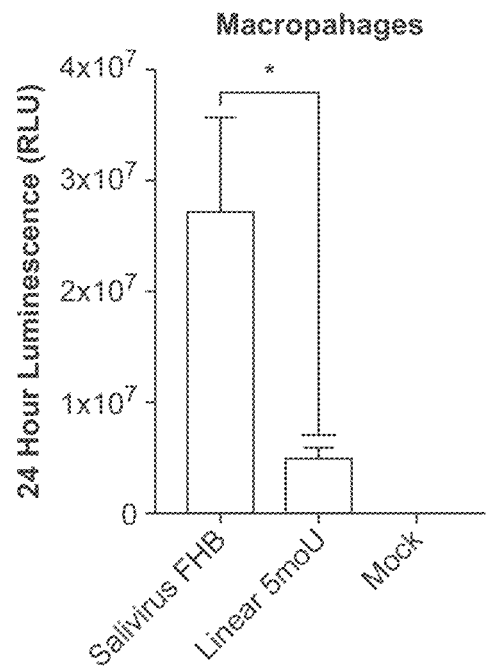
Figure 8C:
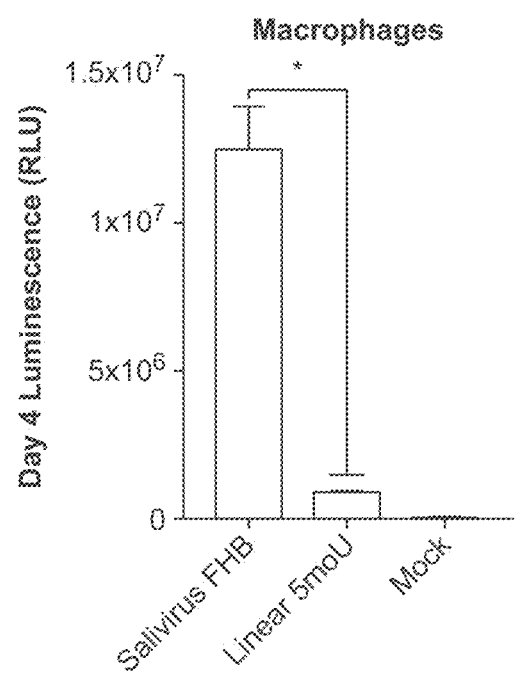

A construct including anabaena intron/exon regions, a *Gaussia* luciferase expression sequence, and a Salivirus FHB IRES was circularized. mRNA including a *Gaussia* luciferase expression sequence and a ~150 nt polyA tail, and modified to replace 100% of uridine with 5-methoxy uridine (5moU) was purchased from Trilink. Expression of circular and modified mRNA was measured in human primary monocytes (FIG. 8A) and human primary macrophages (FIG. 8B). Luminescence from secreted *Gaussia* luciferase in supernatant was measured 24 hours after electroporation of 60,000 cells with 1 µg of each RNA species. Luminescence was also measured 4 days after electroporation of human primary macrophages with media changes every 24 hours (FIG. 8C). The difference in luminescence was statistically significant in each case ($p<0.05$).

Example 12

Expression and Functional Stability by IRES in Primary T Cells

Figure 9A:
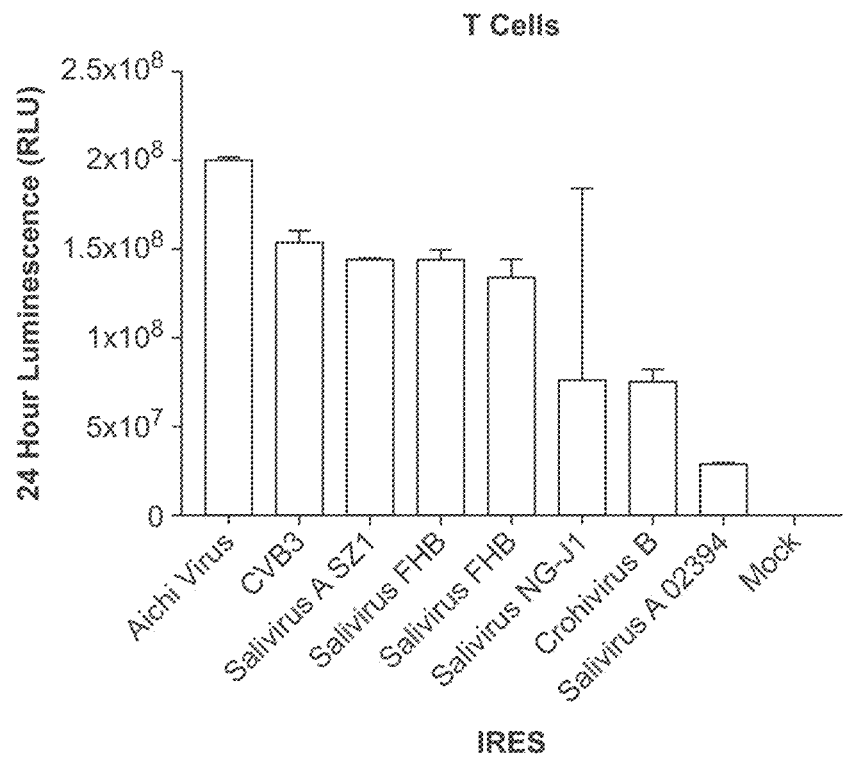
FIG. 9A and FIG. 9B depict relative luminescence over 3 days (FIG. 9A) in supernatant of primary T cells after transduction with circular RNA comprising a *Gaussia* luciferase expression sequence and varying IRES sequences or 24 hour luminescence (FIG. 9B).

Constructs including anabaena intron/exon regions, a *Gaussia* luciferase expression sequence, and a subset of previously tested IRES were circularized and reaction products were purified by size exclusion HPLC. 150,000 primary human CD3+ T cells were electroporated with 1 µg of each circRNA. Luminescence from secreted *Gaussia* luciferase in supernatant was measured 24 hours after electroporation (FIG. 9A). Aichi Virus and CVB3 IRES constructs had the most expression at 24 hours.

Figure 9B:
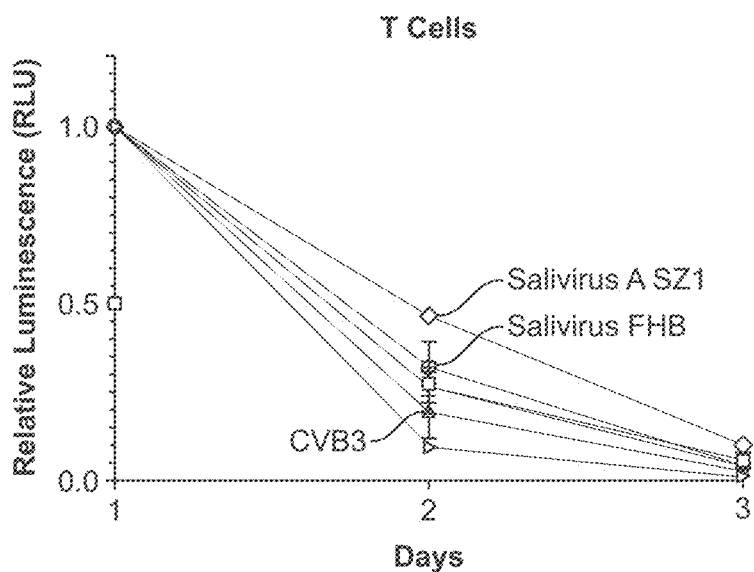

Luminescence was also measured every 24 hours after electroporation for 3 days in order to compare functional stability of each construct (FIG. 9B). The construct with a Salivirus A SZ1 TRES was the most stable.

Example 13

Figure 10A:
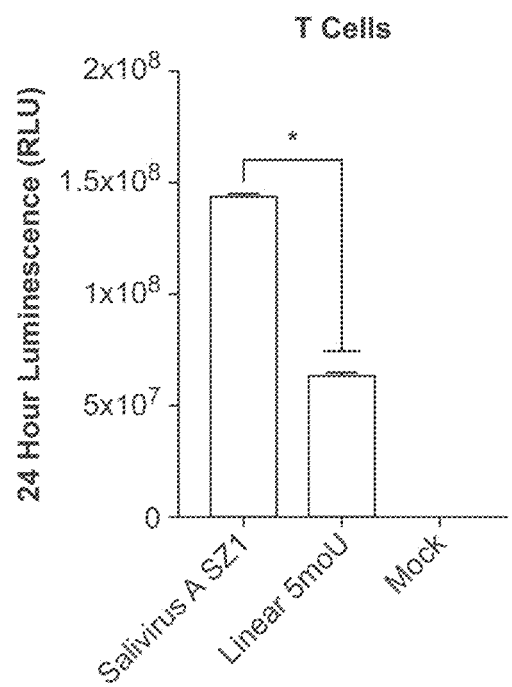
FIGS. 10A-10C depict 24 hour luminescence in supernatant of primary T cells (FIG. 10A) after transduction with circular RNA or modified linear RNA comprising a *Gaussia* luciferase expression sequence, or relative luminescence over 3 days (FIG. 10B), and 24 hour luminescence in PBMCs (FIG. 10C).

Expression and Functional Stability of Circular and Linear RNA in Primary T Cells and PBMCs Constructs including anabaena intron/exon regions, a *Gaussia* luciferase expression sequence, and a Salivirus A SZ1 IRES or Salivirus FHB IRES were circularized. mRNA including a *Gaussia* luciferase expression sequence and a ~150 nt polyA tail, and modified to replace 100% of uridine with 5-methoxy uridine (5moU) and was purchased from Trilink. Expression of Salivirus A SZ1 IRES HPLC purified circular and modified mRNA was measured in human primary CD3+ T cells. Expression of Salivirus FHB HPLC purified circular, unpurified circular and modified mRNA was measured in human PBMCs. Luminescence from secreted *Gaussia* luciferase in supernatant was measured 24 hours after electroporation of 150,000 cells with 1 µg of each RNA species. Data for primary human T cells is in FIGS. 10A and 10B, and data for PBMCs is in FIG. 10C. The difference in expression between the purified circular RNA and unpurified circular RNA or linear RNA was significant in each case ($p<0.05$).

Figure 10B:
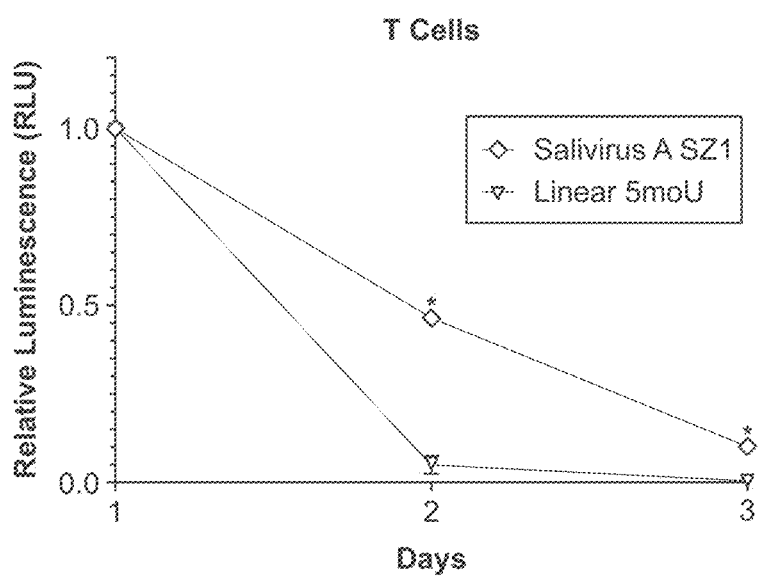
Figure 10C:
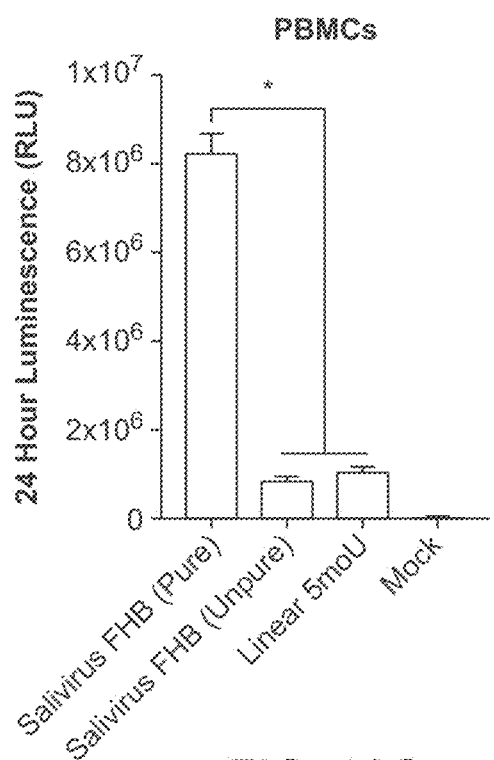

Luminescence from secreted *Gaussia* luciferase in primary T cell supernatant was measured every 24 hours after electroporation over 3 days in order to compare construct functional stability. Data is shown in FIG. 10B. The difference in relative luminescence from the day 1 measurement between purified circular RNA and linear RNA was significant at both day 2 and day 3 for primary T cells.

Example 14

Circularization Efficiency by Permutation Site in Anabaena Intron.

Figure 11A:
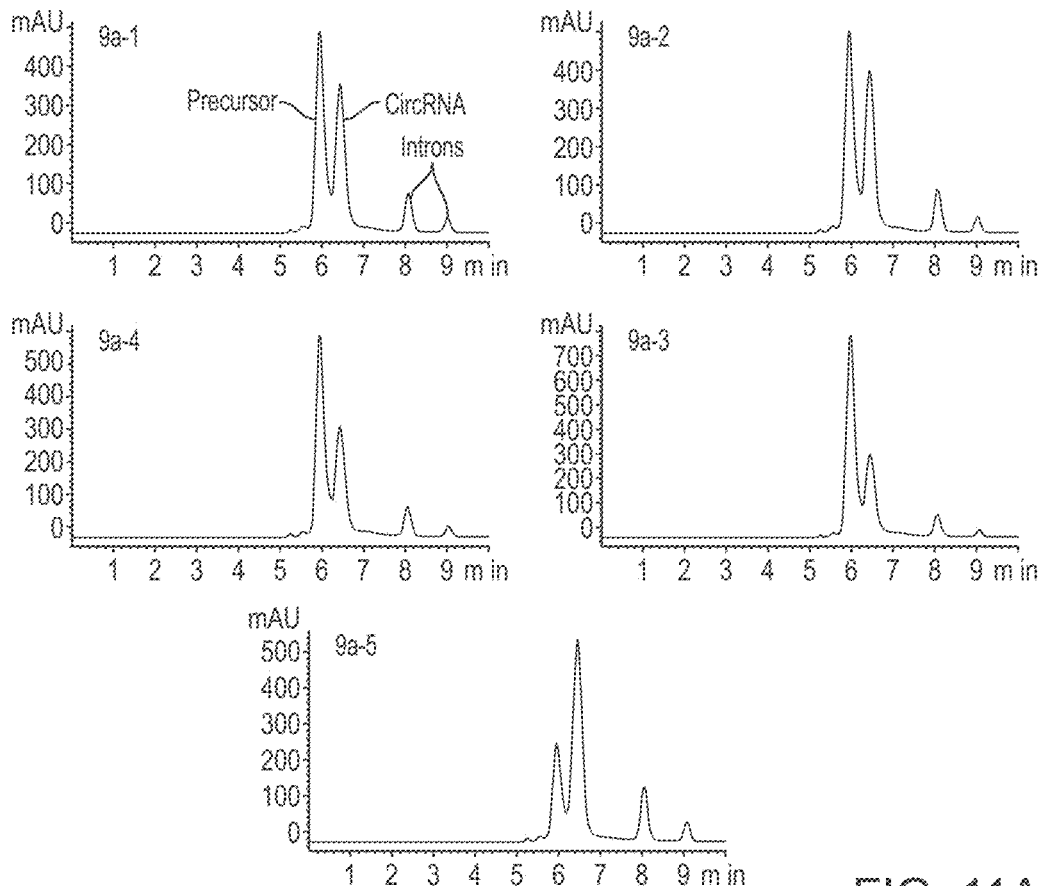
FIG. 11A and FIG. 11B depict HPLC chromatograms (FIG. 11A) and circularization efficiencies (FIG. 11B) of RNA constructs having different permutation sites.

RNA constructs including a CVB3 IRES, a *Gaussia* luciferase expression sequence, anabaena intron/exon regions, spacers, internal duplex regions, and homology arms were produced. Circularization efficiency of constructs using the traditional anabaena intron permutation site and 5 consecutive permutations sites in P9 was measured by HPLC. HPLC chromatograms for the 5 consecutive permutation sites in P9 are shown in FIG. 11A.

Figure 11B:
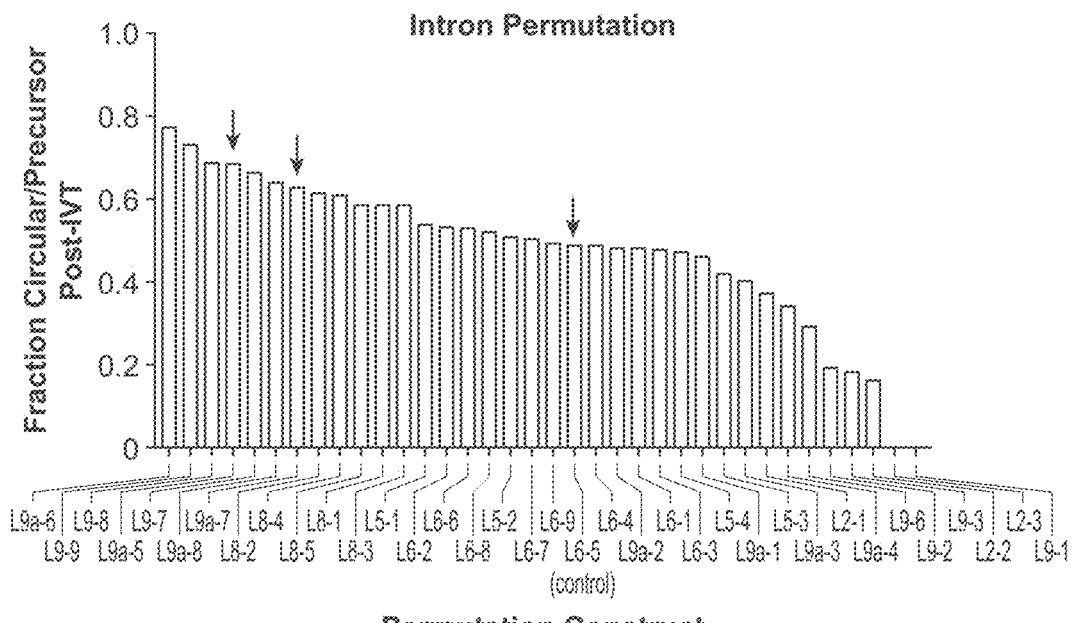

Circularization efficiency was measured at a variety of permutation sites. Circularization efficiency is defined as the area under the HPLC chromatogram curve for each of: circRNA/(circRNA+precursor RNA). Ranked quantification of circularization efficiency at each permutation site is in FIG. 11B. 3 permutation sites (indicated in FIG. 111B) were selected for further investigation.

Circular RNA in this example was circularized by in vitro transcription (IVT) then purified via spin column. Circularization efficiency for all constructs would likely be higher if the additional step of incubation with $Mg^{2+}$ and guanosine nucleotide were included; however, removing this step allowed for comparison between, and optimization of, circular RNA constructs. This level of optimization is especially useful for maintaining high circularization efficiency with large RNA constructs, such as those encoding chimeric antigen receptors.

Example 15

Circularization Efficiency of Alternative Introns

Figure 12A:
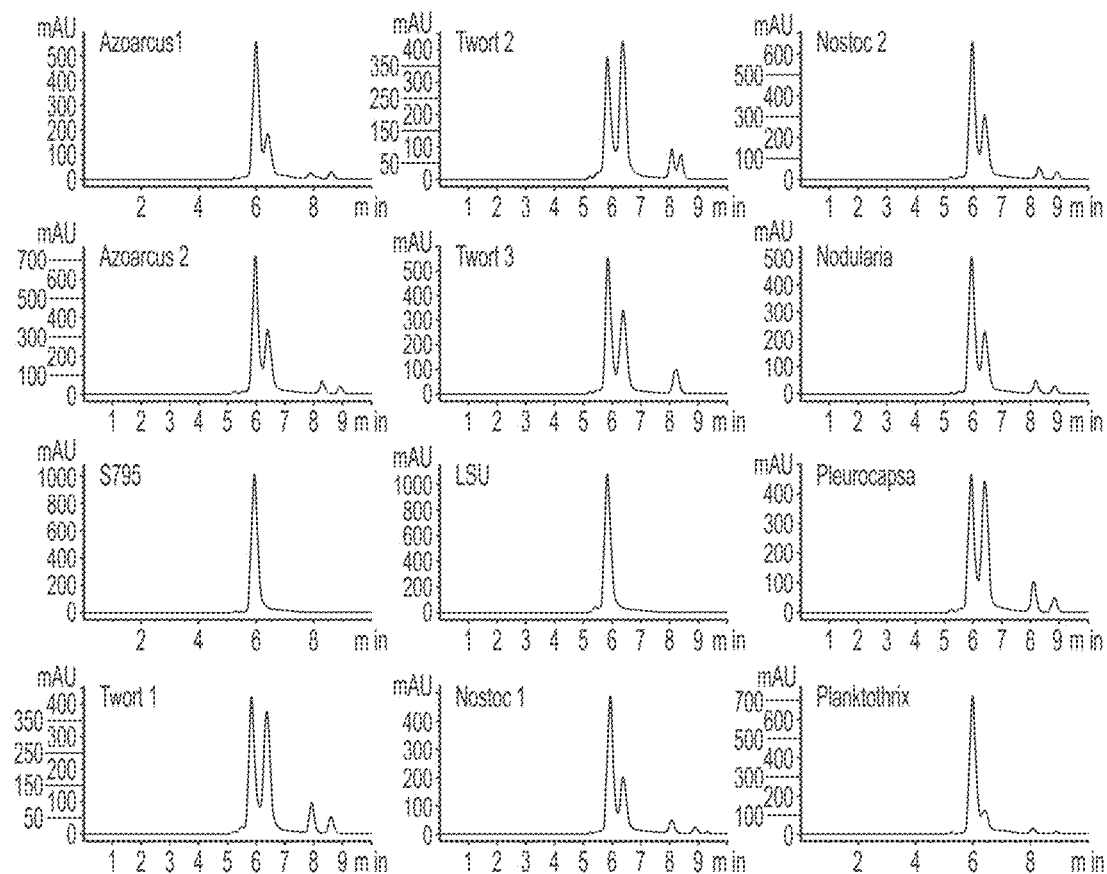
FIG. 12A and FIG. 12B depict HPLC chromatograms (FIG. 12A) and circularization efficiencies (FIG. 12B) of RNA constructs having different introns and/or permutation sites.
Figure 12B:
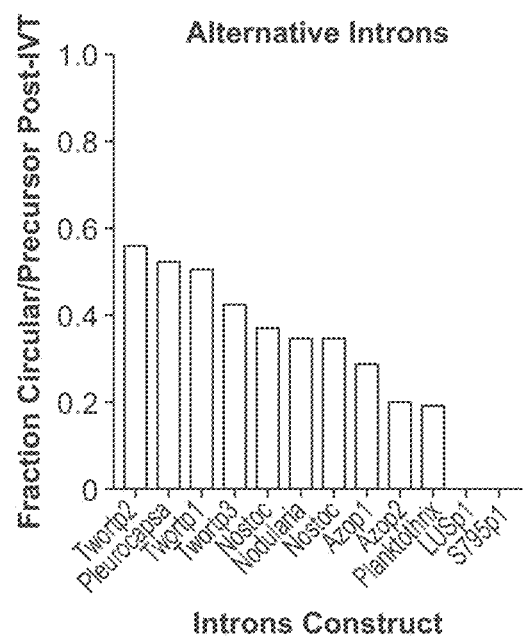

Precursor RNA containing a permuted group 1 intron of variable species origin or permutation site and several constant elements including: a CVB3 IRES, a *Gaussia* luciferase expression sequence, spacers, internal duplex regions, and homology arms were created. Circularization data can be found in FIG. 12. FIG. 12A shows chromatograms resolving precursor, CircRNA and introns. FIG. 12B provides ranked quantification of circularization efficiency, based on the chromatograms shown in FIG. 12A, as a function of intron construct.

Circular RNA in this example was circularized by in vitro transcription (IVT) then spin column purification. Circularization efficiency for all constructs would likely be higher if the additional step of incubation with $Mg^{2+}$ and guanosine nucleotide were included; however, removing this step allows for comparison between, and optimization of, circular RNA constructs. This level of optimization is especially useful for maintaining high circularization efficiency with large RNA constructs, such as those encoding chimeric antigen receptors.

Example 16

Circularization Efficiency by Homology Arm Presence or Length

Figure 13A:
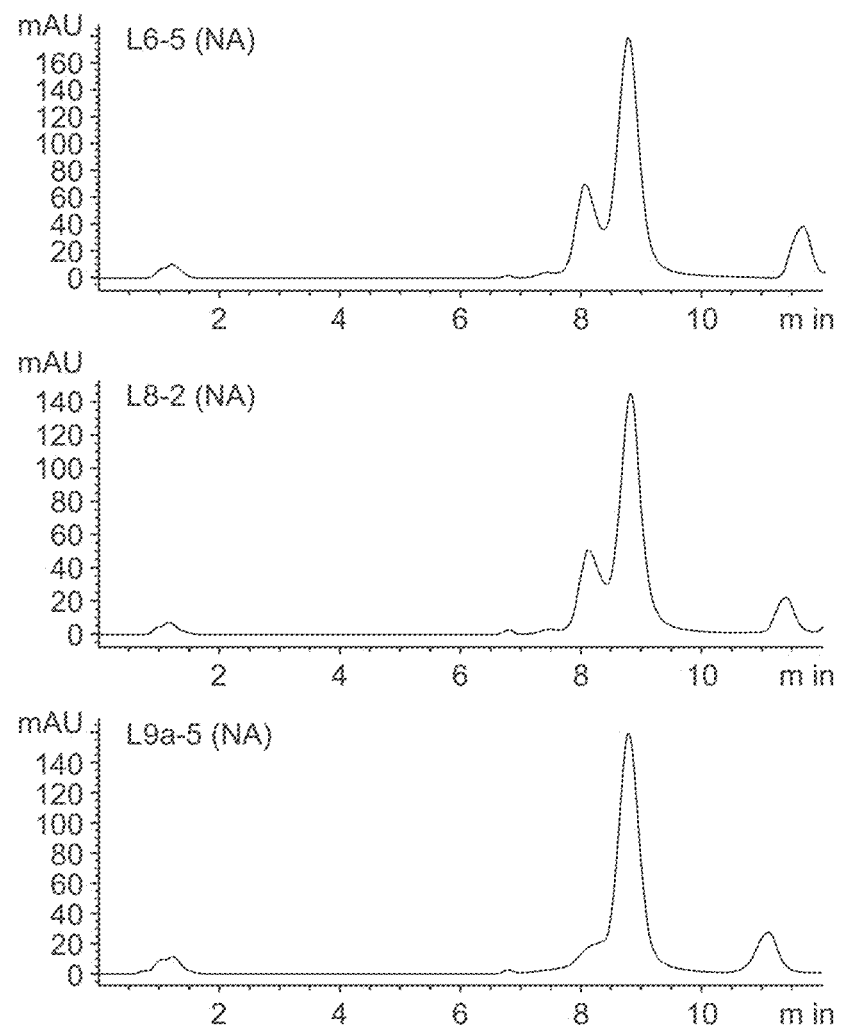
FIG. 13A and FIG. 13B depict HPLC chromatograms (FIG. 13A) and circularization efficiencies (FIG. 13B) of 3 RNA constructs with or without homology arms.
Figure 13B:
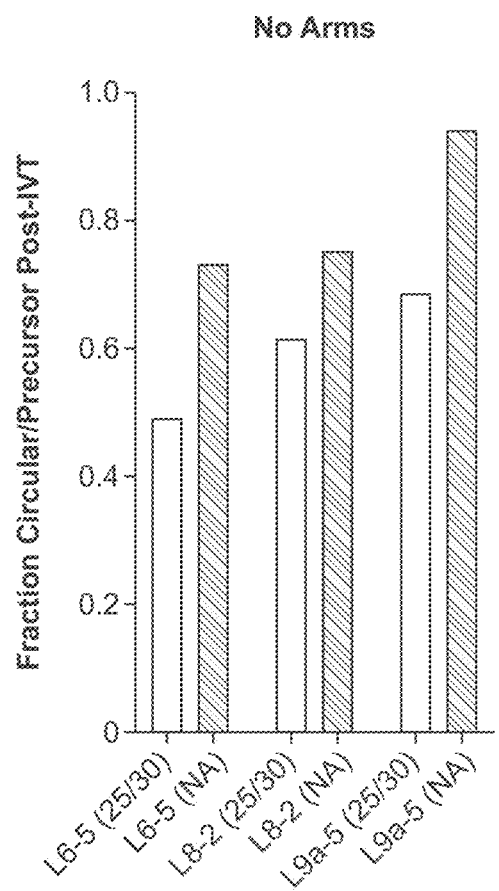

RNA constructs including a CVB3 IRES, a *Gaussia* luciferase expression sequence, anabaena intron/exon regions, spacers, and internal duplex regions were produced. Constructs representing 3 anabaena intron permutation sites were tested with 30 nt, 25% GC homology arms or without homology arms ("NA"). These constructs were allowed to circularize without the step of incubation with $Mg^{2+}$. Circularization efficiency was measured and compared. Data can be found in FIG. 13. Circularization efficiency was higher for each construct lacking homology arms. FIG. 13A provides ranked quantification of circularization efficiency; FIG. 13B provides chromatograms resolving precursor, circRNA and introns.

Figure 14:
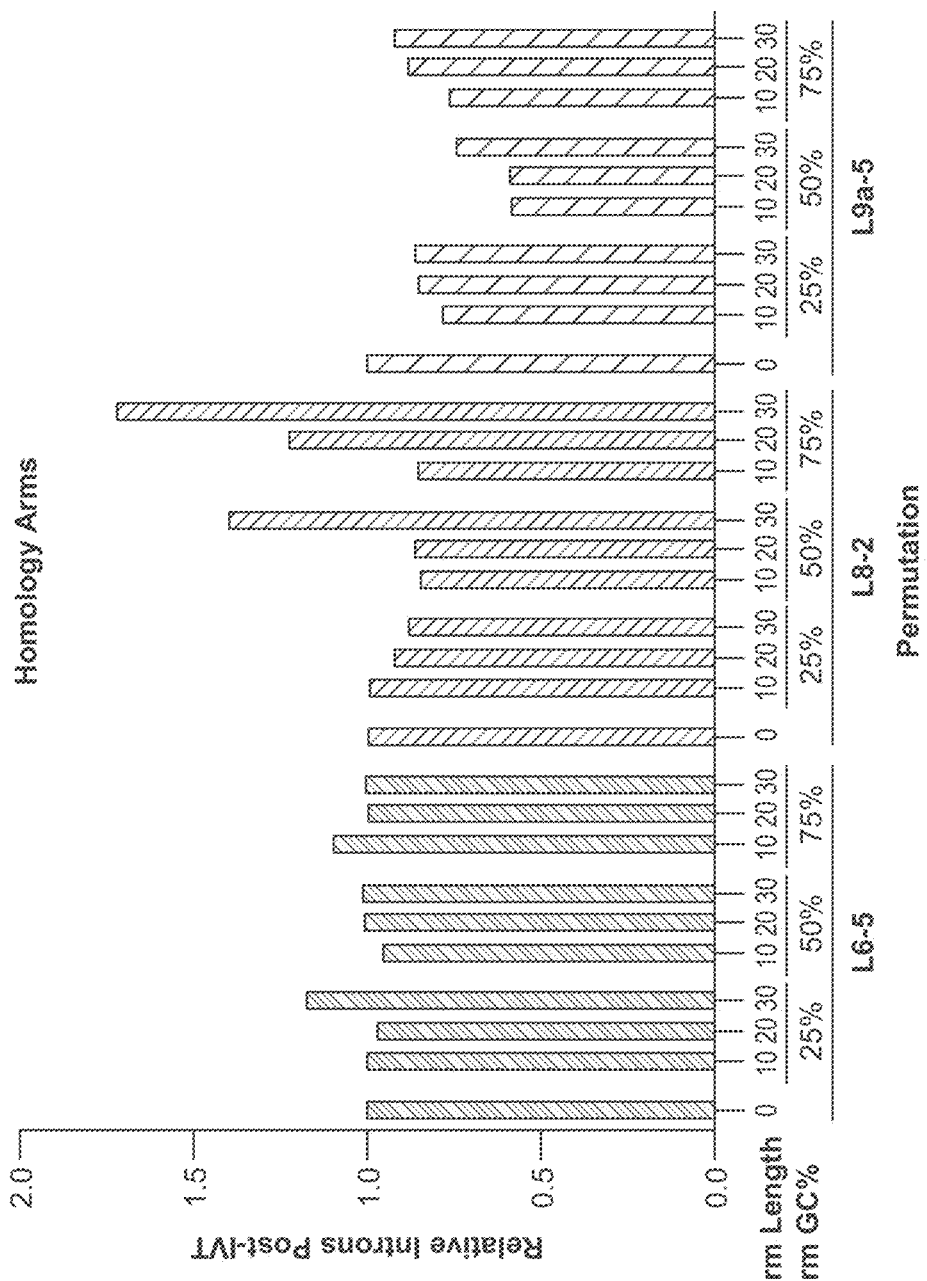
FIG. 14 depicts circularization efficiencies of 3 RNA constructs without homology arms or with homology arms having various lengths and GC content.

For each of the 3 permutation sites, constructs were created with 10 nt, 20 nt, and 30 nt arm length and 25%, 50%, and 75% GC. Splicing efficiency of these constructs was measured and compared to constructs without homology arms (FIG. 14). Splicing efficiency is defined as the proportion of free introns relative to the total RNA in the splicing reaction.

Figure 15A:
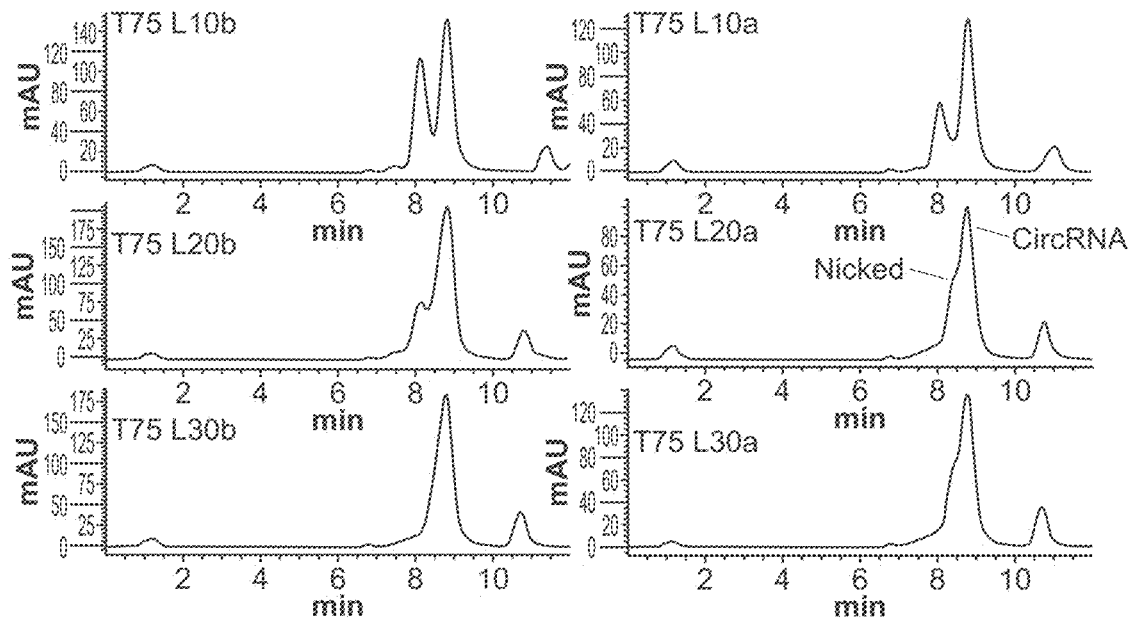
FIGS. 15A and 15B depict HPLC chromatograms showing the contribution of strong homology arms to improved splicing efficiency, the relationship between circularization efficiency and nicking in select constructs, and combinations of permutations sites and homology arms hypothesized to demonstrate improved circularization efficiency.

FIG. 15A (left) contains HPLC chromatograms showing the contribution of strong homology arms to improved splicing efficiency. Top left: 75% GC content, 10 nt homology arms. Center left: 75% GC content, 20 nt homology arms. Bottom left: 75% GC content, 30 nt homology arms.

FIG. 15A (right) shows HPLC chromatograms indicating increased splicing efficiency paired with increased nicking, appearing as a shoulder on the circRNA peak. Top right: 75% GC content, 10 nt homology arms. Center right: 75% GC content, 20 nt homology arms. Bottom right: 75% GC content, 30 nt homology arms.

Figure 15B:
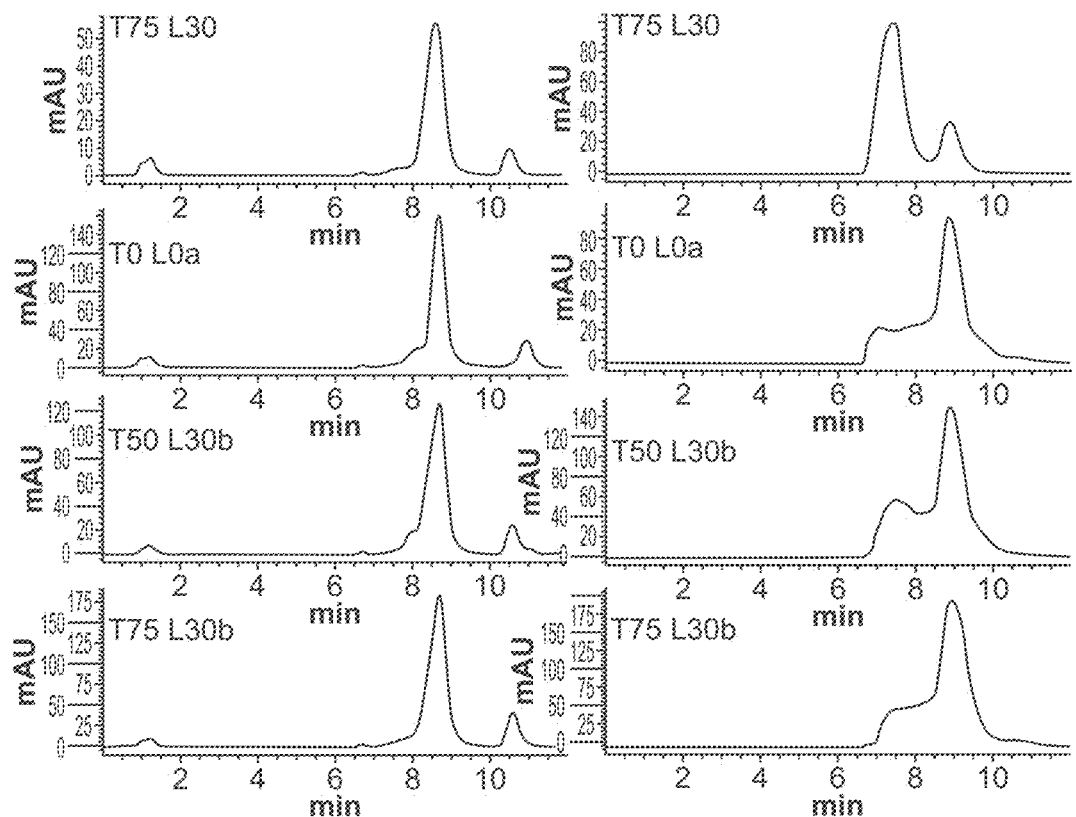

FIG. 15B (left) shows select combinations of permutation sites and homology arms hypothesized to demonstrate improved circularization efficiency.

FIG. 15B (right) shows select combinations of permutation sites and homology arms hypothesized to demonstrate improved circularization efficiency, treated with *E. coli* polyA polymerase.

Circular RNA in this example was circularized by in vitro transcription (IVT) then spin-column purified. Circularization efficiency for all constructs would likely be higher if an additional $Mg^{2+}$ incubation step with guanosine nucleotide were included; however, removing this step allowed for comparison between, and optimization of, circular RNA constructs. This level of optimization is especially useful for maintaining high circularization efficiency with large RNA constructs, such as those encoding chimeric antigen receptors.

Example 17

Circular RNA Encoding Chimeric Antigen Receptors

Figure 16:
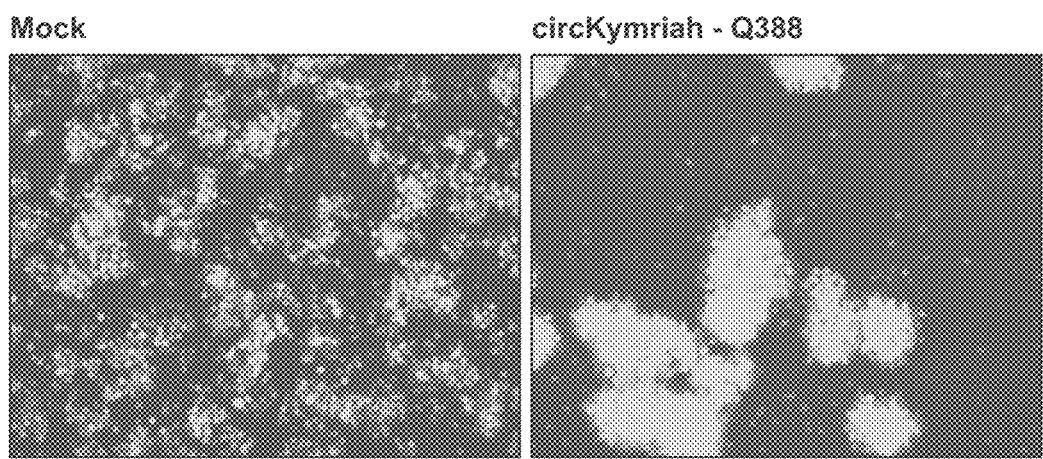
FIG. 16 shows fluorescent images of T cells mock electroporated (left) or electroporated with circular RNA encoding a CAR (right) and co-cultured with Raji cells expressing GFP and firefly luciferase.

Constructs including anabaena intron/exon regions, a Kymriah chimeric antigen receptor (CAR) expression sequence, and a CVB3 IRES were circularized. 100,000 human primary CD3+ T cells were electroporated with 500 ng of circRNA and co-cultured for 24 hours with Raji cells stably expressing GFP and firefly luciferase. Effector to target ratio (E:T ratio) 0.75:1. 100,000 human primary CD3+ T cells were mock electroporated and co-cultured as a control (FIG. 16).

Figure 17:
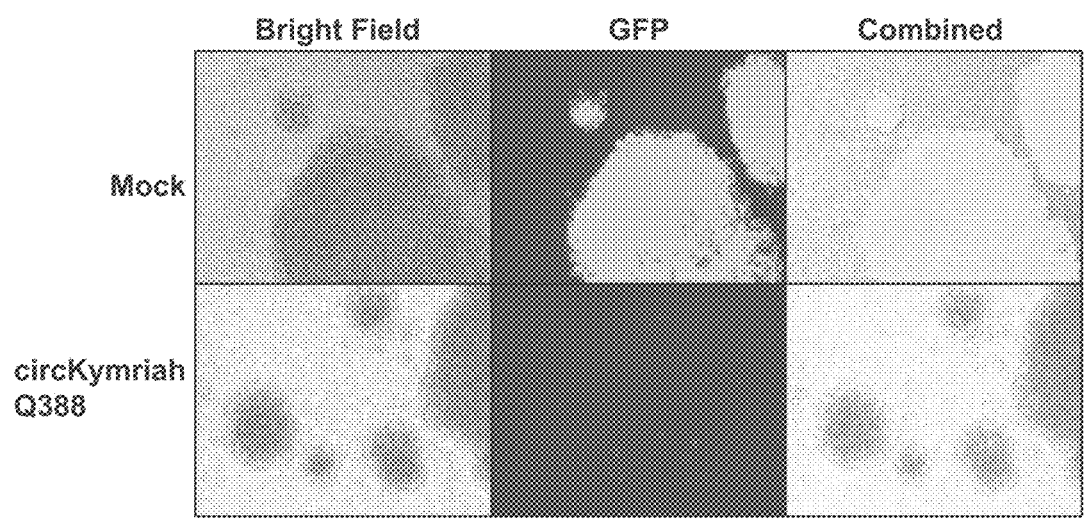
FIG. 17 shows bright field (left), fluorescent (center), and overlay (right) images of T cells mock electroporated (top) or electroporated with circular RNA encoding a CAR (bottom) and co-cultured with Raji cells expressing GFP and firefly luciferase.

Sets of 100,000 human primary CD3+ T cells were mock electroporated or electroporated with 1 µg of circRNA then co-cultured for 48 hours with Raji cells stably expressing GFP and firefly luciferase. E:T ratio 10:1 (FIG. 17).

Figure 18:
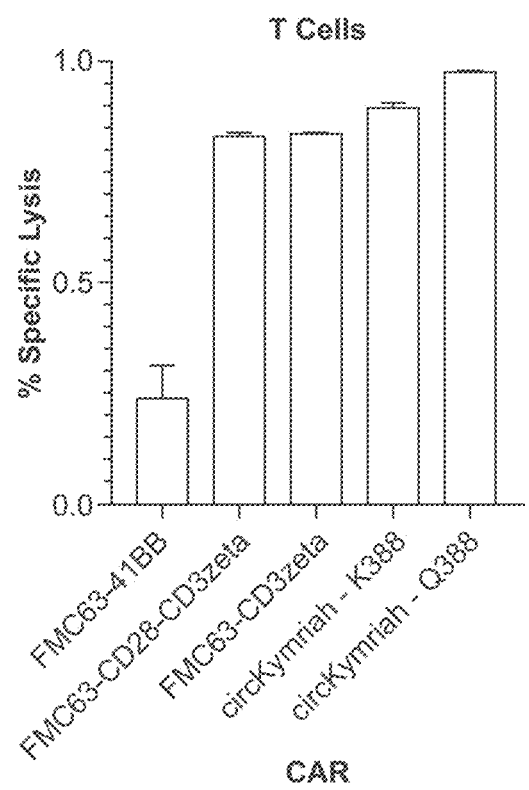
FIG. 18 depicts specific lysis of Raji target cells by T cells mock electroporated or electroporated with circular RNA encoding different CAR sequences.

Quantification of specific lysis of Raji target cells was determined by detection of firefly luminescence (FIG. 18). 100,000 human primary CD3+ T cells either mock electroporated or electroporated with circRNA encoding different CAR sequences were co-cultured for 48 hours with Raji cells stably expressing GFP and firefly luciferase. % Specific lysis defined as 1-[CAR condition luminescence]/[mock condition luminescence]. E:T ratio 10:1.

Example 18

Figure 19A:
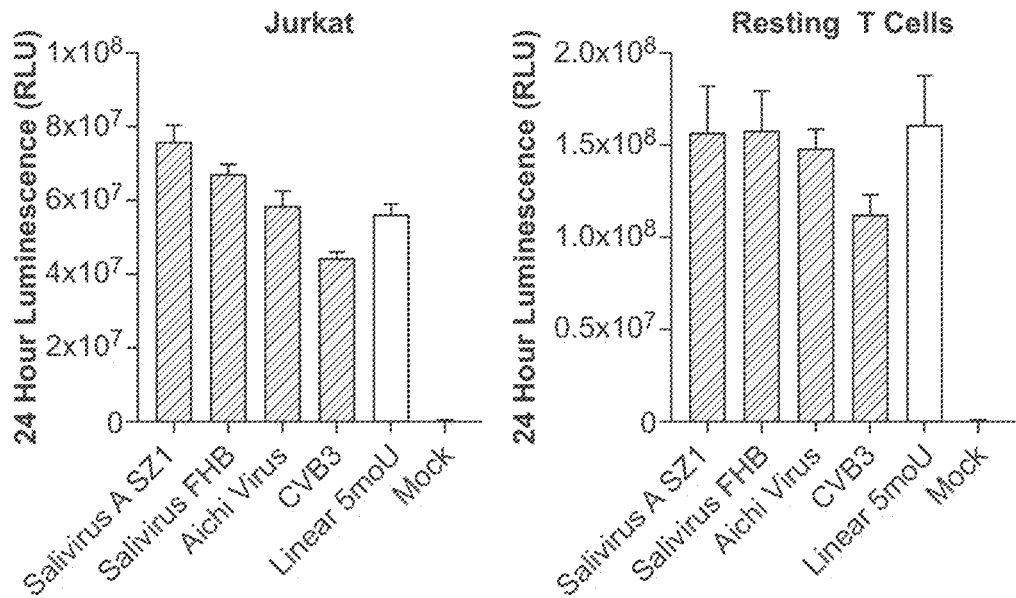
FIG. 19A and FIG. 19B depict luminescence in supernatants of Jurkat cells (left) or resting primary human CD3+ T cells (right) 24 hours after transduction with linear or circular RNA comprising a *Gaussia* luciferase expression sequence and varying IRES sequences (FIG. 19A), and relative luminescence over 3 days (FIG. 19B).

Expression and Functional Stability of Circular and Linear RNA in Jurkat Cells and Resting Human T Cells Constructs including anabaena intron/exon regions, a *Gaussia* luciferase expression sequence, and a subset of previously tested IRES were circularized and reaction products were purified by size exclusion HPLC. 150,000 Jurkat cells were electroporated with 1 µg of circular RNA or 5moU-mRNA. Luminescence from secreted *Gaussia* luciferase in supernatant was measured 24 hours after electroporation (FIG. 19A left). 150,000 resting primary human CD3+ T cells (10 days post-stimulation) were electroporated with 1 µg of circular RNA or 5moU-mRNA. Luminescence from secreted *Gaussia* luciferase in supernatant was measured 24 hours after electroporation (FIG. 19A right).

Figure 19B:
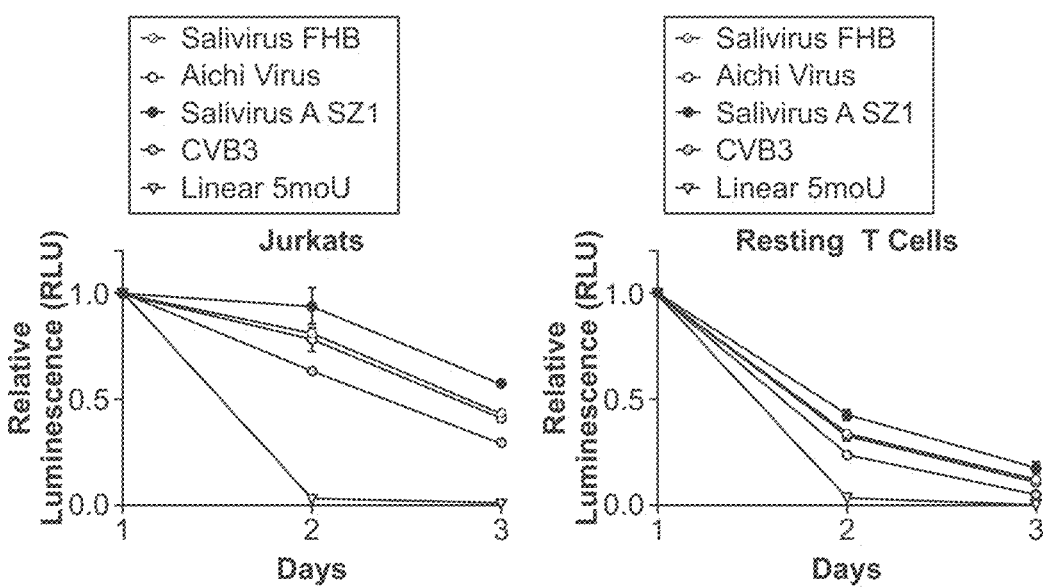

Luminescence from secreted *Gaussia* luciferase in supernatant was measured every 24 hours after electroporation, followed by complete media replacement. Functional stability data is shown in FIG. 19B. Circular RNA had more functional stability than linear RNA in each case, with a more pronounced difference in Jurkat cells.

Example 19

Figure 20A:
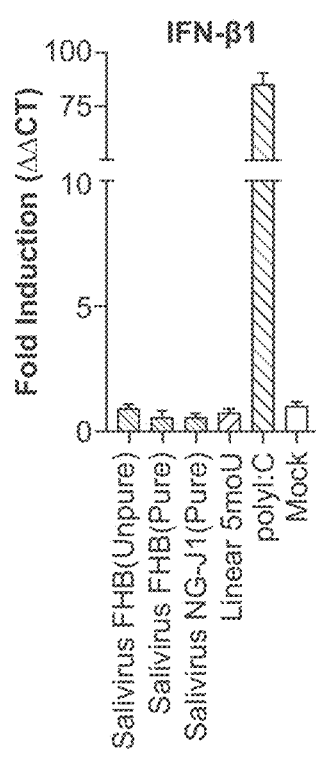
FIGS. 20A-20F depict transcript induction of IFN-β1 (FIG. 20A), RIG-I (FIG. 20B), IL-2 (FIG. 20C), IL-6 (FIG. 20D), IFNγ (FIG. 20E), and TNFα (FIG. 20F) after electroporation of human CD3+ T cells with modified linear, unpurified circular, or purified circular RNA.
Figure 20B:
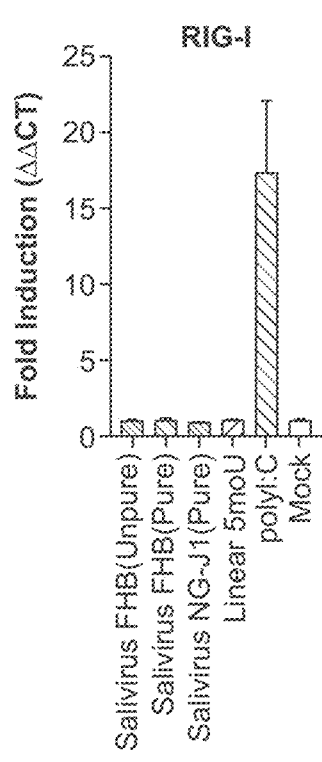
Figure 20C:
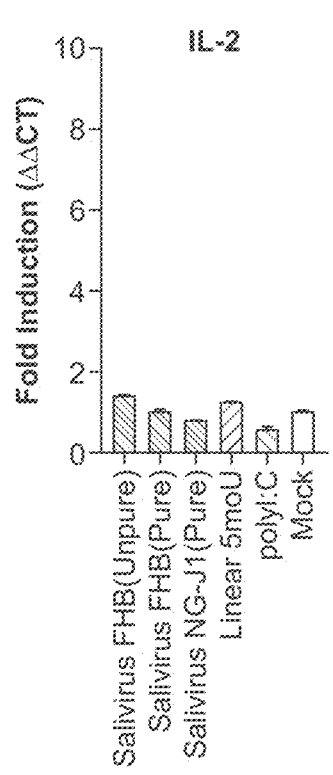
Figure 20D:
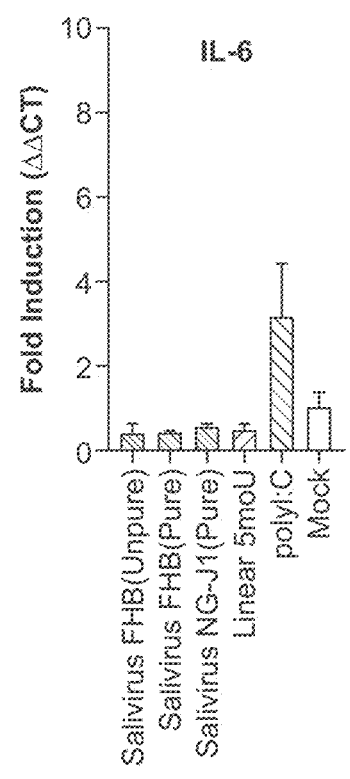
Figure 20E:
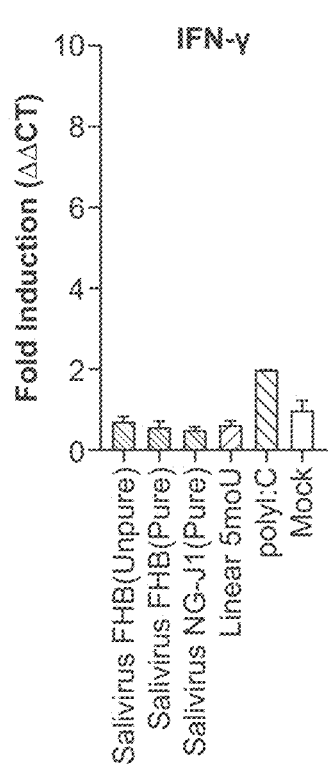
Figure 20F:
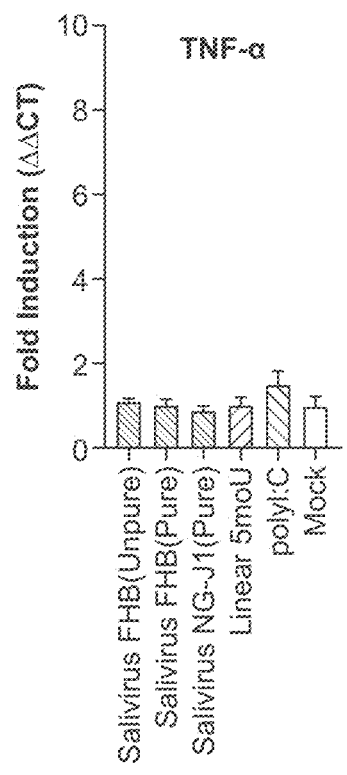

IFN-β1, RIG-I, IL-2, IL-6, IFNγ, and TNFα Transcript Induction of Cells Electroporated with Linear RNA or Varying Circular RNA Constructs Constructs including anabaena intron/exon regions, a *Gaussia* luciferase expression sequence, and a subset of previously tested IRES were circularized and reaction products were purified by size exclusion HPLC. 150,000 CD3+ human T cells were electroporated with 1 µg of circular RNA, 5moU-mRNA, or immunostimulatory positive control poly inosine:cytosine. IFN-β1 (FIG. 20A), RIG-I (FIG. 20B), IL-2 (FIG. 20C), IL-6 (FIG. 20D), IFN-γ (FIG. 20E), and TNF-α (FIG. 20F) transcript induction was measured 18 hours after electroporation.

Example 20

Specific lysis of target cells and IFNγ transcript induction by CAR expressing cells electroporated with different amounts of circular or linear RNA; specific lysis of target and non-target cells by CAR expressing cells at different E:T ratios.

Figure 21A:
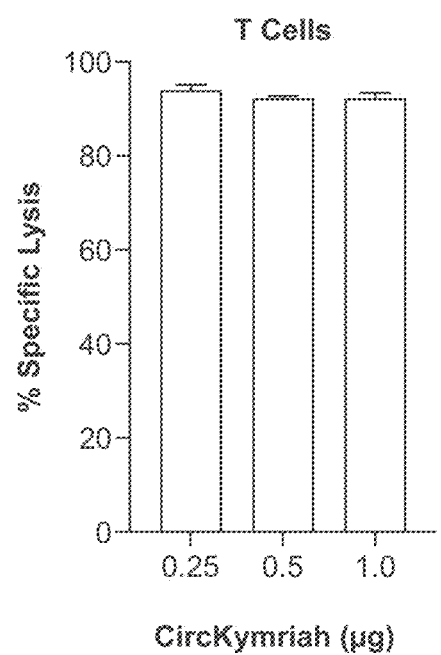
FIG. 21A and FIG. 21B depict specific lysis of Raji target cells by human primary CD3+ T cells electroporated with circRNA encoding a CAR as determined by detection of firefly luminescence (FIG. 21A), and IFNγ transcript induction 24 hours after electroporation with different quantities of circular or linear RNA encoding a CAR sequence (FIG. 21B).
Figure 21B:
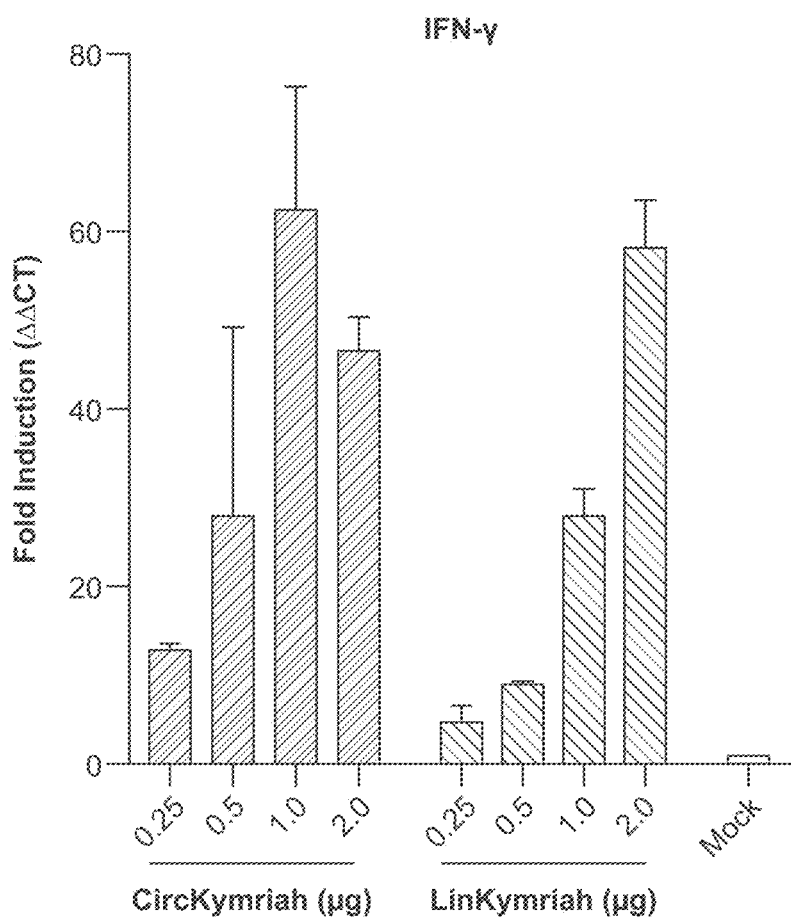

Constructs including anabaena intron/exon regions, an anti-CD19 CAR expression sequence, and a CVB3 IRES were circularized and reaction products were purified by size exclusion HPLC. 150,000 human primary CD3+ T cells either mock electroporated or electroporated with different quantities of circRNA encoding an anti-CD19 CAR sequence were co-cultured for 12 hours with Raji cells stably expressing GFP and firefly luciferase at an E:T ratio of 2:1. Specific lysis of Raji target cells was determined by detection of firefly luminescence (FIG. 21A). % Specific lysis was defined as 1-[CAR condition luminescence]/[mock condition luminescence]. IFNγ transcript induction was measured 24 hours after electroporation (FIG. 21).

Figure 22A:
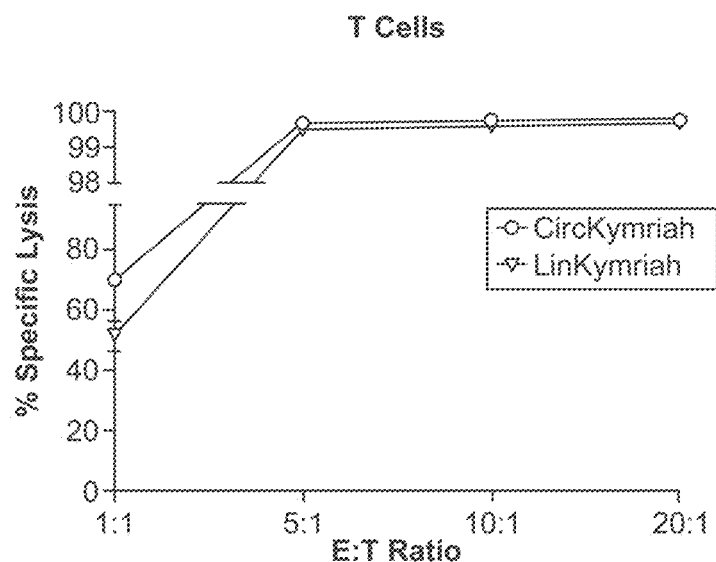
FIG. 22A and FIG. 22B depict specific lysis of target or non-target cells by human primary CD3+ T cells electroporated with circular or linear RNA encoding a CAR at different E:T ratios as determined by detection of firefly luminescence.

150,000 human primary CD3+ T cells were either mock electroporated or electroporated with 500 ng circRNA or m1ψ-mRNA encoding an anti-CD19 CAR sequence, then co-cultured for 24 hours with Raji cells stably expressing firefly luciferase at different E:T ratios. Specific lysis of Raji target cells was determined by detection of firefly luminescence (FIG. 22A). Specific lysis was defined as 1-[CAR condition luminescence]/[mock condition luminescence].

Figure 22B:
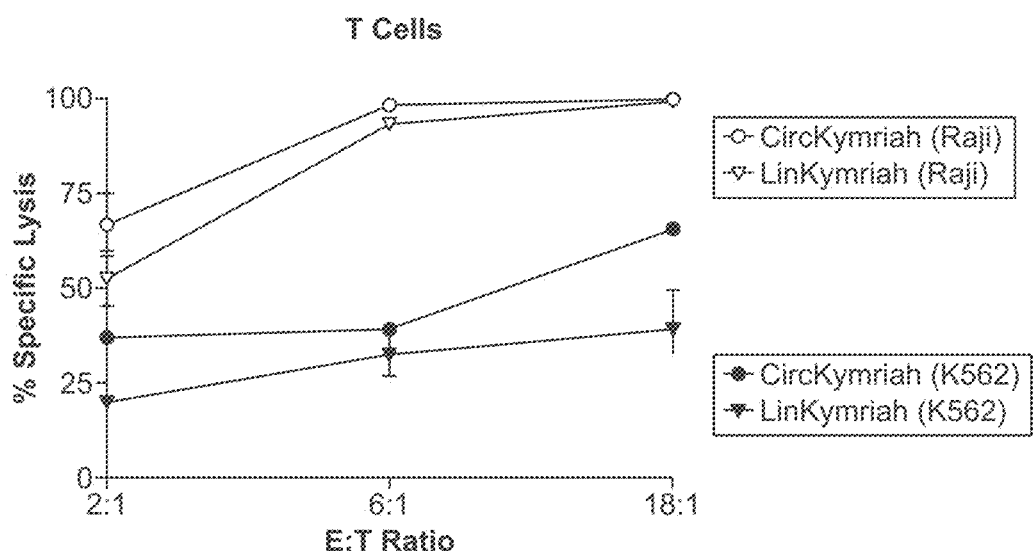

CAR expressing T cells were also co-cultured for 24 hours with Raji or K562 cells stably expressing firefly luciferase at different E:T ratios. Specific lysis of Raji target cells or K562 non-target cells was determined by detection of firefly luminescence (FIG. 22B). % Specific lysis is defined as 1-[CAR condition luminescence]/[mock condition luminescence].

Example 21

Figure 23:
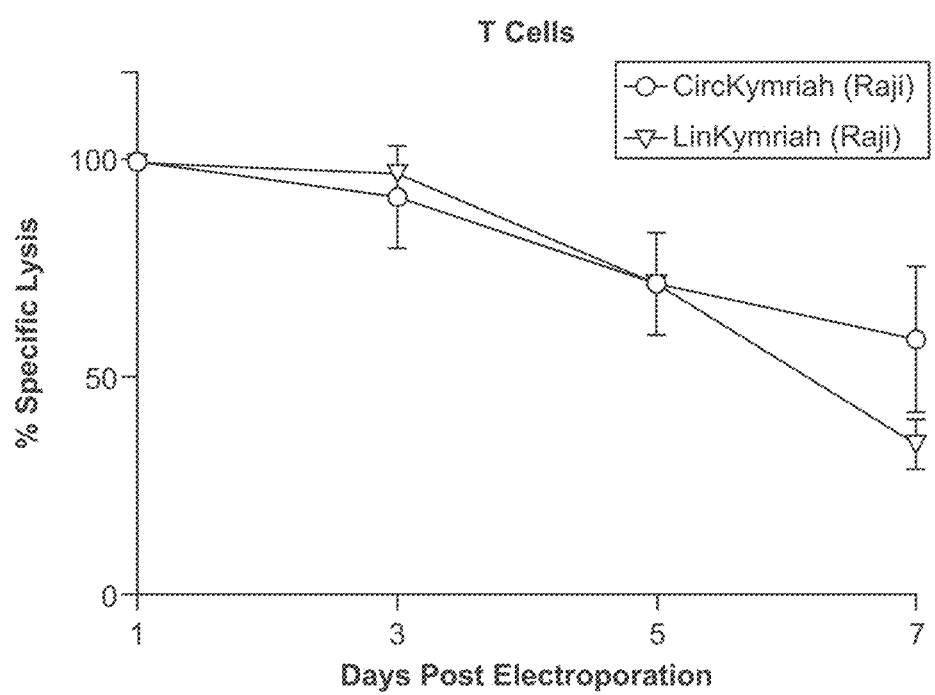
FIG. 23 depicts specific lysis of target cells by human CD3+ T cells electroporated with RNA encoding a CAR at 1, 3, 5, and 7 days post electroporation.

Specific Lysis of Target Cells by T Cells Electroporated with Circular RNA or Linear RNA Encoding a CAR Constructs including anabaena intron/exon regions, an anti-CD19 CAR expression sequence, and a CVB3 IRES were circularized and reaction products were purified by size exclusion HPLC. Human primary CD3+ T cells were electroporated with 500 ng of circular RNA or an equimolar quantity of m1ψ-mRNA, each encoding a CD19-targeted CAR. Raji cells were added to CAR-T cell cultures over 7 days at an E:T ratio of 10:1. % Specific lysis was measured for both constructs at 1, 3, 5, and 7 days (FIG. 23).

Example 22

Figure 24:
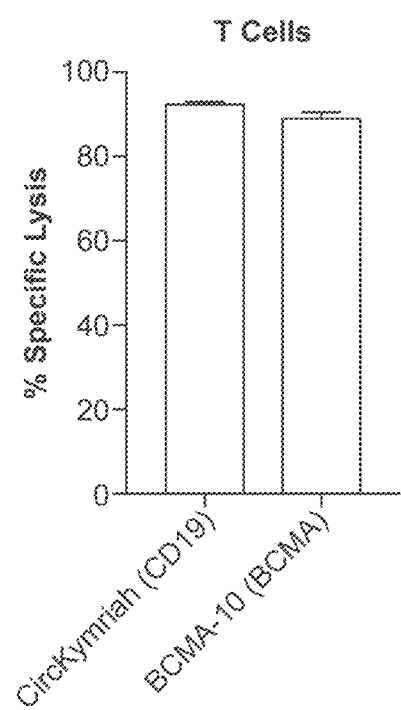
FIG. 24 depicts specific lysis of target cells by human CD3+ T cells electroporated with circular RNA encoding a CD19 or BCMA targeted CAR.
Figure 25A:
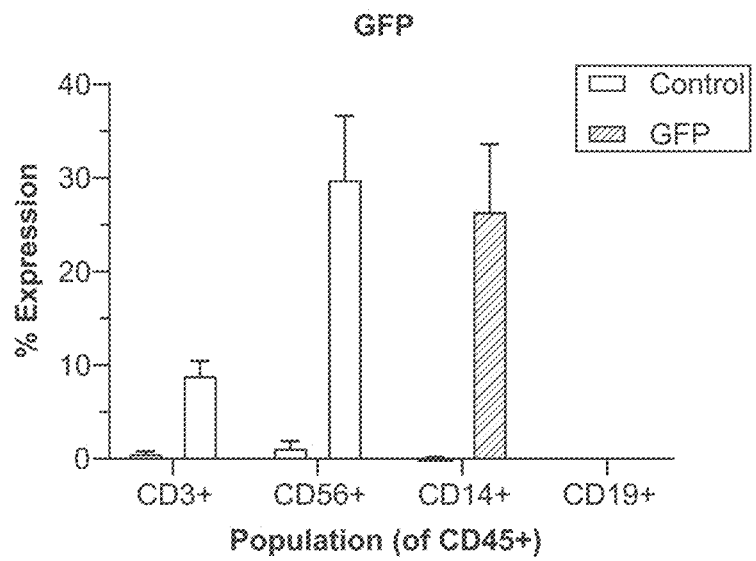
FIG. 25A and FIG. 25B show the expression of GFP (FIG. 25A) and CD19 CAR (FIG. 25B) in human PBMCs after incubating with testing lipid nanoparticle containing circular RNA encoding either GFP or CD19 CAR.
Figure 25B:
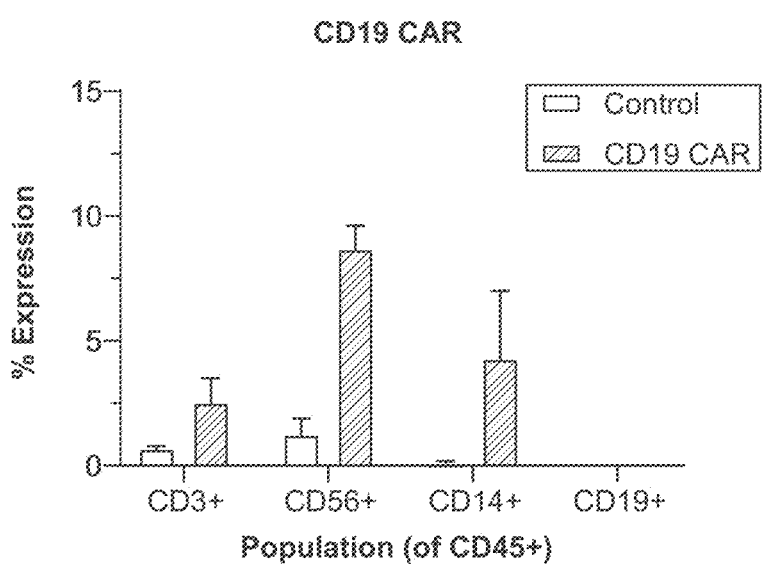

Specific Lysis of Raji Cells by T Cells Expressing an Anti-CD19 CAR or an Anti-BCMA CAR Constructs including anabaena intron/exon regions, anti-CD19 or anti-BCMA CAR expression sequence, and a CVB3 IRES were circularized and reaction products were purified by size exclusion HPLC. 150,000 primary human CD3+ T cells were electroporated with 500 ng of circRNA, then were co-cultured with Raji cells at an E:T ratio of 2:1. % Specific lysis was measured 12 hours after electroporation (FIG. 24).

Example 23

Expression, Functional Stability, and Cytokine Transcript Induction of Circular and Linear RNA Expressing Antigens Constructs including one or more antigen expression sequences are circularized and reaction products are purified by size exclusion HPLC. Antigen presenting cells are electroporated with circular RNA or mRNA.

In vitro antigen production is measured via ELISA. Optionally, antigen production is measured every 24 hours after electroporation. Cytokine transcript induction or release is measured 18 hours after electroporation of antigen presenting cells with circular or linear RNA encoding antigens. The tested cytokines may include IFN-β1, RIG-I, IL-2, IL-6, IFNγ, RANTES, and TNFα.

In vitro antigen production and cytokine induction are measured using purified circRNA, purified circRNA plus antisense circRNA, and unpurified circRNA in order to find the ratio that best preserves expression and immune stimulation.

Example 24

In Vivo Antigen and Antibody Expression in Animal Models

To assess the ability of antigen encoding circRNAs to facilitate antigen expression and antibody production in vivo, escalating doses of RNA encoding one or more antigens is introduced into mice via intramuscular injection.

Mice are injected once, blood collected after 28 days, then injected again, with blood collected 14 days thereafter. Neutralizing antibodies against antigen of interest is measured via ELISA.

Example 25

Protection Against Infection

To assess the ability of antigen encoding circRNAs to protect against or cure an infection, RNA encoding one or more antigens of a virus (such as influenza) is introduced into mice via intramuscular injection.

Mice receive an initial injection and boost injections of circRNA encoding one or more antigens. Protection from a virus such as influenza is determined by weight loss and mortality over 2 weeks.

Example 26

Example 26A: Synthesis of Compounds

Synthesis of representative ionizable lipids of the invention are described in PCT applications PCT/US2016/052352, PCT/US2016/068300, PCT/US2010/061058, PCT/US2018/058555, PCT/US2018/053569, PCT/US2017/028981, PCT/US2019/025246, PCT/US2018/035419, PCT/US2019/015913, PCT/US2020/063494, and US applications with publication numbers 20190314524, 20190321489, and 20190314284, the contents of each of which are incorporated herein by reference in their entireties.

Example 26B: Synthesis of Compounds

Synthesis of representative ionizable lipids of the invention are described in US patent publication number US20170210697A1, the contents of which is incorporated herein by reference in its entirety.

Example 27

Protein Expression by Organ

Circular or linear RNA encoding FLuc was generated and loaded into transfer vehicles with the following formulation: 50% ionizable lipid represented by

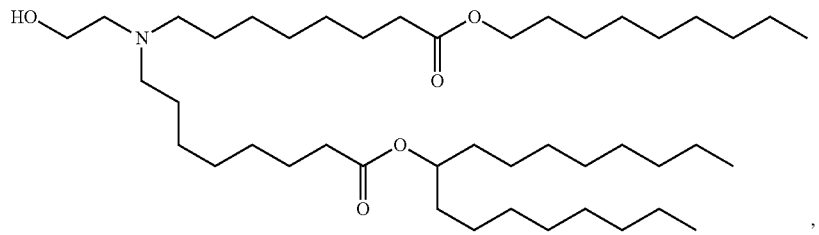 [SMILES: CCCCCCCCCOC(=O)CCCCCCCN(CCO)CCCCCCCC(=O)OC(CCCCCCCC)CCCCCCCC]

10% DSPC, 1.5% PEG-DMG, 38.5% cholesterol. CD-1 mice were dosed at 0.2 mg/kg and luminescence was measured at 6 hours (live IVIS) and 24 hours (live IVIS and ex vivo IVIS). Total Flux (photons/second over a region of interest) of the liver, spleen, kidney, lung, and heart was measured.

Example 28

Distribution of Expression in the Spleen

Circular or linear RNA encoding GFP is generated and loaded into transfer vehicles with the following formulation: 50% ionizable Lipid represented by

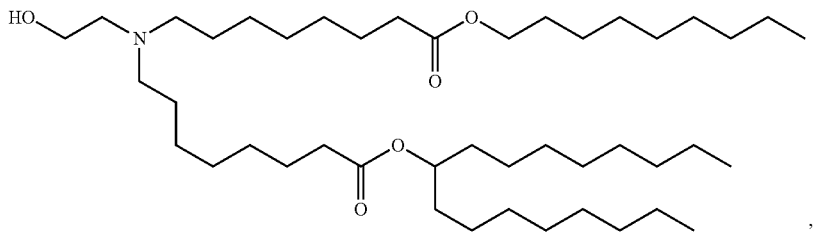 [SMILES: CCCCCCCCCOC(=O)CCCCCCCN(CCO)CCCCCCCC(=O)OC(CCCCCCCC)CCCCCCCC]

10% DSPC, 1.5% PEG-DMG, 38.5% cholesterol. The formulation is administered to CD-1 mice. Flow cytometry is run on spleen cells to determine the distribution of expression across cell types.

Example 29

Example 29A: Production of Nanoparticle Compositions

In order to investigate safe and efficacious nanoparticle compositions for use in the delivery of circular RNA to cells, a range of formulations are prepared and tested. Specifically, the particular elements and ratios thereof in the lipid component of nanoparticle compositions are optimized.

Nanoparticles can be made in a 1 fluid stream or with mixing processes such as microfluidics and T-junction mixing of two fluid streams, one of which contains the circular RNA and the other has the lipid components.

Lipid compositions are prepared by combining an ionizable lipid, optionally a helper lipid (such as DOPE, DSPC, or oleic acid obtainable from Avanti Polar Lipids, Alabaster, AL), a PEG lipid (such as 1,2-dimyristoyl-sn-glycerol methoxypolyethylene glycol, also known as PEG-DMG, obtainable from Avanti Polar Lipids, Alabaster, AL), and a structural lipid such as cholesterol at concentrations of about, e.g., 40 or 50 mM in a solvent, e.g., ethanol. Solutions should be refrigerated for storage at, for example, −20° C. Lipids are combined to yield desired molar ratios (see, for example, Tables 17a and 17b below) and diluted with water and ethanol to a final lipid concentration of e.g., between about 5.5 mM and about 25 mM.

TABLE 17a

| Formulation number | Description |
|---|---|
| 1 | Aliquots of 50 mg/mL ethanolic solutions of C12-200, DOPE, Chol and DMG-PEG2K (40:30:25:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 2 | Aliquots of 50 mg/mL ethanolic solutions of DODAP, DOPE, cholesterol and DMG-PEG2K (18:56:20:6) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. Final concentration = 1.35 mg/mL EPO circRNA (encapsulated). Zave = 75.9 nm (Dv(50) = 57.3 nm; Dv(90) = 92.1 nm). |
| 3 | Aliquots of 50 mg/mL ethanolic solutions of HGT4003, DOPE, cholesterol and DMG-PEG2K (50:25:20:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 4 | Aliquots of 50 mg/mL ethanolic solutions of ICE, DOPE and DMG-PEG2K (70:25:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 5 | Aliquots of 50 mg/mL ethanolic solutions of HGT5000, DOPE, cholesterol and DMG-PEG2K (40:20:35:5) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. Final concentration = 1.82 mg/mL EPO mRNA (encapsulated). Zave = 105.6 nm (Dv(50) = 53.7 nm; Dv(90) = 157 nm). |

TABLE 17a-continued

| Formulation number | Description |
|---|---|
| 6 | Aliquots of 50 mg/mL ethanolic solutions of HGT5001, DOPE, cholesterol and DMG-PEG2K (40:20:35:5) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 7 | Aliquots of 50 mg/mL ethanolic solutions of HGT5001, DOPE, cholesterol and DMG-PEG2K (35:16:46.5:2.5) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 8 | Aliquots of 50 mg/mL ethanolic solutions of HGT5001, DOPE, cholesterol and DMG-PEG2K (40:10:40:10) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |

In some embodiments, transfer vehicle has a formulation as described in Table 17a.

TABLE 17b

| Composition (mol %) | Components |
|---|---|
| 40:20:38.5:1.5 | Compound:Phospholipid:Phytosterol*:PEG-DMG |
| 45:15:38.5:1.5 | Compound:Phospholipid:Phytosterol*:PEG-DMG |
| 50:10:38.5:1.5 | Compound:Phospholipid:Phytosterol*:PEG-DMG |
| 55:5:38.5:1.5 | Compound:Phospholipid:Phytosterol*:PEG-DMG |
| 60:5:33.5:15 | Compound:Phospholipid:Phytosterol*:PEG-DMG |
| 45:20:33.5:1.5 | Compound:Phospholipid:Phytosterol*:PEG-DMG |
| 50:20:28.5:1.5 | Compound:Phospholipid:Phytosterol*:PEG-DMG |
| 55:20:23.5:1.5 | Compound:Phospholipid:Phytosterol*:PEG-DMG |
| 60:20:18.5:1.5 | Compound:Phospholipid:Phytosterol*:PEG-DMG |
| 40:15:43.5:1.5 | Compound:Phospholipid:Phytosterol*:PEG-DMG |
| 50:15:33.5:1.5 | Compound:Phospholipid:Phytosterol*:PEG-DMG |
| 55:15:28.5:1.5 | Compound:Phospholipid:Phytosterol*:PEG-DMG |
| 60:15:23.5:1.5 | Compound:Phospholipid:Phytosterol*:PEG-DMG |
| 40:10:48.5:1.5 | Compound:Phospholipid:Phytosterol*:PEG-DMG |
| 45:10:43.5:1.5 | Compound:Phospholipid:Phytosterol*:PEG-DMG |
| 55:10:33.5:1.5 | Compound:Phospholipid:Phytosterol*:PEG-DMG |
| 60:10:28.5:1.5 | Compound:Phospholipid:Phytosterol*:PEG-DMG |
| 40:5:53.5:1.5 | Compound:Phospholipid:Phytosterol*:PEG-DMG |
| 45:5:48.5:1.5 | Compound:Phospholipid:Phytosterol*:PEG-DMG |
| 50:5:43.5:1.5 | Compound:Phospholipid:Phytosterol*:PEG-DMG |
| 40:20:40:0 | Compound:Phospholipid:Phytosterol*:PEG-DMG |
| 45:20:35:0 | Compound:Phospholipid:Phytosterol*:PEG-DMG |
| 50:20:30:0 | Compound:Phospholipid:Phytosterol*:PEG-DMG |
| 55:20:25:0 | Compound:Phospholipid:Phytosterol*:PEG-DMG |
| 60:20:20:0 | Compound:Phospholipid:Phytosterol*:PEG-DMG |
| 40:15:45:0 | Compound:Phospholipid:Phytosterol*:PEG-DMG |

In some embodiments, transfer vehicle has a formulation as described in Table 17b.

For nanoparticle compositions including circRNA, solutions of the circRNA at concentrations of 0.1 mg/ml in deionized water are diluted in a buffer, e.g., 50 mM sodium citrate buffer at a pH between 3 and 4 to form a stock solution. Alternatively, solutions of the circRNA at concentrations of 0.15 mg/ml in deionized water are diluted in a buffer, e.g., 6.25 mM sodium acetate buffer at a pH between 3 and 4.5 to form a stock solution.

Nanoparticle compositions including a circular RNA and a lipid component are prepared by combining the lipid solution with a solution including the circular RNA at lipid component to circRNA wt:wt ratios between about 5:1 and about 50:1. The lipid solution is rapidly injected using, e.g., a NanoAssemblr microfluidic based system at flow rates between about 10 ml/min and about 18 ml/min or between about 5 ml/min and about 18 ml/min into the circRNA solution, to produce a suspension with a water to ethanol ratio between about 1:1 and about 4:1.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, IL) with a molecular weight cutoff of 10 kDa or 20 kDa. The formulations are then dialyzed overnight at 4° C. The resulting nanoparticle suspension is filtered through 0.2 m sterile filters (Sarstedt, Nümbrecht, Germany) into glass vials and sealed with crimp closures. Nanoparticle composition solutions of 0.01 mg/ml to 0.15 mg/ml are generally obtained.

The method described above induces nano-precipitation and particle formation.

Alternative processes including, but not limited to, T-junction and direct injection, may be used to achieve the same nano-precipitation. B. Characterization of nanoparticle compositions A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of circRNA in nanoparticle compositions. 100 µL of the diluted formulation in 1×PBS is added to 900 µL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of circRNA in the nanoparticle composition can be calculated based on the extinction coefficient of the circRNA used in the composition and on the difference between the absorbance at a wavelength of, for example, 260 nm and the baseline value at a wavelength of, for example, 330 nm.

A QUANT-IT™ RIBOGREEN® RNA assay (Invitrogen Corporation Carlsbad, CA) can be used to evaluate the encapsulation of circRNA by the nanoparticle composition. The samples are diluted to a concentration of approximately 5 µg/mL or 1 µg/mL in a TE buffer solution (10 mM Tris-HCl, 1 mM EDTA, pH 7.5). 50 µL of the diluted samples are transferred to a polystyrene 96 well plate and either 50 µL of TE buffer or 50 µL of a 2-4% Triton X-100 solution is added to the wells. The plate is incubated at a temperature of 37° C. for 15 minutes. The RIBOGREEN® reagent is diluted 1:100 or 1:200 in TE buffer, and 100 µL of this solution is added to each well. The fluorescence intensity can be measured using a fluorescence plate reader (Wallac Victor 1420 Multilabel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free circRNA is determined by dividing the fluorescence intensity of the intact sample (without addition of Triton X-100) by the fluorescence value of the disrupted sample (caused by the addition of Triton X-100).

Example 29B: In Vivo Formulation Studies

In order to monitor how effectively various nanoparticle compositions deliver circRNA to targeted cells, different nanoparticle compositions including circRNA are prepared and administered to rodent populations. Mice are intravenously, intramuscularly, intraarterially, or intratumorally administered a single dose including a nanoparticle composition with a lipid nanoparticle formulation. In some instances, mice may be made to inhale doses. Dose sizes may range from 0.001 mg/kg to 10 mg/kg, where 10 mg/kg describes a dose including 10 mg of a circRNA in a nanoparticle composition for each 1 kg of body mass of the mouse. A control composition including PBS may also be employed.

Upon administration of nanoparticle compositions to mice, dose delivery profiles, dose responses, and toxicity of particular formulations and doses thereof can be measured by enzyme-linked immunosorbent assays (ELISA), bioluminescent imaging, or other methods. Time courses of protein expression can also be evaluated. Samples collected from the rodents for evaluation may include blood and tissue (for example, muscle tissue from the site of an intramuscular injection and internal tissue); sample collection may involve sacrifice of the animals.

Higher levels of protein expression induced by administration of a composition including a circRNA will be indicative of higher circRNA translation and/or nanoparticle composition circRNA delivery efficiencies. As the non-RNA components are not thought to affect translational machineries themselves, a higher level of protein expression is likely indicative of a higher efficiency of delivery of the circRNA by a given nanoparticle composition relative to other nanoparticle compositions or the absence thereof.

Example 30

Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the transfer vehicle compositions in 1×PBS in determining particle size and 15 mM PBS in determining zeta potential.

Ultraviolet-visible spectroscopy can be used to determine the concentration of a therapeutic and/or prophylactic (e.g., RNA) in transfer vehicle compositions. 100 µL of the diluted formulation in 1×PBS is added to 900 µL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of therapeutic and/or prophylactic in the transfer vehicle composition can be calculated based on the extinction coefficient of the therapeutic and/or prophylactic used in the composition and on the difference between the absorbance at a wavelength of, for example, 260 nm and the baseline value at a wavelength of, for example, 330 nm.

For transfer vehicle compositions including RNA, a QUANT-IT™ RIBOGREEN® RNA assay (Invitrogen Corporation Carlsbad, CA) can be used to evaluate the encapsulation of RNA by the transfer vehicle composition. The samples are diluted to a concentration of approximately 5 µg/mL or 1 µg/mL in a TE buffer solution (10 mM Tris-HCl, 1 mM EDTA, pH 7.5). 50 µL of the diluted samples are transferred to a polystyrene 96 well plate and either 50 µL of TE buffer or 50 µL of a 2-4% Triton X-100 solution is added to the wells. The plate is incubated at a temperature of 37° C. for 15 minutes. The RIBOGREEN® reagent is diluted 1:100 or 1:200 in TE buffer, and 100 µL of this solution is added to each well. The fluorescence intensity can be measured using a fluorescence plate reader (Wallac Victor 1420 Multilablel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Example 31

T Cell Targeting

To target transfer vehicles to T-cells, T cell antigen binders, e.g., anti-CD8 antibodies, are coupled to the surface of the transfer vehicle. Anti-T cell antigen antibodies are mildly reduced with an excess of DTT in the presence of EDTA in PBS to expose free hinge region thiols. To remove DTT, antibodies are passed through a desalting column. The heterobifunctional cross-linker SM(PEG)24 is used to anchor antibodies to the surface of circRNA-loaded transfer vehicles (Amine groups are present in the head groups of PEG lipids, free thiol groups on antibodies were created by DTT, SM(PEG)24 cross-links between amines and thiol groups). Transfer vehicles are first incubated with an excess of SM(PEG)24 and centrifuged to remove unreacted cross-linker. Activated transfer vehicles are then incubated with an excess of reduced anti-T cell antigen antibody. Unbound antibody is removed using a centrifugal filtration device.

Example 32

RNA Containing Transfer Vehicle Using RV88.

In this example RNA containing transfer vehicles are synthesized using the 2-D vortex microfluidic chip with the cationic lipid RV88 for delivery of circRNA.

lipid 14:0-PEG2K PE is prepared at a concentration of 4 mg/ml also in a borosilica glass vial. Dissolution of lipids at stock concentrations is attained by sonication of the lipids in ethanol for 2 m. The solutions are then heated on an orbital tilting shaker set at 170 rpm at 37° C. for 10 min. Vials are then equilibrated at 26° C. for a minimum of 45 min. The lipids are then mixed by adding volumes of stock lipid as shown in Table 18b. The solution is then adjusted with ethanol such that the final lipid concentration was 7.92 mg/ml.

TABLE 18b

| Composition | MW | % | nmoles | mg | Stock (mg/ml) | ul | Ethanol (ul) |
|---|---|---|---|---|---|---|---|
| RV88 | 794.2 | 40% | 7200 | 5.72 | 10 | 571.8 | 155.3 |
| DSPC | 790.15 | 10% | 1800 | 1.42 | 10 | 142.2 | |
| Cholesterol | 386.67 | 48% | 8640 | 3.34 | 10 | 334.1 | |
| PEG2K | 2693.3 | 2% | 360 | 0.97 | 4 | 242.4 | |

RNA is prepared as a stock solution with 75 mM Citrate buffer at pH 6.0 and a concentration of RNA at 1.250 mg/ml. The concentration of the RNA is then adjusted to 0.1037 mg/ml with 75 mM citrate buffer at pH 6.0, equilibrated to 26° C. The solution is then incubated at 26° C. for a minimum of 25 min.

The microfluidic chamber is cleaned with ethanol and neMYSIS syringe pumps are prepared by loading a syringe with the RNA solution and another syringe with the etha-

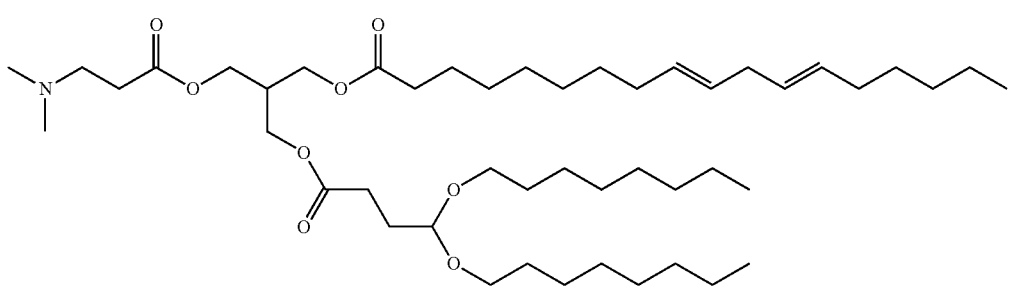

RV88

TABLE 18a

| Materials and Instrument | Vendor | Cat # |
|---|---|---|
| 1M Tris-HCl, pH 8.0, Sterile | Teknova | T1080 |
| 5M Sodium Chloride solution | Teknova | S0250 |
| QB Citrate buffer, pH 6.0 (100 mM) | Teknova | Q2446 |
| Nuclease-free water | Ambion | AM9937 |
| Triton X-100 | Sigma-Aldrich | T8787-100ML |
| RV88 | GVK bio | |
| DSPC | Lipoid | 556500 |
| Cholesterol | Sigma | C3045-5G |
| PEG2K | Avanti Polar Lipids | 880150 |
| Ethanol | Acros Organic | 615090010 |
| 5 mL Borosilicate glass vials | Thermo Scientific | ST5-20 |
| PD MiniTrap G-25 Desalting Columns | GE Healthcare | VWR Cat. #95055-984 |
| Quant-iT RiboGreen RNA Assay kit | Molecular Probes/ Life Technologies | R11490 |
| Black 96-well microplates | Greiner | 655900 |

RV88, DSPC, and cholesterol all being prepared in ethanol at a concentration of 10 mg/ml in borosilica vials. The nolic lipid. Both syringes are loaded and under the control of neMESYS software. The solutions are then applied to the mixing chip at an aqueous to organic phase ratio of 2 and a total flow rate of 22 ml/min (14.67 ml/min for RNA and 7.33 ml/min for the lipid solution. Both pumps are started synchronously. The mixer solution that flowed from the microfluidic chip is collected in 4×1 ml fractions with the first fraction being discarded as waste. The remaining solution containing the RNA-liposomes is exchanged by using G-25 mini desalting columns to 10 mM Tris-HCl, 1 mM EDTA, at pH 7.5. Following buffer exchange, the materials are characterized for size, and RNA entrapment through DLS analysis and Ribogreen assays, respectively.

Example 33

RNA Containing Transfer Vehicle Using RV94.

In this example, RNA containing liposome are synthesized using the 2-D vortex microfluidic chip with the cationic lipid RV94 for delivery of circRNA.

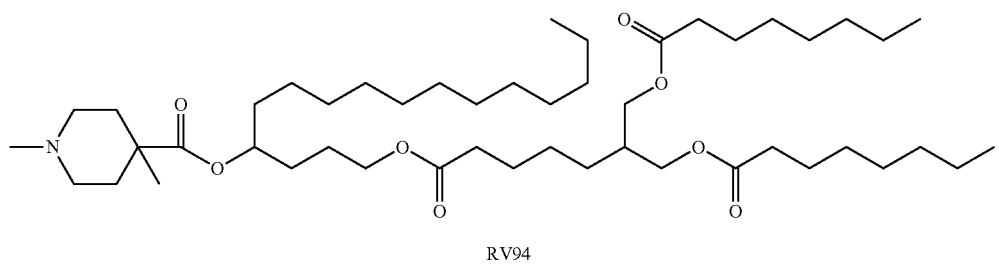 [SMILES: CCCCCCCCCCCCC(CCCOC(=O)CCCCC(COC(=O)CCCCCCC)COC(=O)CCCCCCC)OC(=O)C1(C)CCN(C)CC1 ; "RV94"]

RV94

TABLE 19

| Materials and Instrument | Vendor | Cat # |
|---|---|---|
| 1M Tris-HCl, pH 8.0, Sterile | Teknova | T1080 |
| 5M Sodium Chloride solution | Teknova | S0250 |
| QB Citrate buffer, pH 6.0 (100 mM) | Teknova | Q2446 |
| Nuclease-free water | Ambion | AM9937 |
| Triton X-100 | Sigma-Aldrich | T8787-100ML |
| RV94 | GVKbio | |
| DSPC | Lipoid | 556500 |
| Cholesterol | Sigma | C3045-5G |
| PEG2K | Avanti Polar Lipids | 880150 |
| Ethanol | Acros Organic | 615090010 |
| 5 mL Borosilicate glass vials | Thermo Scientific | ST5-20 |
| PD MiniTrap G-25 Desalting Columns | GE Healthcare | VWR Cat. #95055-984 |
| Quant-iT RiboGreen RNA Assay kit | Molecular Probes/ Life Technologies | R11490 |
| Black 96-well microplates | Greiner | 655900 |

The lipids were prepared as in Example 29 using the material amounts named in Table 20 to a final lipid concentration of 7.92 mg/ml.

TABLE 20

| Composition | MW | % | nmoles | mg | Stock (mg/ml) | ul | Ethanol (ul) |
|---|---|---|---|---|---|---|---|
| RV94 | 808.22 | 40% | 2880 | 2.33 | 10 | 232.8 | 155.3 |
| DSPC | 790.15 | 10% | 720 | 0.57 | 10 | 56.9 | |
| Cholesterol | 386.67 | 48% | 3456 | 1.34 | 10 | 133.6 | |
| PEG2K | 2693.3 | 2% | 144 | 0.39 | 4 | 97.0 | |

The aqueous solution of circRNA is prepared as a stock solution with 75 mM Citrate buffer at pH 6.0 the circRNA at 1.250 mg/ml. The concentration of the RNA is then adjusted to 0.1037 mg/ml with 75 mM citrate buffer at pH 6.0, equilibrated to 26° C. The solution is then incubated at 26° C. for a minimum of 25 min.

The microfluidic chamber is cleaned with ethanol and neMYSIS syringe pumps are prepared by loading a syringe with the RNA solution and another syringe with the ethanolic lipid. Both syringes are loaded and under the control of neMESYS software. The solutions are then applied to the mixing chip at an aqueous to organic phase ratio of 2 and a total flow rate of 22 ml/min (14.67 ml/min for RNA and 7.33 ml/min for the lipid solution. Both pumps are started synchronously. The mixer solution that flowed from the microfluidic chip is collected in 4×1 ml fractions with the first fraction being discarded as waste. The remaining solution containing the circRNA-transfer vehicles is exchanged by using G-25 mini desalting columns to 10 mM Tris-HCl, 1 mM EDTA, at pH 7.5, as described above. Following buffer exchange, the materials are characterized for size, and RNA entrapment through DLS analysis and Ribogreen assays, respectively. The biophysical analysis of the liposomes is shown in Table 21.

TABLE 21

| Sample Name | N:P Ratio | TFR ml/min | Ratio (aqueous/ org phase) | RNA encap- sulation amount (µg/ml) | RNA encap- sulation yield % | size d.nm | PDI |
|---|---|---|---|---|---|---|---|
| SAM-RV94 | 8 | 22 | 2 | 31.46 | 86.9 | 113.1 | 0.12 |

Example 34

General Protocol for in Line Mixing

Individual and separate stock solutions are prepared—one containing lipid and the other circRNA. Lipid stock containing a desired lipid or lipid mixture, DSPC, cholesterol and PEG lipid is prepared by solubilized in 90% ethanol. The remaining 10% is low pH citrate buffer. The concentration of the lipid stock is 4 mg/mL. The pH of this citrate buffer can range between pH 3 and pH 5, depending on the type of lipid employed. The circRNA is also solubilized in citrate buffer at a concentration of 4 mg/mL. 5 mL of each stock solution is prepared.

Stock solutions are completely clear and lipids are ensured to be completely solubilized before combining with circRNA. Stock solutions may be heated to completely solubilize the lipids. The circRNAs used in the process may be unmodified or modified oligonucleotides and may be conjugated with lipophilic moieties such as cholesterol.

The individual stocks are combined by pumping each solution to a T-junction. A dual-head Watson-Marlow pump was used to simultaneously control the start and stop of the two streams. A 1.6 mm polypropylene tubing is further downsized to 0.8 mm tubing in order to increase the linear flow rate. The polypropylene line (ID=0.8 mm) are attached to either side of a T-junction. The polypropylene T has a linear edge of 1.6 mm for a resultant volume of 4.1 mm³. Each of the large ends (1.6 mm) of polypropylene line is placed into test tubes containing either solubilized lipid stock or solubilized circRNA. After the T-junction, a single tubing is placed where the combined stream exited. The tubing is then extended into a container with 2× volume of PBS, which is rapidly stirred. The flow rate for the pump is at a setting of 300 rpm or 110 mL/min. Ethanol is removed and exchanged for PBS by dialysis. The lipid formulations are then concentrated using centrifugation or diafiltration to an appropriate working concentration.

C57BL/6 mice (Charles River Labs, MA) receive either saline or formulated circRNA via tail vein injection. At various time points after administration, serum samples are collected by retroorbital bleed. Serum levels of Factor VII protein are determined in samples using a chromogenic assay (Biophen FVTI, Aniara Corporation, OH). To determine liver RNA levels of Factor VII, animals are sacrificed and livers are harvested and snap frozen in liquid nitrogen. Tissue lysates are prepared from the frozen tissues and liver RNA levels of Factor VII are quantified using a branched DNA assay (QuantiGene Assay, Panomics, CA).

FVII activity is evaluated in FVTI siRNA-treated animals at 48 hours after intravenous (bolus) injection in C57BL/6 mice. FVII is measured using a commercially available kit for determining protein levels in serum or tissue, following the manufacturer's instructions at a microplate scale. FVII reduction is determined against untreated control mice, and the results are expressed as % Residual FVII. Two dose levels (0.05 and 0.005 mg/kg FVII siRNA) are used in the screen of each novel liposome composition.

Example 36 circRNA Formulation Using Preformed Vesicles

Cationic lipid containing transfer vehicles are made using the preformed vesicle method. Cationic lipid, DSPC, cholesterol and PEG-lipid are solubilized in ethanol at a molar ratio of 40/10/40/10, respectively. The lipid mixture is added to an aqueous buffer (50 mM citrate, pH 4) with mixing to a final ethanol and lipid concentration of 30% (vol/vol) and 6.1 mg/mL respectively and allowed to equilibrate at room temperature for 2 min before extrusion. The hydrated lipids are extruded through two stacked 80 nm pore-sized filters (Nuclepore) at 22° C. using a Lipex Extruder (Northern Lipids, Vancouver, BC) until a vesicle diameter of 70-90 nm, as determined by Nicomp analysis, is obtained. For cationic lipid mixtures which do not form small vesicles, hydrating the lipid mixture with a lower pH buffer (50 mM citrate, pH 3) to protonate the phosphate group on the DSPC headgroup helps form stable 70-90 nm vesicles.

The FVII circRNA (solubilised in a 50 mM citrate, pH 4 aqueous solution containing 30% ethanol) is added to the vesicles, pre-equilibrated to 35° C., at a rate of ~5 mL/min with mixing. After a final target circRNA/lipid ratio of 0.06 (wt wt) is achieved, the mixture is incubated for a further 30 min at 35° C. to allow vesicle re-organization and encapsulation of the FVII RNA. The ethanol is then removed and the external buffer replaced with PBS (155 mM NaCl, 3 mM Na2HPO4, ImM KH2P04, pH 7.5) by either dialysis or tangential flow diafiltration. The final encapsulated circRNA-to-lipid ratio is determined after removal of unencapsulated RNA using size-exclusion spin columns or ion exchange spin columns.

Example 37

Example 37A: Expression of Trispecific Antigen Binding Proteins from Engineered Circular RNA Circular RNAs are designed to include: (1) a 3' post splicing group I intron fragment; (2) an Internal Ribosome Entry Site (IRES); (3) a trispecific antigen-binding protein coding region; and (4) a 3' duplex region. The trispecific antigen-binding protein regions are constructed to produce an exemplary trispecific antigen-binding protein that will bind to a target antigen, e.g., GPC3.

Example 37B: Generation of a scFv CD3 Binding Domain

The human CD3epsilon chain canonical sequence is Uniprot Accession No. P07766. The human CD3gamma chain canonical sequence is Uniprot Accession No. P09693. The human CD3delta chain canonical sequence is Uniprot Accession No. P043234. Antibodies against CD3epsilon, CD3gamma or CD3delta are generated via known technologies such as affinity maturation. Where murine anti-CD3 antibodies are used as a starting material, humanization of murine anti-CD3 antibodies is desired for the clinical setting, where the mouse-specific residues may induce a human-anti-mouse antigen (HAMA) response in subjects who receive treatment of a trispecific antigen-binding protein described herein. Humanization is accomplished by grafting CDR regions from murine anti-CD3 antibody onto appropriate human germline acceptor frameworks, optionally including other modifications to CDR and/or framework regions.

Human or humanized anti-CD3 antibodies are therefore used to generate scFv sequences for CD3 binding domains of a trispecific antigen-binding protein. DNA sequences coding for human or humanized VL and VH domains are obtained, and the codons for the constructs are, optionally, optimized for expression in cells from *Homo sapiens*. The order in which the VL and VH domains appear in the scFv is varied (i.e. VL-VH, or VH-VL orientation), and three copies of the "G4S" or "G4S" (SEQ ID NO: 124) subunit (G4S)$_3$ (SEQ ID NO: 125) connect the variable domains to create the scFv domain. Anti-CD3 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD3-expressing cells.

Example 37C: Generation of a scFv Glypican-3 (GPC3) Binding Domain

Glypican-3 (GPC3) is one of the cell surface proteins present on Hepatocellular Carcinoma but not on healthy normal liver tissue. It is frequently observed to be elevated in hepatocellular carcinoma and is associated with poor prognosis for HCC patients. It is known to activate Wnt signalling. GPC3 antibodies have been generated including MDX-1414, HN3, GC33, and YP7.

A scFv binding to GPC-3 or another target antigen is generated similarly to the above method for generation of a scFv binding domain to CD3.

Example 37D: Expression of Trispecific Antigen-Binding Proteins In Vitro

A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted trispecific antigen-binding proteins are generated by transfection of suspension-adapted cells. During selection with the antibiotic Hygromycin B viable cell densities are measured twice a week, and cells are centrifuged and resuspended in fresh selection medium at a maximal density of 0.1×10$^6$ viable cells/mL. Cell pools stably expressing trispecific antigen-binding proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Trispecific antigen-binding proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Example 37E: Purification of Trispecific Antigen-Binding Proteins

Trispecific antigen-binding proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL Purity and homogeneity (typically >90%) of final samples are assessed by SDS PAGE under reducing and non-reducing conditions, followed by immunoblotting using an anti-(half-life extension domain) or anti idiotype antibody as well as by analytical SEC, respectively. Purified proteins are stored at aliquots at −80° C. until use.

Example 38

Expression of Engineered Circular RNA with a Half-Life Extension Domain has Improved Pharmacokinetic Parameters than without a Half-Life Extension Domain The trispecific antigen-binding protein encoded on a circRNA molecule of Example 37 is administered to cynomolgus monkeys as a 0.5 mg/kg bolus injection intramuscularly. Another cynomolgus monkey group receives a comparable protein encoded on a circRNA molecule in size with binding domains to CD3 and GPC-3 but lacking a half-life extension domain. A third and fourth group receive a protein encoded on a circRNA molecule with CD3 and half-life extension domain binding domains and a protein with GPC-3 and half-life extension domains, respectively. Both proteins encoded by circRNA are comparable in size to the trispecific antigen-binding protein. Each test group consists of 5 monkeys. Serum samples are taken at indicated time points, serially diluted, and the concentration of the proteins is determined using a binding ELISA to CD3 and/or GPC-3.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where c(t) is the plasma concentration at time t, A and B are intercepts on the Y-axis, and $\alpha$ and $\beta$ are the apparent first-order rate constants for the distribution and elimination phases, respectively. The a-phase is the initial phase of the clearance and reflects distribution of the protein into all extracellular fluid of the animal, whereas the second or β-phase portion of the decay curve represents true plasma clearance. Methods for fitting such equations are well known in the art. For example, $A=D/V(\alpha-k21)/(\alpha-\beta)$, $B=D/V(\beta-k21)/(\alpha-\beta)$, and $\alpha$ and $\beta$ (for $\alpha>\beta$) are roots of the quadratic equation: $r^2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif). Pharmacokinetic parameters are computed as described in Ritschel W A and Kearns G L, 1999, EST: Handbook Of Basic Pharmacokinetics Including Clinical Applications, 5th edition, American Pharmaceutical Assoc., Washington, D C.

It is expected that the trispecific antigen-binding protein encoded on a circRNA molecule of Example 37 has improved pharmacokinetic parameters such as an increase in elimination half-time as compared to proteins lacking a half-life extension domain.

Example 39

Cytotoxicity of the Trispecific Antigen-Binding Protein

The trispecific antigen-binding protein encoded on a circRNA molecule of Example 37 is evaluated in vitro on its mediation of T cell dependent cytotoxicity to GPC-3+ target cells.

Fluorescence labeled GPC3 target cells are incubated with isolated PBMC of random donors or T-cells as effector cells in the presence of the trispecific antigen-binding protein of Example 37. After incubation for 4 h at 37° C. in a humidified incubator, the release of the fluorescent dye from the target cells into the supernatant is determined in a spectrofluorimeter. Target cells incubated without the trispecific antigen-binding protein of Example 37 and target cells totally lysed by the addition of saponin at the end of the incubation serve as negative and positive controls, respectively.

Based on the measured remaining living target cells, the percentage of specific cell lysis is calculated according to the following formula: [1-(number of living targets(sample)/number of living targets(spontaneous))]×100%. Sigmoidal dose response curves and EC50 values are calculated by non-linear regression/4-parameter logistic fit using the GraphPad Software. The lysis values obtained for a given antibody concentration are used to calculate sigmoidal dose-response curves by 4 parameter logistic fit analysis using the Prism software.

Example 40

Lipid Nanoparticle Formulation with Circular RNA

Lipid Nanoparticles (LNPs) were formed using a Precision Nanosystems Ignite instrument with a 'NextGen' mixing chamber. Ethanol phase contained ionizable Lipid 10c-7, DSPC, Cholesterol, and DSPE-PEG 2000 (Avanti Polar Lipids Inc.) at a weight ratio of 16:1:4:1 or 62:4:33:1 molar ratio was combined with an aqueous phase containing circular RNA and 25 mM sodium acetate buffer at pH 5.2. A 3:1 aqueous to ethanol mixing ratio was used. The formulated LNP then were dialyzed in 1 L of water and exchanged 2 times over 18 hours. Dialyzed LNPs were filtered using 0.2 µm filter. Prior to in vivo dosing, LNPs were diluted in PBS. LNP sizes were determined by dynamic light scattering. A cuvette with 1 mL of 20 µg/mL LNPs in PBS (pH 7.4) was measured for Z-average using the Malvern Panalytical Zetasizer Pro. The Z-average and polydispersity index were recorded.

40.1 Formulation of Lipids 10c-7 and 10c-8

Lipid Nanoparticles (LNPs) were formed using a Precision Nanosystems Ignite instrument with a 'NextGen' mixing chamber. Ethanol phase contained ionizable Lipid 10c-7 or Lipid 10c-28, DOPE, Cholesterol, and DSPE-PEG 2000 (Avanti Polar Lipids Inc.) at a weight ratio of 16:1:4:1 or 62:4:33:1 molar ratio was combined with an aqueous phase containing circular RNA and 25 mM sodium acetate buffer at pH 5.2. A 3:1 aqueous to ethanol mixing ratio was used. The formulated LNPs were then dialyzed in 1 L of water and exchanged 2 times over 18 hours. Dialyzed LNPs were filtered using 0.2 µm filter. Prior to in vivo dosing, LNPs were diluted in PBS. LNP sizes were determined by dynamic light scattering. A cuvette with 1 mL of 20 µg/mL LNPs in PBS (pH 7.4) was measured for Z-average using the Malvern Panalytical Zetasizer Pro. The Z-average and polydispersity index were recorded.

Example 41

In Vitro Delivery of Green Fluorescent Protein (GFP) or Chimeric Antigen Receptor (CAR)

Human PBMCs (Stemcell Technologies) were transfected with LNP encapsulating GFP and examined by flow cytometry. PBMCs from five different donors (PBMC A-E) were incubated in vitro with one LNP composition, containing circular RNA encoding either GFP or CD19-CAR (200 ng), at 37° C. in RPMI, 2% human serum, IL-2 (10 ng/mL), and 50 µM BME. PBMCs incubated without LNP were used as a negative control. After 24, 48, or 72 hours post-LNP incubation, cells were analyzed for CD3, CD19, CD56, CD14, CD11b, CD45, fixable live dead, and payload (GFP or CD19-CAR).

Representative data are presented in FIGS. 27A and 27B, showing that the tested LNP is capable of delivering circular RNA into primary human immune cells resulting in protein expression.

Example 42

Multiple IRES Variants can Mediate Expression of Murine CD19 CAR In Vitro

Multiple circular RNA constructs, encoding anti-murine CD19 CAR, contains unique IRES sequences and were lipotransfected into 1C1C7 cell lines. Prior to lipotransfection, 1C1C7 cells are expanded for several days in complete RPMI Once the cells expanded to appropriate numbers, 1C1C7 cells were lipotransfected (Invitrogen RNAiMAX) with four different circular RNA constructs. After 24 hours, 1C1C7 cells were incubated with His-tagged recombinant murine CD19 (Sino Biological) protein, then stained with a secondary anti-His antibody. Afterwards, the cells were analyzed via flow cytometry.

Figure 26:
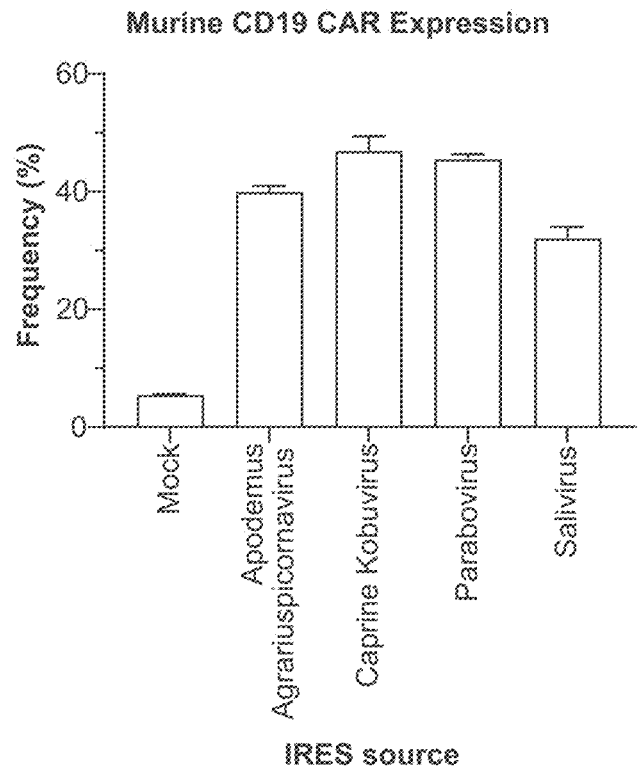
FIG. 26 depicts the expression of an anti-murine CD19 CAR in 1C1C7 cells lipotransfected with circular RNA comprising an anti-murine CD19 CAR expression sequence and varying IRES sequences.

Representative data are presented in FIGS. 26, showing that IRES sourced from the indicated virus (apodemus agrarius picornavirus, caprine kobuvirus, parabovirus, and salivirus) are capable of driving expression of an anti-mouse CD19 CAR in murine T cells.

Example 43

Murine CD19 CAR Mediates Tumor Cell Killing In Vitro

Circular RNA encoding anti-mouse CD19 CAR were electroporated into murine T cells to evaluate CAR-mediated cytotoxicity. For electroporation, T cells were electroporated with circular RNA encoding anti-mouse CD19 CAR using ThermoFisher's Neon Transfection System then rested overnight. For the cytotoxicity assay, electroporated T cells were co-cultured with Fluc+ target and non-target cells at 1:1 ratio in complete RPMI containing 10% FBS, IL-2 (10 ng/mL), and 50 uM BME and incubated overnight at 37° C. Cytotoxicity was measured using a luciferase assay system 24 hours post-co-culture (Promega Brightglo Luciferase System) to detect lysis of Fluc+ target and non-target cells. Values shown are calculated relative to the untransfected mock signal.

Figure 27:
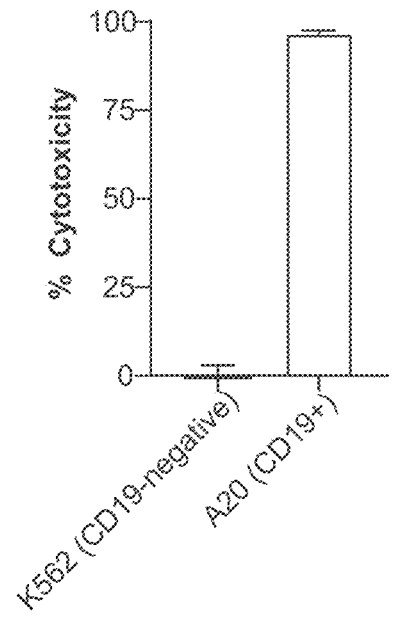
FIG. 27 shows the cytotoxicity of an anti-murine CD19 CAR to murine T cells. The CD19 CAR is encoded by and expressed from a circular RNA, which is electroporated into the murine T cells.

Representative data are presented in FIG. 27, showing that an anti-mouse CD19 CAR expressed from circular RNA is functional in murine T cells in vitro.

Example 44

CD19 CAR Expressed from Circular RNA has Higher Yield and Greater Cytotoxic Effect Compared to that Expressed from mRNA Circular RNA encoding anti-CD19 chimeric antigen receptor, which includes, from N-terminus to C-terminus, a FMC63-derived scFv, a CD8 transmembrane domain, a 4-1BB costimulatory domain, and a CD3ζ intracellular domain, were electroporated into human peripheral T cells to evaluate surface expression and CAR-mediated cytotoxicity. For comparison, circular RNA-electroporated T cells were compared to mRNA-electroporated T cells in this experiment. For electroporation, CD3+ T cells were isolated from human PBMCs using commercially available T cell isolation kits (Miltenyi Biotec) from donor human PBMCs. After isolation, T cells were stimulated with anti-CD3/anti-CD28 (Stemcell Technologies) and expanded over 5 days at 37° C. in complete RPMI containing 10% FBS, IL-2 (10 ng/mL), and 50 uM BME. Five days post stimulation, T cells were electroporated with circular RNA encoding anti-human CD19 CAR using ThermoFisher's Neon Transfection System and then rested overnight. For the cytotoxicity assay, electroporated T cells were co-cultured with Fluc+ target and non-target cells at 1:1 ratio in complete RPMI containing 10% FBS, IL-2 (10 ng/mL), and 50 uM BME and incubated overnight at 37° C. Cytotoxicity was measured using a luciferase assay system 24 hours post-co-culture (Promega Brightglo Luciferase System) to detect lysis of Fluc+ target and non-target cells. Furthermore, an aliquot of electroporated T cells were taken and stained for live dead fixable staining, CD3, CD45, and chimeric antigen receptors (FMC63) at the day of analysis.

Figure 28A:
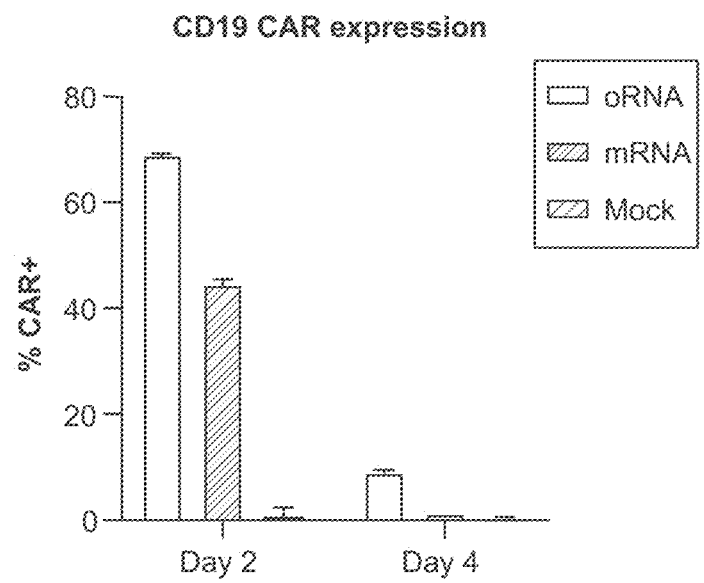
FIG. 28A and FIG. 28B compare the expression level of an anti-human CD19 CAR expressed from a circular RNA with that expressed from a linear mRNA.
Figure 28B:
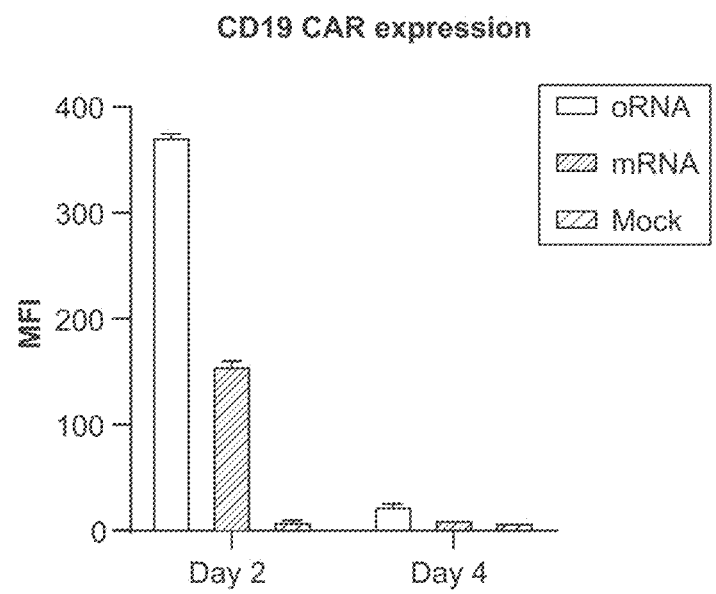
Figure 29A:
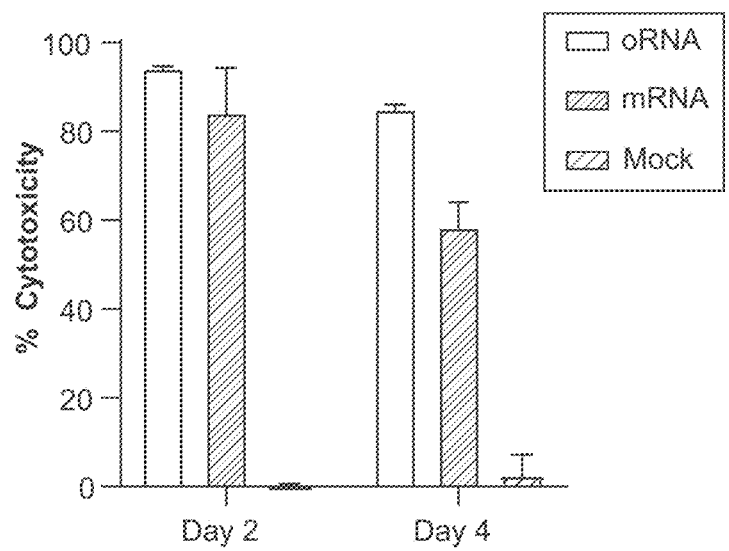
FIG. 29A and FIG. 29B compare the cytotoxic effect of an anti-human CD19 CAR expressed from a circular RNA with that expressed from a linear mRNA
Figure 29B:
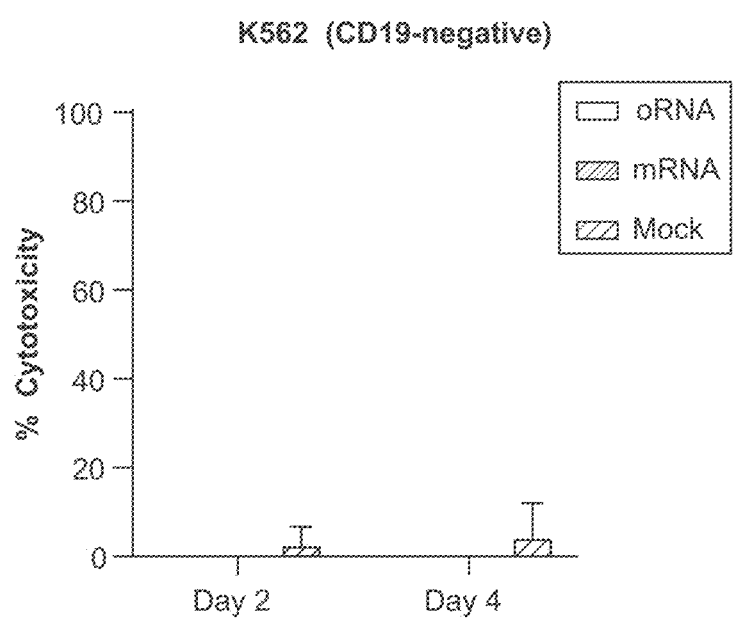

Representative data are presented in FIGS. 28 and 29. FIGS. 28A and 28B show that an anti-human CD19 CAR expressed from circular RNA is expressed at higher levels and longer than an anti-human CD19 CAR expressed from linear mRNA. FIGS. 29A and 29B show that an anti-human CD19 CAR expressed from circular RNA is exerts a greater cytotoxic effect relative to anti-human CD19 CAR expressed from linear mRNA.

Example 45

Functional Expression of Two CARs from a Single Circular RNA

Circular RNA encoding chimeric antigen receptors were electroporated into human peripheral T cells to evaluate surface expression and CAR-mediated cytotoxicity. The purpose of this study is to evaluate if circular RNA encoding for two CARs can be stochastically expressed with a 2A (P2A) or an IRES sequence. For electroporation, CD3+ T cells were commercially purchased (Cellero) and stimulated with anti-CD3/anti-CD28 (Stemcell Technologies) and expanded over 5 days at 37° C. in complete RPMI containing 10% FBS, IL-2 (10 ng/mL), and 50 uM BME. Four days post stimulation, T cells were electroporated with circular RNA encoding anti-human CD19 CAR, anti-human CD19 CAR-2A-anti-human BCMA CAR, and anti-human CD19 CAR-IRES-anti-human BCMA CAR using ThermoFisher's Neon Transfection System then rested overnight. For the cytotoxicity assay, electroporated T cells were co-cultured with Fluc+K562 cells expressing human CD19 or BCMA antigens at 1:1 ratio in complete RPMI containing 10% FBS, IL-2 (10 ng/mL), and 50 uM BME and incubated overnight at 37° C. Cytotoxicity was measured using a luciferase assay system 24 hours post-co-culture (Promega BrightGlo Luciferase System) to detect lysis of Fluc+ target cells.

Figure 30:
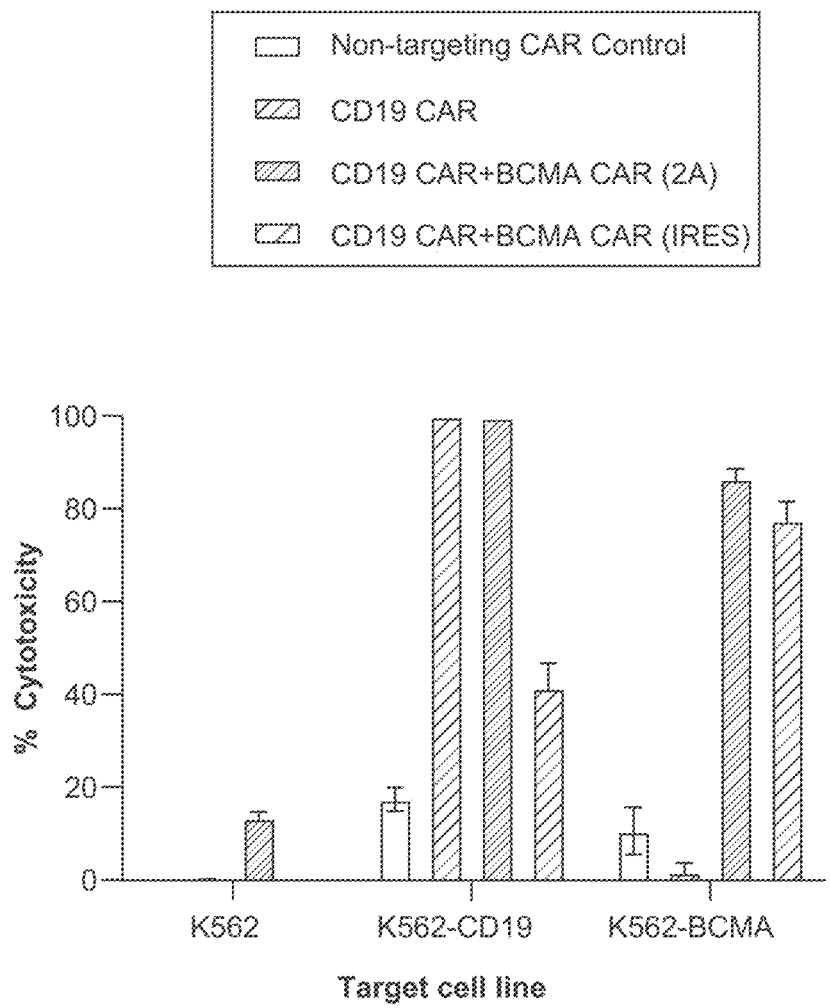
FIG. 30 depicts the cytotoxicity of two CARs (anti-human CD19 CAR and anti-human BCMA CAR) expressed from a single circular RNA in T cells.

Representative data are presented in FIG. 30, showing that two CARs can be functionally expressed from the same circular RNA construct and exert cytotoxic effector function.

Example 46

Example 46A: Built-In polyA Sequences and Affinity-Purification to Produce Immue-Silent Circular RNA PolyA sequences (20-30 nt) were inserted into the 5' and 3' ends of the RNA construct (precursor RNA with built-in polyA sequences in the introns). Precursor RNA and introns can alternatively be polyadenylated post-transcriptionally using, e.g., *E. coli*. polyA polymerase or yeast polyA polymerase, which requires the use of an additional enzyme.

Circular RNA in this example was circularized by in vitro transcription (IVT) and affinity-purified by washing over a commercially available oligo-dT resin to selectively remove polyA-tagged sequences (including free introns and precursor RNA) from the splicing reaction. The IVT was performed with a commercial IVT kit (New England Biolabs) or a customerized IVT mix (Orna Therapeutics), containing guanosine monophosphate (GMP) and guanosine triphosphate (GTP) at different ratios (GMP:GTP=8, 12.5, or 13.75). In some embodiments, GMP at a high GMP:GTP ratio may be preferentially included as the first nucleotide, yielding a majority of monophosphate-capped precursor RNAs. As a comparison, the circular RNA product was alternatively purified by the treatment with Xrn1, Rnase R, and Dnase I (enzyme purification).

Immunogenicity of the circular RNAs prepared using the affinity purification or enzyme purification process were then assessed. Briefly, the prepared circular RNAs were transfected into A549 cells. After 24 hours, the cells were lysed and interferon beta-1 induction relative to mock samples was measured by qPCR. 3p-hpRNA, a triphosphorylated RNA, was used as a positive control.

Figure 31A:
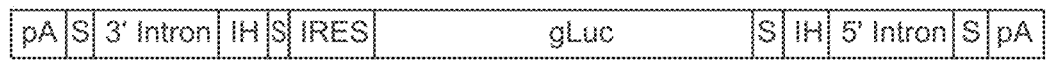
FIG. 31A depicts an exemplary RNA construct design with built-in polyA sequences in the introns.
Figure 31B:
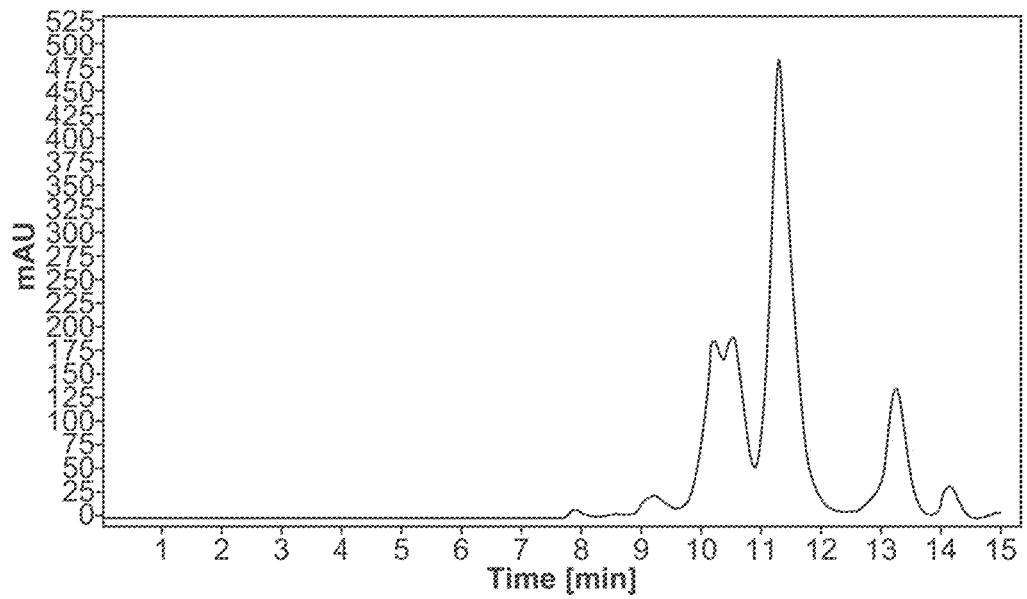
FIG. 31B shows the chromatography trace of unpurified circular RNA.
Figure 31C:
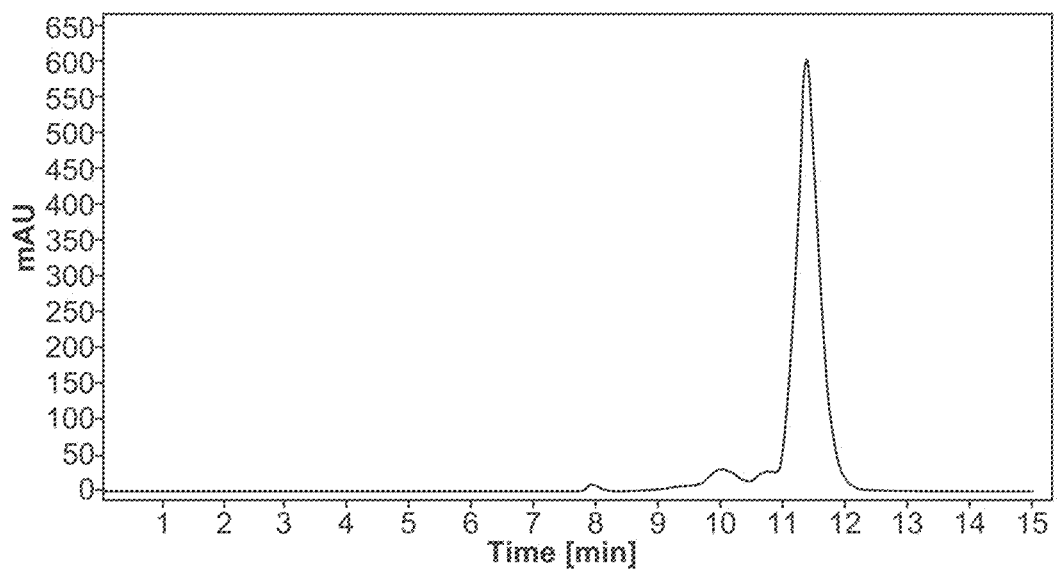
FIG. 31C shows the chromatography trace of affinity-purified circular RNA.
Figure 31D:
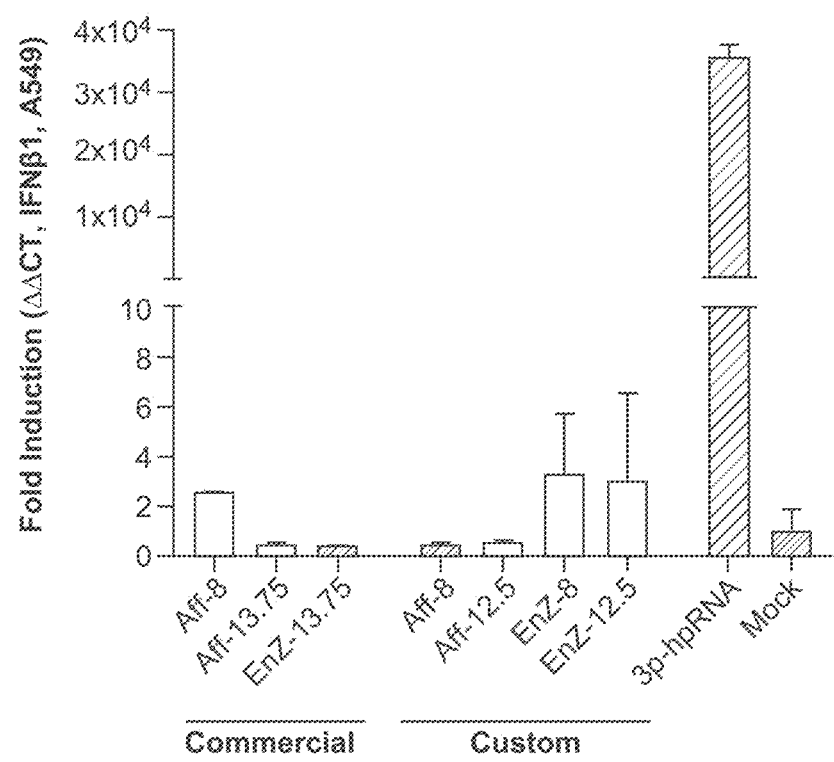
FIG. 31D shows the immunogenicity of the circular RNAs prepared with varying IVT conditions and purification methods. (Commercial=commercial IVT mix; Custom=customerized IVT mix; Aff=affinity purification; Enz=enzyme purification; GMP:GTP ratio=8, 12.5, or 13.75).

FIGS. 31B and 31C show that the negative selection affinity purification removes non-circular products from splicing reactions when polyA sequences are included on elements that are removed during splicing and present in unspliced precursor molecules. FIG. 31D shows circular RNAs prepared with tested IVT conditions and purification methods are all immunoquiescent. These results suggest the negative selection affinity purification is equivalent or superior to enzyme purification for circular RNA purification and that customized circular RNA synthesis conditions (IVT conditions) may reduce the reliance on GMP excess to achieve maximal immunoquiescence.

Example 46B: Dedicated Binding Site and Affinity-Purification for Circular RNA Production Instead of polyA tags, one can include specifically design sequences (DBS, dedicated binding site).

Instead of a polyA tag, a dedicated binding site (DBS), such as a specifically designed complementary oligonucleotide that can bind to a resin, may be used to selectively deplete precursor RNA and free introns. In this example, DBS sequences (30 nt) were inserted into the 5' and 3' ends of the precursor RNA. RNA was transcribed and the transcribed product was washed over a custom complementary oligonucleotide linked to a resin.

Figure 32A:
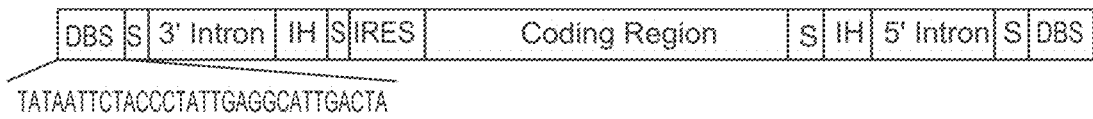
FIG. 32A depicts an exemplary RNA construct design with a dedicated binding sequence as an alternative to polyA for hybridization purification.
Figure 32B:
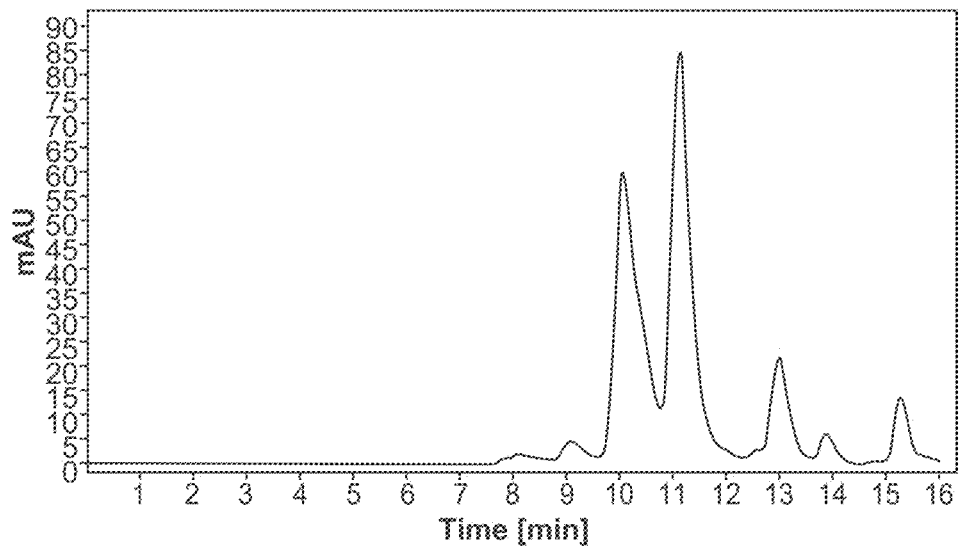
FIG. 32B shows the chromatography trace of unpurified circular RNA.
Figure 32C:
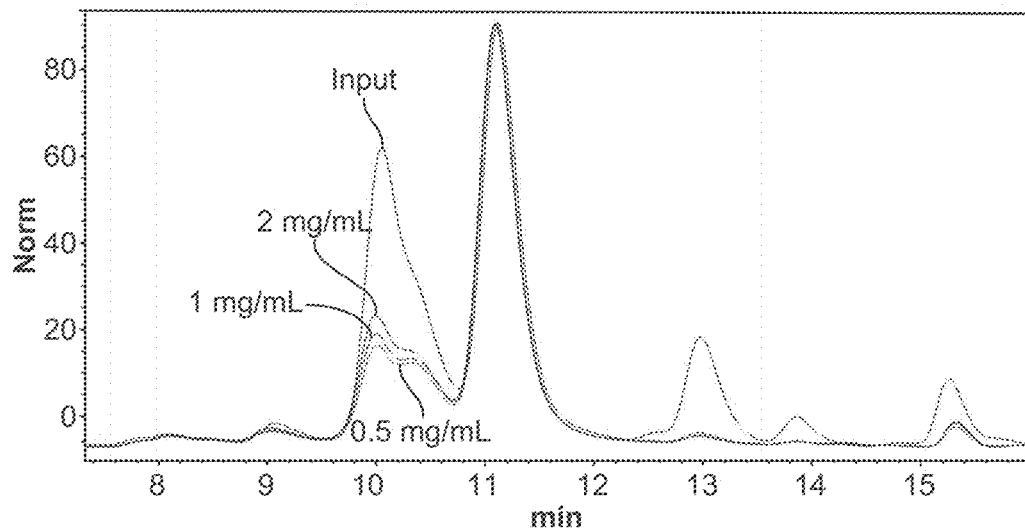
FIG. 32C shows the chromatography trace of affinity-purified circular RNA.

FIGS. 32B and 32C demonstrates that including the designed DBS sequence in elements that are removed during splicing enables the removal of unspliced precursor RNA and free intron components in a splicing reaction, via negative affinity purification.

Example 46C: Production of a Circular RNA Encoding Dystrophin

Figure 33A:
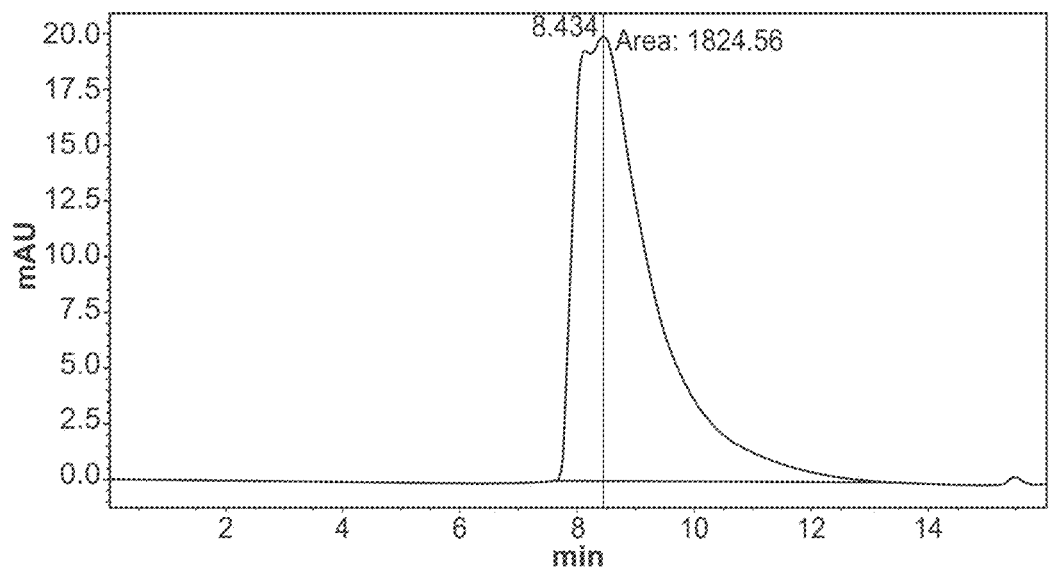
FIG. 33A shows the chromatography trace of unpurified circular RNA encoding dystrophin.
Figure 33B:
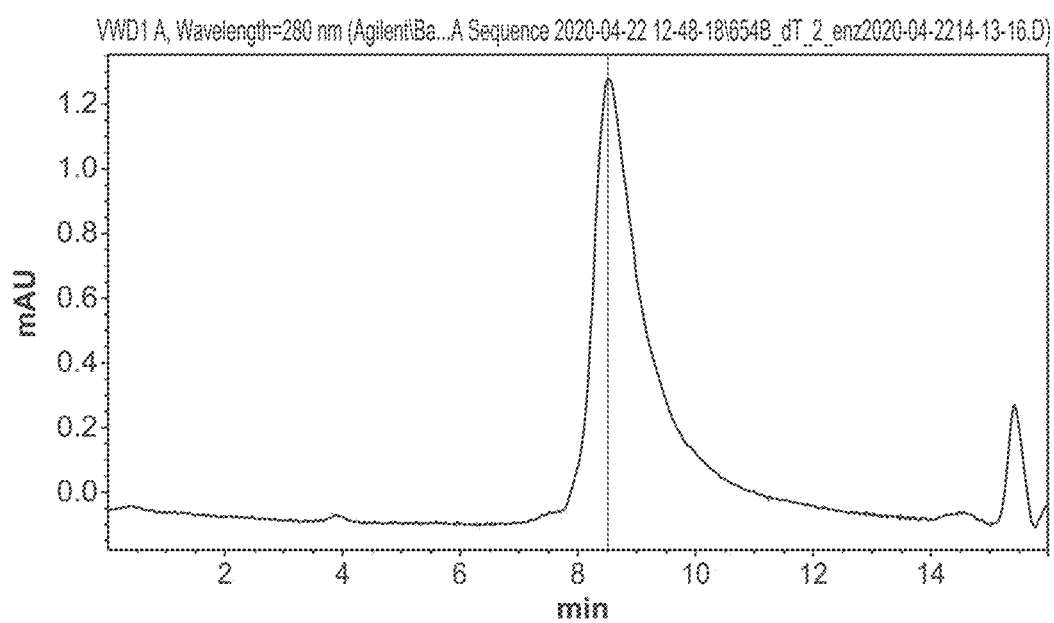
FIG. 33B shows the chromatography trace of enzyme-purified circular RNA encoding dystrophin.

A 12 kb12,000 nt circular RNA encoding dystrophin was produced by in vitro transcription of RNA precursors followed by enzyme purification using a mixture of Xrn1, DNase 1, and RNase R to degrade remaining linear components. FIG. 33 shows that the circular RNA encoding dystrophin was successfully produced.

Example 47

5' Spacer Between 3' Intron Fragment and the IRES Improves Circular RNA Expression Expression level of purified circRNAs with different 5' spacers between the 3' intron fragment and the IRES in Jurkat cells were compared. Briefly, luminescence from secreted *Gaussia* luciferase in supernatant was measured 24 hours after electroporation of 60,000 cells with 250 ng of each RNA.

Additionally, stability of purified circRNAs with different 5' spacers between the 3' intron fragment and the IRES in Jurkat cells were compared. Briefly, luminescence from secreted *Gaussia* luciferase in supernatant was measured over 2 days after electroporation of 60,000 cells with 250 ng of each RNA and normalized to day 1 expression.

Figure 34A:
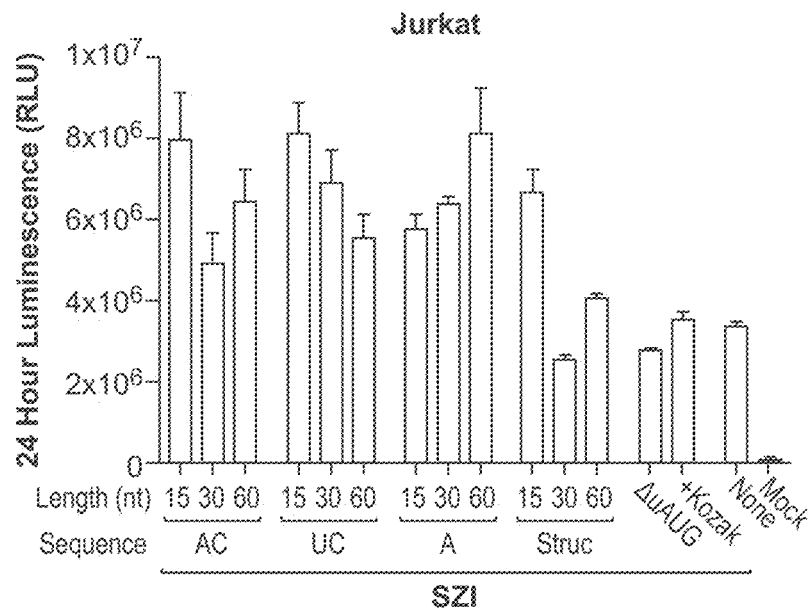
FIG. 34A and FIG. 34B compare the expression (FIG. 34A) and stability (FIG. 34B) of purified circRNAs with different 5' spacers between the 3' intron fragment/5' internal duplex region and the IRES in Jurkat cells. (AC=only A and C were used in the spacer sequence; UC=only U and C were used in the spacer sequence.)
Figure 34B:
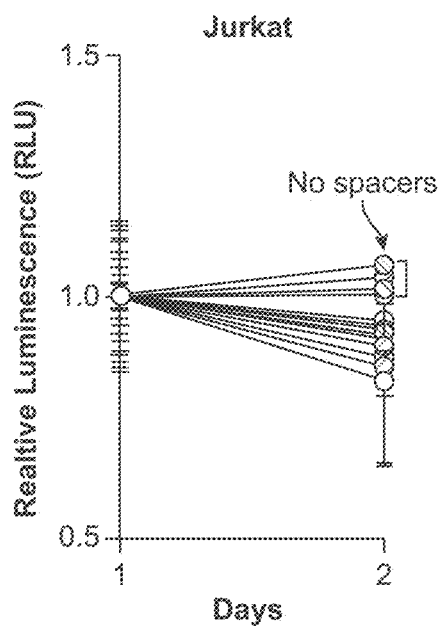

The results are shown in FIGS. 34A and 34B, indicating that adding a spacer can enhance IRES function and the importance of sequence identity and length of the added spacer. A potential explanation is that the spacer is added right before the IRES and likely functions by allowing the TRES to fold in isolation from other structured elements such as the intron fragments.

Example 48

This example describes deletion scanning from 5' or 3' end of the caprine kobuvirus IRES. TRES borders are generally poorly characterized and require empirical analysis, and this example can be used for locating the core functional sequences required for driving translation. Briefly, circular RNA constructs were generated with truncated IRES elements operably linked to a *Gaussia* luciferase coding sequence. The truncated TRES elements had nucleotide sequences of the indicated lengths removed from the 5' or 3' end. Luminescence from secreted *Gaussia* luciferase in supernatant was measured 24 and 48 hours after electroporation of primary human T cells with RNA. Stability of expression was calculated as the ratio of the expression level at the 48-hour time point relative to that at the 24-hour time point.

Figure 35:
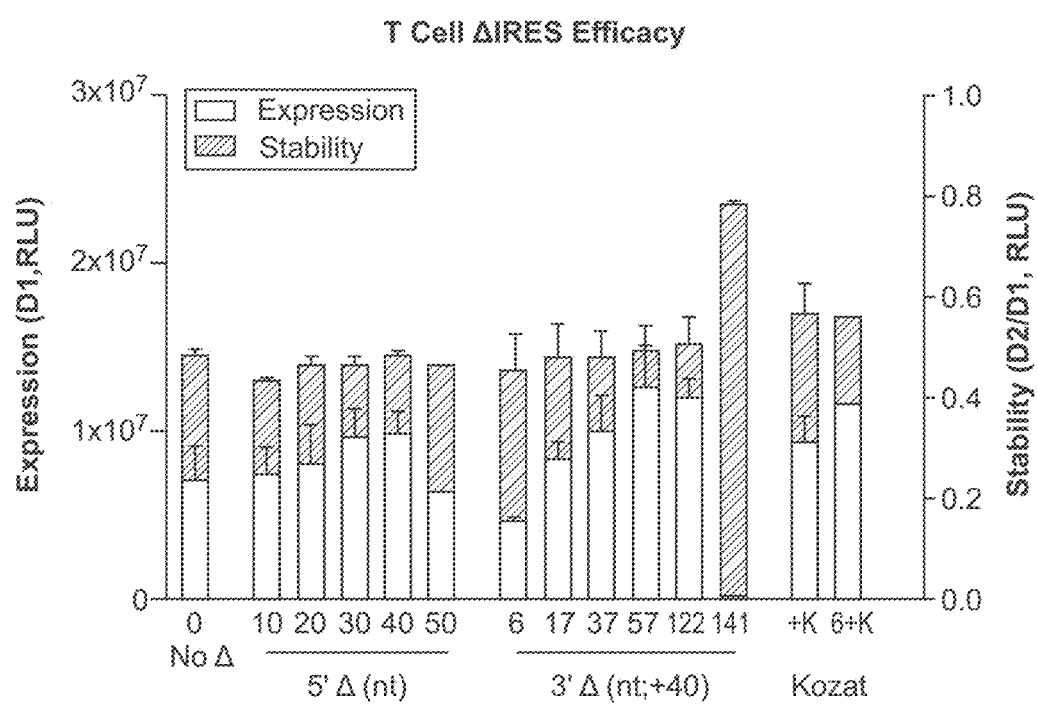
FIG. 35 shows luminescence expression levels and stability of expression in primary T cells from circular RNAs containing the original or modified IRES elements indicated.

As shown in FIG. 35, deletion of more than 40 nucleotides from the 5' end of the IRES reduced expression and disrupted IRES function. Stability of expression was relatively unaffected by the truncation of the IRES element but expression level was substantially reduced by deletion of 141 nucleotides from the 3' end of the IRES, whereas deletion of 57 or 122 nucleotides from the 3' end had a positive impact on the expression level.

It was also observed that deletion of the 6-nucleotide pre-start sequence reduced the expression level of the luciferase reporter. Replacement of the 6-nucleotide sequence with a classical kozak sequence (GCCACC) did not have a significant impact but at least maintained expression.

Example 49

This example describes modifications (e.g., truncations) of selected IRES sequences, including Caprine Kobuvirus (CKV) IRES, Parabovirus IRES, Apodemus Picornavirus (AP) IRES, Kobuvirus SZAL6 IRES, Crohivirus B (CrVB) IRES, CVB3 IRES, and SAFV IRES. The sequences of the IRES elements are provided in SEQ ID NOs: 55-96. Briefly, circular RNA constructs were generated with truncated IRES elements operably linked to a *Gaussia* luciferase coding sequence. HepG2 cells were transfected with the circular RNAs. Luminescence in the supernatant was assessed 24 and 48 hours after transfection. Stability of expression was calculated as the ratio of the expression level at the 48-hour time point relative to that at the 24-hour time point.

Figure 36:
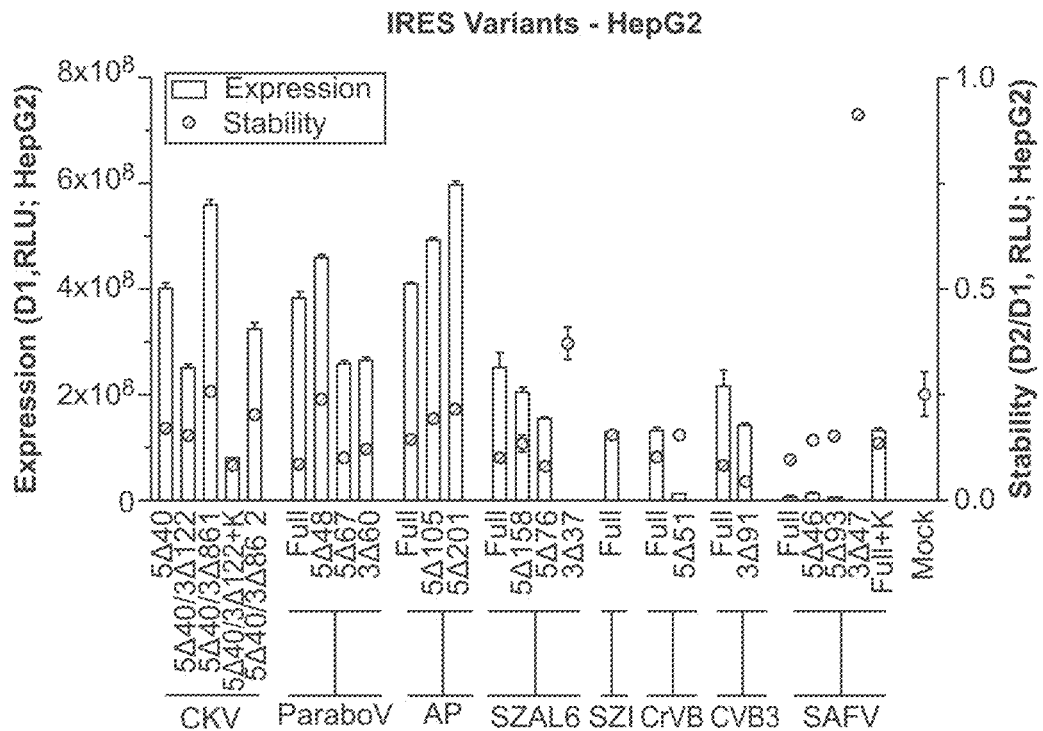
FIG. 36 shows luminescence expression levels and stability of expression in HepG2 cells from circular RNAs containing the original or modified IRES elements indicated.

As shown in FIG. 36, truncations had variable effects depending on the identity of the IRES, which may depend on the initiation mechanism and protein factors used for translation, which often differs between IRESs. 5' and 3' deletions can be effectively combined, for example, in the context of CKV IRES. Addition of a canonical Kozak sequence in some cases significantly improved expression (as in SAFV, Full vs Full+K) or diminished expression (as in CKV, 5d40/3d122 vs 5d40/3d122+K).

Example 50

This example describes modifications of CK-739, AP-748, and PV-743 IRES sequences, including mutations at the translation initiation elements. Briefly, circular RNA constructs were generated with modified IRES elements operably linked to a *Gaussia* luciferase coding sequence. Luminescence from secreted *Gaussia* luciferase in supernatant was measured 24 and 48 hours after transfection of 1C1C7 cells with RNA.

Figure 37:
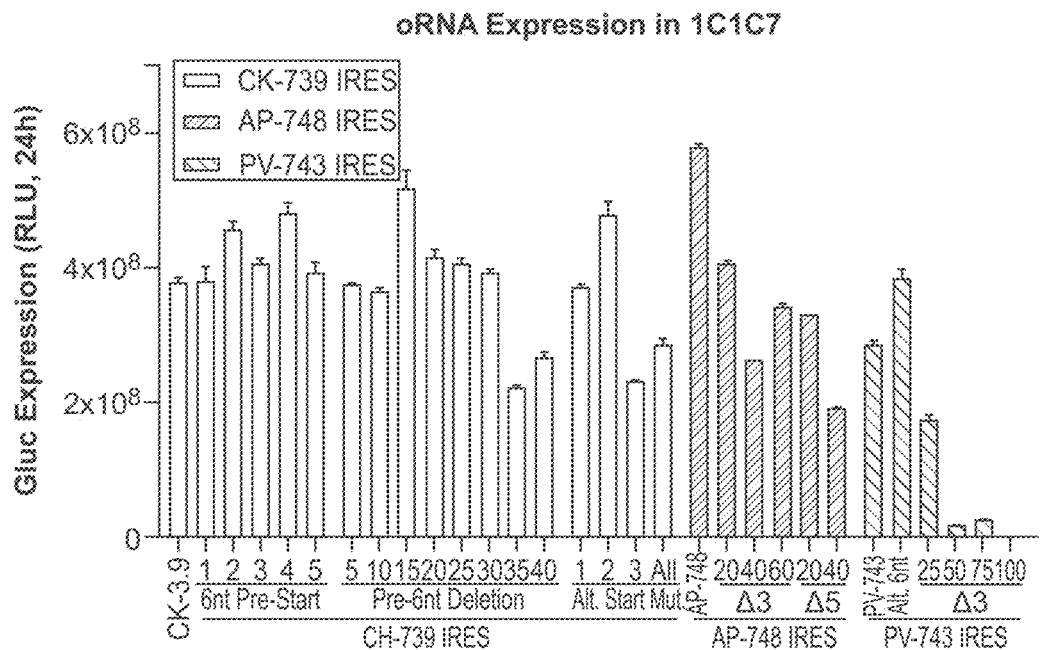
FIG. 37 shows luminescence expression levels and stability of expression in 1C1C7 cells from circular RNAs containing the original or modified IRES elements indicated.

CUG was the most commonly found alternative start site but many others were also characterized. These triplets can be present in the IRES scanning tract prior to the start codon and can affect translation of correct polypeptides. Four alternative start site mutations were created, with the IRES sequences provided in SEQ ID NOs: 97-99. As shown in FIG. 37, mutations of alternative translation initiation sites in the CK-739 IRES affected translation of correct polypeptides, positively in some instances and negatively in other instances. Mutation of all the alternative translation initiation sites reduced the level of translation.

Alternative Kozak sequences, 6 nucleotides before start codon, can also affect expression levels. The 6-nucleotide sequence upstream of the start codon were gTcacG, aaagtc, gTcacG, gtcatg, gcaaac, and acaacc, respectively, in CK-739 IRES and Sample Nos. 1-5 in the "6 nt Pre-Start" group. As shown in FIG. 37, substitution of certain 6-nucleotide sequences prior to the start codon affected translation.

It was also observed that 5' and 3' terminal deletions in AP-748 and PV-743 IRES sequences reduced expression. However, in the CK-739 IRES, which had a long scanning tract, translation was relatively unaffected by deletions in the scanning tract.

Example 51

This example describes modifications of selected IRES sequences by inserting 5' and/or 3' untranslated regions (UTRs) and creating IRES hybrids. Briefly, circular RNA constructs were generated with modified IRES elements operably linked to a *Gaussia* luciferase coding sequence. Luminescence from secreted *Gaussia* luciferase in supernatant was measured 24 and 48 hours after transfection of HepG2 cells with RNA.

Figure 53A:
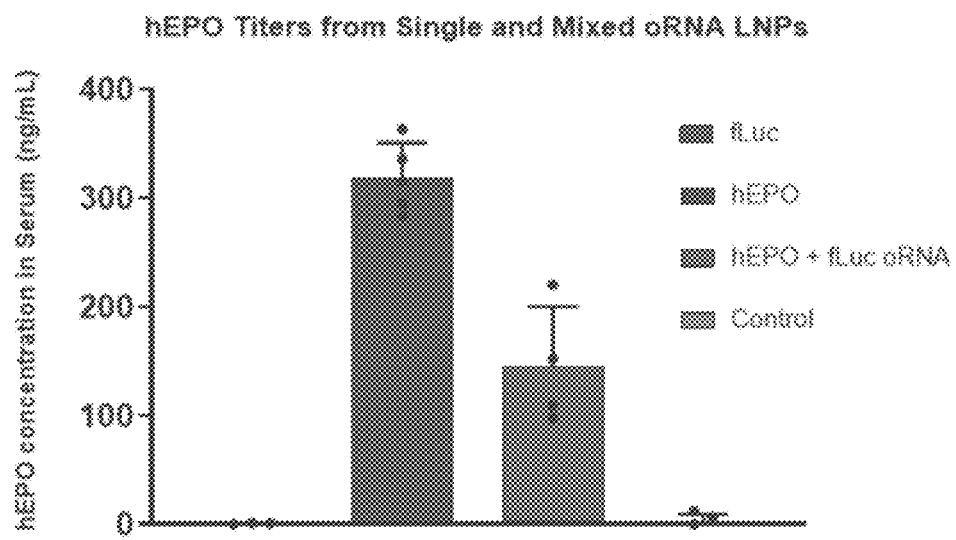
FIG. 53A and FIG. 53B illustrate expression of multiple circular RNAs from a single lipid formulation.

IRES sequences with UTRs inserted are provided in SEQ ID NOs: 100-104, 106-110 and GTCACG. As shown in FIG. 53, insertion of 5' UTR right after the 3' end of the IRES and before the start codon slightly increased the translation from Caprine Kobuvirus (CK) IRES but in some instances abrogated translation from Salivirus SZ1 IRES. Insertion of 3' UTR right after the stop cassette had no impact on both TRES sequences.

Figure 38:
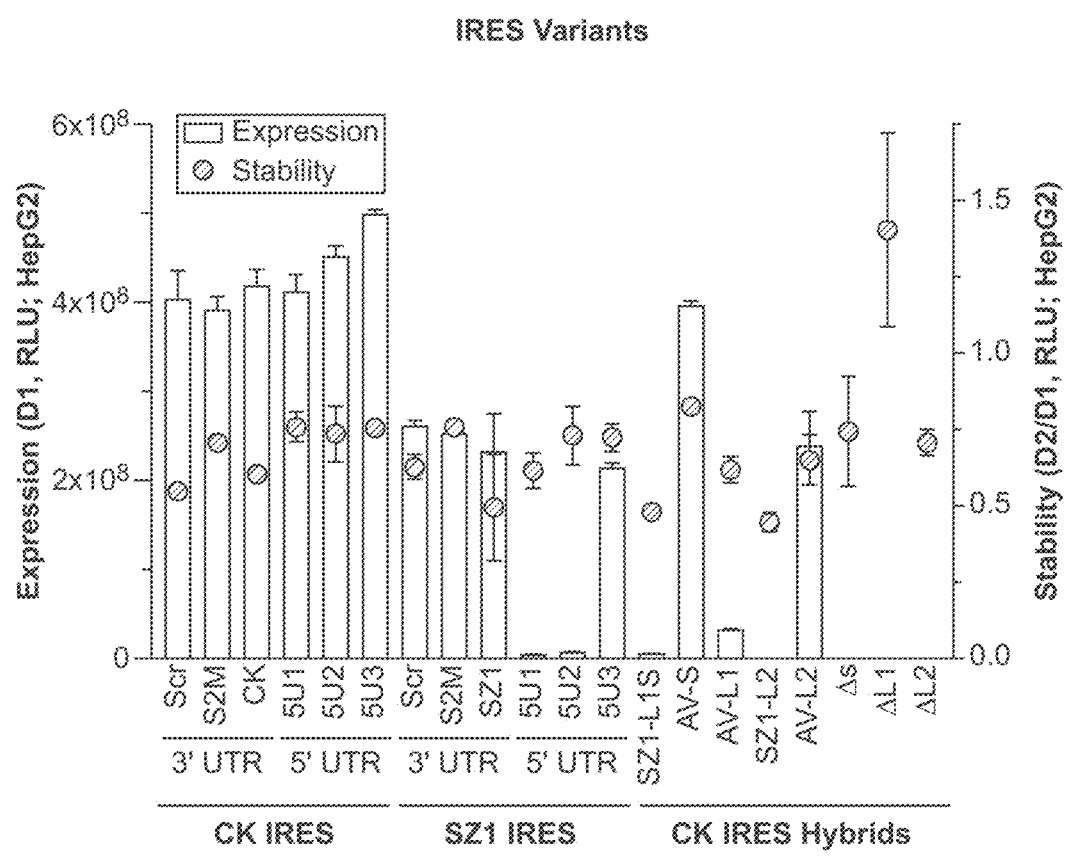
FIG. 38 shows luminescence expression levels and stability of expression in HepG2 cells from circular RNAs containing IRES elements with untranslated regions (UTRs) inserted or hybrid IRES elements. "Scr" means Scrambled, which was used as a control.

Hybrid CK IRES sequences are provided in SEQ ID NOs: 100-104, 106-110 and GTCACG. CK TRES was used as a base, and specific regions of the CK TRES were replaced with similar-looking structures from other IRES sequences, for example, SZ1 and AV (Aichivirus). As shown in FIG. 38, certain hybrid synthetic TRES sequences were functional, indicating that hybrid IRES can be constructed using parts from distinct TRES sequences that show similar predicted structures while deleting these structures completely abrogates IRES function.

Example 52

This example describes modifications of circular RNAs by introducing stop codon or cassette variants. Briefly, circular RNA constructs were generated with IRES elements operably linked to a *Gaussia* luciferase coding sequence followed by variable stop codon cassettes, which included a stop codon in each frame and two stop codons in the reading frame of the *Gaussia* luciferase coding sequence. 1C1C7 cells were transfected with the circular RNAs. Luminescence in supernatant was assessed 24 and 48 hours after transfection.

Figure 39:
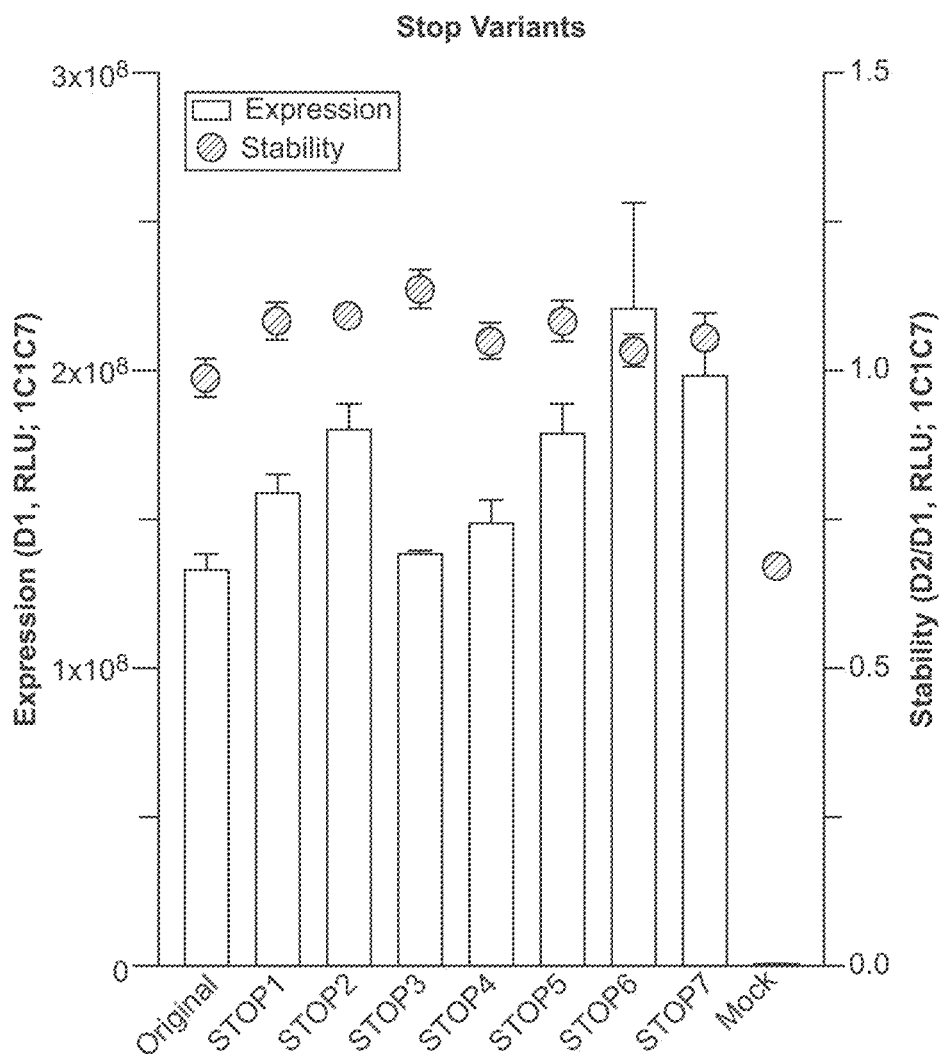
FIG. 39 shows luminescence expression levels and stability of expression in 1C1C7 cells from circular RNAs containing an IRES and variable stop codon cassettes operably linked to a gaussian luciferase coding sequence.

The sequences of the stop codon cassettes are set forth in SEQ ID NOs: 112-115, 117-118 and TAA. As shown in FIG. 39, certain stop codon cassettes improved expression levels, although they had little impact on expression stability. In particular, a stop cassette with two frame 1 (the reading frame of the *Gaussia* luciferase coding sequence) stop codons, the first being TAA, followed by a frame 2 stop codon and a frame 3 stop codon, is effective for promoting functional translation.

Example 53

This example describes modifications of circular RNAs by inserting 5' UTR variants. Briefly, circular RNA constructs were generated with IRES elements with 5' UTR variants inserted between the 3' end of the IRES and the start codon, the IRES being operably linked to a *Gaussia* luciferase coding sequence. 1C1C7 cells were transfected with the circular RNAs. Luminescence in supernatant was assessed 24 and 48 hours after transfection.

Figure 40:
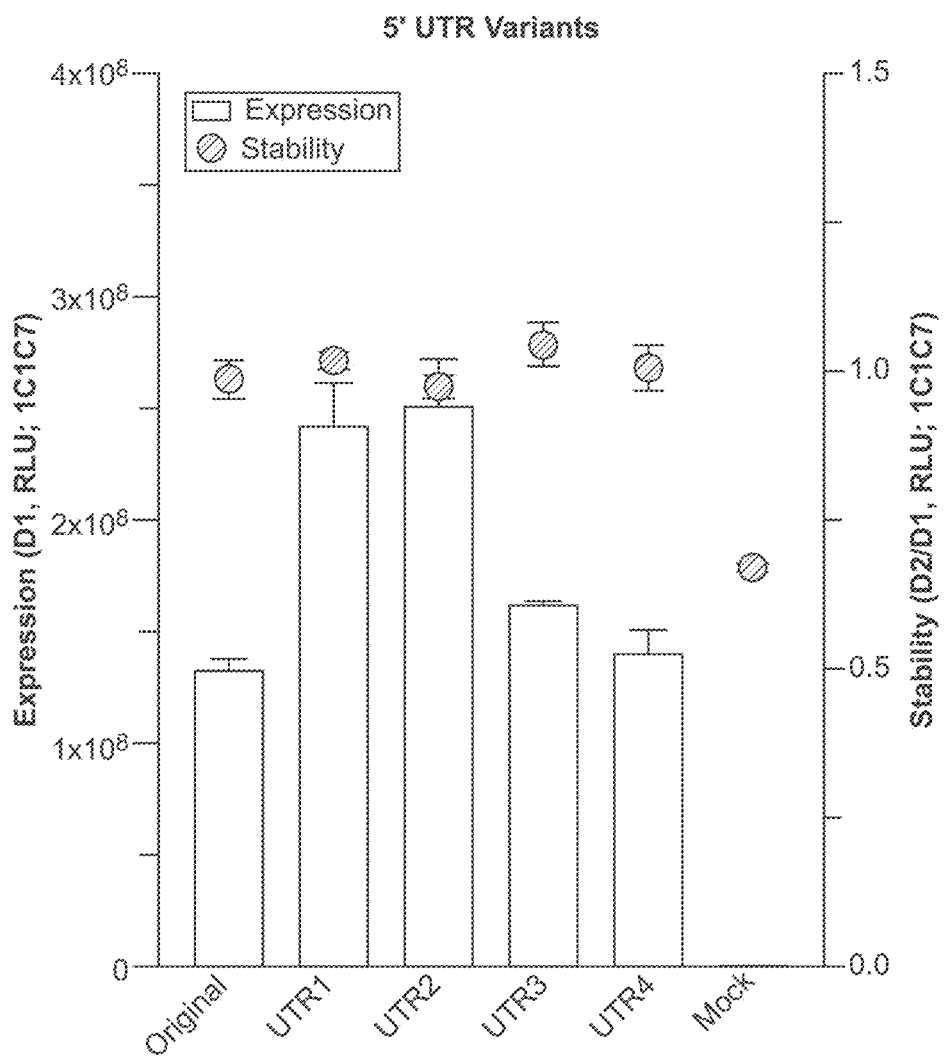
FIG. 40 shows luminescence expression levels and stability of expression in 1C1C7 cells from circular RNAs containing an IRES and variable untranslated regions (UTRs) inserted before the start codon of a gaussian luciferase coding sequence.

The sequences of the 5' UTR variants are set forth in SEQ ID NOs: 120-121, GTCACG, and AGCCACC. As shown in FIG. 40, a CK IRES with a canonical Kozak sequence (UTR4) was more effective when a 36-nucleotide unstructured/low GC spacer sequence was added (UTR2), suggesting that the GC-rich Kozak sequences may interfere with core IRES folding. Using a higher-GC/structured spacer with a kozak sequence did not show the same benefit (UTR3), possibly due to interference with IRES folding by the spacer itself. Mutating the kozak sequence to gTcacG (UTR1) enhanced translation to the same level as the Kozak+spacer alternative without the need for a spacer.

Example 54

This example describes the impact of miRNA target sites in circular RNAs on expression levels. Briefly, circular RNA constructs were generated with IRES elements operably linked to a human erythropoietin (hEPO) coding sequence, where 2 tandem miR-122 target sites were inserted into the construct. miR-122-expressing Huh7 cells were transfected with the circular RNAs. hEPO expression in supernatant was assessed 24 and 48 hours after transfection by sandwich ELISA.

Figure 41:
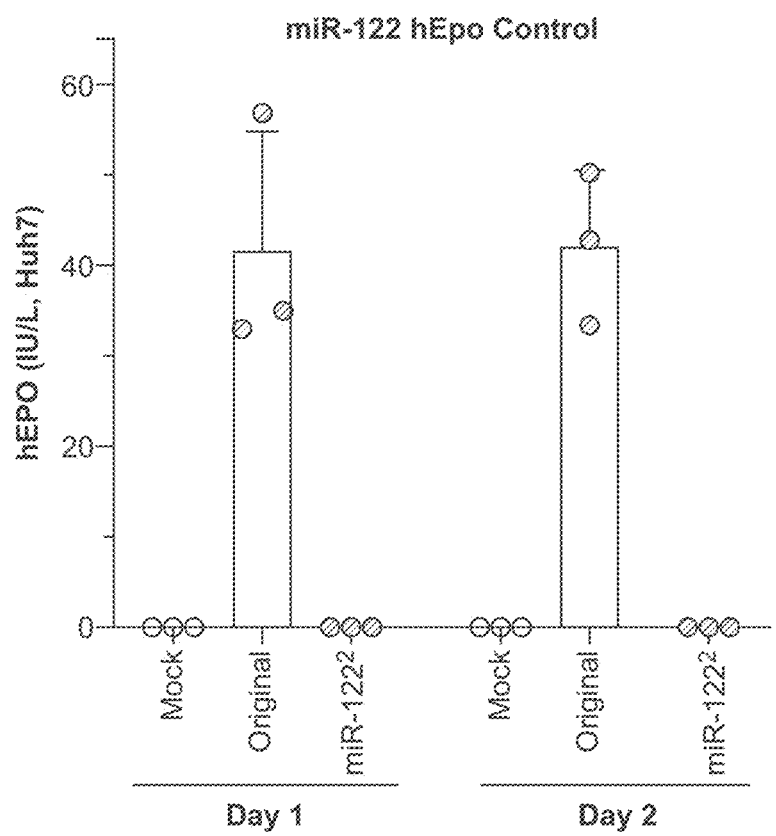
FIG. 41 shows expression levels of human erythropoietin (hEPO) in Huh7 cells from circular RNAs containing two miR-122 target sites downstream from the hEPO coding sequence.

As shown in FIG. 41, the hEPO expression level was obrogated where the miR-122 target sites were inserted into the circular RNA. This result demonstrates that expression from circular RNA can be regulated by miRNA. As such, cell type- or tissue-specific expression can be achieved by incorporating target sites of the miRNAs expressed in the cell types in which expression of the recombinant protein is undesirable.

Example 55

LNP and Circular RNA Construct Containing Anti-CD19 CAR Reduces B Cells in the Blood and Spleen In Vivo Circular RNA constructs encoding an anti-CD19 CAR expression were encapsulated within lipid nanoparticles as described above. For comparison, circular RNAs encoding luciferase expression were encapsulated within separate lipid nanoparticle.

Figure 42A:
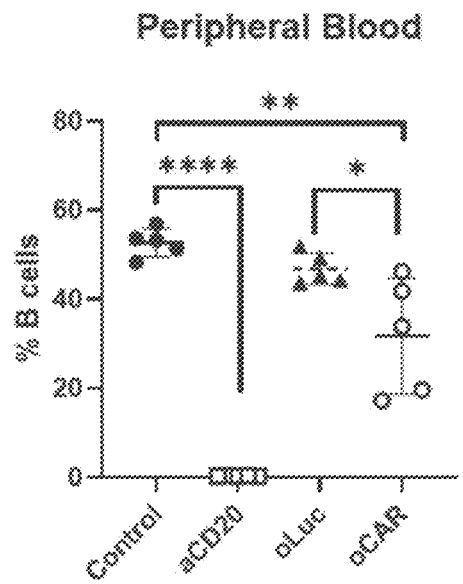
FIG. 42A and FIG. 42B show CAR expression levels in the peripheral blood (FIG. 42A) and spleen (FIG. 42B) when treated with LNP encapsulating circular RNA that expresses anti-CD19 CAR. Anti-CD20 (aCD20) and circular RNA encoding luciferase (oLuc) were used for comparison.
Figure 42B:
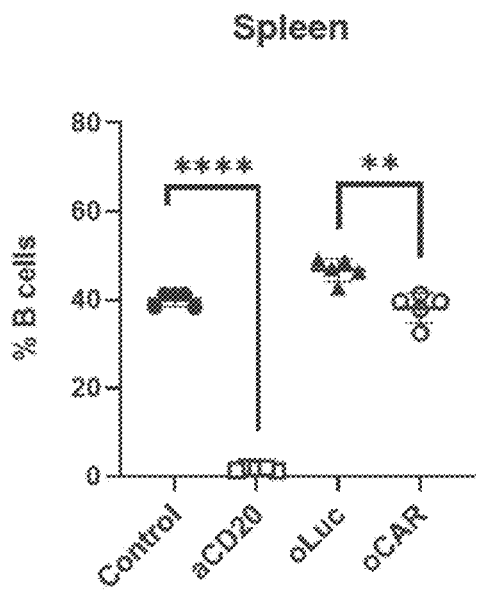
Figure 43A:
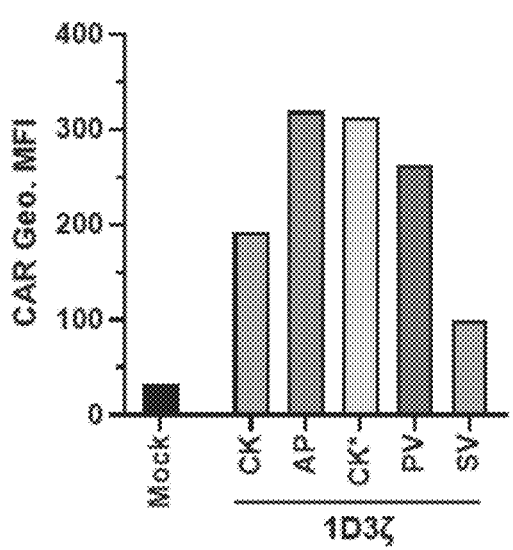
FIGS. 43A-43C show the overall frequency of anti-CD19 CAR expression, the frequency of anti-CD19 CAR expression on the surface of cells and effect on anti-tumor response of IRES specific circular RNA encoding anti-CD19 CARs on T-cells.
Figure 43B:
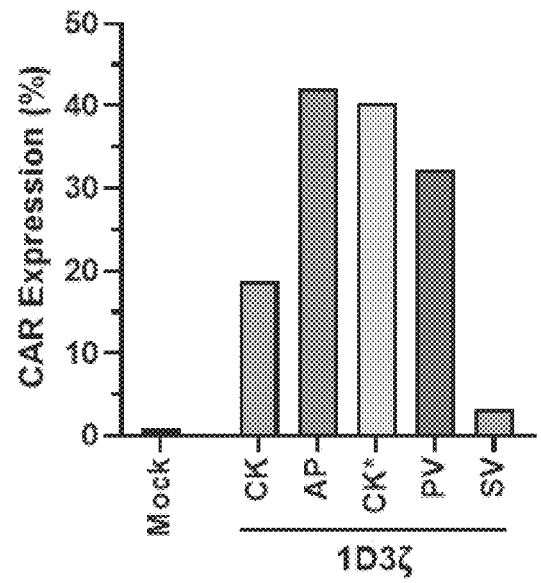
Figure 43C:
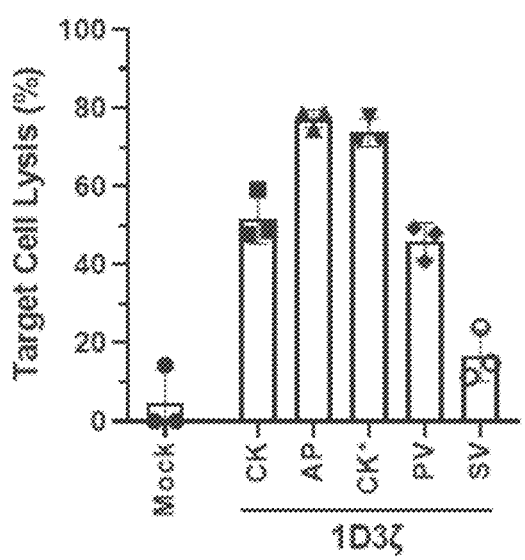
Figure 44:
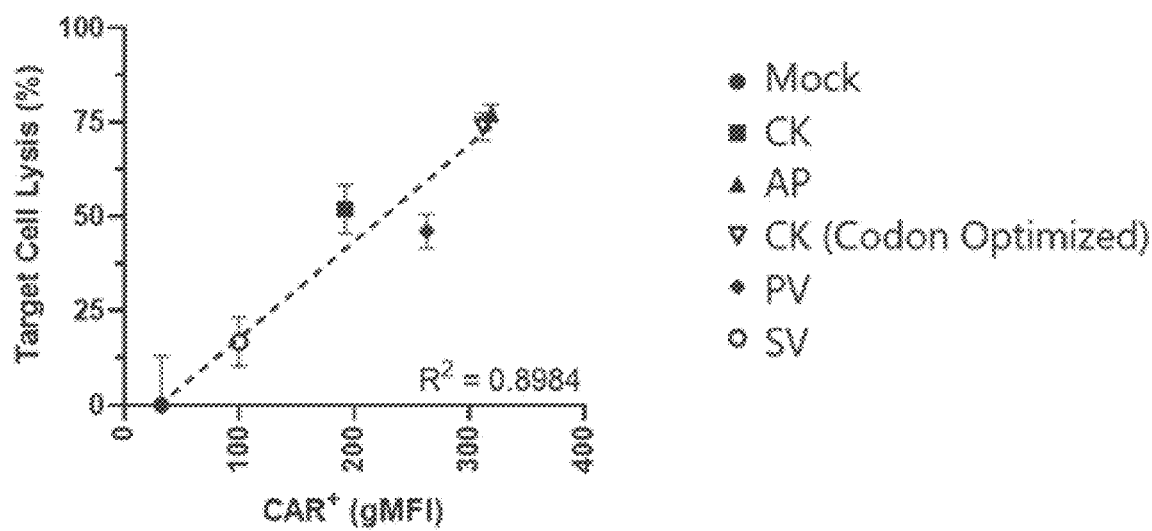
FIG. 44 shows CAR expression levels of A20 FLuc target cells when treated with IRES specific circular RNA constructs.

C57BL/6 mice at 6 to 8 weeks old were injected with either LNP solution every other day for a total of 4 LNP injections within each mouse. 24 hours after the last LNP injection, the mice's spleen and blood were harvested, stained, and analyzed via flow cytometry. As shown in FIG. 42A and FIG. 42B, mice containing LNP-circular RNA constructs encoding an anti-CD19 CAR led to a statistically significant reduction in CD19+ B cells in the peripheral blood and spleen compared to mice treated with LNP-circular RNA encoding a luciferase.

Example 56

IRES Sequences Contained within Circular RNA Encoding CARs Improves CAR Expressions and Cytotoxicity of T-Cells Activated murine T-cells were electroporated with 200 ng of circular RNA constructs containing a unique IRES and a murine anti-CD19 1D3ζ CAR expression sequence. The IRES contained in these constructs were derived either in whole or in part from a Caprine Kobuvirus, Apodemus Picornavirus, Parabovirus, or Salivirus. A Caprine Kobuvirus derived IRES was additionally codon optimized. As a control, a circular RNA containing a wild-type zeta mouse CAR with no IRES was used for comparison. The T-cells were stained for the CD-19 CAR 24 hours post electroporation to evaluate for surface expression and then co-cultured with A20 Fluc target cells. The assay was then evaluated for cytotoxic killing of the Fluc+ A20 cells 24 hours after co-culture of the T-cells with the target cells.

As seen in FIGS. 43A, 43B, 43C, and 44, the unique IRES were able to increase the frequency that the T-cells expressed the CAR protein and level of CAR expression on the surface of the cells. The increase frequency of expression of the CAR protein and level of CAR expression on the surface of cells lead to an improved anti-tumor response.

Example 57

Cytosolic and Surface Proteins Expressed from Circular RNA Construct in Primary Human T-Cells Circular RNA construct contained either a sequence encoding for a fluorescent cytosolic reporter or a surface antigen reporter. Fluorescent reporters included green fluorescent protein, mCitrine, mWasabi, Tsapphire. Surface reporters included CD52 and Thy1.1$^{bio}$. IN Primary human T-cells were activated with an anti-CD3/anti-CD28 antibody and electroporated 6 days post activation of the circular RNA containing a reporter sequence. T-cells were harvested and analyzed via flow cytometry 24 hours post electroporation. Surface antigens were stained with commercially available antibodies (e.g., Biolegend, Miltenyi, and BD).

Figure 45A:
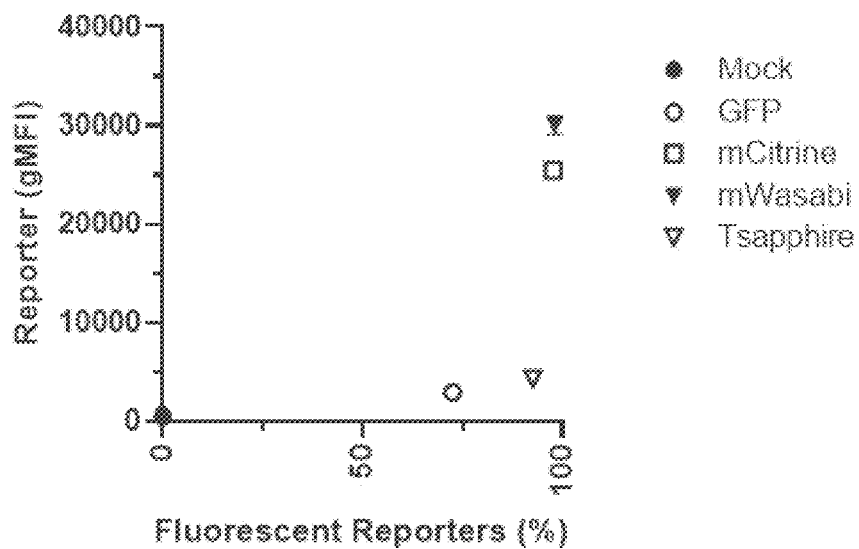
FIG. 45A and FIG. 45B show luminescence expression levels for cytosolic (FIG. 45A) and surface (FIG. 45B) proteins from circular RNA in primary human T-cells.
Figure 45B:
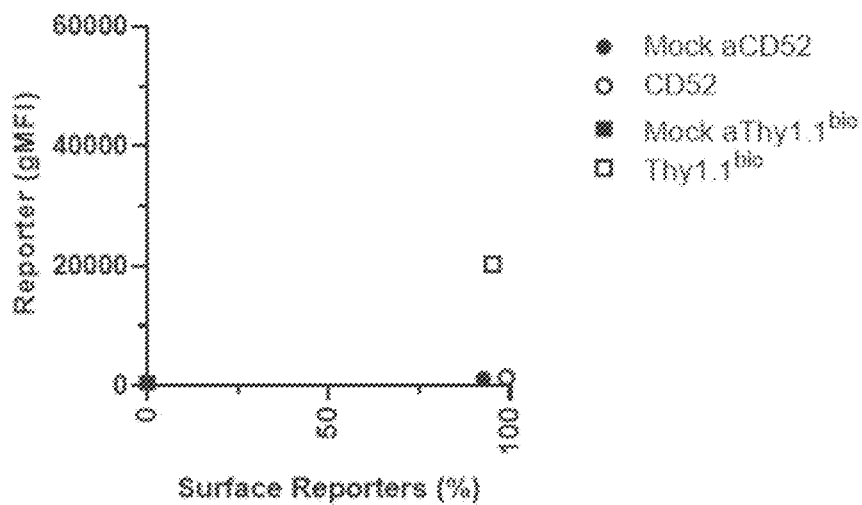
Figure 46A:
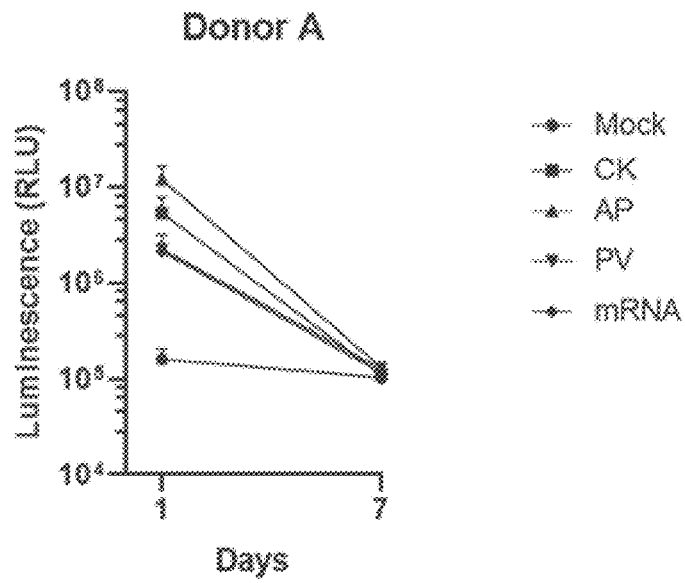
FIGS. 46A-46G show luminescence expression in human T-cells when treated with IRES specific circular constructs. Expression in circular RNA constructs were compared to linear mRNA.
Figure 46B:
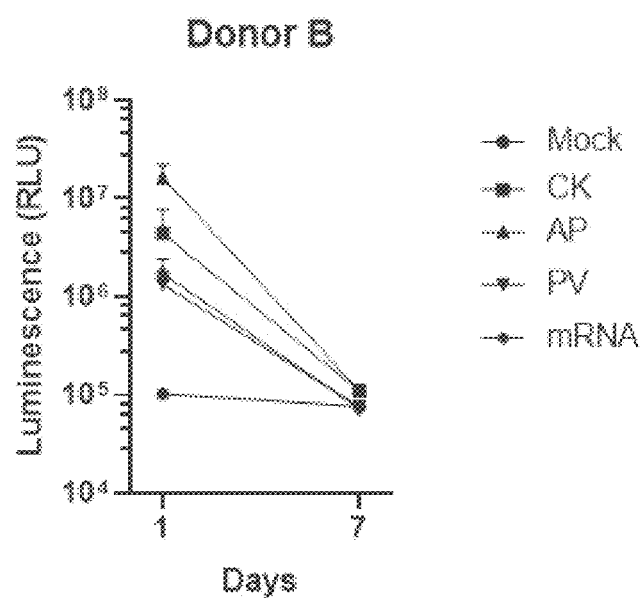
Figure 46C:
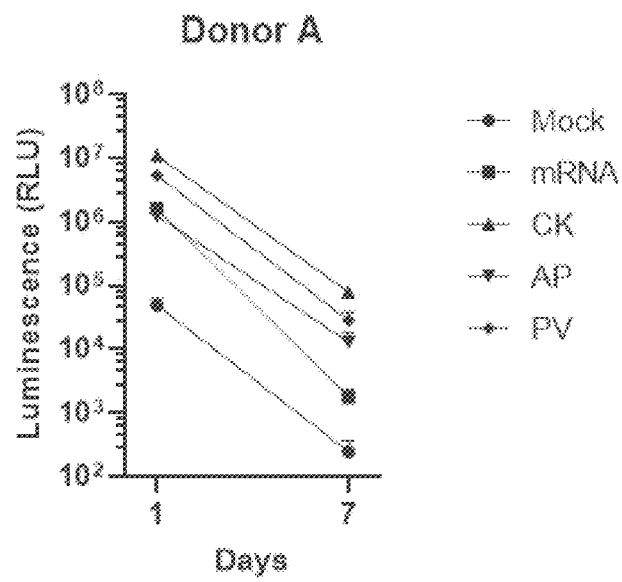
Figure 46D:
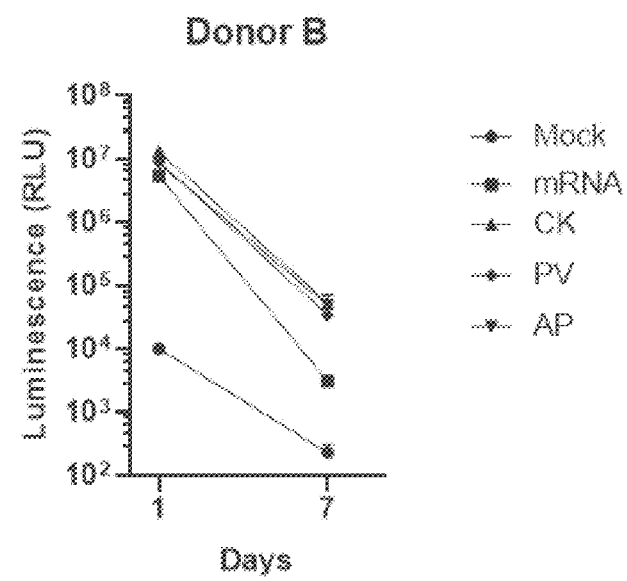
Figure 46E:
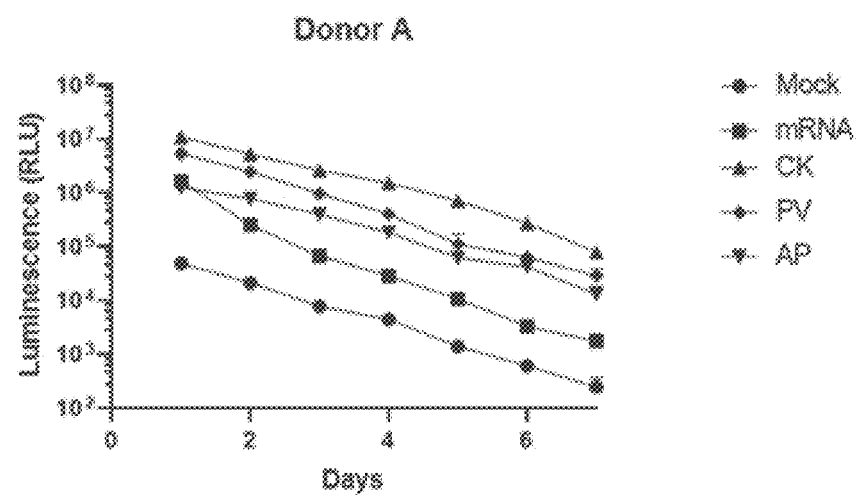
Figure 46F:
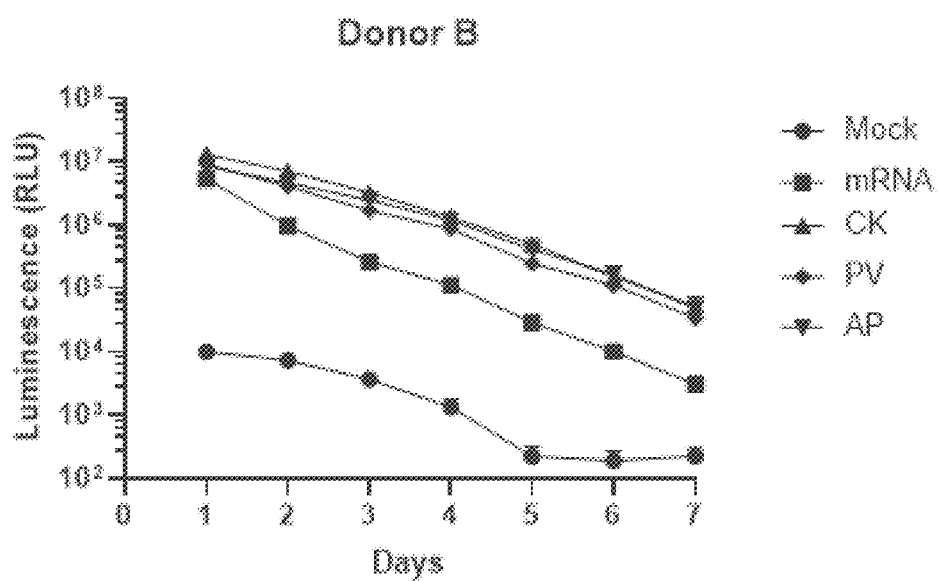
Figure 46G:
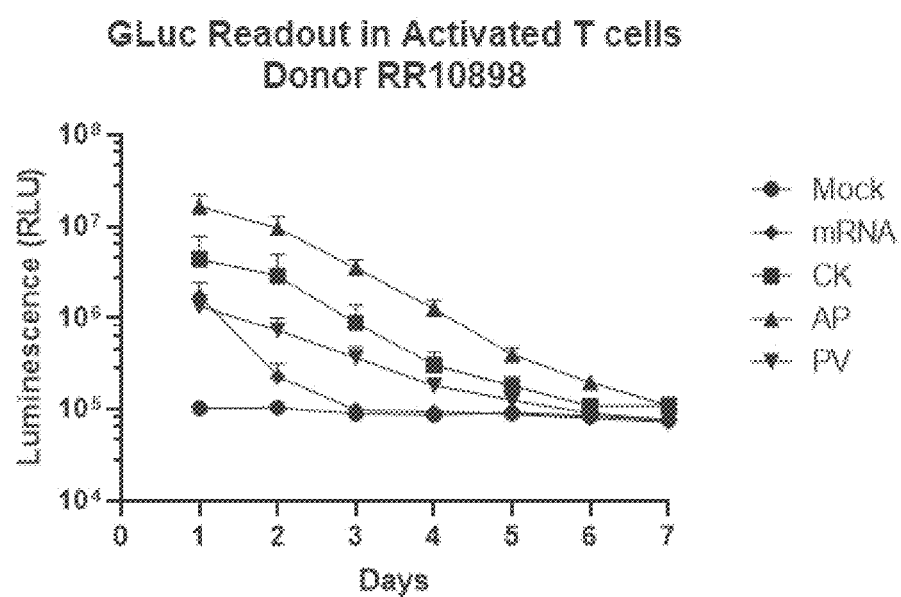

As seen in FIG. 45A and FIG. 45B, cytosolic and surface proteins can be expressed from circular RNA encoding the proteins in primary human T-cells.

Example 58

Circular RNAs Containing Unique IRES Sequences have Improved Translation Expression Over Linear mRNA Circular RNA constructs contained a unique IRES along with an expression sequence for Firefly luciferase (FLuc).

Human T-cells from 2 donors were enriched and stimulated with anti-CD3/anti-CD28 antibodies. After several days of proliferation, activated T cells were harvested and electroporated with equal molar of either mRNA or circular RNA expressing FLuc payloads. Various IRES sequences, including those derived from Caprine Kobuvirus, Apodemus Picornavirus, and Parabovirus, were studied to evaluate expression level and durability of the payload expression across 7 days. Across the 7 days, the T-cells were lysed with Promega Brightglo to evaluate for bioluminsences.

As shown in FIGS. 46C, 46D, 46E, 46F, and 46G, the presence of an IRES within a circular RNA can increase translation and expression of a cytosolic protein by orders of magnitude and can improve expression compared to linear mRNA. This was found consistent across multiple human T-cell donors.

Example 59

Example 59A: LNP-Circular RNA Encoding Anti-CD19 Mediates Human T-Cell Killing of K562 Cells Circular RNA constructs contained a sequence encoding for anti-CD19 antibodies. Circular RNA constructs were then encapsulated within a lipid nanoparticle (LNP).

Human T-cells were stimulated with anti-CD3/anti-CD28 and left to proliferate up to 6 says. At day 6, LNP-circular RNA and ApoE3 (1 μg/mL) were co-cultured with the T-cells to mediate transfection. 24 hours later, Fluc+K562 cells were electroporated with 200 ng of circular RNA encoding anti-CD19 antibodies and were later co-cultured at day 7. 48 hours post co-culture, the assay was assessed for CAR expression and cytotoxic killing of K562 cells through Fluc expression.

Figure 47A:
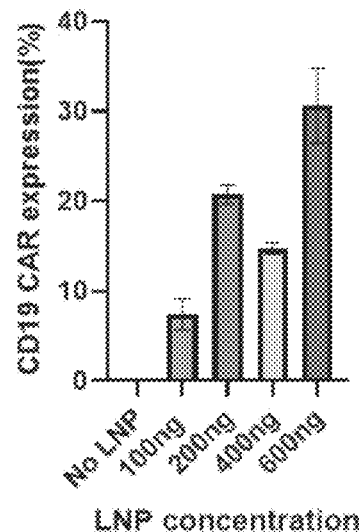
FIG. 47A and FIG. 47B show anti-CD19 CAR and anti-BCMA CAR (FIG. 47B) expression in human T-cells following treatment of a lipid nanoparticle encompassing a circular RNA that encodes either an anti-CD19 or anti-BCMA CAR to a firefly luciferase expressing K562 cell.
Figure 47B:
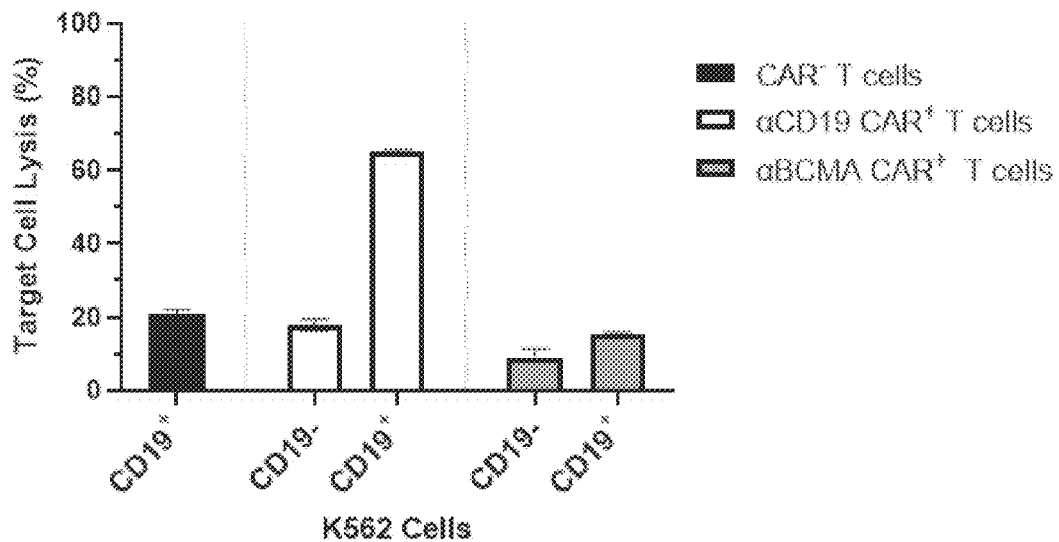

As shown in FIG. 47A and FIG. 47B, there is T-cell expression of anti-CD19 CAR from the LNP-mediated delivery of a CAR in vitro to T-cells and its capability to lyse tumor cells in a specific, antigen dependent manner in engineered K562 cells.

Example 59B: LNP-Circular RNA Encoding Anti-BCMA Antibody Mediates Human T-Cell Killing of K562 Cells Circular RNA constructs contained a sequence encoding for anti-BCMA antibodies. Circular RNA constructs were then encapsulated within a lipid nanoparticle (LNP).

Human T-cells were stimulated with anti-CD3/anti-CD28 and left to proliferate up to 6 says. At day 6, LNP-circular RNA and ApoE3 (1 μg/mL) were co-cultured with the T-cells to mediate transfection. 24 hours later, Fluc+K562 cells were electroporated with 200 ng of circular RNA encoding anti-BCMA antibodies and were later co-cultured at day 7. 48 hours post co-culture, the assay was assessed for CAR expression and cytotoxic killing of K562 cells through Fluc expression.

As shown in FIG. 47B, there is T-cell expression of BCMA CAR from the LNP-mediated delivery of a CAR in vitro to T-cells and its capability to lyse tumor cells in a specific, antigen dependent manner in engineered K562 cells.

Example 60

Anti-CD19 CAR T-Cells Exhibit Anti-Tumor Activity In Vitro.

Human T-cells were activated with anti-CD3/anti-CD28 and electroporated once with 200 ng of anti-CD19 CAR-expressing circular RNA. Electroporated T-cells were co-cultured with FLuc+ Nalm6 target cells and non-target Fluc+K562 cells to evaluate CAR-mediated killing. After 24 hours post co-culture, the T-cells were lysed and examined for remanent FLuc expression by target and non-target cells to evaluate expression and stability of expression across 8 days total.

Figure 48A:
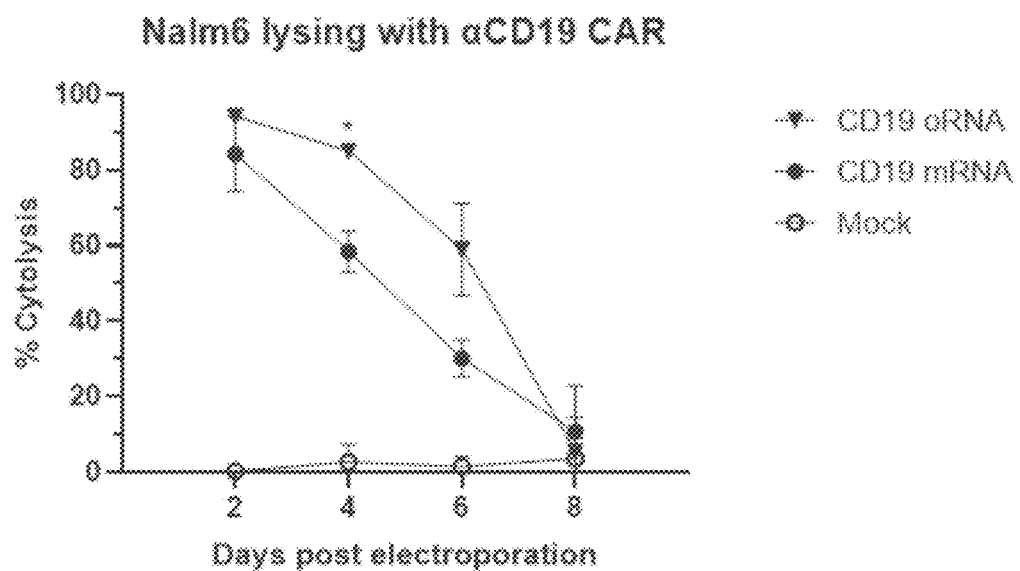
FIG. 48A and FIG. 48B show anti-CD19 CAR expression levels resulting from delivery via electroporation in vitro of a circular RNA encoding an anti-CD19 CAR in a specific antigen-dependent manner.
Figure 48B:
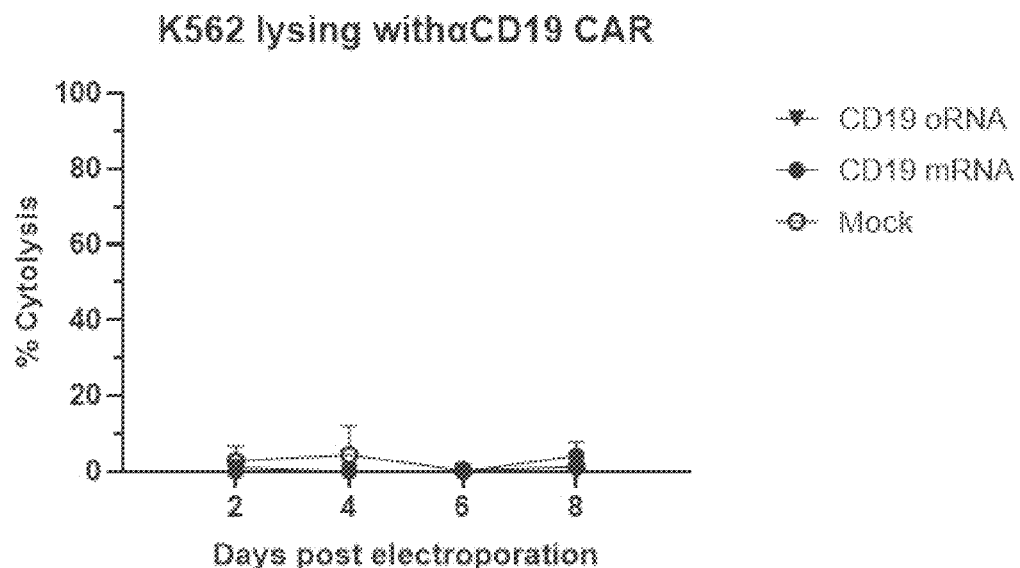
Figure 49A:
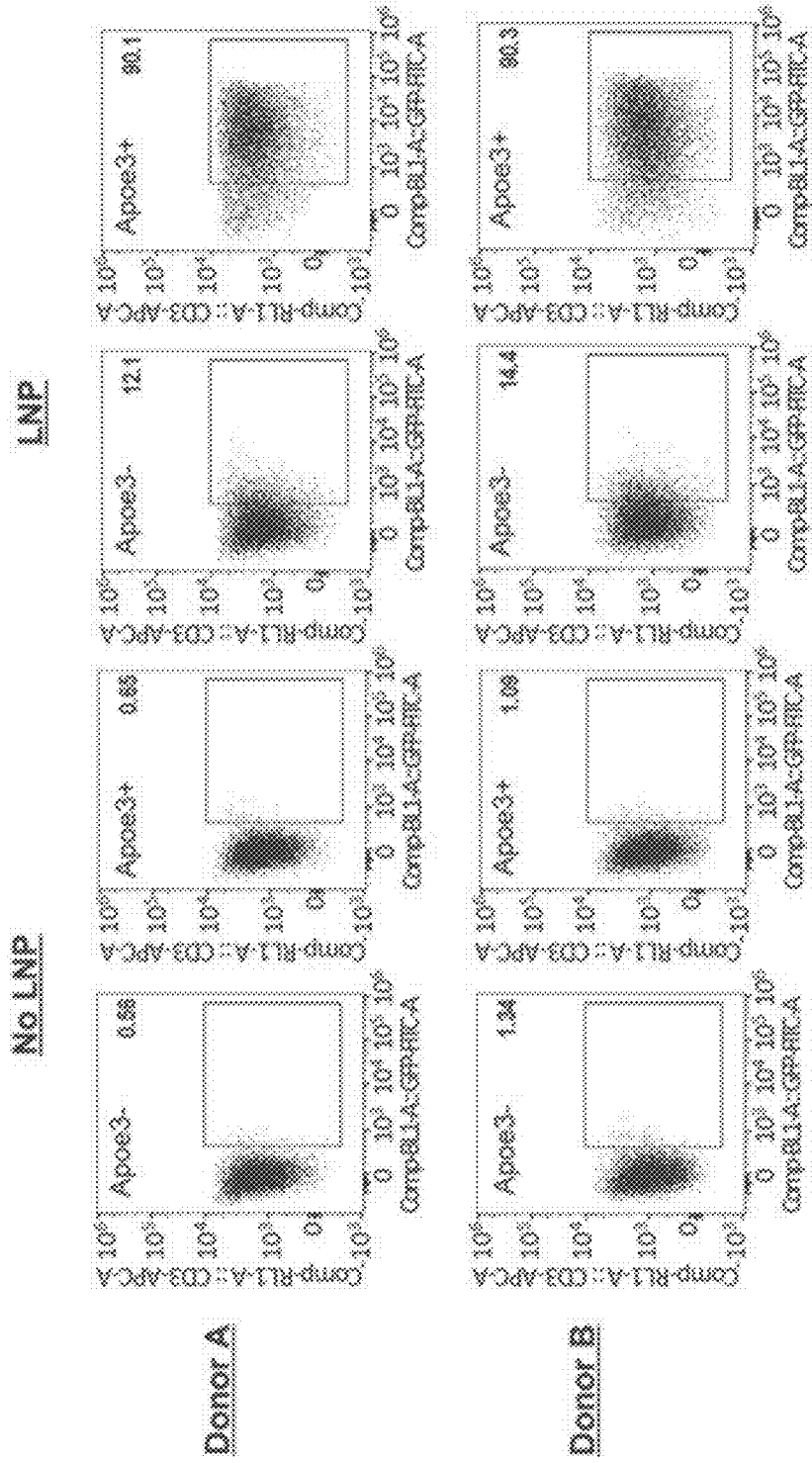
FIGS. 49A-49E show transfection of LNP mediated by use of ApoE3 in solutions containing LNP and circular RNA expressing green fluorescence protein (GFP).
Figure 49B:
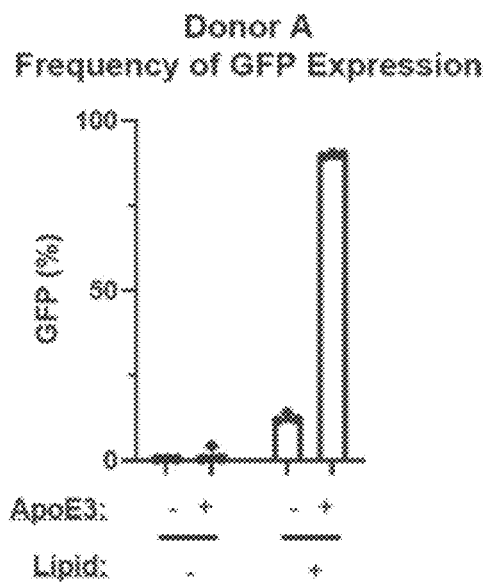
Figure 49C:
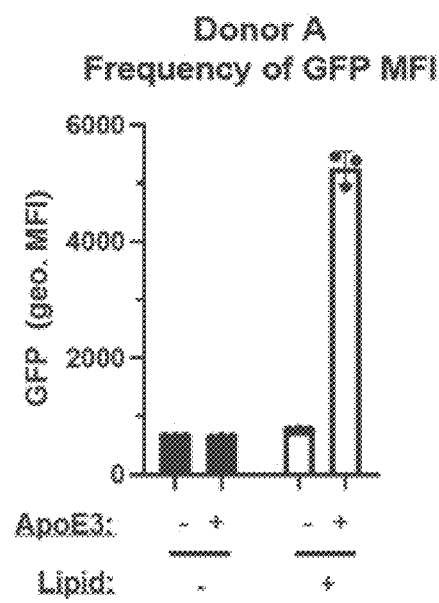
Figure 49D:
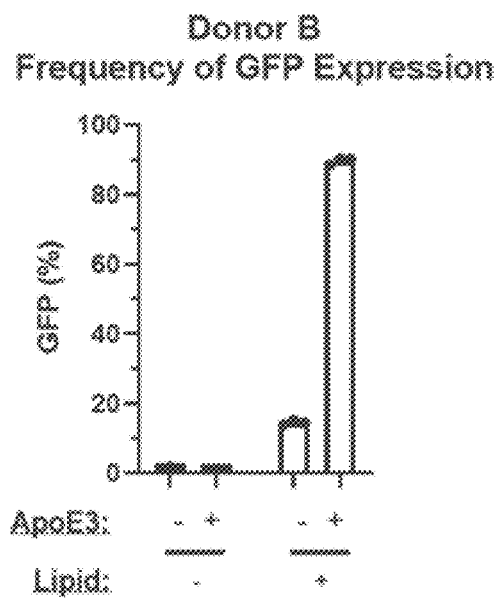
Figure 49E:
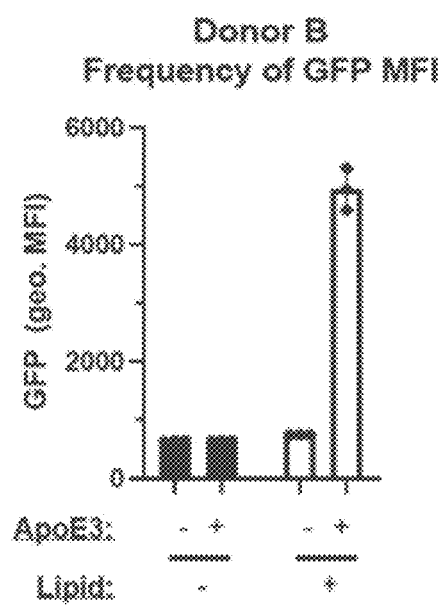

As shown in FIGS. 48A and 48B, T-cells express circular RNA CAR constructs in specific, antigen-dependent manner. Results also shows improved cytotoxicity of circular RNAs encoding CARs compared to linear mRNA encoding CARs and delivery of a functional surface receptor.

Example 61

Effective LNP Transfection of Circular RNA Mediated with ApoE3

Human T-cells were stimulated with anti-CD3/anti-CD28 and left to proliferate up to 6 days. At day 6, lipid nanoparticle (LNP) was and circular RNA expressing green fluorescence protein solution with or without ApoE3 (1 μg/mL) were co-cultured with the T-cells. 24 hours later, the T-cells were stained for live/dead T-cells and the live T-cells were analyzed for GFP expression on a flow cytometer.

As shown by FIGS. 49A, 49B, 49C, 49D, and 49E, efficient LNP transfection can be mediated by ApoE3 on activated T-cells, followed by significant payload expression. These results were exhibited across multiple donors.

Example 62

This example illustrates expression of SARS-CoV2 spike protein expression in vitro. Circular RNA encoding SARS-CoV2 stabilized spike protein was transfected into 293 cells using MessengerMax Transfection Reagent. 24 hours after transfection, the 293 cells were stained with a CR3022 anti-spike primary antibody and APC-labeled secondary antibody.

Figure 50A:
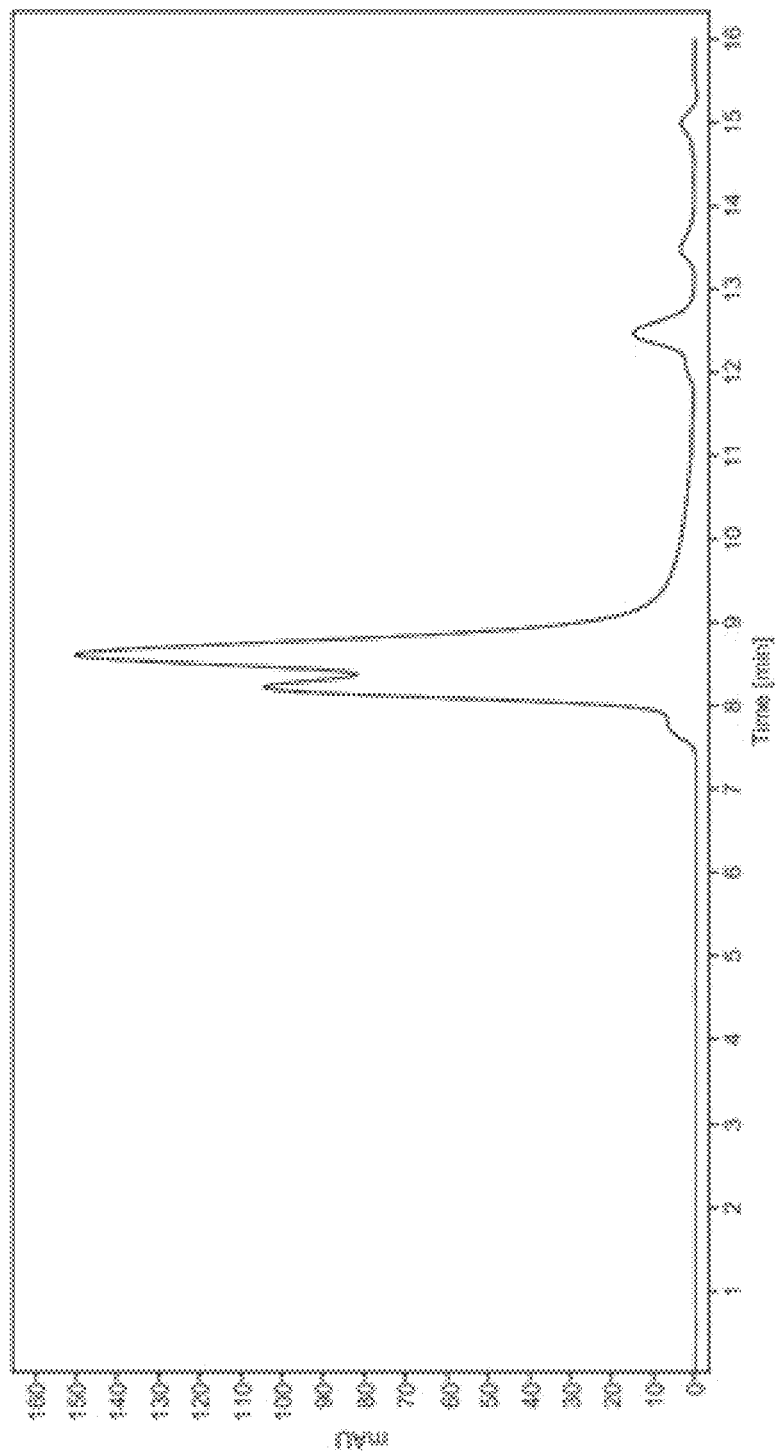
FIGS. 50A-50C show circularization efficiency of an RNA molecule encoding a stabilized (double proline mutant) SARS-CoV2 spike protein.
Figure 50B:
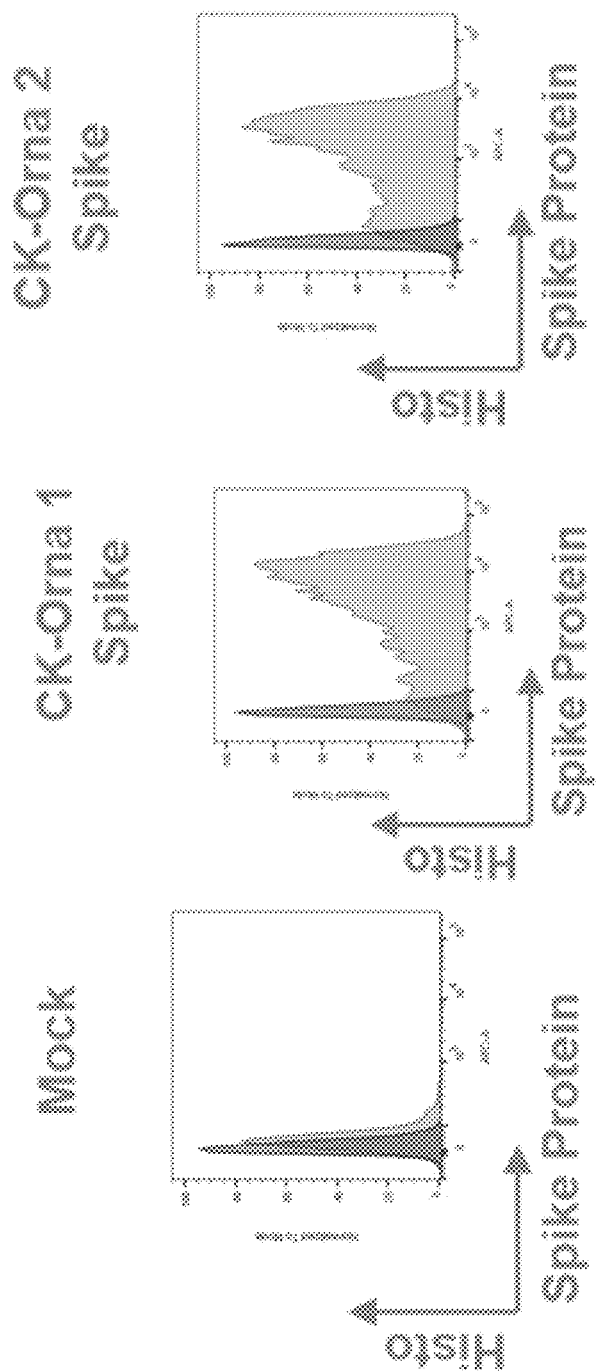
Figure 50C:
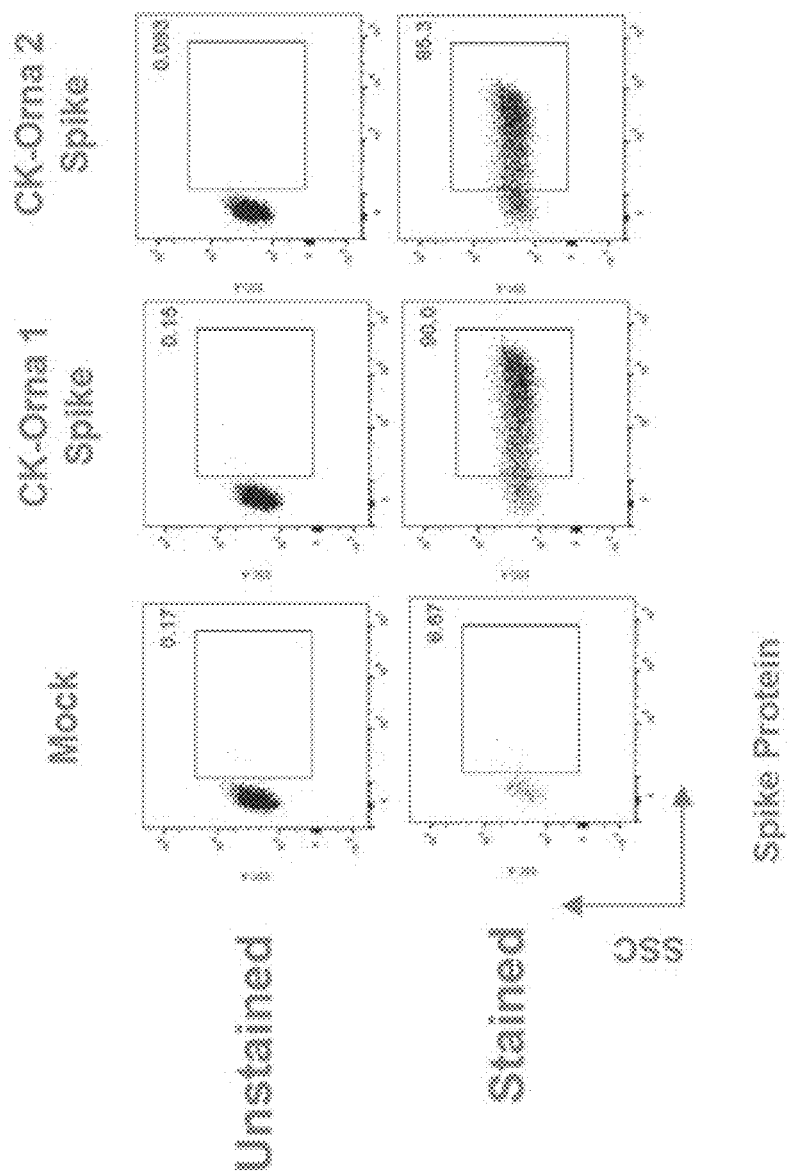
Figure 51:
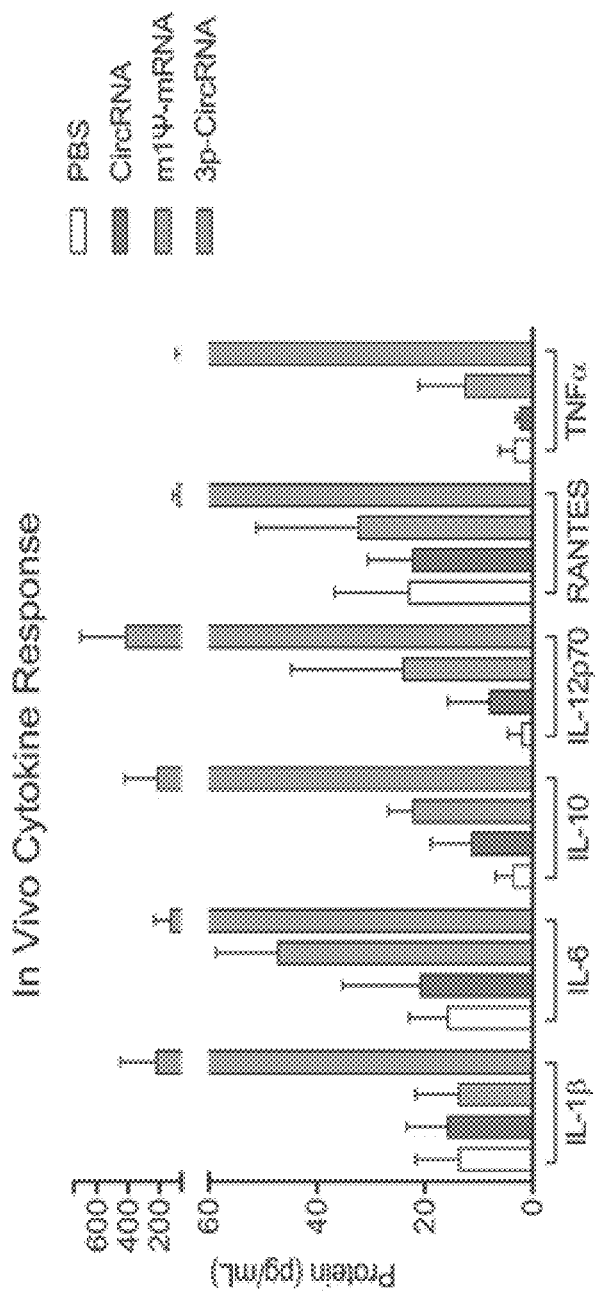
FIG. 51 provides multiple controlled adjuvant strategies. CircRNA as indicated on the figure entails an unpurified sense circular RNA splicing reaction using GTP as an indicator molecule in vitro. 3p-circRNA entails a purified sense circular RNA as well as a purified antisense circular RNA mixed containing triphosphorylated 5' termini.
Figure 52A:
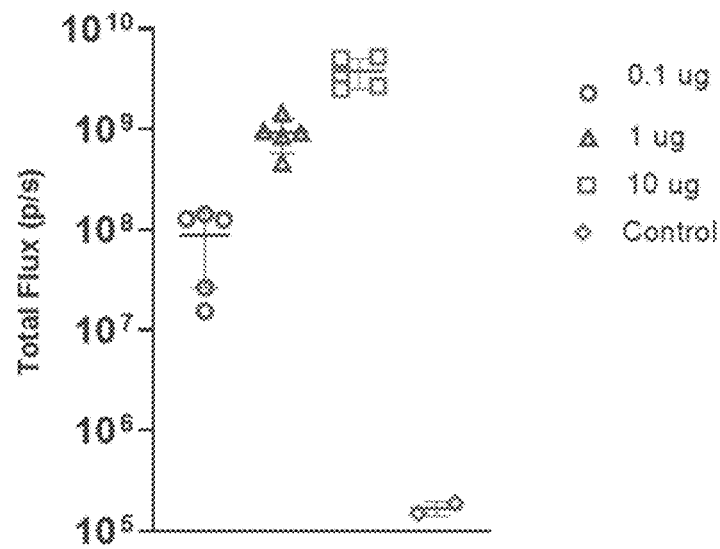
FIGS. 52A-52C illustrate an intramuscular delivery of LNP containing circular RNA constructs.
Figure 52B:
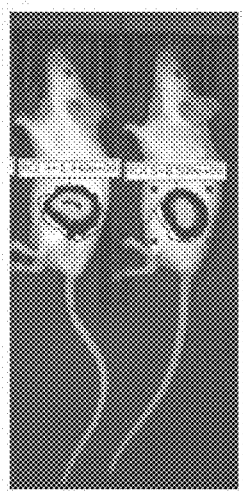
Figure 52C:
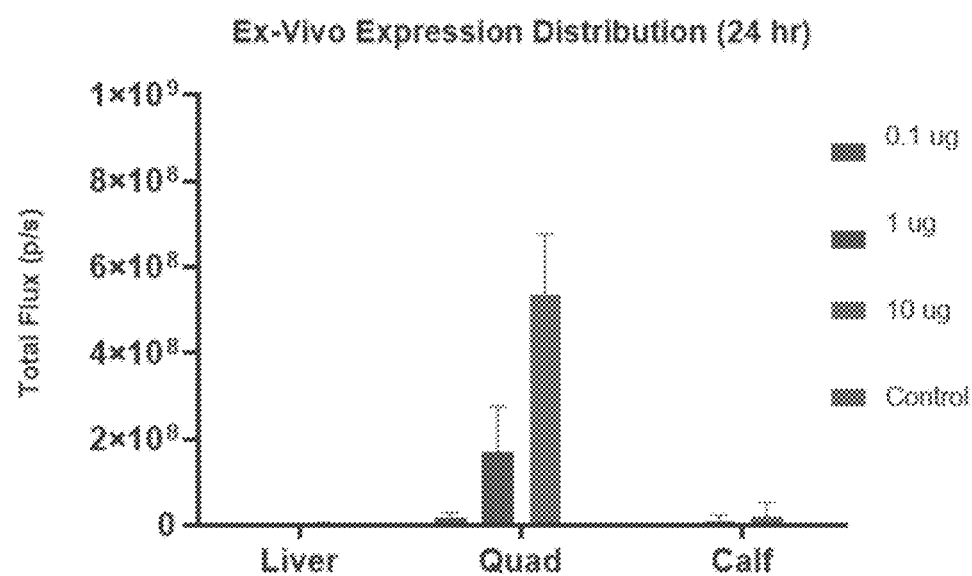
Figure 53B:
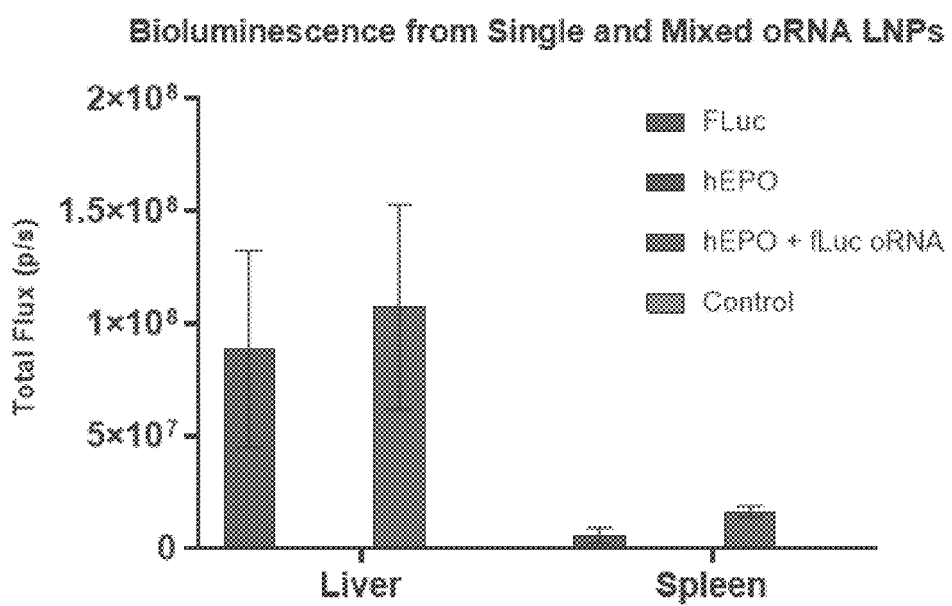
Figure 54A:
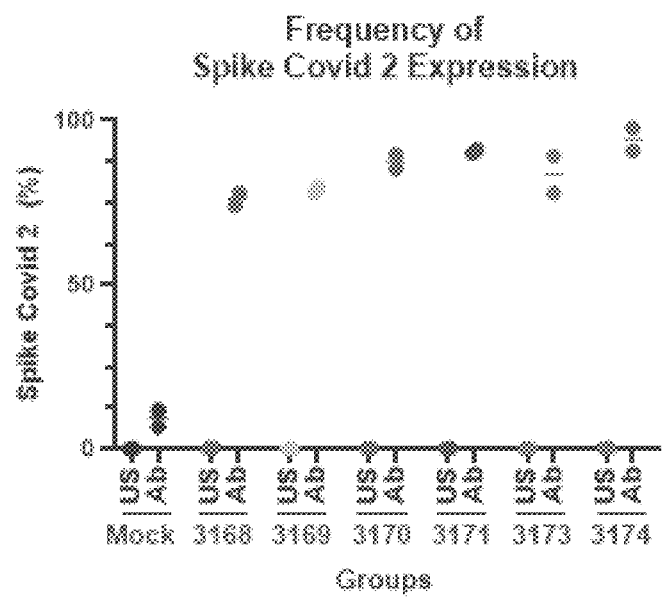
FIGS. 54A-54C illustrate SARS-CoV2 spike protein expression of circular RNA encoding spike SARS-CoV2 proteins.
Figure 54B:
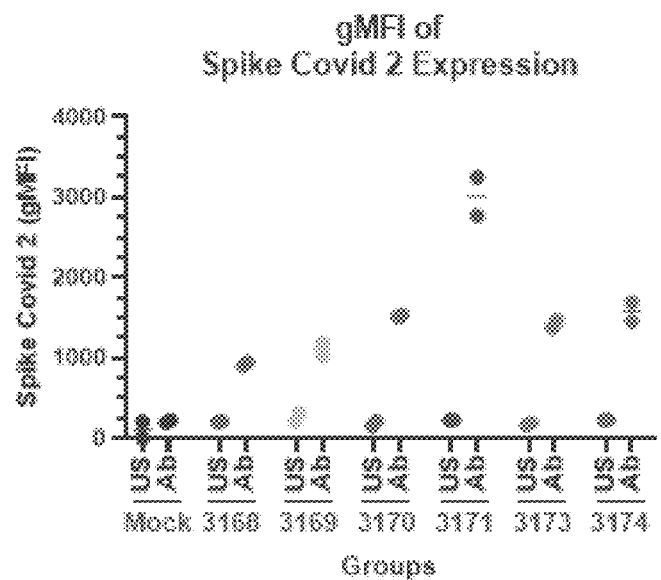
Figure 54C:
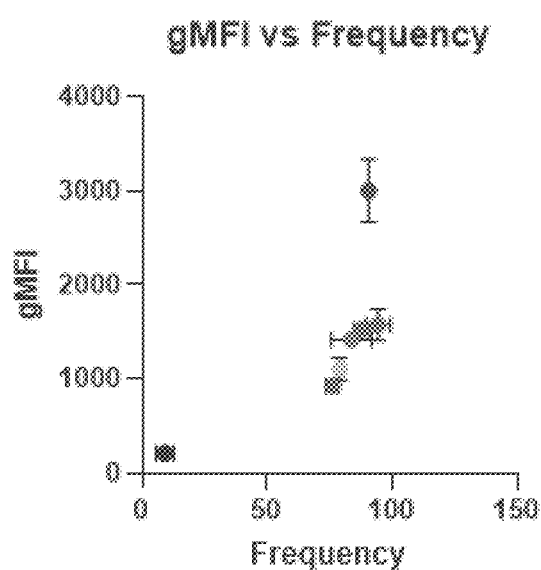
Figure 55:
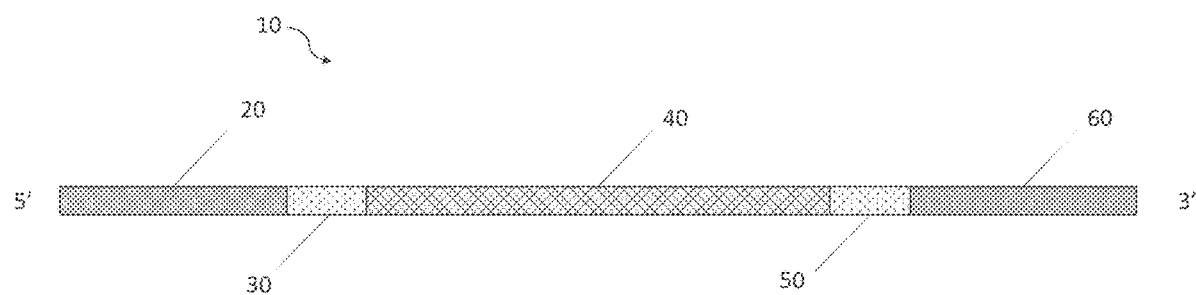
FIG. 55 depicts a general sequence construct of a linear RNA polynucleotide precursor (10). The sequence as provided is illustrated in a 5' to 3' order of a 5' enhanced intron element (20), a 5' enhanced exon element (30), a core functional element (40), a 3' enhanced exon element (50) and a 3' enhanced intron element (60).
Figure 56:
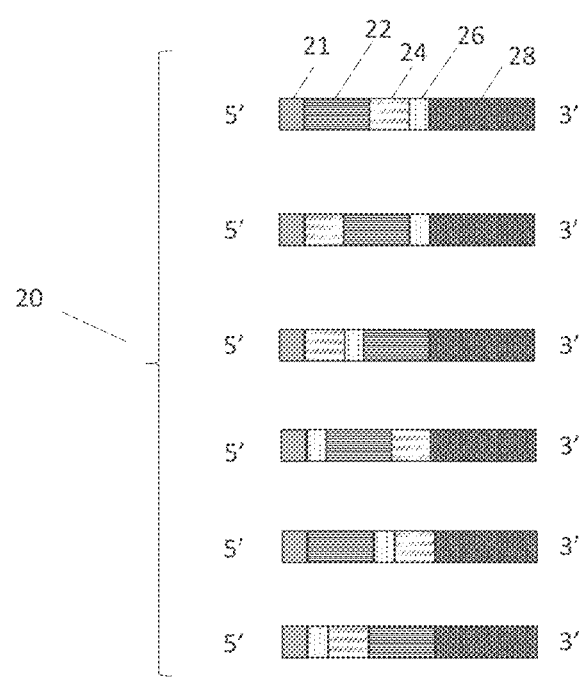
FIG. 56 depicts various exemplary iterations of the 5' enhanced exon element (20). As illustrated, one iteration of the 5' enhanced exon element (20) comprises in a 5' to 3' order in the following order: a leading untranslated sequence (21), a 5' affinity tag (22), a 5' external duplex region (24), a 5' external spacer (26), and a 3' intron fragment (28).
Figure 57:
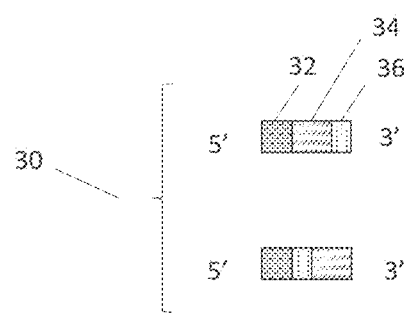
FIG. 57 depicts various exemplary iterations of the 5' enhanced exon element (30). As illustrated, one iteration of the 5' enhanced exon element (30) comprises in a 5' to 3' order: a 3' exon fragment (32), a 5' internal duplex region (34), and a 5' internal spacer (36).
Figure 58:
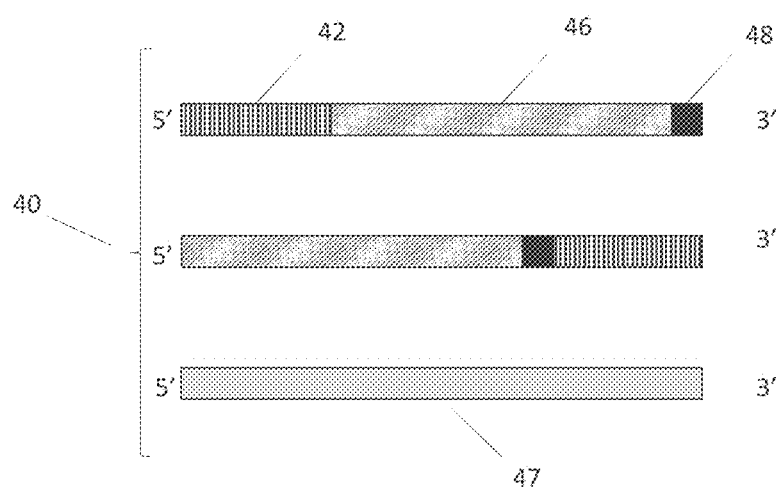
FIG. 58 depicts various exemplary iterations of the core functional element (40). As illustrated, one iteration of the core functional element (40) comprises a TIE (42), a coding region (46) and a stop region (e.g., a stop codon or stop cassette) (48). Another iteration is illustrated to show the core functional element (47) comprising a noncoding region (47).
Figure 59:
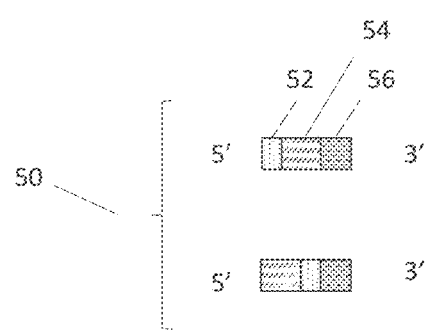
FIG. 59 depicts various exemplary iterations of the 3' enhanced exon element (50). As illustrated, one of the iterations of the 3' enhanced exon element (50) comprises, in the following 5' to 3' order: a 3' internal spacer (52), a 3' internal duplex region (54), and a 5' exon fragment (56).
Figure 60:
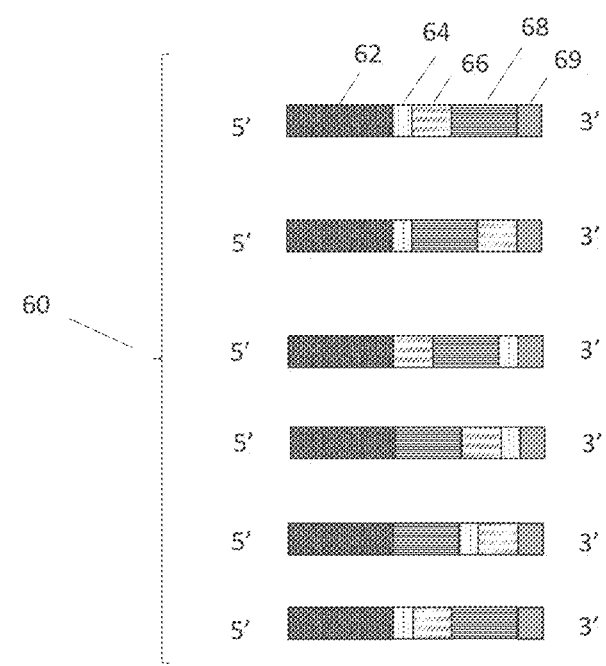
FIG. 60 depicts various exemplary iterations of the 3' enhanced intron element (60). As illustrated, one of the iterations of the 3' enhanced intron element (60) comprises, in the following order, a 5' intron fragment (62), a 3' external spacer (64), a 3' external duplex region (66), a 3' affinity tag (68) and a terminal untranslated sequence (69).
Figure 61:
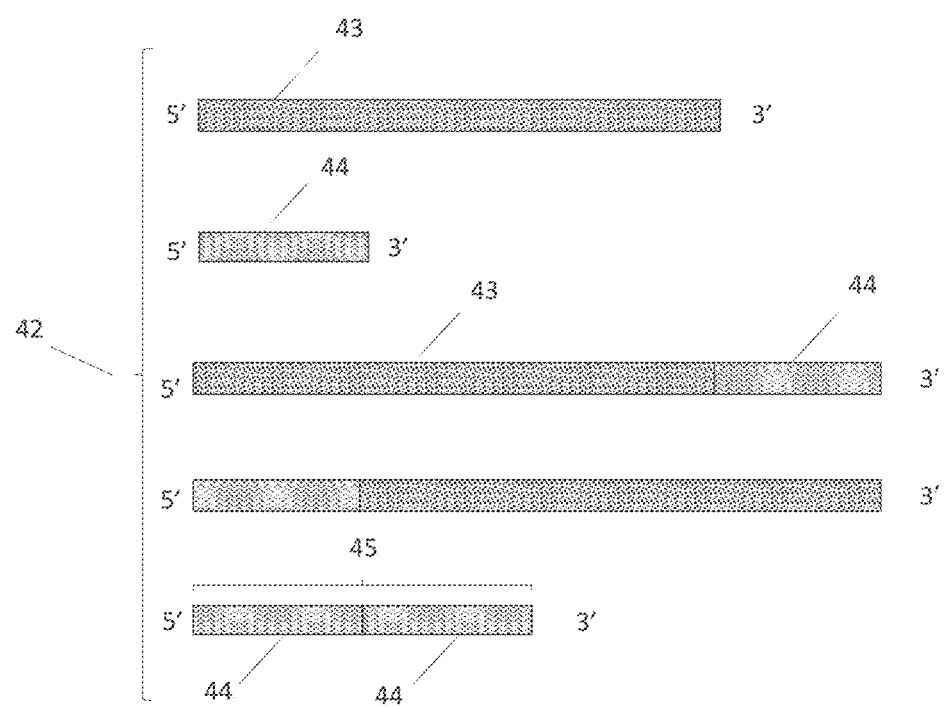
FIG. 61 depicts various exemplary iterations a translation initiation element (TIE) (42). TIE (42) sequence as illustrated in one iteration is solely an IRES (43). In another iteration, the TIE (42) is an aptamer (44). In two different iterations, the TIE (42) is an aptamer (44) and IRES (43) combination. In another iteration, the TIE (42) is an aptamer complex (45).
Figure 62:
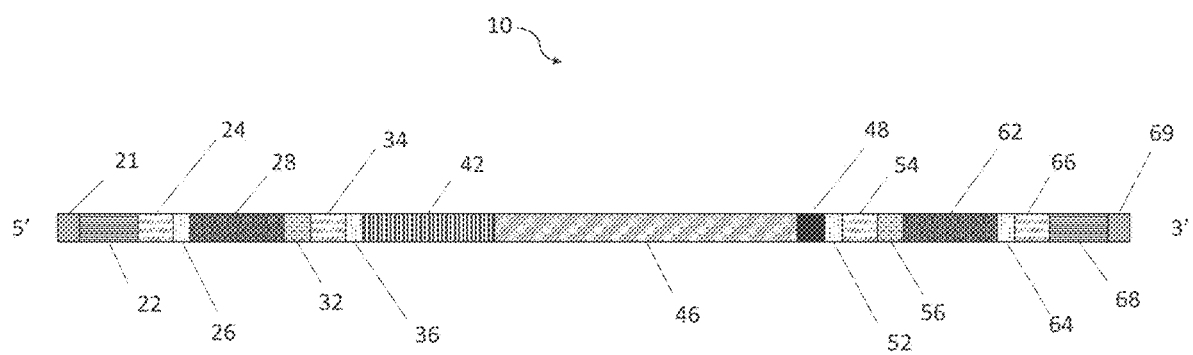
FIG. 62 illustrates an exemplary linear RNA polynucleotide precursor (10) comprising in the following 5' to 3' order, a leading untranslated sequence (21), a 5' affinity tag (22), a 5' external duplex region (24), a 5' external spacer (26), a 3' intron fragment (28), a 3' exon fragment (32), a 5' internal duplex region (34), a 5' internal spacer (36), a TIE (42), a coding element (46), a stop region (48), a 3' internal spacer (52), a 3' internal duplex region (54), a 5' exon fragment (56), a 5' intron fragment (62), a 3' external spacer (64), a 3' external duplex region (66), a 3' affinity tag (68) and a terminal untranslated sequence (69).
Figure 63:
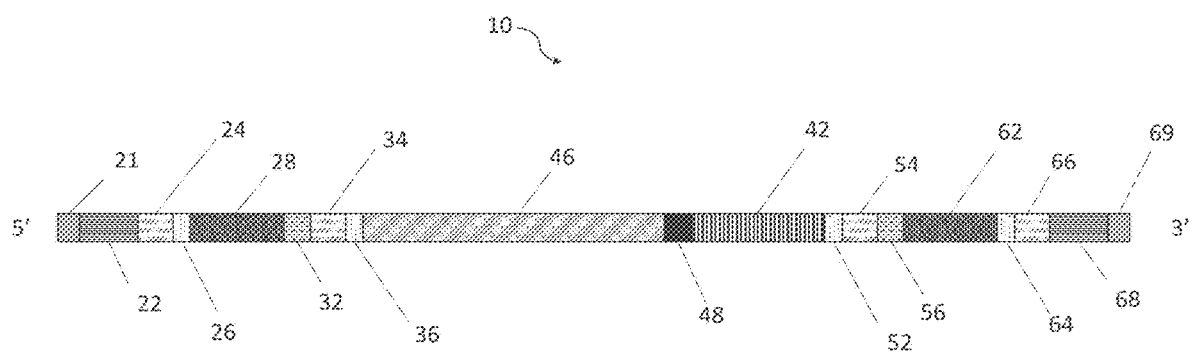
FIG. 63 illustrates an exemplary linear RNA polynucleotide precursor (10) comprising in the following 5' to 3' order, a leading untranslated sequence (21), a 5' affinity tag (22), a 5' external duplex region (24), a 5' external spacer (26), a 3' intron fragment (28), a 3' exon fragment (32), a 5' internal duplex region (34), a 5' internal spacer (36), a coding element (46), a stop region (48), a TIE (42), a 3' internal spacer (52), a 3' internal duplex region (54), a 5' exon fragment (56), a 5' intron fragment (62), a 3' external spacer (64), a 3' external duplex region (66), a 3' affinity tag (68) and a terminal untranslated sequence (69).
Figure 64:
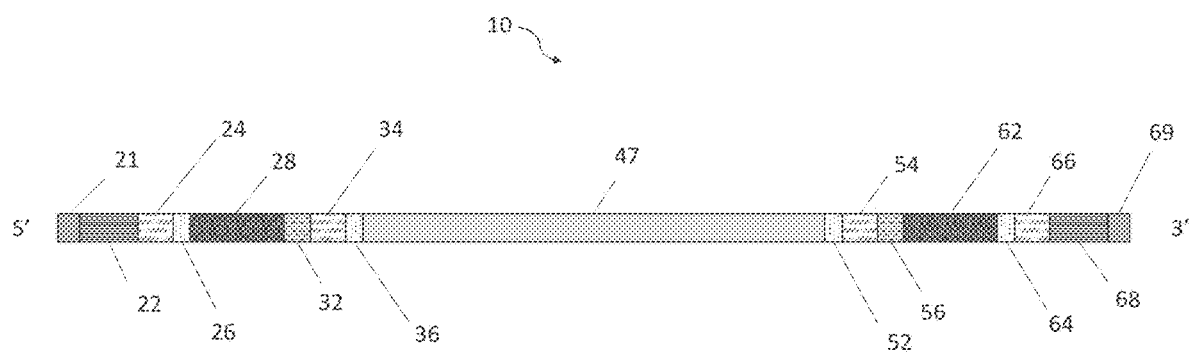
FIG. 64 illustrates an exemplary linear RNA polynucleotide precursor (10) comprising in the following 5' to 3' order, a leading untranslated sequence (21), a 5' affinity tag (22), a 5' external duplex region (24), a 5' external spacer (26), a 3' intron fragment (28), a 3' exon fragment (32), a 5' internal duplex region (34), a 5' internal spacer (36), a noncoding element (47), a 3' internal spacer (52), a 3' internal duplex region (54), a 5' exon fragment (56), a 5' intron fragment (62), a 3' external spacer (64), a 3' external duplex region (66), a 3' affinity tag (68) and a terminal untranslated sequence (69).
Figure 65:
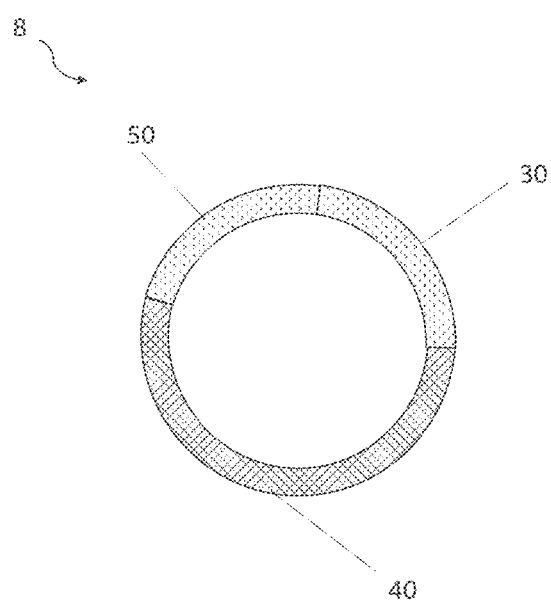
FIG. 65 illustrates the general circular RNA (8) structure formed post splicing. The circular RNA as depicted includes a 5' exon element (30), a core functional element (40) and a 3' exon element (50).
Figure 66A:
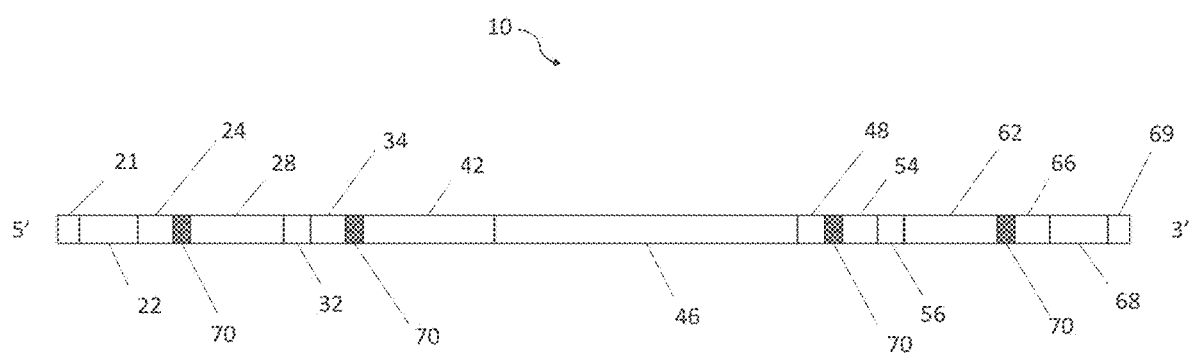
FIGS. 66A-66E illustrate the various ways an accessory element (70) (e.g., a miRNA binding site) may be included in a linear RNA polynucleotide.
Figure 66B:
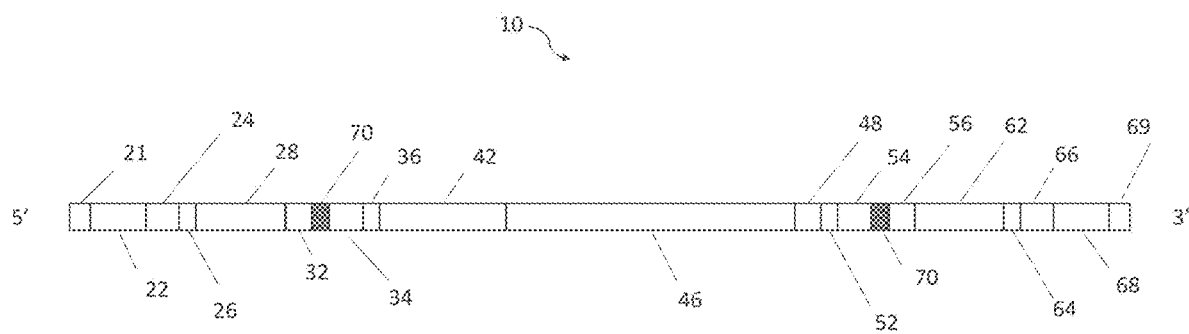
Figure 66C:
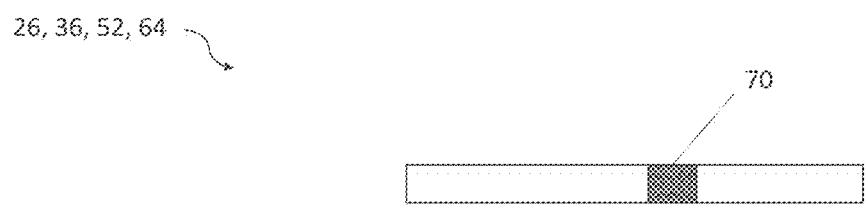
Figure 66D:
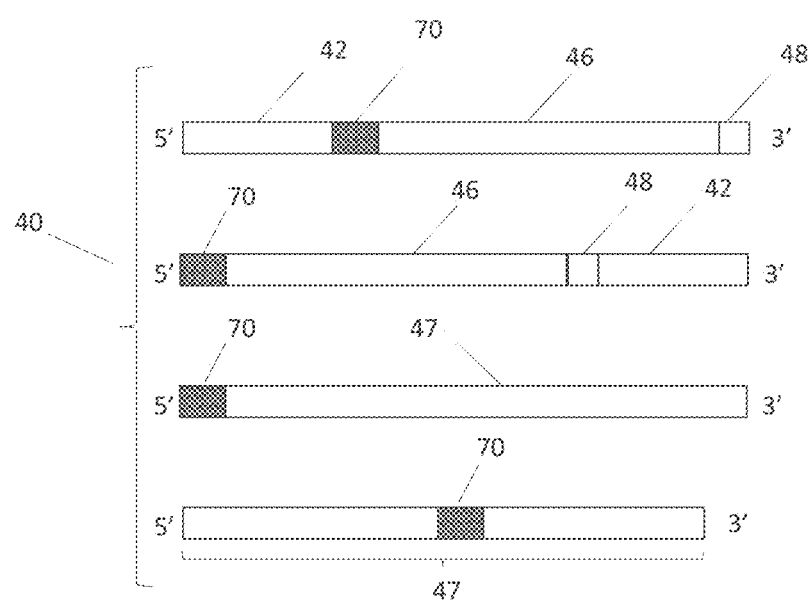
Figure 66E:
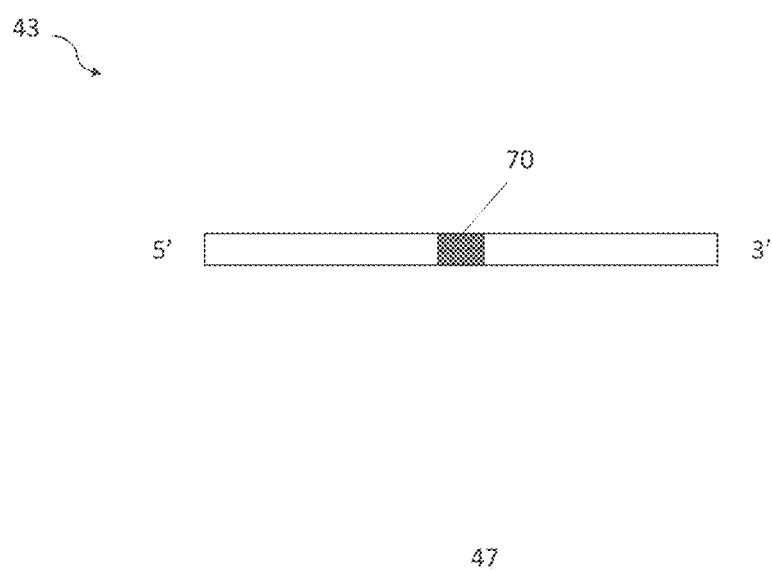

FIG. 50A shows circularization efficiency of roughly 4.5 kb SARS-Cov2 stabilized spike protein-encoding RNA resulting from an in vitro transcription reaction. FIG. 50B and FIG. 73C show SARS-CoV2 stabilized spike protein expression on 293 cells after the circular RNA transfection with MessengerMax Transfection Reagent relative to mock transfected cells.

FIG. 54A and FIG. 54B show SARS-CoV2 stabilized spike protein expression by percentage of cells and gMFI on 293 cells after transfection of a panel of circular RNAs, containing variable IRES sequences, codon optimized coding regions, and stabilized SARS-CoV2 spike proteins, using MessengerMax Transfection Reagent. FIG. 54C shows the relationship between MFI and percentage.

Example 63

This example shows in vivo cytokine response after IV injection of 0.2 mg/kg circRNA preparations encapsulated in a lipid nanoparticle formulation. circRNA splicing reactions synthesized with GTP as a precursor RNA initiator and splicing nucleotide incited greater cytokine responses than purified circRNA and linear m1ψ-mRNA due to the presence of triphosphorylated 5' termini in the splicing reaction. Levels of IL-1β, IL-6, IL-10, IL-12p70, RANTES, TNFα were measured from blood drawn 6 hours following intravenous injection of the LNP-formulated circRNA preparation. Mice injected with PBS were used as a control.

As seen in FIG. 51, circRNA splicing reactions synthesized with GTP as a precursor RNA initiator and splicing nucleotide incite greater cytokine responses than purified circRNA and linear m1ψ-mRNA due to the presence of triphosphorylated 5' termini in the splicing reaction.

Example 64

This example illustrates intramuscular delivery of varying doses of lipid nanoparticle containing circular RNAs. Mice were dosed with either 0.1 μg, 1 μg, or 10 μg of circRNA formulated in lipid nanoparticles. Whole body IVIS imagine was conducted at 6 hours following an injection of luciferin (FIG. 52A and FIG. 52B). Ex vivo IVIS imaging was conducted at 24-hour. Flux values for liver, quad, and calf are shown in FIG. 52C. FIG. 53B and FIG. 53C show that the expression of the circular RNA is present in the muscle tissue of the mice.

Example 65

This example illustrates expression of multiple circular RNAs in LNP formulations. Circular RNA constructs encoding either hEPO or fLuc were dosed in a single and mixed set of LNPs. hEPO concentration in the serum (FIG. 53A) and total flux by IVIS imaging (FIG. 53B) was determined. The results show that the circular RNA hEPO or fLuc constructs individually formulated or co-formulated expressed protein efficiently.

Example 66

Example 66A: Hepatocyte Plating and Culture

Primary human hepatocytes (PHH), primary mouse hepatocytes (PMH), primary cynomolgus monkey hepatocytes (PCH) were thawed and resuspended in hepatocyte thawing medium (Xenotech, cat #K8600/K8650) followed by centrifugation. The supernatant was discarded, and the pelleted cells were resuspended in hepatocyte plating medium (Xenotech, cat #K8200). Cells were counted via hemocytometer and plated on Bio-coat collagen-I coated 96-well plates at a density of 25,000 cells/well for PHH, 25,000 cells/well for PMH, and 50,000 cells/well for PCH in 100 µL of plating media. Plated cells were allowed to settle and adhere for 6 hours in a tissue culture incubator at 37° C. and 5% $CO_2$ atmosphere. After incubation cells were checked for monolayer formation after which the plating media was aspirated and replaced with 100 ul of culture media (Xenotech, cat #K8300). Media was replaced every 24 hours for the duration of the experiment.

Example 66B: In Vitro Screening of LNP Formulated Circular RNA Encoding Firefly Luciferase in Primary Human, Mouse, and Cynomolgus Monkey Hepatocytes A circular RNA construct comprising a TIE and a coding element encoding for firefly luciferase was produced and transfected into LNPs. Various concentrations of LNPs formulated with the circularized RNA (oRNA) were diluted in hepatocyte media supplemented with 3% fetal bovine serum (FBS) (ThermoFisher, cat #A3160401). Media was aspirated from the cells prior to addition of 100 µL of LNP/FBS/media mixture to the cells.

Luciferase activity was detected in primary human (FIG. 67A), mouse (FIG. 67B), and cynomolgus monkey (FIG. 67C) hepatocyte. 24 hours post-transfection plates were removed from the incubator and allowed to equilibrate to room temperature for 15 mins. A volume of 100 µL of Firefly Luciferase one-step glow assay working solution (Pierce, cat #16196) was added to each well. The plate was placed on a microplate shaker (ThermoFisher, cat #S72050) and mixed at 300 rpm for 3 min. Post-mixing, the plate was allowed to incubate at room temperature for 10 min. Luminescence was read using a Varioskan or Bio-Tek Cytation5 instrument.

Figure 67A:
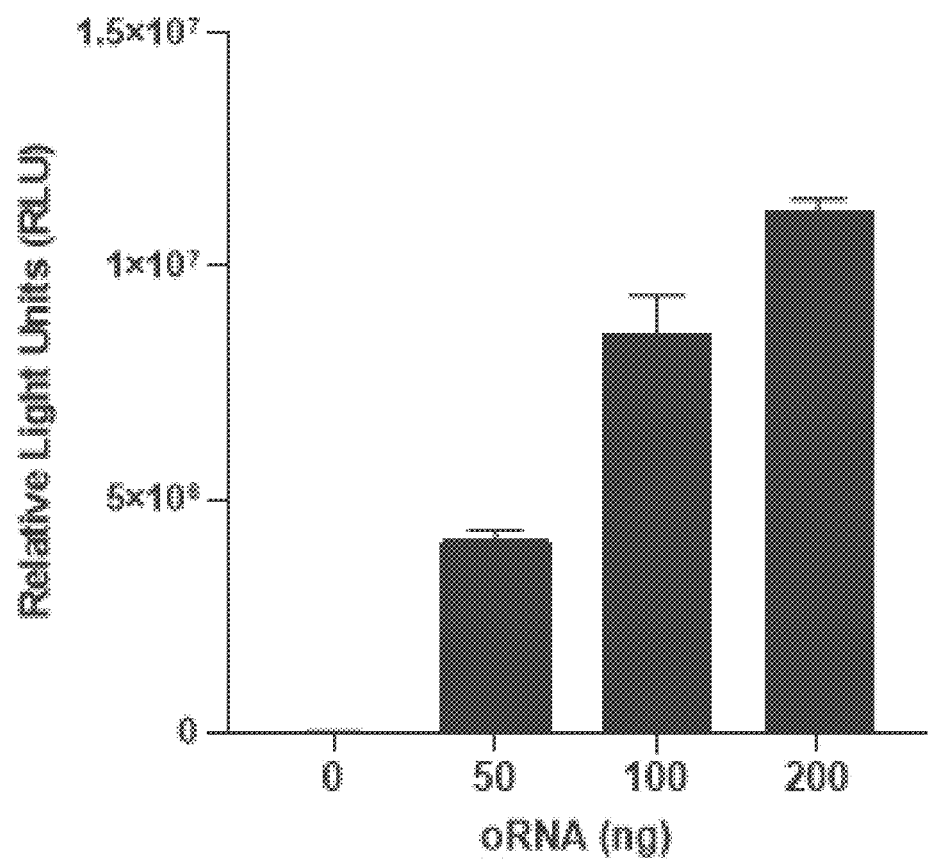
FIGS. 67A-67C illustrate a screening of a LNP formulated with circular RNA encoding firefly luciferase and having a TIE in primary human (FIG. 67A), mouse (FIG. 67B), and cynomolgus monkey (FIG. 67C) hepatocyte with varying dosages in vitro.
Figure 67B:
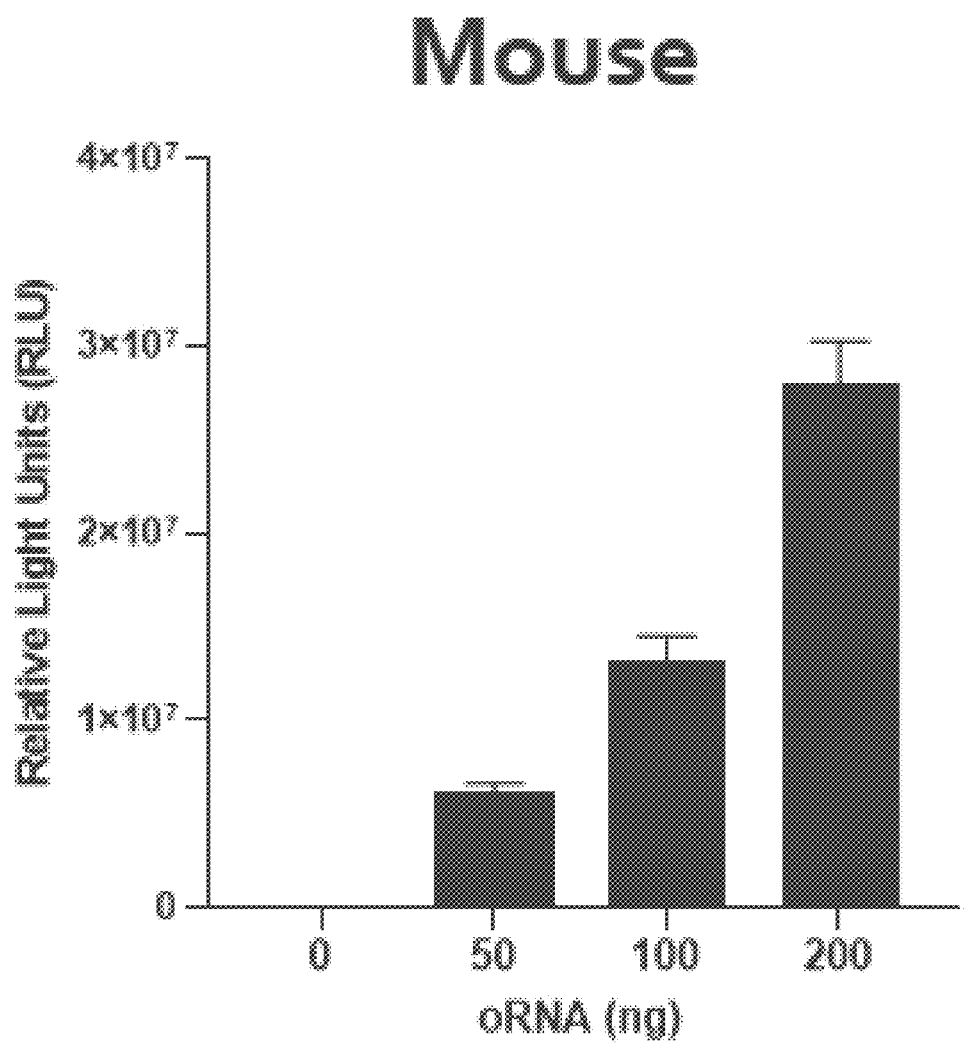
Figure 67C:
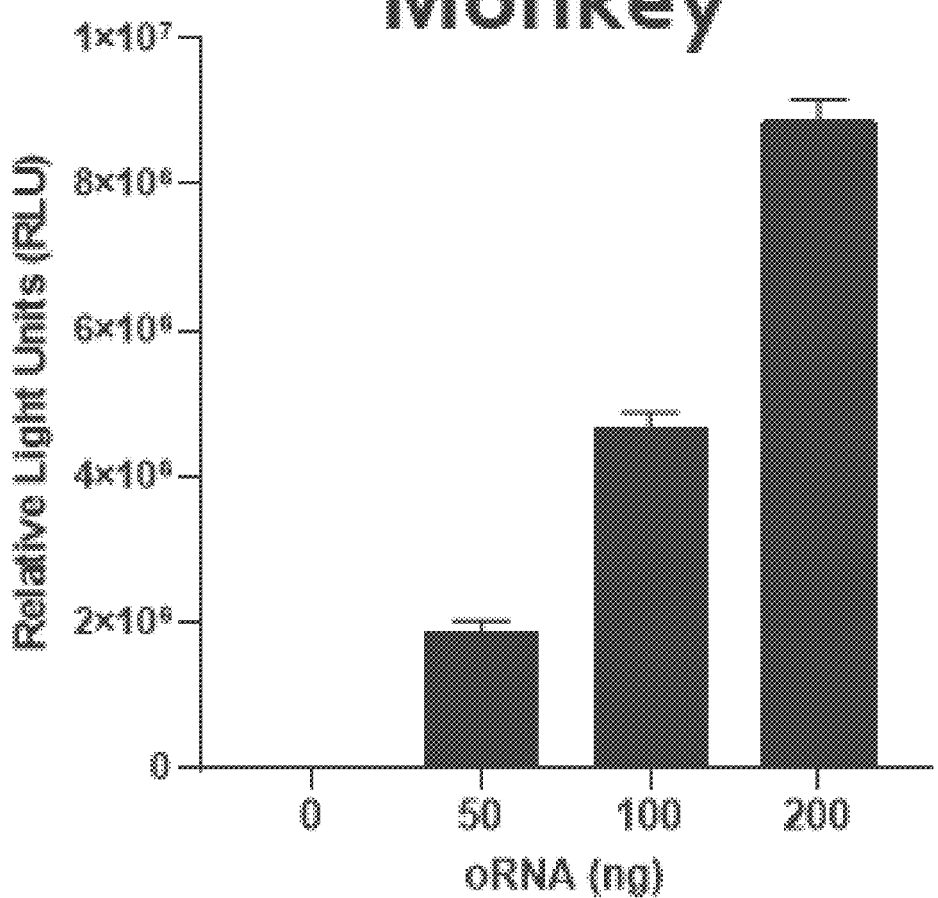

As seen in FIG. 67A, FIG. 67B, and FIG. 67C, TIE containing circular RNAs are capable of driving firefly luciferase protein expression in primary hepatocytes from multiple species in a dose-dependent manner when transfected in vitro with an LNP.

Example 66C: In Vitro Screening of LNP Formulated Circular RNA Encoding Firefly Luciferase in Multiple Primary Human Hepatocyte Donors A circular RNA construct comprising a TIE and a coding element encoding for firefly luciferase was produced and transfected into LNPs. Various concentrations of LNPs formulated with the circularized RNA (oRNA) were diluted in hepatocyte media supplemented with 3% fetal bovine serum (FBS) (ThermoFisher, cat #A3160401). Media was aspirated from the cells prior to addition of 100 ul of LNP/FBS/media mixture to the cells.

Luciferase activity was detected in primary human (FIG. 68A), mouse (FIG. 68B), and cynomolgus monkey (FIG. 68C) hepatocyte. 24 hours post-transfection plates were removed from the incubator and allowed to equilibrate to room temperature for 15 mins. A volume of 100 µL of Firefly Luciferase one-step glow assay working solution (Pierce, cat #16196) was added to each well. The plate was placed on a microplate shaker (ThermoFisher, cat #S72050) and mixed at 300 rpm for 3 min. Post-mixing, the plate was allowed to incubate at room temperature for 10 min. Luminescence was read using a Varioskan or Bio-Tek Cytation5 instrument.

Figure 68A:
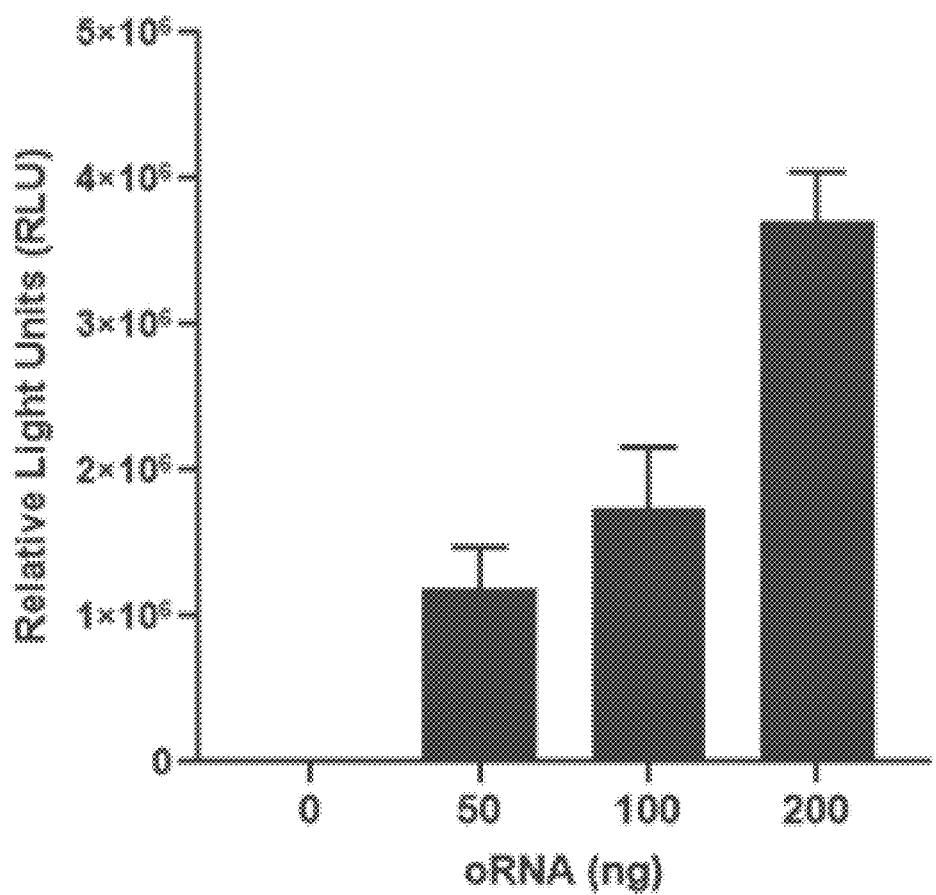
FIGS. 68A-68C illustrates a screening of a LNP formulated with circular RNA encoding firefly luciferase and having a TIE, in primary human hepatocyte from three different donors with varying dosages in vitro.
Figure 68B:
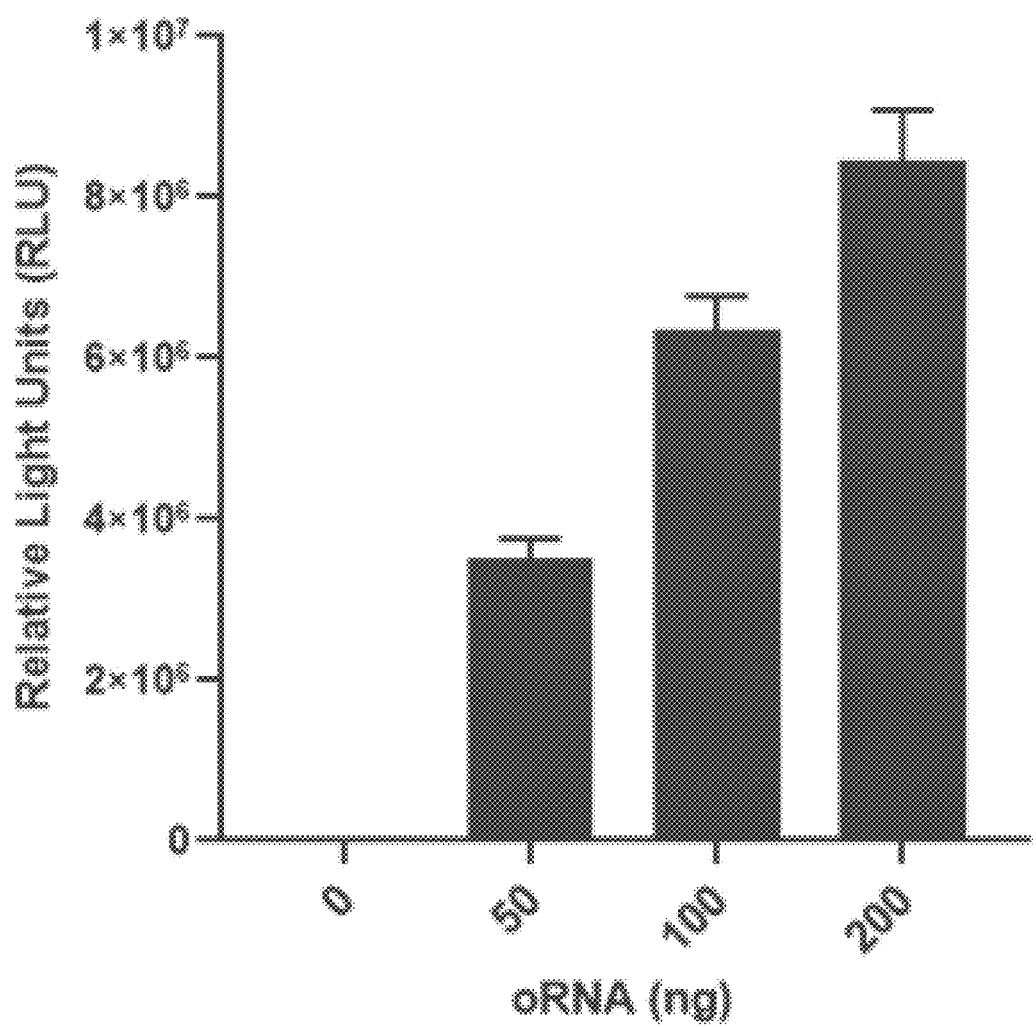
Figure 68C:
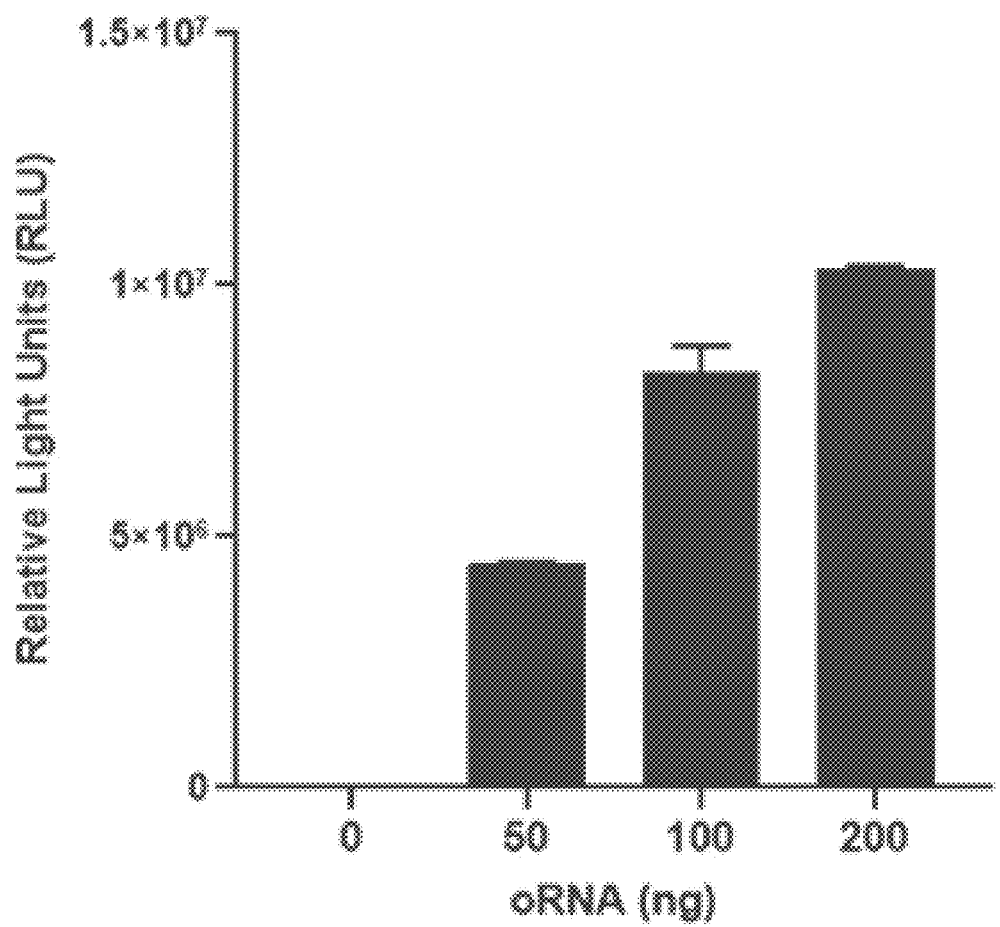

As seen in FIG. 68A, FIG. 68B, and FIG. 68C, TIE containing circular RNAs are capable of driving firefly luciferase protein expression in primary hepatocytes from multiple human donors in a dose-dependent manner when transfected in vitro with an LNP.

Example 67

In Vitro Expression of LNP Formulated with Circular RNA Encoding for GFP in Multiple Human Cell Models A circular RNA construct was produced comprising a TIE and coding element encoding for a GFP protein. LNP were formulated with the circular RNA construct. Then various concentrations of the LNP containing the circular RNA construct were diluted in hepatocyte media supplemented with 3% fetal bovine (FBS) (ThermoFisher, cat #A3160401). Media was aspirated from the cells prior to addition of 100 ul of LNP/FBS/media mixture to the cells.

HeLa (human cervical adenocarcinoma; ATCC, cat #CCL-2), HEK293 (human embryonic kidney; ATCC, cat #CRL-1573), and HUH7 (human liver hepatocellular carcinoma; JCRB, cat #JCRB0403) were transfected as previously described with LNP formulated oRNAs. Twenty-four hours post-transfection, the media was removed and the cells were trypsinized. The trypsinized cells were neutralized with PBS supplemented with 10% FBS, harvested, and transferred to a tube. The tube was centrifuged to pellet the cells and the supernatant was aspirated. The pellet was stored at −80° C. prior to lysis. For lysis the cells were thawed on ice and were lysed with 100 µL/well RIPA buffer (Boston Bio Products, Cat. BP-115) plus freshly added 1 mM DTT, and 250 U/mL Benzonase (EMD Millipore, cat #71206-3), and protease inhibitor mixture consisting of complete protease inhibitor cocktail (Sigma, cat #11697498001). Cells were kept on ice for 30 minutes at which time NaCl (1M final concentration) was added. Cell lysates were thoroughly mixed and retained on ice for 30 min. The whole cell extracts (WCE) were centrifuged to pellet debris. A Bradford assay (Bio-Rad, cat #500-0001)

was used to assess protein content of the lysates. The Bradford assay procedure was completed according to the manufacturer's protocol. Extracts were stored at −20° C. prior to use. Western blots were performed to assess GFP protein levels. Whole cell extract lysates were mixed with Laemmli buffer and denatured at 95° C. for 10 min. Western blots were run using the NuPage system on 4-12% Bis-Tris gels (ThermoFisher, cat #NP0335BOX) according to the manufacturer's protocol followed by wet transfer onto 0.45 m nitrocellulose membrane (ThermoFisher, cat #LC2001). After transfer membranes were rinsed thoroughly with water and stained with Ponceau S solution (Boston Bio Products, cat #ST-180) to confirm complete and even transfer. Blots were blocked using 5% Dry Milk in TBS for 30 minutes on a lab rocker at room temperature. Blots were rinsed with 1xTBST (Boston BioProducts, cat #IBB-180) and probed with mouse dylight 680-tagged anti-GFP monoclonal antibody (ThermoFisher, cat #MA515256D680) at 1:1,000 in 1xTBST. Anti-3-ACTIN OR GAPDH WAS USED AS A LOADING CONTROL (THERMOFISHER, CAT #AM4302/AM4300) AT 1:4,000 IN 1xTBST AND INCUBATED SIMULTANEOUSLY WITH THE GFP PRIMARY ANTIBODY. BLOTS WERE SEALED IN A BAG AND KEPT OVERNIGHT AT 4° C. ON A LAB ROCKER. AFTER INCUBATION, BLOTS WERE RINSED 3 TIMES FOR 5 MINUTES EACH IN 1xTBST AND PROBED WITH MOUSE SECONDARY ANTIBODIES (THERMOFISHER, CAT #PI35519) AT 1:25,000 EACH IN 1xTBST FOR 30 MINUTES AT ROOM TEMPERATURE. AFTER INCUBATION, BLOTS WERE RINSED 3 TIMES FOR 5 MINUTES EACH IN 1xTBST. BLOTS WERE VISUALIZED AND ANALYZED USING A LICOR ODYSSEY SYSTEM.

Figure 69:
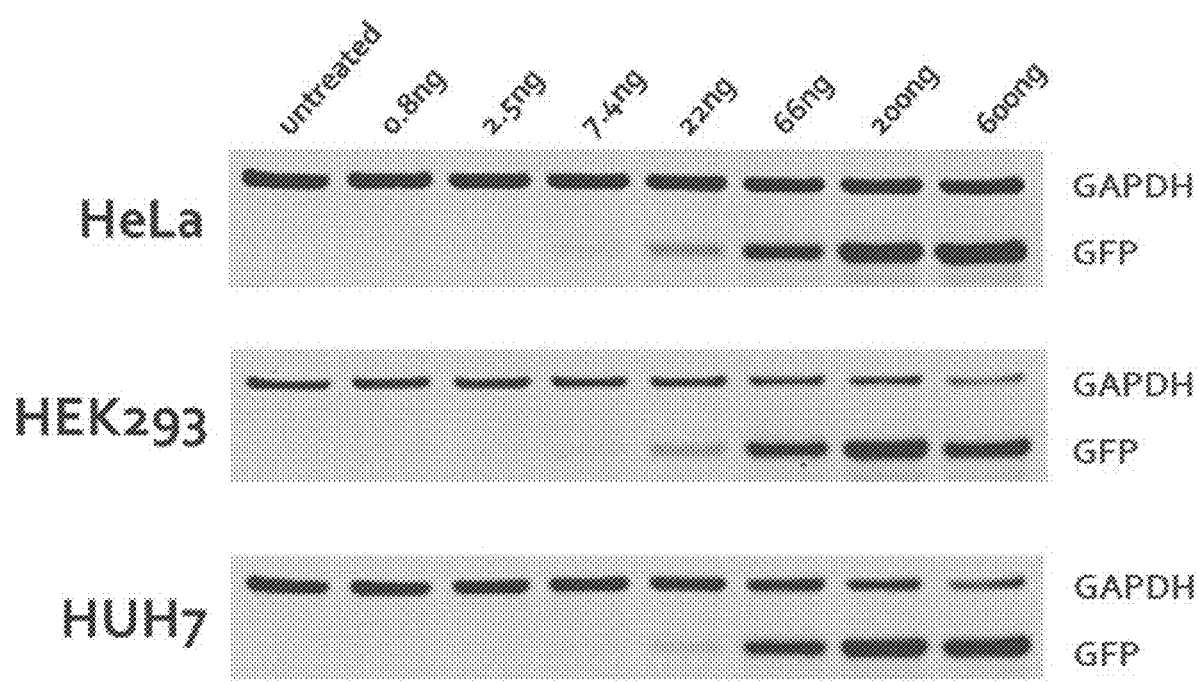
FIG. 69 illustrates in vitro expression of LNP formulated with circular RNA encoding for GFP and having a TIE, in HeLa, HEK293, and HUH7 human cell models.

As shown in FIG. 69, TIE-containing circular RNA is capable of expressing GFP protein in diverse human cell lines (e.g., HeLa, HEK293, and HUH7 cells) in a dose dependent manner when transfected in vitro with an LNP.

Example 68

In Vitro Expression of LNP Formulated with Circular RNA Encoding for GFP in Primary Human Hepatocytes.

A circular RNA construct was produced comprising a TIE and coding element encoding for a GFP protein. Various concentrations of LNP containing circularized RNA (oRNA) were diluted in hepatocyte media supplemented with 3% fetal bovine serum (FBS) (ThermoFisher, cat #A3160401). Media was aspirated from the cells prior to addition of 100 µL of LNP/FBS/media mixture to the cells.

Primary human hepatocytes (PHH) were thawed and resuspended in hepatocyte thawing medium (Xenotech, cat #K8600/K8650) followed by centrifugation. The supernatant was discarded, and the pelleted cells were resuspended in hepatocyte plating medium (Xenotech, cat #K8200). Cells were counted via hemocytometer and plated on Bio-coat collagen-I coated 96-well plates at a density of 25,000 cells/well for PHH, 25,000 cells/well for PMH, and 50,000 cells/well for PCH in 100 ul of plating media. Plated cells were allowed to settle and adhere for 6 houra in a tissue culture incubator at 37° C. and 5% $CO_2$ atmosphere. After incubation cells were checked for monolayer formation after which the plating media was aspirated and replaced with 100 ul of culture media (Xenotech, cat #K8300). Media was replaced every 24 hours for the duration of the experiment.

Primary human hepatocytes were transfected as previously described with LNP formulated oRNAs. Twenty-four hours post-transfection, the media was removed and the cells were trypsinized. The trypsinized cells were neutralized with PBS supplemented with 10% FBS, harvested, and transferred to a tube. The tube was centrifuged to pellet the cells and the supernatant was aspirated. The pellet was stored at −80° C. prior to lysis. For lysis the cells were thawed on ice and were lysed with 100 µL/well RIPA buffer (Boston Bio Products, Cat. BP-115) plus freshly added 1 mM DTT, and 250 U/ml Benzonase (EMD Millipore, cat #71206-3), and protease inhibitor mixture consisting of complete protease inhibitor cocktail (Sigma, cat #11697498001). Cells were kept on ice for 30 minutes at which time NaCl (1M final concentration) was added. Cell lysates were thoroughly mixed and retained on ice for 30 min. The whole cell extracts (WCE) were centrifuged to pellet debris. A Bradford assay (Bio-Rad, cat #500-0001) was used to assess protein content of the lysates. The Bradford assay procedure was completed according to the manufacturer's protocol. Extracts were stored at −20° C. prior to use. Western blots were performed to assess GFP protein levels. Whole cell extract lysates were mixed with Laemmli buffer and denatured at 95° C. for 10 min. Western blots were run using the NuPage system on 4-12% Bis-Tris gels (ThermoFisher, cat #NP0335BOX) according to the manufacturer's protocol followed by wet transfer onto 0.45 m nitrocellulose membrane (ThermoFisher, cat #LC2001). After transfer membranes were rinsed thoroughly with water and stained with Ponceau S solution (Boston Bio Products, cat #ST-180) to confirm complete and even transfer. Blots were blocked using 5% Dry Milk in TBS for 30 minutes on a lab rocker at room temperature. Blots were rinsed with 1xTBST (Boston BioProducts, cat #IBB-180) and probed with mouse dylight 680-tagged anti-GFP monoclonal antibody (ThermoFisher, cat #MA515256D680) at 1:1,000 in 1xTBST. Anti-3-actin or GAPDH was used as a loading control (ThermoFisher, cat #AM4302/AM4300) at 1:4,000 in 1xTBST and incubated simultaneously with the GFP primary antibody. Blots were sealed in a bag and kept overnight at 4° C. on a lab rocker. After incubation, blots were rinsed 3 times for 5 minutes each in 1xTBST and probed with mouse secondary antibodies (ThermoFisher, cat #PI35519) at 1:25,000 each in 1xTBST for 30 minutes at room temperature. After incubation, blots were rinsed 3 times for 5 minutes each in 1xTBST. Blots were visualized and analyzed using a Licor Odyssey system.

Figure 70:
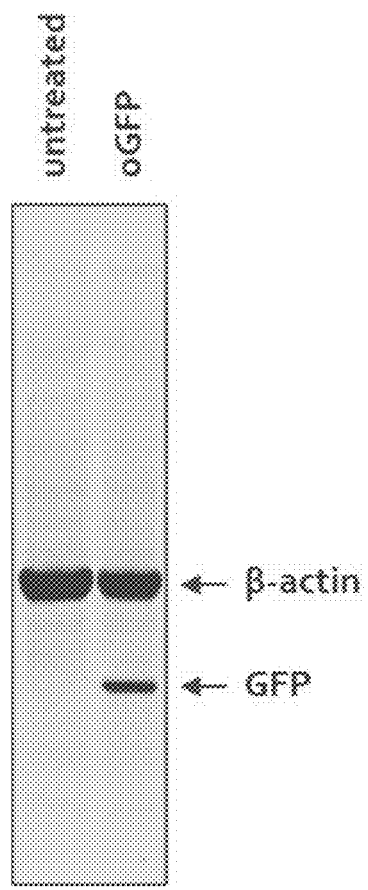
FIG. 70 illustrates in vitro expression of LNP formulated with circular RNAs encoding a GFO protein and having a TIE, in primary human hepatocytes.

As shown in the western blot in FIG. 70, circular RNAs containing a TIE is capable of successfully encoding a GFP protein in primary human hepatocytes when transfected in vivo with an LNP.

Example 69

In Vitro Expression of Firefly Luciferase in Circular RNA Encoding Firefly Luciferase in Mouse Myoblast and Primary Human Skeletal Muscle Myoblast Cells Using Lipofectamine A circular RNA construct comprising a TIE and coding element encoding firefly luciferase protein.

Primary human skeletal muscle (HSkM) cells (Lonza, cat #20TL356514) were thawed in a 37° C. water bath and plated at recommended seeding density (3,000 to 5,000 per $cm^2$) in SkGM-2 BulletKit growth media (Lonza, cat #CC-3245) and allowed to grow overnight. Cells were detached using ReagentPack subculture reagents (Lonza, cat #CC-5034) and plated on tissue culture grade 96-well plates at recommended seeding density and allowed to grow overnight in a tissue culture incubator at 37° C. and 5% CO₂ atmosphere or to 70-80% confluency with growth media changed every 2 days.

For one 96-well plate reaction, 0.3 µL of Lipofectamine-3000 transfection reagent (Lipo3K) (ThermoFisher, cat #L3000015) was mixed with 5 µL Opti-MEM reduced serum media (ThermoFisher, cat #51985091). In a separate tube, per reaction, firefly luciferase (f.luc) oRNA (at 10-200 ng) was combined with 5 µL Opti-MEM and 0.2 µL P3000™ enhancer reagent (ThermoFisher, cat #L3000015). Equal volumes of Lipo3K/Opti-MEM mix was combined with oRNA/Opti-MEM mix and incubated at room temperature for 15 min. The Lipo3K/oRNA mixture was added to each well to be transfected and placed in a tissue culture incubator at 37° C. and 5% CO₂ atmosphere for 24 hours.

After 24 hours, the transfection plates were removed from the incubator and allowed to equilibrate to room temperature for 15 minutes. A volume of 100 µL of firefly luciferase one-step glow assay working solution (Pierce, cat #16196) was added to each well. The plate was placed on a microplate shaker (ThermoFisher, cat #S72050) and mixed at 300 rpm for 3 minutes. Post-mixing, the plate was allowed to incubate at room temperature for 10 minutes. Luminescence was read using a Varioskan or Bio-Tek Cytation5 instrument.

Figure 71A:
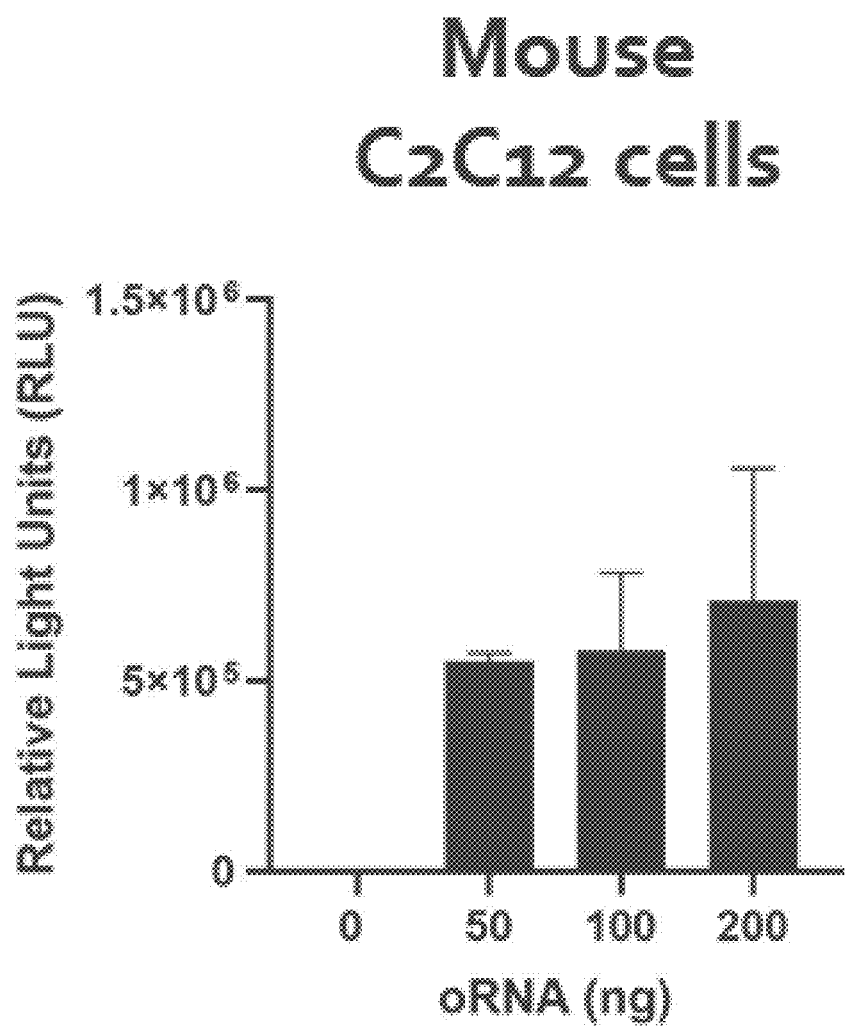
FIG. 71A and FIG. 71B illustrate in vitro expression of circular RNA encoding firefly luciferase and having a TIE, in mouse myoblast (FIG. 71A) and primary human muscle myoblast (FIG. 71B) cells.
Figure 71B:
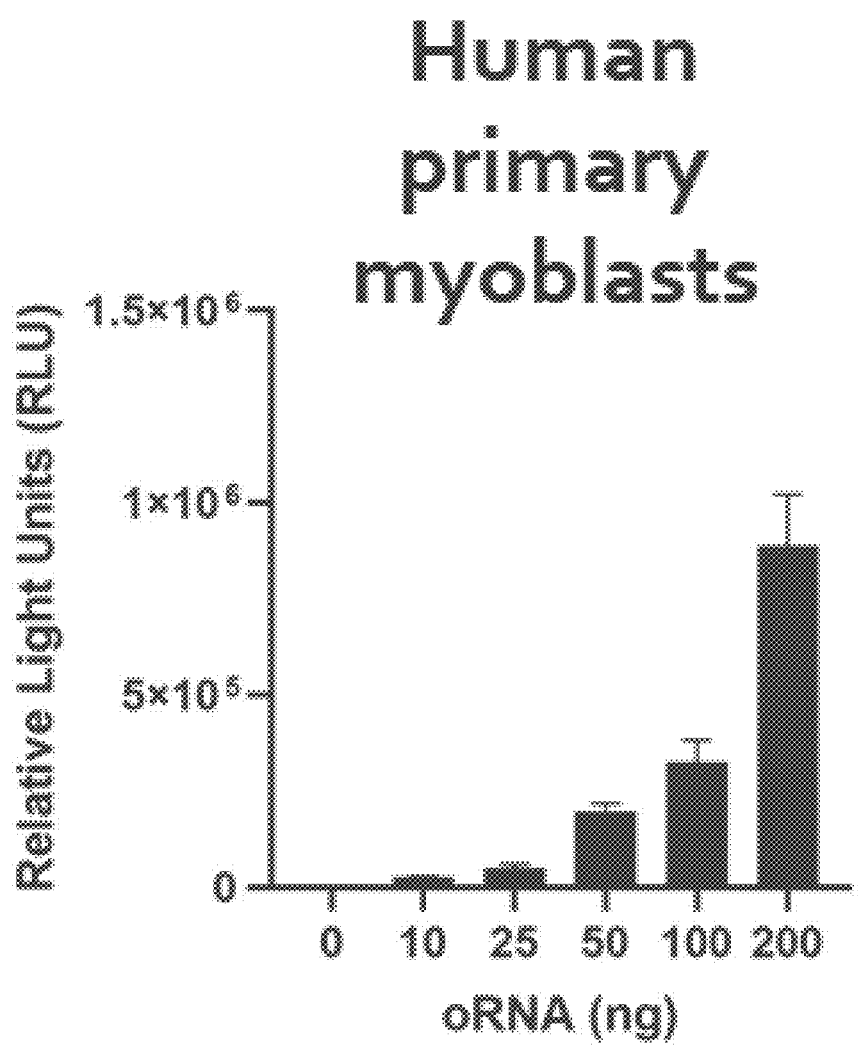

As shown in FIG. 71A and FIG. 71B, circular RNAs comprising a TIE is capable of driving firefly luciferase protein expression in myoblasts from different species in a dose-dependent manner when transfected in vitro with lipofectamine.

Example 70

In Vitro Expression of Firefly Luciferase in Circular RNA Encoding Firefly Luciferase in Differentiated Primary Human Skeletal Muscles Myotubes A circular RNA construct comprising a TIE and coding element encoding firefly luciferase protein.

Primary human skeletal muscle (HSkM) cells (Lonza, cat #20TL356514) were thawed in a 37° C. water bath and plated at recommended seeding density (3,000 to 5,000 per cm²) in SkGM-2 BulletKit growth media (Lonza, cat #CC-3245) and allowed to grow overnight. Cells were detached using ReagentPack subculture reagents (Lonza, cat #CC-5034) and plated on tissue culture grade 96-well plates at recommended seeding density and allowed to grow overnight in a tissue culture incubator at 37° C. and 5% CO₂ atmosphere or to 70-80% confluency with growth media changed every 2 days. Once cells reached 70-80% confluency, growth media was removed, cells were washed twice in 1×PBS (Gibco, cat #10010023) and changed to differentiation media consisting of F-10 (1×) (Gibco, cat #11550-043) supplemented with 2% Horse Serum (Gibco, cat #26050088) and 1% Pen-Strep (Gibco, cat #15140-122). Media was changed daily for 5 to 6 days until nearly all myoblasts had fused to form myotubes.

For one 96-well plate reaction, 0.3 µL of Lipofectamine-3000 transfection reagent (Lipo3K) (ThermoFisher, cat #L3000015) was mixed with 5ul Opti-MEM reduced serum media (ThermoFisher, cat #51985091). In a separate tube, per reaction, firefly luciferase (f.luc) oRNA (at 10-200 ng) was combined with 5 µL Opti-MEM and 0.2 µL P3000™ enhancer reagent (ThermoFisher, cat #L3000015). Equal volumes of Lipo3K/Opti-MEM mix was combined with oRNA/Opti-MEM mix and incubated at room temperature for 15 min. The Lipo3K/oRNA mixture was added to each well to be transfected and placed in a tissue culture incubator at 37° C. and 5% CO₂ atmosphere for 24 hours.

After 24 hours, transfection plates were removed from the incubator and allowed to equilibrate to room temperature for 15 minutes. A volume of 100 µL of Firefly Luc one-step glow assay working solution (Pierce, cat #16196) was added to each well. The plate was placed on a microplate shaker (ThermoFisher, cat #S72050) and mixed at 300 rpm for 3 minutes. Post-mixing, the plate was allowed to incubate at room temperature for 10 minutes. Luminescence was read using a Varioskan or Bio-Tek Cytation5 instrument.

Figure 72A:
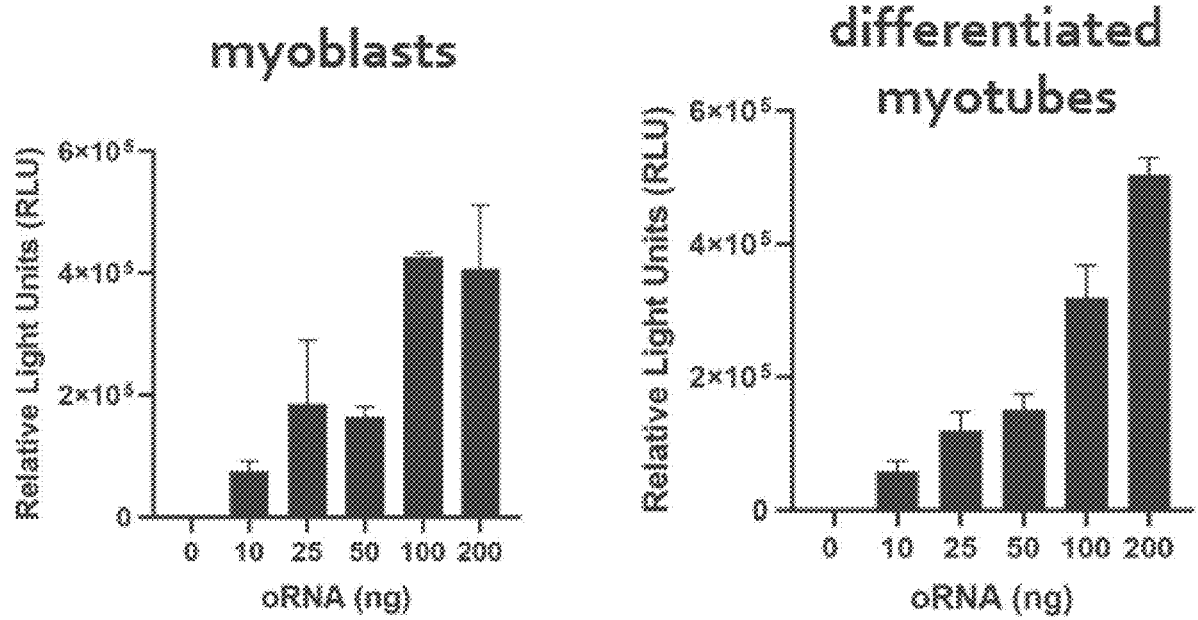
FIG. 72A and FIG. 72B illustrate in vitro expression of circular RNA encoding for firefly luciferase and having a TIE, in myoblasts and differentiated primary human skeletal muscle myotubes.
Figure 72B:
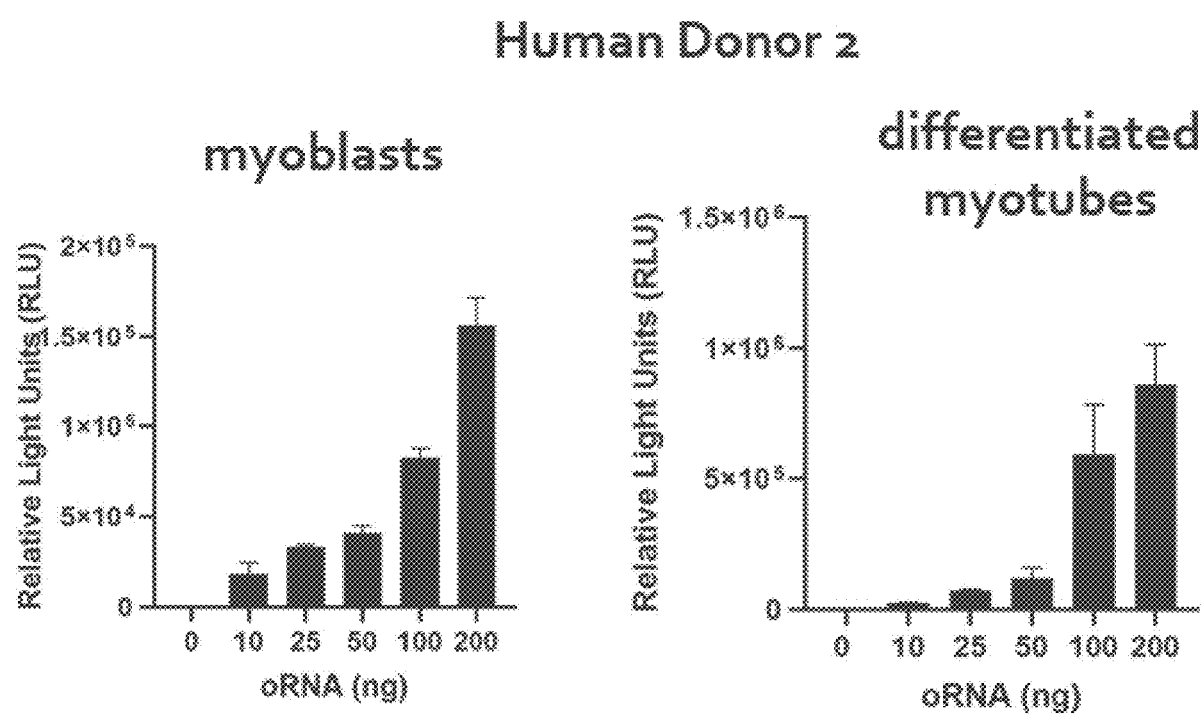

As shown in FIG. 72A and FIG. 72B, a circular RNA comprising a TIE is capable of driving firefly luciferase protein expression in primary muscles cells through differentiated states (e.g., in myoblast and differentiated myotubes) in multiple human donors in a dose-dependent manner when transfected in vitro with lipofectamine.

Example 71

Cell-Free In Vitro Translation of Circular RNAs Containing TIEs

A cell-free rabbit reticulocyte in vitro translation assay (Promega, cat #L4540) was completed to characterize protein products from various RNA templates. Both linear mRNA and circular oRNA templates were used in the assay and reaction components were assembled according to the manufacturer's protocol. Prior to assay, RNA templates were denatured at 65° C. for 3 minutes and immediately cooled on ice. All reaction components were assembled on ice. Flexi Rabbit Reticulocyte kit components, complete amino acid mixture (Promega, cat #L5061), RNAsin TIEuclease inhibitor (Promega, cat #N2111), and transcend tRNA (Promega, cat #L5061) were added to denatured RNA templates. The reaction was vortexed to mix and incubated at 30° C. for 60 minutes and then placed on ice.

The reaction mixture was added to 1× sample buffer (ThermoFisher, cat #NP0007) and heated at 70° C. for 15 minutes. The denatured protein sample was loaded onto 4-12% Bis-Tris gels (ThermoFisher, cat #NPO335BOX). Gel electrophoresis was completed, and the gel was wet transferred onto 0.45 m nitrocellulose membrane (ThermoFisher, cat #LC2001). Post-transfer, the membrane was blocked for 1 hour with rocking in freshly made TBS with 0.5% Tween-20 (Boston Bioproducts Inc Cat #IBB-180). The membrane was incubated for 45 min with rocking with streptavidin-AP (Promega, cat #V5591) at a 1:2,500 dilution. The membrane was rinsed with four cycles of: twice with TBST and twice with deionized water for 1 min per rinse. The membrane was incubated with Western Blue substrate (Promega, cat #S3841) for 45 minutes and the membrane was rinsed in water and scanned on a LICOR Odyssey CLx imaging system.

Figure 73A:
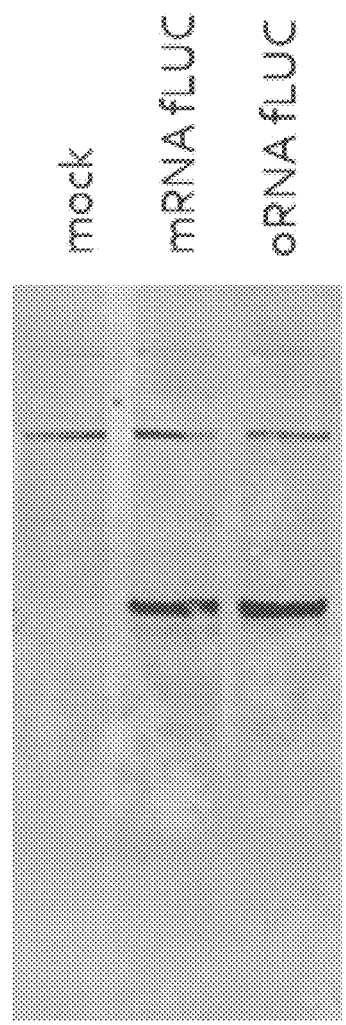
FIG. 73A and FIG. 73B illustrate cell-free in vitro translation of circular RNA of variable sizes.
Figure 73B:
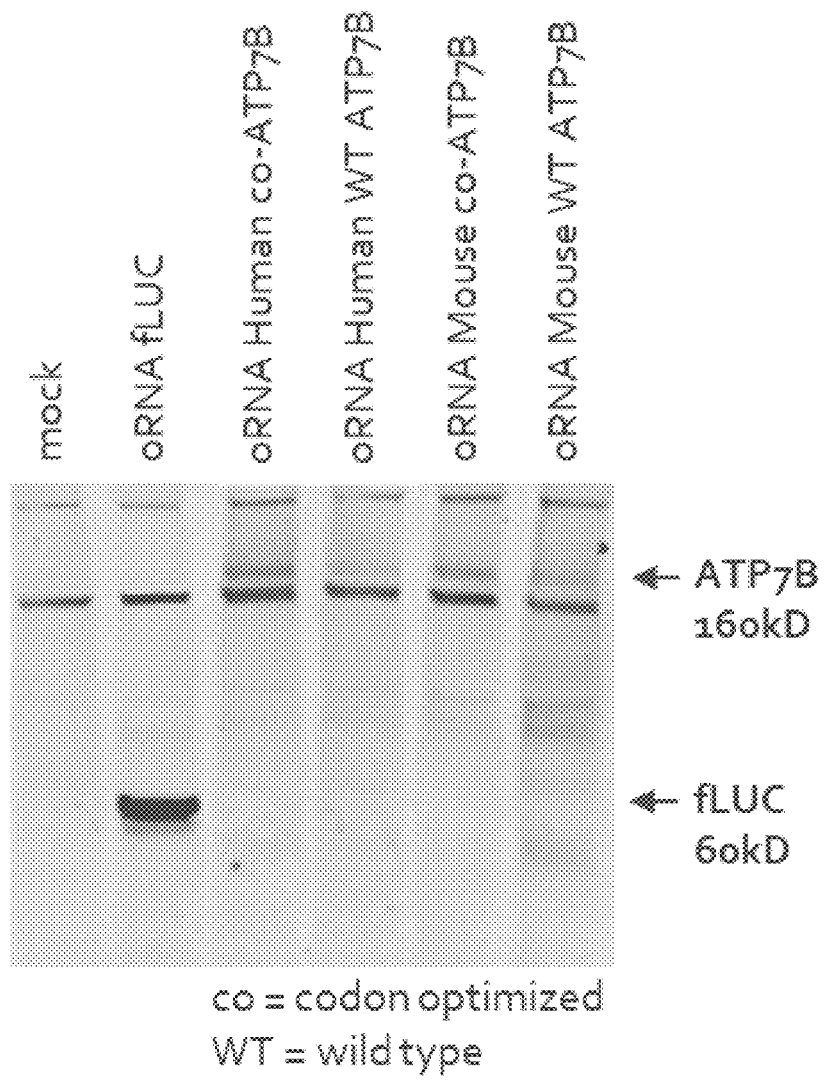

As shown in FIG. 73A and FIG. 73B, a circular RNA comprising a TIE is capable of driving protein expression in a cell-free lysate, independent of any cell type. FIG. 73A illustrates expression of firefly luciferase from a linear or circular RNA input. FIG. 73B illustrates expression of human and mouse ATP7B proteins with different codon optimization (co) approaches compared to wild-type native sequence (WT). The codon optimized-circular RNAs expressing ARP7B protein and the circular RNA expressing firefly luciferase shoed protein full-length protein expression.

Example 72

TIE Selection Methodology

Putative TIEs were identified for activity assessment from sequences in GenBank. Briefly, Riboviria and Unclassified Virus sequences greater than 1 kb in length were identified. 5' and intergenic UTRs were extracted based on putative CDS start and end sites with a minimum length cutoff of 250 nt. Reverse sequences were also collected for negative sense CDS annotations. For genuses not expected to contain TIE sequences, a few noncoding regions per genus were selected at random. Duplicates, >10 nt repeat-containing sequences, sequences with both XbaI and BamHI sites, and low-quality sequences (non acgt) were culled, then sequences were clustered through CDHit with an 80% sequence similarity cutoff for clustering; representative sequences from each cluster were selected for further study. For unclassified sequences or sequences expected to contain a TIE, all 5' and intergenic UTRs were selected; duplicates, >10 nt repeat-containing sequences, sequences with both XbaI and BamHI sites, and low-quality sequences (non acgt) were culled, then sequences were clustered through CDHit with a 95% (low risk, known IRESs) sequence similarity cutoff for clustering; representative sequences from each cluster were selected for further study. For both strategies, sequences shorter than 300 nt or unable to be synthesized due to sequence complexity were eliminated.

Example 73

Example 73A: TIE Activity in Primary Human T Cells

Nucleic acid sequences containing putative TIEs were inserted into a circular RNA (oRNA) construct prior to the start codon of a *Gaussia* luciferase reporter sequence. oRNA containing the TIE was synthesized and purified. Purified oRNA was formulated into lipid nanoparticles. LNP-oRNA was transfected into T cells in vitro. Supernatant was harvested and replaced 24 and 48 hours after transfection, and *Gaussia* luciferase expression from oRNA was determined using a coelenterazine-containing detection reagent and luminometer. Higher luminescence at 24 hours indicates higher TIE function. Higher luminescence at 48 hours relative to 24 hours indicates higher oRNA stability due to TIE function.

Example 73B: TIE Activity in Primary Human Hepatocytes

Nucleic acid sequences containing putative TIEs were inserted into a circular RNA (oRNA) construct prior to the start codon of a *Gaussia* luciferase reporter sequence. oRNA containing the TIE was synthesized and purified. Purified oRNA was formulated into lipid nanoparticles. LNP-oRNA was transfected into hepatocytes in vitro. Supernatant was harvested and replaced 24 and 48 hours after transfection, and *Gaussia* luciferase expression from oRNA was determined using a coelenterazine-containing detection reagent and luminometer. Higher luminescence at 24 hours indicates higher TIE function. Higher luminescence at 48 hours relative to 24 hours indicates higher oRNA stability due to TIE function.

Example 73C: TIE Activity in Primary Human Myotubes

Nucleic acid sequences containing putative TIEs were inserted into a circular RNA (oRNA) construct prior to the start codon of a *Gaussia* luciferase reporter sequence. oRNA containing the TIE was synthesized and purified. Purified oRNA was formulated into lipid nanoparticles. LNP-oRNA was transfected into human myotubes in vitro. Supernatant was harvested and replaced 24 and 48 hours after transfection, and *Gaussia* luciferase expression from oRNA was determined using a coelenterazine-containing detection reagent and luminometer. Higher luminescence at 24 hours indicates higher TIE function. Higher luminescence at 48 hours relative to 24 hours indicates higher oRNA stability due to TIE function.

Example 74

TIE Tissue Tropism

Select TIE-containing oRNAs were formulated into LNPs. LNP-oRNAs were transfected into T cells, hepatocytes, and myotubes. Supernatant was harvested and replaced 24 and 48 hours after transfection, and *Gaussia* luciferase expression from oRNA was determined using a coelenterazine-containing detection reagent and luminometer. Higher luminescence at 24 hours indicates higher TIE function. Higher luminescence at 48 hours relative to 24 hours may indicate higher oRNA stability due to TIE function. TIE activity was compared between cell types and differences resulting from TIE tissue preference were noted. Differences may be a result of the TIE engaging proteins that show tissue-specific expression and promoting enhanced translation initiation, degradation, or stability.

Example 75

Example 75A: TIE Deletion Scanning

Select TIE sequences with progressive deletions from either the 5' end or 3' end of the TIE were inserted into a circular RNA (oRNA) construct prior to the start codon of a *Gaussia* luciferase reporter sequence. oRNA containing the TIE variant was synthesized and purified. Purified oRNA was formulated into lipid nanoparticles. LNP-oRNA was transfected into human primary T cells. Supernatant was harvested and replaced 24 and 48 hours after transfection, and *Gaussia* luciferase expression from oRNA was determined using a coelenterazine-containing detection reagent and luminometer. Higher luminescence at 24 hours indicates higher TIE function. Higher luminescence at 48 hours relative to 24 hours may indicate higher oRNA stability due to TIE function. Expression or stability impairment due to progressive deletions identifies the core functional unit of the TIE.

Example 75B: TIE Variant Generation and Identification

Select TIE-containing oRNA synthesis plasmids were subjected to error-prone PCR to introduce random mutations into the PCR product. PCR product was used as a template for oRNA synthesis. Purified oRNA was formulated into LNPs and transfected into primary human T cells. Polysome fractions were harvested from T cells at 6, 24, 48, and 72 hours post-transfection by HPLC. RNA associated with each polysome fraction was extracted from polysome fractions and sequenced by NGS. TIE mutation enrichment in each polysome fraction at each time point was analyzed to identify mutations that 1) maintain or improve translation activity from the TIE and/or 2) improve stability of the oRNA.

Example 75C: TIE Single and Multi-Variant Validation

Nucleic acid sequences containing putative beneficial TIE mutations from example 6 alone or in combination were inserted into a circular RNA (oRNA) construct prior to the start codon of a *Gaussia* luciferase reporter sequence. oRNA containing the TIE variant was synthesized and purified. Purified oRNA was formulated into lipid nanoparticles. LNP-oRNA was transfected into human primary T cells. Supernatant was harvested and replaced 24 and 48 hours after transfection, and *Gaussia* luciferase expression from oRNA was determined using a coelenterazine-containing detection reagent and luminometer. Higher luminescence at 24 hours indicates higher TIE function. Higher luminescence at 48 hours relative to 24 hours indicates higher oRNA stability due to TIE function.

Example 76

Example 76A: Selection of Eukaryotic TIEs

Selection of eukaryotic TIEs. Putative eukaryotic TIEs were identified using several databases. TIEs selected include sequences 40-1578 nucleotides in length and may or may not contain identified modification (m6A) sites.

Example 76B: TIEs Containing Modified Nucleotides (m6A)

Nucleic acid sequences containing putative TIEs were inserted into a circular RNA (oRNA) construct preceding the coding region of a *Gaussia* luciferase reporter sequence. oRNAs were synthesized with a titration of modified nucleotide. Purified oRNA was formulated into lipid nanoparticles. LNP-oRNAs were transfected into T cells, hepatocytes, and myotubes. Supernatant was harvested and replaced 24 and 48 hours after transfection, and *Gaussia* luciferase expression from oRNA was determined using a coelenterazine-containing detection reagent and luminometer. Higher luminescence of modified nucleotide containing TIEs at 24 hours indicates necessity for modification for enhanced function. Higher luminescence at 48 hours relative to 24 hours indicates modified nucleotide containing TIEs enhance stability of oRNA.

Example 77

Expression of TIEs in Cells Undergoing Oxidative and/or Hypoxic Stress

Nucleic acid sequences containing putative TIEs were inserted into a circular RNA (oRNA) construct preceding the coding region of a *Gaussia* luciferase reporter sequence. Purified oRNA was formulated into lipid nanoparticles. Hepatocytes were treated with hydrogen peroxide to induce oxidative stress or CoCl2 to induce hypoxic stress. LNP-oRNA was transfected into hepatocytes (under hypoxic stress, oxidative stress, or untreated) in vitro. Supernatant was harvested and replaced 24 and 48 hours after transfection, and *Gaussia* luciferase expression from oRNA was determined using a coelenterazine-containing detection reagent and luminometer. Higher luminescence at 24 hours indicates higher TIE function. Higher luminescence at 48 hours relative to 24 hours may indicate higher oRNA stability due to TIE function.

Example 78

Aptamer as a TIE

Nucleic acid sequences containing aptamers against translation initiation factors (ie eIF4E, eIF4G, eIF4a) were inserted into a circular RNA (oRNA) construct preceding the coding region of a *Gaussia* luciferase reporter sequence. Purified oRNA was formulated into lipid nanoparticles. LNP-oRNAs were transfected into hepatocytes. Supernatant was harvested and replaced 24 and 48 hours after transfection, and *Gaussia* luciferase expression from oRNA was determined using a coelenterazine-containing detection reagent and luminometer. Higher luminescence at 24 hours indicates higher TIE function. Higher luminescence at 48 hours relative to 24 hours may indicate higher oRNA stability due to TIE function.

Example 79

Tandem TIEs

Select combinations of viral, eukaryotic, and/or aptamer TIEs were inserted into a circular RNA (oRNA) construct preceding the coding region of a *Gaussia* luciferase reporter sequence. oRNAs were synthesized with a titration of modified nucleotide. Purified oRNA was formulated into lipid nanoparticles. LNP-oRNAs were transfected into T cells, hepatocytes, and myotubes. Supernatant was harvested and replaced 24 and 48 hours after transfection, and *Gaussia* luciferase expression from oRNA was determined using a coelenterazine-containing detection reagent and luminometer. Higher luminescence of constructs containing multiple TIEs at 24 hours indicates a synergy of TIEs. Higher luminescence at 48 hours relative to 24 hours may indicate having multiple TIEs in one construct enhance stability of oRNA.

Example 80

Example 80A: Coding Aptamers to Enhance Cap-Independent Translation

Certain aptamers that bind to eIF4E, eIF4a, and other translation initiators are known to inhibit translation by forcing the proteins to adopt a non-functional conformation. Nucleic acid sequences containing aptamers against translation initiation factors (ie eIF4E, eIF4a) were inserted into a circular RNA (oRNA) construct preceding a functional TIE and the coding region of a *Gaussia* luciferase reporter sequence. Purified oRNA was formulated into lipid nanoparticles. LNP-oRNAs were transfected into hepatocytes. Supernatant was harvested and replaced 24 and 48 hours after transfection, and *Gaussia* luciferase expression from oRNA was determined using a coelenterazine-containing detection reagent and luminometer. Higher luminescence at 24 hours indicates a preference for cap-independent translation. Higher luminescence at 48 hours relative to 24 hours indicates higher oRNA stability due to inhibition of cap-dependent translation.

Example 80B: Coding Aptamers to Enhance Cap-Independent Translation

Cotransfection of oRNA and aptamers. Certain aptamers that bind to eIF4E, eIF4a, and other translation initiators are known to inhibit translation by forcing the proteins to adopt a non-functional conformation. Nucleic acid sequences containing aptamers against translation initiation factors (ie eIF4E, eIF4a) were co-transfected with a circular RNA (oRNA) containing a TIE and the coding region of a *Gaussia* luciferase reporter. Purified aptamer and oRNA were formulated into lipid nanoparticles together. LNP-oRNAs were transfected into hepatocytes. Supernatant was harvested and replaced 24 and 48 hours after transfection, and *Gaussia* luciferase expression from oRNA was determined using a coelenterazine-containing detection reagent and luminometer. Higher luminescence at 24 hours indicates a preference for cap-independent translation. Higher luminescence at 48 hours relative to 24 hours may indicate higher oRNA stability due to inhibition of cap-dependent translation.

Example 81

Example 81.1 Synthesis of heptadecan-9-yl 8-((3-hydroxypropyl)(2-hydroxytetradecyl)amino)octanoate (Lipid 10e-1)

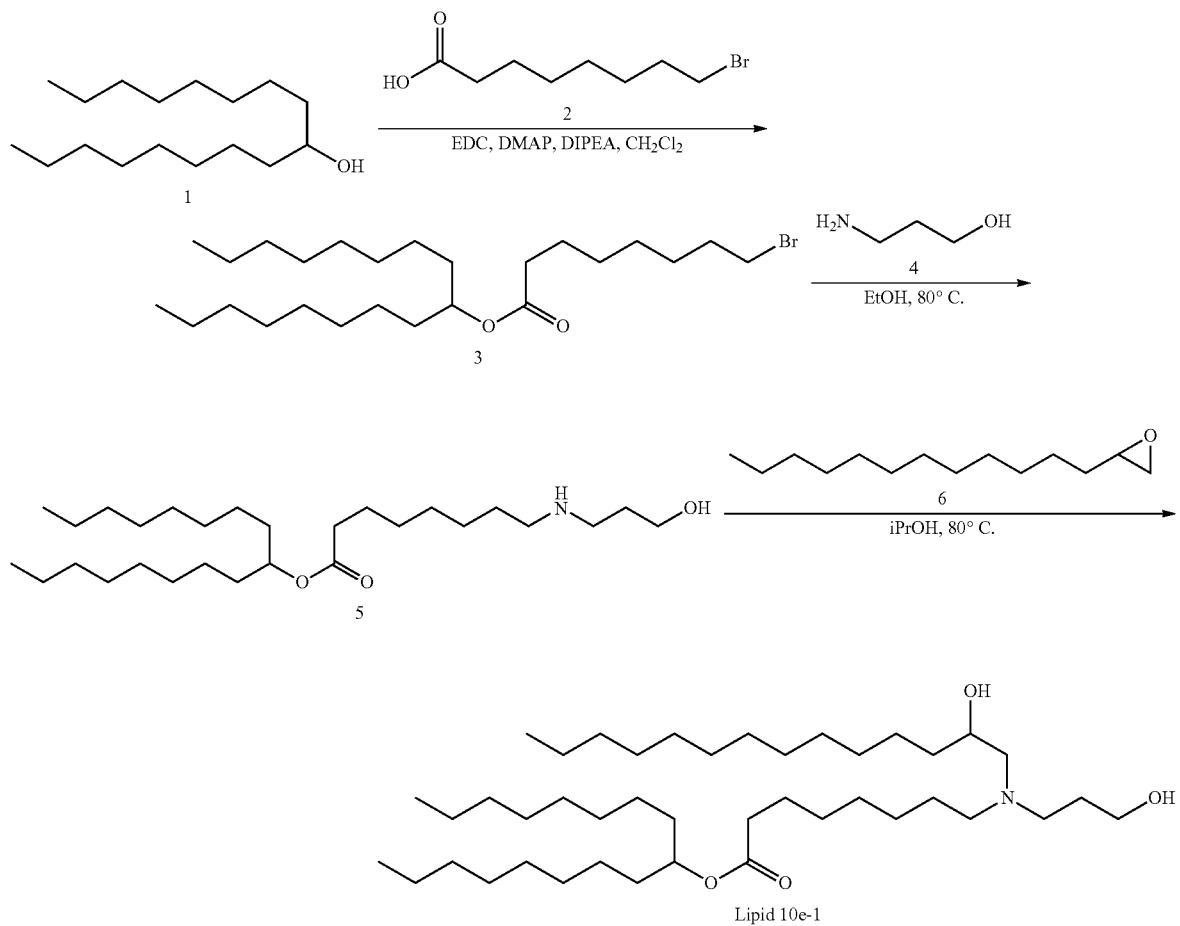

To a mixture of 8-bromooctanoic acid 2 (10 g, 44.82 mmol) and heptadecan-9-ol 1 (9.6 g, 37.35 mmol) in $CH_2Cl_2$ (300 mL) was added DMAP (900 mg, 7.48 mmol), DIPEA (26 mL, 149.7 mmol) and EDC (10.7 g, 56.03 mmol). The

Example 81.1.1 Synthesis of heptadecan-9-yl 8-bromooctanoate (3)

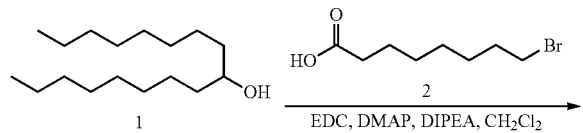

reaction was stirred at room temperature overnight. After concentration of the reaction mixture, the crude residue was dissolved in ethyl acetate (300 mL), washed with 1N HCl, sat. $NaHCO_3$, water and Brine. The organic layer was dried over anhydrous $Na_2SO_4$. The solvent was evaporated, and the crude residue was purified by flash chromatography ($SiO_2$: Hexane=100% to 30% of EtOAc in Hexane) and colorless oil product 3 was obtained (5 g, 29%).

$^1$H NMR (300 MHz, $CDCl_3$): δ ppm 4.86 (m, 1H), 3.39 (t, J=7.0 Hz, 2H), 2.27 (t, J=7.6 Hz, 2H), 1.84 (m, 2H), 1.62 (m, 2H), 1.5-1.4 (m, 8H), 1.35-1.2 (m, 26H), 0.87 (t, J=6.7 Hz, 6H).

Example 81.1.2 Synthesis of heptadecan-9-yl 8-((3-hydroxypropyl)amino)octanoate (5)

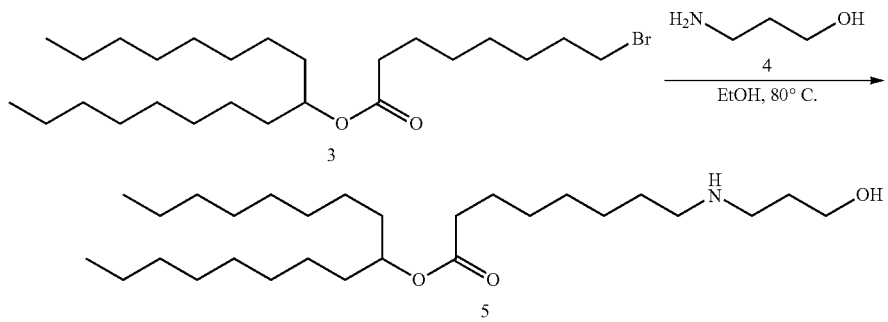

A solution of 1-octylnonyl 8-bromooctanoate 3 (7.4 g, 16.03 mmol) in EtOH (200 mL) was added 3-amino-1-propanol 4 (24.4 mL, 320 mmol) and the reaction solution was heated at 70° C. overnight. MS showed the expected product: [APCI]: [MH]+456.4. After concentration of the reaction mixture, the crude residue was dissolved in methyl tert-butyl ether (500 mL), washed with sat. NaHCO$_3$, water and Brine. The organic layer was dried over anhydrous Na$_2$SO$_4$. The solvent was evaporated, and the crude residue was purified by flash chromatography (SiO$_2$: CH$_2$Cl$_2$=100% to 10% of MeOH in CH$_2$C$_2$ with 1% NH$_4$OH) and colorless oil product 5 was obtained (6.6 g, 88%).

$^1$H NMR (300 MHz, CDCl$_3$): δ ppm 4.84 (m, 1H), 3.80 (t, J=5.5 Hz, 2H), 2.87 (t, J=5.76 Hz, 2H), 2.59 (t, J=7.2 Hz, 2H), 2.27 (t, J=7.6 Hz, 2H), 1.68 (m, 2H), 1.62 (m, 2H), 1.5-1.4 (m, 5H), 1.35-1.2 (m, 32H), 0.87 (t, J=6.7 Hz, 6H). MS (APCI+): 456.4 (M+1).

Example 81.1.3 Synthesis of heptadecan-9-yl 8-((3-hydroxypropyl)(2-hydroxytetradecyl)amino)octanoate (7)

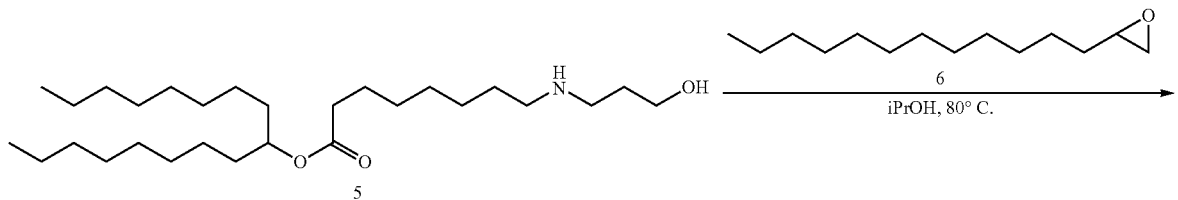

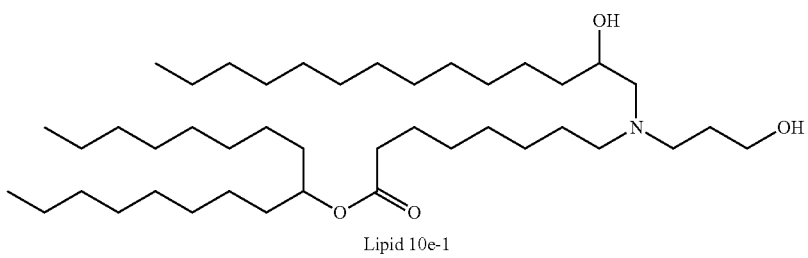

Lipid 10e-1

A mixture of compound 5 (6.6 g, 14.5 mmol) and 1,2-epoxytetradecane (3.68 g, 17.4 mmol) in isopropanol (150 mL) was heated to reflux for overnight. MS showed the expected product: [APCI]: [MH]$^+$668.6. The reaction mixture was concentrated, and crude product was purified flash chromatography (SiO$_2$: CH$_2$Cl$_2$=100% to 10% of MeOH in CH$_2$C$_2$ with 1% NH$_4$OH) to obtained Lipid 10e-1 as colorless oil (6.34 g, 65%).

$^1$H NMR (300 MHz, CDCl$_3$): δ ppm 4.85 (m, 1H), 3.76 (t, J=5.49 Hz, 2H), 3.68 (m, 1H), 2.75 (m, 1H), 2.59 (m, 2H), 2.38 (m, 3H), 2.27 (m, 2H), 1.58-1.68 (m, 2H), 1.48 (m, 6H), 1.24 (m, 56H), 0.87 (m, 9H). MS (APCI+): 668.6 (M+1).

Example 81.2 Synthesis of Di(undecan-3-yl) 8,8'-((3-hydroxypropyl)azanediyl)bis(7-hydroxyoctanoate) (10e-7)

$^1$H NMR (300 MHz, CDCl$_3$): δ ppm 5.88-5.72 (m, 1H), 5.02-4.91 (m, 1H), 4.80 (m, 1H), 2.28 (t, J=7.4 Hz, 2H), 2.05-2.03 (m, 2H), 1.62-1.49 (m, 6H), 1.37-1.25 (m, 16H), 0.87 (t, J=7.4 Hz, 6H).

Example 81.2.2 Synthesis of undecan-3-yl 6-(oxiran-2-yl)hexanoate (4)

To a mixture of undecan-3-yl oct-7-enoate 3 (17.2 g, 58.1 mmol) in CH$_2$Cl$_2$ (300 mL) was added meta-chloroperoxybenzoic acid (mCPBA, <77%) (19.5 g, 87 mmol) in one portion at 0° C. ice-water bath. The reaction was stirred at room temperature overnight. The white precipitate (meta-benzoic acid) was filtered and the filtrate was diluted with CH$_2$Cl$_2$ (200 mL), washed with 10% Na$_2$S$_2$O$_3$, sat. NaHCO$_3$, water and Brine. The organic layer was dried over anhydrous Na$_2$SO$_4$. The solvent was evaporated and the

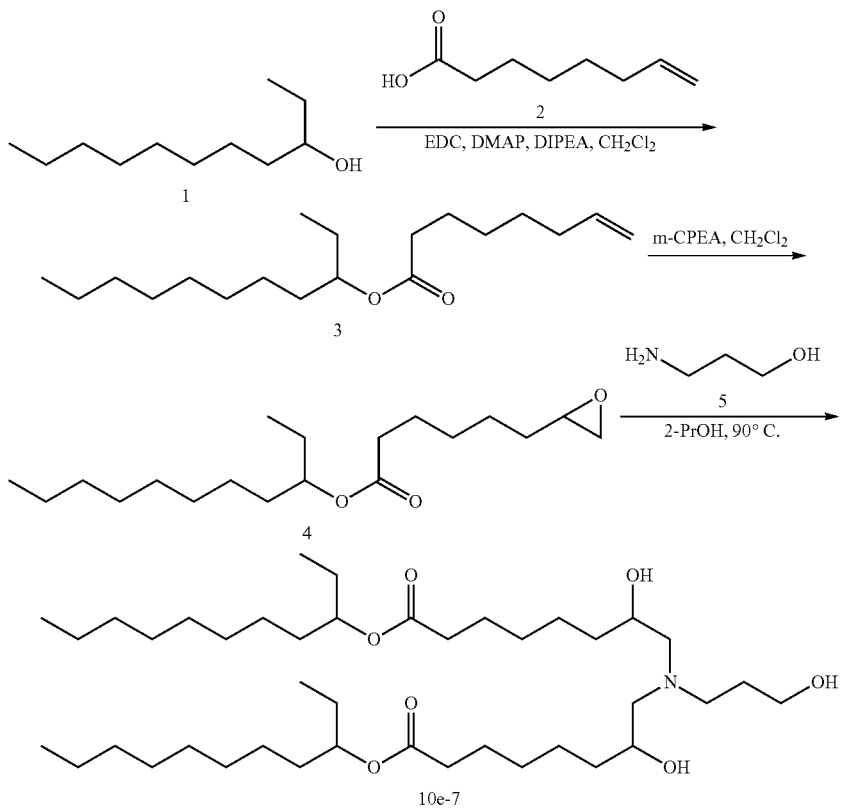

Example 81.2.1 Synthesis of undecan-3-yl oct-7-enoate (3)

To a mixture of oct-7-enoic acid 2 (10 g, 70.3 mmol) and undecan-3-ol 1 (10 g, 58.6 mmol) in CH$_2$Cl$_2$ (300 mL) was added DMAP (1.4 g, 11.6 mmol), DIPEA (40 mL, 232 mmol) and EDC (16.9 g, 87.9 mmol). The reaction was stirred at room temperature overnight. After concentration of the reaction mixture, the crude residue was dissolved in tert-butylmethyl ether (500 mL), washed with 1N HCl, sat. NaHCO$_3$, water and Brine. The organic layer was dried over anhydrous Na$_2$SO$_4$. The solvent was evaporated and the crude residue was purified by flash chromatography (SiO$_2$: Hexane=100% to 20% of EtOAc in Hexane) and colorless oil product 3 was obtained (17.2 g, 98%).

crude residue was purified by flash chromatography (SiO$_2$: Hexane=100% to 30% of EtOAc in Hexane) and colorless oil product 3 was obtained (17.1 g, 97%).

$^1$H NMR (300 MHz, CDCl$_3$): δ ppm 4.80 (m, 1H), 2.89-2.86 (m, 1H), 3.39 (t, J=7.0 Hz, 2H), 2.74 (t, J=4.7 Hz, 1H), 2.47 (dd, J=4.9, 2.2 Hz, 1H), 2.28 (t, J=7.4 Hz, 1H), 1.74-1.46 (m, 10H), 1.35-1.2 (m, 13H) 0.87 (m, 6H).

Example 81.2.3 Synthesis of Di(undecan-3-yl) 8,8'-((3-hydroxypropyl)azanediyl)bis(7-hydroxyoctanoate) (10e-7)

A solution of undecan-3-yl 6-(oxiran-2-yl)hexanoate 4 (8 g, 25.6 mmol) in isopropanol (50 mL) was added 3-amino-1-propanol (769.1 mg, 10.2 mmol) and the reaction solution was heated at 90° C. overnight. MS showed the expected product: [APCI]: [MH]700.6. After concentration of the reaction mixture, the crude residue was purified by flash chromatography (SiO$_2$: CH$_2$Cl$_2$=100% to 10% of MeOH in CH$_2$Cl$_2$) and colorless oil product was obtained (5.1 g, 71%).

$^1$H NMR (300 MHz, CDCl$_3$): δ ppm 4.81 (m, 2H), 3.80 (m, 2H), 3.73 (m, 2H), 2.78 (m, 2H), 2.52-2.43 (m, 4H), 2.28 (t, J=7.3 Hz, 2H), 1.68-1.48 (m, 15H), 1.35-1.17 (m, 37H), 0.88-0.83 (m, 12H). MS (APCI+): 700.6 (M+1).

Example 82

Lipid Nanoparticle Formulation Procedure

A Zetasizer Nano ZS (Malvern Instruments Ltd, Malvern, Worcestershire, UK) was used to determine the particle size, the polydispersity index (PDI), and zeta potential of the nanoparticle compositions in 1×PBS in determining particle size and 15 mM PBS in determining zeta potential. A cuvette with 1 mL of 20 µg/mL LNPs in PBS (pH 7.4) was measured for Z-average using the Malvern Panalytical Zetasizer Pro. The Z-average and polydispersity index were recorded. LNP sizes were determined by dynamic light scattering.

Ultraviolet-visible spectroscopy can be used to determine the concentration of circRNA in nanoparticle compositions. 100 µL of the diluted formulation in 1×PBS is added to 900 µL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of circRNA in the nanoparticle composition can be calculated based on the extinction coefficient of the circRNA used in the composition and on the difference between the absorbance at a wavelength of, for example, 260 nm and the baseline value at a wavelength of, for example, 330 nm.

For the transfer vehicle's pKa, a TNS assay was conducted. 5 µL of 60 µg/mL 2-(p-toluidino) naphthalene-6-sulfonic acid (TNS) and 5 µL of 30 µg of RNA/mL lipid nanoparticles were added in to wells with HEPES buffer ranging from pH 2-12. The mixture was then shaken at room temperature for 5 minutes, and read for fluorescence (excitation 322 nm, emission 431 nm) using a plate reader. The inflection point of the fluorescence signal was calculated to determine the particle's pK$_a$.

For transfer vehicle compositions including RNA, a QUANT-IT™ RIBOGREEN® RNA assay (Invitrogen Corporation Carlsbad, CA) can be used to evaluate the encapsulation of RNA by the transfer vehicle composition. Nanoparticle solutions were diluted in tris-ethylenediaminetetraacetic acid (TE) buffer at a theoretical oRNA concentration of 2 µg/mL. Standard oRNA solutions diluted in TE buffer were made ranging from 2 µg/mL to 0.125 µg/mL. The particles and standards were plated in a black 96-well plate with both TE buffer and 4% Triton-X separately (Triton-X was used as a surfactant to lyse the nanoparticles). After an incubation (37° C. at 350 rpm for 15 minutes), Quant-iT™ RiboGreen™ RNA reagent was added to all wells and a second incubation was performed (37° C. at 350 rpm for 3 minutes). Fluorescence was measured using a SPECTRAmax® GEMINI XS microplate spectrofluorometer (Molecular Devices Corporation Sunnyvale, CA). The concentration of oRNA in each particle solution was calculated using the standard curve. The encapsulation efficiency was calculated from the ratio of oRNA detected between lysed and unlysed particles.

Example 83

Expression of mOX40L in Splenic Immune Cells.

Lipid nanoparticles comprising Lipid 1 of Table 10e and Lipid 15 of Table 10f were formulated with circular RNA encoding for mOX40L at an ionizable lipid to phosphate ratio (IL:P) of 5.7. The ionizable lipid:helper lipid:cholesterol:PEG-lipid molar ratio of these LNPs was 50:10:38.5:1.5. Dialysis of the LNPs were performed using PBS. C57BL/6 female mice (6-8 weeks, n=4) were dosed at either LNP comprising Lipid 1 of Table 10e or the Lipid 15 of Table 10f at 1 mg/kg intravenously. At 24 hours, the spleen from the mice were collected for flow cytometry analysis. mOX40L transfection of Lipid 1 of Table 10e and Lipid 15 of Table 10f were compared in T cells, myeloid cells, B cells, and NK cells.

Figure 74:
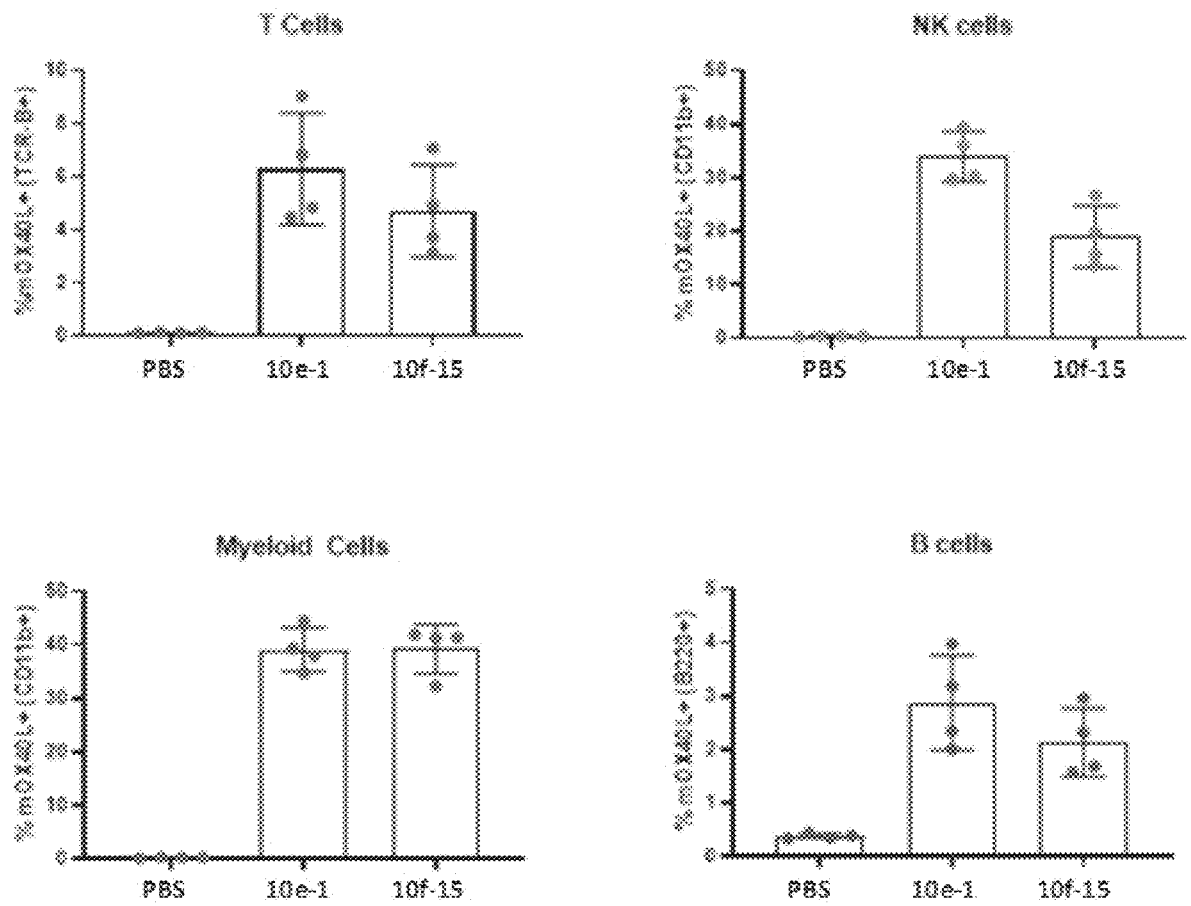
FIG. 74 illustrates mOX40L expression in the spleen of mice from LNPs comprising either Lipid 1 of Table 10e (10e-1) or Lipid 15 of Table 10f (10f-15), at a lipid to phosphate ratio (IL:P) of 5.7 (5.7 A parameters formulation) encapsulating circular RNA encoding for mOX40L.

As shown in FIG. 74, Lipid 1 of Table 10e resulted in comparable or higher levels of mOX40L transfection in splenic immune cells compared to those comprising Lipid 15 of Table 10f.

| Formulation | Ionizable Lipid | Helper Lipid | PEG-Lipid | Dialysis | Z-Average (nm) | PDI | RNA Encapsulation Efficiency (%) |
|---|---|---|---|---|---|---|---|
| 10e-1 (5.7A) | Table 10e, Lipid 1 | DSPC | DMG-PEG(2000) | 1X PBS | 79 | 0.03 | 95 |
| 10f-15 (5.7A) | Table 10f, Lipid 15 | DSPC | DMG-PEG(2000) | 1X PBS | 69 | 0.09 | 98 |

Example 84

Fluorescent Expression of Circular RNA Encompassed within LNP Formulations Compared to Linear RNA Encompassed within LNP Formulations.

LNPs were made to either contain circular RNAs encoding for firefly luciferase or linear RNAs (mRNA) encoding for firefly luciferase. The LNPs containing linear RNAs were also modified with 5-methoxyuridine (5-moU). These LNPs were formulated to contain Lipid 1 or Lipid 7 of Table 10e, wherein the ionizable lipid:helper lipid:cholesterol:PEG-lipid molar ratio of these LNPs was 50:10:38.5:1.5. Dialysis of the LNP was performed using 1×PBS. Size of the LNP construct, polydispersion index (PDI), and RNA entrapment was determined.

As seen in the table below, encapsulation efficiency of circular RNA in each of the LNP formulations was greater than that of linear RNA in the same formulations.

| Formulation | Ionizable Lipid | Helper Lipid | PEG-Lipid | RNA | Z-Average (nm) | PDI | RNA Encapsulation Efficiency (%) |
|---|---|---|---|---|---|---|---|
| 10e-1 (5.7A) | Table 10e, Lipid 1 | DSPC | DMG-PEG(2000) | FLuc oRNA | 82 | 0.05 | 95 |
| | | | | FLuc mRNA 5MoU | 89 | 0.05 | 90 |
| 10e-7 (5.7A) | Table 10e, Lipid 7 | DSPC | DMG-PEG(2000) | oRNA | 86 | 0.02 | 97 |
| | | | | FLuc mRNA 5MoU | 86 | 0.04 | 94 |

Example 85

Formulated LNPs Undergoing Dialysis Using Either PBS or TSS.

LNPs were formulated with circular RNA at a ionizable lipid to phosphate ratio (IL:P) of 5.7 and a ionizble lipid: helper lipid:cholesterol:PEG-lipid ratio of 50:10:38.5:1.5. These LNPs then underwent dialysis using either 1×PBS or 1×TSS. Both formulated LNPs had greater than 90% encapsulation efficiency ratio of the circular RNAs.

| Formulation | Ionizable Lipid | Helper Lipid | PEG-Lipid | Dialysis | Z-Average (nm) | PDI | RNA Encapsulation Efficiency (%) |
|---|---|---|---|---|---|---|---|
| 10e-1 (5.7A) | Table 10e, Lipid 1 | DSPC | DMG-PEG(2000) | 1X PBS | 87 | 0.06 | 94 |
| | | | | 1X TSS | 68 | 0.04 | 92 |

Example 86

Mouse Splenic Protein Expression Post-Treatment of LNP-Circular RNAs Encoding for Firefly Luciferase with Varying B-Hydroxyl Groups in the Ionizable Lipid C57BL/6 mice (female, 6-8 weeks, n=4 per group) were injected intravenously with 0.5 mg/kg circular RNA encoding for firefly luciferase encapsulated in LNPs or PBS control. The LNPs were formulated with different ionizable lipids (Table 10e, Lipid 85, 86, 89, or 90, or Table 10f Lipid 22) and formulated as described in the table below. After 6 hr, mice were injected intraperitoneally with D-luciferin (200 µL at 15 mg/mL). After 15 minutes, mice were euthanized and their spleens were collected. Whole tissue luminescence was measured ex vivo using an IVIS Spectrum In Vivo Imaging system (PerkinElmer) and total flux was quantified using Living Image® software (PerkinElmer).

Figure 75:
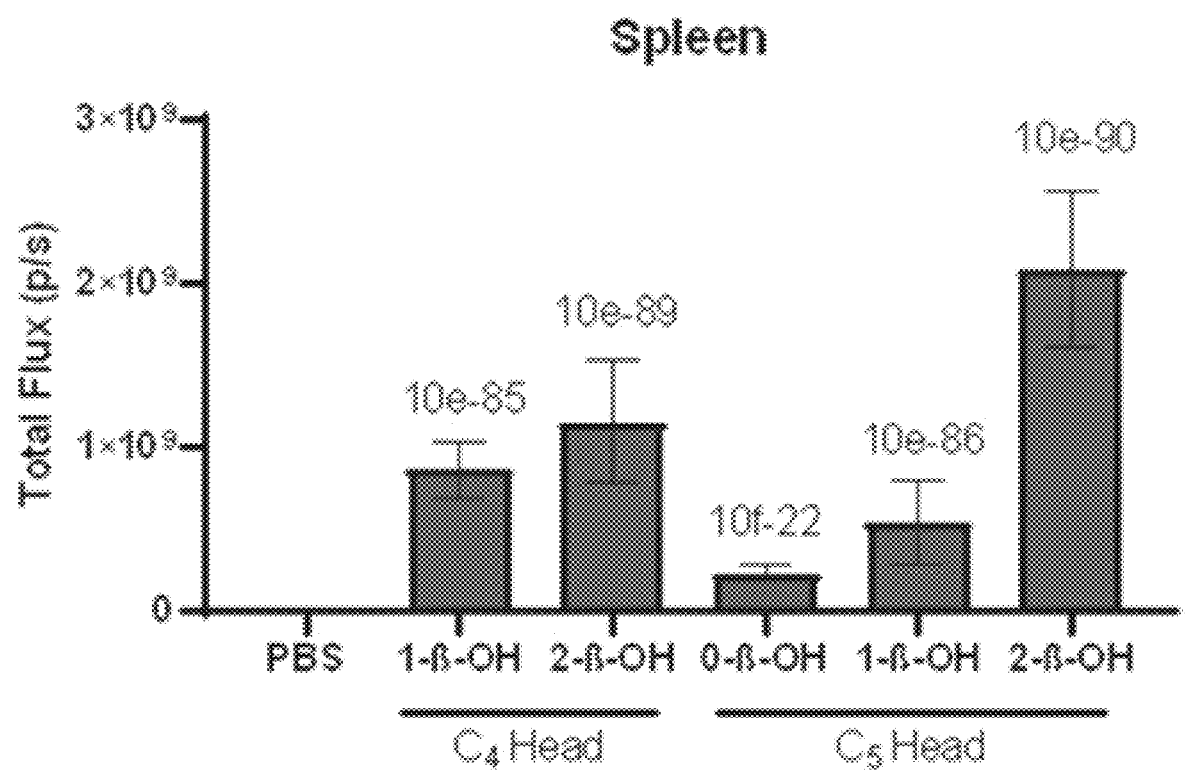
FIG. 75 illustrates circular RNA expression of firefly luciferase delivered using LNPs formulated with ionizable lipids comprising varying numbers of β-hydroxyl groups or a negative control (PBS). Ionizable lipids used comprise left to right: Table 10e, Lipid 85 (10e-85); Table 10e, Lipid 89 (10e-89); Table 10f, Lipid 22 (10f-22); Table 10e, Lipid 86 (10e-86); and Table 10e, Lipid 90 (10e-90).

As shown in FIG. 75, increasing luciferase expression in the spleen was correlated with increasing numbers of B-hydroxyl groups present in the ionizable lipid component of the LNP.

Example 87

Mouse whole splenic protein expression post-treatment of LNP-circular RNAs encoding for firefly luciferase and comprising ionizable lipids from Table 10e C57BL/6 mice (female, 6-8 weeks, n=4 per group) were injected intravenously with 0.5 mg/kg circular RNA encoding for firefly luciferase encapsulated in LNPs or PBS control. The LNPs were formulated with different ionizable lipids from Table 10e Lipid 1, Lipid 85, Lipid 38, Lipid 34, Lipid 45, Lipid 86, Lipid 88, Lipid 89, Lipid 90). LNPs were formulated with circular RNA at a ionizable lipid to phosphate ratio (IL:P) of 5.7 and a ionizble lipid:helper lipid:cholesterol:PEG-lipid ratio of 50:10:38.5:1.5. After 6 hr, mice were injected intraperitoneally with D-luciferin (200 µL at 15 mg/mL). After 15 minutes, mice were euthanized and their spleens were collected. Whole tissue luminescence was measured ex vivo using an IVIS Spectrum In Vivo Imaging system (PerkinElmer) and total flux was quantified using Living Image® software (PerkinElmer).

Figure 76:
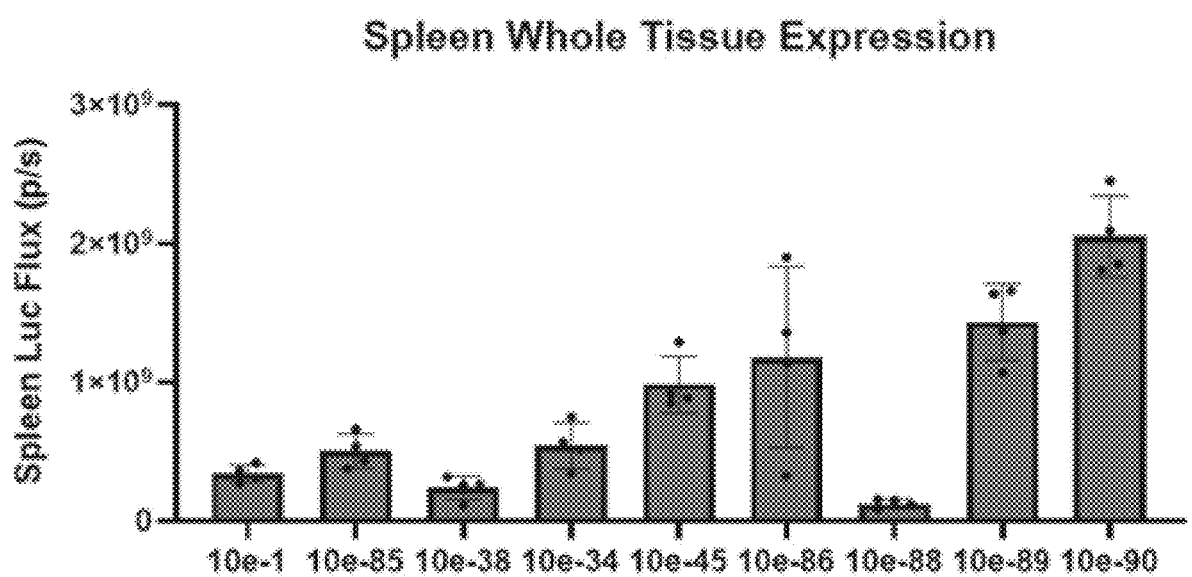
FIG. 76 illustrates oRNA expression of firefly luciferase in the spleen delivered using LNPs formulated with ionizable lipids from Table 10e (from left to right: lipids 1, 85, 38, 34, 45, 86, 88, 89, 90) post intravenous administration. Total luciferase flux was measured in the spleen.

As seen in FIG. 76 the LNP-circular RNAs were able to express firefly luciferase in spleen of the mice post intravenous administration of the construct.

Example 88

Expression of mOX40L in Splenic T Cells.

Lipid nanoparticles comprising ionizable lipids from Table 10e (Lipid 1, 16, 85, 34, 45, 86, 88, 89, 90) or PBS (negative control) formulated with circular RNA encoding for mOX40L at an ionizable lipid to phosphate ratio (IL:P) of 5.7. The ionizable lipid:helper lipid: cholesterol:PEG-lipid molar ratio of these LNPs was 50:10:38.5:1.5.

| Formulation | Ionizable Lipid | Helper Lipid | PEG-Lipid | Ionizable lipid:Helper lipid:Cholesterol:PEG-lipid (mol %) | Z-Average (nm) | PDI | RNA Encapsulation Efficiency (%) |
|---|---|---|---|---|---|---|---|
| 10e-85 (5.7A) | Table 10e, Lipid 85 | DSPC | DMG-PEG(2000) | 50:10:38.5:1.5 | 81 | 0.08 | 91 |
| 10e-89 (5.7A) | Table 10e, Lipid 89 | DSPC | DMG-PEG(2000) | 50:10:38.5:1.5 | 82 | 0.04 | 92 |
| 10f-22 (5.7A) | Table 10f, Lipid 22 | DSPC | DMG-PEG(2000) | 50:10:38.5:1.5 | 78 | 0.08 | 93 |
| 10e-86 (5.7A) | Table 10e, Lipid 86 | DSPC | DMG-PEG(2000) | 50:10:38.5:1.5 | 79 | 0.1 | 92 |
| 10e-90 (5.7A) | Table 10e, Lipid 90 | DSPC | DMG-PEG(2000) | 50:10:38.5:1.5 | 86 | 0.04 | 92 |

C57BL/6 female mice (6-8 weeks, n=4) were dosed at 1 mg/kg intravenously. At 24 hours, the spleen from the mice were collected for flow cytometry analysis, tested for weight loss and measured for serum alanine aminotransferase (ALT) after blood collection. mOX40L expression was measured in splenic T cells.

Figure 77:
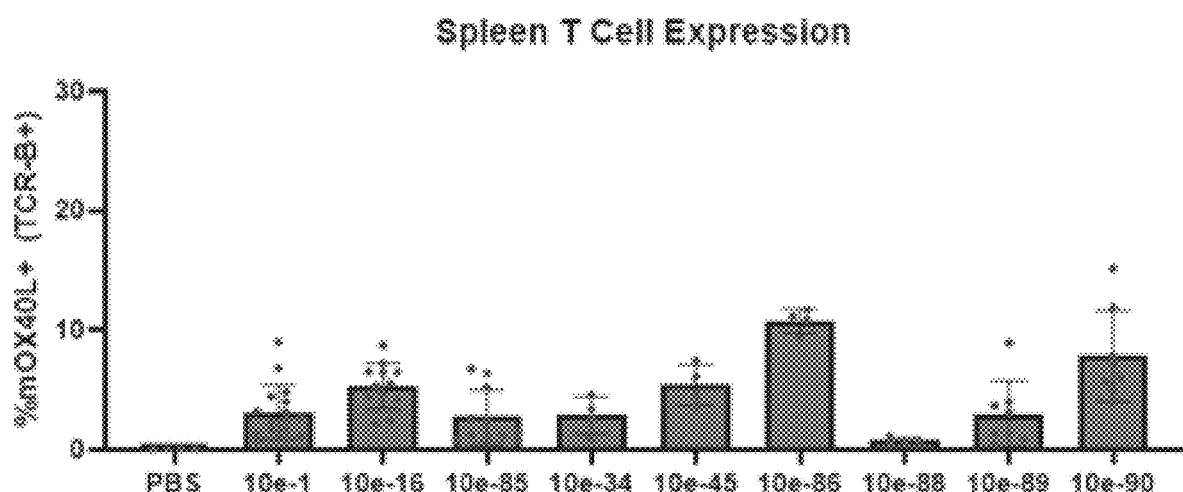
FIG. 77 illustrates splenic T cell expression post intravenous administration of circular RNA encoding for mOX40L delivered using LNPs comprising an ionizable lipid from Table 10e (from left to right: Lipid 1, Lipid 85, Lipid 38, Lipid 34, Lipid 45, Lipid 86, Lipid 88, Lipid 89, Lipid 90).

As shown in FIG. 77, Lipid 1 of Table 10e resulted in expression of mOX40L in splenic T cells. No substantial adverse effects were measured pertaining to weight loss or ALT.

| Formulation | Ionizable Lipid | Helper Lipid | PEG-Lipid | Ionizable lipid:Helper lipid:Cholesterol:PEG-lipid (mol %) | Z-Average (nm) | PDI | RNA Encapsulation Efficiency (%) |
|---|---|---|---|---|---|---|---|
| 10e-1 (5.7A) | Table 10e, Lipid 1 | DSPC | DMG-PEG(2000) | 50:10:38.5:1.5 | 73 | 0.05 | 94 |
| 10e-16 (5.7A) | Table 10e, Lipid 16 | DSPC | DMG-PEG(2000) | 50:10:38.5:1.5 | 76 | 0.10 | 95 |
| 10e-85 (5.7A) | Table 10e, Lipid 85 | DSPC | DMG-PEG(2000) | 50:10:38.5:1.5 | 74 | 0.04 | 95 |
| 10e-34 (5.7A) | Table 10e, Lipid 34 | DSPC | DMG-PEG(2000) | 50:10:38.5:1.5 | 72 | 0.03 | 97 |
| 10e-45 (5.7A) | Table 10e, Lipid 45 | DSPC | DMG-PEG(2000) | 50:10:38.5:1.5 | 75 | 0.04 | 98 |
| 10e-86 (5.7A) | Table 10e, Lipid 86 | DSPC | DMG-PEG(2000) | 50:10:38.5:1.5 | 79 | 0.05 | 94 |
| 10e-88 (5.7A) | Table 10e, Lipid 88 | DSPC | DMG-PEG(2000) | 50:10:38.5:1.5 | 67 | 0.01 | 95 |
| 10e-89 (5.7A) | Table 10e, Lipid 89 | DSPC | DMG-PEG(2000) | 50:10:38.5:1.5 | 73 | 0.01 | 95 |
| 10e-90 (5.7A) | Table 10e, Lipid 90 | DSPC | DMG-PEG(2000) | 50:10:38.5:1.5 | 87 | 0.02 | 94 |

Example 89

Level of B Cell Depletion Post Treatment of LNP-Circular RNTAs Encoding for aCD19-CAR C57B3L/6 mice (female, 6-8 weeks, n=4 per group) were injected intravenously with 1 mg/kg circular RNA encoding for an aCD19-CAR encapsulated in LNPs or control circular RNA encoding for mWasabi encapsulated in LNPs on Days 0, 2, 5, and 7. The LNPs were formed with different ionizable lipids (Table 10e, Lipid 1, 16, 85, 45, 86, or 90). LNPs were formulated with circular RNA at a ionizable lipid to phosphate ratio (IL:P) of 5.7 and a ionizable lipid:helper lipid:cholesterol:PEG-lipid ratio of 50:10:38.5:1.5. On day 8, Cardiac punctures were performed to collect blood, and blood was stained, fixed, and lysed with BD FACS Lysis Solution per the manufacturer's protocol. To assess the frequency of B cells in the blood, single cell suspensions were stained for dead cells (LiveDead Near IR, Invitrogen) and stained with anti-mouse antibodies (CD45, 30-F11, or BUV563 [blood], BD; CD3, 17A2, APC, Biolegend; B220, RA3-6B2, PE, Biolegend; CD11b, M1/70, BV421, Biolegend) at 1:200. Flow cytometry was performed using a BD FACSSymphony flow cytometer. B Cell depletion was defined by the percentage of B220+ B cells of live, CD45+ immune cells.

Figure 78:
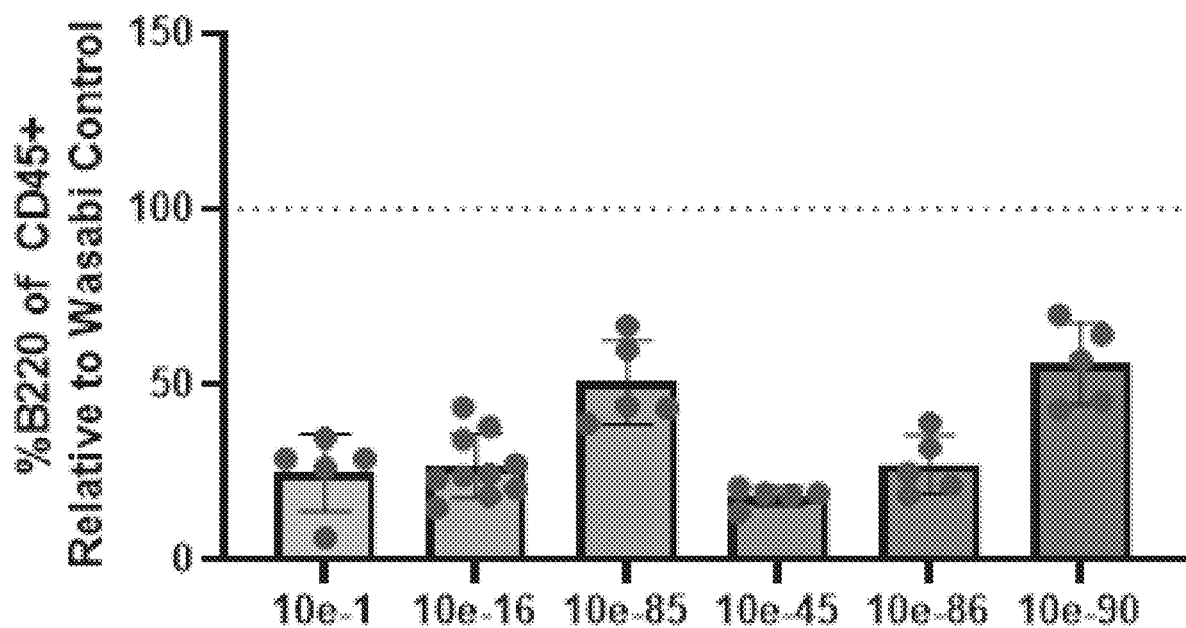
FIG. 78 illustrates B cell depletion within mice when treated with a circular RNA encoding a CD-19 chimeric antigen receptor (CAR) protein encapsulated in mice. The circular RNAs were delivered via an LNP comprising an ionizable lipid from Table 10e (1, 16, 85, 45, 86, or 90).

Resulting blood B cell aplasia is illustrated in FIG. 78. As shown in FIG. 78, the LNP-circular RNA constructs were able to express an aCD19-CAR.

Example 90

Tumor Growth Kinetics Post Administration of LNP-oRNA Construct in a Nalm6 Model NSG mice were engrafted with Nalm6-luciferase tumor cells and 3 days later were engrafted with human PBMCs. Starting the following day, the mice were treated 4 times every other day with vehicle (PBS) or anti-CD19 LNP-oCAR compounds at a dose of 2 mg/kg. LNPs were formulated with circular RNA at a ionizable lipid to phosphate ratio (IL:P) of 5.7 and a ionizble lipid:helper lipid:cholesterol:PEG-lipid ratio of 50:10:38.5:1.5. Animals were then whole-body imaged via IVIS to monitor luciferase expression from Nalm6 cells. Nalm6 tumor burden is plotted as total flux of luciferase expression at each imaging timepoint.

Figure 79:
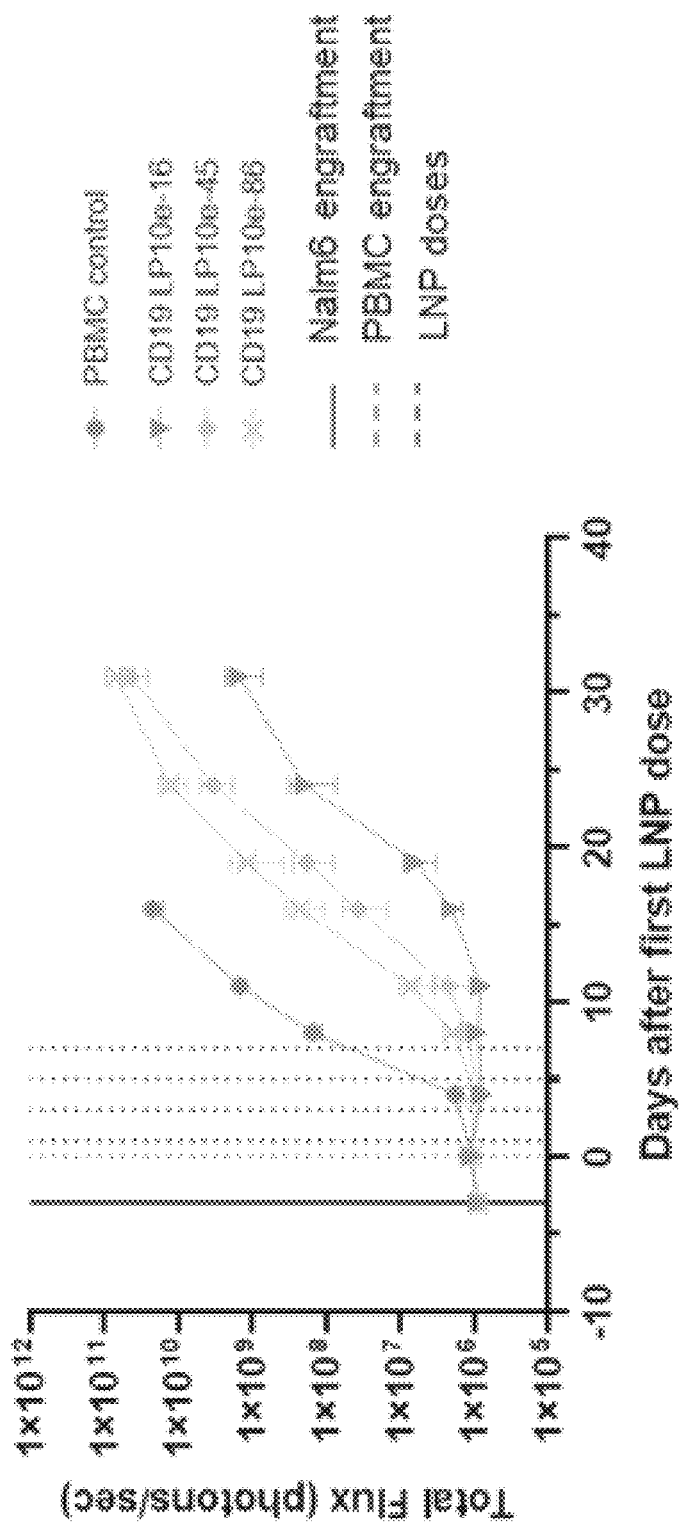
FIG. 79 illustrates tumor growth kinetics in a Nalm6 model post administration of LNP-oRNA constructs in Table 10e, lipids 16, 45, or 86. Total flux of the tested mice was measured.

As shown in FIG. 79, all three anti-CD19 oCAR LNPs each comprising of a different ionizable lipid were capable of slowing tumor growth in this Nalm6 model.

INCORPORATION BY REFERENCE

All publications, patents, and patent applications mentioned in this specification are herein incorporated by reference to the same extent as if each individual publication, patent, or patent application was specifically and individually indicated as being incorporated by reference herein.

What is claimed is:

1. An ionizable lipid represented by Formula (13*):

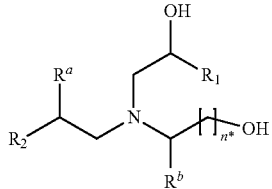

Formula (13*)

or a pharmaceutically acceptable salt thereof, wherein:

n* is an integer from 1 to 7;

$R^a$ is hydrogen;

$R^b$ is hydrogen or C1-C6 alkyl;

$R^1$ and $R^2$ are each independently unsubstituted, linear, or branched $C_6$-$C_{30}$ alkyl or —$(CH_2)_qC(O)(CH_2)_rCH(R^8)(R^9)$, wherein one of $R^1$ and $R^2$ is an unsubstituted, linear or branched $C_6$-$C_{30}$ alkyl, wherein:

q is an integer from 0 to 12, r is 0, $R^8$ is $R^{10}$, and $R^9$ and $R^{10}$ are independently unsubstituted linear $C_1$-$C_{12}$ alkyl or unsubstituted linear $C_2$-$C_{12}$ alkenyl.

2. The ionizable lipid of claim 1, wherein the ionizable lipid is represented by Formula (13a-1), Formula (13a-2), or Formula (13a-3):

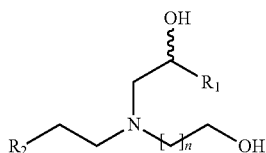

Formula (13a-1)

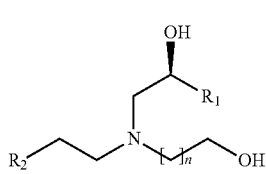

Formula (13a-2)

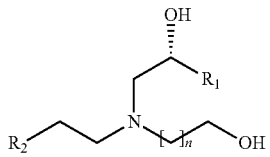

Formula (13a-3)

wherein n is 1, 2, 3, 4, or 5.

3. The ionizable lipid of claim 1, wherein q is 3, 4, 5, or 6.

4. The ionizable lipid of claim 1, wherein $R^b$ is hydrogen.

5. The ionizable lipid of claim 1, wherein $R^b$ is $C_1$-$C_6$ alkyl.

6. The ionizable lipid of claim 1, wherein $R^9$ and $R^{10}$ are the same.

7. The ionizable lipid of claim 1, wherein $R^9$ and $R^{10}$ are different.

8. The ionizable lipid of claim 1, wherein $R^9$ and $R^{10}$ are each independently unsubstituted linear $C_4$-$C_8$ alkyl.

9. The ionizable lipid of claim 1, wherein $R^9$ and $R^{10}$ are each independently unsubstituted linear $C_6$-$C_8$ alkyl.

10. The ionizable lipid of claim 1, wherein $R^1$ is unsubstituted, linear, or branched $C_6$-$C_{30}$ alkyl.

11. The ionizable lipid of claim 1, wherein $R^2$ is —$(CH_2)_qC(O)O(CH_2)_rCH(R^8)(R^9)$.

12. The ionizable lipid of claim 1, wherein $R^1$ and $R^2$ are each independently selected from:

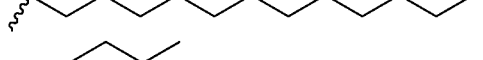

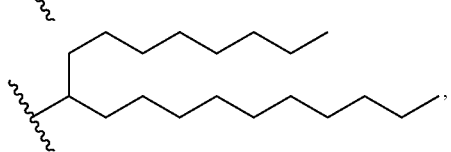

471

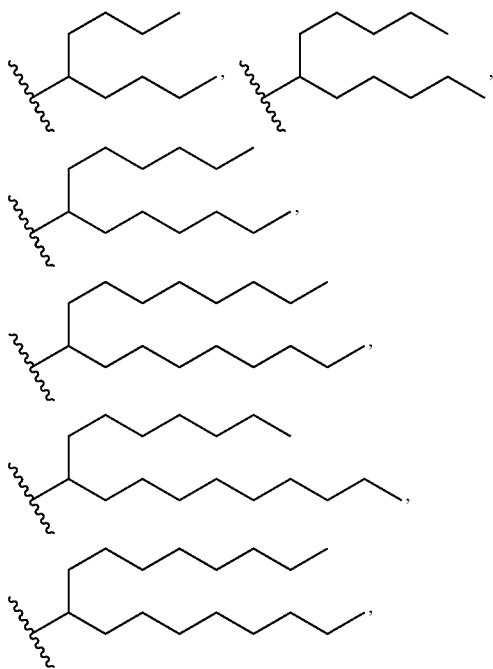

472

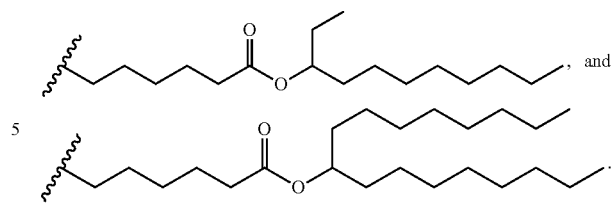, and

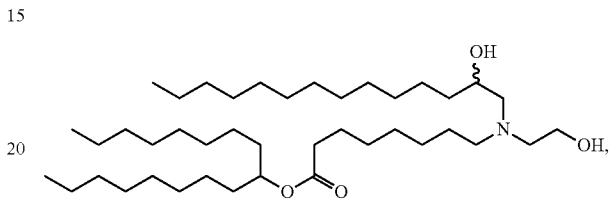.

13. The ionizable lipid of claim 12, wherein $R^1$ and $R^2$ are the same.

14. The ionizable lipid of claim 12, wherein $R^1$ and $R^2$ are different.

15. The ionizable lipid of claim 1, wherein the ionizable lipid is:

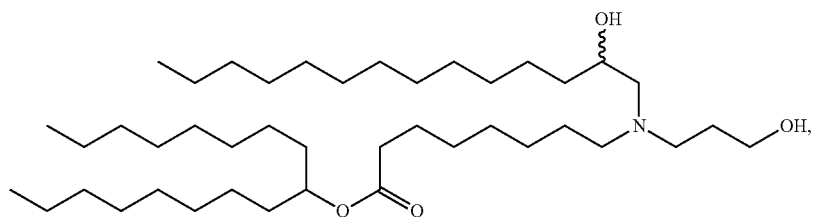 [SMILES: CCCCCCCCCCCCC(O)CN(CCCO)CCCCCCCC(=O)OC(CCCCCCCC)CCCCCCCC]

or is a pharmaceutically acceptable salt thereof.

16. The ionizable lipid of claim 1, wherein the ionizable lipid is:

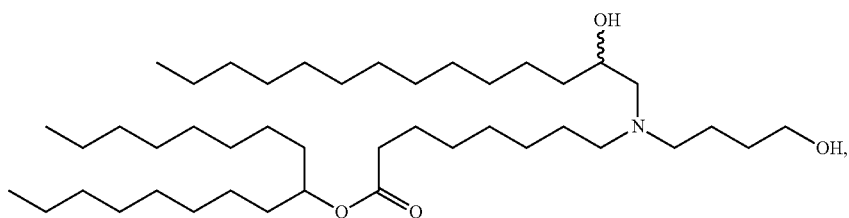 [SMILES: CCCCCCCCCCCCC(O)CN(CCCCO)CCCCCCCC(=O)OC(CCCCCCCC)CCCCCCCC]

or is a pharmaceutically acceptable salt thereof.

17. The ionizable lipid of claim 1, wherein the ionizable lipid is:

or is a pharmaceutically acceptable salt thereof.

18. The ionizable lipid of claim 1, wherein the ionizable lipid is:

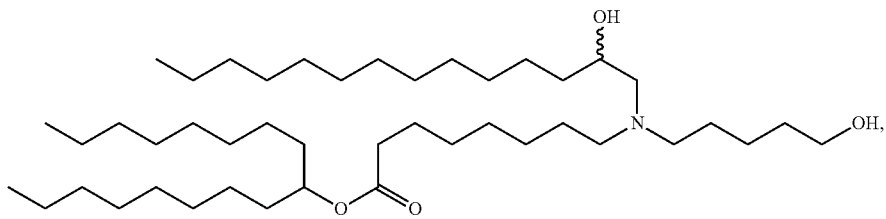 [SMILES: CCCCCCCCCCCCC(O)CN(CCCCCO)CCCCCCCC(=O)OC(CCCCCCCC)CCCCCCCC]

or is a pharmaceutically acceptable salt thereof.

19. An ionizable lipid represented by Formula (13):

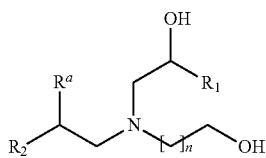

Formula (13)

or a pharmaceutically acceptable salt thereof, wherein:
- n is 1, 2, 3, or 4;
- $R^a$ is hydrogen;
- $R^1$ is unsubstituted linear $C_6$-$C_{30}$ alkyl;
- $R^2$ is —$(CH_2)_q C(O)O(CH_2)_r CH(R^8)(R^9)$, wherein:
  - q is 3, 4, 5, or 6,
  - r is 0,
  - $R^8$ is $R^{10}$, and
  - $R^9$ and $R^{10}$ are independently unsubstituted linear $C_2$-$C_8$ alkyl.

20. The ionizable lipid of claim 19, wherein $R^9$ and $R^{10}$ are the same.

21. The ionizable lipid of claim 19, wherein $R^9$ and $R^{10}$ are different.

22. The ionizable lipid of claim 19, wherein $R^9$ and $R^{10}$ are each independently unsubstituted linear $C_4$-$C_8$ alkyl.

23. The ionizable lipid of claim 19, wherein $R^9$ and $R^{10}$ are each independently unsubstituted linear $C_6$-$C_8$ alkyl.

24. A pharmaceutical composition comprising the ionizable lipid of claim 19.

25. The pharmaceutical composition of claim 24, wherein the pharmaceutical composition further comprises a RNA polynucleotide.

26. The pharmaceutical composition of claim 25, wherein the RNA polynucleotide is a linear RNA polynucleotide.

27. The pharmaceutical composition of claim 25, wherein the RNA polynucleotide is a circular RNA polynucleotide.

28. The pharmaceutical composition of claim 24, wherein the pharmaceutical composition further comprises:
- a helper lipid, wherein the helper lipid is DOPE or DSPC, cholesterol, and
- a PEG-lipid, wherein the PEG-lipid is DSPE-PEG (2000) or DMG-PEG (2000).

\* \* \* \* \*